US008618329B2

(12) United States Patent
Itoh et al.

(10) Patent No.: US 8,618,329 B2
(45) Date of Patent: Dec. 31, 2013

(54) IMINOPROPENE COMPOUND AND USE THEREOF

(71) Applicant: Sumitomo Chemical Company, Limited, Tokyo (JP)

(72) Inventors: Shigeyuki Itoh, Osaka (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/762,708

(22) Filed: Feb. 8, 2013

(65) Prior Publication Data
US 2013/0150392 A1 Jun. 13, 2013

Related U.S. Application Data

(60) Division of application No. 13/222,512, filed on Aug. 31, 2011, now Pat. No. 8,410,316, which is a division of application No. 11/878,392, filed on Jul. 24, 2007, now Pat. No. 8,084,644, which is a continuation-in-part of application No. PCT/JP2006/322698, filed on Nov. 8, 2006.

(30) Foreign Application Priority Data

Dec. 1, 2005 (JP) ................................. 2005-347646
May 26, 2006 (JP) ................................. 2006-146381

(51) Int. Cl.
*C07C 321/18* (2006.01)
(52) U.S. Cl.
USPC .............................................. 568/44; 568/39
(58) Field of Classification Search
None
See application file for complete search history.

(56) References Cited

U.S. PATENT DOCUMENTS

| 3,742,051 A | 6/1973 | McLaughlin et al. |
| 5,691,333 A | 11/1997 | Wu et al. |
| 5,994,359 A | 11/1999 | Grote et al. |

FOREIGN PATENT DOCUMENTS

| EP | 0 317 266 A2 | 5/1989 |
| IE | 32360 B1 | 7/1973 |

OTHER PUBLICATIONS

Sawanishi et al Chemical and Pharmaceutical Bulletin, 1987, 35(8), 3175-3181.*
W. Kantlehner et al., "Umsetzungen von tert-Butoxy-N,N,N',N'-tetramethylmethandiamin mit NH- und CH-aciden Verbindungen", Liebigs Ann. Chem., 1980, pp. 344-357.
A. Robin et al., "Synthesis of pyridone and pyridine rings by [4+2] hetero-cyclocondensation", Tetrahedron Letters, vol. 45, 2004, pp. 9557-9559.
H. Sawanishi et al., "Studies on Diazepines. XXVI. Syntheses of 6H-1,4-Diazepines and 1-Acyl-1H-1,4-diazepines from 4-Pyridyl Azides", Chem. Pharm. Bull., vol. 35, No. 8, 1987, pp. 3175-3181.
S.I. Kaimanakova et al., "Acetals of Lactams and Acid Amides", translated from Khimiya Geterotsiklicheskikh Soedinenii, No. 11, Nov. 1982, pp. 1553-1557.
Beilstein Records (BRN): 8421559. May 16, 2000.
Irina A. Motorina and David S. Grierson, "An Intramolecular 1-Azadiene Diels-Alder Approach to the Preparation of Synthetic Equivalents of Pyridine", Tetrahedron Letters, vol. 40, 1999, pp. 7211-7214.
Dr. Ch. Jutz et al., "Vinyloge Guanidinium- und w,w-Diaminoacryl-amidinium-Saize", Agnew, Chem., vol. 78, No. 15, (1966), p. 747.

\* cited by examiner

*Primary Examiner* — Yevegeny Valenrod
(74) *Attorney, Agent, or Firm* — Sughrue Mion, PLLC

(57) ABSTRACT

The compound (I) or a salt thereof has an excellent controlling activity against pests. Then the compound (I) or a salt thereof is useful for an active ingredient of a pesticidal composition.

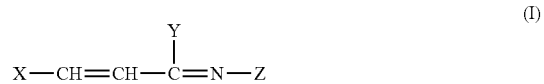

8 Claims, No Drawings

IMINOPROPENE COMPOUND AND USE THEREOF

CROSS-REFERENCE TO RELATED APPLICATIONS

This is a divisional of U.S. application Ser. No. 13/222,512 filed Aug. 31, 2011, now U.S. Pat. No. 8,410,316, which is a divisional of U.S. application Ser. No. 11/878,392 filed Jul. 24, 2007, now U.S. Pat. No. 8,084,644, which is a continuation-in-part application of PCT/JP2006/322698, filed Nov. 8, 2006, which claims priority to Japanese Application No. 2005-347646 filed Dec. 1, 2005 and to Japanese Application No. 2006-146381 filed May 26, 2006, the above-noted applications incorporated herein by reference in their entirety.

TECHNICAL FIELD

The present invention relates to an iminopropene compound and pesticidal use thereof.

BACKGROUND ART

Heretofore, the development of pesticides has been carried out and many compounds which are effective for controlling pest have been found. However, their activity is not always sufficient. Accordingly, there are further demands for developing novel compounds having pest-controlling activity.

DISCLOSURE OF INVENTION

The present invention is intended to provide a compound having superior pest-controlling activity.

The present inventor has intensively studied in order to find a compound having superior pest-controlling activity and, as a result, has found that an iminopropene compound represented by the formula (I) has superior pest-controlling activity. Thus, the present invention has been completed.

That is, the present invention provides as follows:

An iminopropene compound given by the formula (I) or a salt thereof:

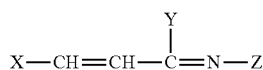

(I)

wherein,

X represents $OX^1$, $NX^2X^3$, $SX^4$, $S(O)_mX^5$, $Si(X^6)_3$ or $N=C(X^7)_2$, Y represents $OY^1$, $NY^2Y^3$, $SY^4$, $SO_2Y^5$ or $N=C(Y^6)_2$, Z represents a cyano group, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{91})Z^A$, $C(=O)OZ^B$, $C(=Q^{92})NZ^{DZE}$, $SO_2Z^F$, $NZ^GZ^H$, $OZ^K$ or $N=C(Z^I)_2$, $X^1$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{11})X^{A1}$, $C(=O)OX^{B1}$, $C(=Q^{12})NX^{D1}X^{E1}$, $SO_2X^{F1}$, $NX^{G1}X^{H1}$ or $N=C(X^{I1})_2$, $X^2$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{A2}$, $C(=O)OX^{B2}$, $C(=Q^{22})NX^{D2}X^{E2}$, $SO_2X^{F2}$, $NX^{G2}X^{H2}$, $N=C(X^{I2})_2$, $OX^{K2}$ or a cyano group, $X^3$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{31})X^{A3}$, $C(=O)OX^{B3}$, $C(=Q^{32})NX^{D3}X^{E3}$ or $SO_2X^{F3}$, alternatively, $X^2$ and $X^3$ represent a ring structure together with the nitrogen which is bonded with each other, $X^4$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{41})X^{A4}$, $C(=O)OX^{B4}$, $C(=Q^{42})NX^{D4}X^{E4}$ or $S(O)_nX^{F4}$, $X^5$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $X^6$s represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or a lower alkoxy group optionally substituted, $X^7$s represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OX^{L7}$, $SX^{M7}$ or $NX^{G7}X^{H7}$, alternatively, represent a ring structure together with the carbon which is bonded with each other, $Y^1$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{51})Y^{A1}$, $C(=O)OY^{B1}$, $C(=Q^{52})NY^{D1}Y^{E1}$, $S(O)_pY^{F1}$ or $N=C(Y^{I1})_2$, $Y^2$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{61})Y^{A2}$, $C(=O)OY^{B2}$, $C(=Q^{62})NY^{D2}Y^{E2}$, $SO_2Y^{F2}$, $NY^{G2}Y^{H2}$, $N=C(Y^{I2})_2$, $OY^{K2}$ or a cyano group, $Y^3$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{71})Y^{A3}$, $C(=O)OY^{B3}$, $C(=Q^{72})NY^{D3}Y^{E3}$ or $SO_2Y^{F3}$, $Y^4$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{81})Y^{A4}$, $C(=O)OY^{B4}$, $C(=Q^{82})NY^{D4}Y^{E4}$ or $S(O)_qY^{F4}$, $Y^5$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Y^6$s represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OY^{L6}$, $SY^{M6}$ or $NY^{G6}Y^{H6}$, alternatively, represent a ring structure together with the carbon which is bonded with each other, $X^{A1}$, $X^{A2}$, $X^{A3}$, $X^{A4}$, $Y^{A1}$, $Y^{A2}$, $Y^{A3}$, $Y^{A4}$ and $Z^A$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $X^{B1}$, $X^{B2}$, $X^{B3}$, $X^{B4}$, $Y^{B1}$, $Y^{B2}$, $Y^{B3}$, $Y^{B4}$ and $Z^B$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $X^{D1}$, $X^{D2}$, $X^{D3}$, $X^{D4}$, $Y^{D1}$, $Y^{D2}$, $Y^{D3}$, $Y^{D4}$ and $Z^D$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or $OG^{a1}$ and $X^{E1}$, $X^{E2}$, $X^{E3}$, $X^{E4}$, $Y^{E1}$, $Y^{E2}$, $Y^{E3}$, $Y^{E4}$ and $Z^E$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ represent a ring structure together with the nitrogen which is bonded with each other, $X^{F1}$, $X^{F2}$, $X^{F3}$, $Y^{F1}$, $Y^{F2}$, $Y^{F3}$ and $Z^F$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $X^{F4}$ and $Y^{F4}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $X^{G1}$, $X^{G2}$, $X^{G7}$, $Y^{G2}$, $Y^{G6}$ and $Z^G$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{G1})G^{A1}$, $C(=O)OG^{B1}$, $C(=Q^{G2})NG^{D1}G^{E1}$ or $SO_2G^{F1}$, and $X^{H1}$, $X^{H2}$, $X^{H7}$, $Y^{H2}$, $Y^{H6}$ and $Z^H$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^{G1}$ and $X^{H1}$, $X^{G2}$ and $X^{H2}$, $X^{G7}$ and $X^{H7}$, $Y^{G2}$ and $Y^{H2}$, $Y^{G6}$ and $Y^{H6}$, and $Z^G$ and $Z^H$ represent a ring structure together with the nitrogen which is bonded with each other, $X^{I1}$, $X^{I2}$, $Y^{I1}$, $Y^{I2}$ and $Z^I$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OG^{a2}$, $SG^{a3}$ or $NG^{G1}G^{H1}$, alternatively, represent a ring structure together with the carbon which is bonded with each other, $X^{K2}$, $Y^{K2}$ and $Z^{K}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{K1})G^{A2}$, $C(=O)OG^{B2}$, $C(=Q^{K2})NG^{D2}G^{E2}$ or $SO_2G^{F2}$, $X^{L7}$, $X^{M7}$, $Y^{L6}$ and $Y^{M6}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{a1}$, $G^{a2}$ and $G^{a3}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{A1}$ and $G^{A2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{B1}$ and $G^{B2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $G^{D1}$ and $G^{D2}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or $OG^{d1}$, and $G^{E1}$ and $G^{E2}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{D1}$ and $G^{E1}$, and $G^{D2}$ and $G^{E2}$ represent a ring structure together with the nitrogen which is bonded with each other, $G^{F1}$ and $G^{F2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $G^{G1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{Ga})G^{A1-1}$, $C(=O)OG^{B1-1}$, $C(=Q^{Gb})NG^{D1-1}G^{E1-1}$ or $SO_2G^{F1-1}$, and $G^{H1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{G1}$ and $G^{H1}$ represent a ring structure together with the nitrogen which is bonded with each other, $G^{d1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{A1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{B1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $G^{D1-1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or OL, and $G^{E1-1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{D1\text{-}1}$ and $G^{E1\text{-}1}$ represent a ring structure together with the nitrogen which is bonded with each other, $G^{F1\text{-}1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, L represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Q^{11}, Q^{12}, Q^{21}, Q^{22}, Q^{31}, Q^{32}, Q^{41}, Q^{42}, Q^{51}, Q^{52}, Q^{61}, Q^{62}, Q^{71}, Q^{72}, Q^{81}, Q^{82}, Q^{91}, Q^{92}, Q^{G1}, Q^{G2}, Q^{K1}, Q^{K2}, Q^{Ga}$ and $Q^{Gb}$ represent each independently oxygen or sulfur, m represents an integer of 1 or 2, n, p and q represent each independently an integer of 0 or 2, here, 1) if X is a benzoyloxy group and Y is a methoxy group, then, Z is not a 2-(benzoylamino)vinyl group, 2) if $X^2$ is a methyl group, then, $X^3$ is not a methyl group, 3) if X is a methoxy group and Y is a trifluoromethylsulfonyloxy group, then, Z is not a 3-vinyloxypropyl group (referred as the compound (I), hereinafter);

a pesticidal composition comprising the compound (I) or a salt thereof as an active ingredient and an inert carrier; and a method for controlling a pest which comprises a step of applying an effective amount of the compound (I) or a salt thereof to a pest or a habitat of pests.

MODE OF CARRYING OUT THE INVENTION

First, the embodiment of the compound (I) is exemplified as following [1] to [33].

[1] An iminopropene compound given by the formula (I) or a salt thereof:

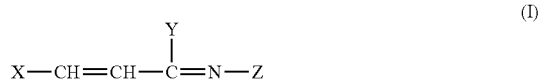
(I)

wherein,

X, Y and Z are defined above.

Here, 1) if X is a benzoyloxy group and Y is a methoxy group, then, Z is not a 2-(benzoylamino)vinyl group, 2) if $X^2$ is a methyl group, then, $X^3$ is not a methyl group, 3) if X is a methoxy group and Y is a trifluoromethylsulfonyloxy group, then, Z is not a 3-vinyloxypropyl group.

[2] The compound according to [1], wherein

X is $OX^1$, $NX^2X^3$, $SX^4$ or $S(O)_2X^5$ (wherein, X and $X^2$ area lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{42}$ (wherein, $Q^{21}$ is an oxygen atom, and $X^{42}$ is a lower alkyl group optionally substituted), $NX^{G1}X^{H1}$ or $N=C(X^{J1})_2$, $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{42}$ (wherein, $Q^{21}$ is an oxygen atom, and $X^{42}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^2$ and $X^3$ are formed a ring structure together with the nitrogen which is bonded with each other), Y is $OY^1$, $NY^2Y^3$ or $SY^4$ (wherein, Y is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{J1})_2$, $Y^2$ and $Y^4$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Y^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^G Z^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[3] The compound according to [2], wherein

X is $SX^4$ (wherein, $X^4$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), Y is $OY^1$, $NY^2Y^3$ or $SY^4$ (wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{I1})_2$, $Y^2$ and $Y^4$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Y^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^G Z^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[4] The compound according to [3], wherein

X is $SX^4$ (wherein, $X^4$ is a lower alkyl group optionally substituted, a higher alkyl group, a lower alkenyl group optionally substituted, a lower cycloalkyl group optionally substituted, an aromatic hydrocarbon group optionally substituted or a heterocyclic group optionally substituted), Y is $OY^1$, $NY^2Y^3$ or $SY^4$ (wherein, $Y^1$ is a lower alkyl group optionally substituted, an aromatic hydrocarbon group optionally substituted, a heterocyclic group optionally substituted or $N=C(Y^{I1})_2$ ($Y^{I1}$s are each independently a lower alkyl group or an aromatic hydrocarbon group), $Y^2$ and $Y^3$ are each independently a lower alkyl group optionally substituted or an aromatic hydrocarbon group optionally substituted, $Y^4$ is a lower alkyl group optionally substituted, a lower cycloalkyl group optionally substituted, a lower alkenyl group optionally substituted, a lower alkynyl group optionally substituted or a heterocyclic group optionally substituted), Z is a lower alkyl group optionally substituted, an aromatic hydrocarbon group optionally substituted, a heterocyclic group optionally substituted, a lower alkoxycarbonyl group, an aromatic hydrocarbon sulfonyl group optionally substituted, an amino group substituted with an aromatic hydrocarbon group and optionally substituted with a lower alkyl group, an aromatic hydrocarbon oxy group, a lower alkoxy group substituted with at least one aromatic hydrocarbon group or a lower alkylidene amino group substituted with at least one aromatic hydrocarbon group.

[5] The compound according to [4], wherein

X is $SX^4$ (wherein, $X^4$ is a lower alkyl group optionally substituted with at least one substituent selected from the group consisting of (1) an aromatic hydrocarbon group optionally substituted with at least one halogen, lower alkyl group or lower alkoxy group and (2) a heterocyclic group optionally substituted with at least one halogen; a higher alkyl group; a lower alkenyl group; a lower cycloalkyl group; an aromatic hydrocarbon group optionally substituted with one or more independent substituent (s) selected from the group consisting of (1) a halogen atom, (2) a nitro group, (3) a lower alkyl group, (4) a lower haloalkyl group and (5) a lower alkoxy group; or a heterocyclic group optionally substituted with one or more lower alkyl group(s)), Y is $OY^1$, $NY^2Y^3$ or $SY^4$ (wherein, $Y^1$ is a lower alkyl group optionally substituted with at least one substituent selected from the group consisting of (1) an aromatic hydrocarbon group optionally substituted with at least one lower alkyl group, (2) an aromatic hydrocarbon group substituted with at least one halogen and (3) a heterocyclic group substituted with at least one halogen; an aromatic hydrocarbon group optionally substituted with one or more independent substituent(s) selected from the group consisting of (1) a halogen, (2) a cyano group, (3) a nitro group, (4) a lower alkyl group, (5) an amino group, (6) a lower alkylthio group, (7) a lower alkylsulfonyl group, (8) a lower cycloalkyl group, (9) an aromatic hydrocarbon group, (10) a lower alkoxycarbonyl group, (11) a lower alkoxy group, (12) a heterocyclic group, (13) a lower alkylene group and (14) a lower alkylenedioxy group; a heterocyclic group; or a lower alkylidene amino group optionally substituted at least one aromatic hydrocarbon group, $Y^2$ is a lower alkyl group optionally substituted with at least one aromatic hydrocarbon group, or an aromatic hydrocarbon group, $Y^3$ is a lower alkyl group, $Y^4$ is a lower alkyl group optionally substituted with at least one substituent selected from the group consisting of (1) an aromatic hydrocarbon group optionally substituted with at least one halogen, (2) an aromatic hydrocarbon group optionally substituted with at least one lower alkyl group and (3) a lower cycloalkyl group; a lower cycloalkyl group; an aromatic hydrocarbon group optionally substituted with one or more independent substituent(s) selected from the group consisting of (1) a halogen, (2) a lower alkyl group optionally substituted with at least one halogen, (3) a lower alkoxy group and (4) a lower haloalkyloxy group; a heterocyclic group optionally substituted with one or more independent substituent (s) selected from the group consisting of (1) a lower alkyl group, (2) a lower haloalkyl group and (3) a heterocyclic group substituted with at least one halogen; a lower alkenyl group optionally substituted with at least one halogen; or a lower alkynyl group), Z is a lower alkyl group substituted with at least one halogen; an aromatic hydrocarbon group optionally substituted with one or more independent substituent(s) selected from the group consisting of (1) a halogen, (2) a nitro group, (3) a cyano group, (4) a lower alkyl group, (5) a lower alkoxy group, (6) a lower haloalkyl group, (7) a lower cycloalkyl group and (8) an aromatic hydrocarbon oxy group; a heterocyclic group; a lower alkoxycarbonyl group; an aromatic hydrocarbon sulfonyl group; an amino group substituted with an aromatic hydrocarbon group and optionally substituted with a lower alkyl group; an aromatic hydrocarbon oxy group; a lower alkoxy group substituted with at least one aromatic hydrocarbon group, or a lower alkylidene amino group substituted with at least one aromatic hydrocarbon group.

[6] The compound according to [2], wherein

X is $OX^1$ (wherein, $X^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $NX^{G1}X^{H1}$, or $N=C(X^{I1})_2$), Y is $OY^1$, $NY^2Y^3$ or $SY^4$ (wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or $N=C(Y^{I1})_2$, $Y^2$ and $Y^4$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted, $Y^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$'s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[7] The compound according to [6], wherein
X is $OX^1$
(wherein, $X^1$ is a lower alkyl group optionally substituted, an aromatic hydrocarbon group optionally substituted, a lower cycloalkyl group optionally substituted, a di-lower alkyl amino group, a lower alkylidene amino group optionally substituted, or a lower cycloalkylidene amino group optionally substituted), Y is $OY^1$ or $SY^4$
(wherein, $Y^1$ and $Y^4$ are each independently a lower alkyl group optionally substituted, or an aromatic hydrocarbon group optionally substituted), Z is an aromatic hydrocarbon group optionally substituted or a heterocyclic group optionally substituted.

[8] The compound according to [7], wherein
X is $OX^1$
(wherein, $X^1$ is a lower alkyl group substituted with at least one aromatic hydrocarbon group optionally substituted with one or more independent substituent(s) selected from the group consisting of (1) a halogen, (2) a lower alkyl group and (3) a lower alkoxy group; lower cycloalkyl group; an aromatic hydrocarbon group optionally substituted with one or more independent substituent(s) selected from the group consisting of (1) a halogen, (2) a lower alkyl group optionally substituted with at least one halogen, (3) a lower alkoxy group, (4) a lower alkoxycarbonyl group, (5) a lower alkanoyl group, (6) a lower alkylthio group, (7) an aromatic hydrocarbon group, (8) a cyano group, (9) a nitro group and (10) an alkylenedioxy group; an alkylidene amino group optionally substituted with at least one aromatic hydrocarbon group; a lower cycloalkylidene amino group; or a di-lower alkyl amino group), Y is $OY^1$ or $SY^4$
(wherein, $Y^1$ is a lower alkyl group substituted with at least one aromatic hydrocarbon group, or an aromatic hydrocarbon group optionally substituted with one or more independent substituent(s) selected from the group consisting of a halogen and a lower alkyl group, $Y^4$ is a lower alkyl group optionally substituted with at least one aromatic hydrocarbon group, or an aromatic hydrocarbon group), Z is an aromatic hydrocarbon group optionally substituted with one or more independent substituent(s) selected from the group consisting of (1) a halogen, (2) a lower cycloalkylthio group, (3) a hydroxyl group, (4) a lower alkyl group optionally substituted with at least one aromatic hydrocarbon group, (5) a lower alkenyl group, (6) a lower alkoxy group optionally substituted with at least one halogen, (7) a lower alkanoyloxy group, (8) an aromatic hydrocarbon group optionally substituted with at least one lower alkyl group or halogen, (9) a heterocyclic group, (10) a lower alkylthio group, (11) a lower alkyl sulfinyl group, (12) a lower alkyl sulfonyl group, (13) an arylthio group, (14) a lower alkoxy carbonyl group, (15) a lower alkanoyl group, (16) an aromatic hydrocarbon carbonyl group, (17) a lower alkynyl group, (18) a lower alkylenedioxy group and (19) a lower alkylene group; or a heterocyclic group.

[9] The compound according to [2], wherein
X is $NX^2X^3$, or $S(O)_2X^5$
(wherein, $X^2$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or $C(=Q^{21})X^{42}$ (wherein, $Q^{21}$ is an oxygen atom, and $X^{42}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted), Y is $OY^1$, $NY^2Y^3$ or $SY^4$
(wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{J1})_2$, $Y^2$ and $Y^4$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Y^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[10] The compound according to [9], wherein
X is $NX^2X^3$, or $S(O)_2X^5$
(wherein, $X^2$ is a lower alkyl group optionally substituted, an aromatic hydrocarbon group optionally substituted, or $C(=Q^{21})X^{A2}$ (wherein, $Q^{21}$ is an oxygen atom, and $X^{A}2$ is a lower alkyl group optionally substituted), $X^3$ is a lower alkyl group optionally substituted, or an aromatic hydrocarbon group optionally substituted, alternatively, $X^2$ and $X^3$ are formed a ring structure together with the nitrogen which is bonded with each other, $X^5$ is an aromatic hydrocarbon group optionally substituted), Y is $OY^1$, or $SY^4$
(wherein, $Y^1$ and $Y^4$ are an aromatic hydrocarbon group optionally substituted), Z is an aromatic hydrocarbon group optionally substituted.
[11] The compound according to [10], wherein
X is $NX^2X^3$, or $S(O)_2X^5$
(wherein, $X^2$ is a lower alkyl group substituted with at least one aromatic hydrocarbon group, an aromatic hydrocarbon group or a lower alkanoyl group, $X^3$ is a lower alkyl group or an aromatic hydrocarbon group, alternatively, $X^2$ and $X^3$ are formed a piperidino group or morpholino group together with the nitrogen which is bonded with each other, $X^5$ is an aromatic hydrocarbon group),
Y is $OY^1$, or $SY^4$
(wherein, Y and $SY^4$ are an aromatic hydrocarbon group),
Z is an aromatic hydrocarbon group.
[12] The compound according to [2], wherein
X is $OX^1$, $NX^2X^3$, $SX^4$ or $S(O)_2X^5$
(wherein, X and $X^2$ area lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{A2}$ (wherein, $Q^{21}$ is an oxygen atom, and $X^{A2}$ is a lower alkyl group optionally substituted), $NX^{G1}X^{H1}$, or $N=C(X^{I1})_2$, $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or $C(=Q^{21})X^{A2}$ (wherein, $Q^{21}$ is an oxygen atom, and $X^{A2}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted, alternatively, $X^2$ and $X^3$ are formed a ring structure together with the nitrogen which is bonded with each other,
Y is $OY^1$
(wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{I1})_2$, Z is a cyano group, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[13] The compound according to [12], wherein

X is $OX^1$, $NX^2X^3$, $SX^4$ or $S(O)_2X^5$ (wherein, $X^1$ is a lower alkyl group optionally substituted, an aromatic hydrocarbon group optionally substituted, a lower cycloalkyl group optionally substituted, a di-lower alkyl amino group, a lower alkylidene amino group optionally substituted, a lower cycloalkylidene amino group optionally substituted, $X^2$ is a lower alkyl group optionally substituted, an aromatic hydrocarbon group optionally substituted, or $C(=Q^{21})X^{A2}$ (wherein, $Q^{21}$ is an oxygen atom, and $X^A2$ is a lower alkyl group optionally substituted), $X^3$ is a lower alkyl group optionally substituted or an aromatic hydrocarbon group optionally substituted, alternatively, $X^2$ and $X^3$ are formed a ring structure together with the nitrogen which is bonded with each other, $X^4$ is a lower alkyl group optionally substituted, a higher alkyl group, a lower cycloalkyl group optionally substituted, a lower cycloalkyl group optionally substituted, an aromatic hydrocarbon group optionally substituted, or a heterocyclic group optionally substituted, $X^5$ is an aromatic hydrocarbon group optionally substituted), Y is $OY^1$ (wherein, $Y^1$ is a lower alkyl group optionally substituted, an aromatic hydrocarbon group optionally substituted, a heterocyclic group optionally substituted or $N=C(Y^{J1})_2$ ($Y^{J1}$s are each independently a lower alkyl group or an aromatic hydrocarbon group)

Z is an aromatic hydrocarbon group optionally substituted, or a heterocyclic group optionally substituted.

[14] The compound according to [13], wherein

X is $OX^1$, $NX^2X^3$, $SX^4$ or $S(O)_2X^5$ (wherein, $X^1$ is a lower alkyl group substituted with at least one aromatic hydrocarbon group optionally substituted with one or more independent substituent(s) selected from the group consisting of (1) a halogen, (2) a lower alkyl group and (3) a lower alkoxy group; an aromatic hydrocarbon group optionally substituted with one or more independent substituent (s) selected from the group consisting of (1) a halogen, (2) a lower alkyl group optionally substituted with at least one halogen, (3) a lower alkoxy group, (4) a lower alkoxycarbonyl group, (5) a lower alkanoyl group, (6) a lower alkylthio group, (7) an aromatic hydrocarbon group, (8) a cyano group, (9) a nitro group and (10) an alkylenedioxy group; a lower cycloalkyl group; an alkylidene amino group optionally substituted with at least one aromatic hydrocarbon group; a lower cycloalkylidene amino group; or a di-lower alkyl amino group, $X^2$ is a lower alkyl group substituted with at least one aromatic hydrocarbon group, an aromatic hydrocarbon group, or a lower alkanoyl group, $X^3$ is a lower alkyl group or an aromatic hydrocarbon group, alternatively, $X^2$ and $X^3$ are formed a piperidino group or a morpholino group together with the nitrogen which is bonded with each other, $X^4$ is a lower alkyl group optionally substituted with at least one substituent selected from the group consisting of (1) an aromatic hydrocarbon group optionally substituted with at least one halogen, lower alkyl group or lower alkoxy group and (2) a heterocyclic group optionally substituted with at least one halogen; a higher alkyl group; a lower alkenyl group; a lower cycloalkyl group; an aromatic hydrocarbon group optionally substituted with one or more independent substituent (s) selected from the group consisting of (1) a halogen atom, (2) a nitro group, (3) a lower alkyl group, (4) a lower haloalkyl group and (5) a lower alkoxy group; or a heterocyclic group optionally substituted with one or more lower alkyl group(s), $X^5$ is an aromatic hydrocarbon group), Y is $OY^1$, (wherein, $Y^1$ is a lower alkyl group optionally substituted with one or more substituent(s) selected from the group consisting of (1) an aromatic hydrocarbon group optionally substituted with at least one lower alkyl group, (2) an aromatic hydrocarbon group substituted with at least one halogen and (3) a heterocyclic group substituted with at least one halogen; an aromatic hydrocarbon group optionally substituted with one or more independent substituent (s) selected from the group consisting of (1) a halogen, (2) a cyano group, (3) a nitro group, (4) a lower alkyl group, (5) an amino group, (6) a lower alkylthio group, (7) a lower alkyl sulfonyl group, (8) a lower cycloalkyl group, (9) an aromatic hydrocarbon group, (10) a lower alkoxycarbonyl group, (11) a lower alkoxy group, (12) a heterocyclic group, (13) a lower alkylenedioxy group and

(14) a lower alkylene group; a heterocyclic group; or a lower alkylidene amino group optionally substituted at least one aromatic hydrocarbon group), Z is an aromatic hydrocarbon group optionally substituted with one or more independent substituent(s) selected from the group consisting of (1) a halogen, (2) a cyano group, (3) a hydroxy group, (4) a lower alkyl group optionally substituted with at least one halogen or aromatic hydrocarbon group, (5) a lower alkenyl group, (6) a lower alkoxy group optionally substituted with at least one halogen, (7) a lower alkanoyl oxy group, (8) an aromatic hydrocarbon group optionally substituted with at least one halogen or lower alkyl group, (9) a heterocyclic group, (10) a lower alkylthio group, (11) a lower alkyl sulfinyl group, (12) a lower alkyl sulfonyl group, (13) an arylthio group, (14) a lower alkoxy carbonyl group, (15) a lower alkanoyl group, (16) an aromatic hydrocarbon carbonyl group, (17) a lower alkynyl group, (18) a lower cycloalkylthio group, (19) a lower alkylene dioxygroup, (20) a lower alkylene group, (21) a lower cycloalkyl group, (22) an aryloxy group and (23) a nitro group; a heterocyclic group.

[15] The compound according to [2], wherein

X is $OX^1$, $NX^2X^3$, $SX^4$ or $S(O)_2X^5$ (wherein, $X^1$ and $X^2$ are a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{A2}$ (wherein, $Q^{21}$ is an oxygen atom, and $X^{A2}$ is a lower alkyl group optionally substituted), $NX^{G1}X^{H1}$ or $N=C(X^{I1})_2$, $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{A2}$ (wherein, $Q^{21}$ is an oxygen atom, and $X^{A2}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^2$ and $X^3$ are formed a ring structure together with the nitrogen which is bonded with each other), Y is $SY^4$ (wherein, $Y^4$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[16] The compound according to [15], wherein

X is $OX^1$, $SX^4$ or $S(O)_2X^5$ (wherein, $X^1$ is an aromatic hydrocarbon group optionally substituted, $X^4$ is a lower alkyl group optionally substituted, a lower cycloalkyl group optionally substituted, an aromatic hydrocarbon group optionally substituted or a heterocyclic group optionally substituted, and $X^5$ is an aromatic hydrocarbon group optionally substituted), Y is $SY^4$ (wherein, $Y^4$ is a lower alkyl group optionally substituted, a higher alkyl group, a lower cycloalkyl group optionally substituted, a lower alkenyl group optionally substituted, a higher alkenyl group, a lower alkynyl group optionally substituted, an aromatic hydrocarbon group optionally substituted or a heterocyclic group optionally substituted), Z is a lower alkyl group optionally substituted, an aromatic hydrocarbon group optionally substituted, a lower alkoxycarbonyl group, an aromatic hydrocarbon sulfonyl group optionally substituted, an amino group substituted with an aromatic hydrocarbon group and optionally substituted with a lower alkyl group, an aromatic hydrocarbon oxy group, a lower alkoxy group substituted with at least one aromatic hydrocarbon group, or a lower alkylidene amino group optionally substituted with at least one aromatic hydrocarbon group.

[17] The compound according to [16], wherein

X is $OX^1$, $SX^4$ or $S(O)_2X^5$ (wherein, $X^1$ represents an aromatic hydrocarbon group, $X^4$ is a lower alkyl group optionally substituted with at least one aromatic hydrocarbon group optionally substituted with one or more independent substituent(s) selected from the group consisting of (1) a halogen, (2) a lower alkyl group and (3) a lower alkoxy group; a lower cycloalkyl group; an aromatic hydrocarbon group optionally substituted with one or more independent substituent(s) selected from the group consisting of (1) a halogen, (2) a lower alkyl group optionally substituted with at least one halogen, (3) a lower alkoxy group, (4) a nitro group; or a heterocyclic group, $X^5$ is an aromatic hydrocarbon group), Y is $SY^4$ (wherein, $Y^4$ is a lower alkyl group optionally substituted with at least one substituent selected from the group consisting of (1) an aromatic hydrocarbon group optionally substituted with at least one halogen, (2) an aromatic hydrocarbon group optionally substituted with at least one lower alkyl group and (3) a lower cycloalkyl group; a higher alkyl group; a lower cycloalkyl group; an aromatic hydrocarbon group optionally substituted with one or more independent substituent(s) selected from the group consisting of (1) a halogen, (2) a lower alkyl group optionally substituted with at least one halogen, (3) a lower alkoxy group and (4) a lower haloalkyloxy group; a heterocyclic group optionally substituted with one or more independent substituent(s) selected from the group consisting of (1) a lower alkyl group, (2) a lower haloalkyl group and (3) a heterocyclic group substituted with at least one halogen; a lower alkenyl group optionally substituted with at least one halogen; a higher alkenyl group; or a lower alkynyl group), Z is a lower alkyl group substituted with at least one halogen; an aromatic hydrocarbon group optionally substituted with one or more independent substituent(s) selected from the group consisting of (1) a halogen, (2) a lower alkyl group and (3) a lower alkoxy group; a lower alkoxycarbonyl group; an aromatic hydrocarbon sulfonyl group optionally substituted; an amino group substituted with an aromatic hydrocarbon group and optionally substituted with a lower alkyl group; an aromatic hydrocarbon oxy group; a lower alkoxy group substituted with at least one aromatic hydrocarbon group; or a lower alkylidene amino group substituted with at least one aromatic hydrocarbon group.

[18] The compound according to [15], wherein

X is $OX^1$, $NX^2X^3$, $SX^4$ or $S(O)_2X^5$ (wherein, $X^1$ and $X^2$ area lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{A2}$ (wherein, $Q^{21}$ is an oxygen atom, and $X^{A2}$ is a lower alkyl group optionally substituted), $NX^{G1}X^{H1}$ or $N=C(X^{I1})_2$, $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{A2}$ (wherein, $Q^{21}$ is an oxygen atom, and $X^{A2}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^2$ and $X^3$ are formed a ring structure together with the nitrogen which is bonded with each other), Y is $SY^4$ (wherein, $Y^4$ is an aromatic hydrocarbon group optionally substituted or a heterocyclic group optionally substituted), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[19] The compound according to [18], wherein

X is $OX^1$, $SX^4$ or $S(O)_2X^5$ (wherein, $X^1$ represents an aromatic hydrocarbon group optionally substituted, $X^4$ is a lower alkyl group optionally substituted, a lower cycloalkyl group optionally substituted, or an aromatic hydrocarbon group optionally substituted, $X^5$ is an aromatic hydrocarbon group optionally substituted), Y is $SY^4$ (wherein, $Y^4$ is an aromatic hydrocarbon group optionally substituted or a heterocyclic group optionally substituted), Z is a lower alkyl group optionally substituted, an aromatic hydrocarbon group optionally substituted, a lower alkoxycarbonyl group, an aromatic hydrocarbon sulfonyl group optionally substituted, an amino group substituted with an aromatic hydrocarbon group and optionally substituted with a lower alkyl group, an aromatic hydrocarbon oxy group, a lower alkoxy group substituted with at least one aromatic hydrocarbon group, or a lower alkylidene amino group optionally substituted with at least one aromatic hydrocarbon group.

[20] The compound according to [19], wherein

X is $OX^1$, $SX^4$ or $S(O)_2X^5$ (wherein, $X^5$ represents an aromatic hydrocarbon group, $X^4$ is a lower alkyl group substituted with at least one aromatic hydrocarbon group, a lower cycloalkyl group, or an aromatic hydrocarbon group optionally substituted with at least one lower alkyl group or lower alkoxy group, $X^5$ is an aromatic hydrocarbon group), Y is $SY^4$ (wherein, $Y^4$ is an aromatic hydrocarbon group optionally substituted with at least one substituent selected from the group consisting of (1) a halogen, (2) a lower alkyl group optionally substituted with at least one halogen and (3) a lower alkoxy group optionally substituted with at least one halogen, or a heterocyclic group optionally substituted with one or more substituent(s) selected from the group consisting of (1) a lower alkyl group optionally substituted with at least one halogen, and (2) a heterocyclic group substituted with at least one halogen), Z is a lower alkyl group substituted with at least one halogen; an aromatic hydrocarbon group optionally substituted with one or more substituent(s) selected from the group consisting of (1) a halogen, (2) a lower alkyl group and (3) a lower alkoxy group; a lower alkoxycarbonyl group; an aromatic hydrocarbon sulfonyl group optionally substituted; an amino group substituted with an aromatic hydrocarbon group and optionally substituted with a lower alkyl group; an aromatic hydrocarbon oxy group; a lower alkoxy group substituted with at least one aromatic hydrocarbon group; or a lower alkylidene amino group substituted with at least one aromatic hydrocarbon group.

[21] The compound according to [15], wherein

X is $OX^1$, $NX^2X^3$, $SX^4$ or $S(O)_2X^5$ (wherein, X and $X^2$ are a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{42}$ (wherein, $Q^{21}$ is an oxygen atom, and $X^{42}$ is a lower alkyl group optionally substituted), $NX^{G1}X^{H1}$ or $N=C(X^{I1})_2$, $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{42}$ (wherein, $Q^{21}$ is an oxygen atom, and $X^{42}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^2$ and $X^3$ are formed a ring structure together with the nitrogen which is bonded with each other), Y is $SY^4$ (wherein, $Y^4$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, or a higher alkynyl group), Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^J)_2$ (wherein, $Z^J$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[22] The compound according to [21], wherein
X is $SX^4$
(wherein, $X^4$ is a lower alkyl group optionally substituted, a lower cycloalkyl group optionally substituted, an aromatic hydrocarbon group optionally substituted, or a heterocyclic group optionally substituted),
Y is $SY^4$
(wherein, $Y^4$ is a lower alkyl group optionally substituted, a higher alkyl group, a lower cycloalkyl group optionally substituted, a lower alkenyl group optionally substituted, a higher alkenyl group, or a lower alkynyl group optionally substituted),
Z is an aromatic hydrocarbon group optionally substituted.

[23] The compound according to [22], wherein
X is $SX^4$
(wherein, $X^4$ is a lower alkyl group optionally substituted with at least one aromatic hydrocarbon group optionally substituted with one or more substituent(s) selected from the group consisting of (1) a halogen, (2) a lower alkyl group and (3) a lower alkoxy group; lower cycloalkyl group; an aromatic hydrocarbon group optionally substituted with one or more substituent (s) selected from the group consisting of (1) a halogen, (2) a lower alkyl group optionally substituted with at least one halogen, (3) a lower alkoxy group, and (4) a nitro group; or a heterocyclic group),
Y is $SY^4$
(wherein, $Y^4$ is a lower alkyl group optionally substituted with at least one substituent selected from the group consisting of (1) an aromatic hydrocarbon group optionally substituted with at least one halogen and (2) a lower cycloalkyl group; a higher alkyl group; a lower cycloalkyl group; a lower alkenyl group optionally substituted with at least one halogen; a higher alkenyl group; or a lower alkynyl group),
Z is an aromatic hydrocarbon group optionally substituted with at least one lower alkyl group.

[24] The compound according to [2], wherein
X is $OX^1$, $NX^2X^3$, $SX^4$ or $S(O)_2X^5$
(wherein, $X^1$ and $X^2$ area lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{A2}$ (wherein, $Q^{21}$ is an oxygen atom, and $X^{A2}$ is a lower alkyl group optionally substituted), $NX^{G1}X^{H1}$ or $N=C(X^{I1})_2$,
$X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{A2}$ (wherein, $Q^{21}$ is an oxygen atom, and $X^{A2}$ is a lower alkyl group optionally substituted),
$X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^2$ and $X^3$ are formed a ring structure together with the nitrogen which is bonded with each other),
Y is $NY^2Y^3$
(wherein, $Y^2$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted,
$Y^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted),
Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted,
$C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted),
$NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or
$N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

[25] The compound according to [24], wherein

X is $SX^4$ (wherein, $X^4$ is an aromatic hydrocarbon group optionally substituted), Y is $NY^2Y^3$ (wherein, $Y^2$ is a lower alkyl group optionally substituted, and $Y^3$ is a lower alkyl group optionally substituted, or an aromatic hydrocarbon group optionally substituted), Z is an aromatic hydrocarbon group optionally substituted.

[26] The compound according to [25], wherein

X is $SX^4$ (wherein, $X^4$ is an aromatic hydrocarbon group optionally substituted with at least one halogen or lower alkyl group), Y is $NY^2Y^3$ (wherein, $Y^2$ is a lower alkyl group optionally substituted with at least one aromatic hydrocarbon group, and $Y^3$ is a lower alkyl group or an aromatic hydrocarbon group), Z is an aromatic hydrocarbon group.

[27] The compound according to [2], wherein

X is $OX^1$, $NX^2X^3$, $SX^4$ or $S(O)_2X^5$ (wherein, $X^1$ and $X^2$ area lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{21})X^{42}$ (wherein, $Q^{21}$ is an oxygen atom, and $X^{42}$ is a lower alkyl group optionally substituted), $NX^{G1}X^{H1}$ or $N=C(X^{J1})_2$, $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{42}$ (wherein, $Q^{21}$ is an oxygen atom, and $X^{42}$ is a lower alkyl group optionally substituted), $X^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^2$ and $X^3$ are formed a ring structure together with the nitrogen which is bonded with each other), Y is $OY^1$, $NY^2Y^3$ or $SY^4$ (wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or $N=C(Y^{J1})_2$, $Y^2$ and $Y^4$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted, $Y^3$ is a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted), Z is a lower alkyl group optionally substituted, a lower cycloalkyl group optionally substituted, a lower alkenyl group optionally substituted, a lower cycloalkenyl group optionally substituted, a lower alkynyl group optionally substituted, an aromatic hydrocarbon group optionally substituted, a heterocyclic group optionally substituted, $C(=O)OZ^B$ (wherein, $Z^B$ is a lower alkyl group optionally substituted, a lower cycloalkyl group optionally substituted, a lower alkenyl group optionally substituted, a lower cycloalkenyl group optionally substituted, a lower alkynyl group optionally substituted, an aromatic hydrocarbon group optionally substituted or a heterocyclic group optionally substituted), $SO_2Z^F$ (wherein, $Z^F$ is a lower alkyl group optionally substituted, a lower cycloalkyl group optionally substituted, a lower alkenyl group optionally substituted, a lower cycloalkenyl group optionally substituted, a lower alkynyl group optionally substituted, an aromatic hydrocarbon group optionally substituted or a heterocyclic group optionally substituted), $NZ^GZ^H$ (wherein, $Z^G$ and $Z^H$ are each independently a hydrogen atom, a lower alkyl group optionally substituted, a lower cycloalkyl group optionally substituted, a lower alkenyl group optionally substituted, a lower cycloalkenyl group optionally substituted, a lower alkynyl group optionally substituted, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a lower cycloalkyl group optionally substituted, a lower alkenyl group optionally substituted, a lower cycloalkenyl group optionally substituted, a lower alkynyl group optionally substituted, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a lower cycloalkyl group optionally substituted, a lower alkenyl group optionally substituted, a lower cycloalkenyl group optionally substituted, a lower alkynyl group optionally substituted, an aromatic hydrocarbon group optionally substituted or a heterocyclic group optionally substituted, alternatively, are formed a ring structure together with the nitrogen which is bonded with each other).

[28] The compound according to [27], wherein

X is $OX^1$, $NX^2X^3$, $SX^4$ or $S(O)_2X^5$ (wherein, $X^1$ is a lower alkyl group optionally substituted, an aromatic hydrocarbon group optionally substituted, a lower cycloalkyl group optionally substituted, a di-lower alkyl amino group, a lower alkylidene amino group optionally substituted or a lower cycloalkylidene amino group optionally substituted, $X^2$ is a lower alkyl group optionally substituted, an aromatic hydrocarbon group optionally substituted, or C(=Q$^{21}$)X$^{A2}$ (wherein, Q$^2$1 is an oxygen atom and X$^A$2 is a lower alkyl group optionally substituted), X$^3$ is a lower alkyl group optionally substituted or an aromatic hydrocarbon group optionally substituted, X$^4$ is a lower alkyl group optionally substituted, a higher alkyl group, a lower alkenyl group optionally substituted, a lower cycloalkyl group optionally substituted, an aromatic hydrocarbon group optionally substituted or a heterocyclic group optionally substituted, and X$^5$ is an aromatic hydrocarbon group optionally substituted), Y is OY$^1$, NY$^2$Y$^3$ or SY$^4$ (wherein, Y$^1$ is a lower alkyl group optionally substituted, an aromatic hydrocarbon group optionally substituted, a heterocyclic group optionally substituted, or N=C(Y$^{T1}$)$_2$, (Y$^{T1}$s are independently a lower alkyl group or an aromatic hydrocarbon group), Y$^2$ and Y$^3$ are each independently a lower alkyl group optionally substituted or an aromatic hydrocarbon group optionally substituted, and Y$^4$ is a lower alkyl group optionally substituted, a higher alkyl group, a lower cycloalkyl group optionally substituted, a lower alkenyl group optionally substituted, a higher alkenyl group, a lower alkynyl group optionally substituted, an aromatic hydrocarbon group optionally substituted or a heterocyclic group optionally substituted), Z is a lower alkyl group optionally substituted, an aromatic hydrocarbon group optionally substituted, a heterocyclic group optionally substituted, a lower alkoxycarbonyl group, an aromatic hydrocarbon sulfonyl group optionally substituted, an amino group substituted with an aromatic hydrocarbon group and optionally substituted with a lower alkyl group, and aromatic hydrocarbon oxy group, a lower alkoxy group substituted with at least one aromatic hydrocarbon group, or a lower alkylidene amino group optionally substituted with at least one aromatic hydrocarbon group.

[29] The compound according to [28], wherein

X is OX$^1$, NX$^2$X$^3$, SX$^4$ or S(O)$_2$X$^5$ (wherein, X$^1$ is a lower alkyl group substituted with at least one aromatic hydrocarbon group optionally substituted with one or more independent substituent(s) selected from the group consisting of (1) a halogen, (2) a lower alkyl group and (3) a lower alkoxy group; an aromatic hydrocarbon group optionally substituted with one or more independent substituent(s) selected from the group consisting of (1) a halogen, (2) a lower alkyl group optionally substituted with at least one halogen, (3) a lower alkoxy group, (4) a lower alkoxycarbonyl group, (5) a lower alkanoyl group, (6) a lower alkylthio group, (7) an aromatic hydrocarbon group, (8) a cyano group, (9) a nitro group and (10) an alkylenedioxy group; a lower cycloalkyl group; an alkylidene amino group optionally substituted with at least one aromatic hydrocarbon group; a lower cycloalkylidene amino group; or a di-lower alkyl amino group, X$^2$ is a lower alkyl group substituted with at least one aromatic hydrocarbon group, an aromatic hydrocarbon group, or a lower alkanoyl group, X$^3$ is a lower alkyl group or an aromatic hydrocarbon group, alternatively, X$^2$ and X$^3$ are formed a piperidino group or a morpholino group together with the nitrogen which is bonded with each other, X$^4$ is an aromatic hydrocarbon group optionally substituted with one or more independent substituent(s) selected from the group consisting of (1) a halogen, (2) a lower alkyl group and (3) a lower alkoxy group; a lower alkyl group optionally substituted with at least one heterocyclic group optionally substituted with at least one halogen; a higher alkyl group; a lower alkenyl group; a lower cycloalkyl group; an aromatic hydrocarbon group optionally substituted with one or more independent substituent(s) selected from the group consisting of (1) a halogen, (2) a nitro group, (3) a lower alkyl group, (4) a halo-lower alkyl group, and (5) a lower alkoxy group; or a heterocyclic group optionally substituted with one or more lower alkyl group(s), X$^5$ is an aromatic hydrocarbon group), Y is OY$^1$, NY$^2$Y$^3$ or SY$^4$ (wherein, Y$^1$ is a lower alkyl group optionally substituted with one or more substituent(s) selected from the group consisting of (1) an aromatic hydrocarbon group optionally substituted with at least one lower alkyl group, (2) an aromatic hydrocarbon group substituted with at least one halogen and (3) a heterocyclic group substituted with at least one halogen; an aromatic hydrocarbon group optionally substituted with one or more independent substituent(s) selected from the group consisting of (1) a halogen, (2) a cyano group, (3) a nitro group, (4) a lower alkyl group, (5) an amino group, (6) a lower alkylthio group, (7) a lower alkylsulfonyl group, (8) a lower cycloalkyl group, (9) an aromatic hydrocarbon group, (10) a lower alkoxycarbonyl group, (11) a lower alkoxy group, (12) a heterocyclic group, (13) a lower alkylene group and (14) a lower alkylenedioxy group; a heterocyclic group; or a lower alkylidene amino group optionally substituted at least one aromatic hydrocarbon group, Y$^2$ is a lower alkyl group optionally substituted with at least one aromatic hydrocarbon group, or an aromatic hydrocarbon group, Y$^3$ is a lower alkyl group, Y$^4$ is a lower alkyl group optionally substituted with one or more substituent(s) selected from the group consisting of (1) an aromatic hydrocarbon group optionally substituted with at least one halogen, (2) an aromatic hydrocarbon group optionally substituted with at least one lower alkyl group and (3) a lower cycloalkyl group; a higher alkyl group; a lower cycloalkyl group; an aromatic hydrocarbon group optionally substituted with one or more independent substituent(s) selected from the group consisting of (1) a halogen, (2) a lower alkyl group optionally substituted with at least one halogen, (3) a lower alkoxy group and (4) a lower haloalkyloxy group; a heterocyclic group optionally substituted with one or more independent substituent(s) selected from the group consisting of (1) a lower alkyl group, (2) a lower haloalkyl group and (3) a heterocyclic group substituted with at least one halogen; a lower alkenyl group optionally substituted with at least one halogen; a higher alkenyl group; or a lower alkynyl group), Z is a lower alkyl group substituted with at least one halogen; an aromatic hydrocarbon group optionally substituted with one or more independent substituent(s) selected from the group consisting of (1) a halogen, (2) a cyano group, (3) a hydroxy group, (4) a lower alkyl group optionally substituted with at least one halogen or aromatic hydrocarbon group, (5) a lower alkenyl group, (6) a lower alkoxy group optionally substituted with at least one halogen, (7) a lower alkanoyl oxy group, (8) an aromatic hydrocarbon group optionally substituted with at least one alkyl or halogen, (9) a heterocyclic group, (10) a lower alkylthio group, (11) a lower alkyl sulfinyl group, (12) a lower alkyl sulfonyl group, (13) an arylthio group, (14) a lower alkoxy carbonyl group, (15) a lower alkanoyl group, (16) an aromatic hydrocarbon carbonyl group, (17) a lower alkynyl group, (18) a lower cycloalkylthio group, (19) a lower alkylenedioxy group, (20) a lower alkylene group and (21) a nitro group; a heterocyclic group; a lower alkoxycarbonyl group; an aromatic hydrocarbon sulfonyl group; an amino group substituted with an aromatic hydrocarbon group and optionally substituted with a lower alkyl group; an aromatic hydrocarbon oxy group; a lower alkoxy group substituted with at least one aromatic hydrocarbon group, or a lower alkylidene amino group substituted with at least one aromatic hydrocarbon group.

[30] The compound according to [2], wherein

X is $OX^1$, $NX^2X^3$, $SX^4$ or $S(O)_2X^5$ (wherein, $X^1$ is a lower alkyl group optionally substituted, an aromatic hydrocarbon group optionally substituted, a lower cycloalkyl group optionally substituted, a di-lower alkylamino group, a lower alkylidene amino group optionally substituted or a lower cycloalkylidene amino group optionally substituted, $X^2$ is a lower alkyl group optionally substituted, an aromatic hydrocarbon group optionally substituted or $C(=Q^{21})X^{42}$ (wherein, $Q^{21}$ is an oxygen atom and $X^{42}$ is a lower alkyl group optionally substituted), $X^3$ is a lower alkyl group optionally substituted or an aromatic hydrocarbon group optionally substituted, $X^4$ is a lower alkyl group optionally substituted, a higher alkenyl group, a lower alkyl group optionally substituted, a lower cycloalkyl group optionally substituted, an aromatic hydrocarbon group optionally substituted or a heterocyclic group optionally substituted, $X^5$ is an aromatic hydrocarbon group optionally substituted), Y is $OY^1$, $NY^2Y^3$ or $SY^4$ (wherein, $Y^1$ is a lower alkyl group optionally substituted, an aromatic hydrocarbon group optionally substituted, a heterocyclic group optionally substituted, or $N=C(Y^{71})_2$ ($Y^{71}$s are independently a lower alkyl group or an aromatic hydrocarbon group, $Y^2$ is an aromatic hydrocarbon group optionally substituted, $Y^3$ is a lower alkyl group optionally substituted or an aromatic hydrocarbon group optionally substituted, $Y^4$ is a lower alkyl group optionally substituted, a higher alkyl group, a lower cycloalkyl group optionally substituted, a lower alkenyl group optionally substituted, a higher alkenyl group, a lower alkynyl group optionally substituted, an aromatic hydrocarbon group optionally substituted or a heterocyclic group optionally substituted), Z is a lower alkyl group optionally substituted, an aromatic hydrocarbon group optionally substituted, a heterocyclic group optionally substituted, a lower alkoxycarbonyl group, an aromatic hydrocarbon sulfonyl group optionally substituted, an amino group substituted with an aromatic hydrocarbon group and optionally substituted with a lower alkyl group, an aromatic hydrocarbon oxy group, a lower alkoxy group substituted with at least one aromatic hydrocarbon group, or a lower alkylidene amino group optionally substituted with at least one aromatic hydrocarbon group.

[31] The compound according to [30], wherein

X is $OX^1$, $NX^2X^3$, $SX^4$ or $S(O)_2X^5$ (wherein, $X^1$ is a lower alkyl group substituted with at least one aromatic hydrocarbon group optionally substituted with one or more independent substituent(s) selected from the group consisting of (1) a halogen, (2) a lower alkyl group and (3) a lower alkoxy group; or an aromatic hydrocarbon group optionally substituted with one or more independent substituent (s) selected from the group consisting of (1) a halogen, (2) a lower alkyl group optionally substituted with at least one halogen, (3) a lower alkoxy group, (4) a lower alkoxycarbonyl group, (5) a lower alkylthio group, (6) an aromatic hydrocarbon group, (7) a cyano group, (8) a nitro group and (9) an alkylenedioxy group, $X^2$ is a lower alkyl group substituted with at least one aromatic hydrocarbon group, an aromatic hydrocarbon group, or a lower alkanoyl group, $X^3$ is a lower alkyl group or an aromatic hydrocarbon group, $X^4$ is a lower alkyl group optionally substituted with one or more substituent(s) selected from the group consisting of (1) an aromatic hydrocarbon group optionally substituted with at least one halogen or lower alkyl group and (2) a heterocyclic group substituted with at least one halogen; a higher alkyl group; a lower alkenyl group; a lower cycloalkyl group; an aromatic hydrocarbon group optionally substituted with one or more independent substituent(s) selected from the group consisting of (1) a halogen, (2) a nitro group, (3) a lower alkyl group, (4) a lower haloalkyl group and (5) a lower alkoxy group; or a heterocyclic group optionally substituted with one or more substituent(s), and $X^5$ is an aromatic hydrocarbon group), Y is $OY^1$, $NY^2Y^3$ or $SY^4$ (wherein, $Y^1$ is a lower alkyl group optionally substituted, an aromatic hydrocarbon group optionally substituted, a heterocyclic group optionally substituted, or $N=C(Y^{71})_2$ ($Y^{71}$s are independently a lower alkyl group or an aromatic hydrocarbon group, $Y^2$ is a lower alkyl group optionally substituted with at least one aromatic hydrocarbon group, $Y^3$ is a lower alkyl group or an aromatic hydrocarbon group, $Y^4$ is a lower alkyl group optionally substituted with one or more substituent(s) selected from the group consisting of (1) an aromatic hydrocarbon group optionally substituted with at least one halogen and (2) a lower cycloalkyl group; a higher alkyl group; a lower cycloalkyl group; a lower alkenyl group optionally substituted with at least one halogen; a higher alkenyl group; a lower alkynyl group; an aromatic hydrocarbon group optionally substituted with one or more substituent (s) selected from the group consisting of (1) a halogen, (2) a lower alkyl group optionally substituted with at least one halogen and a lower alkoxy group optionally substituted with at least one halogen; or a heterocyclic group optionally substituted with one or more substituent selected from the group consisting of (1) a lower alkyl group optionally substituted with at least one halogen and (2) a heterocyclic group substituted with at least one halogen), Z is a lower alkyl group substituted with at least one halogen; an aromatic hydrocarbon group optionally substituted with one or more independent substituent(s) selected from the group consisting of (1) a halogen, (2) a cyano group, (3) a hydroxy group, (4) a lower alkyl group optionally substituted with at least one halogen or aromatic hydrocarbon group, (5) a lower alkenyl group, (6) a lower alkoxy group optionally substituted with at least one halogen, (7) a lower alkanoyl oxy group, (8) an aromatic hydrocarbon group optionally substituted with at least one alkyl or halogen, (9) a heterocyclic group, (10) a lower alkylthio group, (11) a lower alkyl sulfinyl group, (12) a lower alkyl sulfonyl group, (13) an arylthio group, (14) a lower alkoxy carbonyl group, (15) a lower alkanoyl group, (16) an aromatic hydrocarbon carbonyl group, (17) a lower alkynyl group, (18) a lower cycloalkylthio group, (19) a lower alkylene dioxygroup, (20) a lower alkylene group and (21) a nitro group; a heterocyclic group; a lower alkoxycarbonyl group; an aromatic hydrocarbon sulfonyl group; an amino group substituted with an aromatic hydrocarbon group and optionally substituted with a lower alkyl group; an aromatic hydrocarbon oxy group; a lower alkoxy group substituted with at least one aromatic hydrocarbon group; or a lower alkylidene amino group substituted with at least one aromatic hydrocarbon group.

[32] The compound according to [1], wherein
X is phenylthio group optionally substituted with at least one substituent selected from the group consisting of a halogen, a methyl group, a trifluoromethyl group and a methoxy group; or phenoxy group optionally substituted with at least one substituent selected from the group consisting of a halogen, a methyl group, a trifluoromethyl group and a methoxy group;
Y is phenylthio group optionally substituted with at least one substituent selected from the group consisting of a halogen, a methyl group, a trifluoromethyl group and a methoxy group; phenoxy group optionally substituted with at least one substituent selected from the group consisting of a halogen, a methyl group, a trifluoromethyl group and a methoxy group; a benzylthio group optionally substituted with at least one substituent selected from the group consisting a halogen, and a methyl group; sec-butylthio group; cyclohexylmethylthio group; or cyclohexylthio group:
Z is phenyl group optionally substituted with at least one substituent selected from the group consisting of a halogen, a methyl group, an isopropyl group, a trifluoromethyl group and a methoxy group.

[33] The compound according to [1], wherein
X is phenylthio group optionally substituted with at least one substituent selected from the group consisting of a halogen, a methyl group, a trifluoromethyl group and a methoxy group; or phenoxy group optionally substituted with at least one substituent selected from the group consisting of a halogen, a methyl group, a trifluoromethyl group and a methoxy group;
Y is phenylthio group optionally substituted with at least one substituent selected from the group consisting of a halogen, a methyl group, a trifluoromethyl group and a methoxy group; phenoxy group optionally substituted with at least one substituent selected from the group consisting of a halogen, a methyl group, a trifluoromethyl group and a methoxy group; or cyclohexylthio group:
Z is phenyl group optionally substituted with at least one substituent selected from the group consisting of a halogen, a methyl group, an isopropyl group, a trifluoromethyl group and a methoxy group.

[AA1] An iminopropene compound of the formula (AAI):

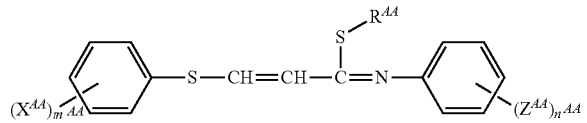

(AAI)

(wherein, $R^{AA}$ represents a $C_{1-3}$ alkyl group substituted with a $C_{3-6}$ cycloalkyl group, $m^{AA}$ represents an integer of 0 to 2, $n^{AA}$ represents an integer of 0 to 2, $X^{AA}$ represents a halogen atom, $C_{1-3}$ alkyl group, $C_{1-3}$ haloalkyl group, $C_{1-4}$ alkoxy group or nitro group, and when $m^{AA}$ is 2, two Xs may be the same or different, and $Z^{AA}$ represents a halogen atom, $C_{1-3}$ haloalkyl group or $C_{1-4}$ alkoxy group, and when $n^{AA}$ is 2, two Zs may be the same or different.).

[AA2] The iminopropene compound according to AA1 wherein in the formula (AAI), $Z^{AA}$ represents a halogen atom or $C_{1-4}$ alkoxy group.

[AB1] An iminopropene compound of the formula (ABI):

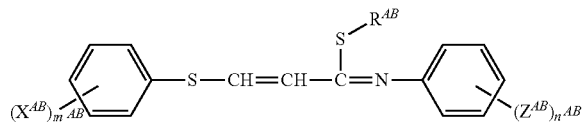

(ABI)

(wherein, $R^{AB}$ represents a $C_{7-10}$ branched alkyl group, or a 3 to 6-membered cycloalkyl group substituted by at least one $C_{1-3}$ alkyl group or condenced with benzene ring, $m^{AB}$ represents an integer of 0 to 2, $n^{AB}$ represents an integer of 0 to 2, $X^{AB}$ represents a halogen atom, $C_{1-3}$ alkyl group, $C_{1-3}$ haloalkyl group, $C_{1-4}$ alkoxy group or nitro group, and when $m^{AB}$ is 2, two Xs may be the same or different, and $Z^{AB}$ represents a halogen atom, $C_{1-3}$ alkyl group, $C_{1-3}$ haloalkyl group or $C_{1-4}$ alkoxy group, and when $n^{AB}$ is 2, two Zs may be the same or different.).

[AB2] The iminopropene compound according to AB1 wherein in the formula (ABI), $R^{AB}$ represents a $C_{7-10}$ branched alkyl group.

[AB3] The iminopropene compound according to AB1 wherein in the formula (ABI), $R^{AB}$ represents a $C_{7-9}$ branched alkyl group.

[AB4] The iminopropene compound according to AB1 wherein in the formula (ABI), $R^{AB}$ represents a 3 to 6-membered cycloalkyl group substituted by at least one $C_{1-3}$ alkyl group.

[AB5] The iminopropene compound according to AB1 wherein in the formula (ABI), $R^{AB}$ represents a cyclohexyl group substituted by at least one $C_{1-3}$ alkyl group.

[AB6] The iminopropene compound according to AB1 wherein in the formula (ABI), $R^{AB}$ represents a 3 to 6-membered cycloalkyl group condenced with benzene ring.

Suitable examples and actual examples of various definitions included the present invention used in the above and following descriptions of the instant specification will be described in detail below.

The term "lower" means a group having 6 or less carbon atoms, unless otherwise stated.

The term "higher" means a group having 7 to 20 carbon atoms, unless otherwise stated.

Suitable examples of "one or more" may include 1 to 6, preferably 1 to 3.

Suitable examples of "lower alkyl group" in the term "lower alkyl group optionally substituted", "lower alkyl group" and "lower alkyl" include linear or branched $C_{1-6}$ alkyl groups, for example, methyl, ethyl, n-propyl, isopropyl, n-butyl, isobutyl, sec-butyl, tert-butyl, n-pentyl, sec-pentyl, isopentyl, neopentyl, n-hexyl, isohexyl and the like.

Suitable examples of "higher alkyl group" include linear or branched $C_{7-20}$ alkyl groups, for example, heptyl, octyl, 3,5-dimethyloctyl, 3,7-dimethyloctyl, nonyl, decyl, undecyl, dodecyl, tridecyl, tetradecyl, hexadecyl, heptadecyl, octadecyl, nonadecyl, icosyl and the like.

Suitable examples of "lower alkenyl group" in the term "lower alkenyl group optionally substituted" and "lower alkenyl group" include linear or branched $C_{2-6}$ alkenyl groups, for example, vinyl, allyl, isopropenyl, isobutenyl, 1-methylallyl, 3-methyl-2-butenyl, 2-pentenyl, 2-hexenyl and the like.

Suitable examples of "higher alkenyl group" include linear or branched $C_{7-20}$ alkenyl groups, for example, heptenyl, octenyl, 3,5-dimethyloctenyl, 3,7-dimethyl-6-octenyl, geranyl and the like.

Suitable examples of "lower alkynyl group" in the term "lower alkynyl group optionally substituted" and "lower alkynyl group" include $C_{2-6}$ alkynyl groups, for example, ethynyl, propargyl, 2-butynyl, 3-butynyl, 3-pentynyl, 3-hexynyl and the like.

Suitable examples of "higher alkynyl group" include linear or branched $C_{7-20}$ alkynyl groups, for example, heptynyl, octynyl, 3,5-dimethyloctynyl 3,7-dimethyloctynyl and the like.

Suitable examples of "lower cycloalkyl group" in the term "lower cycloalkyl group optionally substituted" and "lower cycloalkyl group" include $C_{3-6}$ cycloalkyl groups, for example, cyclopropyl, cyclobutyl, cyclopentyl, cyclohexyl and the like, and preferably may be $C_{4-6}$ cycloalkyl groups, most preferably cyclohexyl.

Suitable examples of "lower cycloalkenyl group" in the term "lower cycloalkenyl group optionally substituted" and "lower cycloalkenyl group" include $C_{3-6}$ cycloalkenyl groups, for example, cyclopropenyl, cyclobutenyl, cyclopentenyl, cyclohexenyl (e.g., 2-cyclohexen-1-yl, 3-cyclohexen-1-yl) and the like, and this "lower cycloalkenyl" may have a lower alkyl.

Suitable examples of "aromatic hydrocarbon group" in the term "aromatic hydrocarbon group optionally substituted", "aromatic hydrocarbon group" and "aryl" include, for example, phenyls optionally having at least one lower alkyl group (e.g., phenyl, mesityl, xylyl, tolyl and the like) and $C_{6-14}$ aromatic hydrocarbon groups such as naphthyl, anthryl, indanyl, tetrahydronaphthyl and the like, and preferably may be phenyl and naphthyl, and this "aromatic hydrocarbon group" may have a suitable substituent such as a lower alkyl, a halogen, a lower alkoxy group, a lower cycloalkyl group and the like.

Suitable examples of "heterocyclic group" in the term "heterocyclic group optionally substituted", and "heterocyclic" part include unsaturated 3 to 8-membered (more preferably, 5 to 6-membered) heteromonocyclic groups containing 1 to 4 nitrogen atoms, for example, pyrrolyl, pyrrolynyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl and the like), tetrazolyl (e.g., 1H-tetrazolyl, 2H-tetrazolyl and the like), and the like; saturated 3 to 8-membered (more preferably, 5 to 6-membered) heteromonocyclic groups containing 1 to 4 nitrogen atoms, for example, pyrrolydinyl, imidazolydinyl, piperidyl, piperidino, piperadinyl and the like; unsaturated condensed heterocyclic groups containing 1 to 4 nitrogen atoms, for example, indolyl, isoindolyl, indolinyl, indolidinyl, benzimidazolyl, quinolyl, isoquinolyl, indazolyl, benzotriazolyl, imidazopyridinyl, imidazothiazolyl and the like; unsaturated 3 to 8-membered (more preferably, 5 to 6-membered) heteromonocyclic groups containing one or two oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl and the like), and the like; saturated 3 to 8-membered (more preferably, 5 to 6-membered) heteromonocyclic groups containing one or two oxygen atoms and 1 to 3 nitrogen atoms, for example, morpholinyl, morpholino and the like; unsaturated condensed heterocyclic groups containing one or two oxygen atoms and 1 to 3 nitrogen atoms, for example, benzoxazolyl, benzoxadiazolyl and the like; unsaturated 3 to 8-membered (more preferably, 5 to 6-membered) heteromonocyclic groups containing one or two sulfur atoms and 1 to 3 nitrogen atoms, for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl and the like), and dihydrothiazinyl and the like; saturated 3 to 8-membered (more preferably, 5 to 6-membered) heteromonocyclic groups containing one or two sulfur atoms and 1 to 3 nitrogen atoms, for example, thiazolidinyl, thiomorpholinyl, thiomorpholino and the like; unsaturated 3 to 8-membered (more preferably, 5 to 6-membered) heteromonocyclic groups containing one or two sulfur atoms, for example, thienyl, dihydrodithiinyl, dihydrodithionyl and the like; saturated heteromonocyclic groups containing one or two sulfur atoms, for example, tetrahydrothienyl, dithianyl and the like; unsaturated condensed heterocyclic groups containing one or two sulfur atoms and containing 1 to 3 nitrogen atoms, for example, benzothiazolyl, benzothiadiazolyl, imidazothiadiazolyl and the like; unsaturated 3 to 8-membered (more preferably, 5 to 6-membered) heteromonocyclic groups containing one or two oxygen atoms, for example, furyl, dihydropyranyl, dioxynyl and the like; saturated 3 to 8-membered (more preferably, 5 to 6-membered) heteromonocyclic groups containing one or two oxygen atoms, for example, tetrahydrofuryl, tetrahydropyranyl, dioxanyl and the like; unsaturated condensed heterocyclic groups containing one or two oxygen atoms, for example, benzofuryl, benzodioxolanyl, benzodioxanyl and the like; unsaturated 3 to 8-membered (more preferably, 5 to 6-membered) heteromonocyclic groups containing an oxygen atom and one or two sulfur atoms, for example, dihydroxathiinyl and the like; unsaturated condensed heterocyclic groups containing one or two sulfur atoms, for example, benzothienyl, benzodithiinyl and the like; unsaturated condensed heterocyclic groups containing an oxygen atom and one or two sulfur atoms, for example, benzoxathiinyl and the like; and this "heterocyclic group" and "heterocyclic" part may have at least one suitable substituent such as a lower alkyl, a halogen, a lower alkoxy group or a lower cycloalkyl group and the like.

Halogen represents fluorine, chlorine, bromine or iodine.

Suitable examples of "lower haloalkyl group" include fluoromethyl, difluoromethyl, trifluoromethyl, chloromethyl, pentafluoroethyl and the like.

Suitable examples of "lower alkoxy group" in the term "lower alkoxy group optionally substituted", "lower alkoxy group" and "lower alkoxy" include linear or branched $C_{1-6}$ alkoxy groups, for example, methoxy, ethoxy, propoxy, isopropoxy, butoxy, isobutoxy, tet-butoxy, pentyloxy, tert-pentyloxy, neo-pentyloxy, hexyloxy, isohexyloxy and the like, preferably, methoxy, ethoxy, propoxy, butoxy, pentyloxy, hexyloxy and isohexyloxy.

Suitable examples of "lower cycloalkyloxy group" in the term "lower cycloalkyloxy group optionally substituted" and "lower cycloalkyloxy group" include $C_{3-6}$ cycloalkyloxy groups such as cyclopropyloxy, cyclobutyloxy, cyclopentyloxy, cyclohexyloxy and the like.

"Acyl group" and "acyl" include aliphatic acyl, aromatic acyl, aryl aliphatic acyl, heterocyclic acyl and heterocyclic aliphatic acyl derived from a carboxylic acid, carbonic acid, carbamic acid, sulfonic acid and the like.

Suitable examples of the above-mentioned "acyl group" include those described below.

carboxy; carbamoyl; mono or di-lower alkylcarbamoyl (e.g., methylcarbamoyl, dimethylcarbamoyl, ethylcarbamoyl, diethylcarbamoyl and the like); mono or diarylcarbamoyl (e.g., phenylcarbamoyl, diphenylcarbamoyl and the like); lower alkylaryl carbamoyl (e.g., methylphenylcarbamoyl and the like); thiocarbamoyl; mono or di-lower alkylthiocarbamoyl (e.g., methylthiocarbamoyl, dimethylthiocarbamoyl, ethylthiocarbamoyl, diethylthiocarbamoyl and the like); mono or diarylthiocarbamoyl (e.g., phenylthiocarbamoyl, diphenylthiocarbamoyl and the like); lower alkylarylthiocarbamoyl (e.g., methylphenylthiocarbamoyl and the like);

aliphatic acyl, for example, lower alkanoyl (e.g., $C_{1-6}$ alkanoyl groups such as formyl, acetyl, propanoyl, butanoyl, 2-methylpropanoyl, pentanoyl, 2,2-dimethylpropanoyl, hexanoyl and the like); higher alkanoyl (e.g., $C_{7-20}$ alkanoyl groups such as heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl and the like); lower alkoxycarbonyl (e.g., $C_{1-6}$ alkoxycarbonyl groups such as methoxycarbonyl, ethoxycarbonyl, propyloxycarbonyl, butoxycarbonyl, t-butoxycarbonyl, t-pentyloxycarbonyl, hexyloxycarbonyl and the like); higher alkoxycarbonyl (e.g., $C_{7-20}$ alkoxycarbonyl groups such as heptyloxycarbonyl, octyloxycarbonyl, nonyloxycarbonyl, decyloxycarbonyl, undecyloxycarbonyl and the like); lower alkylsulfonyl (e.g., $C_{1-6}$ alkylsulfonyl groups such as methylsulfonyl, ethylsulfonyl, propylsulfonyl, isopropylsulfonyl, n-butylsuofonyl, tert-butylsulfonyl, n-pentylsulfonyl, hexylsulfonyl and the like); higher alkylsulfonyl (e.g., $C_{7-20}$alkylsulfonyl groups such as heptylsulfonyl, octylsulfonyl, nonylsulfonyl, decylsulfonyl, dodecylsulfonyl, pentadecylsulfonyl and the like); lower alkoxysulfonyl (e.g., $C_{1-6}$ alkoxysulfonyl groups such as methoxysulfonyl, ethoxysulfonyl, propoxysulfonyl, butoxysulfonyl, tert-butoxysulfonyl, pentyloxysulfonyl, hexyloxysulfonyl and the like); higher alkoxysulfonyl (e.g., $C_{7-20}$ alkoxysulfonyl groups such as heptyloxysulfonyl, octyloxysulfonyl, nonyloxysulfonyl, decyloxysulfonyl, undecyloxysulfonyl and the like);

aromatic acyl, for example, aroyl (e.g., benzoyl, toluoyl, naphthoyl and the like); aryl lower alkanoyl (e.g., phenyl ($C_{1-6}$) alkanoyl groups such as phenylacetyl, phenylpropanoyl, phenylbutanoyl, phenylisobutanoyl, phenylpentanoyl, phenylhexanoyl and the like, naphthyl ($C_{1-6}$) alkanoyl groups such as naphthylacetyl, naphthylpropanoyl, naphthylbutanoyl and the like); aryl lower alkenoyl (e.g., phenyl ($C_{3-6}$) alkenoyl groups such as phenylpropenoyl, phenylbutenoyl, phenylmethacryloyl, phenylpentenoyl, phenylhexenoyl and the like, naphthyl ($C_{1-6}$) alkenoyl groups such as naphthylpropenoyl, naphthylbutenoyl and the like); aryl lower alkoxycarbonyl (e.g., phenyl ($C_{1-6}$) alkoxycarbonyl groups such as benzyloxycarbonyl and the like, fluorenyl ($C_{1-6}$) alkoxycarbonyl groups such as fluorenylmethyloxycarbonyl and the like); aryloxycarbonyl (e.g., phenoxycarbonyl, naphthyloxycarbonyl and the like); aryloxy lower alkanoyl (e.g., phenoxyacetyl, phenoxypropionyl and the like); arylglyoxyloyl (e.g., phenylglyoxyloyl, naphthylglyoxyloyl and the like); arylsulfonyl optionally having 1 to 4 lower alkyls (e.g., phenylsulfonyl, p-tolylsulfonyl and the like) and the like; and heterocyclic acyl for example, heterocyclic carbonyl; heterocyclic lower alkanoyl (e.g., heterocyclic ($C_{1-6}$) alkanoyl groups such as heterocyclic acetyl, heterocyclic propanoyl, heterocyclic butanoyl, heterocyclic pentanoyl, heterocyclic hexanoyl and the like); heterocyclic lower alkenoyl (e.g., heterocyclic ($C_{1-6}$) alkenoyl groups such as heterocyclic propenoyl, heterocyclic butenoyl, heterocyclic pentenoyl, heterocyclic hexenoyl and the like); heterocyclic glyoxyloyl and the like. Here, for suitable "heterocyclic" part in the terms "heterocyclic carbonyl", "heterocyclic lower alkanoyl", "heterocyclic lower alkenoyl" and "heterocyclic glyoxyloyl", the "heterocyclic" part described above can be referred to.

Suitable examples of "lower alkylideneamino group" include $C_{1-6}$ alkylideneaminoxy groups (e.g., ethylideneamino, propylideneamino, isopropylideneamino, cyclohexylideneamino and the like).

Suitable examples of "lower alkylideneaminoxy group" include $C_{1-6}$ alkylideneamino groups (e.g., ethylideneaminoxy, propylideneaminoxy, isopropylideneaminoxy, cyclohexylideneaminoxy and the like).

Suitable examples of "lower alkylidenehydrazino group" include $C_{1-6}$ alkylidenehydrazino groups (e.g., ethylidenehydrazino, propylidenehydrazino, isopropylidenehydrazino, cyclohexylidenehydrazino and the like).

Suitable examples of "lower alkylidenehydrazono group" include $C_{1-6}$ alkylidenehydrazono groups (e.g., ethylidenehydrazono, propylidenehydrazono, isopropylidenehydrazono, cyclohexylidenehydrazono and the like).

Suitable examples of "lower alkanoyloxy group" include $C_{1-6}$ alkanoyloxy groups (e.g., formyloxy, acetyloxy, propanoyloxy, butanoyloxy, 2-methylpropanoyloxy, pentanoyloxy, 2,2-dimethylpropanoyloxy, hexanoyloxy and the like).

Suitable examples of "lower alkylthio group" include $C_{1-6}$ alkylthio groups (e.g., methylthio, ethylthio, propylthio and the like).

Suitable examples of "lower alkylsulfinyl group" include $C_{1-6}$ alkylsulfinyl groups (e.g., methylsulfinyl group, ethylsulfinyl group, propylsulfinyl group and the like).

Suitable examples of "lower alkylsulfonyl group" include $C_{1-6}$ alkylsulfonyl groups (e.g., methylsulfonyl group, ethylsulfonyl group, propylsulfonyl group and the like).

Suitable examples of "arylthio group" include a phenylthio group, mesitylthio group, xylylthio group, tolylthio group, naphthylthio group and the like.

In the compound (I), X represents $OX^1$, $NX^2X^3$, $SX^4$, $S(O)_mX^5$, $Si(X^6)_3$ or $N=C(X^7)_2$.

$X^1$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{11})X^{A1}$, $C(=O)OX^{B1}$, $C(=Q^{12})NX^{D1}X^{E1}$, $SO_2X^{F1}$, $NX^{G1}X^{H1}$ or $N=C(X^{I1})_2$, and preferably mentioned is a lower alkyl group optionally substituted or an aromatic hydrocarbon group optionally substituted, and particularly preferably mentioned is a lower alkyl group substituted with at least one aromatic hydrocarbon group or an aromatic hydrocarbon group optionally substituted.

For the above-mentioned "lower alkyl group" in the term "lower alkyl group optionally substituted" for $X^1$, the "lower alkyl group" described above can be referred to.

For the above-mentioned "higher alkyl group" for $X^1$, the "higher alkyl group" described above can be referred to.

For the above-mentioned "lower cycloalkyl group" in the term "lower cycloalkyl group optionally substituted" for $X^1$, the "lower cycloalkyl group" described above can be referred to.

For the above-mentioned "lower alkenyl group" in the term "lower alkenyl group optionally substituted" for $X^1$, the "lower alkenyl group" described above can be referred to.

For the above-mentioned "higher alkenyl group" for $X^1$, the "higher alkenyl group" described above can be referred to.

For the above-mentioned "lower cycloalkenyl group" in the term "lower cycloalkenyl group optionally substituted" for $X^1$, the "lower cycloalkenyl group" described above can be referred to.

For the above-mentioned "lower alkynyl group" in the term "lower alkynyl group optionally substituted" for $X^1$, the "lower alkynyl group" described above can be referred to.

For the above-mentioned "higher alkynyl group" for $X^1$, the "higher alkynyl group" described above can be referred to.

For the above-mentioned "aromatic hydrocarbon group" in the term "aromatic hydrocarbon group optionally substituted" for $X^1$, the "aromatic hydrocarbon group" described above can be referred to.

For the above-mentioned "heterocyclic group" in the term "heterocyclic group optionally substituted" for $X^1$, the "heterocyclic group" described above can be referred to.

Suitable examples of substituents in the terms "lower alkyl group optionally substituted", "lower cycloalkyl group optionally substituted", "lower alkenyl group optionally substituted", "lower cycloalkenyl group optionally substituted" and "lower alkynyl group optionally substituted" for $X^1$ include a lower alkyl group, a lower alkenyl group, a lower alkynyl group, a lower alkoxy group, a lower alkanoyloxy group, a lower haloalkyl group (e.g., fluoromethyl, difluoromethyl, trifluoromethyl and the like), a lower haloalkyloxy group (e.g., fluoromethoxy, difluoromethoxy, trifluoromethoxy and the like), a hydroxyl group, a nitro group, a cyano group, a carboxyl group, a sulfo group, an oxo, a halogen, a lower cycloalkyl group, a lower cycloalkenyl group, an aromatic hydrocarbon group optionally substituted, a heterocyclic group optionally substituted, an acyl group, a lower alkylideneamino group, a lower alkylideneaminoxy group, a lower alkylidenehydrazino group, a lower alkylidenehydrazono group, a group represented by the formula: —SO$_T$X$^{1A}$,
a group represented by the formula: —OX$^{1B}$,
a group represented by the formula: —N(X$^{1C}$)$_2$,
a group represented by the formula: —ON(X$^{1D}$)$_2$,
a group represented by the formula: =NX$^{1E}$,
a group represented by the formula: =NOX$^{1F}$,
a group represented by the formula: =N(X$^{1G}$)N(X$^{1H}$)$_2$,
a group represented by the formula: =NN(X$^{1I}$)$_2$,
a group represented by the formula: —C(=Q$^{1A}$)N(X$^{1J}$)$_2$,
a group represented by the formula: —C(=Q$^{1B}$)N(X$^{1K}$)N(X$^{1L}$)$_2$, and the like, and the number of the substituent is in a substitutable range and 1 to 5, preferably 1 to 3.

In the above-mentioned formulae, T represents an integer of 0, 1 or 2, $X^{1A}$ represents a hydrogen atom, a lower alkyl group, a lower cycloalkyl group, a lower alkenyl group, a lower cycloalkenyl group, a lower alkynyl group, an aromatic hydrocarbon group or a heterocyclic group, $X^{1B}$, $X^{1C}$, $X^{1D}$, $X^{1E}$, $X^{1F}$, $X^{1G}$, $X^{1H}$, $X^{1I}$, $X^{1J}$, $X^{1K}$ and $X^{1L}$ represent each independently a hydrogen atom, a lower alkyl group, a lower cycloalkyl group, a lower alkenyl group, a lower cycloalkenyl group, a lower alkynyl group, an aromatic hydrocarbon group, heterocyclic group, an acyl group, a group represented by the formula: —SO$_2$X$^{1P}$, or
a group represented by the formula: —C(=Q$^{1C}$)N(X$^{1Q}$)$_2$.

Here, $X^{1P}$ and $X^{1Q}$ represent each independently a lower alkyl group, a lower cycloalkyl group, a lower alkenyl group, a lower cycloalkenyl group, a lower alkynyl group, an aromatic hydrocarbon group or a heterocyclic group, and Q$^{1A}$, Q$^{1B}$ and Q$^{1C}$ represent each independently an oxygen atom or a sulfur atom.

When the substituent in the terms "lower alkyl group optionally substituted", "lower cycloalkyl group optionally substituted", "lower alkenyl group optionally substituted", "lower cycloalkenyl group optionally substituted" and "lower alkynyl group optionally substituted" is an acyl group, C$_{1-6}$ alkylideneamino group, C$_{1-6}$ alkylideneaminoxy group, C$_{1-6}$ alkylidenehydrazino group or C$_{1-6}$ alkylidenehydrazono group, or, when one or more of $X^{1A}$, $X^{1B}$, $X^{1C}$, $X^{1D}$, $X^{1E}$, $X^{1F}$, $X^{1G}$, $X^{1H}$, $X^{1I}$, $X^{1J}$, $X^{1K}$, $X^{1L}$, $X^{1P}$ and $X^{1Q}$ are a lower alkyl group, a lower cycloalkyl group, a lower alkenyl group, a lower cycloalkenyl group or a lower alkynyl group, these groups may be further substituted with a nitro group, a cyano group, a carboxyl group, a sulfo group, an oxo, a halogen, an aromatic hydrocarbon group, a lower cycloalkyl group, a lower cycloalkenyl group, a heterocyclic group, an acyl group, a lower alkylideneamino group, a lower alkylideneaminoxy group, a lower alkylidenehydrazino group, a lower alkylidenehydrazono group, a group represented by the formula: —SO$_U$X$^{2A}$,
a group represented by the formula: —OX$^{2B}$,
a group represented by the formula: —N(X$^{2C}$)$_2$,
a group represented by the formula: —ON(X$^{2D}$)$_2$,
a group represented by the formula: =NX$^{2E}$,
a group represented by the formula: =NOX$^{2F}$,
a group represented by the formula: =N(X$^{2G}$)N(X$^{2H}$)$_2$,
a group represented by the formula: =NN(X$^{2I}$)$_2$,
a group represented by the formula: —C(=Q$^{2A}$)N(X$^{2J}$)$_2$,
a group represented by the formula: —C(=Q$^{2B}$)N(X$^{2K}$)N(X$^{2L}$)$_2$, and the like. In this case, the number of the substituent is preferably 1 to 3.

In the above-mentioned formulae, U represents an integer of 0, 1 or 2, $X^{2A}$ represents a hydrogen atom, a lower alkyl group, a lower cycloalkyl group, a lower alkenyl group, a lower cycloalkenyl group, a lower alkynyl group, an aromatic hydrocarbon group optionally substituted or a heterocyclic group optionally substituted, and $X^{2B}$, $X^{2C}$, $X^{2D}$, $X^{2E}$, $X^{2F}$, $X^{2G}$, $X^{2H}$, $X^{2I}$, $X^{2J}$, $X^{2K}$ and $X^{2L}$ represent each independently a hydrogen atom, a lower alkyl group, a lower cycloalkyl group, a lower alkenyl group, a lower cycloalkenyl group, a lower alkynyl group, an aromatic hydrocarbon group, a heterocyclic group, an acyl group, a group represented by the formula: —SO$_2$X$^{2P}$, or
a group represented by the formula: —C(=Q$^{2C}$)N(X$^{2Q}$)$_2$.

Here, $X^{2P}$ and $X^{2Q}$ represent each independently a lower alkyl group, a lower cycloalkyl group, a lower alkenyl group, a lower cycloalkenyl group, a lower alkynyl group, an aromatic hydrocarbon group or a heterocyclic group.

Q$^{2A}$, Q$^{2B}$ and Q$^{2C}$ represent each independently an oxygen atom or a sulfur atom.

When the "substituent" in the terms "lower alkyl group optionally substituted", "lower cycloalkyl group optionally substituted", "lower alkenyl group optionally substituted", "lower cycloalkenyl group optionally substituted" and "lower alkynyl group optionally substituted" represents an aromatic hydrocarbon group, a lower cycloalkyl group, a lower cycloalkenyl group or a heterocyclic group, or, when one or more of $X^{1A}$, $X^{1B}$, $X^{1C}$, $X^{1D}$, $X^{1E}$, $X^{1F}$, $X^{1G}$, $X^{1H}$, $X^{1I}$, $X^{1J}$, $X^{1K}$, $X^{1L}$, $X^{1P}$ and $X^{1Q}$ represent an aromatic hydrocarbon group, a lower cycloalkyl group, a lower cycloalkenyl group or a heterocyclic group, these groups may be further substituted with a lower alkyl group, a lower alkoxy group, a lower haloalkyl group (e.g., fluoromethyl, difluoromethyl, trifluoromethyl and the like), a nitro group, a cyano group, a carboxyl group, a sulfo group, a halogen, a lower cycloalkyl group, a lower alkenyl group, a lower cycloalkenyl group, a lower alkynyl group, an aromatic hydrocarbon optionally substituted, a heterocyclic group optionally substituted, an acyl group, a lower alkylideneamino group, a lower alkylideneaminoxy group, a lower alkylidenehydrazino group, a lower alkylidenehydrazono group, a group represented by the formula: —SO$_V$X$^{3A}$,
a group represented by the formula: —OX$^{3B}$,
a group represented by the formula: —N(X$^{3C}$)$_2$,
a group represented by the formula: —ON(X$^{3D}$)$_2$,
a group represented by the formula: =NX$^{3E}$,
a group represented by the formula: =NOX$^{3F}$,
a group represented by the formula: =N(X$^{3G}$)N(X$^{3H}$)$_2$,
a group represented by the formula: =NN(X$^{3I}$)$_2$,
a group represented by the formula: —C(=Q$^{3A}$)N(X$^{3J}$)$_2$, or
a group represented by the formula: —C(=Q$^{3B}$)N(X$^{3K}$)N(X$^{3L}$)$_2$. In this case, the number of the substituent is preferably 1 to 3.

In the above-mentioned formulae, V represents an integer of 0, 1 or 2, $X^{3A}$ represents a hydrogen atom, a lower alkyl group, a lower cycloalkyl group, a lower alkenyl group, a lower cycloalkenyl group, a lower alkynyl group, an aromatic hydrocarbon group or a heterocyclic group, $X^{3B}, X^{3C}, X^{3D}, X^{3E}, X^{3F}, X^{3G}, X^{3H}, X^{3I}, X^{3J}, X^{3K}$ and $X^{3L}$ represent each independently a hydrogen atom, a lower alkyl group, a lower cycloalkyl group, a lower alkenyl group, a lower cycloalkenyl group, a lower alkynyl group, an aromatic hydrocarbon group, a heterocyclic group, an acyl group, a group represented by the formula: $—SO_2X^{3P}$, or a group represented by the formula: $—C(=Q^{3C})N(X^{3Q})_2$.

Here, $X^{3P}$ and $X^{3Q}$ represent each independently a lower alkyl group, a lower cycloalkyl group, a lower alkenyl group, a lower cycloalkenyl group, a lower alkynyl group, an aromatic hydrocarbon group or a heterocyclic group.

$Q^{3A}, Q^{3B}$ and $Q^{3C}$ represent each independently an oxygen atom or sulfur atom.

Further, the aromatic hydrocarbon group, lower cycloalkyl group, lower cycloalkenyl group or heterocyclic group has at least one substituent, or when one or more of $X^{1A}, X^{1B}, X^{1C}, X^{1D}, X^{1E}, X^{1F}, X^{1G}, X^{1H}, X^{1I}, X^{1J}, X^{1K}, X^{1L}, X^{1P}$ and $X^{1Q}$ are an aromatic hydrocarbon group, a lower cycloalkyl group or a lower cycloalkenyl group, the 3 to 8-membered heterocyclic group has at least one substituent, and when these substituents are an acyl group, alkylideneamino group, alkylideneaminoxy group, alkylidenehydrazino group or alkylidenehydrazono group, or when one or more of $X^{3A}, X^{3B}, X^{3C}, X^{3D}, X^{3E}, X^{3F}, X^{3G}, X^{3H}, X^{3I}, X^{3J}, X^{3K}, X^{3L}, X^{3P}$ and $X^{3Q}$ are a lower alkyl group, a lower cycloalkyl group, a lower alkenyl group, a lower cycloalkenyl group or a lower alkynyl group, these groups may be further substituted with a nitro group, a cyano group, a carboxyl group, a sulfo group, an oxo, a halogen, an aromatic hydrocarbon group, a lower cycloalkyl group, a lower cycloalkenyl group, a heterocyclic group, an acyl group, a lower alkylideneamino group, a lower alkylideneaminoxy group, a lower alkylidenehydrazino group, a lower alkylidenehydrazono group, a group represented by the formula: $—SO_WX^{4A}$,
a group represented by the formula: $—OX^{4B}$,
a group represented by the formula: $—N(X^{4C})_2$,
a group represented by the formula: $—ON(X^{4D})_2$,
a group represented by the formula: $=NX^{4E}$,
a group represented by the formula: $=NOX^{4F}$,
a group represented by the formula: $=N(X^{4G})N(X^{4H})_2$,
a group represented by the formula: $=NN(X^{4I})_2$,
a group represented by the formula: $—C(=Q^{4A})N(X^{4J})_2$ or
a group represented by the formula: $—C(=Q^{4B})N(X^{4K})N(X^{4L})_2$. In this case, the number of the substituent is preferably 1 to 3.

In the above-mentioned formulae, W represents an integer of 0, 1 or 2, $X^{4A}$ represents a hydrogen atom, a lower alkyl group, a lower cycloalkyl group, a lower alkenyl group, a lower cycloalkenyl group, a lower alkynyl group, an aromatic hydrocarbon group or a heterocyclic group, and $X^{4B}, X^{4C}, X^{4D}, X^{4E}, X^{4F}, X^{4G}, X^{4H}, X^{4I}, X^{4J}, X^{4K}$ and $X^{4L}$ represent each independently a hydrogen atom, a lower alkyl group, a lower cycloalkyl group, a lower alkenyl group, a lower cycloalkenyl group, a lower alkynyl group, an aromatic hydrocarbon group, a heterocyclic group, an acyl group, a group represented by the formula: $—SO_2X^{4P}$, or
a group represented by the formula: $—C(=Q^{4C})N(X^{4Q})_2$.

Here, $X^{4P}$ and $X^{4Q}$ represent each independently a lower alkyl group, a lower cycloalkyl group, a $C_{2-6}$ alkenyl group, a lower cycloalkenyl group, a lower alkynyl group, an aromatic hydrocarbon group or a heterocyclic group, $Q^{4A}, Q^{4B}$ and $Q^{4C}$ represent each independently an oxygen atom or a sulfur atom.

Suitable examples of substituents in the term "aromatic hydrocarbon group optionally substituted" for $X^1$ include a lower alkyl group, a lower alkenyl group, a lower alkynyl group, a lower alkoxy group, a lower alkanoyloxy group, a lower haloalkyl group (e.g., fluoromethyl, difluoromethyl, trifluoromethyl and the like), a lower haloalkyloxy group (e.g., fluoromethoxy, difluoromethoxy, trifluoromethoxy and the like), a hydroxyl group, a nitro group, a cyano group, a carboxyl group, a sulfo group, a halogen, a lower cycloalkyl group, a lower cycloalkenyl group, an aromatic hydrocarbon group optionally substituted, a heterocyclic group optionally substituted, a nacyl group, a lower alkylideneamino group, a lower alkylideneaminoxy group, a lower alkylidenehydrazino group, a lower alkylidenehydrazono group, a group represented by the formula: $—SO_KX^{5A}$,
a group represented by the formula: $—OX^{5B}$,
a group represented by the formula: $—N(X^{5C})_2$,
a group represented by the formula: $—ON(X^{5D})_2$,
a group represented by the formula: $=NX^{5E}$,
a group represented by the formula: $=NOX^{5F}$,
a group represented by the formula: $=N(X^{5G})N(X^{5H})_2$,
a group represented by the formula: $=NN(X^{5I})_2$,
a group represented by the formula: $—C(=Q^{5A})N(X^{5J})_2$,
a group represented by the formula: $—C(=Q^{5B})N(X^{5K})N(X^{5L})_2$, and the like, and the number of the substituent is preferably 1 to 5, more preferably 1 to 3.

In the above-mentioned formulae, $_K$ represents an integer of 0, 1 or 2, $X^{5A}$ represents a hydrogen atom, a lower alkyl group, a lower cycloalkyl group, a lower alkenyl group, a lower cycloalkenyl group, a lower alkynyl group, an aromatic hydrocarbon group or a heterocyclic group, $X^{5B}, X^{5C}, X^{5D}, X^{5E}, X^{5F}, X^{5G}, X^{5H}, X^{5I}, X^{5J}, X^{5K}$ and $X^{5L}$ represent each independently a hydrogen atom, a lower alkyl group, a lower cycloalkyl group, a lower alkenyl group, a lower cycloalkenyl group, a lower alkynyl group, an aromatic hydrocarbon group, a heterocyclic group, acyl group, a group represented by the formula: $—SO_2X^{5P}$, or
a group represented by the formula: $—C(=Q^{5C})N(X^{5Q})_2$.

Here, $X^{5P}$ and $X^{5Q}$ represent each independently a lower alkyl group, a lower cycloalkyl group, a lower alkenyl group, a lower cycloalkenyl group, a lower alkynyl group, an aromatic hydrocarbon group or a heterocyclic group, and $Q^{5A}, Q^{5B}$ and $Q^{5C}$ represent each independently an oxygen atom or sulfur atom.

When the substituent in the "aromatic hydrocarbon group optionally substituted" is an acyl group, alkylideneamino group, alkylideneaminoxy group, alkylidenehydrazino group or alkylidenehydrazono group, or, when one or more of $X^{5A}, X^{5B}, X^{5C}, X^{5D}, X^{5E}, X^{5F}, X^{5G}, X^{5H}, X^{5I}, X^{5J}, X^{5K}, X^{5L}, X^{5P}$ and $X^{5Q}$ are a lower alkyl group, a lower cycloalkyl group, a lower alkenyl group, a lower cycloalkenyl group or a lower alkynyl group, these groups may be further substituted with 1 to 3 substituents selected from the group consisting of a nitro group, a cyano group, a carboxyl group, a sulfo group, an oxo, a halogen, an aromatic hydrocarbon group, a heterocyclic group, an acyl group, a lower alkylideneamino group, a lower alkylideneaminoxy group, a lower alkylidenehydrazino group, a lower alkylidenehydrazono group, a group represented by the formula: $—SO_LX^{6A}$,
a group represented by the formula: $—OX^{6B}$, a group represented by the formula: —N($X^{6C}$)$_2$,
a group represented by the formula: —ON($X^{6D}$)$_2$,
a group represented by the formula: =N$X^{6E}$,
a group represented by the formula: =NO$X^{6F}$,
a group represented by the formula: —N($X^{6G}$)N($X^{6H}$)$_2$,
a group represented by the formula: —NN($X^{6I}$)$_2$,
a group represented by the formula: —C(=$Q^{6A}$)N($X^{6J}$)$_2$,
a group represented by the formula: —C(=$Q^{6B}$) N($X^{6K}$)N($X^{6L}$)$_2$, and the like.

In the above-mentioned formulae, $_L$ represents an integer of 0, 1 or 2, $X^{6A}$ represents a hydrogen atom, a lower alkyl group, a lower cycloalkyl group, a lower alkenyl group, a lower cycloalkenyl group, a lower alkynyl group, an aromatic hydrocarbon group or a heterocyclic group, and $X^{6B}$, $X^{6C}$, $X^{6D}$, $X^{6E}$, $X^{6F}$, $X^{6G}$, $X^{6H}$, $X^{6I}$, $X^{6J}$, $X^{6K}$ and $X^{6L}$ represent each independently a hydrogen atom, a lower alkyl group, a lower cycloalkyl group, a lower alkenyl group, a lower cycloalkenyl group, a lower alkynyl group, an aromatic hydrocarbon group, a heterocyclic group, an acyl group, a group represented by the formula: —SO$_2$$X^{6P}$, or
a group represented by the formula: —C(=$Q^{6C}$)N($X^{6Q}$)$_2$.

Here, $X^{6P}$ and $X^{6Q}$ represent each independently a lower alkyl group, a lower cycloalkyl group, a lower alkenyl group, a lower cycloalkenyl group, a lower alkynyl group, an aromatic hydrocarbon group or a heterocyclic group, and $Q^{6A}$, $Q^{6B}$ and $Q^{6C}$ represent each independently an oxygen atom or a sulfur atom.

When the substituent in the "aromatic hydrocarbon group optionally substituted" is an aromatic hydrocarbon group, a lower cycloalkyl group, a lower cycloalkenyl group or a heterocyclic group, or when one or more of $X^{5A}$, $X^{5B}$, $X^{5C}$, $X^{5D}$, $X^{5E}$, $X^{5F}$, $X^{5G}$, $X^{5H}$, $X^{5I}$, $X^{5J}$, $X^{5K}$, $X^{5L}$, $X^{5P}$ and $X^{5Q}$ are an aromatic hydrocarbon group, a lower cycloalkyl group or a heterocyclic group, these groups may be further substituted with 1 to 3 substituents selected from the group consisting of a nitro group, a cyano group, a carboxyl group, a sulfo group, a halogen, a lower alkyl group, a lower cycloalkyl group, a lower alkenyl group, a lower cycloalkenyl group, a lower alkynyl group, an aromatic hydrocarbon group, a heterocyclic group, an acyl group, a lower alkylideneamino group, a lower alkylideneaminoxy group, a lower alkylidenehydrazino group, a lower alkylidenehydrazono group, a group represented by the formula: —SO$_M$$X^{7A}$,
a group represented by the formula: —O$X^{7B}$,
a group represented by the formula: —N($X^{7C}$)$_2$,
a group represented by the formula: —ON($X^{7D}$)$_2$,
a group represented by the formula: =N$X^{7E}$,
a group represented by the formula: =NO$X^{7F}$,
a group represented by the formula: —N($X^{7G}$)N($X^{7H}$)$_2$,
a group represented by the formula: =NN($X^{7I}$)$_2$,
a group represented by the formula: —C(=$Q^{7A}$)N($X^{7J}$)$_2$,
a group represented by the formula: —C(=$Q^{7B}$) N($X^{7K}$)N($X^{7L}$)$_2$, and the like.

In the above-mentioned formulae, $_M$ represents an integer of 0, 1 or 2, $X^{7A}$ represents a hydrogen atom, a lower alkyl group, a lower cycloalkyl group, a lower alkenyl group, a lower cycloalkenyl group, a lower alkynyl group, an aromatic hydrocarbon group or a heterocyclic group, $X^{7B}$, $X^{7C}$, $X^{7D}$, $X^{7E}$, $X^{7F}$, $X^{7G}$, $X^{7H}$, $X^{7I}$, $X^{7J}$, $X^{7K}$ and $X^{7L}$ represent each independently a hydrogen atom, a lower alkyl group, a lower cycloalkyl group, a lower alkenyl group, a lower cycloalkenyl group, a $C_{2-6}$ alkynyl group, an aromatic hydrocarbon group, a heterocyclic group, acyl group, a group represented by the formula: —SO$_2$$X^{7P}$, or
a group represented by the formula: —C(=$Q^{7C}$)N($X^{7Q}$)$_2$.

Here, $X^{7P}$ and $X^{7Q}$ represent each independently a lower alkyl group, a lower cycloalkyl group, a lower alkenyl group, a lower cycloalkenyl group, a lower alkynyl group, an aromatic hydrocarbon group or a heterocyclic group, and $Q^{7A}$, $Q^{7B}$ and $Q^{7C}$ represent each independently an oxygen atom or a sulfur atom.

As the substituent in the "heterocyclic group optionally substituted" for $X^1$, the same substituents as exemplified for the substituent of the "aromatic hydrocarbon group optionally substituted" are mentioned.

$X^2$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, C(=$Q^{21}$) $X^{A2}$, C(=O)O$X^{B2}$, C(=$Q^{22}$) N$X^{D2}$$X^{E2}$, SO$_2$$X^{F2}$, N$X^{G2}$$X^{H2}$, N=C($X^{I2}$)$_2$, O$X^{K2}$ or a cyano group, and preferably mentioned is a lower alkyl group optionally substituted, an aromatic hydrocarbon group optionally substituted, or C(=$Q^{21}$)$X^{A2}$ (here, $Q^{21}$ represents an oxygen atom, and $X^{A2}$ represents a lower alkyl group optionally substituted), and particularly preferably mentioned is a lower alkyl group substituted with at least one aromatic hydrocarbon group, an aromatic hydrocarbon group or a lower alkanoyl group.

For the above-mentioned "lower alkyl group" in the term "lower alkyl group optionally substituted" for $X^2$, the "lower alkyl group" described above can be referred to.

For the above-mentioned "higher alkyl group" for $X^2$, the "higher alkyl group" described above can be referred to.

For the above-mentioned "lower cycloalkyl group" in the term "lower cycloalkyl group optionally substituted" for $X^2$, the "lower cycloalkyl group" described above can be referred to.

For the above-mentioned "lower alkenyl group" in the term "lower alkenyl group optionally substituted" for $X^2$, the "lower alkenyl group" described above can be referred to.

For the above-mentioned "higher alkenyl group" for $X^2$, the "higher alkenyl group" described above can be referred to.

For the above-mentioned "lower cycloalkenyl group" in the term "lower cycloalkenyl group optionally substituted" for $X^2$, the "lower cycloalkenyl group" described above can be referred to.

For the above-mentioned "lower alkynyl group" in the term "lower alkynyl group optionally substituted" for $X^2$, the "lower alkynyl group" described above can be referred to.

For the above-mentioned "higher alkynyl group" for $X^2$, the "higher alkynyl group" described above can be referred to.

For the above-mentioned "aromatic hydrocarbon group" in the term "aromatic hydrocarbon group optionally substituted" for $X^2$, the "aromatic hydrocarbon group" described above can be referred to.

For the above-mentioned "heterocyclic group" in the term "heterocyclic group optionally substituted" for $X^2$, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $X^2$, the "substituent" for $X^1$ describe above can be referred to.

For $X^{B2}$, $Q^{22}$, $X^{D2}$, $X^{E2}$, $X^{F2}$, $X^{G2}X^{H2}$, $X^{I2}$ and $X^{K2}$ for $X^2$, groups described later can be referred to.

$X^3$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{31})X^{A3}$, $C(=O)OX^{B3}$, $C(=Q^{32})NX^{D3}X^{E3}$ or $SO_2X^{F3}$, and preferably mentioned is a lower alkyl group optionally substituted, or an aromatic hydrocarbon group optionally substituted, and particularly preferably mentioned is a lower alkyl group or an aromatic hydrocarbon group.

For the above-mentioned "lower alkyl group" in the term "lower alkyl group optionally substituted" for $X^3$, the "lower alkyl group" described above can be referred to.

For the above-mentioned "higher alkyl group" for $X^3$, the "higher alkyl group" described above can be referred to.

For the above-mentioned "lower cycloalkyl group" in the term "lower cycloalkyl group optionally substituted" for $X^3$, the "lower cycloalkyl group" described above can be referred to.

For the above-mentioned "lower alkenyl group" in the term "lower alkenyl group optionally substituted" for $X^3$, the "lower alkenyl group" described above can be referred to.

For the above-mentioned "lower cycloalkenyl group" in the term "lower cycloalkenyl group optionally substituted" for $X^3$, the "lower cycloalkenyl group" described above can be referred to.

For the above-mentioned "lower alkynyl group" in the term "lower alkynyl group optionally substituted" for $X^3$, the "lower alkynyl group" described above can be referred to.

For the above-mentioned "higher alkynyl group" for $X^3$, the "higher alkynyl group" described above can be referred to.

For the above-mentioned "aromatic hydrocarbon group" in the term "aromatic hydrocarbon group optionally substituted" for $X^3$, the "aromatic hydrocarbon group" described above can be referred to.

For the above-mentioned "heterocyclic group" in the term "heterocyclic group optionally substituted", the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $X^3$, the "substituent" for $X^1$ describe above can be referred to.

For $X^{A3}$, $X^{B3}$, $Q^{32}$, $X^{D3}$, $X^{E3}$ and $X^{F3}$ for $X^3$, groups described later can be referred to.

For the "ring structure" represented by $X^2$ and $X^3$ together with the nitrogen which is bonded with each other, the same structures as the below-mentioned "ring structure" represented by $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ together with the nitrogen which is bonded with each other are mentioned.

$X^4$ represents a lower alkyl group optionally substituted, a higher alkyl group, a lower cycloalkyl group optionally substituted, a lower alkenyl group optionally substituted, a lower cycloalkenyl group optionally substituted, a higher alkenyl group, a lower alkynyl group optionally substituted, a higher alkynyl group, an aromatic hydrocarbon group optionally substituted, a heterocyclic group optionally substituted, $C(=Q^{41})X^{A4}$, $C(=O)OX^{B4}$, $C(=Q^{42})NX^{D4}X^{E4}$ or $S(O)_nX^{F4}$, and preferably mentioned is a lower alkyl group optionally substituted, a higher alkyl group, a lower alkenyl group optionally substituted, a lower cycloalkyl group optionally substituted, an aromatic hydrocarbon group optionally substituted or a heterocyclic group optionally substituted, and particularly preferably mentioned is a lower alkyl group optionally substituted, a higher alkyl group, a lower cycloalkyl group, a lower alkenyl group, an aromatic hydrocarbon group optionally substituted or a heterocyclic group optionally substituted.

For the above-mentioned "lower alkyl group" in the term "lower alkyl group optionally substituted" for $X^4$, the "lower alkyl group" described above can be referred to.

For the substituent in the term "lower alkyl group optionally substituted" for $X^4$, the "substituent" for $X^1$ described above can be referred to, and preferably mentioned is an aromatic hydrocarbon group optionally substituted or a heterocyclic group optionally substituted, and particularly preferably mentioned is an aromatic hydrocarbon optionally substituted with at least one halogen or a heterocyclic group substituted with at least one halogen.

For the above-mentioned "higher alkyl group" for $X^4$, the "higher alkyl group" described above can be referred to.

For the above-mentioned "lower cycloalkyl group" in the term "lower cycloalkyl group optionally substituted" for $X^4$, the "lower cycloalkyl group" described above can be referred to.

For the above-mentioned "lower alkenyl group" in the term "lower alkenyl group optionally substituted" for $X^4$, the "lower alkenyl group" described above can be referred to.

For the above-mentioned "higher alkenyl group" for $X^4$, the "higher alkenyl group" described above can be referred to.

For the above-mentioned "lower cycloalkenyl group" in the term "lower cycloalkenyl group optionally substituted" for $X^4$, the "lower cycloalkenyl group" described above can be referred to.

For the above-mentioned "lower alkynyl group" in the term "lower alkynyl group optionally substituted" for $X^4$, the "lower alkynyl group" described above can be referred to.

For the above-mentioned "higher alkynyl group" for $X^4$, the "higher alkynyl group" described above can be referred to.

For the above-mentioned "aromatic hydrocarbon group" in the term "aromatic hydrocarbon group optionally substituted" for $X^4$, the "aromatic hydrocarbon group" described above can be referred to.

For the substituent in the above-mentioned term "aromatic hydrocarbon group optionally substituted" for $X^4$, the "substituent" for $X^1$ described above can be referred to, and preferably mentioned is a halogen, a nitro group, a lower alkyl group, a lower haloalkyl group or a lower alkoxy group.

For the above-mentioned "heterocyclic group" in the term "heterocyclic group optionally substituted" for $X^4$, the "heterocyclic group" described above can be referred to.

For the substituent in the above-mentioned term "heterocyclic group optionally substituted" for $X^4$, the "substituent" for $X^1$ described above can be referred to, and preferably mentioned is a lower alkyl group.

For the substituent in the terms "lower cycloalkyl group optionally substituted", "lower alkenyl group optionally substituted", "lower cycloalkenyl group optionally substituted"

and "lower alkynyl group optionally substituted" for $X^4$, the "substituent" for $X^1$ described above can be referred to.

For $Q^{41}$, $X^{A4}$, $X^{B4}$, $Q^{42}$, $X^{D4}$, $X^{E4}$ and $X^{F4}$ for $X^4$, groups described later can be referred to.

$X^5$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted and preferably mentioned is an aromatic hydrocarbon group optionally substituted, and particularly mentioned is an aromatic hydrocarbon group.

For the above-mentioned "lower alkyl group" in the term "lower alkyl group optionally substituted" for $X^5$, the "lower alkyl group" described above can be referred to.

For the above-mentioned "higher alkyl group" for $X^5$, the "higher alkyl group" described above can be referred to.

For the above-mentioned "lower cycloalkyl group" in the term "lower cycloalkyl group optionally substituted" for $X^5$, the "lower cycloalkyl group" described above can be referred to.

For the above-mentioned "lower alkenyl group" in the term "lower alkenyl group optionally substituted" for $X^5$, the "lower alkenyl group" described above can be referred to.

For the above-mentioned "higher alkenyl group" for $X^5$, the "higher alkenyl group" described above can be referred to.

For the above-mentioned "lower cycloalkenyl group" in the term "lower cycloalkenyl group optionally substituted" for $X^5$, the "lower cycloalkenyl group" described above can be referred to.

For the above-mentioned "lower alkynyl group" in the term "lower alkynyl group optionally substituted" for $X^5$, the "lower alkynyl group" described above can be referred to.

For the above-mentioned "higher alkynyl group" for $X^5$, the "higher alkynyl group" described above can be referred to.

For the above-mentioned "aromatic hydrocarbon group" in the term "aromatic hydrocarbon group optionally substituted" for $X^5$, the "aromatic hydrocarbon group" described above can be referred to.

For the above-mentioned "heterocyclic group" in the term "heterocyclic group optionally substituted" for $X^5$, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $X^5$, the "substituent" for $X^1$ described above can be referred to.

$X^6$s represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or a lower alkoxy group optionally substituted.

For the above-mentioned "lower alkyl group" in the term "lower alkyl group optionally substituted" for $X^6$, the "lower alkyl group" described above can be referred to.

For the above-mentioned "higher alkyl group" for $X^6$, the "higher alkyl group" described above can be referred to.

For the above-mentioned "lower cycloalkyl group" in the term "lower cycloalkyl group optionally substituted" for $X^6$, the "lower cycloalkyl group" described above can be referred to.

For the above-mentioned "lower alkenyl group" in the term "lower alkenyl group optionally substituted" for $X^6$, the "lower alkenyl group" described above can be referred to.

For the above-mentioned "higher alkenyl group" for $X^6$, the "higher alkenyl group" described above can be referred to.

For the above-mentioned "lower cycloalkenyl group" in the term "lower cycloalkenyl group optionally substituted" for $X^6$, the "lower cycloalkenyl group" described above can be referred to.

For the above-mentioned "lower alkynyl group" in the term "lower alkynyl group optionally substituted" for $X^6$, the "lower alkynyl group" described above can be referred to.

For the above-mentioned "higher alkynyl group" for $X^6$, the "higher alkynyl group" described above can be referred to.

For the above-mentioned "aromatic hydrocarbon group" in the term "aromatic hydrocarbon group optionally substituted" for $X^6$, the "aromatic hydrocarbon group" described above can be referred to.

For the above-mentioned "heterocyclic group" in the term "heterocyclic group optionally substituted" for $X^6$, the "heterocyclic group" described above can be referred to.

For the above-mentioned "lower alkoxy group" in the term "lower alkoxy group optionally substituted" for $X^6$ the "lower alkoxy group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted", "heterocyclic group optionally substituted" and "lower alkoxy group optionally substituted" for $X^6$, the "substituent" for $X^1$ described above can be referred to.

$X^7$s represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OX^{L7}$, $SX^{M7}$ or $NX^{G7}X^{H7}$, alternatively, represent a reig structure together with the carbon atom which is bonded with each other.

For the above-mentioned "lower alkyl group" in the term "lower alkyl group optionally substituted" for $X^7$, the "lower alkyl group" described above can be referred to.

For the above-mentioned "higher alkyl group" for $X^7$, the "higher alkyl group" described above can be referred to.

For the above-mentioned "lower cycloalkyl group" in the term "lower cycloalkyl group optionally substituted" for $X^7$, the "lower cycloalkyl group" described above can be referred to.

For the above-mentioned "lower alkenyl group" in the term "lower alkenyl group optionally substituted" for $X^7$, the "lower alkenyl group" described above can be referred to.

For the above-mentioned "higher alkenyl group" for $X^7$, the "higher alkenyl group" described above can be referred to.

For the above-mentioned "lower cycloalkenyl group" in the term "lower cycloalkenyl group optionally substituted" for $X^7$, the "lower cycloalkenyl group" described above can be referred to.

For the above-mentioned "lower alkynyl group" in the term "lower alkynyl group optionally substituted" for $X^7$, the "lower alkynyl group" described above can be referred to.

For the above-mentioned "higher alkynyl group" for $X^7$, the "higher alkynyl group" described above can be referred to.

For the above-mentioned "aromatic hydrocarbon group" in the term "aromatic hydrocarbon group optionally substituted" for $X^7$, the "aromatic hydrocarbon group" described above can be referred to.

For the above-mentioned "heterocyclic group" in the term "heterocyclic group optionally substituted" for $X^7$, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $X^7$, the "substituent" for $X^1$ described above can be referred to.

For the "heterocyclic group" in the term "heterocyclic group optionally substituted" for X, the "heterocyclic group" described above can be referred to, and preferably mentioned is a heterocyclic group, particularly preferably mentioned is a piperidino group or morpholino group.

For $X^{L7}$, $X^{M7}$, $X^{G7}$ and $X^{H7}$, groups described below can be referred to.

The "ring structure" represented by $X^7$s together with the carbon which is bonded with each other means a 3 to 8-membered cyclic group composed of the carbon atom as a ring constituent atom, and mentioned are 3 to 8-membered (preferably, 5 to 6-membered) cyclic groups composed of the carbon atom as a ring constituent atom, and optionally having 1 to 3 hetero atoms such as a nitrogen atom optionally oxidized, an oxygen atom, a sulfur atom optionally mono or di-oxidized, and the like such as, for example, cyclopentylidene, cyclohexylidene, cycloheptylidene, cyclooctylidene, cyclopentenylidene, cyclohexenylidene, cycloheptenylidene, cyclooctenylidene, cyclopentadienylidene, cyclohexadienylidene, cycloheptadienylidene, cyclooctadienylidene, tetrahydrofuranylidene, dihydrofuranylidene, tetrahydropyranylidene, dihydropyranylidene, pyranylidene, dioxolanylidene, dioxolylidene, dioxanylidene, dioxinylidene, tetrahydrothiophenylidene, dihydrothiophenylidene, tetrahydrothiopyranylidene, dihydrothiopyranylidene, thiopyranylidene, dithiolanylidene, dithiolylidene, dithianylidene, dithiinylidene, 2H-dihydropyrrolylidene, 2H-pyrrolylidene, 3H-pyrrolylidene, 2H-imidazolylidene, 3H-triazolylidene and the like; and groups obtained by condensing a benzene ring or 3 to 8-membered (preferably, 5 to 6-membered) heterocyclic group (the heterocyclic group has 1 to 4 nitrogen atom(s) optionally oxidized, oxygen atom(s), or sulfur atom(s) optionally mono or di-oxidized) with the above-mentioned cyclic group.

The "3 to 8-membered cyclic group composed of the carbon atom as a ring constituent atom" may be substituted with the same substituent as exemplified for the substituent on "aromatic hydrocarbon group optionally substituted" for $X^1$. The number of the substituent is in a substitutable range and 1 to 5, preferably 1 to 3.

$Q^{XA1}$, $Q^{XA2}$, $Q^{XA3}$, $Q^{XA4}$, $Q^{XA5}$, $Q^{XA6}$, $Q^{XA7}$, $Q^{XA8}$, $Q^{XB1}$, $Q^{XB2}$, $Q^{XB3}$, $Q^{XB4}$, $Q^{XB5}$ and $Q^{XB6}$ represent each independently an oxygen atom or a sulfur atom.

$R^{XA1}$, $R^{XA2}$, $R^{XA3}$, $R^{XA4}$, $R^{XA5}$, $R^{XA6}$, $R^{XA7}$, $R^{XA8}$, $R^{XA9}$, $R^{XA10}$, $R^{XA11}$, $R^{XA12}$, $Q^{YB1}$, $Q^{YB2}$, $Q^{YB3}$, $Q^{YB4}$, $Q^{YB5}$, $Q^{YB6}$, $Q^{YB7}$, $Q^{YB8}$ and $Q^{YB9}$ represent each independently a hydrogen atom, a lower alkyl group, a lower cycloalkyl group, a lower alkenyl group, a lower cycloalkenyl group, a lower alkynyl group or an aromatic hydrocarbon group.

In the compound (I), Y represents $OY^1$, $NY^2Y^3$, $SY^4$, $SO_2Y^5$ or $N=C(Y^6)_2$.

$Y^1$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{51})X^{A1}$, $C(=O)OY^{B1}$, $C(=Q^{52})NY^{D1}Y^{E1}$, $S(O)_pY^{F1}$ or $N(Y^{I1})_2$, and preferably mentioned is a lower alkyl group optionally substituted, an aromatic hydrocarbon group optionally substituted or a heterocyclic group optionally substituted, and particularly preferably mentioned is a lower alkyl optionally substituted, an aromatic hydrocarbon group optionally substituted or a heterocyclic group.

For the above-mentioned "lower alkyl group" in the term "lower alkyl group optionally substituted" for $Y^1$, the "lower alkyl group" described above can be referred to.

For the substituent in the term "lower alkyl group optionally substituted" for $Y^1$, the "substituent" for $X^1$ describe above can be referred to, and preferably mentioned is an aromatic hydrocarbon group optionally substituted or a heterocyclic group optionally substituted, and particularly preferably mentioned is an aromatic hydrocarbon optionally substituted with at least one lower alkyl or halogen or a heterocyclic group substituted with at least one halogen.

For the above-mentioned "higher alkyl group" for $Y^1$, the "higher alkyl group" described above can be referred to.

For the above-mentioned "lower cycloalkyl group" in the term "lower cycloalkyl group optionally substituted" for $Y^1$, the "lower cycloalkyl group" described above can be referred to.

For the above-mentioned "lower alkenyl group" in the term "lower alkenyl group optionally substituted" for $Y^1$, the "lower alkenyl group" described above can be referred to.

For the above-mentioned "higher alkenyl group" for $Y^1$, the "higher alkenyl group" described above can be referred to.

For the above-mentioned "lower cycloalkenyl group" in the term "lower cycloalkenyl group optionally substituted" for $Y^1$, the "lower cycloalkenyl group" described above can be referred to.

For the above-mentioned "lower alkynyl group" in the term "lower alkynyl group optionally substituted" for $Y^1$, the "lower alkynyl group" described above can be referred to.

For the above-mentioned "higher alkynyl group" for $Y^1$, the "higher alkynyl group" described above can be referred to.

For the above-mentioned "aromatic hydrocarbon group" in the term "aromatic hydrocarbon group optionally substituted" for $Y^1$, the "aromatic hydrocarbon group" described above can be referred to.

For the substituent in the term "aromatic hydrocarbon group optionally substituted" for $Y^1$, the "substituent" for $X^1$ described above can be referred to, and preferably mentioned are a halogen, a lower alkyl group, a cyano group and a nitro group.

For the above-mentioned "heterocyclic group" in the term "heterocyclic group optionally substituted" for $Y^1$, the "heterocyclic group" described above can be referred to.

For the substituent in the term "heterocyclic group optionally substituted" for $Y^1$, the "substituent" for $X^1$ described above can be referred to.

For the substituent in the terms "lower cycloalkyl group optionally substituted", "lower alkenyl group optionally substituted", "lower cycloalkenyl group optionally substituted" and "lower alkynyl group optionally substituted" for $Y^1$, the "substituents" for $X^1$ described above can be referred to.

For $Q^{51}$, $Y^{A1}$, $Y^{B1}$, $Q^{52}$, $Y^{D1}$, $Y^{E1}$, $Y^{F1}$ and $Y^{I1}$, groups described later can be referred to.

$Y^2$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{61})Y^{A2}$, $C(=O)OY^{B2}$, $C(=Q^{62})NY^{D2}Y^{E2}$, $SO_2Y^{F2}$, $NY^{G2}Y^{H2}$, $N=C(Y^{I2})_2$, $OY^{K2}$ or a cyano group, and preferably mentioned is a lower alkyl group optionally substituted, or an aromatic hydrocarbon group optionally substituted, and particularly mentioned is a lower alkyl group optionally substituted or an aromatic hydrocarbon group.

For the above-mentioned "lower alkyl group" in the term "lower alkyl group optionally substituted" for $Y^2$, the "lower alkyl group" described above can be referred to.

For the substituent in the term "lower alkyl group optionally substituted" for $Y^2$, the "substituent" for $X^1$ described above can be referred to, and preferably mentioned is an aromatic hydrocarbon group.

For the above-mentioned "higher alkyl group" for $Y^2$, the "higher alkyl group" described above can be referred to.

For the above-mentioned "lower cycloalkyl group" in the term "lower cycloalkyl group optionally substituted" for $Y^2$, the "lower cycloalkyl group" described above can be referred to.

For the above-mentioned "lower alkenyl group" in the term "lower alkenyl group optionally substituted" for $Y^2$, the "lower alkenyl group" described above can be referred to.

For the above-mentioned "higher alkenyl group" for $Y^2$, the "higher alkenyl group" described above can be referred to.

For the above-mentioned "lower cycloalkenyl group" in the term "lower cycloalkenyl group optionally substituted" for $Y^2$, the "lower cycloalkenyl group" described above can be referred to.

For the above-mentioned "lower alkynyl group" in the term "lower alkynyl group optionally substituted" for $Y^2$, the "lower alkynyl group" described above can be referred to.

For the above-mentioned "higher alkynyl group" for $Y^2$, the "higher alkynyl group" described above can be referred to.

For the above-mentioned "aromatic hydrocarbon group" in the term "aromatic hydrocarbon group optionally substituted" for $Y^2$, the "aromatic hydrocarbon group" described above can be referred to.

For the above-mentioned "heterocyclic group" in the term "heterocyclic group optionally substituted" for $Y^2$, the "heterocyclic group" described above can be referred to.

For the substituent in the terms "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $Y^2$, the "substituents" for $X^1$ described above can be referred to.

For $Q^{61}$, $Y^{A2}$, $Y^{B2}$, $Q^{62}$, $Y^{D2}$, $Y^{E2}$, $Y^{F2}$, $Y^{G2}$, $Y^{H2}$, $Y^{I2}$ and $Y^{K2}$, groups described later can be referred to.

$Y^3$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{71})Y^{A3}$, $C(=O)OY^{B3}$, $C(=Q^{72})NY^{D3}Y^{E3}$ or $SO_2Y^{F3}$, and preferably mentioned is a lower alkyl group optionally substituted, and particularly mentioned is a lower alkyl group.

For the above-mentioned "lower alkyl group" in the term "lower alkyl group optionally substituted" for $Y^3$, the "lower alkyl group" described above can be referred to.

For the above-mentioned "higher alkyl group" for $Y^3$, the "higher alkyl group" described above can be referred to.

For the above-mentioned "lower cycloalkyl group" in the term "lower cycloalkyl group optionally substituted" for $Y^3$, the "lower cycloalkyl group" described above can be referred to.

For the above-mentioned "lower alkenyl group" in the term "lower alkenyl group optionally substituted" for $Y^3$, the "lower alkenyl group" described above can be referred to.

For the above-mentioned "higher alkenyl group" for $Y^3$, the "higher alkenyl group" described above can be referred to.

For the above-mentioned "lower cycloalkenyl group" in the term "lower cycloalkenyl group optionally substituted" for $Y^3$, the "lower cycloalkenyl group" described above can be referred to.

For the above-mentioned "lower alkynyl group" in the term "lower alkynyl group optionally substituted" for $Y^3$, the "lower alkynyl group" described above can be referred to.

For the above-mentioned "higher alkynyl group" for $Y^3$, the "higher alkynyl group" described above can be referred to.

For the above-mentioned "aromatic hydrocarbon group" in the term "aromatic hydrocarbon group optionally substituted" for $Y^3$, the "aromatic hydrocarbon group" described above can be referred to.

For the above-mentioned "heterocyclic group" in the term "heterocyclic group optionally substituted" for $Y^3$, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $Y^3$, the "substituents" for $X^1$ described above can be referred to.

For $Q^{71}$, $Y^{A3}$, $Y^{B3}$, $Q^{72}$, $Y^{D3}$, $Y^{E3}$ and $Y^{F3}$, groups described later can be referred to.

$Y^4$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{81})Y^{A4}$, $C(=O)OY^{B4}$, $C(=Q^{82})NY^{D4}Y^{E4}$ or $S(O)_q Y^{F4}$, and preferably mentioned is a lower alkyl group optionally substituted, a higher alkyl group, a lower cycloalkyl group optionally substituted, a lower alkenyl group optionally substituted, a higher alkenyl group, an aromatic hydrocarbon group optionally substituted or a heterocyclic group optionally substituted, and particularly mentioned is a lower alkyl group optionally substituted, a lower cycloalkyl group optionally substituted, a lower alkenyl group optionally substituted, an aromatic hydrocarbon group optionally substituted or a heterocyclic group.

For the above-mentioned "lower alkyl group" in the term "lower alkyl group optionally substituted" for $Y^4$, the "lower alkyl group" described above can be referred to.

For the substituent in the term "lower alkyl group optionally substituted" for $Y^4$, the "substituents" for $X^1$ describe above can be referred to, and preferably mentioned is an aromatic hydrocarbon group optionally substituted, and particularly preferably mentioned is an aromatic hydrocarbon group substituted with at least one halogen.

For the above-mentioned "higher alkyl group" for $Y^4$, the "higher alkyl group" described above can be referred to.

For the above-mentioned "lower cycloalkyl group" in the term "lower cycloalkyl group optionally substituted" for $Y^4$, the "lower cycloalkyl group" described above can be referred to.

For the above-mentioned "lower alkenyl group" in the term "lower alkenyl group optionally substituted" for $Y^4$, the "lower alkenyl group" described above can be referred to.

For the above-mentioned "higher alkenyl group" for $Y^4$, the "higher alkenyl group" described above can be referred to.

For the above-mentioned "lower cycloalkenyl group" in the term "lower cycloalkenyl group optionally substituted" for $Y^4$, the "lower cycloalkenyl group" described above can be referred to.

For the above-mentioned "lower alkynyl group" in the term "lower alkynyl group optionally substituted" for $Y^4$, the "lower alkynyl group" described above can be referred to.

For the above-mentioned "higher alkynyl group" for $Y^4$, the "higher alkynyl group" described above can be referred to.

For the above-mentioned "aromatic hydrocarbon group" in the term "aromatic hydrocarbon group optionally substituted" for $Y^4$, the "aromatic hydrocarbon group" described above can be referred to.

For the substituent in the term "aromatic hydrocarbon group optionally substituted" for $Y^4$, the "substituents" for $X^1$ describe above can be referred to, and preferably mentioned are a halogen, a lower haloalkyl group, a lower alkoxy group and a lower haloalkyloxy group.

For the above-mentioned "heterocyclic group" in the term "heterocyclic group optionally substituted" for $Y^4$, the "heterocyclic group" described above can be referred to.

For the substituent in the terms "lower cycloalkyl group optionally substituted", "lower alkenyl group optionally substituted", "lower cycloalkenyl group optionally substituted", "lower alkynyl group optionally substituted" and "heterocyclic group optionally substituted" for $Y^4$, the "substituents" for $X^1$ describe above can be referred to.

For $Q^{81}$, $Y^{A4}$, $Y^{B4}$, $Q^{82}$, $Y^{D4}$, $Y^{E4}$ and $Y^{F4}$, groups described later can be referred to.

$Y^5$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the above-mentioned "lower alkyl group" in the term "lower alkyl group optionally substituted" for $Y^5$, the "lower alkyl group" described above can be referred to.

For the above-mentioned "higher alkyl group" for $Y^5$, the "higher alkyl group" described above can be referred to.

For the above-mentioned "lower cycloalkyl group" in the term "lower cycloalkyl group optionally substituted" for $Y^5$, the "lower cycloalkyl group" described above can be referred to.

For the above-mentioned "lower alkenyl group" in the term "lower alkenyl group optionally substituted" for $Y^5$, the "lower alkenyl group" described above can be referred to.

For the above-mentioned "higher alkenyl group" for $Y^5$, the "higher alkenyl group" described above can be referred to.

For the above-mentioned "lower cycloalkenyl group" in the term "lower cycloalkenyl group optionally substituted" for $Y^5$, the "lower cycloalkenyl group" described above can be referred to.

For the above-mentioned "lower alkynyl group" in the term "lower alkynyl group optionally substituted" for $Y^5$, the "lower alkynyl group" described above can be referred to.

For the above-mentioned "higher alkynyl group" for $Y^5$, the "higher alkynyl group" described above can be referred to.

For the above-mentioned "aromatic hydrocarbon group" in the term "aromatic hydrocarbon group optionally substituted" for $Y^5$, the "aromatic hydrocarbon group" described above can be referred to.

For the above-mentioned "heterocyclic group" in the term "heterocyclic group optionally substituted" for $Y^5$, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $Y^5$, the "substituent" for $X^1$ described above can be referred to.

$Y^6$s represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OY^{L6}$, $SY^{M6}$ or $NY^{G6}Y^{H6}$, alternatively, represent a ring structure together with the carbon which is bonded with each other.

For the above-mentioned "lower alkyl group" in the term "lower alkyl group optionally substituted" for $Y^6$, the "lower alkyl group" described above can be referred to.

For the above-mentioned "higher alkyl group" for $Y^6$, the "higher alkyl group" described above can be referred to.

For the above-mentioned "lower cycloalkyl group" in the term "lower cycloalkyl group optionally substituted" for $Y^6$, the "lower cycloalkyl group" described above can be referred to.

For the above-mentioned "lower alkenyl group" in the term "lower alkenyl group optionally substituted" for $Y^6$, the "lower alkenyl group" described above can be referred to.

For the above-mentioned "higher alkenyl group" for $Y^6$, the "higher alkenyl group" described above can be referred to.

For the above-mentioned "lower cycloalkenyl group" in the term "lower cycloalkenyl group optionally substituted" for $Y^6$, the "lower cycloalkenyl group" described above can be referred to.

For the above-mentioned "lower alkynyl group" in the term "lower alkynyl group optionally substituted" for $Y^6$, the "lower alkynyl group" described above can be referred to.

For the above-mentioned "higher alkynyl group" for $Y^6$, the "higher alkynyl group" described above can be referred to.

For the above-mentioned "aromatic hydrocarbon group" in the term "aromatic hydrocarbon group optionally substituted" for $Y^6$, the "aromatic hydrocarbon group" described above can be referred to.

For the above-mentioned "heterocyclic group" in the term "heterocyclic group optionally substituted" for $Y^6$, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $Y^6$, the "substituent" for $X^1$ described above can be referred to.

For $Y^{L6}, Y^{M6}, Y^{G6}$ and $Y^{H6}$, groups described below can be referred to.

For the "ring structure" represented by $Y^6$s together with the carbon which is bonded with each other, the same structures as the above-mentioned "ring structure" represented by $X^7$s together with the carbon which is bonded with each other are mentioned.

In the compound (I), Z represents a cyano group, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O^{91})Z^A$, $C(=O)OZ^B$, $C(=O^{92})NZ^DZ^E$, $SO_2Z^F$, $NZ^GZ^H$, $OZ^K$ or $N=C(Z^I)_2$, and preferably mentioned is an aromatic hydrocarbon group optionally substituted, heterocyclic group optionally substituted or $SO_2Z^F$ (wherein, $Z^F$ is an aromatic hydrocarbon group optionally substituted), and particularly preferably mentioned is an aromatic hydrocarbon group optionally substituted, heterocyclic group or $SO_2Z^F$ (wherein, $Z^F$ is an aromatic hydrocarbon group).

For the above-mentioned "lower alkyl group" in the term "lower alkyl group optionally substituted" for Z, the "lower alkyl group" described above can be referred to.

For the above-mentioned "higher alkyl group" for Z, the "higher alkyl group" described above can be referred to.

For the above-mentioned "lower cycloalkyl group" in the term "lower cycloalkyl group optionally substituted" for Z, the "lower cycloalkyl group" described above can be referred to.

For the above-mentioned "lower alkenyl group" in the term "lower alkenyl group optionally substituted" for Z, the "lower alkenyl group" described above can be referred to.

For the above-mentioned "higher alkenyl group" for Z, the "higher alkenyl group" described above can be referred to.

For the above-mentioned "lower cycloalkenyl group" in the term "lower cycloalkenyl group optionally substituted" for Z, the "lower cycloalkenyl group" described above can be referred to.

For the above-mentioned "lower alkynyl group" in the term "lower alkynyl group optionally substituted" for Z, the "lower alkynyl group" described above can be referred to.

For the above-mentioned "higher alkynyl group" for Z, the "higher alkynyl group" described above can be referred to.

For the above-mentioned "aromatic hydrocarbon group" in the term "aromatic hydrocarbon group optionally substituted" for Z, the "aromatic hydrocarbon group" described above can be referred to.

For the substituent in the term "aromatic hydrocarbon group optionally substituted" for Z, the "substituent" for $X^1$ described above can be referred to, and preferably mentioned is a halogen, a nitro group, a cyano group, a hydroxy group, a lower alkyl group, a lower haloalkyl group, a lower alkenyl group, a lower alkoxy group, a lower alkanoyloxy group, an aromatic hydrocarbon group, a heterocyclic group, a lower alkylthio group, a lower alkylsulfinyl group, a lower alkylsulfonyl group or an arylthio group.

For the above-mentioned "heterocyclic group" in the term "heterocyclic group optionally substituted" for Z, the "heterocyclic group" described above can be referred to.

For the substituent in the terms "lower alkyl group optionally substituted", "lower cycloalkyl group optionally substituted", "lower alkenyl group optionally substituted", "lower cycloalkenyl group optionally substituted", "lower alkynyl group optionally substituted" and "heterocyclic group optionally substituted" for Z, the "substituents" for $X^1$ described above can be referred to.

For $Q^{91}, Z^A, Z^B, Q^{92}, Z^D, Z^E, Z^F, Z^G, Z^H, Z^K$ and $Z^I$, groups described later can be referred to.

$X^{A1}, X^{A2}, X^{A3}, X^{A4}, Y^{A1}, Y^{A2}, Y^{A3}, Y^{A4}$ and $Z^A$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the above-mentioned "lower alkyl group" in the term "lower alkyl group optionally substituted" for $X^{A1}, X^{A2}, X^{A3}, X^{A4}, Y^{A1}, Y^{A2}, Y^{A3}, Y^{A4}$ and $Z^A$, the "lower alkyl group" described above can be referred to.

For the above-mentioned "lower cycloalkyl group" in the term "lower cycloalkyl group optionally substituted" for $X^{A1}, X^{A2}, X^{A3}, X^{A4}, Y^{A1}, Y^{A2}, Y^{A3}, Y^{A4}$ and $Z^A$, the "lower cycloalkyl group" described above can be referred to.

For the above-mentioned "lower alkenyl group" in the term "lower alkenyl group optionally substituted" for $X^{A1}, X^{A2}, X^{A3}, X^{A4}, Y^{A1}, Y^{A2}, Y^{A3}, Y^{A4}$ and $Z^A$, the "lower alkenyl group" described above can be referred to.

For the above-mentioned "lower cycloalkenyl group" in the term "lower cycloalkenyl group optionally substituted" for $X^{A}1, X^{A2}, X^{A3}, X^{A4}, Y^{A1}, Y^{A2}, Y^{A3}, Y^{A4}$ and $Z^A$, the "lower cycloalkenyl group" described above can be referred to.

For the above-mentioned "lower alkenyl group" in the term "lower alkynyl group optionally substituted" for $X^{A1}, X^{A2}, X^{A3}, X^{A4}, Y^{A1}, Y^{A2}, Y^{A3}, Y^{A4}$ and $Z^A$, the "lower alkenyl group" described above can be referred to.

For the above-mentioned "aromatic hydrocarbon group" in the term "aromatic hydrocarbon group optionally substituted" for $X^{A1}, X^{A2}, X^{A3}, X^{A4}, Y^{A1}, Y^{A2}, Y^{A3}, Y^{A4}$ and $Z^A$, the "aromatic hydrocarbon group" described above can be referred to.

For the above-mentioned "heterocyclic group" in the term "heterocyclic group optionally substituted" for $X^{A1}, X^{A2}, X^{A3}, X^{A4}, Y^{A1}, Y^{A2}, Y^{A3}, Y^{A4}$ and $Z^A$, the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $X^{A1}, X^{A2}, X^{A3}, X^{A4}, Y^{A1}, Y^{A2}, Y^{A3}, Y^{A4}$ and $Z^A$, the "substituents" for $X^1$ describe above can be referred to.

$X^{B1}, X^{B2}, X^{B3}, X^{B4}, Y^{B1}, Y^{B2}, Y^{B3}, Y^{B4}$ and $Z^B$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted.

For the above-mentioned "lower alkyl group" in the term "lower alkyl group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "lower alkyl group" described above can be referred to.

For the above-mentioned "lower cycloalkyl group" in the term "lower cycloalkyl group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "lower cycloalkyl group" described above can be referred to.

For the above-mentioned "lower alkenyl group" in the term "lower alkenyl group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "lower alkenyl group" described above can be referred to.

For the above-mentioned "lower cycloalkenyl group" in the term "lower cycloalkenyl group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "lower cycloalkenyl group" described above can be referred to.

For the above-mentioned "lower alkenyl group" in the term "lower alkynyl group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "lower alkenyl group" described above can be referred to.

For the above-mentioned "aromatic hydrocarbon group" in the term "aromatic hydrocarbon group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "aromatic hydrocarbon group" described above can be referred to.

For the above-mentioned "heterocyclic group" in the term "heterocyclic group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$, the "substituents" for $X^1$ describe above can be referred to.

The above-mentioned "amino group optionally substituted" for $X^{B1}$, $X^{B2}$, $X^{B3}$, $X^{B4}$, $Y^{B1}$, $Y^{B2}$, $Y^{B3}$, $Y^{B4}$ and $Z^B$ represents a mono or diamino group optionally substituted with a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an acyl group optionally substituted, a carbamoyl group optionally substituted or a group represented by —SO$_2$R (wherein, R represents a lower alkyl group optionally substituted, higher alkyl group, lower cycloalkyl group optionally substituted, lower alkenyl group optionally substituted, higher alkenyl group, lower cycloalkenyl group optionally substituted, lower alkynyl group optionally substituted, higher alkynyl group, or aromatic hydrocarbon group optionally substituted).

For the above-mentioned "lower alkyl group" in the term "lower alkyl group optionally substituted" as a substituent on "amino group optionally substituted", the "lower alkyl group" described above can be referred to.

For the above-mentioned "lower cycloalkyl group" in the term "lower cycloalkyl group optionally substituted" as a substituent on "amino group optionally substituted", the "lower cycloalkyl group" described above can be referred to.

For the above-mentioned "lower alkenyl group" in the term "lower alkenyl group optionally substituted" as a substituent on "amino group optionally substituted", the "lower alkenyl group" described above can be referred to.

For the above-mentioned "lower cycloalkenyl group" in the term "lower cycloalkenyl group optionally substituted" as a substituent on "amino group optionally substituted", the "lower cycloalkenyl group" described above can be referred to.

For the above-mentioned "lower alkenyl group" in the term "lower alkenyl group optionally substituted" as a substituent on "amino group optionally substituted", the "lower alkenyl group" described above can be referred to.

For the above-mentioned "aromatic hydrocarbon group" in the term "aromatic hydrocarbon group optionally substituted" as a substituent on "amino group optionally substituted", the "aromatic hydrocarbon group" described above can be referred to.

For the above-mentioned "heterocyclic group" in the term "heterocyclic group optionally substituted" as a substituent on "amino group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted" as a substituent on "amino group optionally substituted", the "substituents" for $X^1$ describe above can be referred to.

The "substituent" on "acyl group optionally substituted" includes, when this acyl group is a lower alkanoyl group or a lower alkoxy carbonyl group, for example, a lower alkylthio group (e.g., $C_{1-6}$ alkylthio groups such as methylthio, ethylthio, n-propylthio, isopropylthio, isobutylthio and the like), a halogen, a lower alkoxy group, a nitro group, a lower alkoxycarbonyl group, an alkoxyimino group (e.g., $C_{1-6}$ alkoxyimino groups such as methoxyimino, ethoxyimino, n-propoxyimino, tert-butoxyimino, n-hexyloxy-imino and the like), and a hydroxyimino group. The number of substituents is in a substitutable range and 1 to 5, preferably 1 to 3.

When this acyl group is an aroyl group, an aryloxycarbonyl group, an aryl lower alkanoyl group, an aryl lower alkoxycarbonyl group, a 5 to 6-membered heterocyclic carbonyl group or a 5 to 6-membered heterocyclic acetyl group, the "substituent" includes, for example, a lower alkyl group, a lower cycloalkyl group, a lower alkenyl group, a lower cycloalkenyl group, a lower alkynyl group, a lower alkoxy group, an acyl group, a nitro group, an amino group, a hydroxyl group, a cyano group, a sulfamoyl group, a mercapto group, a halogen, a lower alkylthio group (e.g., $C_{1-6}$ alkylthio groups such as methylthio, ethylthio, n-propylthio, isobutylthio and the like) and the like. The number of substituents is in a substitutable range and 1 to 5, preferably 1 to 3.

The "substituent" on "carbamoyl group optionally substituted" includes a lower alkyl group, a lower cycloalkyl group, a lower alkenyl group, a lower cycloalkenyl group, a lower alkynyl group, an aromatic hydrocarbon group, a heterocyclic group and an acyl group.

The "carbamoyl group" is optionally substituted with one or two substituent(s) described above.

$X^{D1}$, $X^{D2}$, $X^{D3}$, $X^{D4}$, $Y^{D1}$, $Y^{D2}$, $Y^{D3}$, $Y^{D4}$ and $Z^D$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or $OG^{a1}$, and $X^{E1}$, $X^{E2}$, $X^{E3}$, $X^{E4}$, $Y^{E1}$, $Y^{E2}$, $Y^{E3}$, $Y^{E4}$ and $Z^E$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted, alternatively, $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ represent a ring structure together with the nitrogen which is bonded with each other.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}$, $X^{B2}$, $X^{B3}$, $X^{B4}$, $Y^{B1}$, $Y^{B2}$, $Y^{B3}$, $Y^{B4}$ and $Z^B$ are mentioned.

The "ring structure" represented by $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$ $Y^{D4}$ and $Y^{E4}$, and $Z^D$ and $Z^E$ together with the nitrogen which is bonded with each other means a 3 to 8-membered heterocyclic group composed of the nitrogen atom as a ring constituent atom, and mentioned are 3 to 8-membered (preferably, 5 to 6-membered) nitrogen-containing heterocyclic groups composed of the nitrogen atom as a ring constituent atom, and optionally having 1 to 3 hetero atoms such as a nitrogen atom optionally oxidized, an oxygen atom, a sulfur atom optionally mono or di-oxidized, and the like such as, for example, 1-aziridinyl, 1-azirinyl, 1-azetyl, 1-azetydinyl, 1-perhydroazepynyl, 1-perhydroazosynyl, 1-pyrrolidinyl, 1-pyrrolinyl, 1-pyrrolyl, 1-pyrazolyl, 1-imidazolyl, 1,2,3-triazol-1- or 2-yl, 1,2,4-triazol-1- or 4-yl, 1H-tetrazol-1-yl, 2H-tetrazol-2-yl, 1-piperidinyl, 4-thiomorpholinyl, 4-morpholinyl, 1-dihydropyridyl, 1-tetrahydropyridyl, 2- or 4-oxodihydropyridin-1-yl, 1-tetrahydropyrimidyl, 1-perhydropyrimidyl, 1-dihydrotriazinyl, 1-tetrahydrotriazinyl, 2-oxodihydrotriazin-1-yl, 1,4-oxazin-4-yl, 1,4-thiazin-4-yl, 1,3-thiazin-3-yl, 1-piperazinyl, 1-perhydropyridazinyl, indol-1-yl, indolin-1-yl, isoindol-2-yl, isoindolin-2-yl, 1H-indazol-1-yl, 2,3-dihydrobenzoxazol-3-yl, 2,3-dihydrobenzothiazol-3-yl, benzotriazol-1-yl, 7-purinyl, 9-carbazoyl and the like; and groups obtained by condensing a benzene ring or 3 to 8-membered (preferably, 5 to 6-membered) heterocyclic group (the heterocyclic group has 1 to 4 nitrogen atom(s) optionally oxidized, oxygen atom(s), or sulfur atom(s) optionally mono or di-oxidized) with the above-mentioned nitrogen-containing heterocyclic group.

The "3 to 8-membered heterocyclic group composed of the nitrogen atom as a ring constituent atom" may be substituted with the same substituent as exemplified for the substituent on "aromatic hydrocarbon group optionally substituted" for $X^1$. The number of the substituent is in a substitutable range and 1 to 5, preferably 1 to 3.

$X^{F1}$, $X^{F2}$, $X^{F3}$, $X^{F4}$, $Y^{F1}$, $Y^{F2}$, $Y^{F3}$, $Y^{F4}$ and $Z^F$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or an amino group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}$, $X^{B2}$, $X^{B3}$, $X^{B4}$, $Y^{B1}$, $Y^{B2}$, $Y^{B3}$, $Y^{B4}$ and $Z^B$ are mentioned.

$X^{G1}$, $X^{G2}$, $X^{G7}$, $Y^{G2}$, $Y^{G6}$ and $Z^G$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{G1})G^{A1}$, $C(=O)OQ^{B1}$, $C(=Q^{G2})NG^{D1}G^{E1}$ or $SO_2G^{F1}$, and $X^{H1}$, $X^{H2}$, $X^{H7}$, $Y^{H2}$, $Y^{H6}$ and $Z^H$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted, alternatively, $X^{G1}$ and $X^{H1}$, $X^{G2}$ and $X^{H2}$, $X^{G7}$ and $X^{H7}$, $Y^{G2}$ and $Y^{H2}$, $Y^{G6}$ and $Y^{H6}$, and $Z^G$ and $Z^H$ represent a ring structure together with the nitrogen which is bonded with each other.

For $Q^{G1}$, $G^{A1}$, $G^{B1}$, $Q^{G2}$, $G^{D1}$, $G^{E1}$ or $G^{F1}$, descriptions below can be referred to.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

For the "ring structure" represented by $X^{G1}$ and $X^{H1}$, $X^{G2}$ and $X^{H2}$, $X^{G7}$ and $X^{H7}$, $Y^{G2}$ and $Y^{H2}$, $Y^{G6}$ and $Y^{H6}$ and $Z^G$ and $Z^H$ together with the nitrogen which is bonded with each other, the same structures as the above-mentioned "ring structure" represented by $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ together with the nitrogen which is bonded with each other are mentioned.

$X^{I1}$, $X^{I2}$, $Y^{I1}$, $Y^{I2}$ and $Z^I$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OG^{a2}$, $SG^{a3}$, or $NG^{G1}G^{H1}$, alternatively, represent a ring structure together with the carbon which is bonded with each other.

For $G^{a2}$, $G^{a3}$, $G^{G1}$ and $G^{H1}$, descriptions below can be referred to.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

For the "ring structure" represented by $X^{I1}$, $X^{I2}$, $Y^{I1}$, $Y^{I2}$ and $Z^I$ together with the carbon which is bonded with each other, the same structures as the above-mentioned "ring structure" represented by $X^7$s together with the carbon which is bonded with each other are mentioned.

$X^{K2}$, $Y^{K2}$ and $Z^K$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{K1})G^{A2}$, $C(=O)OG^{B2}$, $C(=Q^{K2})NG^{D2}G^{E2}$ or $SO_2G^{F2}$.

For $Q^{K1}$, $G^{A2}$, $G^{B2}$, $Q^{K2}$, $G^{D2}$, $G^{E2}$ or $G^{F2}$, descriptions below can be referred to.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

$X^{L7}$, $X^{M7}$, $Y^{L6}$ and $Y^{M6}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkenyl group optionally substituted", the "lower alkenyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

$G^{a1}$, $G^{a2}$ and $G^{a3}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkenyl group" in the term "lower alkynyl group optionally substituted", the "lower alkenyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

$G^{A1}$ and $G^{A2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkenyl group" in the term "lower alkynyl group optionally substituted", the "lower alkenyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

$G^{B1}$ and $G^{B2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkenyl group" in the term "lower alkynyl group optionally substituted", the "lower alkenyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}, X^{B2}, X^{B3}, X^{B4}, Y^{B1}, Y^{B2}, Y^{B3}, Y^{B4}$ and $Z^B$ are mentioned.

$G^{D1}$ and $G^{D2}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or $OG^{d1}$, and $G^{E1}$ and $G^{E2}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, or a heterocyclic group optionally substituted, alternatively, $G^{D1}$ and $G^{E1}$, and $G^{D2}$ and $G^{E2}$ represent a ring structure together with the nitrogen which is bonded with each other.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", the "substituents" for $X^1$ described above can be referred to.

As the "amino group optionally substituted", the same "amino groups optionally substituted" as exemplified for $X^{B1}, X^{B2}, X^{B3}, X^{B4}, Y^{B1}, Y^{B2}, Y^{B3}, Y^{B4}$ and $Z^B$ are mentioned.

For the "ring structure" represented by $G^{D1}$ and $G^{E1}$, and $G^{D2}$ and $G^{E2}$ together with the nitrogen which is bonded with each other, the same structures as the above-mentioned "ring structure" formed by $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ together with the nitrogen which is bonded with each other are mentioned.

$G^{F1}$ and $G^{F2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or an amino group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}$, $X^{B2}$, $X^{B3}$, $X^{B4}$, $Y^{B1}$, $Y^{B2}$, $Y^{B3}$, $Y^{B4}$ and $Z^B$ are mentioned.

$G^{G1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{Ga})G^{A1-1}$, $C(=O)OG^{B1-1}$, $C(=Q^{Gb})NG^{D1-1}G^{E1-1}$ or $SO_2G^{F1-1}$, and $G^{H1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{G1}$ and $G^{H1}$ represent a ring structure together with the nitrogen which is bonded with each other.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

For the "ring structure" represented by $G^{G1}$ and $G^{H1}$ together with the nitrogen which is bonded with each other, the same structures as the above-mentioned "ring structure" represented by $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ together with the nitrogen which is bonded with each other are mentioned.

For $Q^{Ga}$, $G^{A1-1}$, $G^{B1-1}$, $Q^{Gb}$, $G^{D1-1}$, $G^{E1-1}$ and $G^{F1-1}$, descriptions below can be referred to.

$G^{A1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

$G^{A1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

$G^{B1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}, X^{B2}, X^{B3}, X^{B4}, Y^{B1}, Y^{B2}, Y^{B3}, Y^{B4}$ and $Z^B$ are mentioned.

$G^{D1-1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or OL, and $G^{E1-1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{D1-1}$ and $G^{E1-1}$ represent a ring structure together with the nitrogen which is bonded with each other.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}, X^{B2}, X^{B3}, X^{B4}, Y^{B1}, Y^{B2}, Y^{B3}, Y^{B4}$ and $Z^B$ are mentioned.

For the "ring structure" represented by $G^{D1-1}$ and $G^{E1-1}$ together with the nitrogen which is bonded with each other, the same structures as the above-mentioned "ring structure" represented by $X^{D1}$ and $X^{E1}$, $X^{D2}$ and $X^{E2}$, $X^{D3}$ and $X^{E3}$, $X^{D4}$ and $X^{E4}$, $Y^{D1}$ and $Y^{E1}$, $Y^{D2}$ and $Y^{E2}$, $Y^{D3}$ and $Y^{E3}$, $Y^{D4}$ and $Y^{E4}$, and $Z^D$ and $Z^E$ together with the nitrogen which is bonded with each other are mentioned.

$G^{F1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

As the "amino group optionally substituted", the same "amino groups optionally substituted" as exemplified for $X^{B1}, X^{B2}, X^{B3}, X^{B4}, Y^{B1}, Y^{B2}, Y^{B3}, Y^{B4}$ and $Z^B$ are mentioned.

L represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted.

For the "lower alkyl group" in the term "lower alkyl group optionally substituted", the "lower alkyl group" described above can be referred to.

For the "lower cycloalkyl group" in the term "lower cycloalkyl group optionally substituted", the "lower cycloalkyl group" described above can be referred to.

For the "lower alkenyl group" in the term "lower alkenyl group optionally substituted", the "lower alkenyl group" described above can be referred to.

For the "lower cycloalkenyl group" in the term "lower cycloalkenyl group optionally substituted", the "lower cycloalkenyl group" described above can be referred to.

For the "lower alkynyl group" in the term "lower alkynyl group optionally substituted", the "lower alkynyl group" described above can be referred to.

For the "aromatic hydrocarbon group" in the term "aromatic hydrocarbon group optionally substituted", the "aromatic hydrocarbon group" described above can be referred to.

For the "heterocyclic group" in the term "heterocyclic group optionally substituted", the "heterocyclic group" described above can be referred to.

For the "substituent" in the terms "lower alkyl group optionally substituted", "lower cycloalkyl group optionally substituted", "lower alkenyl group optionally substituted", "lower cycloalkenyl group optionally substituted", "lower alkynyl group optionally substituted", "aromatic hydrocarbon group optionally substituted" and "heterocyclic group optionally substituted", the "substituents" for $X^1$ described above can be referred to.

$Q^{11}, Q^{12}, Q^{21}, Q^{22}, Q^{31}, Q^{32}, Q^{41}, Q^{42}, Q^{51}, Q^{52}, Q^{61}, Q^{62}, Q^{71}, Q^{72}, Q^{81}, Q^{82}, Q^{91}, Q^{92}, Q^{G1}, Q^{G2}, Q^{K1}, Q^{K2}, Q^{Ga}$ and $Q^{Gb}$ represent each independently an oxygen atom or a sulfur atom.

m represents an integer of 1 or 2, and n, p and q represent each independently an integer of 0 or 2.

The compound (I) can be produced, for example, by the following Production Methods 1 to 7.

Production Method 1

The compound (I) can be produced by reacting a compound represented by the formula (II):

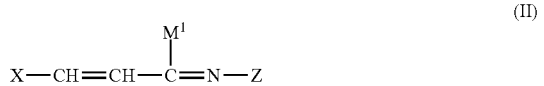

(wherein, $M^1$ represents a leaving group, and other symbols are as defined above) with a compound represented by the formula (III):

(symbols in the formula are as defined above).

As the leaving group represented by $M^1$, for example, halogens, acyloxy groups ($C_{1-10}$ acyloxy groups such as $C_{1-6}$ alkylcarbonyloxy groups optionally substituted with 1 to 3 halogen(s) such as a formyloxy group, acetoxy group, propionyloxy group, trifluoroacetoxy group and the like; $C_{7-9}$ benzoyloxy groups optionally substituted with at least one lower alkyl group such as a benzoyloxy group, 4-methylbenzoyloxy group and the like; $C_{1-6}$ alkoxycarbonyloxy groups such as methoxycarbonyloxy, t-butoxycarbonyloxy and the like) or groups represented by the formula: $R^P SO_r$ (wherein, $R^P$ represents a lower alkyl group or a phenyl optionally substituted with at least one lower alkyl group, and r is an integer of 0, 1 or 2) and the like can be used.

In this reaction, the amount of the compound represented by the above-mentioned formula (III) is not particularly restricted, and may be used in large excess amount as a solvent, and preferably, it is about 0.8 to 5 equivalents for the compound represented by the formula (II).

A good result may be obtained in some cases by presence of a base or action of a base before or after the reaction, for the purpose of promoting the reaction and reducing by-products. As such a base, there can be used alcoholates of alkali metals such as, for example, sodium ethylate, sodium methylate, potassium tert-butoxide and the like; organic bases such as, for example, triethylamine, diisopropylethylamine, pyridine, 4-dimethylaminopyridine, N,N-dimethylaniline and the like; inorganic bases such as, for example, potassium carbonate, sodium carbonate, sodium hydroxide, potassium hydroxide, sodium hydrogen carbonate, potassium hydrogen carbonate and the like; metal hydrides such as, for example, lithium hydride, sodium hydride, potassium hydride and the like; or organic lithium reagents such as, for example, butyllithium, lithium diisopropylamide and the like. The amount of the base to be used is not particularly restricted providing it does not adversely affect the reaction, and it can also be used in large excess amount for acting as a solvent simultaneously.

In this reaction, a salt of a compound represented by the formula (III) and a base, previously prepared, can also be used. As such a salt, alkali metal salts of lithium, sodium and potassium, and alkaline earth metal salts of magnesium and calcium are suitable, among others. The amount of the salt is not particularly restricted and the salt may be used in large excess amount, and preferably, it is about 0.8 to 5 equivalents for the compound represented by the formula (II).

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof, water, further, mixed solvents of these compounds with water.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, concentration, concentration under reduced pressure, liquid nature conversion, transference dissolution, solvent extraction, distillation, crystallization, re-crystallization, chromatography and the like.

Production Method 2

The compound (I) can be produced by reacting a compound represented by the formula (IV):

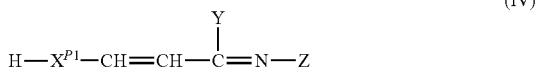
(IV)

(wherein, $X^{P1}$ represents O, S, NH or $NX^2$, and other symbols are as defined above) with a compound represented by the formula (V):

$$X^{P2}\text{-}M^2 \quad (V)$$

(wherein, $X^{P2}$ represents $X^1$, $X^3$ or $X^4$, $M^2$ represents a leaving group).

As the leaving group represented by $M^2$, for example, halogens, acyloxy groups ($C_{1-10}$ acyloxy groups such as $C_{1-6}$ alkylcarbonyloxy groups optionally substituted with 1 to 3 halogen(s) such as a formyloxy group, acetoxy group, propionyloxy group, trifluoro acetoxy group and the like; $C_{7-9}$ benzoyloxy groups optionally substituted with at least one alkyl group such as a benzoyloxy group, 4-methylbenzoyloxy group and the like; $C_{1-6}$ alkoxycarbonyloxy groups such as methoxycarbonyloxy, t-butoxycarbonyloxy and the like) or groups represented by the formula: $R^P SO_r$ (wherein, $R^P$ represents a lower alkyl group or a phenyl optionally substituted with at least one lower alkyl group, and r is an integer of 0, 1 or 2) and the like can be used.

In this reaction, the amount of the compound represented by the above-mentioned formula (V) is not particularly restricted, and may be used in large excess amount as a solvent, and preferably, it is about 0.8 to 5 equivalents for the compound represented by the formula (IV).

A good result may be obtained in some cases by presence of a base or action of a base before or after the reaction, for the purpose of promoting the reaction and reducing by-products. As such a base, there can be used alcoholates of alkali metals such as, for example, sodium ethylate, sodium methylate, potassium tert-butoxide and the like; organic bases such as, for example, triethylamine, diisopropylethylamine, pyridine, 4-dimethylaminopyridine, N,N-dimethylaniline and the like; inorganic bases such as, for example, potassium carbonate, sodium carbonate, sodium hydroxide, potassium hydroxide, sodium hydrogen carbonate, potassium hydrogen carbonate and the like; metal hydrides such as, for example, lithium hydride, sodium hydride, potassium hydride and the like; or organic lithium reagents such as, for example, butyllithium, lithium diisopropylamide and the like. The amount of the base to be used is not particularly restricted providing it does not adversely affect the reaction, and it can also be used in large excess amount for acting as a solvent simultaneously.

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof, water, further, mixed solvents of these compounds with water.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, concentration, concentration under reduced pressure, liquid nature conversion, transference dissolution, solvent extraction, distillation, crystallization, re-crystallization, chromatography and the like.

Production Method 3

The compound (I) can be produced by reacting a compound represented by the formula (VI):

(VI)

(wherein, symbols are as defined above) with a compound represented by the formula (VII):

$$X\text{—}H \quad (VII)$$

(wherein, symbols are as defined above).

In this reaction, the amount of the compound represented by the above-mentioned formula (VII) is not particularly restricted, and may be used in large excess amount as a solvent, and preferably, it is about 0.8 to 5 equivalents for the compound represented by the formula (IV).

A good result may be obtained in some cases by presence of a base or action of a base before or after the reaction, for the purpose of promoting the reaction and reducing by-products. As such a base, there can be used alcoholates of alkali metals such as, for example, sodium ethylate, sodium methylate, potassium tert-butoxide and the like; organic bases such as, for example, triethylamine, diisopropylethylamine, pyridine, 4-dimethylaminopyridine, N,N-dimethylaniline and the like; inorganic bases such as, for example, potassium carbonate, sodium carbonate, sodium hydroxide, potassium hydroxide, sodium hydrogen carbonate, potassium hydrogen carbonate and the like; metal hydrides such as, for example, lithium hydride, sodium hydride, potassium hydride and the like; or organic lithium reagents such as, for example, butyllithium, lithium diisopropylamide and the like. The amount of the base to be used is not particularly restricted providing it does not adversely affect the reaction, and it can also be used in large excess amount for acting as a solvent simultaneously.

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof, water, further, mixed solvents of these compounds with water.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, concentration, concentration under reduced pressure, liquid nature conversion, transference dissolution, solvent extraction, distillation, crystallization, re-crystallization, chromatography and the like.

Production Method 4

The compound (I) can be produced by hydrogenating a compound represented by the formula (IIX):

(IIX)

(wherein, symbols are as defined above). As the hydrogenating reagent, a hydrogen gas, formic acid, hydride reagents (e.g., sodium borohydride, potassium borohydride, sodium cyanoborohydride and the like) can be used.

In this reaction, the amount of the above-mentioned hydrogenating reagent is not particularly restricted, and may be used in large excess amount, and preferably, it is about 0.8 to 5 equivalents.

A good result may be obtained in some cases by using a catalyst, for the purpose of promoting the reaction and reducing by-products. As such a catalyst, for example, transition metal catalysts such as palladium-carbon, palladium-barium sulfate, Lindlar catalyst (palladium-calcium carbonate (lead poisoning)), platinum-carbon, platinum oxide and the like can be used. The amount of the catalyst to be used is not particularly restricted providing it does not adversely affect the reaction, and preferably, it is 0.001 to 0.1 wt % for the compound represented by the formula (IIX).

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof, water, further, mixed solvents of these compounds with water.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, concentration, concentration under reduced pressure, liquid nature conversion, transference dissolution, solvent extraction, distillation, crystallization, re-crystallization, chromatography and the like.

Production Method 5

The compound (I) can be produced by reacting a compound represented by the formula (IX):

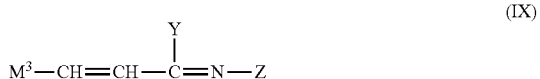

(IX)

(wherein, $M^3$ represents a leaving group, and other symbols are as defined above) with a compound represented by the formula (VII):

(VII)

(symbols in the formula are as defined above).

As the leaving group represented by $M^3$, for example, halogens, acyloxy groups ($C_{1-10}$ acyloxy groups such as $C_{1-6}$ alkylcarbonyloxy groups optionally substituted with 1 to 3 halogen(s) such as a formyloxy group, acetoxy group, propionyloxy group, trifluoroacetoxy group and the like; $C_{7-9}$ benzoyloxy groups optionally substituted with at least one lower alkyl group such as a benzoyloxy group, 4-methylbenzoyloxy group and the like; $C_{1-6}$ alkoxycarbonyloxy groups such as methoxycarbonyloxy, t-butoxycarbonyloxy and the like), lower alkoxy groups ($C_{1-6}$ alkoxy groups such as methoxy group, ethoxy group, propoxy group and the like), aryloxy groups ($C_{6-10}$ aryloxy groups optionally substituted with at least one lower alkyl group such as a phenoxy, group, 4-methylphenoxy group, 2-naphthoxy group and the like), di-lower alkylamino groups (di-$C_{1-6}$ alkylamino groups such as a dimethylamino group, diethylamino group and the like) or groups represented by the formula: $R^P SO_r$ (wherein, $R^P$ represents a lower alkyl group or a phenyl optionally substituted with at least one lower alkyl group, and r is an integer of 0, 1 or 2) and the like can be used.

In this reaction, the amount of the compound represented by the above-mentioned formula (VII) is not particularly restricted, and may be used in large excess amount as a solvent, and preferably, it is about 0.8 to 5 equivalents for the compound represented by the formula (IX).

A good result may be obtained in some cases by presence of a base or action of a base before or after the reaction, for the purpose of promoting the reaction and reducing by-products. As such a base, there can be used alcoholates of alkali metals such as, for example, sodium ethylate, sodium methylate, potassium tert-butoxide and the like; organic bases such as, for example, triethylamine, diisopropylethylamine, pyridine, 4-dimethylaminopyridine, N,N-dimethylaniline and the like; inorganic bases such as, for example, potassium carbonate, sodium carbonate, sodium hydroxide, potassium hydroxide, sodium hydrogen carbonate, potassium hydrogen carbonate and the like; metal hydrides such as, for example, lithium hydride, sodium hydride, potassium hydride and the like; or organic lithium reagents such as, for example, butyllithium, lithium diisopropylamide and the like. The amount of the base to be used is not particularly restricted providing it does not adversely affect the reaction, and it can also be used in large excess amount for acting as a solvent simultaneously.

In this reaction, a salt of a compound represented by the formula (VII) and a base, previously prepared, can also be used. Alkali metal salts of lithium, sodium and potassium, and alkaline earth metal salts of magnesium and calcium are suitable, among others. The amount of the salt is not particularly restricted and the salt may be used in large excess amount, and preferably, it is about 0.8 to 5 equivalents for the compound represented by the formula (IX).

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof, water, further, mixed solvents of these compounds with water.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, concentration, concentration under reduced pressure, liquid nature conversion, transference dissolution, solvent extraction, distillation, crystallization, re-crystallization, chromatography and the like, and after separation and/or purification.

Production Method 6

The compound (I) can be produced by reacting a compound represented by the formula (X):

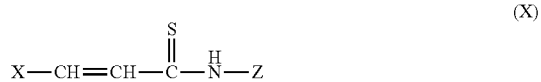

(X)

(wherein, symbols are as defined above) with a compound represented by the formula (XI):

(XI)

(wherein, $Y^{P1}$ represents an alkyl group optionally substituted, alkenyl group optionally substituted or alkynyl group optionally substituted, $M^4$ represents a leaving group and other symbols are as defined above).

As the leaving group represented by $M^4$, for example, halogens, acyloxy groups ($C_{1-10}$ acyloxy groups such as $C_{1-6}$ alkylcarbonyloxy groups optionally substituted with 1 to 3 halogen(s) such as a formyloxy group, acetoxy group, propionyloxy group, trifluoro acetoxy group and the like; $C_{7-9}$ benzoyloxy groups optionally substituted with at least one alkyl group such as a benzoyloxy group, 4-methylbenzoyloxy group and the like; $C_{1-6}$ alkoxycarbonyloxy groups such as methoxycarbonyloxy, t-butoxycarbonyloxy and the like) or groups represented by the formula: $R^P SO_r$ (wherein, $R^P$ represents a lower alkyl group or a phenyl optionally substituted with at least one lower alkyl group, and r is an integer of 0, 1 or 2) and the like can be used.

In this reaction, the amount of the compound represented by the above-mentioned formula (XI) is not particularly restricted, and may be used in large excess amount as a solvent, and preferably, it is about 0.8 to 5 equivalents for the compound represented by the formula (X).

A good result may be obtained in some cases by presence of a base or action of a base before or after the reaction, for the purpose of promoting the reaction and reducing by-products. As such a base, there can be used alcoholates of alkali metals such as, for example, sodium ethylate, sodium methylate, potassium tert-butoxide and the like; organic bases such as, for example, triethylamine, diisopropylethylamine, pyridine, 4-dimethylaminopyridine, N,N-dimethylaniline and the like; inorganic bases such as, for example, potassium carbonate, sodium carbonate, sodium hydroxide, potassium hydroxide, sodium hydrogen carbonate, potassium hydrogen carbonate and the like; metal hydrides such as, for example, lithium hydride, sodium hydride, potassium hydride and the like; or organic lithium reagents such as, for example, butyllithium, lithium diisopropylamide and the like. The amount of the base to be used is not particularly restricted providing it does not adversely affect the reaction, and it can also be used in large excess amount for acting as a solvent simultaneously.

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof, water, further, mixed solvents of these compounds with water.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, pulverization, concentration, concentration under reduced pressure, liquid nature conversion, transference dissolution, solvent extraction, distillation, crystallization, re-deposition, re-crystallization, chromatography, high performance liquid chromatography (HPLC), demineralized resin column chromatography and the like.

Production Method 7

The compound (I) can be produced by reacting a compound represented by the formula (XII):

(wherein, symbols are as defined above) with a compound represented by the formula (XIII):

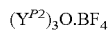

(wherein, $Y^{P2}$ represents an alkyl group optionally substituted, alkenyl group optionally substituted or alkynyl group optionally substituted).

In this reaction, the amount of the compound represented by the above-mentioned formula (XIII) is not particularly restricted, and may be used in large excess amount as a solvent, and preferably, it is about 0.8 to 5 equivalents for the compound represented by the formula (XII).

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, and mixed solvents thereof.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, pulverization, concentration, concentration under reduced pressure, liquid nature conversion, transference dissolution, solvent extraction, distillation, crystallization, re-deposition, re-crystallization, chromatography, high performance liquid chromatography (HPLC), demineralized resin column chromatography and the like.

The compound produced by the above-mentioned production methods can also be further subjected to methods known per se, for example, alkylation, alkenylation, alkynylation, acylation, amination, sulfidation, sulfinylation, sulfonation, oxidation, reduction, halogenation, nitration, cross coupling reaction and the like to convert its substituent into other desired substituent.

The compound obtained by the above-mentioned production methods can be separated and/or purified by conventional methods, for example, pulverization, concentration, concentration under reduced pressure, liquid nature conversion, transference dissolution, solvent extraction, distillation, crystallization, re-deposition, re-crystallization, chromatography, high performance liquid chromatography (HPLC), demineralized resin column chromatography and the like.

Reference Production Method

A method for producing a compound to be used for production of the compound (I) will be described below.

A compound (II) wherein $M^1$ represents a halogen atom can be obtained by reacting a compound represented by the formula (XIV):

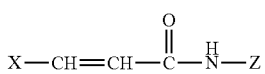

with a halogenating agent.

As the halogenating agent which can be used in this reaction, thionyl chloride, sulfuryl chloride, phosphorus oxychloride, phosphorus pentachloride, carbon tetrachloride, carbon tetrabromide and the like are mentioned.

In this reaction, the amount of the above-mentioned halogenating reagent is not particularly restricted, and may be used in large excess amount as a solvent, and preferably, it is about 0.8 to 5 equivalents for the compound represented by the formula (XIV).

A good result may be obtained in some cases by presence of a base or action of a base before or after the reaction, for the purpose of promoting the reaction and reducing by-products. As such a base, there can be used organic bases such as, for example, triethylamine, diisopropylethylamine, pyridine, 4-dimethylaminopyridine, N,N-dimethylaniline and the like; metal hydrides such as, for example, lithium hydride, sodium hydride, potassium hydride and the like; organic lithium reagents such as, for example, butyllithium, lithium diisopropylamide and the like; or phosphorus compounds such as, for example, triphenylphosphine and the like. The amount of the base to be used is not particularly restricted providing it does not adversely affect the reaction, and it can also be used in large excess amount for acting as a solvent simultaneously.

This reaction can be carried out using a suitable solvent. Such a solvent is not particularly restricted providing it does not react with a reaction substrate, reaction reagent and product to give a by-product, and those dissolving both the reaction substrate and the reaction reagent are desirable. Used as such a solvent are, for example, aliphatic hydrocarbons such as pentane, hexane, heptane, petroleum ether and the like, aromatic hydrocarbons such as benzene, toluene, xylene and the like, esters such as methyl acetate, ethyl acetate, ethyl formate, ethyl propionate and the like, ketones such as acetone, methyl ethyl ketone and the like, ethers such as diethyl ether, dipropyl ether, diisopropyl ether, dibutyl ether, tetrahydrofuran, dioxane and the like, nitriles such as acetonitrile, propionitrile and the like, acid amides such as dimethylformamide, dimethylacetamide and the like, sulfoxides such as dimethyl sulfoxide and the like, sulfones such as sulfolane and the like, phosphoric amides such as hexamethylphosphoramide and the like, halogenated hydrocarbons such as dichloromethane, chloroform, 1,2-dichloroethane, carbon tetrachloride and the like, aromatic amines such as pyridine, picoline, lutidine, quinoline and the like, and mixed solvents thereof.

The reaction temperature is usually about −50 to 200° C., preferably about −30 to 150° C. The reaction time is generally about 0.1 to 96 hours, preferably 0.1 to 72 hours, more preferably about 0.1 to 24 hours.

The resultant compound can be separated and/or purified by means known per se, for example, filtration, pulverization, concentration, concentration under reduced pressure, transference dissolution, solvent extraction, distillation, crystallization, re-deposition, re-crystallization and the like, and after separation and/or purification, alternatively as the reaction mixture itself, may be used as a raw material for the subsequent reaction. The compound as a starting substance in this reaction is a known compound or can be produce by known methods (Chem. Pharm. Bull. 48, P1854, 2000, and the like).

The compound represented by the formula (III) belongs to, for example, thiols, alcohols, phenols, primary or secondary amines, and these are known compounds or can be produced by known methods.

The compound represented by the formula (VI) is a known compound or can be produced by known methods (Chem. Lett. P1261, 1989, Chem. Berichte 109, P1643, 1976, and the like).

The compound represented by the formula (VII) belongs to, for example, thiols, alcohols, phenols, primary or secondary amines, and these are known compounds or can be produced by known methods.

The compound represented by the formula (IIX) is a known compound or can be produced by known methods (Chem. Lett. P1261, 1989, and the like).

The compounds to be produced by the above-mentioned Production Methods 1 to 7 and Reference Production Method can also be further subjected to methods known per se, for example, alkylation, alkenylation, alkynylation, arylation, hetero arylation, acylation, amination, sulfidation, sulfinylation, sulfonation, oxidation, reduction, halogenation, nitration and the like to convert its substituent into other desired substituent.

The compounds to be obtained by the above-mentioned Production Methods 1 to 7 and Reference Production Method can be separated and/or purified by conventional methods, for example, pulverization, concentration, concentration under reduced pressure, liquid nature conversion, transference dissolution, solvent extraction, distillation, crystallization, re-deposition, re-crystallization, chromatography, high performance liquid chromatography (HPLC), demineralized resin column chromatography and the like.

The compounds to be obtained by the above-mentioned Production Methods 1 to 7 and Reference Production Method can also be obtained in the form of hydrate, and hydrates thereof are also included in the range of the present invention.

Regarding the compound (I), an acidic group such as a sulfonyl group, carboxyl group in a substituent in the molecule can form an pesticidally acceptable base salt of an inorganic base, organic base and the like, and a basic group such as a basic nitrogen atom in the molecule, an amino group in the substituent, and the like can form an pesticidally acceptable acid-addition salt of an inorganic acid, organic acid and the like.

The inorganic base salts include, for example, salts of alkali metals (sodium, potassium and the like), alkaline earth metals (calcium and the like) and ammonia, and the organic base salts include, for example, salts with dimethylamine, triethylamine, N,N-dimethylaniline, piperazine, pyrrolidine, piperidine, pyridine, 2-phenylethylamine, benzylamine, ethanolamine, diethanolamine, 1,8-diazabicyclo[5.4.0]undecene (hereinafter, abbreviated as DBU), and the like.

The inorganic acid-addition salts include, for example, salts with hydrochloric acid, hydrobromic acid, hydroiodic acid, sulfuric acid, nitric acid, phosphoric acid and perchloric acid, and the organic acid-addition salts include, for example, salts with formic acid, acetic acid, propionic acid, oxalic acid, succinic acid, benzoic acid, p-toluenesulfonic acid, methanesulfonic acid and trifluoroacetic acid, and the like.

Each of the compounds (I) may contain steric isomers such as optical isomers based on one or more asymmetric carbon atom(s) and geometric isomers based on one or more double bond(s), and the like. Such isomers and mixtures thereof are also entirely included in the range of the present invention.

The compounds (I) can include isomers such as tautomers, geometric isomers, steric isomers and the like, and in the present invention, these isomers and mixtures thereof are all included in the formula (I).

Some of the compounds (I) are in the form of solvate (for example, hydrate and the like), and these forms are also included in the range of the present invention.

Some of the compounds (I) are in the form of crystal and/or amorphous substance, and these forms are also included in the range of the present invention.

In the present invention, some of the compounds are in the form of pro-drug, and these forms are also included in the range of the present invention.

The compound (I) is effective for controlling a hygiene pest and an animal and plant parasitic pest, and exhibits a strong insecticidal activity by treating an animal and a plant which are parasitized by a pest. In addition, the compound (I) have little phytotoxic effects on a plant, and have little toxicity to fishes and, thus, have both safe and advantageous nature as an agent for controlling pests for hygiene, the livestock industry, pets, horticulture and agriculture.

When the compound (I) is used as a pesticide, in particular, as an insecticide, the compound is used in a form which general pesticides and veterinary drugs can take, that is, a dosage form such as an emulsion, a solution, a microemulsion, a flowable formulation, an oil solution, a wettable powder, a powder, a granule, a fine granule, a seed coating agent, a smoking agent, a tablet, a microcapsule, a spray formulation, an aerosol, a carbon dioxide formulation, a heat fumigate formulation such as mosquito coil, electric mosquito tablet and electric insecticidal solution, an EW agent, an ointment, a poison bait, a capsule, a pellet, an injectable, a resinous formulation, a shampoo preparation and the like, by dissolving or dispersing one kind or two kinds or more (preferably, one kind or more, and not more than three kinds) of the compound (I) or a salt thereof as an active ingredient in a suitable liquid carrier, or mixing with or being adsorbed on a suitable solid carrier depending on a use purpose. To these preparations, if needed, an emulsifying agent, a suspending agent, a developer, a penetrant, a wetting agent, a thickener, a stabilizer or the like may be added, and they can be prepared by a method known per se. Namely, the pesticidal composition of the present invention comprises the compound (I) or a salt thereof as an active ingredient and an inert carrier.

As a liquid carrier (solvent) to be used, for example, solvents such as water, alcohols (e.g. methyl alcohol, ethyl alcohol, n-propyl alcohol, isopropyl alcohol, benzyl alcohol, ethylene glycol etc.), ketones (e.g. acetone, methyl ethyl ketone, methyl isobutyl ketone, cyclohexanone etc.), ethers (e.g. tetrahydrofuran, ethylene glycol monomethyl ether, diethylene glycol monomethyl ether, diethylene glycol mono ethyl ether, propylene glycol monomethyl ether etc,), aliphatic hydrocarbons (e.g. kerosine, kerosene, fuel oil, machine oil etc.), aromatic hydrocarbons (e.g. toluene, xylene, solvent naphtha, methylnaphthalene etc.), halogenated hydrocarbons (e.g. dichloromethane, chloroform, carbon tetrachloride etc.), acid amides (e.g. N,N-dimethylformamide, N,N-dimethylacetamide, N-methylpyrrolidone etc.), esters (e.g. ethyl acetate, butyl acetate, fatty acid glycerin ester, γ-butyrolactone etc.), nitriles (e.g. acetonitrile, propionitrile etc.), carbonates (e.g.

propylene carbonate etc.), vegetable oils (e.g. rapeseed oil, cotton seed oil etc.), and the like are suitable. These can be appropriately used by mixing one kind or two kinds or more (preferably one kind or more, and not more than three kinds) at a suitable ratio.

As a solid carrier (diluent, bulking agent), a vegetable powder (e.g. soybean powder, tobacco powder, wheat powder, wood meal etc.), a mineral powder (e.g. clays such as kaolin, bentonite, acid clay etc., talcs such as talc powder, agalmatolite powder etc., silicas such as diatomaceous earth, mica powder etc.), alumina, a sulfur powder, an active carbon, calcium carbonate, potassium chloride, ammonium sulfate, sodium hydrogen carbonate, lactose, urea and the like are used, and these can be appropriately used by mixing one kind or two kinds or more (preferably one kind or more, and not more than three kinds) at a suitable ratio.

As a gaseous carrier, for example, fluorocarbon, butane gas, LPG (liquid petroleum gas), dimethyl ether, carbon dioxide and the like is used and these can be appropriately used by mixing one kind or two kinds at a suitable ratio.

In addition, as an ointment base materials, for example, one kind or two kinds or more (preferably, one kind or more, and not more than three kinds) of materials selected from the group consisting of polyethylene glycol, pectin, polyhydric alcohol ester of higher fatty acid such as monostearic acid glycerin ester and the like, cellulose derivative such as methylcellulose and the like, sodium alginate, bentonite, higher alcohol, polyhydric alcohol such as glycerin and the like, vaseline, white vaseline, liquid paraffin, lard, various vegetable oils, lanolin, dehydrated lanolin, hardened oil, resins and the like, or these materials wherein following various surfactants are added thereto are appropriately used.

As a surfactant used as an emulsifying agent, a developer, a penetrant, a dispersant and the like, depending on the necessity, nonionic and anionic surfactants such as soaps, polyoxyethylene alkyl aryl ethers [e.g. Neugen (trade name), E•A142 (trade name); manufactured by Dai-ichi Kogyo Seiyaku Co., Ltd., Nonal (trade name); manufactured by Toho Chemical Industries Co., Ltd.], alkyl sulfate salts [e.g. Emar 10 (trade name), Emar 40 (trade name); manufactured by Kao Corporation], alkylbenzene sulfonic acid salts [e.g. Neogen (trade name), Neogen T(trade name); manufactured by Dai-ichi Kogyo Seiyaku Co., Ltd., Neoperex; manufactured by Kao Corporation], polyethylene alkylethers [e.g., Neugen ET-135 (trade name); manufactured by Dai-ichi Kogyo Seiyaku Co., Ltd.], polyoxyethylene polyoxypropylene block copolymers [e.g., Nonipol PE-64 (trade name); manufactured by Sanyo Chemical Industries, Ltd.], polyhydric alcohol esters [e.g. Tween 20 (trade name), Tween 80 (trade name); manufactured by Kao Corporation], alkylsulfosuccinic acid salts [e.g. Sanmolin OT20 (trade name); manufactured by Sanyo Chemical Industries, Ltd., Newcalgen EX70 (trade name); manufactured by Takemoto Oil & Fat Co., Ltd.], alkylnaphthalene sulfonic acid salts [e.g. Newcalgen WG-1 (trade name); manufactured by Takemoto Oil & Fat Co., Ltd.], alkenyl sulfonic acid salts [e.g. Solpol 5115 (trade name); manufactured by Toho Chemical Industries Co., Ltd.] and the like are appropriately used and these can be appropriately used by mixing one kind or two kinds at a suitable ratio. In addition, the compound (I) can also be used appropriately by compounding with, for example, other insecticide (pyrethroid insecticide, organic phosphorus insecticide, carbamate insecticide, neonicotinoid insecticide, natural insecticide etc.), an acaricide, a machine oil, a nematocide, a herbicide, a plant hormone agent, a plant growth regulating substance, an fungicidal agent (e.g. copper fungicidal agent, organic chlorine fungicidal agent, organic sulfur fungicidal agent, phenol fungicidal agent etc.), a synergist, an attractant, a repellent, a drug harm alleviating agent, a pigment, a fertilizer, an animal feed (feed for livestock such as cow, pig and hence chicken, feed for pet animal such as dog and cat, feed for raised fish such as young yellowtail and sea bream), veterinary medicaments (medicaments for treating or preventing diseases of livestock, pet animal, raised fish), a veterinary nutrient and the like.

The ratio of the compound (I) contained in the pesticidal composition of the present invention is usually about 0.1 to 80% by weight, preferably about 1 to 20% by weight relative to the total amount of the composition. Specifically, when the compound is used as an emulsion, a solution or a wettable powder (e.g. granular wettable powder), usually about 1 to 80% by weight, preferably about 1 to 20% by weight is suitable. When used as an oil solution or a powder, usually about 0.1 to 50% by weight, preferably about 0.1 to 20% by weight is suitable. When used in a granule, usually about 1 to 50% by weight, preferably about 1 to 20% by weight is suitable.

Other pesticidaly active ingredient (e.g. an insecticide, a herbicide, an acaricide and/or a fungicide) which is compounded in the pesticidal composition of the present invention is used usually in the range of about 0.1 to 80% by weight, preferably about 1 to 20% by weight relative to the total amount of the preparation.

The content of an additive other than the aforementioned active ingredients differs depending on a kind or a content of an active ingredient or a dosage form of a preparation, and is usually about 0.001 to 99.9% by weight, preferably about 1 to 99% by weight. More specifically, it is preferable to add a surfactant at usually about 1 to 20% by weight, more preferably about 1 to 15% by weight, a flowing aid at about 1 to 20% by weight, and a carrier at about 1 to 90% by weight, preferably at about 1 to 70% by weight relative to the total amount of the composition. Specifically, when a solution is prepared, it is preferable to add a surfactant at usually about 1 to 20% by weight, preferably 1 to 10% by weight, and water at about 20 to 90% by weight. An emulsion or a wettable powder (e.g. granular wettable powder) should be diluted with water appropriately (e.g. about 100 to 5.000-fold) for use to spray.

Typical examples of fungicidal agent, plant hormone agent, plant growth regulating substance, herbicide, and pesticide such as insecticide, acaricide and nematocide and the like (including isomers and salts thereof) which can be used by mixing with the compound (I) or salts thereof of the present invention are shown below.

(1) Organic Phosphorous Compounds

Acephate, Aluminium phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, Hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion and the like;

(2) Carbamate Compounds

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb and the like;

(3) Synthetic Pyrethroid Compounds

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, 2,3,5,6-tetrafluoro-4-(methoxymethyl)benzyl (EZ)-(1RS,3RS; 1RS,3SR)-2,2-dimethyl-3-prop-1-enylcycloprop anecarboxylate, 2,3,5,6-tetrafluoro-4-methylbenzyl (EZ)-(1RS,3RS; 1RS,3SR)-2,2-dimethyl-3-prop-1-enylcyclopropanecarboxylate, 2,3,5,6-tetrafluoro-4-(methoxymethyl)benzyl (1RS,3RS; 1RS,3SR)-2,2-dimethyl-3-(2-methyl-1-propenyl)cyclo propanecarboxylate and the like;

(4) Nereistoxin Compounds

Cartap, bensultap, thiocyclam, monosultap, bisultap and the like;

(5) Neonicotinoid Compounds

Imidacloprid, nitenpyram, acetamiprid, thiamethoxam, thiacloprid, dinotefuran, clothianidin and the like;

(6) Benzoylurea Compounds

Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron and the like;

(7) Phenylpyrazole Compounds

Acetoprole, ethiprole, fipronil, vaniliprole, pyriprole, pyrafluprole and the like;

(8) Bt Toxins

Live spores and produced crystal toxin derived from *bacillus thuringiensis*, and a mixture thereof;

(9) Hydrazine Compounds

Chromafenozide, halofenozide, methoxyfenozide, tebufenozide and the like;

(10) Organic Chlorine Compounds

Aldrin, dieldrin, dienochlor, endosulfan, methoxychlor and the like;

(11) Natural Insecticides

Machine oil, nicotine-sulfate and the like;

(12) Other Insecticides

Avermectin-B, bromopropylate, buprofezin, chlorphenapyr, cyromazine, D-D (1,3-Dichloropropene), emamectin-benzoate, fenazaquin, flupyrazofos, hydroprene, indoxacarb, metoxadiazone, milbemycin-A, pymetrozine, pyridalyl, pyriproxyfen, spinosad, sulfluramid, tolfenpyrad, triazamate, flubendiamide, SI-0009, cyflumetofen, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, nidinotefuran, Potassium oleate, protrifenbute, spiromesifen, Sulfur, metaflumizone, spirotetramat, pyrifluquinazon, Chlorantraniliprole, a compound represented by formula (A)

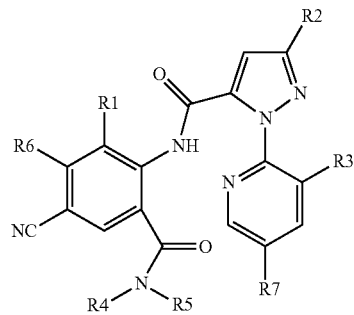

(A)

[wherein, $R^1$ represents a methyl group, a chlorine atom, a bromine atom or a fluorine atom, $R^2$ represents a fluorine atom, a chlorine atom, a bromine atom, $C_{1-4}$haloalkyl group or $C_{1-4}$haloalkoxy group, $R^3$ represents a fluorine atom, a chlorine atom or a bromine atom, $R^4$ represents a hydrogen atom; $C_{1-4}$ alkyl group optionally substituted with a methoxy group, one or more of halogen atom(s), a cyano group, a methylthio group, a methylsulfinyl group or a methylsulfonyl group; $C_{3-4}$ alkenyl; $C_{3-4}$ alkynyl; or $C_{3-5}$ cycloalkyl, $R^5$ represents a hydrogen atom or a methyl group, $R^6$ represents a hydrogen atom, a fluorine atom or a chlorine atom, $R^7$ represents a hydrogen atom, a fluorine atom or a chlorine atom] and the like.

Acaricides (Active ingredients for acaricide) include, for example, acequinocyl, amitraz, benzoximate, bifenazate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, Pyrimidifen, tebufenpyrad, tetradifon, spirodiclofen, amidoflumet and the like.

Nematocides (Active ingredients of nematocide) include, for example, DCIP, fosthiazate, levamisol, methylsothiocyanate, morantel tartarate and the like.

Fungicides include, for example, acibenzolar-S-methyl, amobam, ampropylfos, anilazine, azoxystrobin, benalaxyl, benodanil, benomyl, benthiavalicarb, benthiazole, bethoxazin, bitertanol, blasticidin-S, Bordeaux mixture, boscalid, bromuconazole, buthiobate, Calcium hypochlorite, Calcium polysulfide, captan, carbendazol, carboxin, carpropamid, chlobenthiazone, chloroneb, chloropicrin, chlorothalonil (TPN), chlorthiophos, Cinnamaldehyde, clozylacon, CNA (2,6-Dichloro-4-nitroaniline), Copper hydroxide, Copper sulfate, cyazofamid, cyfluphenamid, cymoxanil, cyproconazole, cyprodinil, cyprofuram, dazomet, debacarb, dichlofluanid, D-D (1,3-Dichloropropene), diclocymet, diclomezine, diethofencarb, difenoconazole, diflumetorim, dimefluazole, dimethirimol, dimethomorph, diniconazole-M, dinocap, edifenphos, epoxiconazole, nickel dimethyldithiocarbamate, etaconazole, ethaboxam, ethirimol, etridiazole, famoxadone, fenamidone, fenarimol, fenbuconazole, Fendazosulam, fenhexamid, fenoxanil, fenpiclonil, fenpropidin, fenpropimorph, fentiazon, fentin hydroxide, ferimzone, fluazinam, fludioxonil, flumetover, flumorph, fluoroimide, fluotrimazole, fluoxastrobin, fluquinconazole, flusilazole, flusulfamide, flutolanil, flutriafol, fosetyl-Al, fthalide, fuberidazole, furalaxyl, furametpyr, furcarbanil, furconazole-cis, hexaconazole, hymexazol, IBP, imazalil, imibenconazole, iminoctadine-albesilate, iminoctadine-triacetate, iodocarb, ipconazole, iprodione, iprovalicarb, isoprothiolane, kasugamycin, kresoxim-methyl, mancozeb, maneb, mepanipyrim, mepronil, metalaxyl, metalaxyl-M, metam-sodium, methasulfocarb, Methyl bromide, metconazole, methfuroxam, metominostrobin, metrafenone, metsulfovax, mildiomycin, milneb, myclobutanil, myclozolin, nabam, orysastrobin, ofurace, oxadixyl, oxolinic acid, oxpoconazole, oxycarboxin, oxytetracycline, pefurazoate, penconazole, pencycuron, picoxystrobin, polycarbamate, polyoxin, Potassium hydrogen carbonate, probenazole, prochloraz, procymidone, propamocarb-hydrochloride, propiconaole, propineb, proquinazid, prothiocarb, prothioconazole, pyracarbolid, pyraclostrobin, pyrazophos, pyributicarb, pyrifenox, pyrimethanil, pyroquilon, quinoxyfen, quintozene (PCNB), silthiopham, simeconazole, sipconazole, Sodium bibarbonate, sodium hypochlorite, spiroxamine, ((E)-2[2-(2,5-dimethylphenoxymethyl)phenyl]-2-m ethoxyimino-N-methylacetamide), streptomycin, Sulfur, tebuconazole, tecloftalam, tetraconazole, thiabendazole, thiadinil, thiram (TMTD), thifluzamide, thiophanatemethyl, tolclofos-methyl, TPN, triadimefon, triadimenol, triazoxide, triclamide, tricyclazole, tridemorph, triflumizole, trifloxystrobin, triforine, triticonazole, validamycin, vinclozolin, viniconazole, zineb, ziram and zoxamide.

Active ingredients of the herbicides, plant hormone agent and plant growth regulators include, for example, Abscisic acid, acetochlor, acifluorfen-sodium, alachlor, alloxydim, ametryn, amicarbazone, amidosulfuron, aminoethoxyvinylglycine, aminopyralid, AC94,377, amiprofos-methyl, ancymidol, asulam, atrazine, aviglycine, azimsulfuron, beflubutamid, benfluralin, benfuresate, bensulfuron-methyl, bensulide (SAP), bentazone, benthiocarb, benzamizole, benzfendizone, benzobicyclon, benzofenap, benzyl adenine, benzylaminopurine, bialaphos, bifenox, Brassinolide, bromacil, bromobutide, butachlor, butafenacil, butamifos, butylate, cafenstrole, Calcium carbonate, Calcium peroxide, carbaryl, chlomethoxynil, chloridazon, chlorimuron-ethyl, chlorphthalim, chlorpropham, chlorsulfuron, chlorthal-dimethyl, chlorthiamid (DCBN), choline chloride, cinidon-ethyl, cinmethylin, cinosulfuron, clethodim, clomeprop, cloxyfonac-sodium, chlormequat chloride, 4-CPA (4-chlorophenoxyacetic acid), cliprop, clofencet, cumyluron, cyanazine, cyclanilide, cyclosulfamron, cyhalofop-butyl, 2,4-Dichlorophenoxyacetic acid salts, dichlorprop (2,4-DP), daimuron, dalapon (DPA), dimethenamid-P, daminozide, dazomet, n-Decyl alcohol, dicamba-sodium (MDBA), dichlobenil (DBN), diflufenican, dikegulac, dimepiperate, dimethametryn, dimethenamid, diquat, dithiopyr, diuron, endothal, epocholeone, esprocarb, ethephon, ethidimuron, ethoxysulfuron, ethychlozate, etobenzanid, fenarimol, fenoxaprop-ethyl, fentrazamide, flazasulfuron, florasulam, fluazifop-butyl, fluazolate, flucarbazone, flufenacet, flufenpyr, flumetralin, flumioxazin, flupropanate-sodium, flupyrsulfuron-methyl-sodium, flurprimidol, fluthiacet-methyl, foramsulfuron, forchlorfenuron, formesafen, gibberellin, glufosinate, glyphosate, halosulfuron-methyl, hexazinone, imazamox, imazapic, imazapyr, imazaquin, imazosulfuron, inabenfide, Indole acetic acid (IAA), Indole butyric acid, iodosulfuron, ioxynil-octanoate, isouron, isoxachlortole, isoxadifen, karbutilate, lactofen, lenacil, linuron, LGC-42153, Maleic hydrazide, mecoprop (MCPP), 2-Methyl-4-chlorophenoxyacetic acid salts, MCPA-thioethyl, 2-Methyl-4-chlorophenoxybutanoic acidethyl ester, mefenacet, mefluidide, mepiquat, mesosulfuron, mesotrione, methyl daimuron, metamifop, metolachlor, metribuzin, metsulfuron-methyl, molinate, naphthylacetic acid, 1-naphthaleneacetamide, naproanilide, napropamide, n-decyl alcohol, nicosulfuron, n-phenylphthalamic acid, orbencarb, oxadiazon, oxaziclomefone, oxine-sulfate, paclobutrazol, paraquat, Pelargonic acid, pendimethalin, penoxsulam, pentoxazone, pethoxamide, phenmedipham, picloram, picolinafen, piperonyl butoxide, piperophos, pretilachlor, primisulfuron-methyl, procarbazone, prodiamine, profluazol, profoxydim, prohexadione-calcium, prohydrojasmon, prometryn, propanil, propoxycarbazone, propyzamide, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac, quiclorac, quinoclamine, quizalofop-ethyl, rimsulfuron, sethoxydim, siduron, simazine, simetryn, Sodium chlorate, sulfosulfuron, swep (MCC), tebuthiuron, tepraloxydim, terbacil, terbucarb (MBPMC), thenylchlor, thiazafluoron, thidiazuron, thifensulfuron-methyl, triaziflam, tribufos, triclopyr, tridiphane, trifloxysulfuron, trifluralin, trinexapac-ethyl, tritosulfuron, uniconazole-P and vemolate (PPTC).

The pesticidal composition of the present invention can also be used further in admixture with a synergist such as piperonyl butoxide, sesamex, sulfoxide, N-(2-ethylhexyl)-8,9,10-trinorborn-5-en-2,3-dicarboxylmide (MGK 264), N-decylimidazole, WARF-antiresistant TBPT, TPP, IBP, PSCP, Iodo methane ($CH_3I$), t-phenylbutenone, diethylmaleate, DMC, FDMC, ETP, ETN and the like, and furthermore, may be used in admixture with a safener such as benoxacor, cloquintocet-mexyl, cyometrinil, daimuron, dichlormid, fenchlorazole-ethyl, fenclorim, flurazole, fluxofenim, furilazole, mefenpyr-diethyl, MG191, naphthalic anhydride and oxabetrinil.

Furthermore, the compound (I) or salts thereof of the present invention may be used by mixture with a controlling agent for an outside-parasitic arthropod such as IGR agents (juvenile hormone-like substances such as methoprene, fenoxycarb and the like, chitin synthase inhibitors such as lufenuron, flufenoxuron, novaluron, hexaflumuron, teflubenzuron, diflubenzuron, triflumuron and the like, insect growth regulating agents such as cyromazine, pyriproxyfen and the like), and neonicotinoid compounds (nitenpyram etc.), or may be used by mixture with a controlling agent for inner parasite such as an above-mentioned IGR agent as in vivo administration agent for animal, a controlling agent for filaria (macrolide compounds such as selamectin, ivermectin, milbemycin, moxidectin etc.) or the like, and further may be used by mixture with an antibacterial agent for animal, vaccine, therapeutic agent, nutritional supplement and bait.

Examples of the pest against which the compound (I) or a salt thereof has an activity include noxious arthropods such as insect pests, acarine pests and the like, and nematode pests.

Specific Examples are Listed Below:

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potatoaphid (*Macrosiphum euphorbiae*), foxglove aphid (*Aulacorthum solani*), oat bird-cherry aphid (*Rhopalosiphumpadi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), and silver leaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottonycushion scale (*Icerya purchasi*); lace bags (Tingidae); psyllids (Psyllidae); etc.

Lepidoptera: —

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Helio*-

*this* spp., and *Helicoverpa* spp.; whites and sulfer butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), *Adoxophye* ssp., oriental tea tortrix (*Homona magnanima*), apple tortrix (*Archips fuscocupreanus*), and *Cydia pomonella*; leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:

Thrips (Thripidae) such as yellow citrus thrips (*Frankliniella occidentalis*), *Thrips parmi*, yellow tea thrips (*Scirtothrips dorsalis*), onion thrip (*Thrips tabaci*), flower thrips (*Frankliniella intonsa*), etc.

Diptera:

Housefly (*Musca domestica*), common mosquito (*Culex popiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), *Ceratitis capitata*, legume leafminer (*Liriomyza trifolii*), etc.

Coleoptera:

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), *Anthonomus grandis*, azuki bean weevil (*Callosobruchus chinensis*), *Sphenophorus venatus*, Japanese beetle (*Popillia japonica*), cupreous chafer (*Anomala cuprea*), corn root worm (*Diabrotica* spp.), Colorado beetle (*Leptinotarsa decemlineata*), click beetle (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*), etc.

Orthoptera:

Asiaticlocust (*Locusta migratoria*), African mole cricket (*Gryllotalpa africana*), rice grasshopper (*Oxya yezoensis*), rice grasshopper (*Oxya japonica*), etc.

Hymenoptera:

Cabbage sawfly (*Athalia rosae*), *Acromyrmex* spp., fire ant (*Solenopsis* spp.), etc.

Nematodes:

Rice white-tip nematode (*Aphelenchoides besseyi*), strawberry bud nematode (*Nothotylenchus acris*), etc.

Dictyoptera:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*), etc.

Acarina:

Spider mites (Tetranychidae) such as two-spotted spider mite (*Tetranychus urticae*); eriophyid mites (Eriophyidae) such as pink citrus rust mite (*Aculops pelekassi*); tarosonemid mites (Tarsonemidae) such as broad mite (*Polyphagotarsonemus latus*); false spider mites (Tenuipalpidae); Tuckerellidae; ticks (Ixodidae) such as *Haemaphysalis longicornis*, *Haemaphysalis flava*, *Dermacentor taiwanicus*, *Ixodes ovatus*, *Ixodes persulcatus*, *Boophilus microplus*, and *Rhipicephalus sanguineus*; acarid mites (Acaridae) such as mold mite (*Tyrophagus putrescentiae*); house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae); *Dermahyssus gallinae*; etc.

Furthermore, the preparation containing the compound (I) or a salt thereof can be used in the field of treatment for disease of livestock and in livestock farming, and also for maintaining public sanitation by exterminating an arthropod and parasite which parasitize inside and/or outside of vertebrates such as human, cow, sheep, goat, pig, poultry, dog, cat, fish and the like. Examples of pests include, for example, *Ixodes* spp., *Boophilus* spp. (e.g. *Boophilus microplus*), *Amblyomma* spp., *Hyalomma* spp., *Rhipicephalus* spp. (e.g. *Rhipicephalus appendiculatus*), *Haemaphysalis* spp., *dermacentor* spp., *Ornithodoros* spp. (e.g. *Ornithodoros moubata*), *Dermahyssus gallinae*, *Ornithonyssus sylviarum*, *Sarcoptes* spp. (e.g. *Sarcoptes scabiei*), *Psoroptes* spp., *Chorioptes* spp., *Demodex* spp., *Eutrombicula* spp., *Aedes* spp. (e.g. *Aedes albopictus*), *Anopheles* spp., *Culex spp*, *Culicodes spp*, *Musca* spp., *Hypoderma* spp., *Gasterophilus* spp., *Haematobia* spp, *Tabanus* spp, *Simulium* spp., *Triatoma* spp., *Phthiraptera* (e.g. *Damalinia* spp., *Linognathus* spp., *Haematopinus* spp), *Ctenocephalides* spp. *Xenosylla* spp), *monomorium pharaonis* and Nematoda (for example, *Trichostrongylus* (e.g. *Nippostrongylus brasiliensis*, *Trichostrongylus axei*, *Trichostrongylus colubriformis*), *Trichinella* (e.g. *Trichinella spiralis*), *Haemonchus contortus*, *Nematodirus* (e.g. *Nematodirus battus*), *Ostertagia circumcincta*, *Cooperia* spp., *Hymenolepis nana*) and the like.

For the method for controlling pests of the present invention, the compound (I) or a salt thereof may be used as it is. But the compound (I) or a salt thereof is usually formulated to the form of above mentioned pesticidal composition of the present invention, and for example, it is applied to a pest or a inhabit of pests in a similar manner as conventional pesticidal composition, then the active ingredient being brought the pests into contact or fed the pests.

Examples of the habitat of pests in the present invention include paddy fields, fields, orchards, uncultivated fields, houses and the like.

As a method for application, for example, a spray treatment, a soil treatment, a seed treatment and a hydroponic solution treatment are exemplified.

The spray treatment in the present invention is a method of treatment for expressing a controlling effect against pests by treating plant surface or pest itself with an active ingredient (the compound (I) or a salt thereof), specifically for example, foliage application, spraying to tree trunk and the like. The soil treatment is a method of treatment for protecting crops from damages by pests, by treating soils, irrigation solutions or the like with an active ingredient in order to penetrate and translocate from the root portion and the like into the plant interior of a crop to be protected from damages such as feeding and the like by pests, and specifically, for example, a planting hole treatment (planting hole spraying, soil-incorporation after planting hole treatment), a plant foot treatment (plant foot spraying, plant foot soil-incorporation, plant foot irrigation, plant foot treatment at latter half of raising seeding period), planting furrow treatment (planting furrow spraying, planting furrow soil-incorporation), planting row treatment (planting row spraying, planting row soil-incorporation, planting row spraying at growing period), planting row treatment at sowing (planting row spraying at sowing, planting row soil-incorporation at sowing), overall treatment (overall spraying, overall soil-incorporation), other spray treatment (foliar granule spraying at growing period, spraying under tree crown or around main stem, soil surface spraying, soil surface incorporation, sowing hole spraying, spraying on the ribbing ground, inter-plant spraying), other irrigation treatment (irrigation into soil, irrigation during raising seeding, injection treatment of pesticide solution, irrigation on plant foot, pesticide solution drip irrigation, chemigation), nursery box treatment (nursery box spraying, nursery box irrigation), nursery tray treatment (nursery tray spraying, nursery tray irrigation), nursery bed treatment (nursery bed spraying, nursery bed irrigation, nursery bed spraying in paddy field, immersion of nursery plant), seed bed soil-incorporation treatment seed (bed soil-incorporation, seed bed soil-incorporation before sowing), other treatment (growing media incorporation, plowing, surface soil-incorporation, soil incorporation into rain dropping, planting spot treatment, flower cluster granule spraying, paste fertilizer mixing), and the like are exemplified. The seed treatment is a method of treatment for expressing a controlling effect against pests by treating seeds, seed tubers, bulbs or the like of a crop to be protected from damages such as feeding and the like by pests directly, or neighborhood thereof, with an active ingredient, and specifically, for example, blowing treatment, painting treatment, immersion treatment, impregnation treatment, application treatment, film coating and a pellet coating treatment are exemplified. The hydroponic solution treatment is a method of treatment for protecting crops from damages by pests, by treating hydroponic solution or the like with an active ingredient in order to penetrate and translocate from the root portion and the like into the plant interior of a crop to be protected from damages such as feeding and the like by pests, and specifically, for example, hydroponic solution incorporation, hydroponic solution mixing, and the like are exemplified.

The amount of application of the compound (I) or a salt thereof in the method for controlling pests of the present invention can be changed depending on the application time, application site, application method and the like, but in general, it is at a rate of about 0.3 to 3000 g, preferably at a rate of about 50 to 3000 g as an amount of the active ingredient (the compound (I) or a salt thereof) per hectare. In addition, when the pesticidal composition of the present invention is a wettable powder or the like, it may be diluted with water to use so that the final concentration of active ingredient comes to the range of about 0.1 to 1,000 ppm, preferably about 10 to 500 ppm.

As an alternative mode, for example, the arthropod and parasite living with said vertebrates can be exterminated in whole body or non-whole body by administering the pesticidal composition of the present invention to inside (internal parts of the body) or outside (body surface) of the above-mentioned vertebrates. The method of administrating to inside includes oral treatment; anus treatment; interplanting; and hypodermic treatment, intermuscular treatment or vein treatment by injection. In addition, sanitary pests arising from the excrement of the animal can be exterminated by feeding a livestock animal.

When the pesticidal composition of the present invention is applied to an animal which a pest is parasitic such as a domestic animal and a pet, the application amount can be varied in wide range according to application method, but, generally, it is preferable that the amount of active ingredient (the compound (I) or a salt thereof) per 1 kg of animal weight is about 0.1 mg to 2000 mg, more preferably about 0.5 mg to 1000 mg.

The present invention will be further illustrated by the following Synthetic Examples, Reference Examples, Formulation Examples and Test Examples; however, the present invention is not limited to these examples.

The elution in the column chromatography for Examples and Reference Production Examples was carried out under the observation by TLC (Thin Layer Chromatography). In the TLC observation, kieselgel $60F_{254}$ (70 to 230 meshes) manufactured by Merck & Co., Inc. was used as TLC plate; the solvent used as an elution solvent in column chromatography was used as developing solvent; and a UV detector was used for detection. Kieselgel 60 (70 to 230 meshes) manufactured by Merck & Co., Inc. was used as silica gel for column chromatography. As a medium pressure preparative high performance liquid chromatography, Ultrapack manufactured by Yamazen, Co., Ltd. (filler: silica gel) has been used. When a mixed solvent was used as developing solvent, the numeric value in parentheses shows a mixing ratio of solvents by volume. NMR spectra were proton NMR, and were determined with JEOL AL-400 (400 MHz) spectrometer and AVANCE 400 (400 MHz) spectrometer using tetramethylsilane as internal standard. All delta values were shown in ppm. The measurement temperature is 25° C. unless otherwise mentioned, and the measurement temperature has been indicated for the rest.

Furthermore, the abbreviations used in the following Examples and Reference Production Examples have the following meanings:
s: singlet, br: broad, brs: broadsinglet, d: doublet, t: triplet, q: quartet, quint: quintet, sext: sextet, sept: septet, Me: methyl group, Et: ethyl group, Ph: phenyl group, Pr-n (or n-Pr): n-propyl, Pr-i (or i-Pr or $^i$Pr): isopropyl, Pr-cyclo (or cyclo-Pr): cyclopropyl, Bu-n (or n-Bu): n-butyl, Bu-i (or i-Bu): isobutyl, Bu-s (or s-Bu): sec-butyl, Bu-t (or t-Bu): tert-butyl, DMF: dimethylformamide, m-CPBA: meta chloro perbenzoic acid. In addition, room temperature means about 15 to 25° C.

EXAMPLE 1

Compound (1): Phenyl N-phenyl-3-(phenylthio)thioacrylimidate

N-phenyl-3-phenylthioacrylamide (0.75 g) was suspended to toluene (10 ml), then thionyl chloride (0.40 ml), one drop of DMF and triethylamine (0.80 ml) were added thereto at room temperature. The mixture was stirred on the 60° C. oil bath for three hours. Then it was cooled and filtered off the insoluble matter. The filtrate was concentrated under reduced pressure. The residue was dissolved to DMF (15 ml). Sodium hydride (55% in oil:0.217 g) was added thereto under ice-cooling, then thiophenol (0.40 ml) was added dropwise over the period for 3 minutes. It was stirred for 2.5 hours. Aqueous saturated sodium chloride solution (10 ml) and water (5 ml) were added to the reaction mixture, and it was extracted with t-butyl methyl ether (15 ml) three times. The organic layers were combined, and washed with aqueous saturated sodium chloride solution (15 ml) three times, dried over anhydrous sodium sulfate, filtered off an inorganic salt, concentrated under reduced pressure, to obtain black oil (1.0 g). It was subjected to silica gel column chromatography (hexane:ethyl acetate=15:1) to obtain phenyl N-phenyl-3-(phenylthio)thioacrylimidate (0.41 g) as light yellow oil.

¹H-NMR (CDCl₃) δ(ppm): 5.68(dJ=15.1 Hz), 5.81 (dJ=10.3 Hz), 6.08(d J=15.1 Hz) total 1H, 6.66-7.58(16H,m)

The stereochemistry of the —CH═CH— bond was mixture of E and Z.

Compounds (2) to (34) were synthesized in a similar manner as the Example 1.

EXAMPLE 2

Compound (2): 4-Chlorophenyl N-phenyl-3-(phenylthio)thioacrylimidate

¹H-NMR (CDCl₃) δ(ppm): 5.46-5.84(1H,m), 6.67-7.52 (15H,m)

The stereochemistry of the —CH═CH— bond was mixture of E and Z.

EXAMPLE 3

Compound (3): 3-Chlorophenyl N-phenyl-3-(phenylthio)thioacrylimidate

¹H-NMR (CDCl₃) δ(ppm): 5.55-5.87(1H,m), 6.67-7.63 (15H,m)

The stereochemistry of the —CH═CH— bond was mixture of E and Z.

EXAMPLE 4

Compound (4): 2-Chlorophenyl N-phenyl-3-(phenylthio)thioacrylimidate

¹H-NMR (CDCl₃) δ(ppm): 5.62-5.87(1H,m), 6.83-7.59 (15H,m)

The stereochemistry of the —CH═CH— bond was mixture of E and Z.

EXAMPLE 5

Compound (5): Benzyl N-phenyl-3-(phenylthio)thioacrylimidate

¹H-NMR (CDCl₃) δ(ppm): 4.31(2H,s), 6.08(1H,d J=15.6 Hz), 6.74(2H,d J=7.3 Hz), 7.05(1H, t J=7.4 Hz), 7.22-7.39 (13H,m).

The stereochemistry of the —CH═CH— bond was E.

EXAMPLE 6

Compound (6): Benzyl N-phenyl-3-(benzylthio)thioacrylimidate

¹H-NMR (CDCl₃) δ(ppm): 3.82(2H,s), 4.30(2H,s), 6.07 (1H,d J=15.6 Hz), 6.73(2H,d J=7.6 Hz), 7.07(1H,t J=7.4 Hz), 7.14-7.39(13H,m).

The stereochemistry of the —CH═CH— bond was E.

EXAMPLE 7

Compound (7): Phenyl N-phenyl-3-(cyclohexylthio)thioacrylimidate

¹H-NMR (CDCl₃) δ(ppm): 1.20-2.00(10H,m), 2.66-2.92 (1H,m), 5.71(0.33H,d J=12.0 Hz), 5.77(0.66H,d J=15.1 Hz), 6.92-7.51(11H,m)

The stereochemistry of the —CH═CH— bond was mixture of E and Z.

EXAMPLE 8

Compound (8): Phenyl N-phenyl-3-(benzylthio)thioacrylimidate

¹H-NMR (CDCl₃) δ(ppm): 3.75(1H, m), 3.86(1H, m), 5.70 (0.5H, d, J=12.0 Hz), 5.79(0.5H, d, J=16.0 Hz), 6.62-7.52 (16H, m)

The stereochemistry of the —CH═CH— bond was mixture of E and Z.

EXAMPLE 9

Compound (9): Phenyl N-phenyl-3-(phenylthio)thioacrylimidate

¹H-NMR (CDCl₃) δ(ppm): 5.81(1H,d J=10.1 Hz), 6.84 (1H,d J=10.1 Hz), 7.08-7.52(15H,m).

The stereochemistry of the —CH═CH— bond was Z.

EXAMPLE 10

Compound (10): 4-Pyridyl N-phenyl-3-(phenylthio)thioacrylimidate

¹H-NMR (CDCl₃) δ(ppm): 5.87(0.7H,d J=15.0 Hz), 6.09 (0.3H,d J=15.2 Hz), 6.73(0.6H,d J=7.7 Hz), 6.84(1.4H,d J=7.7 Hz), 7.08-7.66(11H,m), 8.43(1.4H,d J=5.8 Hz), 8.54 (0.6H,d J=4.8H).

The stereochemistry of the —CH═CH— bond was E.

EXAMPLE 11

Compound (11): 3,4-Dichlorophenyl N-phenyl-3-(phenylthio)thioacrylimidate m.p.: 99.5-100.5° C.

¹H-NMR (CDCl₃) δ(ppm): 5.38(0.8H, d J=14.7 Hz), 6.06 (0.2H,d J=15.5 Hz), 6.67(0.4H,d J=7.6 Hz), 6.87(1.6H,d J=7.6 Hz), 6.99-7.64(12H,m).

The stereochemistry of the —CH═CH— bond was E.

EXAMPLE 12

Compound (12): Phenyl N-(2-methoxyphenyl)-3-(phenylthio)thioacrylimidate

¹H-NMR (CDCl₃) δ(ppm): 3.90(3H,s), 5.86(1H,dJ=10.2 Hz), 6.86(1H, d J=10.2 Hz), 6.95-7.03(4H, m), 7.09-7.16(1H, m), 7.22-7.38(4H, m), 7.40-7.52(5H, m).

The stereochemistry of the —CH═CH— bond was Z.

EXAMPLE 13

Compound (13): 4-Chlorobenzyl N-phenyl-3-(4-chlorobenzylthio)thioacrylimidate

¹H-NMR (CDCl₃) δ(ppm): 3.78(2H,s), 4.24(2H,s), 6.00 (1H,d J=16.0 Hz), 6.67(2H,d J=7.7 Hz), 7.00-7.75(12H,m).

The stereochemistry of the —CH═CH— bond was E.

EXAMPLE 14

Compound (14): 2-Naphtyl N-phenyl-3-(phenylthio)thioacrylimidate $^1$H-NMR (CDCl$_3$) δ(ppm): 5.50-5.70(0.7H,m), 5.80-5.90 (0.3H,m), 6.81-7.87(18H,m)

The stereochemistry of the —CH═CH— bond was mixture of E and Z.

EXAMPLE 15

Compound (15): 3,4-Dichlorophenyl N-phenyl-3-(phenylthio)thioacrylimidate $^1$H-NMR (CDCl$_3$) δ(ppm): 5.37(0.1H, d J=14.6 Hz), 5.81 (0.9H,d J=10.2 Hz), 6.86-7.59(14H,m)

The stereochemistry of the —CH═CH— bond was mixture of E and Z.

EXAMPLE 16

Compound (16): 3,5-Dichlorophenyl N-phenyl-3-(phenylthio)thioacrylimidate $^1$H-NMR (CDCl$_3$) δ(ppm): 5.46(0.7H, d J=14.6 Hz), 6.06 (0.3H,d J=15.4 Hz), 6.68-7.66(14H,m)

The stereochemistry of the —CH═CH— bond was mixture of E and Z.

EXAMPLE 17

Compound (17): Phenyl N-(4-chlorophenyl)-3-(phenylthio)thioacrylimidate $^1$H-NMR (CDCl$_3$) δ(ppm): 5.66(1H,d J=14.85 Hz), 6.84 (2H,d J=8.45 Hz), 7.24-7.38(12H,m), 7.56(1H,d J=14.85 Hz).

The stereochemistry of the —CH═CH— bond was E.

EXAMPLE 18

Compound (18): Phenyl N-(4-chlorophenyl)-3-(phenylthio)thioacrylimidate $^1$H-NMR (CDCl$_3$) δ(ppm): 5.80(1H, d J=10.14 Hz), 6.86 (1H,d J=10.14 Hz), 6.99-7.05(2H,m), 7.22-7.53(12H,m).

The stereochemistry of the —CH═CH— bond was Z.

EXAMPLE 19

Compound (19): 2,4-Dichlorophenyl N-phenyl-3-(phenylthio)thioacrylimidate $^1$H-NMR (CDCl$_3$) δ(ppm): 5.44(0.5H, d J=14.2 Hz), 5.74 (0.3H,d J=10.1 Hz), 6.05(0.2H,d J=15.9 Hz), 6.66-7.63(14H, m)

The stereochemistry of the —CH═CH— bond was mixture of E and Z.

EXAMPLE 20

Compound (20): 2,5-Dichlorophenyl N-phenyl-3-(phenylthio)thioacrylimidate $^1$H-NMR (CDCl$_3$) δ(ppm): 5.60(0.7H, d J=14.7 Hz), 5.79 (0.1H,d J=10.4 Hz), 6.05(0.2H,d J=15.0 Hz), 6.68-7.65(14H, m)

The stereochemistry of the —CH═CH— bond was mixture of E and Z.

EXAMPLE 21

Compound (21): 4-Bromophenyl N-phenyl-3-(phenylthio)thioacrylimidate m.p.: 93-95° C.

$^1$H-NMR (CDCl$_3$) δ(ppm): 5.49(0.83H, d J=14.4 Hz), 6.06 (0.17H,d J=16.1 Hz), 6.65-7.59(15H,m).

The stereochemistry of the —CH═CH— bond was E.

EXAMPLE 22

Compound (22): 4-Bromophenyl N-phenyl-3-(phenylthio)thioacrylimidate $^1$H-NMR (CDCl$_3$) δ(ppm): 5.49(0.1H, d J=14.7 Hz), 5.79 (0.9H,d J=9.9 Hz), 6.87-7.59(15H,m)

The stereochemistry of the —CH═CH— bond was mixture of E and Z.

EXAMPLE 23

Compound (23): Phenyl N-(3-chlorophenyl)-3-(phenylthio)thioacrylimidate $^1$H-NMR (CDCl$_3$) δ(ppm): 5.65(0.63H, d J=14.73 Hz), 5.80(0.29H, d J=10.63 Hz), 6.00(0.08H, d J=14.97 Hz), 6.73-7.17(3H,m), 7.17-7.63(11.92H,m), 7.78(0.08H,d J=14.97 Hz)

The stereochemistry of the —CH═CH— bond was mixture of E and Z.

EXAMPLE 24

Compound (24): Phenyl N-phenyl-3-(phenylthio)thioacrylimidate $^1$H-NMR (CDCl$_3$) δ(ppm): 5.68(1H,d J=14.5 Hz), 6.88-6.94(2H,m), 7.05-7.40(13H,m), 7.55(1H,d J=14.5 Hz).

The stereochemistry of the —CH═CH— bond was E.

EXAMPLE 25

Compound (25): 4-Trifluoromethylphenyl N-phenyl-3-(phenylthio)thioacrylimidate $^1$H-NMR (CDCl$_3$) δ(ppm): 5.58(0.42H, d J=14.7 Hz), 5.79 (0.42H,d J=9.9 Hz), 6.08(0.16H, d J=15.5 Hz), 6.67-7.64 (15H,m)

The stereochemistry of the —CH═CH— bond was mixture of E and Z.

EXAMPLE 26

Compound (26): 4-Methoxyphenyl N-phenyl-3-(phenylthio)thioacrylimidate $^1$H-NMR (CDCl$_3$) δ(ppm): 3.85(3H,s), 5.59(0.83H, d J=14.6 Hz), 6.06(0.17H,d J=15.6 Hz), 6.64-7.56(15H,m).

The stereochemistry of the —CH═CH— bond was E.

EXAMPLE 27

Compound (27): 4-Methoxyphenyl N-phenyl-3-(4-methoxyphenylthio)thioacrylimidate $^1$H-NMR (CDCl$_3$) δ(ppm): 3.83(3H,s), 3.84(3H,s), 5.40 (0.83H, d J=14.2 Hz), 5.85(0.17H,d J=15.5 Hz), 6.60-7.52 (14H,m).

The stereochemistry of the —CH═CH— bond was E.

EXAMPLE 28

Compound (28): Phenyl N-(4-methylphenyl)-3-phenylthiothioacrylimidate $^1$H-NMR (CDCl$_3$) δ(ppm): 2.37(3H,s), 5.80(1H,dJ=9.9 Hz), 6.82(1H,d J=9.9 Hz), 7.00(2H,d J=8.2 Hz), 7.18-7.53 (12H,m).

The stereochemistry of the —CH═CH— bond was Z.

EXAMPLE 29

Compound (29): Phenyl N-(4-methylphenyl)-3-phenylthiothioacrylimidate $^1$H-NMR (CDCl$_3$) δ(ppm): 2.37(3H,s), 5.68(0.36H, d J=14.7 Hz), 6.01(0.64H,d J=14.6 Hz), 6.83(2H,d J=8.2 Hz), 7.12-7.55(12.36H,m), 7.85(0.64H,d J=14.6 Hz).

The stereochemistry of the —CH═CH— bond was E.

EXAMPLE 30

Compound (30): 4-Trifluoromethoxyphenyl N-phenyl-3-(phenylthio)thioacrylimidate $^1$H-NMR (CDCl$_3$) δ(ppm): 5.58(0.5H, d J=14.7 Hz), 5.79 (0.5H,d J=10.1 Hz), 6.88-7.54(15H,m)

The stereochemistry of the —CH═CH— bond was mixture of E and Z.

EXAMPLE 31

Compound (31): 1-Naphtyl N-phenyl-3-(phenylthio)thioacrylimidate $^1$H-NMR (CDCl$_3$) δ(ppm): 5.31(0.38H, d J=14.6 Hz), 5.56 (0.38H, d J=10.2 Hz), 5.68(0.24H, d J=14.9 Hz), 6.61-8.34 (18H,m)

The stereochemistry of the —CH═CH— bond was mixture of E and Z.

EXAMPLE 32

Compound (32): Phenyl N-(3-methylphenyl)-3-phenylthiothioacrylimidate $^1$H-NMR (CDCl$_3$) δ(ppm): 2.40(3H,s), 5.81(1H, d J=9.9 Hz), 6.83(1H,d J=9.9 Hz), 6.86-6.92(2H,m), 6.94-7.00(1H, m), 7.20-7.55(11H,m).

The stereochemistry of the —CH═CH— bond was Z.

EXAMPLE 33

Compound (33): Phenyl N-(3-methylphenyl)-3-phenylthiothioacrylimidate $^1$H-NMR (CDCl$_3$) δ(ppm): 2.35(2.5H,s) 2.35(2.5H,s) 2.40 (0.5H,s), 5.68(0.84H, d J=14.5 Hz), 5.81(0.16H, d J=9.9 Hz), 6.69-6.75(3H,m), 6.83(0.16H,d J=9.9 Hz), 6.89-6.94(2H,m), 7.18-7.57(9.84H,m)

The stereochemistry of the —CH═CH— bond was mixture of E and Z.

EXAMPLE 34

Compound (34): 2,3-Dichlorophenyl N-phenyl-3-(phenylthio)thioacrylimidate $^1$H-NMR (CDCl$_3$) δ(ppm): 5.54(0.5H, d J=14.6 Hz), 5.77 (0.38H,d J=10.2 Hz), 6.05(0.12H,d J=15.4 Hz), 6.67-7.62 (14H,m)

The stereochemistry of the —CH═CH— bond was mixture of E and Z.

EXAMPLE 35

Compound (35): Phenyl N-phenyl-3-(phenoxy)thioacrylimidate N-phenyl-3-phenoxyacrylamide (1.5 g) was suspended to toluene (80 ml), then thionyl chloride (0.82 ml), triethylamine (1.8 ml) and one drop of DMF were added thereto at room temperature. The mixture was stirred on the 60° C. oil bath for three hours. Then it was cooled and filtered off the insoluble matter. The filtrate was concentrated under reduced pressure. The residue was dissolved to DMF (80 ml). Sodium salt of thiophenol (0.82 g) was added to it under ice-cooling, and stirred for 2 hours. t-Butyl methyl ether (250 ml) was added to the reaction mixture. It was successively washed with 1N aqueous sodium hydroxide solution, water and aqueous saturated sodium chloride solution, dried over anhydrous sodium sulfate, filtered off an inorganic salt, concentrated under reduced pressure. The residue was isolated and purified by silica gel column chromatography (hexane: ethyl acetate=20:1) to obtain phenyl N-phenyl-3-(phenoxy) thioacrylimidate (0.28 g) as yellow oil.

$^1$H-NMR (CDCl$_3$) δ(ppm): 5.64(0.7H, d, J=12.0 Hz), 5.98 (0.3H,d, J=12.0 Hz), 6.75(0.6H,d,J=7.6 Hz), 6.91-7.44 (13.8H,m), 7.59(0.6H,d, J=6.6 Hz), 7.68(1H,d, J=12.0 Hz)

The stereochemistry of the —CH═CH— bond was mixture of E and Z.

EXAMPLE 36

Compound (36): Phenyl N-phenylsulfonyl-3-(phenylthio)thioacrylimidate

N-phenylsulfonyl-3-phenylthioacrylamide (0.50 g) was suspended to toluene (10 ml), then thionyl chloride (0.20 ml), triethylamine (0.40 ml) and one drop of DMF were added thereto at room temperature. The mixture was stirred on the 60° C. oil bath for three hours. Then it was cooled and filtered off the insoluble matter. The filtrate was concentrated under reduced pressure. The residue was dissolved to DMF (8 ml). DMF (2 ml) solution of sodium salt of thiophenol (0.30 g) was added thereto under ice-cooling, and it was stirred at room temperature for 1.5 hours. Ethyl acetate (80 ml) was added to the reaction mixture, and it was successively washed with 1N aqueous sodium hydroxide solution, water and aqueous saturated sodium chloride solution, dried over anhydrous sodium sulfate, filtered off an inorganic salt, concentrated under reduced pressure. The residue was isolated and purified by silica gel column chromatography (hexane:ethyl acetate=10:1) to obtain phenyl N-phenylsulfonyl-3-(phenylthio)thioacrylimidate (0.14 g) as light yellow oil.

$^1$H-NMR (CDCl$_3$) δ(ppm): 6.01(0.67H, d J=14.7 Hz), 6.35 (0.33H,d J=9.9 Hz), 7.20(0.33H,d J=9.9 Hz), 7.31-7.51(15H, m), 7.85(0.67H,d J=14.7 Hz)

The stereochemistry of the —CH═CH— bond was mixture of E and Z.

EXAMPLE 37

Compound (37): Phenyl N-phenyl-3-(phenylthio)acrylimidate N-phenyl-3-phenylthioacrylamide (0.766 g) was suspended to toluene (15 ml), then thionyl chloride (0.33 ml) and triethylamine (0.62 ml) were added thereto at room temperature. The mixture was stirred on the 60° C. oil bath for three hours. Then it was filtered off the insoluble matter. The filtrate was concentrated under reduced pressure. The residue was dissolved to DMF (15 ml). Sodium hydride (55% in oil: 0.226 g) was added thereto under ice-cooling, then phenol (0.303 g) was added. It was stirred for 2.5 hours under ice-cooling and for overnight at room temperature. Aqueous saturated sodium chloride solution (15 ml) and water (5 ml) were added to the reaction mixture, and it was extracted with ethyl acetate (20 ml) and t-butyl methyl ether (15 ml) twice. The organic layers were combined, and washed with aqueous saturated sodium chloride solution (15 ml) three times, dried over anhydrous sodium sulfate, filtered off an inorganic salt, concentrated under reduced pressure to obtain black oil (0.88 g). It was subjected to silica gel column chromatography (hexane:ethyl acetate=15:1) to obtain phenyl N-phenyl-3-(phenylthio)acrylimidate (0.2 g) as light yellow oil.

$^1$H-NMR (CDCl$_3$) δ(ppm): 5.65-5.90(1H, m), 6.72-7.72 (16H, m)

The stereochemistry of the —CH═CH— bond was mixture of E and Z.

Compounds (38) to (98) were synthesized in a similar manner as the Example 37.

EXAMPLE 38

Compound (38): Phenyl 3-(phenoxy)-N-phenylacrylimidate $^1$H-NMR (CDCl$_3$) δ(ppm): 5.74(1H, d, J=12.4 Hz), 6.78-6.81(2H, m), 7.00-7.44(13H, m), 7.80(1H, d, J=12.4 Hz)

The stereochemistry of the —CH═CH— bond was E.

EXAMPLE 39

Compound (39): Phenyl N-(2-chlorophenyl)-3-(phenylthio)acrylimidate $^1$H-NMR (CDCl$_3$) δ(ppm): 5.69(0.83H, d J=15.2 Hz), 5.81 (0.17H, d J=15.0 Hz), 6.73(0.83H, d J=7.7 Hz), 6.88-7.00 (0.83H, m), 7.05-7.55(12.34H, m), 7.74(0.83H,d J=15.2 Hz), 8.00(0.17H, d J=15.0 Hz)

The stereochemistry of the —CH═CH— bond was mixture of E and Z.

EXAMPLE 40

Compound (40): Phenyl N-(3-chlorophenyl)-3-(phenylthio)acrylimidate $^1$H-NMR (CDCl$_3$) δ(ppm): 5.75(0.83H, d J=15.0 Hz), 5.81 (0.17H, d J=15.0 Hz), 6.56-6.63(0.83H, m), 6.71-6.77 (0.83H, m), 6.92-7.54(12.34H, m), 7.74(0.83H,d J=15.0 Hz), 8.00(0.17H, d J=15.0 Hz)

The stereochemistry of the —CH═CH— bond was mixture of E and Z.

EXAMPLE 41

Compound (41): Phenyl N-(4-chlorophenyl)-3-(phenylthio)acrylimidate $^1$H-NMR (CDCl$_3$) δ(ppm): 5.76(1H, d J=15.1 Hz), 6.64 (2H, d J=8.5 Hz), 7.05-7.56(12H, m), 7.72(1H, d J=15.1 Hz)

The stereochemistry of the —CH═CH— bond was mixture of E and Z.

EXAMPLE 42

Compound (42): Phenyl N-(2-methoxyphenyl)-3-(phenylthio)acrylimidate $^1$H-NMR (CDCl$_3$) δ(ppm): 3.75(3H,s), 5.82(1H,dJ=15.1 Hz), 6.69(1H, d J=6.5 Hz), 6.78-7.03(5H, m), 7.21-7.50(8H, m), 7.66(1H, d J=15.1 Hz).

The stereochemistry of the —CH═CH— bond was E.

EXAMPLE 43

Compound (43): Phenyl N-(4-chlorophenyl)-3-(phenoxy)acrylimidate m.p.: 98-100° C.

$^1$H-NMR (CDCl$_3$) δ(ppm): 5.70(1H, d, J=12.0 Hz), 6.72-6.74(2H, m), 7.05-7.41(12H, m), 7.83(1H, d, J=12.0 Hz).

The stereochemistry of the —CH═CH— bond was E.

EXAMPLE 44

Compound (44): Phenyl N-(3-methoxyphenyl)-3-(phenylthio)acrylimidate $^1$H-NMR (CDCl$_3$) δ(ppm): 3.75(3H,s), 5.91(1H, d J=15.0 Hz), 6.27-6.35(2H, m), 6.53-6.60(1H, m), 6.82(2H,dJ=7.5 Hz), 6.92(1H, d J=7.5 Hz), 7.07-7.52(8H, m), 7.70(1H,d J=15.0 Hz).

The stereochemistry of the —CH═CH— bond was E.

EXAMPLE 45

Compound (45): Phenyl N-(3-chlorophenyl)-3-(phenoxy)acrylimidate $^1$H-NMR (CDCl$_3$) δ(ppm): 5.71(1H, d, J=12.0 Hz), 6.68 (1H, d, J=8.0 Hz), 6.81(1H, s), 6.99-7.41(12H, m), 7.83(1H, d, J=12.0 Hz).

The stereochemistry of the —CH═CH— bond was E.

EXAMPLE 46

Compound (46): Phenyl N-(4-methoxyphenyl)-3-(phenylthio)acrylimidate $^1$H-NMR (CDCl$_3$) δ(ppm): 3.77(3H,s), 5.94(1H,d J=15.1 Hz), 6.67(2H, d J=8.7 Hz), 6.74-6.86(6H, m), 6.92(2H, t J=7.5 Hz), 7.17-7.54(4H, m), 7.68(1H, d J=15.1 Hz).
The stereochemistry of the —CH=CH— bond was E.

EXAMPLE 47

Compound (47): Phenyl N-(4-pyridyl)-3-(phenylthio)acrylimidate $^1$H-NMR (CDCl$_3$) δ(ppm): 5.81(0.83H, d J=15.2 Hz), 6.13 (0.17H, d J=9.9 Hz), 7.08(1H, d J=8.5 Hz), 7.32-7.57 (12.17H, m), 8.00(0.83H, d J=15.2 Hz)
The stereochemistry of the —CH=CH— bond was mixture of E and Z.

EXAMPLE 48

Compound (48): Phenyl N-(2-fluorophenyl)-3-(phenylthio)acrylimidate $^1$H-NMR (CDCl$_3$) δ(ppm): 5.78(d, J=15.5 Hz), 5.81(d, J=15.5 Hz) total 1H, 6.72-6.80(0.67H, m), 6.91-7.58(13.33H, m), 7.75(0.67H,d, J=15.0 Hz), 8.00(0.33H, d, J=15.0 Hz)
The stereochemistry of the —CH=CH— bond was mixture of E and Z.

EXAMPLE 49

Compound (49): Phenyl N-(3-pyridyl)-3-(phenylthio)acrylimidate $^1$H-NMR (CDCl$_3$) δ(ppm): 5.72(d J=15.2 Hz), 5.82(d J=10.9 Hz) total 1H, 7.08-7.53(12.3H, m), 7.79(0.7H, d J=15.2 Hz), 8.03-8.08(1H, m), 8.22-8.31(1H, m)
The stereochemistry of the —CH=CH— bond was mixture of E and Z.

EXAMPLE 50

Compound (50): Phenyl N-(4-fluorophenyl)-3-(phenylthio)acrylimidate $^1$H-NMR (CDCl$_3$) δ(ppm): 5.80(d, J=15.5 Hz), 5.81(d, J=15.5 Hz) total 1H, 6.63-6.68(2H, m), 6.86-6.93(2H, m), 7.18-7.56(10H, m), 7.71(0.8H, d, J=15.5 Hz) 8.00(0.2H, d, J=15.5 Hz)
The stereochemistry of the —CH=CH— bond was mixture of E and Z.

EXAMPLE 51

Compound (51): Phenyl N-(3-fluorophenyl)-3-(phenylthio)acrylimidate $^1$H-NMR (CDCl$_3$) δ(ppm): 5.78(d, J=15.2 Hz), 5.81(d, J=14.7 Hz) total 1H, 6.40-6.53(2H, m), 6.65-6.73(1H, m), 7.05-7.55(11H, m), 7.73(0.7H, d, J=15.2 Hz) 8.00(0.3H, d, J=14.7 Hz).
The stereochemistry of the —CH=CH— bond was E.

EXAMPLE 52

Compound (52): Phenyl N-(4-trifluoromethylphenyl)-3-(phenylthio)acrylimidate $^1$H-NMR (CDCl$_3$) δ(ppm): 5.60(0.77H,d, J=15.0 Hz), 5.75 (0.15H,d, J=1 0.6 Hz), 5.81(0.04H,d, J=14.7 Hz), 5.82(0.04H,d, J=10.4 Hz), 6.73-6 0.82(2H, m), 7.13-7.62 (12.19H, m), 7.75(0.77H, d, J=15.0 Hz) 8.00(0.04H, d, J=15.0 Hz)
The stereochemistry of the —CH=CH— bond was mixture of E and Z.

EXAMPLE 53

Compound (53): Phenyl N-(4-bromophenyl)-3-(phenylthio)acrylimidate $^1$H-NMR (CDCl$_3$) δ(ppm): 5.74(d, J=14.5 Hz), 5.81(d, J=15.2 Hz) total 0.95H, 6.13(0.05H,d, J=10.1 Hz), 6.59(1H, d, J=8.5 Hz), 7.06-7.11(0 0.57H, m), 7.14-7.56(12.48H, m), 7.72(0.63H, d, J=15.2 Hz), 8.00(0.32H,d, J=14.5 Hz)
The stereochemistry of the —CH=CH— bond was mixture of E and Z.

EXAMPLE 54

Compound (54): Phenyl N-(4-methylphenyl)-3-(phenylthio)acrylimidate $^1$H-NMR (CDCl$_3$) δ(ppm): 2.29(3H,s), 5.81(0.17H, d J=15.2 Hz), 5.94(0.83H, d J=15.2 Hz), 6.63(2H, d J=8.2 Hz), 6.98-7.57(12H, m), 7.67(0.83H, d J=15.2 Hz), 8.00(0.17H, d J=15.2 Hz).
The stereochemistry of the —CH=CH— bond was E.

EXAMPLE 55

Compound (55): Phenyl N-(4-nitrophenyl)-3-(phenylthio)acrylimidate $^1$H-NMR (CDCl$_3$) δ(ppm): 5.57(0.77H, dJ=15.2 Hz), 5.67 (dJ=15.2 Hz), 5.72(d J=10.3 Hz) total 0.23H, 6.79(2H, d J=8.7 Hz), 7.13-7.54(10.23H, m), 7.81(0.77H, d J=15.2 Hz), 8.03-8.12(1.54H,m), 8.12-8.21(0.46H,m)
The stereochemistry of the —CH=CH— bond was mixture of E and Z.

EXAMPLE 56

Compound (56): Phenyl N-(4-methylphenyl)-3-(phenoxy)acrylimidate m.p.: 73-74° C.
$^1$H-NMR (CDCl$_3$) δ(ppm): 2.29(3H,s), 5.78(1H, d J=12.1 Hz), 6.70(2H, d J=7.7 Hz), 7.05-7.07(4H, m), 7.12-7.25(4H, m), 7.33-7.40(4H, m), 7.79(1H, d J=12.1 Hz).
The stereochemistry of the —CH=CH— bond was E.

EXAMPLE 57

Compound (57): Phenyl N-(4-methoxyphenyl)-3-(phenoxy)acrylimidate $^1$H-NMR (CDCl$_3$) δ(ppm): 3.77(3H,s), 5.80(1H, d J=12.1 Hz), 6.72-6.97(4H, m), 7.05-7.07(2H, m), 7.12-7.24(4H, m), 7.33-7.39(4H, m), 7.80(1H,d J=12.1 Hz).
The stereochemistry of the —CH=CH— bond was E.

EXAMPLE 58

Compound (58): Phenyl N-(2-chlorophenyl)-3-(phenoxy)acrylimidate $^1$H-NMR (CDCl$_3$) δ(ppm): 5.59(1H, d J=12.0 Hz), 6.81 (1H, d J=7.5 Hz), 6.93-6.97(1H, m), 7.06-7.07(2H, m), 7.13-7.21(3H, m), 7.30-7.42(7H, m), 7.84(1H,d J=12.0 Hz).
The stereochemistry of the —CH=CH— bond was E.

EXAMPLE 59

Compound (59): Phenyl N-(3,4-dichlorophenyl)-3-(phenoxy)acrylimidate $^1$H-NMR (CDCl$_3$) δ(ppm): 5.67(1H, d J=11.8 Hz), 6.64 (1H, dd J=8.5, 2.4 Hz), 6.91(1H, d J=2.4 Hz), 7.07(2H, d J=8.0 Hz), 7.15-7.41(9H, m), 7.85(1H,d J=11.8 Hz).
The stereochemistry of the —CH=CH— bond was E.

EXAMPLE 60

Compound (60): Benzyl N-phenyl-3-(phenylthio)acrylimidate m.p.: 77-81° C.
$^1$H-NMR (CDCl$_3$) δ(ppm): 5.29(1.67H,s), 5.43(0.33H,s), 5.75(0.16H, d J=10.9 Hz), 5.81(0.84H, d J=15.2 Hz), 6.75-7.62(16H, m)
The stereochemistry of the —CH=CH— bond was mixture of E and Z.

EXAMPLE 61

Compound (61): 3-Methylbenzyl N-phenyl-3-(phenylthio)acrylimidate $^1$H-NMR (CDCl$_3$) δ(ppm): 2.37(2.25H,s), 2.39(0.75H,s), 5.25(1.5H,s), 5.39(0.5H,s), 5.75(0.25H,d J=10.9 Hz), 5.80 (0.75H,d J=15.2 Hz), 6.75-7.47(15H, m)
The stereochemistry of the —CH=CH— bond was mixture of E and Z.

EXAMPLE 62

Compound (62): Phenyl N-(4-cyanophenyl)-3-(phenylthio)acrylimidate $^1$H-NMR (CDCl$_3$) δ(ppm): 5.58(0.91H, d J=14.9 Hz), 5.71 (0.09H,d J=10.9 Hz), 6.72-6.96(3H, m), 7.10-7.61(11.09H, m), 7.79(0.91H, d J=14.9 Hz)
The stereochemistry of the —CH=CH— bond was mixture of E and Z.

EXAMPLE 63

Compound (63): Phenyl N-(4-ethylphenyl)-3-(phenylthio)acrylimidate $^1$H-NMR (CDCl$_3$) δ(ppm): 1.21(3H,t J=7.5 Hz), 2.58(2H, q J=7.5 Hz), 5.81(0.21H, d J=15.0 Hz), 5.93(0.79H,d J=15.4 Hz), 6.65(2H,d J=8.0 Hz), 7.01-7.57(12H, m), 7.67(0.79H, d J=15.4 Hz), 8.00(0.21H, d J=15.0 Hz).
The stereochemistry of the —CH=CH— bond was E.

EXAMPLE 64

Compound (64): Phenyl N-(3,5-dichlorophenyl)-3-(phenoxy)acrylimidate $^1$H-NMR (CDCl$_3$) δ(ppm): 5.66(1H, d J=12.0 Hz), 6.71 (2H,s), 7.02-7.25(6H,m), 7.36-7.39(5H,m), 7.86(1H,d J=12.0 Hz).
The stereochemistry of the —CH=CH— bond was E.

EXAMPLE 65

Compound (65): Phenyl N-(3,4,5-trichlorophenyl)-3-(phenoxy)acrylimidate $^1$H-NMR (CDCl$_3$) δ(ppm): 5.65(1H, d J=11.8 Hz), 6.85 (2H,s), 7.08-7.10(2H,m), 7.16-7.23(4H,m), 7.36-7.42(4H, m), 7.87(1H,d J=11.2 Hz).
The stereochemistry of the —CH=CH— bond was E.

EXAMPLE 66

Compound (66): 3-Pyridyl N-phenyl-3-(phenoxy)acrylimidate $^1$H-NMR (CDCl$_3$) δ(ppm): 5.88(1H, d J=15.0 Hz), 6.69-6.75(2H,m), 6.98-7.05(1H,m), 7.18-7.61(9H,m), 7.72(1H,d J=15.0 Hz), 8.40-8.55(2H,m).
The stereochemistry of the —CH=CH— bond was E.

EXAMPLE 67

Compound (67): 4-Chlorobenzyl N-phenyl-3-(phenylthio)acrylimidate $^1$H-NMR (CDCl$_3$) δ(ppm): 5.25(1.6H,s),5.38(0.4H,s), 5.74(0.2H,d J=11.1 Hz),5.79(0.8H,d J=15.2 Hz),6.72-7.55 (15H, m)
The stereochemistry of the —CH=CH— bond was mixture of E and Z.

EXAMPLE 68

Compound (68): 2-Chloropyridine-5-ylmethyl N-phenyl-3-(phenylthio)acrylimidate $^1$H-NMR (CDCl$_3$) δ(ppm): 5.29(1.6H,s), 5.41(0.4H,s), 5.74(0.2H,d J=11.1 Hz), 5.78(0.8H,d J=15.2 Hz), 6.71-7.44 (12H, m), 7.73(0.8H,d J=8.2 Hz), 7.91(0.2H,d J=8.1 Hz), 8.47(0.8H,s), 8.64(0.2H,s)
The stereochemistry of the —CH=CH— bond was mixture of E and Z.

EXAMPLE 69

Compound (69): Phenyl N-(3-methylphenyl)-3-(phenoxy)acrylimidate $^1$H-NMR (CDCl$_3$) δ(ppm): 2.29(3H,s), 5.77(1H, d J=11.8 Hz), 6.59-6.62(2H, m), 6.83(1H,d J=7.5 Hz), 7.05-7.24(7H, m), 7.35-7.40(4H, m), 7.80(1H,d J=11.8 Hz).
The stereochemistry of the —CH=CH— bond was E.

EXAMPLE 70

Compound (70): Phenyl N-(3,4-dimethylphenyl)-3-(phenoxy)acrylimidate $^1$H-NMR (CDCl$_3$) δ(ppm): 2.21(6H,s),5.81(1H, d J=11.8 Hz), 6.53-6.59(2H, m), 7.00-7.07(3H, m), 7.12-7.18(2H, m), 7.23-7.25(2H, m), 7.33-7.39(4H, m), 7.78(1H,d J=11.8 Hz).
The stereochemistry of the —CH═CH— bond was E.

EXAMPLE 71

Compound (71): Phenyl N-[3-(1-methylethyl)phenyl]-3-(phenoxy)acrylimidate $^1$H-NMR (CDCl$_3$) δ(ppm): 1.22(6H,d J=6.8 Hz),2.84(1H, sept J=6.8 Hz), 5.76(1H, d J=11.8 Hz), 6.60-6.66(2H, m), 6.88(1H, d J=7.5 Hz), 7.06(2H,d J=7.7 Hz), 7.14-7.25(5H, m), 7.33-7.40(4H, m), 7.79(1H,d J=11.8 Hz).
The stereochemistry of the —CH═CH— bond was E.

EXAMPLE 72

Compound (72): Phenyl N-[4-(1-methylethyl)phenyl]-3-(phenylthio)acrylimidate $^1$H-NMR (CDCl$_3$) δ(ppm): 1.21(6H,dJ=6.8 Hz), 2.84(1H, sept J=6.8 Hz), 5.81(0.07H, d J=15.4 Hz),5.92(0.93H, d J=15.4 Hz), 6.65(2H, d J=8.2 Hz), 7.01-7.58(12H, m), 7.68 (0.93H, d J=15.4 Hz), 8.01(0.07H,d J=15.4 Hz).
The stereochemistry of the —CH═CH— bond was E.

EXAMPLE 73

Compound (73): Phenyl N-(4-propylphenyl)-3-(phenylthio)acrylimidate $^1$H-NMR (CDCl$_3$) δ(ppm): 0.91(3H,t J=7.2 Hz),2.22(2H, sept J=7.2 Hz), 2.52(2H,t J=7.2 Hz), 5.81(0.09H, d J=15.2 Hz), 5.92(0.91H, d J=15.3 Hz), 6.64(2H, d J=8.5 Hz), 6.97-7.56(12H, m), 7.68(0.91H, d J=15.3 Hz), 8.01(0.09H,d J=15.2 Hz).
The stereochemistry of the —CH═CH— bond was E.

EXAMPLE 74

Compound (74): Phenyl N-[4-(1-methylethyl)phenyl]-3-(phenoxy)acrylimidate $^1$H-NMR (CDCl$_3$) δ(ppm): 1.23(6H,dJ=6.9 Hz),2.85(1H, sept J=6.9 Hz), 5.81(1H, d J=12.1 Hz), 6.71-6.73(2H, m), 7.05-7.18(6H, m), 7.22-7.25(2H, m), 7.33-7.39(4H, m), 7.79 (1H, d J=12.1 Hz).
The stereochemistry of the —CH═CH— bond was E.

EXAMPLE 75

Compound (75): Phenyl N-(4-fluorophenyl)-3-(phenoxy)acrylimidate $^1$H-NMR (CDCl$_3$) δ(ppm): 5.72(1H, d J=11.8 Hz), 6.71-6.77(2H, m), 6.92-6.97(2H, m), 7.05-7.08(2H, m), 7.14-7.23 (4H, m), 7.33-7.41(4H, m),7.82(1H, d J=11.8 Hz).
The stereochemistry of the —CH═CH— bond was E.

EXAMPLE 76

Compound (76): Phenyl N-[4-(1,1-dimethylethyl)phenyl]-3-(phenylthio)acrylimidate $^1$H-NMR (CDCl$_3$) δ(ppm): 1.59(9H,s), 5.81(0.33H,d J=15.0 Hz), 5.92(0.67H, d J=15.0 Hz), 6.65(2H, d J=8.5 Hz), 7.06-7.57(12H, m), 7.67(0.67H, d J=15.0 Hz), 8.00(0.33H, d J=15.0 Hz).
The stereochemistry of the —CH═CH— bond was E.

EXAMPLE 77

Compound (77): Phenyl N-(4-bromophenyl)-3-(phenoxy)acrylimidate $^1$H-NMR (CDCl$_3$) δ(ppm): 5.69(1H, d J=11.8 Hz), 6.68 (2H, d J=8.7 Hz), 7.05-7.07(2H, m), 7.14-7.22(4H, m), 7.34-7.41(6H, m), 7.82(1H, d J=11.8 Hz).
The stereochemistry of the —CH═CH— bond was E.

EXAMPLE 78

Compound (78): Phenyl N-(3-methoxyphenyl)-3-(phenoxy)acrylimidate $^1$H-NMR (CDCl$_3$) δ(ppm): 3.77(3H,s), 5.77(1H, d J=12.1 Hz), 6.31-6.39(2H, m), 6.57-6.59(1H, m), 7.06(2H, d J=7.7 Hz), 7.14-7.24(5H, m), 7.33-7.41(4H, m), 7.80(1H, d J=12.1 Hz).
The stereochemistry of the —CH═CH— bond was E.

EXAMPLE 79

Compound (79): Phenyl 3-benzylthio-N-phenyl-acrylimidate $^1$H-NMR (CDCl$_3$) δ(ppm): 3.89(2H,s), 5.84(1H, dJ=15.2 Hz), 6.72(2H, d J=7.2 Hz), 7.01-7.05(1H, m), 7.14-7.31(10H, m), 7.34-7.38(2H, m), 7.58(1H, d J=15.2 Hz).
The stereochemistry of the —CH═CH— bond was E.

EXAMPLE 80

Compound (80): PhenylN-(4-iodophenyl)-3-(phenoxy) acrylimidate $^1$H-NMR (CDCl$_3$) δ(ppm): 5.69(1H, d J=12.0 Hz),6.57 (2H, d J=8.5 Hz), 7.06(2H,dJ=8.0 Hz), 7.11-7.21(4H,m), 7.34-7.41(4H,m), 7.55(2H, d J=8.5 Hz), 7.81(1H, d J=12.0 Hz).
The stereochemistry of the —CH═CH— bond was E.

EXAMPLE 81

Compound (81): Phenyl N-(indan-5-yl)-3-(phenoxy) acrylimidate $^1$H-NMR (CDCl$_3$) δ(ppm): 2.01-2.09(2H, m), 2.83-2.86 (4H, m), 5.83(1H, d J=12.0 Hz), 6.55-6.57(1H, m), 6.67(1H, brs), 7.05-7.24(7H, m), 7.33-7.39(4H, m), 7.78(1H, d J=12.0 Hz).
The stereochemistry of the —CH═CH— bond was E.

EXAMPLE 82

Compound (82): 2,5-Dichlorophenyl N-[4-(1-methylethyl)phenyl]-3-(phenylthio)acrylimidate $^1$H-NMR (CDCl$_3$) δ(ppm): 1.21(6H,d J=6.8 Hz), 2.84(1H, sept J=6.8 Hz), 5.87(1H, d J=15.1 Hz), 6.64-7.48(12H, m), 7.73(1H, d J=15.1 Hz).
The stereochemistry of the —CH=CH— bond was E.

EXAMPLE 83

Compound (83): 2-Naphtyl N-[4-(1-methylethyl)phenyl]-3-(phenylthio)acrylimidate $^1$H-NMR (CDCl$_3$) δ(ppm): 1.21(6H,dJ=6.8 Hz), 2.83(1H, sept J=6.8 Hz), 5.96(1H, d J=15.0 Hz), 6.66-7.82(17H, m).
The stereochemistry of the —CH=CH— bond was E.

EXAMPLE 84

Compound (84): Phenyl N-(4-methylthiophenyl)-3-(phenoxy)acrylimidate $^1$H-NMR (CDCl$_3$) δ(ppm): 2.45(3H,s), 5.75(1H,dJ=11.8 Hz), 6.57(2H, d, J=8.5 Hz), 7.06(2H,d, J=7.7 Hz), 7.13-7.23 (6H,m), 7.34-7.41(4H, m), 7.81(1H, d, J=11.8 Hz).
The stereochemistry of the —CH=CH— bond was E.

EXAMPLE 85

Compound (85): 5,6,7,8-Tetrahydro-2-naphtyl N-[4-(1-methylethyl)phenyl]-3-(phenylthio)acrylimidate $^1$H-NMR (CDCl$_3$) δ(ppm): 1.21(6H,d J=7.0 Hz), 1.72-1.82(4H, m), 2.67-2.90(5H, m), 5.89(1H, d J=14.9 Hz), 6.61-6.67(2H, m), 6.85-7.52(10H, m), 7.64(1H, d J=19.9 Hz).
The stereochemistry of the —CH=CH— bond was E.

EXAMPLE 86

Compound (86): Phenyl N-(benzo-1,4-dioxane-6-yl)-3-(phenoxy)acrylimidate $^1$H-NMR (CDCl$_3$) δ(ppm): 4.17-4.25(4H, m), 5.83(1H, d J=12.0 Hz), 6.28-6.35(2H, m), 6.75(1H, d J=8.5 Hz), 7.06-7.08(2H, m), 7.15-7.21(4H, m), 7.33-7.39(4H, m), 7.78(1H, d J=12.0 Hz).
The stereochemistry of the —CH=CH— bond was E.

EXAMPLE 87

Compound (87): 3-Methylphenyl N-[4-(1-methylethyl)phenyl]-3-(phenylthio)acrylimidate $^1$H-NMR (CDCl$_3$) δ(ppm): 1.21(6H,d J=7.0 Hz), 2.34(3H, s), 2.83(1H, sept J=7.0 Hz), 5.91(1H, dJ=15.2 Hz), 6.64-7.47 (13H, m), 7.65(1H, d J=15.2 Hz).
The stereochemistry of the —CH=CH— bond was E.

EXAMPLE 88

Compound (88): 4-Methylphenyl N-[4-(1-methylethyl)phenyl]-3-(phenylthio)acrylimidate $^1$H-NMR (CDCl$_3$) δ(ppm): 1.21(6H,d J=6.9 Hz), 2.31(3H, s), 2.83(1H, sept J=6.9 Hz), 5.90(1H,dJ=15.2 Hz), 6.62-7.44 (13H, m), 7.66(1H, d J=15.2 Hz).
The stereochemistry of the —CH=CH— bond was E.

EXAMPLE 89

Compound (89): 4-(1-Methylethyl)phenyl N-[4-(1-methylethyl)phenyl]-3-(phenylthio)acrylimidate $^1$H-NMR (CDCl$_3$) δ(ppm): 1.20-1.23(12H,m), 2.85(2H, m), 5.91(1H, d J=15.2 Hz), 6.64-7.43(13H, m), 7.66(1H, d J=15.2 Hz).
The stereochemistry of the —CH=CH— bond was E.

EXAMPLE 90

Compound (90): 4-(1,1-Dimethylethyl)phenyl N-[4-(1-methylethyl)phenyl]-3-(phenylthio)acrylimidate $^1$H-NMR (CDCl$_3$) δ(ppm): 1.21(6H,d J=6.8 Hz), 1.31(9H, s), 2.83(1H, sept J=6.8 Hz), 5.91(1H,dJ=15.1 Hz), 6.64-7.47 (13H,m), 7.65(1H, d J=15.1 Hz).
The stereochemistry of the —CH=CH— bond was E.

EXAMPLE 91

Compound (91): 2,3-Dimethylphenyl N-[4-(1-methylethyl)phenyl]-3-(phenylthio)acrylimidate $^1$H-NMR (CDCl$_3$) δ(ppm): 1.20(6H,dJ=7.2 Hz), 2.16(3H, s), 2.29(3H,s), 2.77-2.88(1H,m), 5.90(1H,dJ=15.6 Hz), 6.56-7.54(12H,m), 7.70(1H,d J=15.6 Hz).
The stereochemistry of the —CH=CH— bond was E.

EXAMPLE 92

Compound (92): 2,5-Difluorophenyl N-[4-(1-methylethyl)phenyl]-3-(phenylthio)acrylimidate $^1$H-NMR (CDCl$_3$) δ(ppm): 1.20(6H,dJ=6.8 Hz),2.84(1H, sept J=6.8 Hz), 5.86(1H, d J=15.2 Hz), 6.64-7.48(12H, m), 7.69(1H, d J=15.2 Hz).
The stereochemistry of the —CH=CH— bond was E.

EXAMPLE 93

Compound (93): 2,4,5-Trichlorophenyl N-[4-(1-methylethyl)phenyl]-3-(phenylthio)acrylimidate $^1$H-NMR (CDCl$_3$) δ(ppm): 1.21(6H,dJ=7.0 Hz),2.84(1H, sept J=7.0 Hz), 5.85(1H, d J=15.2 Hz), 6.63-7.48(11H, m), 7.73(1H, d J=15.2 Hz)
The stereochemistry of the —CH=CH— bond was E.

EXAMPLE 94

Compound (94): 1-Naphtyl N-[4-(1-methylethyl)phenyl]-3-(phenylthio)acrylimidate $^1$H-NMR (CDCl$_3$) δ(ppm): 1.19(6H,d J=7.0 Hz),2.81(1H, sept J=7.0 Hz), 6.00(1H, d J=15.2 Hz), 6.58(1H, d J=8.2 Hz),7.01-7.97(15H, m).
The stereochemistry of the —CH=CH— bond was E.

EXAMPLE 95

Compound (95): 4-Cyanophenyl N-[4-(1-methylethyl)phenyl]-3-(phenylthio)acrylimidate $^1$H-NMR (CDCl$_3$) δ(ppm): 1.22(6H,d J=7.1 Hz), 2.85(1H, sept J=7.1 Hz), 5.89(1H, d J=15.1 Hz), 6.64(2H, d J=8.3 Hz), 7.07-7.69(12H, m).
The stereochemistry of the —CH=CH— bond was E.

EXAMPLE 96

Compound (96): 4-Nitrophenyl N-[4-(1-methylethyl)phenyl]-3-(phenylthio)acrylimidate $^1$H-NMR (CDCl$_3$) δ(ppm): 1.22(6H,d J=7.2 Hz),2.85(1H, sept J=7.2 Hz), 5.90(1H, d J=15.2 Hz), 6.65(2H, d J=8.2 Hz), 7.08-7.45(9H, m), 7.69(1H,d J=15.2 Hz), 8.24(2H,d J=8.9 Hz).
The stereochemistry of the —CH=CH— bond was E.

EXAMPLE 97

Compound (97): Benzo-1,3-dioxol-5-yl N-[4-(1-methylethyl)phenyl]-3-(phenylthio)acrylimidate $^1$H-NMR (CDCl$_3$) δ(ppm): 1.21(6H,d J=6.8 Hz),2.84(1H, sept J=6.8 Hz), 5.88(1H, d J=15.2 Hz), 5.95(2H,s), 6.61-7.44 (12H, m), 7.64(1H, d J=15.2 Hz).
The stereochemistry of the —CH=CH— bond was E.

EXAMPLE 98

Compound (98): Phenyl 3-(phenoxy)-N-(4-phenylthiophenyl)acrylimidate $^1$H-NMR (CDCl$_3$) δ(ppm): 5.74(1H, d J=12.0 Hz),6.78 (2H, d J=8.5 Hz), 7.06-7.24(11H, m), 7.34-7.41(6H, m), 7.84 (0.83H, d J=12.0 Hz), 7.99(0.17H, d J=12.0 Hz).
The stereochemistry of the —CH=CH— bond was E.

EXAMPLE 99

Compound (99): Phenyl N-phenyl-3-(phenylsulfonyl)acrylimidate

Phenyl N-phenyl-3-(phenylthio)acrylimidate (3.65 g) was dissolved to chloroform (50 ml), m-CPBA (70%: 5.42 g) was added thereto in five portion under ice-cooling, then it was stirred for two hours at the same temperature. Then chloroform (50 ml) and aqueous saturated sodium bicarbonate solution (75 ml) were added and extracted. The organic layer was washed with aqueous saturated sodium chloride solution (50 ml), dried, distilled off the solvent. The residue was subjected to silica gel column chromatography (hexane:ethyl acetate=3:1) to obtain phenyl N-phenyl-3-(phenylsulfonyl) acrylimidate (2.08 g) as light yellow crystal.
m.p.: 110-116° C.
$^1$H-NMR (CDCl$_3$) δ(ppm): 6.73-6.75H (2H, m), 7.04(1H, d, J=15.0 Hz), 7.10-7.91(14H, m)
The stereochemistry of the —CH=CH— bond was mixture of E and Z.

EXAMPLE 100

Compound (100): Phenyl 3-(2-bromophenylthio)-N-phenylacrylimidate

Sodium hydride (60% in oil: 0.026 g) was suspended to DMF (2 ml), and 2-bromothiophenol (0.10 g) was added thereto under ice-cooling. Furthermore, phenyl N-phenyl-3-(phenylsulfonyl)acrylimidate (0.20 g) was added thereto, and stirred for one hour under ice-cooling. After the reaction, water and ethyl acetate were added to the reaction mixture, and extracted. The organic layer was washed with aqueous saturated sodium chloride solution, dried, and distilled off the solvent. The residue was subjected to silica gel column chromatography (hexane:ethyl acetate=10:1) to obtain phenyl 3-(2-bromophenylthio)-N-phenylacrylimidate (0.19 g).
$^1$H-NMR (CDCl$_3$) δ(ppm): 5.90(1H,d, J=15.1 Hz), 6.74 (2H,d, J=7.6 Hz), 6.98-7.64(13H, m).
The stereochemistry of the —CH=CH— bond was E.

Compounds (101) to (130) were synthesized in a similar manner as the Example 100

EXAMPLE 101

Compound (101): Phenyl 3-(3-bromophenylthio)-N-phenylacrylimidate $^1$H-NMR (CDCl$_3$) δ(ppm): 5.92(1H,d, J=15.2 Hz), 6.73 (2H,d, J=7.7 Hz), 6.98-7.67(13H, m).
The stereochemistry of the —CH=CH— bond was E.

EXAMPLE 102

Compound (102): Phenyl 3-(4-bromophenylthio)-N-phenylacrylimidate $^1$H-NMR (CDCl$_3$) δ(ppm): 5.85(1H,d, J=15.4 Hz), 6.71 (2H,d, J=7.8 Hz), 7.02-7.46(12H,m), 7.62(1H, d, J=15.1 Hz).
The stereochemistry of the —CH=CH— bond was E.

EXAMPLE 103

Compound (103): Phenyl 3-(4-fluorophenylthio)-N-phenylacrylimidate $^1$H-NMR (CDCl$_3$) δ(ppm): 5.76(1H,d, J=15.2 Hz), 6.70 (2H,d, J=7.2 Hz), 6.98-7.42(12H, m), 7.61(1H, d, J=15.2 Hz).
The stereochemistry of the —CH=CH— bond was E.

EXAMPLE 104

Compound (104): Phenyl 3-(2-fluorophenylthio)-N-phenylacrylimidate $^1$H-NMR (CDCl$_3$) δ(ppm): 5.81(1H,d, J=14.9 Hz), 6.72 (2H,d, J=7.3 Hz), 6.97-7.46(12H, m), 7.58(1H, d, J=15.1 Hz).
The stereochemistry of the —CH=CH— bond was E.

EXAMPLE 105

Compound (105): Phenyl 3-(2-methylphenylthio)-N-phenylacrylimidate $^1$H-NMR (CDCl$_3$) δ(ppm): 2.38(3H,s),5.65(1H,d, J=15.0 Hz), 6.69(2H, d, J=7.5 Hz), 6.95-7.42(12H, m), 7.61(1H, d, J=15.0 Hz).
The stereochemistry of the —CH=CH— bond was E.

EXAMPLE 106

Compound (106): Phenyl 3-(3-methylphenylthio)-N-phenylacrylimidate $^1$H-NMR (CDCl$_3$) δ(ppm): 2.32(3H,s),5.87(1H,d, J=15.2 Hz), 6.73(2H, d, J=7.2 Hz), 6.98-7.39(12H, m), 7.69(1H,d, J=15.2 Hz).
The stereochemistry of the —CH=CH— bond was E.

EXAMPLE 107

Compound (107): Phenyl 3-(3-methoxyphenylthio)-N-phenylacrylimidate $^1$H-NMR (CDCl$_3$) δ(ppm): 3.79(3H,s), 5.91(1H,d, J=15.2 Hz), 6.73(2H, d, J=7.5 Hz), 6.83-7.39(12H, m), 7.70(1H, d, J=15.0 Hz).
The stereochemistry of the —CH═CH— bond was E.

EXAMPLE 108

Compound (108): Phenyl 3-(4-nitrophenylthio)-N-phenylacrylimidate $^1$H-NMR (CDCl$_3$) δ(ppm): 6.15(1H,d, J=15.2 Hz), 6.76 (2H,d, J=7.2 Hz), 7.03-7.53(10H, m), 7.70(1H,d, J=15.2 Hz), 8.19(2H, d, J=8.9 Hz).
The stereochemistry of the —CH═CH— bond was E.

EXAMPLE 109

Compound (109): Phenyl N-phenyl-3-(4-pyridylthio)acrylimidate $^1$H-NMR (CDCl$_3$) δ(ppm): 6.23(1H,d, J=15.4 Hz), 6.78 (2H,d, J=7.3 Hz), 7.04-7.42(10H,m), 7.74(1H,d, J=15.4 Hz), 8.52(2H,d, J=6.1 Hz).
The stereochemistry of the —CH═CH— bond was E.

EXAMPLE 110

Compound (110): Phenyl N-phenyl-3-(2-trifluoromethylphenylthio)acrylimidate $^1$H-NMR (CDCl$_3$) δ(ppm): 5.88(1H,d, J=15.0 Hz), 6.72 (2H,d, J=7.5 Hz), 6.98-7.70(13H,m).
The stereochemistry of the —CH═CH— bond was E.

EXAMPLE 111

Compound (111): Phenyl N-phenyl-3-(3-trifluoromethylphenylthio)acrylimidate m.p.: 79-81° C.
$^1$H-NMR (CDCl$_3$) δ(ppm): 5.90(1H,d, J=15.2 Hz), 6.72 (2H,d, J=7.5 Hz), 6.98-7.68(13H,m).
The stereochemistry of the —CH═CH— bond was E.

EXAMPLE 112

Compound (112): Phenyl 3-(3,5-dichlorophenylthio)-N-phenylacrylimidate m.p.: 126-131° C.
$^1$H-NMR (CDCl$_3$) δ(ppm): 5.97(1H,d, J=15.2 Hz), 6.74 (2H,d, J=7.2 Hz), 7.01-7.41(11H, m), 7.60(1H, d, J=15.2 Hz).
The stereochemistry of the —CH═CH— bond was E.

EXAMPLE 113

Compound (113): Phenyl 3-(3-fluorophenylthio)-N-phenylacrylimidate $^1$H-NMR (CDCl$_3$) δ(ppm): 5.94(1H,d, J=15.2 Hz), 6.74 (2H,d, J=7.7 Hz), 6.97-7.40(12H, m), 7.66(1H, d, J=15.2 Hz).
The stereochemistry of the —CH═CH— bond was E.

EXAMPLE 114

Compound (114): Phenyl N-phenyl-3-(2-pyrimidinylthio)acrylimidate $^1$H-NMR (CDCl$_3$) δ(ppm): 6.26(1H,d, J=15.9 Hz), 6.80 (2H,d, J=8.0 Hz), 7.04-7.43(9H, m), 8.59-8.63(3H, m).
The stereochemistry of the —CH═CH— bond was E.

EXAMPLE 115

Compound (115): Phenyl N-phenyl-3-(2-pyridylthio)acrylimidate $^1$H-NMR (CDCl$_3$) δ(ppm): 6.21(1H,d, J=15.7 Hz), 6.79 (2H,d, J=7.2 Hz), 7.02-7.59(11H, m), 8.49-8.53(2H, m).
The stereochemistry of the —CH═CH— bond was E.

EXAMPLE 116

Compound (116): Phenyl 3-(1-methyl-2-imidazolylthio)-N-phenylacrylimidate $^1$H-NMR (CDCl$_3$) δ(ppm): 3.63(3H,s), 5.71(1H,d, J=15.2 Hz), 6.71(2H, d, J=7.5 Hz), 6.95-7.39(10H, m), 7.61(1H, d, J=15.0 Hz).
The stereochemistry of the —CH═CH— bond was E.

EXAMPLE 117

Compound (117): Phenyl 3-(4-chlorophenylthio)-N-phenylacrylimidate m.p.: 75.5° C.
$^1$H-NMR (CDCl$_3$) δ(ppm): 5.84(1H, d J=15.1 Hz), 6.69-6.76(2H, m), 6.98-7.05(1H, m), 7.15-7.44(11H, m), 7.62(1H, d J=15.1 Hz).
The stereochemistry of the —CH═CH— bond was E.

EXAMPLE 118

Compound (118): Phenyl 3-(4-methylphenylthio)-N-phenylacrylimidate $^1$H-NMR (CDCl$_3$) δ(ppm): 2.33(3H,s), 5.79(1H,d, J=15.2 Hz), 6.71(2H, d, J=7.2 Hz), 6.97-7.38(12H, m), 7.66(1H, d, J=15.2 Hz).
The stereochemistry of the —CH═CH— bond was E.

EXAMPLE 119

Compound (119): Phenyl 3-(2,4-dimethylphenylthio)-N-phenylacrylimidate $^1$H-NMR (CDCl$_3$) δ(ppm): 2.28(3H, s), 2.33(3H, s), 5.53 (1H, d, J=15.0 Hz), 6.66(2H, d, J=7.5 Hz), 6.94-7.38(11H, m), 7.57(1H, d, J=15.2 Hz).
The stereochemistry of the —CH═CH— bond was E.

EXAMPLE 120

Compound (120): Phenyl 3-(2,5-dimethylphenylthio)-N-phenylacrylimidate $^1$H-NMR (CDCl$_3$) δ(ppm): 2.27(3H, s), 2.33(3H, s), 5.63 (1H, d, J=15.0 Hz), 6.69(2H, d, J=7.5 Hz), 6.95-7.39(11H, m), 7.60(1H, d, J=15.2 Hz).
The stereochemistry of the —CH═CH— bond was E.

EXAMPLE 121

Compound (121): Phenyl 3-(3,5-dimethylphenylthio)-N-phenylacrylimidate $^1$H-NMR (CDCl$_3$) δ(ppm): 2.28(6H,s), 5.85(1H,d, J=15.0 Hz), 6.73(2H, d, J=7.2 Hz), 6.92-7.39(11H, m), 7.69(1H, d, J=15.2 Hz).
The stereochemistry of the —CH═CH— bond was E.

EXAMPLE 122

Compound (122): Phenyl 3-[2-(1-methylethyl)phenylthio]-N-phenylacrylimidate $^1$H-NMR (CDCl$_3$) δ(ppm): 1.18(6H, d, J=7.5 Hz), 3.36-3.43(1H, m), 5.65(1H,d, J=15.0 Hz), 6.67(2H,d, J=7.2 Hz), 6.93-7.42(12H, m), 7.64(1H, d, J=15.0 Hz).
The stereochemistry of the —CH═CH— bond was E.

EXAMPLE 123

Compound (123): Phenyl N-phenyl-3-(4-trifluoromethylphenylthio)acrylimidate $^1$H-NMR (CDCl$_3$) δ(ppm): 5.97(1H, d, J=15.0 Hz), 6.73 (2H, d, J=7.3 Hz), 6.99-7.59(12H, m), 7.67(1H, d, J=15.2 Hz).
The stereochemistry of the —CH═CH— bond was E.

EXAMPLE 124

Compound (124): Phenyl 3-(4,6-dimethyl-2-pyrimidinylthio)-N-phenylacrylimidate m.p.: 175-178° C.
$^1$H-NMR (CDCl$_3$) δ(ppm): 2.44(6H,s), 6.24(1H,d, J=15.9 Hz), 6.80(3H, d, J=6.9 Hz), 7.04-7.43(8H, m), 8.63(1H, d, J=15.9 Hz).
The stereochemistry of the —CH═CH— bond was E.

EXAMPLE 125

Compound (125): Phenyl 3-(3-chlorophenylthio)-N-phenylacrylimidate m.p.: 85° C.
$^1$H-NMR (CDCl$_3$) δ(ppm): 5.92(1H, d, J=15.2 Hz), 6.73 (2H, d, J=7.5 Hz), 7.01(1H, t, J=7.5 Hz), 7.15-7.45(11H, m), 7.64(1H, d, J=15.2 Hz).
The stereochemistry of the —CH═CH— bond was E.

EXAMPLE 126

Compound (126): Phenyl 3-(2-chlorophenylthio)-N-phenylacrylimidate $^1$H-NMR (CDCl$_3$) δ(ppm): 5.88(1H, d, J=15.0 Hz), 6.69-6.92(2H, m), 6.95-7.12(1H, m), 7.14-7.51(11H, m), 7.52(1H, d, J=15.0 Hz).
The stereochemistry of the —CH═CH— bond was E.

EXAMPLE 127

Compound (127): Phenyl 3-(2-chloro-5-pyridinylmethylthio)-N-phenylacrylimidate $^1$H-NMR (CDCl$_3$) δ(ppm): 3.85(2H,s), 5.77(1H,d, J=15.2 Hz), 6.70(2H, d, J=6.7 Hz), 7.02-7.52(11H,m), 8.23(1H,s).
The stereochemistry of the —CH═CH— bond was E.

EXAMPLE 128

Compound (128): Phenyl 3-(2-chloro-5-thiazolylmethylthio)-N-phenylacrylimidate $^1$H-NMR (CDCl$_3$) δ(ppm): 4.00(2H,s), 5.84(1H, d, J=15.1 Hz), 6.71-7.40(11H, m), 7.49(1H, d, J=15.1 Hz).
The stereochemistry of the —CH═CH— bond was E.

EXAMPLE 129

Compound (129): Phenyl 3-(2-chloro-5-thienylmethylthio)-N-phenylacrylimidate $^1$H-NMR (CDCl$_3$) δ(ppm): 4.00(2H,s), 5.86(1H, d, J=15.2 Hz), 6.52-7.39(12H, m), 7.53(1H,d, J=15.0 Hz).
The stereochemistry of the —CH═CH— bond was E.

EXAMPLE 130

Compound (130): Phenyl 3-(4-methylphenylthio)-N-(phenyl)thioacrylimidate $^1$H-NMR (CDCl$_3$) δ(ppm): 2.33(3H,s), 5.58(1H, d, J=14.5 Hz), 6.90-7.56(15H, m).
The stereochemistry of the —CH═CH— bond was E.

EXAMPLE 131

Compound (131): Phenyl N-phenyl-3-(N'-acetyl-N'-phenylamino)acrylimidate

To DMF (3 ml) solution of acetanilide (0.14 g) was added sodium hydride (60% in oil: 0.043 g) under ice-cooling, and DMF (2 ml) solution of phenyl N-phenyl-3-(phenylsulfonyl) acrylimidate (0.30 g) was added dropwise. It was stirred for two hours under ice-cooling and for one hour at room temperature. Ethyl acetate (100 ml) was added to the reaction mixture and was successively washed with water and aqueous saturated sodium chloride solution. The organic layer was dried over anhydrous magnesium sulfate, concentrated under reduced pressure. The residue was isolated and purified by silica gel column chromatography (hexane:ethyl acetate=3:1) to obtain phenyl N-phenyl-3-(N'-acetyl-N'-phenylamino) acrylimidate (0.050 g) as yellow crystal.
m.p.: 120° C.
$^1$H-NMR (CDCl$_3$) δ(ppm): 1.94(3H,s), 4.72(1H,d, J=14.0 Hz), 6.57(2H, d, J=7.5 Hz), 6.85-6.87(1H, m), 7.03-7.22(7H, m), 7.35-7.39(5H, m), 8.66(1H, d, J=14.0 Hz).
The stereochemistry of the —CH═CH— bond was E.

EXAMPLE 132

Compound (132): Phenyl 3-(N'-methyl-N'-phenylamino)-N-phenylacrylimidate phenyl 3-(phenoxy)-N-phenylacrylimidate (0.39 g) was dissolved to acetonitrile (5 ml), and N-methylaniline (0.20 g) and catalytic amount of N,N-dimethylaminopyridine were added at room temperature. It was stirred for two hours at the same temperature and for eight hours under heat refluxing. It was concentrated under reduced pressure. The residue was subjected to silica gel column chromatography (hexane:ethyl acetate=10:1) to obtain phenyl 3-(N'-methyl-N'-phenylamino)-N-phenylacrylimidate (0.17 g) as light brown crystal.

m.p.: 130-132° C.
$^1$H-NMR (CDCl$_3$) δ(ppm): 3.11(3H,s), 4.92(1H,d, J=16.0 Hz), 6.86(2H, d, J=8.0 Hz), 6.99-7.38(13H, m), 7.95(1H, d, J=16.0 Hz).

The stereochemistry of the —CH=CH— bond was E.
Compounds (133) to (135) were synthesized in a similar manner as the Example 132.

EXAMPLE 133

Compound (133): Phenyl 3-(N'-benzyl-N'-methylamino)-N-phenylacrylimidate $^1$H-NMR (CDCl$_3$) δ(ppm): 2.65(3H, s), 4.28(2H, s), 4.51 (0.25H, d, J=4.0 Hz), 4.59(0.75H, d, J=16.0 Hz), 6.76-7.46 (15H, m), 7.62(0.75H, d, J=16.0 Hz), 8.93(0.25H, d, J=4.0 Hz)

The stereochemistry of the —CH=CH— bond was mixture of E and Z.

EXAMPLE 134

Compound (134): Phenyl N-phenyl-3-(piperidino)acrylimidate m.p.: 127-128° C.
$^1$H-NMR (CDCl$_3$) δ(ppm): 1.56(6H, brs), 3.07(4H, brs), 4.58(1H, d, J=16.0 Hz), 6.82(2H,d, J=4.0 Hz), 6.94-6.97(1H, m), 7.11-7.37(8H, m).

The stereochemistry of the —CH=CH— bond was E.

EXAMPLE 135

Compound (135): Phenyl 3-(morphorino)-N-phenylacrylimidate m.p.: 146-147° C.
$^1$H-NMR (CDCl$_3$) δ(ppm): 3.10(4H,t, J=4.0 Hz), 3.68(4H, t, J=4.0 Hz), 4.67(1H,d, J=16.0 Hz), 6.81(2H,d, J=4.0 Hz), 6.95-6.99(1H, m), 7.11-7.38(8H, m).

The stereochemistry of the —CH=CH— bond was E.

EXAMPLE 136

Compound (136): Phenyl 3-ethylthio-N-phenylacrylimidate Ethanethiol (0.11 ml) was dissolved to DMF (3 ml), and sodium hydride (60% in oil: 60 mg) was added under ice-cooling, and stirred for 30 minutes at the same temperature. Phenyl 3-phenoxy-N-phenylacrylimidate (0.30 g) was dissolved to DMF (2 ml), and the obtained solution was added to the above mentioned thiolate solution under ice-cooling, and stirred for two hours at the same temperature and for two hours at room temperature. Ethyl acetate (100 ml) was added to the reaction solution, and it was successively washed with 1N aqueous sodium hydroxide solution, water and aqueous saturated sodium chloride solution, dried over magnesium sulfate (anhydrous), concentrated under reduced pressure. The residue was subjected to silica gel column chromatography (hexane:ethyl acetate=10:1) to obtain phenyl 3-ethylthio-N-phenylacrylimidate (0.14 g) as yellow oil.

$^1$H-NMR (CDCl$_3$) δ(ppm): 1.29(3H,t, J=8.0 Hz), 2.71(2H, q, J=8.0 Hz), 5.80(1H, d, J=16.0 Hz), 6.78(2H, d, J=8.0 Hz), 7.00-7.03(1H, m), 7.15-7.27(5H, m), 7.36-7.40(2H, m), 7.60 (1H, d, J=16.0 Hz).

The stereochemistry of the —CH=CH— bond was E.
Compounds (137) to (147) were synthesized in a similar manner as the Example 136.

EXAMPLE 137

Compound (137): Phenyl N-phenyl-3-(propylthio)acrylimidate $^1$H-NMR (CDCl$_3$) δ(ppm): 0.95(3H, t, J=8.0 Hz), 1.60-1.69(2H,m), 2.66(2H,t, J=8.0 Hz), 5.80(1H,d, J=16.0 Hz), 6.78(2H,d, J=8.0 Hz), 7.00-7.03(1H,m), 7.15-7.27(5H,m), 7.36-7.40(2H,m), 7.59(1H, d, J=16.0 Hz).

The stereochemistry of the —CH=CH— bond was E.

EXAMPLE 138

Compound (138): Phenyl 3-hexylthio-N-phenylacrylimidate $^1$H-NMR (CDCl$_3$) δ(ppm): 0.88(3H, t, J=8.0 Hz), 1.23-1.34(6H,m), 1.55-1.64(2H,m), 2.67(2H, t, J=8.0 Hz), 5.79 (1H, d, J=16.0 Hz), 6.78(2H, d, J=8.0 Hz), 7.00-7.03(1H, m), 7.15-7.27(5H, m), 7.36-7.40(2H, m), 7.60(1H, d, J=16.0 Hz).

The stereochemistry of the —CH=CH— bond was E.

EXAMPLE 139

Compound (139): Phenyl 3-(1-methylethylthio)-N-phenylacrylimidate $^1$H-NMR (CDCl$_3$) δ(ppm): 1.32(6H, d, J=8.0 Hz), 3.19 (1H, sept., J=8.0 Hz), 5.85(1H,d, J=16.0 Hz), 6.79(2H,d, J=8.0 Hz), 6.99-7.03(1H,m), 7.16-7.26(5H,m), 7.36-7.40 (2H,m), 7.62(1H, d, J=16.0 Hz).

The stereochemistry of the —CH=CH— bond was E.

EXAMPLE 140

Compound (140): Phenyl 3-(1,1-dimethylethylthio)-N-phenylacrylimidate m.p.: 134-136° C.
$^1$H-NMR (CDCl$_3$) δ(ppm): 1.42(9H,s), 5.97(1H,d, J=16.0 Hz), 6.77(2H, d, J=8.0 Hz), 6.99-7.03(1H,m), 7.16-7.26(5H, m), 7.37-7.41(2H, m), 7.72(1H,d, J=16.0 Hz).

The stereochemistry of the —CH=CH— bond was E.

EXAMPLE 141

Compound (141): Phenyl N-phenyl-3-(2-phenylethylthio)acrylimidate $^1$H-NMR (CDCl$_3$) δ(ppm): 2.85-2.97(4H, m), 5.87(1H, d, J=16.0 Hz), 6.80(2H, d, J=8.0 Hz), 7.01-7.06(3H, m), 7.16-7.29(8H, m), 7.37-7.41(2H, m), 7.58(1H, d, J=16.0 Hz).

The stereochemistry of the —CH=CH— bond was E.

EXAMPLE 142

Compound (142): Phenyl 3-dodecylthio-N-phenylacrylimidate $^1$H-NMR (CDCl$_3$) δ(ppm): 0.88(3H,t, J=6.8 Hz), 1.22-1.34(18H, m), 1.56-1.64(2H, m), 2.67(2H,t, J=7.5 Hz), 5.79

(1H,d, J=15.2 Hz), 6.78(2H, d, J=7.5 Hz), 6.99-7.03(1H, m), 7.16-7.26(5H, m), 7.36-7.40(2H, m), 7.60(1H, d, J=15.2 Hz).
The stereochemistry of the —CH=CH— bond was E.

EXAMPLE 143

Compound (143): Phenyl 3-allylthio-N-phenylacrylimidate $^1$H-NMR (CDCl$_3$) δ(ppm): 3.33(2H,d, J=7.0 Hz), 5.00 (1H,d, J=10.9 Hz), 5.12(1H,d, J=10.1 Hz), 5.70-5.80(1H, m), 5.89(1H, d, J=15.6 Hz), 6.76(2H, d, J=7.5 Hz), 7.02(1H, t, J=7.4 Hz), 7.15-7.26(5H, m), 7.35-7.39(2H,m), 7.54(1H,d, J=15.6 Hz).
The stereochemistry of the —CH=CH— bond was E.

EXAMPLE 144

Compound (144): Phenyl 3-(2-naphtylthio)-N-phenylacrylimidate $^1$H-NMR (CDCl$_3$) δ(ppm): 5.93(1H,d, J=15.2 Hz), 6.72 (2H,d, J=7.5 Hz), 6.92-6.94(1H, m), 7.13-7.22(5H, m), 7.35-7.39(2H, m), 7.45-7.53(3H, m), 7.75-7.83(4H, m), 7.92(1H, brs).
The stereochemistry of the —CH=CH— bond was E.

EXAMPLE 145

Compound (145): Phenyl N-phenyl-3-(1-phenylethylthio)acrylimidate $^1$H-NMR (CDCl$_3$) δ(ppm): 1.60(3H,d, J=7.0 Hz), 4.14-4.20(1H, m), 5.80(1H, d, J=15.2 Hz), 6.68(2H, d, J=7.2 Hz), 7.03(1H, t, J=7.4 Hz), 7.13-7.37(12H, m), 7.49(1H, d, J=15.2 Hz).
The stereochemistry of the —CH=CH— bond was E.

EXAMPLE 146

Compound (146): Phenyl 3-(4-methoxyphenylthio)-N-phenylacrylimidate $^1$H-NMR (CDCl$_3$) δ(ppm): 3.79(3H,s), 5.69(1H,d, J=16.00 Hz), 6.69(1H, d, J=8.0 Hz), 6.84(2H, d, J=8.0 Hz), 6.95-7.38(11H, m), 7.62(1H, d, J=16.0 Hz).
The stereochemistry of the —CH=CH— bond was E.

EXAMPLE 147

Compound (147): Benzyl 3-benzyloxy-N-phenylacrylimidate $^1$H-NMR (CDCl$_3$) δ(ppm): 4.73(2H,s), 5.27(1H, d, J=12.4 Hz) 5.30(2H,s), 6.78-6.80(2H, m), 7.01-7.06(1H, m), 7.22-7.48(13H, m).
The stereochemistry of the —CH=CH— bond was E.

EXAMPLE 148

Compound (148): Phenyl 3-methylthio-N-phenylacrylimidate

Phenyl 3-phenoxy-N-phenylacrylimidate (0.30 g) was dissolved to THF (5 ml), sodium salt of methyl mercaptan (0.075 g) was added thereto and stirred for four hours at room temperature. Ethyl acetate (50 ml) was added to the reaction solution, and it was successively washed with water and aqueous saturated of sodium chloride solution, dried over magnesium sulfate (anhydrous), concentrated under reduced pressure. The residue was subjected to silica gel column chromatography (hexane:ethyl acetate=10:1) to obtain phenyl 3-methylthio-N-phenylacrylimidate (0.20 g) as yellow oil.
$^1$H-NMR (CDCl$_3$) δ(ppm): 2.22(3H,s), 5.72(1H,d, J=16.0 Hz), 6.79(2H, d, J=8.0 Hz), 7.00-7.04(1H, m), 7.17-7.27(5H, m), 7.36-7.40(2H, m), 7.65(1H, d, J=16.0 Hz).
The stereochemistry of the —CH=CH— bond was E.

EXAMPLE 149

Compound (149): N-Benzyl-N-methyl-N'-phenyl-3-phenylthioacrylamidine

N-phenyl-3-phenylthioacrylamide (0.77 g) was suspended to toluene (15 ml), then one drop of DMF and thionyl chloride (0.52 ml) was added thereto at room temperature. The mixture was stirred on the 60° C. oil bath for one hour. Then it was cooled and concentrated under reduced pressure. The residue was dissolved to THF (15 ml). Benzyl methyl amine (0.77 ml) was added thereto at room temperature and stirred for 4.5 hours. The unsolved matter was filtered off and concentrated to obtain brown oil (1.39 g). It was subjected to activated alumina column chromatography (hexane:ethyl acetate=20:1) to obtain N-benzyl-N-methyl-N'-phenyl-3-(phenylthio) acrylamidine (0.22 g) as light yellow oil.
$^1$H-NMR (CDCl$_3$) δ(ppm): 2.95(3H,s), 4.59(1.4H,s), 4.62 (0.6H,s), 5.94(0.7H,d, J=16.2 Hz), 6.01(0.3H,d, J=10.6 Hz), 6.45(0.3H,d, J=10.6 Hz), 6.53(0.7H,d, J=16.2 Hz), 6.67-6.90 (2H,m), 7.13-7.38(13H, m)
The stereochemistry of the —CH=CH— bond was mixture of E and Z.

EXAMPLE 150

Compound (150): Ethyl N-phenyl-3-(phenylthio)acrylimidate

N-phenyl-3-(phenylthio)acrylamide (2.0 g) was dissolved to chloroform (10 ml), and 7.8 ml of tetrafluoroboric acid triethyloxonium—dichloromethane 1 mol/L solution was added thereto dropwise under ice-cooling. It was stirred for one hour at room temperature, 50° C. for two hours and for five hours under heat refluxing. After cooling, ice-water was added to the reaction solution, then the chloroform layer was separated. The chloroform layer was washed with water, dried and distilled off the solvent. The residue was subjected to silica gel column chromatography (hexane/ethyl acetate=15/1) to obtain ethyl N-phenyl-3-(phenylthio) acrylimidate (0.15 g) as oil.
$^1$H-NMR (CDCl$_3$) δ(ppm): 1.35(1.8H, t, J=8.4 Hz), 1.51 (1.2H, t, J=8.4 Hz), 4.28(1.2H, q, J=8.4 Hz), 4.39(0.8H, q, J=8.4 Hz), 5.72(0.4H, d, J=11.1 Hz), 5.78(0.6H, d, J=15.2 Hz), 6.71-7.48(11H, m)
The stereochemistry of the —CH=CH— bond was mixture of E and Z.

EXAMPLE 151

Compound (151): Ethyl 3-ethylthio-N-phenylacrylimidate

To DMF (5 ml) solution of phenyl N-phenyl-3-phenoxyacrylimidate (0.30 g) was added sodium salt of ethyl mercaptan (0.10 g) under ice-cooling, and stirred for three hours at the same temperature. Ethyl acetate (80 ml) was added to the reaction solution, and it was successively washed with water and aqueous saturated sodium chloride solution, dried over anhydrous magnesium sulfate and concentrated under reduced pressure. DMF (5 ml) and sodium salt of ethyl mercaptan (0.1 g) were added to the residue, and stirred for three hours at room temperature. Ethyl acetate (80 ml) was added to the reaction solution and it was successively washed with water and aqueous saturated sodium chloride solution, dried over anhydrous magnesium sulfate and concentrated under reduced pressure. The residue was isolated and purified by silica gel column chromatography (hexane:ethyl acetate=10:1) to obtain ethyl N-phenyl-3-(ethylthio)acrylimidate (0.14 g) as yellow oil.

$^1$H-NMR (CDCl$_3$) δ(ppm): 1.24(3H,t, J=7.3 Hz), 1.34(3H, t, J=7.3 Hz), 2.65(2H, q, J=7.3 Hz), 3.07(2H, q, J=7.3 Hz), 6.01(1H,d, J=15.6 Hz), 6.78(2H, d, J=7.6 Hz), 7.03-7.06(1H, m), 7.23-7.31(3H, m).

The stereochemistry of the —CH=CH— bond was E.

EXAMPLE 152

Compound (152): N-Methyl-N-phenyl-N'-phenyl-3-(4-chlorophenylthio)acrylamidine

N-methyl-N-phenyl-N'-phenylpropynamidine (0.23 g) was dissolved to chloroform (5 ml), chloroform (5 ml) solution of 4-chlorothiophenol (0.14 g) was added dropwise under ice-cooling and stirred for 14 hours at room temperature. The reaction solution was concentrated under reduced pressure. The residue was purified by silica gel column chromatography (hexane:ethyl acetate=7:1) to obtain N-methyl-N-phenyl-N'-phenyl-3-(4-chlorophenylthio)acrylamidine (0.22 g) as light yellow oil.

$^1$H-NMR (CDCl$_3$) δ(ppm): 3.41(3H,s),5.72(0.8H, d, J=15.9 Hz), 5.92(0.2H, d, J=10.3 Hz),6.52-7.41(15H, m)

The stereochemistry of the —CH=CH— bond was mixture of E and Z.

Compound (153) was synthesized in a similar manner as the Example 152.

EXAMPLE 153

Compound (153): N,N-Dimethyl-N'-phenyl-3-(4-methylphenylthio)acrylamidine $^1$H-NMR (CDCl$_3$) δ(ppm): 2.30(2.4H,s), 2.32(0.6H,s), 2.98(4.8H,s), 3.08(1.2H,s), 5.77(0.8H,d, J=15.8 Hz), 5.83 (0.2H,d, J=10.7 Hz), 6.42(0.2H,d, J=10.7 Hz), 6.45(0.8H,d, J=15.8 Hz), 6.68-7.73(2H, m), 6.81-7.29(7H, m)

The stereochemistry of the —CH=CH— bond was mixture of E and Z.

EXAMPLE 154

Compound (154): Phenyl N-(4-hydroxyphenyl)-3-(phenoxy)acrylimidate

To chloroform (80 ml) solution of phenyl N-(4-methoxyphenyl)-3-(phenoxy)acrylimidate (2.4 g) was added dropwise with borone tribromide dichloromethane solution (1.0M: 14.0 ml) under ice-cooling and stirred for one hour at the same temperature and 2.5 hours at room temperature. Chloroform (200 ml) was added to the reaction solution and it was successively washed with water and aqueous saturated sodium chloride solution, dried over anhydrous magnesium sulfate and concentrated under reduced pressure. The residue was separated and purified by silica gel column chromatography (hexane:ethyl acetate=3:1) to obtain phenyl N-(4-hydroxyphenyl)-3-(phenoxy)acrylimidate (0.46 g) as white crystal.

m.p.: 110° C.

$^1$H-NMR (CDCl$_3$) δ(ppm): 4.73(1H,brs), 5.79(1H, d J=11.8 Hz), 6.66-6.72(4H, m), 7.06-7.39(10H, m), 7.79(1H,d J=11.8 Hz).

The stereochemistry of the —CH=CH— bond was E.

EXAMPLE 155

Compound (155): Phenyl N-(4-acetoxyphenyl)-3-(phenoxy)acrylimidate

Potassium carbonate (0.075 g) and acetyl chloride (0.035 ml) were added to DMF (3 ml) solution of phenyl N-(4-hydroxyphenyl)-3-(phenoxy)acrylimidate (0.15 g) at room temperature and stirred for two hours at the same temperature and for three hours at 50° C. t-Butyl methyl ether (80 ml) was added to the reaction solution, and it was successively washed with water and aqueous saturated sodium chloride solution, dried over anhydrous magnesium sulfate, concentrated under reduced pressure. The residue was separated and purified by silica gel column chromatography (hexane:ethyl acetate=4:1) to obtain phenyl N-(4-acetoxyphenyl)-3-(phenoxy)acrylimidate (0.11 g) as colorless oil.

$^1$H-NMR (CDCl$_3$) δ(ppm): 2.27(3H,s), 5.79(1H, d J=11.8 Hz), 6.78-6.80(2H, m), 6.98-7.00(2H, m), 7.06-7.08(2H, m), 7.15-7.23(4H, m), 7.34-7.40(4H, m), 7.82(1H,d J=11.8 Hz).

The stereochemistry of the —CH=CH— bond was E.

EXAMPLE 156

Compound (156): Phenyl N-(4-ethynylphenyl)-3-(phenoxy)acrylimidate

Phenyl N-(4-iodophenyl)-3-(phenoxy)acrylimidate (0.40 g), bis(acetonitrile) dichloro palladium (II) (0.016 g) and copper iodide (I) (0.006 g) were suspended to dioxane (5 ml). Diisopropylamine (0.090 ml), tri-t-butylphosphine (10 wt % in hexane: 0.24 g) and trimethylsilyl acetylene (0.12 g) were added thereto under ice-cooling, and stirred for eight hours at room temperature. t-Butyl methyl ether (50 ml) was added to the reaction solution, and was successively washed with water and aqueous saturated sodium chloride solution, dried over anhydrous magnesium sulfate and concentrated under reduced pressure. The residue was separated and purified by silica gel column chromatography (hexane:ethyl acetate=4:1) to obtain white crystal (0.15 g).

The above-mentioned crystal was dissolved to methanol (5 ml), potassium carbonate (0.010 g) was added and stirred for four hours at room temperature. The reaction solution was concentrated under reduced pressure. The residue was separated and purified by silica gel column chromatography (hexane:ethyl acetate=5:1) to obtain phenyl N-(4-ethynylphenyl)-3-(phenoxy)acrylimidate (0.12 g) as yellow solid.

$^1$H-NMR (CDCl$_3$) δ(ppm): 3.02(1H,s), 5.68(1H, d J=11.8 Hz), 6.75(2H, d J=8.2 Hz), 7.06(2H, d J=7.7 Hz), 7.14-7.22 (4H, m), 7.34-7.41(6H, m), 7.82(1H,d J=11.8 Hz).

The stereochemistry of the —CH=CH— bond was E.

EXAMPLE 157

Compound (157): Phenyl N-(4-vinylphenyl)-3-(phenoxy)acrylimidate

Phenyl N-(4-iodophenyl)-3-(phenoxy)acrylimidate (0.50 g), bis(benzylideneacetone)palladium (0) (0.023 g) and cesium carbonate (0.82 g) were suspended to dioxane (15 ml). Tri-t-butylphosphine (10 wt % in hexane: 0.24 g) and tributyl(vinyl)tin (0.44 g) were added thereto and it was stirred for four hours at room temperature and 60° C. for five hours. The unsolved matter was filtered off, and the filtrate was concentrated under reduced pressure. The residue was separated and purified by silica gel column chromatography (hexane:ethyl acetate=30:1) to obtain phenyl N-(4-vinylphenyl)-3-(phenoxy)acrylimidate (0.29 g) as yellow oil.

$^1$H-NMR (CDCl$_3$) δ(ppm): 5.15(1H, d J=11.6 Hz), 5.65 (1H, d J=18.4 Hz), 5.76(1H, d J=12.1 Hz), 6.63-6.70(1H,m), 6.76(2H, d J=8.2 Hz), 7.06(2H, d J=7.7 Hz), 7.13-7.22(4H, m), 7.31-7.41(6H, m), 7.80(1H,d J=12.1 Hz).

The stereochemistry of the —CH=CH— bond was E.

EXAMPLE 158

Compound (158): Phenyl N-(4-biphenyl)-3-(phenoxy)acrylimidate

Phenyl N-(4-iodophenyl)-3-(phenoxy)acrylimidate (0.30 g), phenylboronic acid (0.091 g), bis(benzylideneacetone)palladium(0) (0.015 g) and cesium carbonate (0.26 g) were suspended to THF (15 ml). Tri-t-butylphosphine (10 wt % in hexane: 0.11 g) was added thereto and stirred for 16 hours at room temperature. The unsolved matter was filtered off, and the filtrate was concentrated under reduced pressure. The residue was separated and purified by silica gel column chromatography (hexane:ethyl acetate=20:1) to obtain phenyl N-(4-biphenyl)-3-(phenoxy)acrylimidate (0.06 g) as light yellow crystal.

$^1$H-NMR (CDCl$_3$) δ(ppm): 5.82(1H, d J=12.1 Hz), 6.88 (2H, d J=8.2 Hz), 7.07(2H, d J=7.7 Hz), 7.13-7.43(11H, m), 7.50-7.52(2H, m), 7.56-7.58(2H, m), 7.83(1H,d J=12.1 Hz).

The stereochemistry of the —CH=CH— bond was E.

Compound (159) was synthesized in a similar manner as the Example 158.

EXAMPLE 159

Compound (159): Phenyl 3-phenoxy-N-(4-(3-thienyl)phenyl)acrylimidate m.p.: 117° C.
$^1$H-NMR (CDCl$_3$) δ(ppm): 5.80(1H, d J=11.8 Hz), 6.84 (2H, d J=8.2 Hz), 7.07(2H, d J=8.0 Hz), 7.13-7.23(4H, m), 7.33-7.42(7H, m), 7.50-7.52(2H, m), 7.82(1H,d J=11.8 Hz).

The stereochemistry of the —CH=CH— bond was E.

EXAMPLE 160

Compound (160): Phenyl N-(4-methylsulfinylphenyl)-3-(phenoxy)acrylimidate

Compound (161): Phenyl N-(4-methylsulfonylphenyl)-3-(phenoxy)acrylimidate

Phenyl N-(4-methylthiophenyl)-3-(phenoxy)acrylimidate (0.50 g) was dissolved to chloroform (15 ml), then chloroform (10 ml) solution of m-chloro perbenzoic acid (0.55 g) was added dropwise under ice-cooling and stirred for five hours at room temperature. Chloroform (50 ml) was added thereto, and it was successively washed with 1N aqueous sodium hydroxide solution, water and aqueous saturated sodium chloride solution, dried over anhydrous magnesium sulfate, concentrated under reduced pressure. The residue was separated and purified by silica gel column chromatography (hexane:ethyl acetate=1:1) to obtain phenyl N-(4-methylsulfinylphenyl)-3-(phenoxy)acrylimidate (0.30 g) as yellow oil and phenyl N-(4-methylsulfonylphenyl)-3-(phenoxy)acrylimidate (0.18 g) as yellow oil.

Compound (160):

$^1$H-NMR (CDCl$_3$) δ(ppm): 2.70(3H,s), 5.65(1H,dJ=11.8 Hz), 6.94(2H, d J=8.2 Hz), 7.06-7.08(2H, m), 7.15-7.23(4H, m), 7.34-7.42(4H, m), 7.56(2H,d J=8.2 Hz), 7.85(1H,d J=11.8 Hz).

The stereochemistry of the —CH=CH— bond was E.

Compound (161):

$^1$H-NMR (CDCl$_3$) δ(ppm): 3.30(3H,s), 5.59(1H, d J=11.8 Hz), 6.95(2H, d J=8.2 Hz), 7.06-7.08(2H, m), 7.17-7.21(4H, m), 7.35-7.40(4H, m), 7.83(2H,d J=8.2 Hz), 7.87(1H,d J=11.8 Hz).

The stereochemistry of the —CH=CH— bond was E.

EXAMPLE 161

Compound (162): Methyl N-phenyl-3-(4-methylphenylthio)thioacrylimidate

Methyl N-phenylpropynthioimidate (0.30 g) was dissolved to chloroform (5 ml), 4-methylthiophenol (0.19 g) was added dropwise under ice-cooling and stirred for 15 hours at room temperature. The reaction solution was concentrated under reduced pressure. The residue was purified by silica gel column chromatography (hexane:ethyl acetate=15:1) to obtain methyl N-phenyl-3-(4-methylphenylthio)thioacrylimidate (0.20 g) as light yellow oil.

$^1$H-NMR (CDCl$_3$) δ(ppm): 2.33(3H,s), 2.43(3H,s), 5.99 (1H, d, J=15.1 Hz), 6.68-6.75(2H, m), 7.00-7.35(8H, m).

The stereochemistry of the —CH=CH— bond was E.

Compounds (163) to (169) were synthesized in a similar manner as the Example 161.

EXAMPLE 162

Compound (163): Methyl N-phenyl-3-(phenylthio)thioacrylimidate $^1$H-NMR (CDCl$_3$) δ(ppm): 2.44(3H,s), 6.09(1H,d, J=15.6 Hz), 6.73(2H, d, J=7.3 Hz), 7.00-7.39(9H, m).

The stereochemistry of the —CH=CH— bond was E.

EXAMPLE 163

Compound (164): Methyl 3-(4-chlorophenylthio)-N-(phenyl)thioacrylimidate $^1$H-NMR (CDCl$_3$) δ(ppm): 2.44(3H,s), 6.04(1H,d, J=16.1 Hz), 6.71(2H, d, J=7.7 Hz), 7.06(1H, br), 7.22-7.31(7H, m).

The stereochemistry of the —CH=CH— bond was E.

EXAMPLE 164

Compound (165): Methyl 3-(4-chlorophenylthio)-N-(phenyl)thioacrylimidate $^1$H-NMR (CDCl$_3$) δ(ppm): 2.41(3H,brs), 6.40(1H,br), 6.90-7.48(10H, m).

The stereochemistry of the —CH=CH— bond was Z.

EXAMPLE 165

Compound (166): Benzyl 3-(4-fluorophenylthio)-N-(phenyl)thioacrylimidate $^1$H-NMR (CDCl$_3$) δ(ppm): 4.30(2H,s), 5.94(1H, d, J=15.6 Hz), 6.67-6.73(1H,m), 6.93-7.09(3H,m), 7.20-7.42(11H,m).
The stereochemistry of the —CH═CH— bond was E.

EXAMPLE 166

Compound (167): Benzyl 3-(4-chlorophenylthio)-N-(phenyl)thioacrylimidate $^1$H-NMR (CDCl$_3$) δ(ppm): 4.31(2H,s), 6.03(1H,d, J=15.5 Hz), 6.72(2H, d, J=7.5 Hz), 7.04-7.10(1H, m), 7.21-7.41 (12H, m).
The stereochemistry of the —CH═CH— bond was E.

EXAMPLE 167

Compound (168): Benzyl 3-(3-methylphenylthio)-N-(phenyl)thioacrylimidate $^1$H-NMR (CDCl$_3$) δ(ppm): 2.30(3H,s), 4.31(2H,s), 6.06 (1H, d, J=15.3 Hz), 6.73(2H, d, J=8.2 Hz), 7.00-7.42(13H, m).
The stereochemistry of the —CH═CH— bond was E.

EXAMPLE 168

Compound (169): Benzyl N-phenyl-3-(3-trifluoromethylphenylthio)thioacrylimidate $^1$H-NMR (CDCl$_3$) δ(ppm): 4.33(2H,s), 6.09(1H,d, J=15.6 Hz), 6.73(2H, d, J=8.2 Hz), 7.02-7.10(1H,def. t), 7.21-7.63 (12H, m).
The stereochemistry of the —CH═CH— bond was E.
Compounds (170) to (173) were synthesized in a similar manner as the Example 37.

EXAMPLE 169

Compound (170): 4-Methylthiophenyl N-[4-(1-methylethyl)phenyl]-3-(phenylthio)acrylimidate $^1$H-NMR (CDCl$_3$) δ(ppm): 1.22(6H,d, J=6.8 Hz), 2.45 (3H,s), 2.84(1H, sept J=6.8 Hz), 5.90(1H, d, J=15.2 Hz), 6.64(2H, d, J=8.2 Hz), 7.05-7.41(11H,m), 7.66(1H, d, J=15.2 Hz).
The stereochemistry of the —CH═CH— bond was E.

EXAMPLE 170

Compound (171): 4-Methylsulfonylphenyl N-[4-(1-methylethyl)phenyl]-3-(phenylthio)acrylimidate $^1$H-NMR (CDCl$_3$) δ(ppm): 1.22(6H, d, J=7.0 Hz), 2.85 (1H, sept J=7.0 Hz), 3.04(3H, s), 5.90(1H, d, J=15.0 Hz), 6.66(2H, d, J=8.5 Hz), 7.08-7.45(9H,m), 7.69(1H,d, J=15.0 Hz, CH), 7.94(2H, d, J=8.7 Hz).
The stereochemistry of the —CH═CH— bond was E.

EXAMPLE 171

Compound (172): 4-Cyclohexylphenyl N-[4-(1-methylethyl)phenyl]-3-(phenylthio)acrylimidate $^1$H-NMR (CDCl$_3$) δ(ppm): 1.21(6H, d, J=6.8 Hz), 1.26-1.40(6H, m), 1.84(4H, m), 2.47(1H, m), 2.84(1H, sept J=6.8 Hz), 5.91(1H, d, J=15.2 Hz), 6.64(2H, d, J=8.2 Hz), 7.04-7.45 (11H, m), 7.65(1H, d, J=15.2 Hz, CH).
The stereochemistry of the —CH═CH— bond was E.

EXAMPLE 172

Compound (173): 3-Biphenyl N-[4-(1-methylethyl)phenyl]-3-(phenylthio)acrylimidate $^1$H-NMR (CDCl$_3$) δ(ppm): 1.21(6H, d, J=6.8 Hz), 2.84 (1H, sept J=6.8 Hz), 5.94(1H, d, J=15.1 Hz), 6.67(2H, d, J=8.0 Hz), 7.05-7.59(16H, m), 7.70(1H, d, J=15.1 Hz).
The stereochemistry of the —CH═CH— bond was E.
Compound (174) was synthesized in a similar manner as the Example 161.

EXAMPLE 173

Compound (174): 1-Methylethyl N-phenyl-3-(phenylthio)thioacrylimidate $^1$H-NMR (CDCl$_3$) δ(ppm): 1.38(6H, d, J=7.8 Hz), 3.82-3.94(1H, m), 6.06(1H,d, J=15.6 Hz), 6.73(2H,d, J=8.0 Hz), 7.03(1H,t, J=7.4 Hz), 7.22-7.40(8H, m).
The stereochemistry of the —CH═CH— bond was E.
Compounds (175) and (176) were synthesized in a similar manner as the Example 37.

EXAMPLE 174

Compound (175): Phenyl N-(4-cyclohexylphenyl)-3-(phenylthio)acrylimidate $^1$H-NMR (CDCl$_3$) δ(ppm): 1.29-1.45(4H, m), 1.68-1.91 (6H, m), 2.38-2.49(1H, m), 5.81(0.21H,d J=15.0 Hz), 5.93 (0.75H, d, J=15.2 Hz), 6.13(0.04H, d, J=9.9 Hz), 6.64(1H, d, J=8.2 Hz), 7.01-7.56(13.04H, m), 7.67(0.75H, d J=15.2 Hz), 8.00(0.21H, d J=15.0 Hz)
The stereochemistry of the —CH═CH— bond was mixture of E and Z.

EXAMPLE 175

Compound (176): Phenyl N-(4-cyclohexylthiophenyl)-3-phenoxyacrylimidate $^1$H-NMR (CDCl$_3$) δ(ppm): 0.87-0.90(2H, m), 1.23-1.33 (4H, m), 1.74-1.76(2H, m), 1.92-1.94(2H, m), 2.98-3.00(1H, m), 5.74(1H, d, J=12.0 Hz), 6.73(2H, d, J=8.3 Hz), 7.07(2H, d, J=8.0 Hz), 7.13-7.22(4H, m), 7.33-7.40(6H, m), 7.82(1H, d, J=12.0 Hz, CH).
The stereochemistry of the —CH═CH— bond was E.

EXAMPLE 176

Compound (177): 4-(1,1-Dimethylethyl)phenyl N-phenyl-3-(phenylthio)thioacrylimidate N-phenyl-3-(phenylthio)acrylamide (0.77 g) was suspended to toluene (15 ml), then thionyl chloride (0.52 ml) and one drop of DMF were added thereto at room temperature. The mixture was stirred on 60° C. oil bath for one hour. The reaction mixture was concentrated under reduced pressure. The residue was dissolved to THF (15 ml).

Sodium hydride (55% in oil: 0.25 g) was suspended to THF (5 ml) under ice-cooling, and 4-(tert-butyl)thiophenol (0.57 ml) was added thereto under ice-cooling. The suspension was added to the above THF solution of the residue under ice-cooling, and stirred at the same temperature for 15 minutes. Then methyliodide (0.1 ml) was added thereto. Aqueous saturated sodium chloride solution (20 ml) and water (10 ml) was added to the reaction mixture and it was extracted with ethyl acetate (20 ml) twice. The organic layers were combined and washed with aqueous saturated sodium chloride solution (20 ml), dried over anhydrous sodium sulfate, filtered off inorganic salt, concentrated under reduced pressure to obtain brown oil (1.36 g). It was subjected to silica gel column chromatography (hexane:ethyl acetate=20:1) to obtain light yellow oil, and it was purified by medium pressure preparative high performance liquid chromatography (hexane:ethyl acetate=99:1) to obtain 4-(1,1-dimethylethyl)phenyl N-phenyl-3-(phenylthio)thioacrylimidate (0.20 g).

$^1$H-NMR (CDCl$_3$) δ(ppm): 1.33(9H, s), 5.83(1H, d J=15.0 Hz), 6.90-7.58(15H,m).

The stereochemistry of the —CH═CH— bond was E.

Compounds (178) and (179) were synthesized in a similar manner as the Example 176.

EXAMPLE 177

Compound (178): 2-Naphtyl N-[4-(1-methylethyl)phenyl]-3-(phenylthio)thioacrylimidate $^1$H-NMR (CDCl$_3$) δ(ppm): 1.24(6H,d J=7.0 Hz), 2.85-2.92(1H, m), 5.55(1H, d J=15.0 Hz), 6.62-8.05(17H, m).

The stereochemistry of the —CH═CH— bond was E.

EXAMPLE 178

Compound (179): 2-Naphtyl N-[4-(1-methylethyl)phenyl]-3-(phenylthio)thioacrylimidate $^1$H-NMR (CDCl$_3$) δ(ppm): 1.28(6H, d J=7.0 Hz), 2.90-2.97(1H, m), 5.83(1H,d J=10.1 Hz), 6.78(1H,d J=9.9 Hz), 7.07(2H,d J=8.2 Hz), 7.25-7.32(5H,m), 7.43(2H, d J=6.7 Hz), 7.53(3H, d J=7.2 Hz), 7.82(3H, d J=8.5 Hz), 8.04(1H, s).

The stereochemistry of the —CH═CH— bond was Z.

Compounds (180) to (185) were synthesized in a similar manner as the Example 37.

EXAMPLE 179

Compound (180): Phenyl N-(4-phenoxyphenyl)-3-(phenylthio)acrylimidate $^1$H-NMR (CDCl$_3$) δ(ppm): 5.81(0.29H,d J=15.1 Hz), 5.90 (0.71H, d, J=15.1 Hz), 6.70(2H,d, J=8.7 Hz), 7.13-7.56(17H, m), 7.72(0.71H, d J=15.1 Hz), 8.00(0.29H, d J=15.1 Hz).

The stereochemistry of the —CH═CH— bond was E.

EXAMPLE 180

Compound (181): 4-Biphenyl N-[4-(1-methylethyl)phenyl]-3-(phenylthio)acrylimidate $^1$H-NMR (CDCl$_3$) δ(ppm): 1.22(6H, d J=6.8 Hz), 2.84 (1H, sept J=6.8 Hz), 5.93(1H, d, J=15.2 Hz), 6.67(2H, d, J=8.2 Hz), 7.06-7.58(16H, m), 7.70(1H, d, J=15.2 Hz).

The stereochemistry of the —CH═CH— bond was E.

EXAMPLE 181

Compound (182): 4-Methoxycarbonylphenyl N-[4-(1-methylethyl)phenyl]-3-(phenylthio)acrylimidate $^1$H-NMR (CDCl$_3$) δ(ppm): 1.22(6H, d, J=7.0 Hz), 2.84 (1H, sept J=7.0 Hz), 3.89(3H, s), 5.91(1H, d, J=15.2 Hz), 6.65(2H, d, J=8.2 Hz), 7.07(2H, d, J=8.2 Hz), 7.14-7.44(7H, m), 7.67(1H, d, J=15.2 Hz), 8.05(2H, d, J=8.7 Hz).

The stereochemistry of the —CH═CH— bond was E.

EXAMPLE 182

Compound (183): 4-(1H-Imidazole-1-yl)phenyl N-[4-(1-methylethyl)phenyl]-3-(phenylthio)acrylimidate $^1$H-NMR (CDCl$_3$) δ(ppm): 1.21(6H, d, J=6.9 Hz), 2.83 (1H, sept), 5.90(1H,d, J=15.2 Hz), 6.62-7.44(16H,m), 7.66 (1H,d, J=15.2 Hz).

The stereochemistry of the —CH═CH— bond was E.

EXAMPLE 183

Compound (184): 4-Methoxyphenyl N-[4-(1-methylethyl)phenyl]-3-(phenylthio)acrylimidate $^1$H-NMR (CDCl$_3$) δ(ppm): 1.21(6H, d, J=6.8 Hz), 2.83 (1H, sept J=6.8 Hz), 3.77(3H, s), 5.90(1H, d, J=15.0 Hz), 6.64(2H, d, J=8.5 Hz), 6.86-7.46(11H, m), 7.66(1H, d, J=15.0 Hz).

The stereochemistry of the —CH═CH— bond was E.

EXAMPLE 184

Compound (185): Phenyl N-[4-(1,1-dimethylethoxy)phenyl]-3-phenoxyacrylimidate $^1$H-NMR (CDCl$_3$) δ(ppm): 1.30(9H, s), 5.76(1H, d, J=12.1 Hz), 6.68-6.70(2H, m), 6.88-6.90(2H, m), 7.07(2H, d, J=8.7 Hz), 7.13-7.23(4H, m), 7.33-7.40(4H, m), 7.81(1H, d, J=12.1 Hz).

The stereochemistry of the —CH═CH— bond was E.

Compounds (186) and (187) were synthesized in a similar manner as the Example 161.

EXAMPLE 185

Compound (186): 2-Propenyl N-phenyl-3-(phenylthio)thioacrylimidate $^1$H-NMR (CDCl$_3$) δ(ppm): 3.73(2H,d, J=7.1 Hz), 5.12 (1H,d, J=17.0 Hz), 5.27(1H, brs), 5.87-6.01(1H,m), 6.08(1H, d, J=15.8 Hz), 6.72(2H, d, J=7.8 Hz), 7.00-7.43(9H, m).

The stereochemistry of the —CH═CH— bond was E.

EXAMPLE 186

Compound (187): Cyclohexyl N-phenyl-3-(phenylthio)thioacrylimidate $^1$H-NMR (CDCl$_3$) δ(ppm): 1.26-1.63(6H, m), 1.65-1.78 (2H, m), 2.02-2.12(2H, m), 3.70-3.81(1H, m), 6.06(1H, d, J=16.0 Hz), 6.68-6.75(2H, d), 6.98-7.07(1H, m), 7.20-7.43 (8H, m).

The stereochemistry of the —CH═CH— bond was E.

Compounds (188) to (190) were synthesized in a similar manner as the Example 37.

EXAMPLE 187

Compound (188): 4-Aminophenyl N-[4-(1-methylethyl)phenyl]-3-(phenylthio)acrylimidate $^1$H-NMR (CDCl$_3$) δ(ppm): 1.21(6H, d, J=7.0 Hz), 2.83 (1H, sept J=7.0 Hz), 5.89(1H, d, J=15.2 Hz), 6.65-7.43(15H, m), 7.65(1H, d, J=15.2 Hz).
The stereochemistry of the —CH=CH— bond was E.

EXAMPLE 188

Compound (189): 2-Naphtyl N-phenyl-3-(phenylthio)acrylimidate $^1$H-NMR (CDCl$_3$) δ(ppm): 5.93(1H,d, J=15.2 Hz), 6.74 (2H,d, J=7.5 Hz), 6.97-7.83(16H, m).
The stereochemistry of the —CH=CH— bond was E.

EXAMPLE 189

Compound (190): 2,5-Dichlorophenyl N-phenyl-3-phenylthioacrylimidate $^1$H-NMR (CDCl$_3$) δ(ppm): 5.84(1H,d, J=15.2 Hz), 6.73 (2H,d, J=7.5 Hz), 6.99-7.44(11H, m), 7.76(1H, d, J=15.2 Hz).
The stereochemistry of the —CH=CH— bond was E.
Compound (191) was synthesized in a similar manner as the Example 161.

EXAMPLE 190

Compound (191): 2-Propynyl N-phenyl-3-(phenylthio)thioacrylimidate $^1$H-NMR (CDCl$_3$) δ(ppm): 2.19(1H,t, J=2.5 Hz), 3.86(2H, d, J=2.7 Hz), 6.10(1H,d, J=15.4 Hz), 6.74(2H,d, J=7.5 Hz), 7.03-7.60(9H,m).
The stereochemistry of the —CH=CH— bond was E.
Compounds (192) and (193) were synthesized in a similar manner as the Example 37.

EXAMPLE 191

Compound (192): 2,5-Dichlorophenyl N-phenyl-3-phenoxyacrylimidate $^1$H-NMR (CDCl$_3$) δ(ppm): 5.71(1H,d, J=12.0 Hz), 6.80 (2H,d, J=7.8 Hz), 6.90-7.43(11H, m), 7.85(1H, d, J=12.0 Hz).
The stereochemistry of the —CH=CH— bond was E.

EXAMPLE 192

Compound (193): 2-Naphtyl N-phenyl-3-phenoxyacrylimidate $^1$H-NMR (CDCl$_3$) δ(ppm): 5.79(1H,d, J=12.0 Hz), 6.82 (2H,d, J=7.3 Hz), 6.97-7.90(16H, m).
The stereochemistry of the —CH=CH— bond was E.

Compound (194) was synthesized in a similar manner as the Example 161.

EXAMPLE 193

Compound (194): 1-Phenethyl N-phenyl-3-(phenylthio)thioacrylimidate $^1$H-NMR (CDCl$_3$) δ(ppm): 1.74(3H, d, J=7.7 Hz), 4.96-5.06(1H, m), 6.04(1H, d, J=15.7 Hz), 6.70(2H,d, J=7.5 Hz), 7.00-7.46(14H,m).
The stereochemistry of the —CH=CH— bond was E.
Compound (195) was synthesized in a similar manner as the Example 100

EXAMPLE 194

Compound (195): Phenyl3-(1-naphtylthio)-N-phenylacrylimidate $^1$H-NMR (CDCl$_3$) δ(ppm): 5.58(1H,d, J=15.0 Hz), 6.52 (2H,d, J=7.2 Hz), 6.85-6.89(1H, m), 6.99-7.03(2H, m), 7.12-7.17(3H, m), 7.32-7.42(3H, m), 7.54-7.62(2H, m), 7.66(1H, d, J=15.0 Hz), 7.71-7.73(1H, m), 7.83-7.88(2H, m), 8.27-8.29(1H, m).
The stereochemistry of the —CH=CH— bond was E.
Compounds (196) and (197) were synthesized in a similar manner as the Example 37.

EXAMPLE 195

Compound (196): Phenyl 3-phenoxy-N-(4-piperidinophenyl)acrylimidate $^1$H-NMR (CDCl$_3$) δ(ppm): 1.53-1.57(2H, m), 1.68-1.73 (4H, m), 3.05-3.08(4H, m), 5.84(1H, d, J=12.1 Hz), 6.71-6.73 (2H, m), 6.86-6.88(2H, m), 7.05-7.07(2H, m), 7.14-7.23(4H, m), 7.33-7.39(4H, m), 7.78(1H, d, J=12.1 Hz).
The stereochemistry of the —CH=CH— bond was E.

EXAMPLE 196

Compound (197): 2,5-Dichlorophenyl N-[4-(1-methylethyl)phenyl]-3-phenoxyacrylimidate $^1$H-NMR (CDCl$_3$) δ(ppm): 1.21(6H, d, J=7.0 Hz), 2.85 (1H, sept J=7.0 Hz), 5.78(1H, d, J=11.8 Hz), 6.73(2H, d, J=8.2 Hz), 7.05-7.37(10H, m), 7.84(1H, d, J=11.8 Hz).
The stereochemistry of the —CH=CH— bond was E.
Compounds (198) and (199) were synthesized in a similar manner as the Example 161.

EXAMPLE 197

Compound (198): 1-Methylethyl N-phenyl-3-(phenoxy)thioacrylimidate $^1$H-NMR (CDCl$_3$) δ(ppm): 1.40(6H, d, J=7.3 Hz), 3.90-4.02(1H, m), 5.94(1H, d, =12.6 Hz), 6.95-7.40(10H,m), 7.52 (1H,d, J=12.5 Hz).
The stereochemistry of the —CH=CH— bond was E.

EXAMPLE 198

Compound (199): Benzyl 3-(4-methylbenzylthio)-N-(phenyl)thioacrylimidate $^1$H-NMR (CDCl$_3$) δ(ppm): 2.32(3H, s), 3.79(2H, s), 4.29 (2H, s), 6.07(1H,d, J=15.4 Hz), 6.78(2H,d, J=7.3 Hz), 7.00-7.40(13H,m).

The stereochemistry of the —CH=CH— bond was E.
Compounds (200) to (204) were synthesized in a similar manner as the Example 37.

EXAMPLE 199

Compound (200): 2,3-Dichlorophenyl N-[4-(1-methylethyl)phenyl]-3-phenoxyacrylimidate $^1$H-NMR (CDCl$_3$) δ(ppm): 1.21(6H, d, J=7.4 Hz), 2.85 (1H, sept J=7.4 Hz), 5.78(1H, d, J=12.0 Hz), 6.72(2H, d, J=8.3 Hz), 7.05-7.38(10H, m), 7.85(1H, d, J=12.0 Hz).
The stereochemistry of the —CH=CH— bond was E.

EXAMPLE 200

Compound (201): 3,5-Dichlorophenyl N-[4-(1-methylethyl)phenyl]-3-phenoxyacrylimidate $^1$H-NMR (CDCl$_3$) δ(ppm): 1.23(6H, d, J=6.8 Hz), 2.87 (1H, sept J=6.8 Hz), 5.78(1H, d, J=12.0 Hz), 6.74(2H, d, J=8.3 Hz), 7.03-7.37(10H, m), 7.73(1H, d, J=12.0 Hz).
The stereochemistry of the —CH=CH— bond was E.

EXAMPLE 201

Compound (202): 2,4-Dichlorophenyl N-[4-(1-methylethyl)phenyl]-3-phenoxyacrylimidate $^1$H-NMR (CDCl$_3$) δ(ppm): 1.21(6H, d, J=6.8 Hz), 2.85 (1H, sept J=6.8 Hz), 5.77(1H, d, J=12.0 Hz), 6.71(2H, d, J=8.3 Hz), 7.05-7.43(10H, m), 7.84(1H, d, J=12.0 Hz).
The stereochemistry of the —CH=CH— bond was E.

EXAMPLE 202

Compound (203): 3-Methylphenyl N-(3,4-dimethylphenyl)-3-phenylthioacrylimidate $^1$H-NMR (CDCl$_3$) δ(ppm): 2.19(6H, s), 2.34(3H, s), 5.96 (1H, d, J=15.0 Hz), 6.47-6.53(2H, m), 6.95-7.43(10H, m), 7.65(1H, d, J=15.0 Hz, CH).
The stereochemistry of the —CH=CH— bond was E.

EXAMPLE 203

Compound (204): Phenyl N-(4-benzylphenyl)-3-phenoxyacrylimidate $^1$H-NMR (CDCl$_3$) δ(ppm): 3.93(2H,s), 5.78(1H,d, J=12.1 Hz), 6.72(2H, d, J=8.5 Hz), 7.05-7.09(4H, m), 7.11-7.40 (13H, m), 7.79(1H, d, J=12.1 Hz).
The stereochemistry of the —CH=CH— bond was E.
Compound (205) was synthesized in a similar manner as the Example 161.

EXAMPLE 204

Compound (205): Benzyl N-phenyl-3-(phenoxy)thioacrylimidate $^1$H-NMR (CDCl$_3$) δ(ppm): 4.36(2H, s), 5.96(1H, d, J=12.3 Hz), 6.77-7.54(16H, m).
The stereochemistry of the —CH=CH— bond was E.
Compound (206) was synthesized in a similar manner as the Example 99.

EXAMPLE 205

Compound (206): Phenyl N-phenyl-3-(phenylsulfonyl)thioacrylimidate m.p.: 69-70° C.
$^1$H-NMR (CDCl$_3$) δ(ppm): 6.86-7.74(m)
The stereochemistry of the —CH=CH— bond was mixture of E and Z.
Compound (207) was synthesized in a similar manner as the Example 37.

EXAMPLE 206

Compound (207): Phenyl N-(4-trifluoromethoxyphenyl)-3-phenoxyacrylimidate $^1$H-NMR (CDCl$_3$) δ(ppm): 5.69(1H,d, J=11.8 Hz), 6.79 (2H,d, J=8.7 Hz), 7.06-7.22(8H, m), 7.34-7.41(4H, m), 7.84 (1H, d, J=11.8 Hz).
The stereochemistry of the —CH=CH— bond was E.
Compound (208) was synthesized in a similar manner as the Example 161.

EXAMPLE 207

Compound (208): Cyclohexyl N-phenyl-3-(phenylthio9thioacrylimidate $^1$H-NMR (CDCl$_3$) δ(ppm): 1.26-2.15(8H, m), 3.22(2H, brs), 3.95(1H, Br), 6.42(1H, d, J=10.1 Hz), 6.90-7.55(11H, m).
The stereochemistry of the —CH=CH— bond was Z.
Compound (209) was synthesized in a similar manner as the Example 37.

EXAMPLE 208

Compound (209): 3-Methylphenyl N-(3,4-dimethylphenyl)-3-phenoxyacrylimidate $^1$H-NMR (CDCl$_3$) δ(ppm): 2.20(3H, s), 2.21(3H, s), 2.36 (3H, s), 5.80(1H, d, J=11.8 Hz), 6.54-6.60(2H, m), 6.96-7.37 (10H, m), 7.76(1H, d, J=12.1 Hz).
The stereochemistry of the —CH=CH— bond was E.
Compound (210) was synthesized in a similar manner as the Example 100.

EXAMPLE 209

Compound (210): 3-Methylphenyl N-(3,4-dimethylphenyl)-3-benzyloxyacrylimidate $^1$H-NMR (CDCl$_3$) δ(ppm): 2.19(6H, s), 2.35(3H, s), 4.80 (2H,s), 5.42(1H,d, J=12.3 Hz), 6.52-7.21(12H,m), 7.62(1H, d, J=12.3 Hz).
The stereochemistry of the —CH=CH— bond was E.
Compounds (211) to (234) were synthesized in a similar manner as the Example 161.

EXAMPLE 210

Compound (211): Benzyl 3-(2-fluorophenylthio)-N-phenyl-thioacrylimidate $^1$H-NMR (CDCl$_3$) δ(ppm): 4.30(2H,s), 6.00(1H,d J=15.7 Hz), 6.73(2H,d J=7.3 Hz), 7.02-7.39(13H,m).
The stereochemistry of the —CH=CH— bond was E.

EXAMPLE 211

Compound (213): Benzyl 3-(3-fluorophenylthio)-N-phenyl-thioacrylimidate $^1$H-NMR (CDCl$_3$) δ(ppm): 4.32(2H,s), 6.00(1H,d J=15.7 Hz), 6.73(2H,d J=7.3 Hz), 7.02-7.39(13H,m).
The stereochemistry of the —CH=CH— bond was E.

EXAMPLE 212

Compound (215): Benzyl 3-(2-chlorophenylthio)-N-phenyl-thioacrylimidate $^1$H-NMR (CDCl$_3$) δ(ppm): 4.32(2H,s), 6.08(1H,d J=15.4 Hz), 6.75(2H,d J=7.3 Hz), 7.03-7.40(13H,m).
The stereochemistry of the —CH=CH— bond was E.

EXAMPLE 213

Compound (217): Benzyl 3-(3-chlorophenylthio)-N-phenyl-thioacrylimidate $^1$H-NMR (CDCl$_3$) δ(ppm): 4.32(2H,s), 6.11(1H,d J=15.7 Hz), 6.74(2H,d J=7.3 Hz), 7.06(1H,t J=7.5 Hz), 7.21-7.34 (10H,m), 7.39(2H,d J=7.3 Hz).
The stereochemistry of the —CH=CH— bond was E.

EXAMPLE 214

Compound (219): Benzyl 3-(4-chlorophenylthio)-N-phenyl-thioacrylimidate $^1$H-NMR (CDCl$_3$) δ(ppm): 4.31(2H,s), 6.03(1H,d J=15.7 Hz), 6.72(2H,d J=7.3 Hz), 7.07(1H,t J=7.5 Hz), 7.22-7.32 (10H,m), 7.38(2H,d J=7.1 Hz).
The stereochemistry of the —CH=CH— bond was E.

EXAMPLE 215

Compound (221): Benzyl 3-(3-bromophenylthio)-N-phenyl-thioacrylimidate $^1$H-NMR (CDCl$_3$) δ(ppm): 4.32(2H,s), 6.10(1H,d J=15.7 Hz), 6.74(2H,d J=7.3 Hz), 7.07(1H,t J=7.5 Hz), 7.16(1H,t J=8.0 Hz), 7.23-7.32(8H,m), 7.39(2H,d J=7.3 Hz), 7.49(1H,s).
The stereochemistry of the —CH=CH— bond was E.

EXAMPLE 216

Compound (223): Benzyl 3-(4-bromophenylthio)-N-phenyl-thioacrylimidate $^1$H-NMR (CDCl$_3$) δ(ppm): 4.31(2H,s), 6.04(1H,d J=15.7 Hz), 6.72(2H,d J=7.3 Hz), 7.08(1H,t J=7.3 Hz), 7.18(2H,d J=8.6 Hz), 7.22-7.32(6H,m), 7.40(4H,t J=8.5 Hz).
The stereochemistry of the —CH=CH— bond was E.

EXAMPLE 217

Compound (225): Benzyl 3-(4-nitrophenylthio)-N-phenyl-thioacrylimidate $^1$H-NMR (CDCl$_3$) δ(ppm): 4.34(2H,s), 6.33(1H,d J=15.7 Hz), 6.77(2H,d J=7.3 Hz), 7.10(1H,t J=7.3 Hz), 7.24-7.43 (10H,m), 8.15(2H,d J=8.8 Hz).
The stereochemistry of the —CH=CH— bond was E.

EXAMPLE 218

Compound (226): Benzyl 3-(2-methylphenylthio)-N-phenyl-thioacrylimidate $^1$H-NMR (CDCl$_3$) δ(ppm): 2.30(3H,s), 4.30(2H,s), 5.83 (1H,d J=15.4 Hz), 6.69(2H,d J=7.3 Hz), 7.02(1H,t J=7.5 Hz), 7.09-7.39(10H,m), 7.38(2H,d J=7.3 Hz).
The stereochemistry of the —CH=CH— bond was E.

EXAMPLE 219

Compound (228): Benzyl 3-(4-methylphenylthio)-N-phenyl-thioacrylimidate $^1$H-NMR (CDCl$_3$) δ(ppm): 2.31(3H,s), 4.30(2H,s), 5.98 (1H,d J=15.4 Hz), 6.72(2H,d J=7.3 Hz), 7.02-7.33(11H,m), 7.38(2H,d J=7.1 Hz).
The stereochemistry of the —CH=CH— bond was E.

EXAMPLE 220

Compound (230): Benzyl N-phenyl-3-(4-trifluoromethylphenylthio)-thioacrylimidate $^1$H-NMR (CDCl$_3$) δ(ppm): 4.32(2H,s), 6.17(1H,d J=15.7 Hz), 6.74(2H,d J=7.3 Hz), 7.07(1H,t J=7.5 Hz), 7.25-7.32 (6H,m), 7.41(4H,t J=8.8 Hz), 7.54(2H,d J=8.3 Hz).
The stereochemistry of the —CH=CH— bond was E.

EXAMPLE 221

Compound (232): Benzyl 3-(3-methoxyphenylthio)-N-phenyl-thioacrylimidate $^1$H-NMR (CDCl$_3$) δ(ppm): 3.77(3H,s), 4.31(2H,s), 6.10 (1H,d J=15.4 Hz), 6.74(2H,d J=7.3 Hz), 6.81(1H,d J=8.1 Hz), 6.87(1H,s), 6.92(1H,d J=7.8 Hz), 7.03-7.40(10H,m).
The stereochemistry of the —CH=CH— bond was E.

EXAMPLE 222

Compound (234): Benzyl 3-(4-methoxyphenylthio)-N-phenyl-thioacrylimidate $^1$H-NMR (CDCl$_3$) δ(ppm): 3.78(3H,s), 4.29(2H,s), 5.87 (1H,d J=15.4 Hz), 6.70(2H,d J=7.3 Hz), 6.80(2H,d J=7.2 Hz), 7.02(1H,t J=7.3 Hz), 7.22-7.31(8H,m), 7.38(2H,d J=6.6 Hz).
The stereochemistry of the —CH=CH— bond was E.

EXAMPLE 223

Compound (235): Benzyl 3-(4-fluorobenzylthio)-N-phenyl-thioacrylimidate

Benzyl N-phenylpropynthioimidate (0.30 g) and 4-fluorobenzylmercaptan were dissolved to chloroform (15 ml), catalytic amount of potassium t-butoxide was added thereto under ice-cooling and stirred at room temperature for 14 hours. The reaction mixture was concentrated under reduced pressure. The residue was purified by silica gel column chromatography (hexane:ethyl acetate=15:1) to obtain benzyl 3-(4-fluorobenzylthio)-N-phenyl-thioacrylimidate (0.15 g) as light yellow oil.

$^1$H-NMR (CDCl$_3$) δ(ppm): 3.79(2H,s), 4.29(2H,s), 6.03 (1H,d J=15.7 Hz), 6.71(2H,d J=7.3 Hz), 6.94(2H,t J=8.7 Hz), 7.05-7.12(3H,m), 7.20(1H,d J=15.4 Hz), 7.24-7.32(5H,m), 7.38(2H,d J=7.1 Hz).

The stereochemistry of the —CH═CH— bond was E.
Compounds (236) to (246) and (257) were synthesized in a similar manner as the Example 223.

EXAMPLE 224

Compound (237): Benzyl 3-(4-methylbenzylthio)-N-phenyl-thioacrylimidate $^1$H-NMR (CDCl$_3$) δ(ppm): 2.32(3H,s),3.78(2H,s),4.29 (2H,s),6.07(1H,d J=15.7 Hz),6.73(2H,d J=7.3 Hz),7.02-7.39 (13H,m).
The stereochemistry of the —CH═CH— bond was E.

EXAMPLE 225

Compound (239): Benzyl 3-(4-chlorobenzylthio)-N-phenyl-thioacrylimidate $^1$H-NMR (CDCl$_3$) δ(ppm): 3.78(2H,s),4.29(2H,s),6.01 (1H,d J=15.4 Hz),6.70(2H,d J=7.3 Hz),7.02-7.32(11H,m), 7.38(2H,d J=7.1 Hz).
The stereochemistry of the —CH═CH— bond was E.

EXAMPLE 226

Compound (241): benzyl 3-(2,4-dichlorobenzylthio)-N-phenyl-thioacrylimidate $^1$H-NMR (CDCl$_3$) δ(ppm): 3.90(2H,s), 4.30(2H,s), 6.01 (1H,d J=15.7 Hz), 6.70(2H,d J=7.3 Hz), 7.06(2H,t J=7.5 Hz), 7.15-7.34(8H,m), 7.38(2H,d J=7.3 Hz).
The stereochemistry of the —CH═CH— bond was E.

EXAMPLE 227

Compound (243): Benzyl 3-(2-methylbenzylthio)-N-phenyl-thioacrylimidate $^1$H-NMR (CDCl$_3$) δ(ppm): 2.27(3H,s), 3.82(2H,s), 4.30 (2H,s), 6.07(1H,d J=15.4 Hz), 6.75(2H,d J=7.3 Hz),7.06 (1H,t J=7.3 Hz), 7.13-7.32(10H,m), 7.39(2H,d J=7.1 Hz).
The stereochemistry of the —CH═CH— bond was E.

EXAMPLE 228

Compound (245): Benzyl 3-(4-methoxybenzylthio)-N-phenyl-thioacrylimidate $^1$H-NMR (CDCl$_3$) δ(ppm): 3.77(2H,s),3.78(3H,s),4.29 (2H,s),6.07(1H,d J=15.4 Hz), 6.73(2H,d J=7.3 Hz), 6.79(2H,d J=8.6 Hz), 7.05-7.39(9H,m), 7.38(2H,d J=7.1 Hz).
The stereochemistry of the —CH═CH— bond was E.
Compounds (247) to (256) and (258) were synthesized in a similar manner as the Example 161.

EXAMPLE 229

Compound (248): Benzyl 3-(2,4-dichlorophenylthio)-N-phenyl-thioacrylimidate $^1$H-NMR (CDCl$_3$) δ(ppm): 4.32(2H,s),6.03(1H,dJ=15.4 Hz),6.73(2H,d J=7.3 Hz), 7.07(1H,t J=7.3 Hz), 7.16-7.40 (11H,m).
The stereochemistry of the —CH═CH— bond was E.

EXAMPLE 230

Compound (250): Benzyl 3-(3,5-dichlorophenylthio)-N-phenyl-thioacrylimidate $^1$H-NMR (CDCl$_3$) δ(ppm): 4.32(2H,s),6.03(1H,d J=15.4 Hz),6.75(2H,d J=7.3 Hz),7.08(2H,t J=7.5 Hz),7.20-7.34(8H, m),7.40(2H,d J=7.1 Hz).
The stereochemistry of the —CH═CH— bond was E.

EXAMPLE 231

Compound (252): Benzyl 3-(2,4-dimethylphenylthio)-N-phenyl-thioacrylimidate $^1$H-NMR (CDCl$_3$) δ(ppm): 2.25(3H,s),2.26(3H,s),4.32 (2H,s),5.71(1H,d J=15.4 Hz),6.67(2H,d J=7.3 Hz),6.90-7.04 (4H,m),7.18-7.31(6H,m),7.38(2H,d J=7.1 Hz).
The stereochemistry of the —CH═CH— bond was E.

EXAMPLE 232

Compound (254): Benzyl N-phenyl-3-(2-pyridylthio)-thioacrylimidate $^1$H-NMR (CDCl$_3$) δ(ppm): 4.35(2H,s),6.40(1H,d J=16.2 Hz),6.81(2H,d J=7.3 Hz),7.09(2H,t J=7.3 Hz),7.18(1H,d J=7.8 Hz)7.26(1H,d J=7.3 Hz),7.32(4H,t J=7.8 Hz),7.43 (2H,d J=7.3 Hz),7.55(1H,t J=7.8 Hz),8.21(1H,d J=16.2 Hz), 8.50(1H,d J=5.0 Hz).
The stereochemistry of the —CH═CH— bond was E.

EXAMPLE 233

Compound (256): Benzyl N-phenyl-3-(2-pyrimidylthio)-thioacrylimidate $^1$H-NMR (CDCl$_3$) δ(ppm): 4.36(2H,s),6.44(1H,d J=16.4 Hz),6.81(2H,d J=7.3 Hz),7.05-7.12(2H,m),7.24-7.35(5H, m),7.44(2H,d J=7.1 Hz),8.30(1H,d J=16.4 Hz),8.57(2H,d J=5.1 Hz).
The stereochemistry of the —CH═CH— bond was E.

EXAMPLE 234

Compound (258): Benzyl 3-(3,4-dichlorophenylthio)-N-phenyl-thioacrylimidate $^1$H-NMR (CDCl$_3$) δ(ppm): 4.32(2H,s),6.06(1H,d, J=15.5 Hz),6.73(2H, d, J=7.5 Hz),7.10-7.43(12H,m).
The stereochemistry of the —CH═CH— bond was E.
Compound (259) was synthesized in a similar manner as the Example 176.

EXAMPLE 235

Compound (259): 4-(1-Methylethyl)phenyl N-(4-methylphenyl)-3-(phenylthio)thioacrylimidate $^1$H-NMR (CDCl$_3$) δ(ppm): 1.23(6H,dJ=7.0 Hz),2.29(3H, s),2.82(1H, sept. J=7.0 Hz), 5.93(1H, d J=15.0 Hz), 6.63(2H, d J=7.8 Hz), 7.02(2H, d J=8.0 Hz), 7.11(2H, d J=8.3 Hz), 7.20-7.42(7H, m), 7.66(1H, d J=15.0 Hz).
The stereochemistry of the —CH═CH— bond was E.
Compound (260) was synthesized in a similar manner as the Example 161.

EXAMPLE 236

Compound (260): Benzyl N-(4-methylphenyl)-3-(phenylthio)thioacrylimidate $^1$H-NMR (CDCl$_3$) δ(ppm): 2.32(3H, s), 4.30(2H, s), 6.13 (1H, d, J=15.7 Hz), 6.65(2H, d, J=8.0 Hz), 7.21-7.39(13H, m).

The stereochemistry of the —CH=CH— bond was E.

EXAMPLE 237

Compound (261): Phenyl N-benzyloxy-3-(phenylthio)thioacrylimidate

Sodium salt of thiophenol (0.14 g) was added to ethanol (5 ml) solution of N-benzyloxy-3-phenylthioacrylimidoyl bromide (0.30 g) at room temperature, then it was heat refluxing for three hours. It was cooled, and chloroform (50 ml) was added to the reaction mixture. It was successively washed with 1N aqueous sodium hydroxide solution, pure water, aqueous saturated sodium chloride solution. The organic layer was dried over anhydrous magnesium sulfate, concentrated under reduced pressure. The residue was purified by silica gel column chromatography (hexane:ethyl acetate=20:1) to obtain phenyl N-benzyloxy-3-(phenylthio)thioacrylimidate (0.14 g) as colorless oil.

$^1$H-NMR (CDCl$_3$) δ(ppm): 5.21(2H,s), 5.49(1H, d, J=15.0 Hz), 6.99(1H, d, J=15.0 Hz), 7.14-7.18(2H, m), 7.21-7.39 (13H, m).

The stereochemistry of the —CH=CH— bond was E.

Compound (262) was synthesized in a similar manner as the Example 36.

EXAMPLE 238

Compound (262): Phenyl N—(N'-Methyl-N'-phenylamino)-3-(phenylthio)thioacrylimidate $^1$H-NMR (CDCl$_3$) δ(ppm): 3.17(3H, s), 5.53(1H, d, J=14.7 Hz), 6.90-6.96(3H, m), 7.20-7.42(13H, m).

The stereochemistry of the —CH=CH— bond was E.

Compounds (263) to (265) were synthesized in a similar manner as the Example 176.

EXAMPLE 239

Compound (263): Phenyl N-(4-fluorophenyl)-3-(phenylthio)thioacrylimidate $^1$H-NMR (CDCl$_3$) δ(ppm): 5.80(1H,dJ=10.2 Hz),6.84(1H, dJ=10.2 Hz), 7.05-7.11(4H, m), 7.25-7.51(10H, m).

The stereochemistry of the —CH=CH— bond was Z.

EXAMPLE 240

Compound (264): Phenyl N-(4-fluorophenyl)-3-(phenylthio)thioacrylimidate $^1$H-NMR (CDCl$_3$) δ(ppm): 5.67(0.77H, d J=14.6 Hz), 5.80 (0.08H, d J=10.0 Hz), 5.99(0.15H, d J=15.4 Hz), 6.62(0.3H, br. m), 6.82-6.61(1.7H, m), 6.99-7.09(2H, m), 7.25-7.57 (11H, m).

The stereochemistry of the —CH=CH— bond was mixture of E and Z.

EXAMPLE 241

Compound (265): 1,1-Dimethylethyl N-(4-methylphenyl)-3-(phenylthio)thioacrylimidate $^1$H-NMR (CDCl$_3$) δ(ppm): 1.38(2.1H, s), 1.56(6.9H, s), 2.31(0.7H, s), 2.32(2.3H, s), 6.07(0.77H, d J=15.5 Hz), 6.15 (0.23H, d J=15.7 Hz), 6.64(d J=8.5 Hz), 6.67(d J=8.2 Hz) total 2H, 7.06-7.09(2H, m), 7.27-7.38(6H, m).

The stereochemistry of the —CH=CH— bond was E.

Compounds (266) and (267) were synthesized in a similar manner as the Example 161.

EXAMPLE 242

Compound (266): Ethyl N-(4-methylphenyl)-3-(phenylthio)thioacrylimidate $^1$H-NMR (CDCl$_3$) δ(ppm): 1.33(3H, t J=7.4 Hz), 2.32(3H, s), 2.89(2H, sept), 6.13(1H,d, J=15.5 Hz), 6.63(2H,d, J=8.2 Hz), 7.05-7.38(8H, m).

The stereochemistry of the —CH=CH— bond was E.

EXAMPLE 243

Compound (267): Ethyl N-(4-methylphenyl)-3-(phenylthio)thioacrylimidate $^1$H-NMR (CDCl$_3$) δ(ppm): 1.28-1.33(3H, m), 2.34(3H, s), 2.91-2.93(2H, m), 6.39(1H, d, J=10.0 Hz), 6.89-7.49(10H, m).

The stereochemistry of the —CH=CH— bond was Z.

Compounds (268) to (277) were synthesized in a similar manner as the Example 100.

EXAMPLE 244

Compound (268): 3-Methylphenyl N-(3,4-dimethylphenyl)-3-(4-fluorophenylthio)acrylimidate $^1$H-NMR (CDCl$_3$) δ(ppm): 2.18(3H,s),2.19(3H,s),2.35 (3H,s),5.80 1H,d J=15.2 Hz),6.45(1H,d J=7.8 Hz),6.50(1H, brs),6.94-7.04(7H,m),7.34-7.42(2H,m),7.55(1H, d J=15.2 Hz).

The stereochemistry of the —CH=CH— bond was E.

EXAMPLE 245

Compound (269): 3-Methylphenyl N-(3,4-dimethylphenyl)-3-(4-chlorophenylthio)acrylimidate $^1$H-NMR (CDCl$_3$) δ(ppm): 2.19(3H,s), 2.20(3H,s), 2.35 (3H,s), 5.88(1H,d J=15.2 Hz), 6.46(1H,d J=7.8 Hz), 6.50(1H, brs), 6.96-7.00(3H,m), 7.22-7.36(6H,m), 7.56(1H,d J=15.2 Hz).

The stereochemistry of the —CH=CH— bond was E.

EXAMPLE 246

Compound (270): 3-Methylphenyl N-(3,4-dimethylphenyl)-3-(4-methylphenylthio)acrylimidate $^1$H-NMR (CDCl$_3$) δ(ppm): 2.18(3H,s), 2.19(3H,s), 2.33 (3H,s), 2.34(3H,s), 5.87(1H,d J=14.9 Hz), 6.47(1H,d J=7.8 Hz), 6.51(1H, brs), 6.94-6.99(4H,m), 7.12-7.14(2H,m), 7.21-7.23(1H,m), 7.30-7.32(2H,m), 7.61(1H, d J=14.9 Hz).

The stereochemistry of the —CH=CH— bond was E.

EXAMPLE 247

Compound (271): 3-Methylphenyl N-(3,4-dimethylphenyl)-3-(4-methoxyphenylthio)acrylimidate $^1$H-NMR (CDCl$_3$) δ(ppm): 2.17(3H,s), 2.18(3H,s), 2.34 (3H,s), 3.80(3H,s), 5.76(1H,d J=15.2 Hz), 6.45(1H,d J=7.8 Hz), 6.49(1H, brs), 6.83-6.86(2H,m), 6.93-6.98(4H,m), 7.20-7.24(1H,m), 7.34-7.36(2H,m), 7.56(1H,d J=15.2 Hz).
The stereochemistry of the —CH=CH— bond was E.

EXAMPLE 248

Compound (272): 3-Methylphenyl N-(3,4-dimethylphenyl)-3-(2-pyridylthio)acrylimidate $^1$H-NMR (CDCl$_3$) δ(ppm): 2.21(6H,s), 2.37(3H,s), 6.25 (1H,d J=15.7 Hz), 6.53(1H,d J=7.8 Hz), 6.59(1H, brs), 6.97-7.14(7H,m), 7.55-7.59(1H,m), 8.45(1H,d J=15.9 Hz), 8.49-8.53(1H,m).
The stereochemistry of the —CH=CH— bond was E.

EXAMPLE 249

Compound (273): 3-Methylphenyl N-(3,4-dimethylphenyl)-3-(2-pyrimidinylthio)acrylimidate $^1$H-NMR (CDCl$_3$) δ(ppm): 2.21(6H,s), 2.38(3H,s), 6.29 (1H,d J=15.9 Hz), 6.54(1H,d J=7.8 Hz), 6.59(1H, brs), 6.98-7.09(6H,m), 8.55(1H, d J=15.9 Hz), 8.58-8.60(2H,m).
The stereochemistry of the —CH=CH— bond was E.

EXAMPLE 250

Compound (274): 3-Methylphenyl N-(3,4-dimethylphenyl)-3-(benzylthio)acrylimidate $^1$H-NMR (CDCl$_3$) δ(ppm): 2.20(3H,s), 2.21(3H,s), 2.35 (3H,s), 3.90(2H,s), 5.90(1H,d J=15.2 Hz), 6.47(1H,d J=7.8 Hz), 6.54(1H, brs), 6.95-7.00(4H,m), 7.20-7.28(6H,m), 7.53 (1H, d J=15.2 Hz).
The stereochemistry of the —CH=CH— bond was E.

EXAMPLE 251

Compound (275): 3-Methylphenyl N-(3,4-dimethylphenyl)-3-(4-fluorobenzylthio)acrylimidate $^1$H-NMR (CDCl$_3$) δ(ppm): 2.20(3H,s), 2.21(3H,s), 2.35 (3H,s), 3.87(2H,s), 5.87(1H,d J=15.2 Hz), 6.46(1H,d J=8.1 Hz), 6.53(1H, brs), 6.89-6.99(7H,m), 7.15-7.18(2H,m), 7.50 (1H, d J=15.2 Hz).
The stereochemistry of the —CH=CH— bond was E.

EXAMPLE 252

Compound (276): 3-Methylphenyl N-(3,4-dimethylphenyl)-3-(4-methylbenzylthio)acrylimidate $^1$H-NMR (CDCl$_3$) δ(ppm): 2.20(3H,s), 2.21(3H,s), 2.33 (3H,s), 2.35(3H,s), 3.86(2H,s), 5.90(1H,dJ=14.9 Hz), 6.47 (1H,dJ=7.8 Hz), 6.54(1H, brs), 6.95-7.00(4H,m), 7.09(4H, brs), 7.21-7.23(1H,m), 7.54(1H,d J=14.9 Hz).
The stereochemistry of the —CH=CH— bond was E.

EXAMPLE 253

Compound (277): 3-Methylphenyl N-(3,4-dimethylphenyl)-3-(4-methoxybenzylthio)acrylimidate $^1$H-NMR (CDCl$_3$) δ(ppm): 2.20(3H,s), 2.21(3H,s), 2.35 (3H,s), 3.80(3H,s), 3.86(2H,s), 5.90(1H,dJ=15.2 Hz), 6.48 (1H,dJ=7.8 Hz), 6.55(1H, brs), 6.80-6.82(2H,m), 6.95-7.00 (4H,m), 7.12-7.14(2H,m), 7.21-7.23(1H,m), 7.55(1H, d J=15.2 Hz).
The stereochemistry of the —CH=CH— bond was E.

Compounds (278) and (279) were synthesized in a similar manner as the Example 176

EXAMPLE 254

Compound (278): 4-Fluorophenyl N-(4-fluorophenyl)-3-(phenylthio)thioacrylimidate $^1$H-NMR (CDCl$_3$) δ(ppm): 5.46(0.83H, d J=14.4 Hz), 5.97 (0.17H, d J=15.6 Hz), 6.59(0.51H, Br), 6.84-7.06(4.49H, m), 7.25-7.32(7H, m), 7.49-7.59(2H, m).
The stereochemistry of the —CH=CH— bond was E.

EXAMPLE 255

Compound (279): 4-Methoxyphenyl N-(4-fluorophenyl)-3-(phenylthio)thioacrylimidate $^1$H-NMR (CDCl$_3$) δ(ppm): 3.80(0.30H,s), 3.83(1.29H,s), 3.85(1.41H, s), 5.57(0.47H,dJ=14.9 Hz), 5.80(0.43H, dJ=10.0 Hz), 5.97(0.10H, d J=15.4 Hz), 6.59(0.2H, Br), 6.78-6.91(3.8H,m), 7.00-7.11(3H, m), 7.21-7.56(7H, m).
The stereochemistry of the —CH=CH— bond was mixture of E and Z.

Compounds (280) to (284) were synthesized in a similar manner as the Example 161

EXAMPLE 256

Compound (280): Propyl N-(4-methylphenyl)-3-(phenylthio)thioacrylimidate $^1$H-NMR (CDCl$_3$) δ(ppm): 1.01(3H,t J=7.3 Hz), 1.70(2H, m), 2.31(3H, s), 3.04(2H,t J=7.2 Hz), 6.13(1H,d, J=15.6 Hz), 6.63(2H, d, J=8.0 Hz), 7.05-7.49(8H, m).
The stereochemistry of the —CH=CH— bond was E.

EXAMPLE 257

Compound (281): Propyl N-(4-methylphenyl)-3-(phenylthio)thioacrylimidate $^1$H-NMR (CDCl$_3$) δ(ppm): 0.99(3H, m), 1.63(2H, m), 2.34 (3H, s), 2.86(2H, m), 6.39(1H, d, J=9.8 Hz), 6.89-7.49(10H, m).
The stereochemistry of the —CH=CH— bond was Z.

EXAMPLE 258

Compound (282): Benzyl N-(4-methylphenyl)-3-(4-chlorobenzylthio)thioacrylimidate $^1$H-NMR (CDCl$_3$) δ(ppm): 2.34(3H, s), 3.79(2H, s), 4.28 (2H, s), 6.05(1H,d, J=15.5 Hz), 6.60(2H,d, J=8.2 Hz), 7.07-7.38(12H,m).
The stereochemistry of the —CH=CH— bond was E.

EXAMPLE 259

Compound (283): Benzyl N-(4-methylphenyl)-3-(4-chlorobenzylthio)thioacrylimidate $^1$H-NMR (CDCl$_3$) δ(ppm): 2.30(3H,s), 3.85(2H, brs), 4.06 (2H, brs), 6.29(1H, brs), 6.70-7.30(14H, m).
The stereochemistry of the —CH=CH— bond was Z.

EXAMPLE 260

Compound (284): Butyl N-(4-methylphenyl)-3-(phenylthio)thioacrylimidate $^1$H-NMR (CDCl$_3$) δ(ppm): 0.92(3H, t J=7.4 Hz), 1.38-1.50 (2H, m), 1.62-1.75(2H, m), 2.31(3H, s), 3.06(2H, t J=7.4 Hz), 6.13(1H, d, J=15.5 Hz), 6.63(2H, d, J=8.2 Hz), 6.75-7.38(8H, m).
The stereochemistry of the —CH=CH— bond was E.
Compound (285) was synthesized in a similar manner as the Example 61.

EXAMPLE 261

Compound (285): 4-Biphenyl N-(4-methylphenyl)-3-(phenylthio)acrylimidate $^1$H-NMR (CDCl$_3$) δ(ppm): 2.29(3H,s), 5.95(1H,dJ=15.4 Hz), 6.66(2H, d J=8.0 Hz), 7.03(2H,d J=8.0 Hz), 7.26-7.59 (14H, m), 7.70(1H, d J=15.4 Hz).
The stereochemistry of the —CH=CH— bond was E.
Compounds (286) to (320) were synthesized in a similar manner as the Example 100.

EXAMPLE 262

Compound (286): 3-Methylphenyl N-(3,4-dimethylphenyl)-3-(2-fluorophenoxy)acrylimidate $^1$H-NMR (CDCl$_3$) δ(ppm): 2.19(3H,s),2.20(3H,s),2.36 (3H,s),5.81(1H,d J=12.1 Hz),6.53(1H,d J=7.8 Hz),6.54(1H, brs),6.96-7.03(4H,m),7.08-7.16(4H,m),7.23-7.27(1H,m), 7.68(1H,d J=12.1 Hz).
The stereochemistry of the —CH=CH— bond was E.

EXAMPLE 263

Compound (287): 3-Methylphenyl N-(3,4-dimethylphenyl)-3-(3-fluorophenoxy)acrylimidate $^1$H-NMR (CDCl$_3$) δ(ppm): 2.20(3H,s),2.21(3H,s),2.37 (3H,s),5.83(1H,d J=11.9 Hz),6.53(1H,d J=7.8 Hz),6.59(1H, brs),6.76-6.80(1H,m),6.83-6.87(2H,m),6.97 7.04(4H,m), 7.23-7.33(2H,m),7.71(1H,d J=11.9 Hz).
The stereochemistry of the —CH=CH— bond was E.

EXAMPLE 264

Compound (288): 3-Methylphenyl N-(3,4-dimethylphenyl)-3-(4-fluorophenoxy)acrylimidate $^1$H-NMR (CDCl$_3$) δ(ppm): 2.19(3H,s), 2.20(3H,s), 2.36 (3H,s), 5.76(1H,d J=12.1 Hz), 6.53(1H,d J=7.8 Hz), 6.58(1H, brs), 6.97-7.03(8H,m), 7.23-7.27(1H,m), 7.67(1H, d J=12.1 Hz).
The stereochemistry of the —CH=CH— bond was E.

EXAMPLE 265

Compound (289): 3-Methylphenyl 3-(2-chlorophenoxy)-N-(3,4-dimethylphenyl)acrylimidate $^1$H-NMR (CDCl$_3$) δ(ppm): 2.19(3H,s),2.20(3H,s),2.36 (3H,s),5.83(1H,d J=11.9 Hz),6.54(1H,d J=7.8 Hz),6.59(1H, brs),6.96-7.03(6H,m),7.07-7.13(2H,m),7.39 7.42(1H,m), 7.66(1H,d J=11.9 Hz).
The stereochemistry of the —CH=CH— bond was E.

EXAMPLE 266

Compound (290): 3-Methylphenyl 3-(3-chlorophenoxy)-N-(3,4-dimethylphenyl)acrylimidate $^1$H-NMR (CDCl$_3$) δ(ppm): 2.20(3H,s),2.21(3H,s),2.37 (3H,s),5.82(1H,d J=12.1 Hz),6.53(1H,d J=7.8 Hz),6.59(1H, brs),6.93-7.06(6H,m),7.11-7.13(1H,m),7.24-7.29(2H,m), 7.69(1H,d J=12.1 Hz).
The stereochemistry of the —CH=CH— bond was E.

EXAMPLE 267

Compound (291): 3-Methylphenyl 3-(4-chlorophenoxy)-N-(3,4-dimethylphenyl)acrylimidate $^1$H-NMR (CDCl$_3$) δ(ppm): 2.20(3H,s),2.21(3H,s),2.36 (3H,s),5.80(1H,d J=12.1 Hz),6.53(1H,d J=7.8 Hz),6.58(1H, brs),6.97-7.03(6H,m),7.23-7.31(3H,m),7.68(1H,d J=12.1 Hz).
The stereochemistry of the —CH=CH— bond was E.

EXAMPLE 268

Compound (292): 3-Methylphenyl N-(3,4-dimethylphenyl)-3-(2-methylphenoxy)acrylimidate $^1$H-NMR (CDCl$_3$) δ(ppm): 2.20(3H,s),2.21(3H,s),2.24 (3H,s),2.36(3H,s),5.73(1H,d J=12.1 Hz),6.55(1H,d J=7.8 Hz),6.60(1H, brs),6.96-7.06(6H,m),7.17-7.18(2H,m),7.22-7.26(1H,m),7.71(1H,d J=12.1 Hz).
The stereochemistry of the —CH=CH— bond was E.

EXAMPLE 269

Compound (293): 3-Methylphenyl N-(3,4-dimethylphenyl)-3-(3-methylphenoxy)acrylimidate $^1$H-NMR (CDCl$_3$) δ(ppm): 2.20(3H,s),2.21(3H,s),2.35 (3H,s),2.36(3H,s),5.77(1H,d J=11.9 Hz),6.54(1H,d J=7.8 Hz),6.59(1H, brs),6.84-6.86(2H,m),6.94-7.04(5H,m),7.19-7.27(2H,m),7.74(1H,d J=11.9 Hz).
The stereochemistry of the —CH=CH— bond was E.

EXAMPLE 270

Compound (294): 3-Methylphenyl N-(3,4-dimethylphenyl)-3-(4-methylphenoxy)acrylimidate $^1$H-NMR (CDCl$_3$) δ(ppm): 2.19(3H,s),2.20(3H,s),2.32 (3H,s),2.36(3H,s),5.75(1H,d J=11.9 Hz),6.54(1H,d J=7.8 Hz),6.59(1H, brs),6.92-7.03(6H,m),7.12-7.14(2H,m),7.23-7.27(1H,m),7.72(1H, d J=11.9 Hz).
The stereochemistry of the —CH=CH— bond was E.

EXAMPLE 271

Compound (295): 3-Methylphenyl N-(3,4-dimethylphenyl)-3-(3-methoxyphenoxy)acrylimidate $^1$H-NMR (CDCl$_3$) δ(ppm): 2.20(3H,s),2.21(3H,s),2.36(3H,s),3.79(3H,s),5.79(1H,d J=12.1 Hz),6.54(1H,d J=7.8 Hz),6.59(2H, brs),6.64-6.70(2H,m),6.96-7.03(4H,m),7.22-7.27(2H,m),7.74(1H,d J=12.1 Hz).

The stereochemistry of the —CH=CH— bond was E.

EXAMPLE 272

Compound (296): 3-Methylphenyl N-(3,4-dimethylphenyl)-3-(4-methoxyphenoxy)acrylimidate $^1$H-NMR (CDCl$_3$) δ(ppm): 2.19(3H,s),2.20(3H,s),2.36(3H,s),3.78(3H,s),5.72(1H,d J=12.1 Hz),6.54(1H,d J=7.8 Hz),6.59(1H, brs),6.84-6.86(2H,m),6.96-7.02(6H,m),7.22-7.26(1H,m),7.68(1H,d J=12.1 Hz).

The stereochemistry of the —CH=CH— bond was E.

EXAMPLE 273

Compound (297): 3-Methylphenyl N-(3,4-dimethylphenyl)-3-(3-trifluoromethylphenoxy)acrylimidate $^1$H-NMR (CDCl$_3$) δ(ppm): 2.20(3H,s),2.21(3H,s),2.37(3H,s),5.85(1H,d J=11.9 Hz),6.54(1H,d J=7.8 Hz),6.59(1H, brs),6.98-7.04(4H,m),7.23-7.29(3H,m),7.39-7.41(1H,m),7.46-7.50(1H,m),7.72(1H,d J=11.9 Hz).

The stereochemistry of the —CH=CH— bond was E.

EXAMPLE 274

Compound (298): 3-Methylphenyl 3-(4-bromophenoxy)-N-(3,4-dimethylphenyl)acrylimidate $^1$H-NMR (CDCl$_3$) δ(ppm): 2.20(3H,s),2.21(3H,s),2.36(3H,s),5.80(1H,d J=11.9 Hz),6.53(1H,d J=7.8 Hz),6.58(1H, brs),6.92-7.03(6H,m),7.23-7.27(1H,m),7.44-7.46(2H,m),7.68(1H,d J=11.9 Hz).

The stereochemistry of the —CH=CH— bond was E.

EXAMPLE 275

Compound (299): 3-Methylphenyl 3-(3,4-difluorophenoxy)-N-(3,4-dimethylphenyl)acrylimidate $^1$H-NMR (CDCl$_3$) δ(ppm): 2.20(3H,s),2.21(3H,s),2.36(3H,s),5.80(1H,d J=11.9 Hz),6.52(1H,d J=7.8 Hz),6.58(1H, brs),6.77-6.81(1H,m),6.87-6.92(1H,m),6.97-7.02(4H,m),7.10-7.17(1H,m),7.23-7.28(1H,m),7.63(1H, d J=11.9 Hz).

The stereochemistry of the —CH=CH— bond was E.

EXAMPLE 276

Compound (300): 3-Methylphenyl 3-(3,4-dichlorophenoxy)-N-(3,4-dimethylphenyl)acrylimidate $^1$H-NMR (CDCl$_3$) δ(ppm): 2.20(3H,s),2.21(3H,s),2.37(3H,s),5.83(1H,d J=11.9 Hz),6.53(1H,d J=7.8 Hz),6.58(1H, brs),6.90-6.93(1H,m),6.98-7.03(4H,m),7.16-7.17(1H,m),7.24-7.28(1H,m),7.39-7.41(1H,m),7.64(1H, d J=11.9 Hz).

The stereochemistry of the —CH=CH— bond was E.

EXAMPLE 277

Compound (301): 3-Methylphenyl N-(3,4-dimethylphenyl)-3-(3,4-dimethylphenoxy)acrylimidate $^1$H-NMR (CDCl$_3$) δ(ppm): 2.20(3H,s), 2.21(3H,s), 2.21(3H,s), 2.24(3H,s), 2.36(3H,s), 5.74(1H,dJ=11.9 Hz), 6.54(1H,dJ=7.8 Hz), 6.59(1H, brs), 6.78(1H,d J=7.8 Hz), 6.82(1H, brs), 6.96-7.08(4H,m), 7.23-7.27(1H,m), 7.22-7.26(1H, m), 7.72(1H, d J=11.9 Hz).

The stereochemistry of the —CH=CH— bond was E.

EXAMPLE 278

Compound (302): 3-Methylphenyl N-(3,4-dimethylphenyl)-3-(6-benzo[1,3]dioxolyloxy)acrylimidate $^1$H-NMR (CDCl$_3$) δ(ppm): 2.19(3H,s),2.20(3H,s),2.36(3H,s),5.71(1H,d J=11.9 Hz),5.96(2H,s),6.48-6.54(2H,m),6.58-6.59(2H,m),6.72-60.74(1H,m),6.96-7.02(4H,m),7.22-7.27(1H,m),7.63(1H,d J=11.9 Hz).

The stereochemistry of the —CH=CH— bond was E.

EXAMPLE 279

Compound (303): 3-Methylphenyl N-(3,4-dimethylphenyl)-3-(4-methoxycarbonylphenoxy)acrylimidate $^1$H-NMR (CDCl$_3$) δ(ppm): 2.20(3H,s),2.21(3H,s),2.37(3H,s),3.91(3H,s),5.88(1H,d J=11.9 Hz),6.54(1H,d J=7.8 Hz),6.59(1H, brs),6.98-7.04(4H,m),7.07-7.10(2H,m),7.24-7.28(1H,m),7.78(1H,d J=11.9 Hz),8.03-8.05(2H,m).

The stereochemistry of the —CH=CH— bond was E.

EXAMPLE 280

Compound (304): 3-Methylphenyl 3-(4-acetylphenoxy)-N-(3,4-dimethylphenyl)acrylimidate $^1$H-NMR (CDCl$_3$) δ(ppm): 2.20(3H,s),2.21(3H,s),2.37(3H,s),2.58(3H,s),5.90(1H,d J=11.9 Hz),6.54(1H,d J=7.8 Hz),6.59(1H, brs),6.98-7.04(4H,m),7.10-7.12(2H,m),7.24-7.29(1H,m),7.79(1H,d J=11.9 Hz),7.97-7.99(2H,m).

The stereochemistry of the —CH=CH— bond was E.

EXAMPLE 281

Compound (305): 3-Methylphenyl N-(3,4-dimethylphenyl)-3-(4-cyanophenoxy)acrylimidate $^1$H-NMR (CDCl$_3$) δ(ppm): 2.20(3H,s),2.21(3H,s),2.37(3H,s),5.92(1H,d J=11.9 Hz),6.53(1H,d J=7.8 Hz),6.58(1H, brs),6.99-7.03(4H,m),7.12-7.15(2H,m),7.24-7.29(1H,m),7.65-7.67(2H,m) 7.79(1H,d J=11.9 Hz).

The stereochemistry of the —CH=CH— bond was E.

EXAMPLE 282

Compound (306): 3-Methylphenyl N-(3,4-dimethylphenyl)-3-(4-nitrophenoxy)acrylimidate $^1$H-NMR (CDCl$_3$) δ(ppm): 2.21(3H,s),2.22(3H,s),2.38(3H,s),5.96(1H,d J=11.9 Hz),6.54(1H,d J=7.8 Hz),6.59(1H, brs),6.99-7.04(4H,m),7.15-7.17(2H,m),7.25-7.27(2H,m),7.77(1H,d J=11.9 Hz),8.25-8.27(1H,m).

The stereochemistry of the —CH=CH— bond was E.

EXAMPLE 283

Compound (307): 3-Methylphenyl N-(3,4-dimethylphenyl)-3-(4-methylthiophenoxy)acrylimidate $^1$H-NMR (CDCl$_3$) δ(ppm): 2.20(3H,s),2.21(3H,s),2.36 (3H,s),2.46(3H,s),5.77(1H,d J=12.1 Hz),6.54(1H,d J=7.8 Hz),6.59(1H, brs),6.97-7.03(6H,m),7.23-7.27(3H,m),7.70 (1H,d J=12.1 Hz).

The stereochemistry of the —CH=CH— bond was E.

EXAMPLE 284

Compound (308): 3-Methylphenyl N-(3,4-dimethylphenyl)-3-(4-phenylphenoxy)acrylimidate $^1$H-NMR (CDCl$_3$) δ(ppm): 2.20(3H,s), 2.21(3H,s), 2.37 (3H,s), 5.83(1H,d J=11.9 Hz), 6.56(1H,d J=7.8 Hz), 6.61(1H, brs), 6.99-7.05(4H,m), 7.11-7.13(2H,m), 7.24-7.26(1H,m), 7.34-7.36(1H,m), 7.41-7.45(2H,m), 7.53-7.57(4H,m), 7.80 (1H, d J=11.9 Hz).

The stereochemistry of the —CH=CH— bond was E.

EXAMPLE 285

Compound (309): 3-Methylphenyl 3-(2-fluorobenzyloxy)-N-(3,4-dimethylphenyl)acrylimidate $^1$H-NMR (CDCl$_3$) δ(ppm): 2.19(6H,s), 2.35(3H,s), 4.88 (2H,s), 5.43(1H,d J=12.4 Hz), 6.50(1H,d J=7.8 Hz), 6.56(1H, brs), 6.93-7.01(5H,m), 7.11-7.16(2H,m), 7.28-7.36(2H,m), 7.61(1H, d J=12.4 Hz).

The stereochemistry of the —CH=CH— bond was E.

EXAMPLE 286

Compound (310): 3-Methylphenyl 3-(3-fluorobenzyloxy)-N-(3,4-dimethylphenyl)acrylimidate $^1$H-NMR (CDCl$_3$) δ(ppm): 2.19(3H,s),2.20(3H,s),2.35 (3H,s),4.80(2H,s),5.40(1H,d J=12.4 Hz),6.49(1H,d J=7.8 Hz),6.56(1H, brs),6.95-7.01(7H,m),7.22-7.24(1H,m),7.29-7.32(1H,m),7.60(1H,d J=12.4 Hz).

The stereochemistry of the —CH=CH— bond was E.

EXAMPLE 287

Compound (311): 3-Methylphenyl 3-(4-fluorobenzyloxy)-N-(3,4-dimethylphenyl)acrylimidate $^1$H-NMR (CDCl$_3$) δ(ppm): 2.20(6H,s),2.35(3H,s),4.77 (2H,s),5.39(1H,d J=12.4 Hz),6.49(1H,d J=7.8 Hz),6.55(1H, brs),6.95-7.06(6H,m),7.22-7.28(3H,m),7.59(1H,d J=12.4 Hz).

The stereochemistry of the —CH=CH— bond was E.

EXAMPLE 288

Compound (312): 3-Methylphenyl 3-(2-chlorobenzyloxy)-N-(3,4-dimethylphenyl)acrylimidate $^1$H-NMR (CDCl$_3$) δ(ppm): 2.19(6H,s),2.35(3H,s),4.94 (2H,s), 1H,d J=12.1 Hz),6.51(1H,d J=8.3 Hz),6.56(1H, brs), 6.91-7.01(3H,m),7.19-7.29(4H,m),7.34-7.49(2H,m),7.62 (1H,d J=12.1 Hz).

The stereochemistry of the —CH=CH— bond was E.

EXAMPLE 289

Compound (313): 3-Methylphenyl 3-(3-chlorobenzyloxy)-N-(3,4-dimethylphenyl)acrylimidate $^1$H-NMR (CDCl$_3$) δ(ppm): 2.19(3H,s),2.20(3H,s),2.35 (3H,s),4H,s),5.39(1H,d J=12.4 Hz),6.49(1H,d J=7.8 Hz), 6.56(1H, brs),6.91-7.00(4H,m),7.22-7.32(5H,m), 1H,d J=12.4 Hz).

The stereochemistry of the —CH=CH— bond was E.

EXAMPLE 290

Compound (314): 3-Methylphenyl 3-(4-chlorobenzyloxy)-N-(3,4-dimethylphenyl)acrylimidate $^1$H-NMR (CDCl$_3$) δ(ppm): 2.19(3H,s),2.20(3H,s),2.35 (3H,s),4.77(2H,s),5.38(1H,d J=12.4 Hz),6.49(1H,d J=7.8 Hz),6.55(1H, brs),6.95-7.00(3H,m),7.20-7.24(3H,m), 7.34 (3H,m),7.59(1H,d J=12.4 Hz).

The stereochemistry of the —CH=CH— bond was E.

EXAMPLE 291

Compound (315): 3-Methylphenyl N-(3,4-dimethylphenyl)-3-(2-methylbenzyloxy)acrylimidate $^1$H-NMR (CDCl$_3$) δ(ppm): 2.19(6H,s),2.29(3H,s),2.35 (3H,s),4.81(2H,s),5.42(1H,d J=12.4 Hz),6.52(1H,d J=7.8 Hz),6.57(1H, brs),6.87-7.01(4H,m),7.17-7.24(5H,m),7.61 (1H, d J=12.4 Hz).

The stereochemistry of the —CH=CH— bond was E.

EXAMPLE 292

Compound (316): 3-Methylphenyl N-(3,4-dimethylphenyl)-3-(3-methylbenzyloxy)acrylimidate $^1$H-NMR (CDCl$_3$) δ(ppm): 2.19(6H,s),2.35(6H,s),4.77 (2H,s),5.41(1H,d J=12.4 Hz),6.50(1H,d J=7.8 Hz),6.57(1H, brs),6.91-7.00(3H,m),7.07-7.15(3H,m),7.07-7.15(3H,m), 7.21-7.26(3H,m),7.61(1H, d J=12.4 Hz).

The stereochemistry of the —CH=CH— bond was E.

EXAMPLE 293

Compound (317): 3-Methylphenyl N-(3,4-dimethylphenyl)-3-(4-methylbenzyloxy)acrylimidate $^1$H-NMR (CDCl$_3$) δ(ppm): 2.19(6H,s),2.35(6H,s),4.76 (2H,s),5.40(1H,d J=12.4 Hz),6.50(1H,d J=7.8 Hz),6.56(1H, brs),6.94-7.00(4H,m),7.16-7.18(3H,m),7.20-7.23(2H,m), 7.60(1H,d J=12.4 Hz).

The stereochemistry of the —CH=CH— bond was E.

EXAMPLE 294

Compound (318): 3-Methylphenyl N-(3,4-dimethylphenyl)-3-(2-methoxybenzyloxy)acrylimidate $^1$H-NMR (CDCl$_3$) δ(ppm): 2.19(6H,s),2.35(3H,s),3.79 (3H,s),4.89(2H,s),5.41(1H,d J=12.4 Hz),6.50(1H,d J=7.8 Hz),6.56(1H, brs),6.86-6.88(1H,m),6.94-7.00(5H,m),7.21-7.33(3H,m),7.62(1H, d J=12.4 Hz).

The stereochemistry of the —CH=CH— bond was E.

EXAMPLE 295

Compound (319): 3-Methylphenyl N-(3,4-dimethylphenyl)-3-(3-methoxybenzyloxy)acrylimidate $^1$H-NMR (CDCl$_3$) δ(ppm): 2.19(3H,s),2.20(3H,s),2.35 (3H,s),3.80(3 H,s),4.79(2H,s),5.41(1H,d J=12.4 Hz),6.50 (1H,d J=7.8 Hz),6.56(1H, brs),6.83-6.88(3H,m),6.95-7.00 (4H,m),7.21-7.29(2H,m),7.61(1H,d J=12.4 Hz).

The stereochemistry of the —CH=CH— bond was E.

EXAMPLE 296

Compound (320): 3-Methylphenyl N-(3,4-dimethylphenyl)-3-(4-methoxybenzyloxy)acrylimidate $^1$H-NMR (CDCl$_3$) δ(ppm): 2.19(6H,s),2.35(3H,s),3.81 (3H,s),4.74(2H,s),5.39(1H,d J=12.4 Hz),6.50(1H,d J=7.8 Hz),6.56(1H, brs),6.87-6.89(2H,m),6.95-7.00(4H,m),7.20-7.23(3H,m),7.60(1H,d J=12.4 Hz).

The stereochemistry of the —CH=CH— bond was E.

Compounds (321) to (324) were synthesized in a similar manner as the Example 161.

EXAMPLE 297

Compound (321): 2-Methylpropyl N-(4-methylphenyl)-3-(phenylthio)thioacrylimidate $^1$H-NMR (CDCl$_3$) δ(ppm): 1.01(6H, d, J=6.5 Hz), 1.93 (1H, sept. J=6.7 Hz), 2.31(3H, s), 2.99(2H, d, J=6.8 Hz), 6.12(1H, d, J=15.5 Hz), 6.62(2H, d, J=8.0 Hz), 7.06(2H, d, J=8.0 Hz), 7.29-7.39(6H, m).

The stereochemistry of the —CH=CH— bond was E.

EXAMPLE 298

Compound (322): 2-Methylpropyl N-(4-methylphenyl)-3-(phenylthio)thioacrylimidate $^1$H-NMR (CDCl$_3$) δ(ppm): 0.97(6H, brs), 1.57(2H, s), 2.34(3H, s), 2.77(1H, brs), 6.38(1H, d, J=9.7 Hz), 6.91-7.49 (10H, m).

The stereochemistry of the —CH=CH— bond was Z.

EXAMPLE 299

Compound (323): Cyclohexyl N-phenyl-3-(cyclohexylthio)thioacrylimidate $^1$H-NMR (CDCl$_3$) δ(ppm): 1.23-2.10(20H, m), 2.84-2.89 (1H, m), 3.76-3.81(1H, m), 6.03(1H, d, J=15.7 Hz), 6.75-7.29 (6H, m).

The stereochemistry of the —CH=CH— bond was E.

EXAMPLE 300

Compound (324): 1-Methylpropyl N-(4-methylphenyl)-3-(phenylthio)thioacrylimidate $^1$H-NMR (CDCl$_3$) δ(ppm): 1.01(3H,t J=7.4 Hz), 1.36(3H, d, J=7.0 Hz), 1.63-1.74(2H,m), 2.34(3H,s), 3.79(1H,m), 6.12 (1H,d, J=15.5 Hz), 6.63(2H, d, J=8.2 Hz), 7.06(2H, d, J=8.0 Hz), 7.29-7.38(6H, m).

The stereochemistry of the —CH=CH— bond was E.

Compound (325) was synthesized in a similar manner as the Example 37.

EXAMPLE 301

Compound (325): Phenyl N-(3-biphenyl)-3-phenoxyacrylimidate $^1$H-NMR (CDCl$_3$) δ(ppm): 5.70(1H,d, J=11.8 Hz), 6.80-7.78(19H,m), 7.85(1H ,d, J=11.8 Hz).

The stereochemistry of the —CH=CH— bond was E.

EXAMPLE 302

Compound (326): Phenyl N-phenoxy-3-(phenylthio)thioacrylimidate

N-phenoxy-3-(phenylthio)acrylamide (0.50 g) was suspended to toluene (5 ml), then phosphorus pentachloride (0.42 g) was added thereto under ice-cooling and stirred at same temperature for 2.5 hours. The reaction mixture was concentrated under reduced pressure. The residue was dissolved to ethanol (15 ml). Sodium salt of thiophenol (0.73 g) was added to the solution under ice-cooling and heat refluxing for 2.5 hours. t-Butyl methyl ether (100 ml) was added to the reaction mixture, washed successively with 1N aqueous sodium hydroxide solution, water and aqueous saturated sodium chloride solution, dried over anhydrous sodium sulfate, filtered off inorganic salt and concentrated under reduced pressure. The residue was purified by medium pressure preparative high performance liquid chromatography (hexane:ethyl acetate=30:11) to obtain phenyl N-(phenoxy)-3-(phenylthio)thioacrylimidate (0.14 g) as yellow oil.

$^1$H-NMR (CDCl$_3$) δ(ppm): 5.45(1H, d, J=15.0 Hz), 7.00-7.04(1H, m), 7.18-7.46(15H, m).

The stereochemistry of the —CH=CH— bond was E.

Compound (327) was synthesized in a similar manner as the Example 302.

EXAMPLE 303

Compound (327): Phenyl N-(phenylamino)-3-(phenylthio)thioacrylimidate $^1$H-NMR (CDCl$_3$) δ(ppm): 6.07(0.41H, d, J=9.0 Hz), 6.55 (0.41H, d, J=9.0 Hz), 6.68(0.59H,d, J=16.3 Hz), 6.88-6.94 (1H,m), 7.00(0.59H, d, J=16.3 Hz), 7.03-7.07(1H,m), 7.19-7.37(12H,m) 7.52-7.54(1H, m), 8.68(0.41H, brs, NH), 8.74 (0.59H, brs, NH).

The stereochemistry of the —CH=CH— bond was mixture of E and Z.

Compounds (328) to (330) were synthesized in a similar manner as the Example 176.

EXAMPLE 304

Compound (328): Isopropyrideneamino N-(4-methylphenyl)-3-(phenylthio)acrylimidate $^1$H-NMR (CDCl$_3$) δ(ppm): 2.06(3H, s), 2.11(3H, s), 2.30 (3H, s), 5.80(1H,dJ=15.4 Hz), 6.73(2H,dJ=7.8 Hz), 7.03(2H, dJ=8.5 Hz), 7.30-7.52(6H, m).

The stereochemistry of the —CH=CH— bond was E.

EXAMPLE 305

Compound (329): 2,3,5,6-Tetrafluorophenyl N-(4-methylphenyl)-3-(phenylthio)acrylimidate $^1$H-NMR (CDCl$_3$) δ(ppm): 2.29(3H,s),5.86(1H,dJ=15.2 Hz),6.64(2H, dJ=8.2 Hz), 6.90-6.95(1H,m),7.04(2H,dJ=7.7 Hz), 7.32-7.38(3H, m), 7.43-7.46(2H,m), 7.74(1H,d J=15.2 Hz).

The stereochemistry of the —CH═CH— bond was E.

EXAMPLE 306

Compound (330): 2,6-Dichlorophenyl N-(4-methylphenyl)-3-(phenylthio)thioacrylimidate $^1$H-NMR (CDCl$_3$) δ(ppm): 2.28(0.39H,s), 2.31(1.86H,s), 2.36(0.75H, s), 5.56(0.62H,dJ=14.9 Hz), 5.67(0.25H, dJ=10.0 Hz), 6.10(0.13H, d J=15.4 Hz), 6.57(0.26H,d J=7.3 Hz), 6.82-7.57(12.74H, m).

The stereochemistry of the —CH═CH— bond was mixture of E and Z.

Compounds (331) and (332) were synthesized in a similar manner as the Example 100.

EXAMPLE 307

Compound (331): 3-Methylphenyl 3-cyclohexylthio-N-(3,4-dimethylphenyl)acrylimidate $^1$H-NMR (CDCl$_3$) δ(ppm): 1.20-1.90(8H,m),2.19(6H,s), 2.36(3H,s), 2.88-2.99(1H, brs), 6.51(1H, d, J=8.4 Hz), 6.57 (1H, s), 6.92-7.02(1H, m), 7.20-7.28(1H, m), 7.55(1H, d, J=15.5 Hz).

The stereochemistry of the —CH═CH— bond was E.

EXAMPLE 308

Compound (332): 3-Methylphenyl N-(3,4-dimethylphenyl)-3-(4-trifluoromethylphenoxy)acrylimidate $^1$H-NMR (CDCl$_3$) δ(ppm): 2.21(6H, s), 2.37(3H, s), 5.89 (1H, d, J=11.8 Hz), 6.54(1H, d, J=8.0 Hz), 6.59(1H, s), 6.59-7.07(4H, m), 7.14(2H, d, J=8.5 Hz), 7.23-7.30(1H, m), 7.62 (2H,d, J=8.7 Hz), 7.76(1H, d, J=11.8 Hz).

The stereochemistry of the —CH═CH— bond was E.

Compounds (333) to (338) were synthesized in a similar manner as the Example 161.

EXAMPLE 309

Compound (333): Cyclopentyl N-(4-methylphenyl)-3-(phenylthio)thioacrylimidate $^1$H-NMR (CDCl$_3$) δ(ppm): 1.59-1.73(6H,m), 2.16(2H, brs), 2.31(3H, s), 3.95(1H, q, J=7.0 Hz), 6.12(1H, d, J=15.6 Hz), 6.63(2H, d, J=8.0 Hz), 7.06(2H, d, J=8.0 Hz), 7.25-7.52 (6H, m).

The stereochemistry of the —CH═CH— bond was E.

EXAMPLE 310

Compound (334): Cyclopentyl N-(4-methylphenyl)-3-(phenylthio)thioacrylimidate $^1$H-NMR (CDCl$_3$) δ(ppm): 1.57-1.71(6H,m), 2.07(2H, brs), 2.34(3H, s), 3.63(1H, brs), 6.47(1H,d, J=10.1 Hz), 6.90 (2H,d, J=7.7 Hz), 6.99(1H,d, J=9.9 Hz), 7.15(2H,d, J=7.7 Hz), 7.30-7.51(5H,m).

The stereochemistry of the —CH═CH— bond was Z.

EXAMPLE 311

Compound (335): 4-Methylbenzyl N-(4-methylphenyl)-3-(phenylthio)thioacrylimidate $^1$H-NMR (CDCl$_3$) δ(ppm): 2.31(3H, s), 2.32(3H, s), 4.27 (2H, s), 6.13(1H,d, J=15.7 Hz), 6.65(2H,d, J=8.2 Hz), 7.07-7.35(12H,m).

The stereochemistry of the —CH═CH— bond was E.

EXAMPLE 312

Compound (336): 4-Methylbenzyl N-(4-methylphenyl)-3-(phenylthio)thioacrylimidate $^1$H-NMR (CDCl$_3$) δ(ppm): 2.32(6H, s), 4.11(2H, brs), 6.38(1H, d, J=10.4 Hz), 6.91-7.47(14H, m).

The stereochemistry of the —CH═CH— bond was Z.

EXAMPLE 313

Compound (337): 4-Chlorobenzyl N-(4-methylphenyl)-3-(phenylthio)thioacrylimidate $^1$H-NMR (CDCl$_3$) δ(ppm): 2.33(3H, s), 4.25(2H, s), 6.11 (1H, d, J=15.5 Hz), 6.62(2H, d, J=8.2 Hz), 7.08(2H, d, J=8.0 Hz), 7.24-7.36(10H, m).

The stereochemistry of the —CH═CH— bond was E.

EXAMPLE 314

Compound (338): 2,4-Dichlorobenzyl N-(4-methylphenyl)-3-(phenylthio)thioacrylimidate $^1$H-NMR (CDCl$_3$) δ(ppm): 2.32(3H, s), 4.37(2H, s), 6.09 (1H, d, J=15.5 Hz), 6.62(2H, d, J=8.2 Hz), 7.07-7.48(11H, m).

The stereochemistry of the —CH═CH— bond was E.

Compounds (339) to (340) were synthesized in a similar manner as the Example 37.

EXAMPLE 315

Compound (339): Phenyl N-(4-benzoylphenyl)-3-phenoxyacrylimidate $^1$H-NMR (CDCl$_3$) δ(ppm): 5.70(1H,d, J=11.8 Hz), 6.80-7.78(19H,m), 7.85(1H,d J=11.8 Hz).

The stereochemistry of the —CH═CH— bond was E.

EXAMPLE 316

Compound (340): Phenyl N-(4-acetylphenyl)-3-phenoxyacrylimidate $^1$H-NMR (CDCl$_3$) δ(ppm): 2.57(3H, s), 5.63(0.75H, d, J=12.0 Hz), 5.68(0.25H, d, J=12.0 Hz), 6.85-7.90(14H, m), 7.58(0.25H,d, J=12.0 Hz), 7.84(0.75H, d, J=12.0 Hz).
The stereochemistry of the —CH=CH— bond was E.
Compounds (341) to (370) were synthesized in a similar manner as the Example 161.

EXAMPLE 317

Compound (341): Cyclohexylmethyl 3-(2-fluorophenylthio)-N-(4-methylphenyl)-thioacrylimidate $^1$H-NMR (CDCl$_3$) δ(ppm): 1.00-1.25(5H,m),1.57-1.86 (6H,m),2.31(3H, s),2.99(2H,d J=6.8 Hz),6.05(1H,d J=15.7 Hz),6.61(2H,d J=8.1 Hz),7.04-7.40(7H,m).
The stereochemistry of the —CH=CH— bond was E.

EXAMPLE 318

Compound (343): Cyclohexylmethyl 3-(3-fluorophenylthio)-N-(4-methylphenyl)-thioacrylimidate $^1$H-NMR (CDCl$_3$) δ(ppm): 1.01-1.26(5H,m),1.59-1.87 (6H,m),2.32(3H, s),3.00(2H,d J=6.8 Hz),6.16(1H,d J=15.4 Hz),6.63(2H,d J=8.3 Hz),6.96-7.33(7H,m).
The stereochemistry of the —CH=CH— bond was E.

EXAMPLE 319

Compound (345): Cyclohexylmethyl 3-(2-chlorophenylthio)-N-(4-methylphenyl)-thioacrylimidate $^1$H-NMR (CDCl$_3$) δ(ppm): 1.01-1.26(5H,m), 1.66-1.87 (6H,m), 2.31(3H,s), 3.00(2H,d J=6.6 Hz), 6.15(1H,d J=15.4 Hz), 6.63(2H,d J=8.3 Hz), 7.06(2H,d J=8.1 Hz), 7.21-7.41 (5H,m).
The stereochemistry of the —CH=CH— bond was E.

EXAMPLE 320

Compound (347): Cyclohexylmethyl 3-(3-chlorophenylthio)-N-(4-methylphenyl)-thioacrylimidate $^1$H-NMR (CDCl$_3$) δ(ppm): 1.01-1.26(5H,m), 1.66-1.87 (6H,m), 2.31(3H,s), 3.00(2H,d J=6.8 Hz), 6.13(1H,d J=15.7 Hz), 6.62(2H,d J=8.1 Hz), 7.07(2H,d J=7.8 Hz), 7.23-7.36 (5H,m).
The stereochemistry of the —CH=CH— bond was E.

EXAMPLE 321

Compound (349): Cyclohexylmethyl 3-(4-chlorophenylthio)-N-(4-methylphenyl)-thioacrylimidate $^1$H-NMR (CDCl$_3$) δ(ppm): 1.01-1.26(5H,m), 1.66-1.86 (6H,m), 2.31(3H, s), 3.00(2H,d J=6.8 Hz), 6.04(1H,d J=15.7 Hz), 6.59(2H,d J=8.1 Hz), 7.06(2H,d J=7.8 Hz), 7.21-7.29 (5H,m).
The stereochemistry of the —CH=CH— bond was E.

EXAMPLE 322

Compound (351): Cyclohexylmethyl 3-(3-bromophenylthio)-N-(4-methylphenyl)-thioacrylimidate $^1$H-NMR (CDCl$_3$) δ(ppm): 1.01-1.26(5H,m), 1.63-1.87 (6H,m), 2.32(3H,s), 3.00(2H,d J=6.8 Hz), 6.13(1H,d J=15.4 Hz), 6.62(2H,d J=8.1 Hz), 7.08(2H,d J=8.1 Hz), 7.18(1H,t J=7.8 Hz), 7.26-7.31(2H,m), 7.41(1H,d J=7.8 Hz), 7.52(1H, s).
The stereochemistry of the —CH=CH— bond was E.

EXAMPLE 323

Compound (353): Cyclohexylmethyl 3-(4-bromophenylthio)-N-(4-methylphenyl)-thioacrylimidate $^1$H-NMR (CDCl$_3$) δ(ppm): 1.01-1.26(5H,m),1.66-1.86 (6H,m),2.33(3H, s),2.99(2H,d J=6.6 Hz),6.06(1H,d J=15.7 Hz),6.59(2H,d J=8.1 Hz),7.06(2H,d J=8.1 Hz),7.21-7.44(5H, m).
The stereochemistry of the —CH=CH— bond was E.

EXAMPLE 324

Compound (354): Cyclohexylmethyl N-(4-methylphenyl)-3-(4-nitrophenylthio)-thioacrylimidate $^1$H-NMR (CDCl$_3$) δ(ppm): 1.02-1.27(5H,m),1.64-1.88 (6H,m),2.33(3H, s),3.03(2H,dJ=6.8 Hz),6.37(1H,dJ=15.7 Hz),6.65(2H,dJ=8.1 Hz), 7.10(2H,d J=8.1 Hz), 7.33(1H, dJ=15.7 Hz), 7.45(2H,d J=8.8 Hz), 8.17(2H,d J=8.8 Hz).
The stereochemistry of the —CH=CH— bond was E.

EXAMPLE 325

Compound (356): Cyclohexylmethyl N-(4-methylphenyl)-3-(2-methylphenylthio)-thioacrylimidate $^1$H-NMR (CDCl$_3$) δ(ppm): 1.01-1.25(5H,m),1.62-1.86 (6H,m),2.30(3H, s),2.32(3H,s),2.98(2H,d J=6.8 Hz), 5.88(1H,d J=15.4 Hz), 6.57(2H,d J=8.1 Hz), 7.02(2H,d J=7.8 Hz), 7.12-7.29(4H,m), 7.35(1H,d J=7.8 Hz).
The stereochemistry of the —CH=CH— bond was E.

EXAMPLE 326

Compound (357): Cyclohexylmethyl N-(4-methylphenyl)-3-(4-methylphenylthio)-thioacrylimidate $^1$H-NMR (CDCl$_3$) δ(ppm): 1.01-1.25(5H,m),1.60-1.85 (6H,m),2.31(3H, s),2.33(3H,s),2.98(2H,d J=6.8 Hz),6.03 (1H,d J=15.4 Hz), 6.60(2H,d J=8.1 Hz), 7.04(2H,d J=8.1 Hz), 7.09-7.34(4H,m), 7.38(1H,d J=8.1 Hz).
The stereochemistry of the —CH=CH— bond was E.

EXAMPLE 327

Compound (359): Cyclohexylmethyl N-(4-methylphenyl)-3-(4-trifluoromethylphenylthio)-thioacrylimidate $^1$H-NMR (CDCl$_3$) δ(ppm): 1.01-1.26(5H,m), 1.66-1.87 (6H,m), 2.32(3H,s), 3.01(2H,d J=6.8 Hz), 6.21(1H,d J=15.7 Hz), 6.62(2H,d J=8.3 Hz), 7.07(2H,d J=7.8 Hz), 7.33(1H,d J=15.7 Hz), 7.45(2H,d J=8.1 Hz), 7.56(2H,d J=8.8 Hz).
The stereochemistry of the —CH=CH— bond was E.

EXAMPLE 328

Compound (361): Cyclohexylmethyl 3-(3-methoxyphenylthio)-N-(4-methylphenyl)-thioacrylimidate $^1$H-NMR (CDCl$_3$) δ(ppm): 1.00-1.25(5H,m), 1.66-1.86 (6H,m), 2.31(3H,s), 2.99(2H,dJ=6.8 Hz), 3.79(3H,s), 6.14 (1H,dJ=15.7 Hz), 6.62(2H,d J=8.1 Hz), 6.83(1H,d J=8.3 Hz), 6.95(1H,d J=7.6 Hz), 7.06(2H,d J=8.1 Hz), 7.23(2H,m), 7.37 (1H,d J=15.7 Hz).
The stereochemistry of the —CH=CH— bond was E.

EXAMPLE 329

Compound (363): Cyclohexylmethyl 3-(4-methoxyphenylthio)-N-(4-methylphenyl)-thioacrylimidate $^1$H-NMR (CDCl$_3$) δ(ppm): 1.02-1.21(5H,m),1.65-1.85 (6H,m),2.31(3H, s),2.97(2H,d J=6.6 Hz),3.79(3H,s),5.92 (1H,d J=15.4 Hz), 6.58(2H,d J=8.3 Hz), 6.82(2H,d J=8.8 Hz), 7.03(2H,d J=8.1 Hz), 7.26-7.30(3H,m).
The stereochemistry of the —CH=CH— bond was E.

EXAMPLE 330

Compound (365): Cyclohexylmethyl 3-(2,4-dichlorophenylthio)-N-(4-methylphenyl)-thioacrylimidate $^1$H-NMR (CDCl$_3$) δ(ppm): 1.01-1.26(5H,m),1.70-1.84 (6H,m),2.33(3H, s),3.00(2H,d J=6.8 Hz),6.05(1H,d J=15.4 Hz),6.60(2H,dJ=8.1 Hz), 7.02(2H,d J=8.1 Hz), 7.18-7.40 (4H,m).
The stereochemistry of the —CH=CH— bond was E.

EXAMPLE 331

Compound (366): Cyclohexylmethyl 3-(3,5-dichlorophenylthio)-N-(4-methylphenyl)-thioacrylimidate $^1$H-NMR (CDCl$_3$) δ(ppm): 1.05-1.26(5H,m), 1.63-1.84 (6H,m), 2.34(3H,s), 3.01(2H,d J=6.8 Hz), 6.17(1H,d J=15.4 Hz), 6.63(2H,d J=8.1 Hz), 7.08-7.23(6H,m).
The stereochemistry of the —CH=CH— bond was E.

EXAMPLE 332

Compound (367): Cyclohexylmethyl 3-(2,4-dimethylphenylthio)-N-(4-methylphenyl)-thioacrylimidate $^1$H-NMR (CDCl$_3$) δ(ppm): 1.00-1.25(5H,m), 1.60-1.85 (6H,m), 2.28(6H,s), 2.30(3H,s), 2.97(2H,dJ=6.8 Hz), 5.76 (1H,dJ=15.4 Hz), 6.55(2H,d J=8.3 Hz), 6.92-7.26(6H,m).
The stereochemistry of the —CH=CH— bond was E.

EXAMPLE 333

Compound (368): Cyclohexylmethyl N-(4-methylphenyl)-3-(2-pyridylthio)-thioacrylimidate $^1$H-NMR (CDCl$_3$) δ(ppm): 1.03-1.28(5H,m), 1.64-1.87 (6H,m), 2.33(3H,s), 3.03(2H,d J=6.8 Hz), 6.43(1H,d J=15.9 Hz), 6.68(2H,d J=8.1 Hz), 7.10(3H,d J=8.1 Hz), 7.20(1H,d J=7.8 Hz), 7.56(1H,d J=7.8 Hz), 8.18(1H,d J=15.9 Hz), 8.54 (1H,d J=7.8 Hz).
The stereochemistry of the —CH=CH— bond was E.

EXAMPLE 334

Compound (370): Cyclohexylmethyl N-(4-methylphenyl)-3-(2-pyrimidinylthio)-thioacrylimidate $^1$H-NMR (CDCl$_3$) δ(ppm): 1.04-1.26(5H,m),1.64-1.88 (6H,m),2.33(3H, s),3.04(2H,d J=6.8 Hz),6.46(1H,d J=16.4 Hz),6.68(2H,dJ=8.1 Hz), 7.08(1H,t J=4.8 Hz), 7.11(2H,d J=8.1 Hz), 8.28(1H,d J=16.4 Hz), 8.60(2H,d J=5.1 Hz).
The stereochemistry of the —CH=CH— bond was E.
Compounds (371) to (384) were synthesized in a similar manner as the Example 223.

EXAMPLE 335

Compound (371): Cyclohexylmethyl 3-benzylthio-N-(4-methylphenyl)-thioacrylimidate $^1$H-NMR (CDCl$_3$) δ(ppm): 1.01-1.25(5H,m),1.66-1.86 (6H,m),2.32(3H, s),2.97(2H,d J=6.8 Hz),3.85(2H,s),6.10 (1H,d J=15.4 Hz),6.61(2H,d J=8.3 Hz),7.07(2H,d J=8.1 Hz), 7.19(2H,d J=7.8 Hz),7.25-7.29(4H,m).
The stereochemistry of the —CH=CH— bond was E.

EXAMPLE 336

Compound (373): Cyclohexylmethyl 3-(4-fluorobenzylthio)-N-(4-methylphenyl)-thioacrylimidate $^1$H-NMR (CDCl$_3$) δ(ppm): 1.02-1.25(5H,m), 1.66-1.85 (6H,m),2.33(3H, s),2.97(2H,d J=6.8 Hz),3.82(2H,s),6.06 (1H,d J=15.4 Hz),6.59(2H,d J=8.1 Hz),6.95(2H,t J=8.7 Hz) 7.06(2H,d J=7.8 Hz),7.12-7.16(2H,m),7.23(1H,d J=15.4 Hz).
The stereochemistry of the —CH=CH— bond was E.

EXAMPLE 337

Compound (375): Cyclohexylmethyl 3-(4-methylbenzylthio)-N-(4-methylphenyl)-thioacrylimidate $^1$H-NMR (CDCl$_3$) δ(ppm): 1.02-1.26(5H,m),1.70-1.83 (6H,m),2.32(3H, s),2.33(3H,s),2.97(2H,d J=6.8 Hz),3.81 (2H,s),6.10(1H,d J=15.4 Hz),6.61(2H,d J=8.1 Hz),7.07-7.08 (6H,m),7.27(1H,d J=15.4 Hz).
The stereochemistry of the —CH=CH— bond was E.

EXAMPLE 338

Compound (377): Cyclohexylmethyl 3-(4-chlorobenzylthio)-N-(4-methylphenyl)-thioacrylimidate $^1$H-NMR (CDCl$_3$) δ(ppm): 1.02-1.25(5H,m), 1.70-1.85 (6H,m), 2.33(3H,s), 2.97(2H,d J=6.6 Hz), 3.81(2H,s), 6.04 (1H,d J=15.4 Hz), 6.58(2H,d J=8.1 Hz), 7.06(2H,d J=8.1 Hz), 7.10(2H,d J=8.3 Hz), 7.14-7.30(3H,m).
The stereochemistry of the —CH=CH— bond was E.

EXAMPLE 339

Compound (379): Cyclohexylmethyl 3-(2,4-dichlorobenzylthio)-N-(4-methylphenyl)-thioacrylimidate $^1$H-NMR (CDCl$_3$) δ(ppm): 1.01-1.23(5H,m), 1.70-1.86 (6H,m), 2.32(3H,s), 2.98(2H,dJ=6.8 Hz), 3.92(2H,s), 6.03 (1H,dJ=15.4 Hz), 6.57(2H,d J=8.1 Hz), 7.04(2H,d J=8.1 Hz), 7.19-7.35(4H,m).
The stereochemistry of the —CH=CH— bond was E.

EXAMPLE 340

Compound (381): Cyclohexylmethyl 3-(2-methyl-benzylthio)-N-(4-methylphenyl)-thioacrylimidate $^1$H-NMR (CDCl$_3$) δ(ppm): 1.00-1.26(5H,m),1.66-1.86 (6H,m),2.30(3H, s),2.31(3H,s),2.98(2H,d J=6.8 Hz),3.85 (2H,s),6.10(1H,d J=15.7 Hz),6.63(2H,d J=8.1 Hz),7.06(2H,d J=8.1 Hz) 7.13-7.18(4H,m),7.30(1H,d J=15.4 Hz).

The stereochemistry of the —CH═CH— bond was E.

EXAMPLE 341

Compound (383): Cyclohexylmethyl 3-(4-methoxy-benzylthio)-N-(4-methylphenyl)-thioacrylimidate $^1$H-NMR (CDCl$_3$) δ(ppm): 1.00-1.25(5H,m),1.66-1.86 (6H,m),2.32(3H, s),2.97(2H,d J=6.8 Hz),3.80(3H,s),3.81 (2H,s),6.10(1H,d J=15.4 Hz),6.62(2H,d J=8.3 Hz),6.81(2H,d J=8.8 Hz),7.07(2H,d J=8.1 Hz),7.11(2H,d J=8.6 Hz),7.27 (1H,d J=15.7 Hz).

The stereochemistry of the —CH═CH— bond was E.
Compound (385) was synthesized in a similar manner as the Example 176.

EXAMPLE 342

Compound (385): 1-Phenylethylideneamino N-(4-methylphenyl)-3-(phenylthio)thioacrylimidate $^1$H-NMR (CDCl$_3$) δ(ppm): 2.17(0.96H,s), 2.31(3H,s), 2.45(2.04H, s), 5.88(0.83H,d J=15.4 Hz), 6.59(0.17H,d J=15.1 Hz), 6.76(2H, d J=8.0 Hz), 6.98-7.08(3H,m), 7.32-7.54(8H,m), 7.74-7.78(2H, m).

The stereochemistry of the —CH═CH— bond was E.
Compound (386) was synthesized in a similar manner as the Example 161.

EXAMPLE 343

Compound (386): 2-Phenylethyl N-(4-methylphenyl)-3-(phenylthio)thioacrylimidate $^1$H-NMR (CDCl$_3$) δ(ppm): 2.32(3H, s), 2.98(2H,t J=7.7 Hz), 3.30(2H, tJ=7.7 Hz), 6.14(1H,d, J=15.6 Hz), 6.64(2H,d, J=8.0 Hz), 7.07(2H, d, J=8.0 Hz), 7.18-7.37(11H, m).

The stereochemistry of the —CH═CH— bond was E.

EXAMPLE 344

Compound (387): Phenyl N-ethoxycarbonyl-3-(phenylthio)thioacrylimidate

N-ethoxycarbonyl-3-(phenylthio)acrylamide (1.20 g) was dissolved to acetonitrile (30 ml), then carbon tetrabromide (2.83 g) and triphenylphosphine (2.23 g) was added thereto and heat refluxing for three hours. The reaction mixture was concentrated under reduced pressure. The residue was subjected to silica gel column chromatography (hexane:ethyl acetate 20:1) to obtain light yellow oil. It was dissolved to DMF (10 ml), then sodium salt of thiophenol (0.63 g) was added thereto under ice cooling and stirred at room temperature for two hours. t-Butyl methyl ether (100 ml) was added to the reaction mixture, washed successively with 1N aqueous sodium hydroxide solution, water and aqueous saturated sodium chloride solution, dried over anhydrous sodium sulfate, filtered off inorganic salt and concentrated under reduced pressure. The residue was purified by medium pressure preparative high performance liquid chromatography to obtain phenyl N-ethoxycarbonyl-3-(phenylthio)thioacrylimidate (0.40 g) as light yellow oil.

$^1$H-NMR (CDCl$_3$) δ(ppm): 1.28(2.3H,t, J=7.2 Hz), 1.40 (0.70H, t, J=7.1 Hz), 4.15(1.5H, q, J=7.2 Hz), 4.30(0.50H, q, J=7.1 Hz), 5.67(0.75H,d, J=14.5 Hz), 5.82(0.25H,d, J=10.1 Hz), 7.00(0.25H, d, J=10.1 Hz), 7.29-7.58(10H, m), 7.78 (0.75H, d, J=14.5 Hz).

The stereochemistry of the —CH═CH— bond was E.
Compounds (388) and (389) were synthesized in a similar manner as the Example 176.

EXAMPLE 345

Compound (388): 3-Methyl-2-butenyl N-(4-methylphenyl)-3-(phenylthio)thioacrylimidate $^1$H-NMR (CDCl$_3$) δ(ppm): 1.71(3H, s), 1.73(3H, s), 2.32 (3H, s), 3.71(2H,d, J=8.0 Hz), 5.32(1H,tJ=8.0 Hz), 6.13(1H, d, J=15.4 Hz), 6.64(2H, d, J=8.3 Hz), 7.07(2H, d, J=7.8 Hz), 7.28-7.37(6H, m).

The stereochemistry of the —CH═CH— bond was E.

EXAMPLE 346

Compound (389): 3,3-Dichloro-2-propenyl N-(4-methylphenyl)-3-(phenylthio)thioacrylimidate $^1$H-NMR (CDCl$_3$)δ(ppm): 2.32(3H, s), 3.80(2H, d, J=7.7 Hz), 6.11-6.15(2H, m), 6.64(2H, d, J=8.2 Hz), 7.08(2H, d, J=8.0 Hz), 7.30-7.38(6H, m).

The stereochemistry of the —CH═CH— bond was E.
Compound (390) was synthesized in a similar manner as the Example 100.

EXAMPLE 347

Compound (390): 3-Methylphenyl N-(3,4-dimethylphenyl)-3-(cyclohexyloxy)acrylimidate $^1$H-NMR (CDCl$_3$)δ(ppm): 1.20-1.92(10H, m), 2.18(6H, s), 2.35(3H, s), 3.77-3.89(1H, m), 5.37(1H, d, J=12.0 Hz), 6.48-6.58(2H, m), 6.92-7.02(4H, m), 7.20-7.27(1H, m), 7.48 (1H, d, J=12.2 Hz).

The stereochemistry of the —CH═CH— bond was E.
Compound (391) was synthesized in a similar manner as the Example 37.

EXAMPLE 348

Compound (391): Phenyl N-(4-methoxycarbonylphenyl)-3-phenoxyacrylimidate $^1$H-NMR (CDCl$_3$)δ(ppm): 3.79(3H, s), 5.64(1H, d, J=12.0 Hz), 6.81-7.36(12H, m), 7.82(1H, d, J=12.0 Hz), 7.94-7.96 (2H, m).

The stereochemistry of the —CH═CH— bond was E.
Compounds (392) to (418) were synthesized in a similar manner as the Example 161.

EXAMPLE 349

Compound (392): 1-Phenethyl 3-(2-fluorophenylthio)-N-(4-methylphenyl)thioacrylimidate $^1$H-NMR (CDCl$_3$)δ(ppm): 1.73(3H,d J=7.1 Hz), 2.32(3H, s), 5.00(1H,q J=7.1 Hz), 6.02(1H,d J=15.4 Hz), 6.60(2H,d J=8.1 Hz), 7.06(2H,d J=8.1 Hz), 7.18(1H,d J=15.4 Hz), 7.23-7.26(2H,m), 7.29-7.37(5H,m), 7.41-7.42(2H,m).

The stereochemistry of the —CH=CH— bond was E.

EXAMPLE 350

Compound (393): 1-Phenethyl 3-(3-fluorophenylthio)-N-(4-methylphenyl)thioacrylimidate $^1$H-NMR (CDCl$_3$)δ(ppm): 1.74(3H,d J=7.3 Hz), 2.32(3H, s), 5.02(1H,q J=7.3 Hz), 6.12(1H,d J=15.9 Hz), 6.61(2H,d J=8.3 Hz), 6.94-6.99(1H,m), 7.03-7.06(3H,m), 7.08(2H,d J=8.3 Hz), 7.25(1H,d J=15.9 Hz), 7.29-7.33(3H,m), 7.41-7.43(2H,m).

The stereochemistry of the —CH=CH— bond was E.

EXAMPLE 351

Compound (394): 1-Phenethyl 3-(4-fluorophenylthio)-N-(4-methylphenyl)thioacrylimidate $^1$H-NMR (CDCl$_3$)δ(ppm): 1.73(3H,d J=7.1 Hz), 2.32(3H, s), 5.00(1H,q J=7.1 Hz), 5.93(1H,d J=15.4 Hz), 6.57(2H,d J=8.1 Hz), 6.95-7.03(3H,m), 7.05(2H,d J=8.1 Hz), 7.19(1H,d J=15.4 Hz), 7.29-7.32(4H,m), 7.40-7.42(2H,m).

The stereochemistry of the —CH=CH— bond was E.

EXAMPLE 352

Compound (396): 1-Phenethyl 3-(2-chlorophenylthio)-N-(4-methylphenyl)thioacrylimidate $^1$H-NMR (CDCl$_3$)δ(ppm): 1.74(3H,d J=7.1 Hz), 2.32(3H, s), 5.02(1H,q J=7.1 Hz), 6.12(1H,d J=15.4 Hz), 6.62(2H,d J=8.3 Hz), 7.06-7.08(2H,m), 7.19-7.23(4H,m), 7.29-7.38(4H,m), 7. 42-7.43(2H,m).

The stereochemistry of the —CH=CH— bond was E.

EXAMPLE 353

Compound (397): 1-Phenethyl 3-(3-chlorophenylthio)-N-(4-methylphenyl)thioacrylimidate $^1$H-NMR (CDCl$_3$)δ(ppm): 1.74(3H,d J=7.1 Hz), 2.32(3H, s), 5.02(1H,q J=7.1 Hz), 6.09(1H,d J=15.7 Hz), 6.61(2H,d J=8.1 Hz), 7.08(2H,d J=8.1 Hz), 7.20-7.24(4H,m), 7.29-7.33(4H,m), 7.41-7.43(2H,m).

The stereochemistry of the —CH=CH— bond was E.

EXAMPLE 354

Compound (398): 1-Phenethyl 3-(4-chlorophenylthio)-N-(4-methylphenyl)thioacrylimidate $^1$H-NMR (CDCl$_3$)δ(ppm): 1.73(3H,d J=7.1 Hz), 2.33(3H, s), 5.01(1H,q J=7.1 Hz), 6.01(1H,d J=15.7 Hz), 6.58(2H,d J=8.3 Hz), 7.06(2H,d J=8.3 Hz), 7.14-7.23(4H,m), 7.29-7.33(4H,m), 7.41-7.42(2H,m).

The stereochemistry of the —CH=CH— bond was E.

EXAMPLE 355

Compound (400): 1-Phenethyl 3-(3-bromophenylthio)-N-(4-methylphenyl)thioacrylimidate $^1$H-NMR (CDCl$_3$)δ(ppm): 1.74(3H,d J=7.1 Hz), 2.33(3H, s), 5.02(1H,q J=7.1 Hz), 6.09(1H,d J=15.4 Hz), 6.60(2H,d J=8.1 Hz), 7.07-7.24(5H,m), 7.29-7.33(3H,m), 7.39-7.43(4H,m).

The stereochemistry of the —CH=CH— bond was E.

EXAMPLE 356

Compound (402): 1-Phenethyl 3-(4-bromophenylthio)-N-(4-methylphenyl)thioacrylimidate $^1$H-NMR (CDCl$_3$)δ(ppm): 1.73(3H,d J=7.1 Hz), 2.34(3H, s), 5.01(1H,q J=7.1 Hz), 6.03(1H,d J=15.7 Hz), 6.58(2H,d J=8.1 Hz), 7.06-7.19(2H,m), 7.22-7.24(3H,m), 7.29-7.34(4H,m), 7. 40-7.42(3H,m).

The stereochemistry of the —CH=CH— bond was E.

EXAMPLE 357

Compound (404): 1-Phenethyl N-(4-methylphenyl)-3-(4-nitrophenylthio)thioacrylimidate $^1$H-NMR (CDCl$_3$)δ(ppm): 1.76(3H,d,J=7.0 Hz), 2.33(3H, s), 5.03(1H,q,J=7.0 Hz), 6.32(1H,d,J=15.4 Hz), 6.63(2H,d, J=8.0 Hz), 7.11(2H,d,J=7.8 Hz), 7.21-7.47(8H,m), 8.15(2H, d,J=8.8 Hz).

The stereochemistry of the —CH=CH— bond was E.

EXAMPLE 358

Compound (405): 1-Phenethyl N-(4-methylphenyl)-3-(2-methylphenylthio)thioacrylimidate $^1$H-NMR (CDCl$_3$)δ(ppm): 1.72(3H,d,J=7.0 Hz), 2.30(3H, s), 2.31(3H,s), 5.00(1H,q,J=7.0 Hz), 5.85(1H,d,J=15.4 Hz), 6.56(2H,d,J=8.3 Hz), 7.00-7.43(12H,m).

The stereochemistry of the —CH=CH— bond was E.

EXAMPLE 359

Compound (407): 1-Phenethyl N-(4-methylphenyl)-3-(4-methylphenylthio)thioacrylimidate $^1$H-NMR (CDCl$_3$)δ(ppm): 1.72(3H,d,J=7.0 Hz), 2.32(6H, s), 5.00(1H,q,J=7.0 Hz), 5.99(1H,d,J=15.4 Hz), 6.59(2H,d, J=8.0 Hz), 7.01-7.44(12H,m).

The stereochemistry of the —CH=CH— bond was E.

EXAMPLE 360

Compound (408): 1-Phenethyl N-(4-methylphenyl)-3-(4-trifluoromethylphenylthio)thioacrylimidate $^1$H-NMR (CDCl$_3$)δ(ppm): 1.74(3H,d,J=7.0 Hz), 2.32(3H, s), 5.02(1H,q,J=7.0 Hz), 6.18(1H,d,J=15.6 Hz), 6.60(2H,d, J=8.0 Hz), 7.03-7.70(12H,m).

The stereochemistry of the —CH=CH— bond was E.

EXAMPLE 361

Compound (409): 1-Phenethyl 3-(3-methoxyphenylthio)-N-(4-methylphenyl)thioacrylimidate $^1$H-NMR (CDCl$_3$)δ(ppm): 1.73(3H,d,J=7.0 Hz), 2.32(3H, s), 3.77(3H,s), 5.02(1H,q,J=7.0 Hz), 6.10(1H,d,J=15.4 Hz), 6.61(2H,d,J=8.0 Hz), 6.73-7.45(12H,m).

The stereochemistry of the —CH=CH— bond was E.

EXAMPLE 362

Compound (410): 1-Phenethyl 3-(4-methoxyphenylthio)-N-(4-methylphenyl)thioacrylimidate $^1$H-NMR (CDCl$_3$)δ(ppm): 1.72(3H,d,J=7.0 Hz), 2.32(3H, s), 3.78(3H,s), 4.99(1H,q,J=7.0 Hz), 5.89(1H,d,J=15.6 Hz), 6.57(2H,d,J=8.0 Hz), 6.80(2H,d, J=8.8 Hz), 7.00-7.45(10H, m).

The stereochemistry of the —CH=CH— bond was E.

EXAMPLE 363

Compound (411): 1-Phenethyl 3-(2,4-dichlorophenylthio)-N-(4-methylphenyl)thioacrylimidate $^1$H-NMR (CDCl$_3$)δ(ppm): 1.73(3H,d,J=7.0 Hz), 2.33(3H, s), 5.02(1H,q,J=7.0 Hz), 6.02(1H,d,J=15.6 Hz), 6.59(2H,d, J=8.0 Hz), 7.03-7.46(11H,m).

The stereochemistry of the —CH=CH— bond was E.

EXAMPLE 364

Compound (412): 1-Phenethyl 3-(3,4-dichlorophenylthio)-N-(4-methylphenyl)thioacrylimidate $^1$H-NMR (CDCl$_3$)δ(ppm): 1.73(3H,d,J=7.0 Hz), 2.33(3H, s), 5.01(1H,q,J=7.0 Hz), 6.04(1H,d,J=15.6 Hz), 6.58(2H,d, J=8.3 Hz), 6.99-7.57(11H,m).

The stereochemistry of the —CH=CH— bond was E.

EXAMPLE 365

Compound (413): 1-Phenethyl 3-(3,5-dichlorophenylthio)-N-(4-methylphenyl)thioacrylimidate $^1$H-NMR (CDCl$_3$)δ(ppm): 1.75(3H,d,J=7.0 Hz), 2.33(3H, d), 5.02(1H,q,J=7.0 Hz), 6.12(1H,d,J=15.6 Hz), 6.61(2H,d, J=8.3 Hz), 7.05-7.56(11H,m).

The stereochemistry of the —CH=CH— bond was E.

EXAMPLE 366

Compound (415): 1-Phenethyl 3-(2,4-dimethylphenylthio)-N-(4-methylphenyl)thioacrylimidate $^1$H-NMR (CDCl$_3$)δ(ppm): 1.72(3H,d,J=7.0 Hz), 2.25(3H, s), 2.27(3H,s), 2.32(3H,s), 4.99(1H,q,J=7.0 Hz), 5.73(1H,d, J=15.4 Hz), 6.53(2H,d,J=8.0 Hz), 6.88-7.45(11H,m).

The stereochemistry of the —CH=CH— bond was E.

EXAMPLE 367

Compound (416): 1-Phenethyl N-(4-methylphenyl)-3-(2-pyridylthio)thioacrylimidate $^1$H-NMR (CDCl$_3$)δ(ppm): 1.77(3H,dJ=7.1 Hz), 2.33(3H, s), 5.05(1H,q J=7.1 Hz), 6.39(1H,d J=16.2 Hz), 6.67(2H,d J=8.1 Hz), 7.11(2H,d J=7.8 Hz), 7.17(1H,d J=8.1 Hz), 7.25 (1H,d J=7.3 Hz), 7.32(3H,t J=7.5 Hz), 7.46(2H,d J=7.1 Hz), 7.54(1H,t J=7.7 Hz), 8.12(1H,d J=16.2 Hz), 8.51(1H,d J=4.8 Hz).

The stereochemistry of the —CH=CH— bond was E.

EXAMPLE 368

Compound (418): 1-Phenethyl N-(4-methylphenyl)-3-(2-pyrimidinylthio)-thioacrylimidate $^1$H-NMR (CDCl$_3$)δ(ppm): 1.78(3H,dJ=7.1 Hz), 2.34(3H, s), 5.06(1H,q J=7.1 Hz), 6.42(1H,d J=16.4 Hz), 6.67(2H,d J=8.1 Hz), 7.06(1H,t J=4.9 Hz), 7.12(2H,d J=7.8 Hz), 7.26 (1H,d J=7.3 Hz), 7.33(2H,t J=7.5 Hz), 7.47(2H,d J=7.1 Hz), 8.22(1H,d J=16.4 Hz), 8.57(2H,d J=4.8 Hz).

The stereochemistry of the —CH=CH— bond was E.
Compounds (419) to (425) were synthesized in a similar manner as the Example 223.

EXAMPLE 369

Compound (419): 1-Phenethyl 3-benzylthio-N-(4-methylphenyl)-thioacrylimidate $^1$H-NMR (CDCl$_3$)δ(ppm): 1.72(3H,d J=7.1 Hz), 2.33(3H, s), 3.81(2H,s), 4.99(1H, q J=7.1 Hz), 6.06(1H,d J=15.4 Hz), 6.58(2H d J=8.3 Hz), 7.07(2H,d J=7.8 Hz), 7.15-7.32(9H,m), 7.41(2H,d J=7.1 Hz).

The stereochemistry of the —CH=CH— bond was E.

EXAMPLE 370

Compound (420): 1-Phenethyl 3-(4-fluorobenzylthio)-N-(4-methylphenyl)-thioacrylimidate $^1$H-NMR (CDCl$_3$)δ(ppm): 1.72(3H,d J=7.1 Hz), 2.33(3H, s), 3.78(2H,s), 4.99(1H,q J=7.1 Hz), 6.02(1H,d J=15.4 Hz), 6.57(2H,d J=8.1 Hz), 6.93(2H,t 8.6 Hz), 7.06-7.14(3H,m), 7.16(1H,d J=15.7 Hz), 7.24(1H,d J=7.3 Hz), 7.30(3H,t J=7.5 Hz), 7.41(2H,d J=7.3 Hz).

The stereochemistry of the —CH=CH— bond was E.

EXAMPLE 371

Compound (421): 1-Phenethyl 3-(4-methylbenzylthio)-N-(4-methylphenyl)-thioacrylimidate $^1$H-NMR (CDCl$_3$)δ(ppm): 1.72(3H,d J=7.1 Hz), 2.32(3H, s), 2.33(3H,s), 3.78(2H,s), 4.99(1H,qJ=7.3 Hz), 6.05(1H, dJ=15.4 Hz), 6.59(2H,dJ=8.3 Hz), 7.06(5H,m), 7.20(1H, dJ=15.4 Hz), 7.24(1H,d J=7.3 Hz), 7.30(3H,t J=7.3 Hz), 7.41 (2H,d J=7.1 Hz).

The stereochemistry of the —CH=CH— bond was E.

EXAMPLE 372

Compound (422): 1-Phenethyl 3-(4-chlorobenzylthio)-N-(4-methylphenyl)-thioacrylimidate $^1$H-NMR (CDCl$_3$)δ(ppm): 1.72(3H,d J=7.1 Hz), 2.34(3H, s), 3.77(2H,s), 4.99(1H,q J=7.1 Hz), 6.00(1H,d J=15.4 Hz), 6.56(2H,d J=8.3 Hz), 7.07(3H,d J=8.3 Hz), 7.14(1H,d J=15.7 Hz), 7.21(2H,d 8.3 Hz), 7.24(1H,d J=7.3 Hz), 7.30(3H,t J=7.3 Hz), 7.41(2H,d J=7.3 Hz).

The stereochemistry of the —CH=CH— bond was E.

EXAMPLE 373

Compound (423): 1-Phenethyl 3-(2,4-dichlorobenzylthio)-N-(4-methylphenyl)-thioacrylimidate $^1$H-NMR (CDCl$_3$)δ(ppm): 1.72(3H,d J=7.1 Hz), 2.33(3H, s), 3.89(2H,s), 4.99(1H,q J=7.1 Hz), 5.98(1H,d J=15.7 Hz), 6.55(2H,d J=8.3 Hz), 7.05(2H,d J=8.1 Hz), 7.16(3H,t J=7.8 Hz), 7.23-7.33(4H,m), 7.41(2H,d J=7.1 Hz).

The stereochemistry of the —CH=CH— bond was E.

EXAMPLE 374

Compound (424): 1-Phenethyl 3-(2-methylbenzylthio)-N-(4-methylphenyl)-thioacrylimidate $^1$H-NMR (CDCl$_3$)δ(ppm): 1.73(3H,d J=7.3 Hz), 2.27(3H, s), 2.32(3H,s), 3.81(2H,s), 5.00(1H,qJ=7.3 Hz), 6.05(1H, dJ=15.7 Hz), 6.60(2H,d J=8.1 Hz), 7.07(2H,d J=8.1 Hz), 7.13-7.25(5H,m), 7.31(3H,t J=7.5 Hz), 7.42(2H,d J=7.1 Hz).

The stereochemistry of the —CH=CH— bond was E.

EXAMPLE 375

Compound (425): 1-Phenethyl 3-(4-methoxybenzylthio)-N-(4-methylphenyl)-thioacrylimidate $^1$H-NMR (CDCl$_3$)δ(ppm): 1.72(3H,d J=7.1 Hz), 2.33(3H, s), 3.77(2H,s), 3.79(3H,s), 4.99(1H,q J=7.1 Hz), 6.05(1H,d J=15.4 Hz), 6.60(2H,d J=8.1 Hz), 6.79(2H,d J=8.6 Hz), 7.07-7.25(5H,m), 7.30(3H,t J=7.5 Hz), 7.41(2H,d J=7.3 Hz).

The stereochemistry of the —CH═CH— bond was E.

Compounds (426) and (427) were synthesized in a similar manner as the Example 302.

EXAMPLE 376

Compound (426): Phenyl N-(1-phenylethylideneamino)-3-(phenylthio)thioacrylimidate $^1$H-NMR (CDCl$_3$)δ(ppm): 2.42(2.7H, s), 2.67(0.3H, s), 5.61(0.9H, d, J=14.7 Hz), 5.70(0.1H, d, J=10.1 Hz), 6.80 (0.1H, d, J=10.1 Hz), 7.29-7.61(13.9H, m), 7.91-7.93(1.8H, m), 8.02-8.04(0.2H, m).

The stereochemistry of the —CH═CH— bond was mixture of E and Z.

EXAMPLE 377

Compound (427): Phenyl N-(2,2,2-trifluoroethyl)-3-(phenylthio)thioacrylimidate $^1$H-NMR (CDCl$_3$)δ(ppm): 3.99(1.5H, q, J=9.5 Hz), 4.08 (0.5H, q, J=9.5 Hz), 5.63(0.75H, d, J=14.7 Hz), 5.68(0.25H, d, J=10.1 Hz), 6.78(0.25H, d, J=10.1 Hz), 7.20-7.53 (10.75H, m).

The stereochemistry of the —CH═CH— bond was mixture of E and Z.

Compounds (428) to (455) were synthesized in a similar manner as the Example 161.

EXAMPLE 378

Compound (428): Isobutyl 3-(2-fluorophenylthio)-N-(4-methylphenyl)thioacrylimidate $^1$H-NMR (CDCl$_3$)δ(ppm): 1.02(6H,d,J=6.8 Hz), 1.88-2.00(1H,m), 2.31(3H,s), 2.98(2H,d,J=6.8 Hz), 6.05(1H,d, J=15.6 Hz), 6.61(2H,d,J=8.5 Hz), 7.02-7.42(7H,m).

The stereochemistry of the —CH═CH— bond was E.

EXAMPLE 379

Compound (429): Isobutyl 3-(3-fluorophenylthio)-N-(4-methylphenyl)thioacrylimidate $^1$H-NMR (CDCl$_3$)δ(ppm): 1.02(6H,d,J=6.8 Hz), 1.88-2.00(1H,m), 2.32(3H,s), 3.00(2H,d,J=6.8 Hz), 6.16(1H,d, J=16.4 Hz), 6.62(2H,d, J=8.5 Hz), 7.05-7.33(6H,m), 7.32 (1H,d, J=16.4 Hz).

The stereochemistry of the —CH═CH— bond was E.

EXAMPLE 380

Compound (431): Isobutyl 3-(4-fluorophenylthio)-N-(4-methylphenyl)thioacrylimidate $^1$H-NMR (CDCl$_3$)δ(ppm): 1.01(6H,d,J=6.5 Hz), 1.88-1.99(1H, m), 2.32(3H, s), 2.98(2H, d, J=7.3 Hz), 5.95(1H,d, J=16.6 Hz), 6.57(2H,d,J=8.3 Hz), 6.96-7.47(7H,m).

The stereochemistry of the —CH═CH— bond was E.

EXAMPLE 381

Compound (432): Isobutyl N-(4-methylphenyl)-3-(4-fluorophenylthio)thioacrylimidate $^1$H-NMR (CDCl$_3$)δ(ppm): 0.97(6H,d,J=6.5 Hz), 1.75-1.86(1H,m), 2.34(3H,s), 2.76(2H,d,J=6.3 Hz), 6.35(1H,d, J=10.1 Hz), 6.30-7.53(9H,m).

The stereochemistry of the —CH═CH— bond was Z.

EXAMPLE 382

Compound (433): Isobutyl 3-(2-chlorophenylthio)-N-(4-methylphenyl)thioacrylimidate $^1$H-NMR (CDCl$_3$)δ(ppm): 1.02(6H,d,J=6.5 Hz), 1.88-2.00(1H,m), 2.31(3H,s), 3.00(2H,d,J=7.0 Hz), 6.15(1H,d, J=15.4 Hz), 6.62(2H,d,J=7.5 Hz), 7.06(1H,d,J=8.0 Hz), 7.01-7.42(6H,m).

The stereochemistry of the —CH═CH— bond was E.

EXAMPLE 383

Compound (434): Isobutyl 3-(3-chlorophenylthio)-N-(4-methylphenyl)thioacrylimidate $^1$H-NMR (CDCl$_3$)δ(ppm): 1.02(6H,d,J=6.3 Hz), 1.89-2.01(1H,m), 2.32(3H,s), 2.99(2H,d,J=6.5 Hz), 6.13(1H,d, J=16.1 Hz), 6.62(2H,d,J=7.0 Hz), 7.08(1H,d,J=8.0 Hz), 7.22-7.38(6H,m).

The stereochemistry of the —CH═CH— bond was E.

EXAMPLE 384

Compound (435): Isobutyl 3-(4-chlorophenylthio)-N-(4-methylphenyl)thioacrylimidate $^1$H-NMR (CDCl$_3$)δ(ppm): 1.02(6H,d,J=6.5 Hz), 1.87-1.99(1H,m), 2.32(3H,s), 2.99(2H,d,J=6.8 Hz), 6.04(1H,d, J=15.4 Hz), 6.59(2H,d,J=8.3 Hz), 7.06(1H,d,J=8.0 Hz), 7.18-7.31(6H,m).

The stereochemistry of the —CH═CH— bond was E.

EXAMPLE 385

Compound (437): Isobutyl 3-(3-bromophenylthio)-N-(4-methylphenyl)thioacrylimidate $^1$H-NMR (CDCl$_3$)δ(ppm): 1.02(6H,d,J=6.8 Hz), 1.89-2.00(1H,m), 2.32(3H,s), 3.00(2H,d,J=6.8 Hz), 6.12(1H,d, J=15.6 Hz), 6.62(2H,d,J=8.3 Hz), 7.05-7.44(7H,m).

The stereochemistry of the —CH═CH— bond was E.

EXAMPLE 386

Compound (438): Isobutyl 3-(4-bromophenylthio)-N-(4-methylphenyl)thioacrylimidate $^1$H-NMR (CDCl$_3$)δ(ppm): 1.02(6H,d,J=6.8 Hz), 1.89-1.99(1H,m), 2.33(3H,s), 2.99(2H,d, J=6.8 Hz), 6.06(1H,d, J=15.6 Hz), 6.59(2H,d,J=7.8 Hz), 7.01-7.46(7H,m).

The stereochemistry of the —CH═CH— bond was E.

EXAMPLE 387

Compound (440): Isobutyl N-(4-methylphenyl)-3-(4-nitrophenylthio)thioacrylimidate $^1$H-NMR (CDCl$_3$)δ(ppm): 1.03(6H,d,J=6.8 Hz), 1.91-2.02(1H,m), 2.32(3H,s), 3.02(2H,d,J=6.5 Hz), 6.37(1H,d, J=16.1 Hz), 6.65(2H,d, J=8.0 Hz), 7.01(2H,d,J=8.3 Hz), 7.33 (1H,d, J=15.6 Hz), 7.45(2H,d,J=8.3 Hz), 8.13(2H,d,J=8.0 Hz).

The stereochemistry of the —CH=CH— bond was E.

EXAMPLE 388

Compound (441): Isobutyl N-(4-methylphenyl)-3-(2-methylphenylthio)thioacrylimidate $^1$H-NMR (CDCl$_3$)δ(ppm): 1.01(6H,d,J=7.0 Hz), 1.88-1.99(1H,m), 2.30(3H,s), 2.32(3H.s), 2.98(2H,d,J=6.5 Hz), 5.88(1H,d,J=15.6 Hz), 6.57(2H,d,J=8.3 Hz), 7.02(1H,d, J=8.0 Hz), 7.10-7.38(6H,m).

The stereochemistry of the —CH=CH— bond was E.

EXAMPLE 389

Compound (443): Isobutyl N-(4-methylphenyl)-3-(4-methylphenylthio)thioacrylimidate $^1$H-NMR (CDCl$_3$)δ(ppm): 1.01(6H,d,J=6.8 Hz), 1.87-1.98(1H,m), 2.31(3H,s), 2.32(3H, s), 2.98(2H,d,J=6.5 Hz), 6.02(1H,d,J=15.4 Hz), 6.60(2H,d,J=8.0 Hz), 7.02-7.38(7H, m).

The stereochemistry of the —CH=CH— bond was E.

EXAMPLE 390

Compound (444): Isobutyl N-(4-methylphenyl)-3-(4-trifluoromethylphenylthio)thioacrylimidate $^1$H-NMR (CDCl$_3$)δ(ppm): 1.02(6H,d,J=6.8 Hz), 1.90-1.99(1H,m), 2.31(3H,s), 3.01(2H,d,J=6.5 Hz), 6.21(1H,d, J=15.4 Hz), 6.62(2H,d,J=8.3 Hz), 7.07(2H,d,J=8.3 Hz), 7.32 (1H,d,J=15.4 Hz), 7.45(2H,d,J=8.5 Hz), 7.57(2H,d,J=8.5 Hz).

The stereochemistry of the —CH=CH— bond was E.

EXAMPLE 391

Compound (446): Isobutyl 3-(3-methoxyphenylthio)-N-(4-methylphenyl)thioacrylimidate $^1$H-NMR (CDCl$_3$)δ(ppm): 1.01(6H,d,J=6.5 Hz), 1.88-1.99(1H,m), 2.31(3H,s), 2.99(2H,d,J=6.5 Hz), 3.79(3H,s), 6.14(1H,d,J=15.4 Hz), 6.62(2H,d,J=8.3 Hz), 6.80-7.25(6H, m), 7.38(1H,d,J=15.4 Hz).

The stereochemistry of the —CH=CH— bond was E.

EXAMPLE 392

Compound (447): Isobutyl 3-(4-methoxyphenylthio)-N-(4-methylphenyl)thioacrylimidate $^1$H-NMR (CDCl$_3$)δ(ppm): 1.01(6H,d,J=6.5 Hz), 1.87-1.98(1H,m), 2.31(3H,s), 2.97(2H,d,J=6.5 Hz), 3.87(3H,s), 5.92(1H,d,J=15.4 Hz), 6.58(2H,d,J=8.0 Hz), 6.82(2H,d, J=8.8 Hz), 7.02(2H,d,J=8.0 Hz), 7.26-7.33(3H,m).

The stereochemistry of the —CH=CH— bond was E.

EXAMPLE 393

Compound (448): Isobutyl 3-(2,4-dichlorophenylthio)-N-(4-methylphenyl)thioacrylimidate $^1$H-NMR (CDCl$_3$)δ(ppm): 1.02(6H,d,J=6.5 Hz), 1.89-2.00(1H,m), 2.32(3H,s), 3.00(2H,d,J=6.3 Hz), 6.05(1H,d, J=15.4 Hz), 6.60(2H,d,J=8.3 Hz), 7.06(2H,d,J=8.0 Hz), 7.18-7.33(4H,m).

The stereochemistry of the —CH=CH— bond was E.

EXAMPLE 394

Compound (449): Isobutyl 3-(3,4-dichlorophenylthio)-N-(4-methylphenyl)thioacrylimidate $^1$H-NMR (CDCl$_3$)δ(ppm): 1.02(6H,d,J=7.0 Hz), 1.89-2.00(1H,m), 2.32(3H,s), 3.00(2H,d,J=6.8 Hz), 6.08(1H,d, J=15.4 Hz), 6.60(2H,d,J=8.3 Hz), 7.03-7.47(6H,m).

The stereochemistry of the —CH=CH— bond was E.

EXAMPLE 395

Compound (450): Isobutyl 3-(3,5-dichlorophenylthio)-N-(4-methylphenyl)thioacrylimidate $^1$H-NMR (CDCl$_3$)δ(ppm): 1.02(6H,d,J=6.8 Hz), 1.89-2.01(1H,m), 2.32(3H,s), 3.01(2H,d,J=6.8 Hz), 6.17(1H,d, J=15.4 Hz), 6.62(2H,d,J=8.0 Hz), 7.06-7.28(6H,m).

The stereochemistry of the —CH=CH— bond was E.

EXAMPLE 396

Compound (451): Isobutyl 3-(2,4-dimethylphenylthio)-N-(4-methylphenyl)thioacrylimidate $^1$H-NMR (CDCl$_3$)δ(ppm): 1.01(6H,d,J=6.5 Hz), 1.87-1.99(1H,m), 2.28(6H,s), 2.31(3H,s), 2.97(2H,d,J=6.8 Hz), 5.77(1H,d,J=15.4 Hz), 6.55(2H,d,J=7.8 Hz), 6.90-7.28(6H, m).

The stereochemistry of the —CH=CH— bond was E.

EXAMPLE 397

Compound (452): Isobutyl N-(4-methylphenyl)-3-(2-pyridylthio)thioacrylimidate $^1$H-NMR (CDCl$_3$)δ(ppm): 1.05(6H,d,J=6.8 Hz), 1.92-2.04(1H,m), 2.32(3H,s), 3.02(2H,d,J=6.5 Hz), 6.43(1H,d, J=15.9 Hz), 6.68(2H,d,J=7.8 Hz), 7.07-7.23(4H,m), 7.52-7.60(1H,m), 8.20(1H,d,J=15.9 Hz), 8.52-8.56(1H,m).

The stereochemistry of the —CH=CH— bond was E.

EXAMPLE 398

Compound (454): Isobutyl N-(4-methylphenyl)-3-(2-pyrimidinylthio)thioacrylimidate $^1$H-NMR (CDCl$_3$)δ(ppm): 1.06(6H,d,J=6.5 Hz), 1.93-2.05(1H,m), 2.32(3H,s), 3.03(2H,d,J=6.5 Hz), 6.47(1H,d, J=16.6 Hz), 6.68(2H,d,J=8.3 Hz), 7.08(1H, t, J=4.8 Hz), 7.11 (2H,d,J=7.5 Hz), 8.29(1H,d,J=16.6 Hz), 2-7.60(1H,m), 8.20 (1H,d,J=16.6 Hz), 8.60(1H,d,J=5.0 Hz).

The stereochemistry of the —CH=CH— bond was E.

Compounds (456) to (467) were synthesized in a similar manner as the Example 223.

EXAMPLE 399

Compound (456): Isobutyl 3-(benzylthio)-N-(4-methylphenyl)thioacrylimidate $^1$H-NMR (CDCl$_3$)δ(ppm): 1.01(6H,d,J=6.8 Hz), 1.87-1.99(1H,m), 2.32(3H,s), 2.97(2H,d,J=6.8 Hz), 3.85(2H,s), 6.10(1H,d,J=15.4 Hz), 6.60(2H,d,J=8.0 Hz), 7.04-7.31(8H, m).
The stereochemistry of the —CH=CH— bond was E.

EXAMPLE 400

Compound (458): Isobutyl 3-(4-fluorobenzylthio)-N-(4-methylphenyl)thioacrylimidate $^1$H-NMR (CDCl$_3$)δ(ppm): 1.01(6H,d,J=6.8 Hz), 1.87-1.99(1H,m), 2.32(3H,s), 2.97(2H,d,J=6.8 Hz), 3.82(2H,s), 6.06(1H,d,J=15.4 Hz), 6.59(2H,d,J=8.3 Hz), 6.91-7.28(7H, m).
The stereochemistry of the —CH=CH— bond was E.

EXAMPLE 401

Compound (460): Isobutyl 3-(4-methylbenzylthio)-N-(4-methylphenyl)thioacrylimidate $^1$H-NMR (CDCl$_3$)δ(ppm): 1.01(6H,d,J=6.8 Hz), 1.87-1.99(1H,m), 2.32(3H,s), 2.33(3H,s), 2.97(2H,d,J=6.8 Hz), 3.82(2H,s), 6.10(1H,d,J=15.4 Hz), 6.61(2H,d,J=8.0 Hz), 7.02-7.31(7H,m).
The stereochemistry of the —CH=CH— bond was E.

EXAMPLE 402

Compound (462): Isobutyl 3-(4-chlorobenzylthio)-N-(4-methylphenyl)thioacrylimidate $^1$H-NMR (CDCl$_3$)δ(ppm): 1.01(6H,d,J=6.8 Hz), 1.87-1.99(1H,m), 2.32(3H,s), 2.97(2H,d,J=6.8 Hz), 3.81(2H,s), 6.04(1H,d,J=15.6 Hz), 6.59(2H,d,J=8.3 Hz), 7.04-7.26(7H, m).
The stereochemistry of the —CH=CH— bond was E.

EXAMPLE 403

Compound (464): Isobutyl 3-(2,4-dichlorobenzylthio)-N-(4-methylphenyl)thioacrylimidate $^1$H-NMR (CDCl$_3$)δ(ppm): 1.01(6H,d,J=6.8 Hz), 1.87-1.99(1H,m), 2.32(3H,s), 2.98(2H,d,J=6.8 Hz), 3.92(2H,s), 6.03(1H,d,J=15.6 Hz), 6.58(2H,d,J=8.3 Hz), 7.02-7.39(6H, m).
The stereochemistry of the —CH=CH— bond was E.

EXAMPLE 404

Compound (465): Isobutyl 3-(2-methylbenzylthio)-N-(4-methylphenyl)thioacrylimidate $^1$H-NMR (CDCl$_3$)δ(ppm): 1.02(6H,d,J=6.8 Hz), 1.87-1.99(1H,m), 2.30(3H,s), 2.31(3H,s), 2.98(2H,d,J=6.8 Hz), 3.85(2H,s), 6.10(1H,d,J=15.6 Hz), 6.62(2H,d,J=8.0 Hz), 7.03-7.20(6H,m), 7.30(1H,d,J=15.6 Hz).
The stereochemistry of the —CH=CH— bond was E.

EXAMPLE 405

Compound (467): Isobutyl 3-(4-methoxybenzylthio)-N-(4-methylphenyl)thioacrylimidate $^1$H-NMR (CDCl$_3$)δ(ppm): 1.01(6H,d,J=6.8 Hz), 1.87-1.99(1H,m), 2.32(3H,s), 2.97(2H,d,J=6.8 Hz), 3.79(3H,s), 3.81(2H,s), 6.10(1H,d,J=15.4 Hz), 6.62(2H,d,J=8.3 Hz), 6.80(2H,d,J=6.8 Hz), 7.04-7.13(4H,m), 7.28(1H,d,J=15.4 Hz).
The stereochemistry of the —CH=CH— bond was E.
Compound (468) was synthesized in a similar manner as the Example 37.

EXAMPLE 406

Compound (468): Phenyl 3-phenoxy-N-(6-quinolyl)acrylimidate $^1$H-NMR (CDCl$_3$)δ(ppm): 5.73(1H, d, J=12.0 Hz), 7.04-8.80(16H, m), 7.87(1H, d, J=12.0 Hz, PHOCH=CHR).
The stereochemistry of the —CH=CH— bond was E.
Compounds (469) to (476) were synthesized in a similar manner as the Example 161.

EXAMPLE 407

Compound (469): Cyclohexyl 3-(4-fluorophenylthio)-N-(phenyl)thioacrylimidate $^1$H-NMR (CDCl$_3$)δ(ppm): 1.20-1.90(8H,m), 2.00-2.21(2H,m), 2.70-2.81(1H,Br), 5.91(1H,d,J=15.6 Hz), 6.69(2H, d,J=7.6 Hz), 6.94-7.38(10H,m).
The stereochemistry of the —CH=CH— bond was E.

EXAMPLE 408

Compound (470): Cyclohexyl N-(4-methylphenyl)-3-(phenylthio)thioacrylimidate $^1$H-NMR (CDCl$_3$)δ(ppm): 1.30(2H, brs), 1.37-1.51(4H, m), 1.71(2H, brs), 2.05(2H, brs), 2.31(3H, s), 3.77(1H, brs), 6.11(1H, d, J=15.7 Hz), 6.63(2H, d, J=8.2 Hz), 7.06(2H, d, J=8.2 Hz), 7.27-7.37(6H, m).
The stereochemistry of the —CH=CH— bond was E.

EXAMPLE 409

Compound (471): Cyclohexyl 3-(4-fluorophenylthio)-N-(4-methylphenyl)thioacrylimidate $^1$H-NMR (CDCl$_3$)δ(ppm): 1.24-1.28(2H, m), 1.37-1.47(4H, m), 1.72(2H, brs), 2.04(2H, brs), 2.31(3H, s), 3.76(1H, brs), 5.94(1H, d, J=15.6 Hz), 6.59(2H, d, J=8.3 Hz), 6.97-7.35(7H, m).
The stereochemistry of the —CH=CH— bond was E.

EXAMPLE 410

Compound (472): Cyclohexyl 3-(4-chlorophenylthio)-N-(4-methylphenyl)thioacrylimidate $^1$H-NMR (CDCl$_3$)δ(ppm): 1.20-1.77(8H,m), 2.02-2.12(2H,m), 2.32(3H,s), 3.70-3.82(1H,m), 6.03(1H,d,J=15.4 Hz), 6.60(2H,d,J=8.0 Hz), 7.06(2H,d,J=8.7 Hz), 7.20-7.30(4H,m).
The stereochemistry of the —CH=CH— bond was E.

EXAMPLE 411

Compound (473): Cyclohexyl N-(4-methylphenyl)-3-(4-methylphenylthio)thioacrylimidate $^1$H-NMR (CDCl$_3$)δ(ppm): 1.20-1.63(6H,m), 1.66-1.78(2H,m), 2.02-2.12(2H,m), 2.31(3H,s), 2.33(3H,s), 3.68-3.81(1H,m), 6.01(1H,d,J=15.5 Hz), 6.61(2H,d,J=8.0 Hz), 7.03-7.33(6H,m).
The stereochemistry of the —CH═CH— bond was E.

EXAMPLE 412

Compound (474): Butyl 3-(4-fluorophenylthio)-N-(4-methylphenyl)thioacrylimidate $^1$H-NMR (CDCl$_3$)δ(ppm): 0.92(3H, t J=7.3 Hz), 1.34-1.50(2H, m), 1.54-1.68(2H,m), 2.31(3H, s), 3.05(2H, t J=7.3 Hz), 5.95(1H, d, J=15.4 Hz), 6.59(2H, d, J=8.0 Hz), 6.97-7.35(7H, m).
The stereochemistry of the —CH═CH— bond was E.

EXAMPLE 413

Compound (475): Butyl 3-(4-chlorophenylthio)-N-(4-methylphenyl)thioacrylimidate $^1$H-NMR (CDCl$_3$)δ(ppm): 0.85-0.96(3H,m), 1.35-1.70(4H,m), 2.32(3H,s), 3.07(2H,t,J=7.3 Hz), 6.09(1H,d,J=15.4 Hz), 6.60(2H,d,J=8.0 Hz), 7.05-7.30(7H,m).
The stereochemistry of the —CH═CH— bond was E.

EXAMPLE 414

Compound (476): Butyl N-(4-methylphenyl)-3-(4-methylphenylthio)thioacrylimidate $^1$H-NMR (CDCl$_3$)δ(ppm): 0.85-1.80(7H,m), 2.31(3H,s), 2.32(3H,s), 3.05(2H,t,J=7.5 Hz), 6.03(1H,d, J=15.4 Hz), 6.61(2H,d,J=8.3 Hz), 7.01-7.35(7H,m).
The stereochemistry of the —CH═CH— bond was E.
Compounds (477) to (480) were synthesized in a similar manner as the Example 176.

EXAMPLE 415

Compound (477): 4,5-Dimethylthiazole-2-yl N-(4-methylphenyl)-3-(phenylthio)thioacrylimidate $^1$H-NMR (CDCl$_3$)δ(ppm): 2.29, 2.31, 2.33, 2.34, 2.36, 2.37(total 9H, s), 5.64(0.52H, d J=15.5 Hz), 5.94(0.37H, d J=9.9 Hz), 6.16(0.11H, d J=15.5 Hz), 6.71-7.20(4H, m), 7.28-7.63(6H, m).
The stereochemistry of the —CH═CH— bond was mixture of E and Z.

EXAMPLE 416

Compound (478): 5-Methyl-1,3,4-thiadiazole-2-yl N-(4-methylphenyl)-3-(phenylthio)thioacrylimidate $^1$H-NMR (CDCl$_3$)δ(ppm): 2.35(3H, s), 2.73(3H, s), 6.19(1H, d J=15.9 Hz), 6.73(2H, d J=8.5 Hz), 7.13(2H, d J=7.8 Hz), 7.35-7.40(5H, m), 7.55(1H, d J=15.9 Hz).
The stereochemistry of the —CH═CH— bond was E.

EXAMPLE 417

Compound (479): 1-Methyl-1H-tetrazole-5-yl N-(4-methylphenyl)-3-(phenylthio)thioacrylimidate $^1$H-NMR (CDCl$_3$)δ(ppm): 2.24(1.3H, s), 2.35(1.7H, s), 3.77(1.3H,s), 3.92(1.7H, s), 6.19(0.56H, d J=15.6 Hz), 6.26(0.44H, d J=15.4 Hz), 6.66-7.16(4H, m), 7.32-7.54(6H, m).
The stereochemistry of the —CH═CH— bond was E.

EXAMPLE 418

Compound (480): 2-Thienyl N-(4-methylphenyl)-3-(phenylthio)thioacrylimidate $^1$H-NMR (CDCl$_3$)δ(ppm): 2.34(2.3H, s), 2.37(0.7H, s), 5.70(0.77H, d J=14.6 Hz), 5.92(0.23H, d J=10.2 Hz), 6.83-7.58(13H, m).
The stereochemistry of the —CH═CH— bond was mixture of E and Z.
Compounds (481) to (487) were synthesized in a similar manner as the Example 161.

EXAMPLE 419

Compound (481): Cyclohexylmethyl N-(4-methylphenyl)-3-(phenylthio)thioacrylimidate $^1$H-NMR (CDCl$_3$)δ(ppm): 0.92-1.90(10H,m), 2.30(3H,s), 2.89-3.02(3H,m), 6.12(1H,d,J=15.2 Hz), 6.62(2H,d,J=7.9 Hz), 7.06(2H,d,J=8.2 Hz), 7.26-7.40(6H,m).
The stereochemistry of the —CH═CH— bond was E.

EXAMPLE 420

Compound (482): Cyclohexylmethyl 3-(4-fluorophenylthio)-N-(4-methylphenyl)thioacrylimidate $^1$H-NMR (CDCl$_3$)δ(ppm): 0.94-1.90(10H,m), 2.32(3H,s), 2.85-3.01(3H,m), 5.95(1H,d,J=15.5 Hz), 6.68(2H,d, J=7.9 Hz), 6.95-7.38(7H,m).
The stereochemistry of the —CH═CH— bond was E.

EXAMPLE 421

Compound (483): 1-Phenylethyl N-(4-methylphenyl)-3-phenylthiothioacrylimidate $^1$H-NMR (CDCl$_3$)δ(ppm): 1.73(3H,d,J=7.0 Hz), 2.32(3H, s), 5.01(1H, q, J=7.0 Hz), 6.09(1H,d,J=15.7 Hz), 6.61(2H,d, J=8.2 Hz), 7.07(2H,d,J=8.0 Hz), 7.20-7.45(11H,m).
The stereochemistry of the —CH═CH— bond was E.

EXAMPLE 422

Compound (484): 1-Phenylpropyl N-(4-methylphenyl)-3-(4-methylphenylthio)thioacrylimidate $^1$H-NMR (CDCl$_3$)δ(ppm): 0.91(3H, t J=7.3 Hz), 1.93-2.17(2H, m), 2.31(6H, s), 4.78(1H, m), 5.97(1H, d, J=15.4 Hz), 6.54(2H, d, J=8.0 Hz), 7.03-7.37(12H, m).
The stereochemistry of the —CH═CH— bond was E.

EXAMPLE 423

Compound (485): 1-Phenylpropyl 3-(4-fluorophenylthio)-N-(4-methylphenyl)thioacrylimidate $^1$H-NMR (CDCl$_3$)δ(ppm): 0.92(3H, t J=7.3 Hz), 1.94-2.17 (2H, m), 2.31(3H, s), 4.79(1H, m), 5.91(1H, d, J=15.4 Hz), 6.53(2H, d, J=8.3 Hz), 6.96-7.37(12H, m).
The stereochemistry of the —CH═CH— bond was E.

EXAMPLE 424

Compound (486): Pentyl N-(4-methylphenyl)-3-(4-methylphenylthio)thioacrylimidate $^1$H-NMR (CDCl$_3$)δ(ppm): 0.89(3H, t J=7.1 Hz), 1.30-1.42 (4H, m), 1.63-1.70(2H, m), 2.31(3H, s), 2.33(3H, s), 3.04(2H, tJ=7.4 Hz), 6.03(1H, d, J=15.7 Hz), 6.61(2H, d, J=8.2 Hz), 7.04-7.37(7H, m).
The stereochemistry of the —CH═CH— bond was E.

EXAMPLE 425

Compound (487): Pentyl 3-(4-fluorophenylthio)-N-(4-methylphenyl)thioacrylimidate $^1$H-NMR (CDCl$_3$)δ(ppm): 0.89(3H, t J=7.1 Hz), 1.29-1.42 (4H, m), 1.63-1.70(2H, m), 2.31(3H, s), 3.04(2H, t J=7.4 Hz), 5.95(1H, d, J=15.5 Hz), 6.59(2H, d, J=8.2 Hz), 6.97-7.35(7H, m).
The stereochemistry of the —CH═CH— bond was E.
Compound (488) was synthesized in a similar manner as the Example 37.

EXAMPLE 426

Compound (488): Phenyl 3-phenoxy-N-(3,4,5-trimethylphenyl)acrylimidate $^1$H-NMR (CDCl$_3$)δ(ppm): 2.10(3H, s), 2.22(6H, s), 5.84 (1H, d, J=12.0 Hz), 6.47(2H, s), 7.03-7.38 (10H, m), 7.77(1H, d, J=12.0 Hz).
The stereochemistry of the —CH═CH— bond was E.
Compound (489) was synthesized in a similar manner as the Example 176.

EXAMPLE 427

Compound (489): 4-Methyl-4H-1,2,4-triazole-3-yl N-(4-methylphenyl)-3-(phenylthio)thioacrylimidate $^1$H-NMR (CDCl$_3$)δ(ppm): 2.24(1.08H, s), 2.28(0.54H, s), 2.34(1.38H, s), 3.49(1.08H, s), 3.53(0.54H, s), 3.62(1.38H, s), 6.16(0.46H, d, J=15.4 Hz), 6.29(0.36H, d, J=15.4 Hz), 6.38(0.18H, dJ=10.2 Hz), 6.72-7.14(5H, m), 7.30-7.55(5H, m), 7.67(0.18H, s), 7.69(0.36H, s), 7.88 (0.46H, s).
The stereochemistry of the —CH═CH— bond was mixture of E and Z.
Compound (490) was synthesized in a similar manner as the Example 37.

EXAMPLE 428

Compound (490): Phenyl 3-phenoxy-N-(3-thienyl)acrylimidate $^1$H-NMR (CDCl$_3$)δ(ppm): 5.95(1H, d, J=11.8 Hz), 6.52 (1H, dd, J$_1$=3.1 Hz, J$_2$=1.2 Hz), 6.70(1H, dd, J$_1$=5.1 Hz, J$_2$=1.2 Hz), 7.07-7.40(11H, m), 7.83(1H, d, J=11.8 Hz).
The stereochemistry of the —CH═CH— bond was E.
Compounds (491) to (494) were synthesized in a similar manner as the Example 100.

EXAMPLE 429

Compound (491): 3-Methylphenyl 3-(1-methylethylideneaminoxy)-N-(3,4-dimethylphenyl)acrylimidate $^1$H-NMR (CDCl$_3$)δ(ppm): 1.92(6H, s), 2.20(6H, s), 2.35 (3H, s), 5.56(1H, d, J=12.4 Hz), 6.52-6.54(1H, m), 6.59(1H, brs.), 6.94-7.01(4H, m), 7.21-7.23(1H, m), 8.01(1H, d, J=12.4 Hz).
The stereochemistry of the —CH═CH— bond was E.

EXAMPLE 430

Compound (492): 3-Methylphenyl N-(3,4-dimethylphenyl)-3-(1-phenylethylideneaminoxy)acrylimidate $^1$H-NMR (CDCl$_3$)δ(ppm): 2.22(6H, s), 2.30(3H, s), 2.36 (3H, s), 5.69(1H, d, J=12.4 Hz), 6.55-6.58(1H, m), 6.62(1H, brs.), 6.95-7.04(4H, m), 7.23-7.27(1H, m), 7.36-7.44(3H, m), 7.63-7.66(2H, m), 8.18(1H, d, J=12.4 Hz).
The stereochemistry of the —CH═CH— bond was E.

EXAMPLE 431

Compound (493): 3-Methylphenyl 3-cyclohexlideneaminoxy-N-(3,4-dimethylphenyl)acrylimidate $^1$H-NMR (CDCl$_3$)δ(ppm): 1.55-1.70(6H, m), 2.19(6H, s), 2.19-2.23(2H, m), 2.35(3H, s), 2.45-2.49(2H, m), 5.54(1H, d, J=12.4 Hz), 6.53-6.55(1H, m), 6.59(1H, brs.), 6.93-7.01(4H, m), 7.23-7.24(1H, m), 8.02(1H, d, J=12.4 Hz).
The stereochemistry of the —CH═CH— bond was E.

EXAMPLE 432

Compound (494): 3-Methylphenyl 3-dimethylaminoxy-N-(3,4-dimethylphenyl)acrylimidate $^1$H-NMR (CDCl$_3$)δ(ppm): 2.19(6H, s), 2.35(3H, s), 2.66 (6H, s), 5.52(1H, d, J=12.6 Hz), 6.51-6.53(1H, m), 6.58(1H, brs.), 6.93-7.01(4H, m), 7.21-7.25(1H, m), 7.62(1H, d, J=12.6 Hz).
The stereochemistry of the —CH═CH— bond was E.
Compounds (495) to (497) were synthesized in a similar manner as the Example 176.

EXAMPLE 433

Compound (495): 1-Methyl-1H-imidazole-2-yl N-(4-methylphenyl)-3-(phenylthio)thioacrylimidate $^1$H-NMR (CDCl$_3$)δ(ppm): 2.25 (0.9H, s), 2.29 (0.8H, s), 2.35 (1.29H, s), 3.55 (0.8H, s), 3.58 (0.77H, s), 3.61 (0.52H, s), 3.63 (0.90H, s), 6.19(0.30H, d J=15.4 Hz), 6.25(d J=9.8 Hz), 6.26(d J=9.8 Hz) total 0.43H, 6.32(0.27H, d J=15.4 Hz), 6.49-7.13(7H, m), 7.29-7.54(6H, m).

EXAMPLE 434

Compound (496): Benzothiazole-2-yl N-(4-methylphenyl)-3-phenylthiothioacrylimidate $^1$H-NMR (CDCl$_3$)δ(ppm): 2.32(1.23H, s), 2.36 (1.14H, s), 2.37 (0.63H, s), 5.75(0.38H, d J=14.6 Hz), 6.11(0.21H, d J=10. Hz), 6.23(0.41H, d J=15.4 Hz), 6.81-8.06(14H, m).

The stereochemistry of the —CH=CH— bond was mixture of E and Z.

EXAMPLE 435

Compound (497): 2-Methylfurane-3-yl N-(4-methylphenyl)-3-(phenylthio)thioacrylimidate $^1$H-NMR (CDCl$_3$)δ(ppm): 2.12 (0.3H, s), 2.16(1.4H, s), 2.18(0.6H, s), 2.22(0.7H, s), 2.29(0.47H, s), 2.33(2.53H, s), 5.41(0.1H, d J=14.1 Hz), 5.53(0.2H, d J=14.4 Hz), 5.69(0.7H, d J=14.9 Hz), 6.18(1H, s), 6.83(2H, dJ=8.3 Hz), 7.14-7.53(9.3H, m), 7.55(0.7H, d J=14.9 Hz).

The stereochemistry of the —CH=CH— bond was mixture of E and Z.

Compounds (498) to (501) were synthesized in a similar manner as the Example 100.

EXAMPLE 436

Compound (498): 3-Methylphenyl N-(3,4-dimethylphenyl)-3-(2-methylfurane-3-ylthio)acrylimidate $^1$H-NMR (CDCl$_3$)δ(ppm): 2.18(3H, s), 2.19(3H, s), 2.26 (3H, s), 2.34(3H,s), 5.72(1H,d,J=15.0 Hz), 6.29(1H,brs.), 6.45-6.50(2H, m), 6.94-6.99(4H, m), 7.21-7.25(2H, m), 7.39 (1H, d, J=15.0 Hz).

The stereochemistry of the —CH=CH— bond was E.

EXAMPLE 437

Compound (499): 3-Methylphenyl N-(3,4-dimethylphenyl)-3-(4,5-dimethylthiazole-2-ylthio)acrylimidate $^1$H-NMR (CDCl$_3$)δ(ppm): 2.20(6H, s), 2.29(3H, s), 2.32 (3H, s), 2.36(3H, s), 6.14(1H, d, J=15.5 Hz), 6.49-6.55(2H, m), 6.97-7.01(4H, m), 7.23-7.27(1H, m), 7.78(1H, d, J=15.5 Hz).

The stereochemistry of the —CH=CH— bond was E.

EXAMPLE 438

Compound (500): 3-Methylphenyl N-(3,4-dimethylphenyl)-3-(thiophene-2-ylmethylthio)acrylimidate $^1$H-NMR (CDCl$_3$)δ(ppm): 2.20(6H, s), 2.35(3H, s), 4.11 (2H, s), 5.94(1H, d, J=15.0 Hz), 6.46-6.54(2H, m), 6.82-6.99 (6H, m), 7.20-7.25(2H, m), 7.53(1H, d, J=15.0 Hz).

The stereochemistry of the —CH=CH— bond was E.

EXAMPLE 439

Compound (501): 3-Methylphenyl N-(3,4-dimethylphenyl)-3-(thiophen-2-ylthio)acrylimidate $^1$H-NMR (CDCl$_3$)δ(ppm): 2.18(6H, s), 2.34(3H, s), 5.82 (1H, d, J=15.2 Hz), 6.45-6.50(2H, m), 6.93-6.99(5H, m), 7.17-7.23(2H, m), 7.41-7.42(1H, m), 7.48(1H, d, J=15.2 Hz).

The stereochemistry of the —CH=CH— bond was E.

Compound (502) was synthesized in a similar manner as the Example 176.

EXAMPLE 440

(502): 4-Trifluoromethylpyrimidine-2-yl N-(4-methylphenyl)-3-(phenylthio)thioacrylimidate $^1$H-NMR (CDCl$_3$)δ(ppm): 2.26(1.86H, s), 2.30(0.27H, s), 2.32(0.87H, s), 6.30(0.09H, dJ=15.0 Hz), 6.41(dJ=15.0 Hz), 6.41(dJ=10.1 Hz) total 0.91H, 6.71-6.92(2H, m), 7.02-7.14 (2H, m), 7.27-7.52(6.38H, m), 7.69(0.62H, d J=15.0 Hz), 8.70(0.62H, d J=5.1 Hz), 8.77(0.29H, d J=4.8 Hz), 8.80(0.09H, d J=4.8 Hz).

The stereochemistry of the —CH=CH— bond was mixture of E and Z.

Compound (503) was synthesized in a similar manner as the Example 37.

EXAMPLE 441

Compound (503): Phenyl N-[4-(1,1-dimethylethylthio)phenyl]-3-phenoxyacrylimidate $^1$H-NMR (CDCl$_3$)δ(ppm): 1.24(9H, s), 5.69(1H, d, J=11.8 Hz), 6.74-7.42 (14H, m), 7.82(1H, d, J=11.8 Hz).

The stereochemistry of the —CH=CH— bond was E.

Compounds (504) and (505) were synthesized in a similar manner as the Example 158.

EXAMPLE 442

Compound (504): Phenyl N-[4-(4-methylphenyl) phenyl]-3-phenoxyacrylimidate $^1$H-NMR (CDCl$_3$)δ(ppm): 2.37(3H, s), 5.83(1H, d, J=12.0 Hz), 6.85-7.43(18H, m), 7.82(1H, d, J=12.0 Hz).

The stereochemistry of the —CH=CH— bond was E.

EXAMPLE 443

Compound (505): Phenyl N-[4-(4-chlorophenyl) phenyl]-3-phenoxyacrylimidate $^1$H-NMR (CDCl$_3$)(ppm): 5.80(1H, d, J=11.8 Hz), 6.86-7.49(18H, m), 7.83(1H, d, J=11.8 Hz).

The stereochemistry of the —CH=CH— bond was E.

Compounds (506) and (507) were synthesized in a similar manner as the Example 176.

EXAMPLE 444

Compound (506): Benzoxazole-2-yl N-(4-methylphenyl)-3-(phenylthio)thioacrylimidate $^1$H-NMR (CDCl$_3$)δ(ppm): 2.16 (1.11H, s), 2.19 (0.63H, s), 2.38 (1.26H, s), 6.22(0.46H, d J=15.5 Hz), 6.31(d J=15.5 Hz), 6.31(d J=10.4 Hz) total 0.58H, 6.78-6.83(1H, m), 7.06-7.23 (3H, m), 7.27-7.55 (8H, m).

The stereochemistry of the —CH=CH— bond was mixture of E and Z.

EXAMPLE 445

Compound (507):4-(4-Chloro-1H-pyrazole-1-yl) pyrimidine-2-yl N-(4-methylphenyl)-3-(phenylthio) thioacrylimidate $^1$H-NMR (CDCl$_3$)δ(ppm): 2.27(1.79H,s), 2.33(0.97H,s), 2.35(0.24H, s), 6.31(0.08H,d J=15.0 Hz), 6.41(d J=14.7 Hz), 6.44(d J=10.1 Hz) total 0.92H, 6.74(1H, dJ=8.2 Hz), 6.92-7.16(3H,m), 7.29-7.40(4H, m), 7.52-7.58 (2H, m, Ar), 7.69-7.73 (2H, m), 8.42(1H, s), 8.50-8.52 (0.68H, m), 8.57(0.32H, d J=5.3 Hz).

The stereochemistry of the —CH=CH— bond was mixture of E and Z.

Compounds (508) to (512) were synthesized in a similar manner as the Example 100.

EXAMPLE 446

Compound (508): 3-Methylphenyl 3-(benzothiazole-2-ylthio)-N-(3,4-dimethylphenyl)acrylimidate $^1$H-NMR (CDCl$_3$)δ(ppm): 2.23(3H, s), 2.24(3H, s), 2.40 (3H, s), 6.61-6.68(2H, m), 6.73(1H, d, J=14.5 Hz), 7.02-7.15 (5H, m), 7.22-7.38(4H, m), 8.29(1H, d, J=14.5 Hz).

The stereochemistry of the —CH=CH— bond was E.

EXAMPLE 447

Compound (509): 3-Methylphenyl 3-(benzoxazole-2-ylthio)-N-(3,4-dimethylphenyl)acrylimidate $^1$H-NMR (CDCl$_3$)δ(ppm): 2.19(3H, s), 2.23(3H, s), 2.40 (3H, s), 6.60-6.69(3H, m), 7.02-7.14(4H, m), 7.28-7.34(4H, m), 7.45-7.47(4H, m), 8.14(1H, d, J=14.2 Hz).

The stereochemistry of the —CH=CH— bond was E.

EXAMPLE 448

Compound (510): 3-Methylphenyl N-(3,4-dimethylphenyl)-3-(5-methyl-1,3,5-thiadiazole-2-ylthio)acrylimidate $^1$H-NMR (CDCl$_3$)δ(ppm): 2.22(3H, s), 2.23(3H, s), 2.37 (3H, s), 2.46(3H, s), 6.54-6.52(3H, m), 6.99-7.06(4H, m), 7.24-7.28(1H, m), 8.54(1H, d, J=13.5 Hz).

The stereochemistry of the —CH=CH— bond was E.

EXAMPLE 449

Compound (511): 3-Methylphenyl N-(3,4-dimethylphenyl)-3-(furane-2-ylmethylthio)acrylimidate $^1$H-NMR (CDCl$_3$)δ(ppm): 2.20(6H, s), 2.35(3H, s), 3.92 (2H, s), 5.96(1H,d,J=15.2 Hz), 6.06(1H,d,J=3.1 Hz), 6.28 (1H,dd,J$_1$=3.1 Hz, J$_2$=1.9 Hz), 6.49(1H,dd,J$_1$=7.8 Hz, J$_2$=2.1 Hz), 6.55(1H, brs), 6.91-7.01(4H, m), 7.22-7.26(1H, m), 7.33 (1H, brs), 7.55(1H, d, J=15.2 Hz).

The stereochemistry of the —CH=CH— bond was E.

EXAMPLE 450

Compound (512): 3-Methylphenyl N-(3,4-dimethylphenyl)-3-(1-methyl-1H-tetrazole-5-ylthio)acrylimidate $^1$H-NMR (CDCl$_3$)δ(ppm): 2.21(6H, s), 2.38(3H, s), 3.89 (3H, s), 6.53-6.60(2H, m), 6.97(1H, d, J=14.2 Hz), 7.01-7.06 (4H, m), 7.25-7.30(1H, m), 8.18(1H, d, J=14.2 Hz).

The stereochemistry of the —CH=CH— bond was E.

Compound (513), (598) and (599) were synthesized in a similar manner as the Example 161.

EXAMPLE 451

Compound (513): 1-Methylpropyl 3-(4-fluorophenylthio)-N-(4-methylphenyl)acrylimidate $^1$H-NMR (CDCl$_3$)δ(ppm): 1.00(3H,t,J=7.4 Hz), 1.36(3H d,J=7.0 Hz), 1.60-1.76(2H,m), 2.32(3H,s), 3.78(1H,sext., J=6.8 Hz), 5.95(1H, d, J=15.5 Hz), 6.59(2H, d, J=8.2 Hz), 6.97-7.35(7H, m).

The stereochemistry of the —CH=CH— bond was E.

EXAMPLE 452

Compound (598): Decyl 3-(4-fluorophenylthio)-N-(4-methylphenyl)acrylimidate $^1$H-NMR (CDCl$_3$)δ(ppm): 0.87(3H, t J=6.8 Hz), 1.25-1.40 (14H, m), 1.62-1.70(2H, m), 2.32(3H, s), 3.04(2H, t J=7.2 Hz), 5.96(1H, dJ=15.5 Hz), 6.59(2H,dJ=8.2 Hz), 6.99(2H, m), 7.04(2H,dJ=8.2 Hz), 7.25(1H, d J=15.2 Hz), 7.32-7.35 (2H, m)

The stereochemistry of the —CH=CH— bond was E.

EXAMPLE 453

Compound (599): Geranyl 3-(4-fluorophenylthio)-N-(4-methylphenyl)acrylimidate $^1$H-NMR (CDCl$_3$)δ(ppm): 1.59(3H, s), 1.67(3H, s), 1.70 (3H, s), 1.94-2.13(4H, m), 2.32(3H,s), 3.71(2H, d, J=7.8 Hz), 5.08(1H, t,J=6.3 Hz), 5.33(1H,t,J=7.8 Hz), 5.96(1H,d,J=15.4 Hz), 6.60(2H, d,J=7.9 Hz), 6.99(2H,t,J=8.7 Hz), 7.05(2H,d, J=7.9 Hz), 7.24(1H, d, J=15.4 Hz), 7.33(2H, dd, J=8.7, 5.1 Hz)

The stereochemistry of the —CH=CH— bond was E.

EXAMPLE AA1

Compound AA10-2: cyclohexylmethyl 3-(4-fluorophenylthio)-N-(phenyl)thioacrylimidate

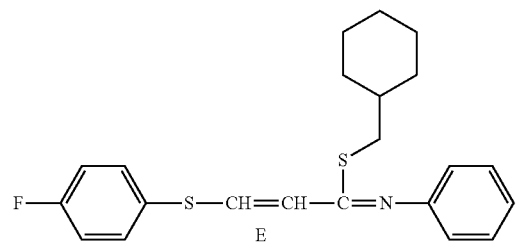 [SMILES: Fc1ccc(SC=CC(=Nc2ccccc2)SCC2CCCCC2)cc1]

Cyclohexylmethyl N-phenylpropynthioimidate (0.34 g) was dissolved to chloroform (8 mL), chloroform (2 mL) solution of 4-fluorothiophenol (0.14 g) was added dropwise under ice-cooling, and then it was stirred at room temperature for 16 hours. The reaction solution was concentrated under reduced pressure. The residue was purified by medium pressure HPLC (hexane/ethyl acetate=98/2) to obtain cyclohexylmethyl 3-(4-fluorophenylthio)-N-(phenyl)thioacrylimidate (0.25 g) as pale yellow oil.

¹H-NMR (CDCl₃)δ(ppm): 0.97-1.28(5H, m), 1.57-1.86 (6H, m), 2.99(2H,d,J=6.8 Hz), 5.93(1H,d,J=15.6 Hz), 6.68 (2H,d,J=7.3 Hz), 6.97-7.35(8H, m)

Below mentioned compounds were synthesized in a similar manner as the Example AA1.

Compound AA10-448: cyclohexylmethyl N-(4-chlorophenyl)-3-(4-fluorophenylthio)thioacrylimidate

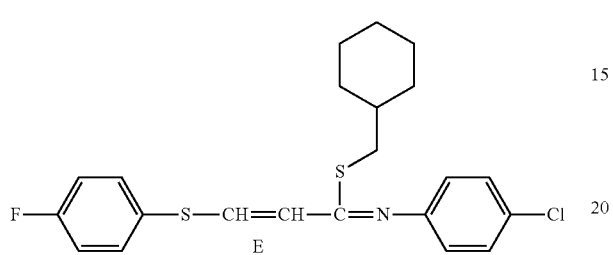

¹H-NMR (CDCl₃)δ(ppm): 0.99-1.25(5H, m), 1.66-1.85 (6H, m), 2.97(2H,d,J=6.8 Hz), 5.84(1H,d,J=15.6 Hz), 6.61 (2H,d,J=8.5 Hz), 7.02(2H,t,J=8.5 Hz), 7.20(2H,d,J=8.5 Hz), 7.30(1H,d,J=15.6 Hz), 7.32-7.36(2H, m)

Compound AA10-894: cyclohexylmethyl 3-(4-fluorophenylthio)-N-(4-methoxyphenyl)thioacrylimidate

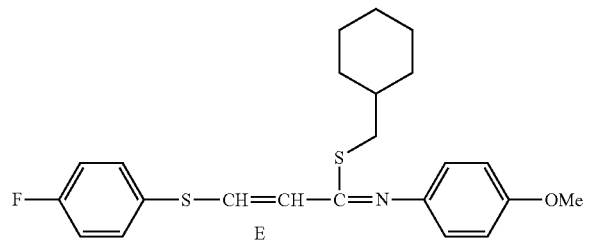 [SMILES: COc1ccc(N=C(C=CSc2ccc(F)cc2)SCC2CCCCC2)cc1]

¹H-NMR (CDCl₃)δ(ppm): 0.97-1.29(5H, m), 1.57-1.86 (6H, m), 2.98(2H,d,J=6.8 Hz), 3.79(3H,s), 5.99(1H,d,J=15.5 Hz), 6.63(2H, d,J=9.0 Hz), 6.80(2H,d,J=8.7 Hz), 7.01(2H,t, J=8.6 Hz), 7.27(1H, d, J=15.5 Hz), 7.34-7.37(2H, m)

Compound AA10-1: cyclohexylmethyl N-phenyl-3-(phenylthio)thioacrylimidate

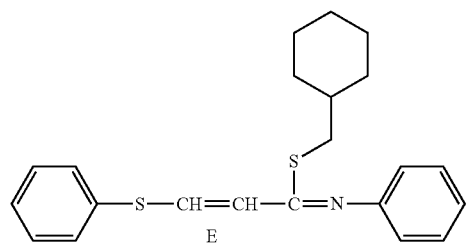 [SMILES: C(=CC(=Nc1ccccc1)SCC1CCCCC1)Sc1ccccc1]

¹H-NMR (CDCl₃)δ(ppm): 0.97-1.28(5H, m), 1.57-1.87 (6H, m), 2.99(2H,d,J=6.8 Hz), 6.07(1H,d,J=15.6 Hz), 6.71 (2H,d,J=7.3 Hz), 7.02(1H, t, J=7.4 Hz), 7.23-7.40(8H, m)

Compound AA10-8: cyclohexylmethyl 3-(4-methylphenylthio)-N-(phenyl)thioacrylimidate

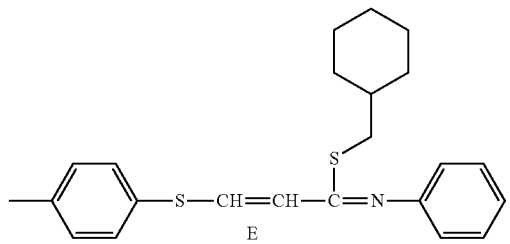 [SMILES: Cc1ccc(SC=CC(=Nc2ccccc2)SCC2CCCCC2)cc1]

¹H-NMR (CDCl₃)δ(ppm): 0.97-1.28(5H, m), 1.57-1.86 (6H, m), 2.32(3H,s), 2.98(2H,d,J=6.8 Hz), 5.98(1H,d,J=15.5 Hz), 6.69(2H, d,J=9.0 Hz), 7.02(1H,t,J=7.4 Hz), 7.10(2H,d, J=8.0 Hz), 7.24(4H, t, J=7.6 Hz), 7.35(1H, d, J=15.5 Hz)

Compound AA7-2: cyclopentylmethyl 3-(4-fluorophenylthio)-N-(phenyl)thioacrylimidate

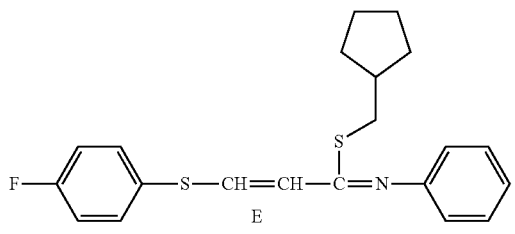 [SMILES: Fc1ccc(SC=CC(=Nc2ccccc2)SCC2CCCC2)cc1]

¹H-NMR (CDCl₃)δ(ppm): 1.23-1.45(2H, m), 1.46-1.88 (6H, m), 2.12-2.21(1H, m), 3.09(2H,d,J=6.8 Hz), 5.92(1H, d, J=16.1 Hz), 6.68(2H, d, J=7.7 Hz), 6.94-7.44(8H, m)

Compound AA11-2: 1-cyclohexylethyl 3-(4-fluorophenylthio)-N-(phenyl)thioacrylimidate

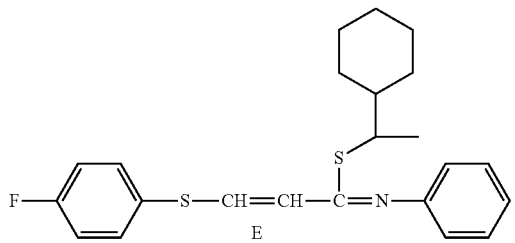 [SMILES: CC(SC(C=CSc1ccc(F)cc1)=Nc1ccccc1)C1CCCCC1]

¹H-NMR (CDCl₃)δ(ppm): 1.06-1.31(5H, m), 1.34(3H, d, J=7.1 Hz), 1.59-1.85(6H, m), 3.81-3.88(1H, m), 5.92(1H, d, J=15.6 Hz), 6.68(2H, d, J=7.3 Hz), 6.96-7.04(3H, m), 7.22-7.34(5H, m)

175

Compound AA10-225: cyclohexylmethyl N-(4-fluorophenyl)-3-(4-fluorophenylthio)thioacrylimidate

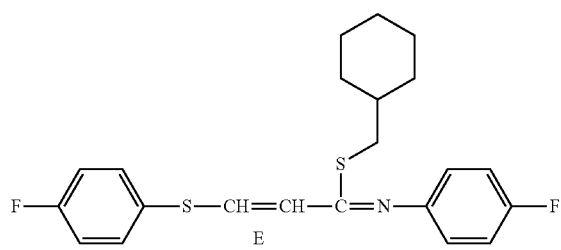 [SMILES: Fc1ccc(N=C(C=CSc2ccc(F)cc2)SCC2CCCCC2)cc1]

$^1$H-NMR (CDCl$_3$)δ(ppm): 0.97-1.25(5H, m), 1.66-1.85 (6H, m), 2.97(2H,d,J=6.8 Hz), 5.88(1H,d,J=15.4 Hz), 6.63 (2H,d,J=8.9 Hz), 6.94(2H,t,J=8.7 Hz), 7.01(2H,t,J=8.5 Hz), 7.30(1H,d,J=15.5 Hz), 7.32-7.37(2H, d, J=8.8 Hz)

Compound AA10-29: cyclohexylmethyl 3-(3-fluorophenylthio)-N-(phenyl)thioacrylimidate

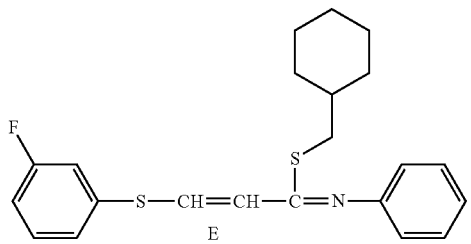

$^1$H-NMR (CDCl$_3$)δ(ppm): 0.99-1.26(5H, m), 1.59-1.87 (6H, m), 3.01(2H,d,J=6.8 Hz), 6.12(1H,d,J=15.7 Hz), 6.72 (2H,d,J=7.6 Hz), 6.96-7.13(4H, m), 7.25-7.35(4H, m)

Compound AA10-31: cyclohexylmethyl 3-(3-chlorophenylthio)-N-(phenyl)thioacrylimidate

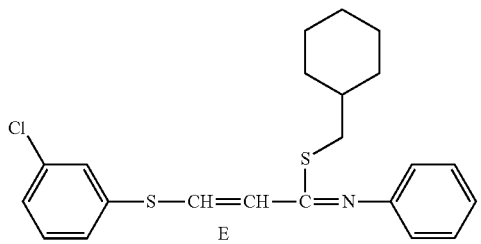 [SMILES: Clc1cccc(SC=CC(=Nc2ccccc2)SCC2CCCCC2)c1]

$^1$H-NMR (CDCl$_3$)δ(ppm): 0.99-1.26(5H, m), 1.59-1.87 (6H, m), 3.01(2H,d,J=6.8 Hz), 6.10(1H,d,J=15.7 Hz), 6.72 (2H,d,J=7.3 Hz), 7.04(1H, t, J=7.3 Hz), 7.23-7.36(7H, m)

176

Compound AA10-4 : cyclohexylmethyl 3-(4-chlorophenylthio)-N-(phenyl)thioacrylimidate

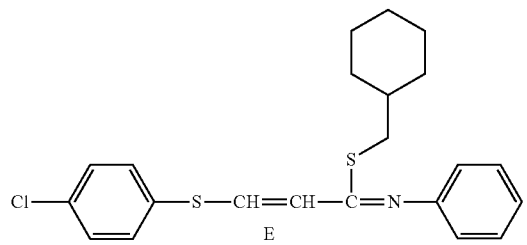 [SMILES: Clc1ccc(SC=CC(=Nc2ccccc2)SCC2CCCCC2)cc1]

$^1$H-NMR (CDCl$_3$)δ(ppm): 1.01-1.28(5H, m), 1.58-1.87 (6H, m), 3.00(2H,d,J=6.8 Hz), 6.02(1H,d,J=15.7 Hz), 6.69 (2H,d,J=7.8 Hz), 7.05(1H,t,J=7.6 Hz), 7.24-7.31(7H, m)

Compound AA10-33: cyclohexylmethyl 3-(3-bromophenylthio)-N-(phenyl)thioacrylimidate

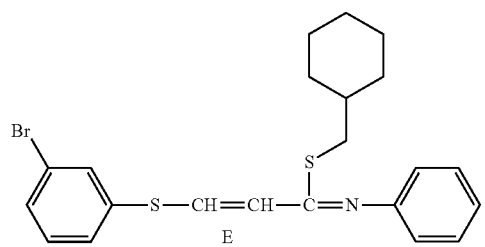

$^1$H-NMR (CDCl$_3$)δ(ppm): 0.99-1.28(5H, m), 1.57-1.87 (6H, m), 3.00(2H,d,J=6.8 Hz), 6.10(1H,d,J=15.4 Hz), 6.72 (2H,d,J=7.3 Hz), 7.04(1H, t, J=7.6 Hz), 7.17(1H, t, J=7.6 Hz), 7.26-7.33(4H, m), 6.41(1H, d, J=7.8 Hz), 7.51(1H, br)

Compound AA10-6: cyclohexylmethyl 3-(4-bromophenylthio)-N-(phenyl)thioacrylimidate

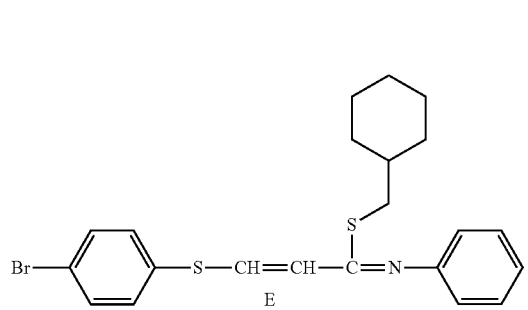

$^1$H-NMR (CDCl$_3$)δ(ppm): 1.02-1.28(5H, m), 1.59-1.87 (6H, m), 3.00(2H,d,J=6.8 Hz), 6.03(1H,d,J=15.4 Hz), 6.69 (2H,d,J=7.6 Hz), 7.05(1H, t, J=7.8 Hz), 7.14-7.43(7H, m)

Compound AA10-35: cyclohexylmethyl 3-(3-methylphenylthio)-N-(phenyl)thioacrylimidate

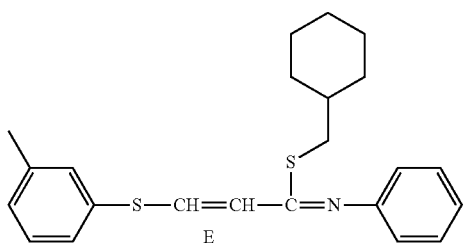 [SMILES: Cc1cccc(SC=CC(=Nc2ccccc2)SCC2CCCCC2)c1]

¹H-NMR (CDCl₃)δ(ppm): 1.01-1.26(5H, m), 1.66-1.87 (6H, m), 2.31(3H,s), 2.99(2H,d,J=6.8 Hz), 6.05(1H,d,J=15.7 Hz), 6.71(2H, d, J=7.6 Hz), 7.02(1H, t, J=7.6 Hz), 7.08-7.31 (6H, m), 7.37(1H, d, J=15.7 Hz)

Compound AA10-51: cyclohexylmethyl 3-(3-methoxyphenylthio)-N-(phenyl)thioacrylimidate

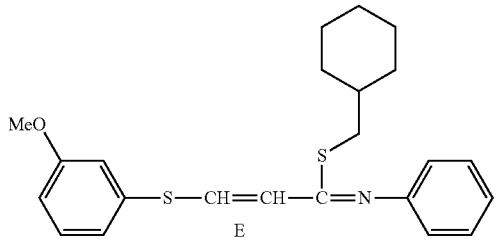 [SMILES: COc1cccc(SC=CC(=Nc2ccccc2)SCC2CCCCC2)c1]

¹H-NMR (CDCl₃)δ(ppm): 1.01-1.28(5H, m), 1.58-1.87 (6H, m), 3.00(2H,d,J=6.6 Hz), 3.78(3H,s), 6.10(1H,d,J=15.4 Hz), 6.72(2H, d, J=7.6 Hz), 6.82(1H, dd, J=8.6, 2.0 Hz), 6.90(1H, br), 6.95(1H, d, J=8.1 Hz), 7.03(1H, t, J=7.8 Hz), 7.20-7.27(3H, m), 7.39(1H, d, J=15.4 Hz)

Compound AA10-40: cyclohexylmethyl N-(phenyl)-3-(3-trifluoromethylphenylthio)thioacrylimidate

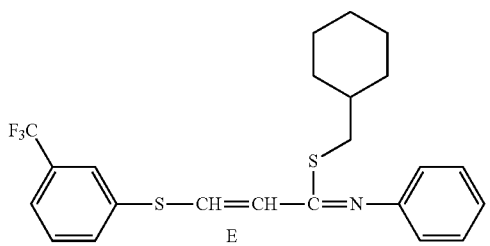 [SMILES: FC(F)(F)c1cccc(SC=CC(=Nc2ccccc2)SCC2CCCCC2)c1]

¹H-NMR (CDCl₃)δ(ppm): 1.03-1.28(5H, m), 1.62-1.89 (6H, m), 3.06(2H,d,J=6.8 Hz), 6.00(1H,d,J=12.1 Hz), 6.78 (2H,d,J=7.3 Hz), 7.06(1H,t,J=7.3 Hz), 7.18(1H,d,J=8.3 Hz), 7.24(1H,br), 7.31(2H, t,J=8.1 Hz), 7.39(1H,d,J=7.8 Hz), 7.45 (1H,d,J=8.1 Hz), 7.51(1H, d, J=12.1 Hz)

Compound AA10-27: cyclohexylmethyl 3-(4-nitrophenylthio)-N-(phenyl)thioacrylimidate

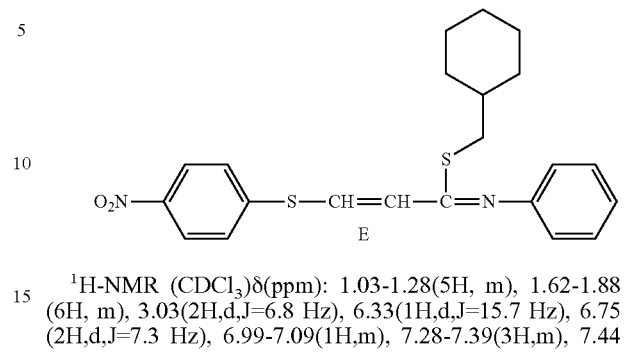

¹H-NMR (CDCl₃)δ(ppm): 1.03-1.28(5H, m), 1.62-1.88 (6H, m), 3.03(2H,d,J=6.8 Hz), 6.33(1H,d,J=15.7 Hz), 6.75 (2H,d,J=7.3 Hz), 6.99-7.09(1H,m), 7.28-7.39(3H,m), 7.44 (2H,d,J=8.8 Hz), 8.17(2H, d, J=8.8 Hz)

EXAMPLE AA2

Compound AA1-2: cyclopropylmethyl 3-(4-fluorophenylthio)-N-(phenyl)thioacrylimidate

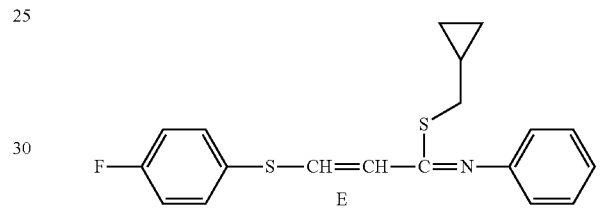

Cyclopropylmethyl N-phenyl-3-(trimethylsilyl)thiopropynimidate (0.91 g) was dissolved in methanol (15 mL), a small amount of potassium carbonate was dissolved thereto at room temperature, and the mixture was stirred for 1 hour. 4-fluorothiophenol (0.35 mL) was added thereto and further stirred for 5.5 hours. The reaction mixture was concentrated under reduced pressure, then the residue was subjected to silica gel column chromatography (hexane/ethyl acetate=20/1), medium pressure HPLC (hexane/ethyl acetate=99.2/0.8-98.5/1.5) to obtain cyclopropylmethyl 3-(4-fluorophenylthio)-N-(phenyl)thioacrylimidate (0.84 g).

¹H-NMR (CDCl₃)δ(ppm): 0.28-0.31(2H, m), 0.55-0.60 (2H, m), 1.06-1.16(1H,m), 3.02(2H,d,J=7.2 Hz), 5.94(1H,d, J=15.5 Hz), 6.69(2H, d, J=7.5 Hz), 6.97-7.05(3H, m), 7.22-7.36(5H, m).

Below mentioned compounds were synthesized in a similar manner as the Example AA2.

Compound AA10-2008: cyclohexylmethyl N-(3-methoxyphenyl)-3-(phenylthio)thioacrylimidate

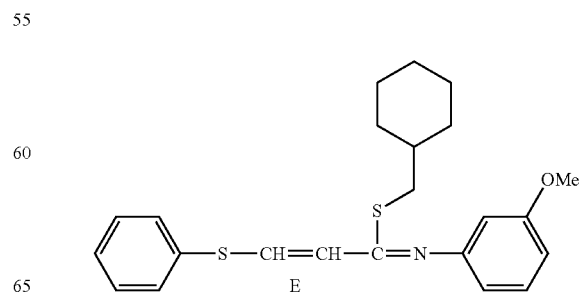

¹H-NMR (CDCl₃)δ(ppm): 0.94-1.31(5H, m), 1.50-1.90 (6H, m), 2.99(2H, d, J=6.8 Hz), 3.78(3H, s), 6.09(1H, d, J=15.4 Hz), 6.24-6.33(2H, m), 6.55-6.63(1H, m), 7.15(1H, t, J=7.9 Hz), 7.24-7.45(6H, m)

Compound AA10-2009: cyclohexylmethyl 3-(4-fluorophenylthio)-N-(3-methoxyphenyl)thioacrylimidate

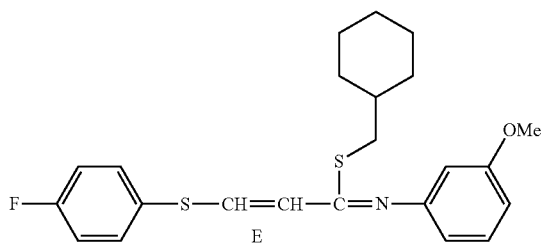 [SMILES: COc1cccc(N=C(C=CSc2ccc(F)cc2)SCC2CCCCC2)c1]

¹H-NMR (CDCl₃)δ(ppm): 0.94-1.30(5H, m), 1.51-1.89 (6H, m), 2.98(2H,d,J=6.8 Hz), 3.78(3H,s), 5.93(1H,d,J=15.7 Hz), 6.24(1H, d, J=2.1 Hz), 6.26(1H, d, J=8.1 Hz), 6.59(1H, dd, J=8.1, 2.1 Hz), 7.00(2H,t,J=8.5 Hz), 7.14(1H,t,J=8.1 Hz), 7.29(1H,d,J=15.7 Hz), 7.34(2H, dd, J=8.5, 5.1 Hz)

Compound AA10-1562: cyclohexylmethyl N-(3-chlorophenyl)-3-(phenylthio)thioacrylimidate

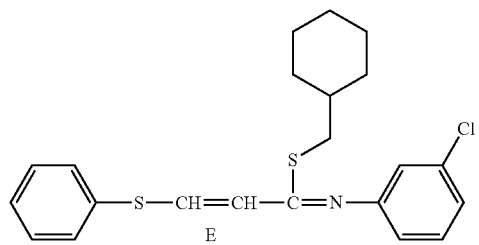 [SMILES: Clc1cccc(N=C(C=CSc2ccccc2)SCC2CCCCC2)c1]

¹H-NMR (CDCl₃)δ(ppm): 0.90-1.33(5H, m), 1.48-1.93 (6H, m), 2.96(2H,d,J=6.6 Hz), 5.91(1H,d,J=15.4 Hz), 6.58 (1H,d,J=7.8 Hz), 6.70(1H, s), 6.99(1H, d, J=7.8 Hz), 7.15 (1H, t, J=7.8 Hz), 7.26-7.46(6H, m)

Compound AA10-1563: cyclohexylmethyl N-(3-chlorophenyl)-3-(4-fluorophenylthio)thioacrylimidate

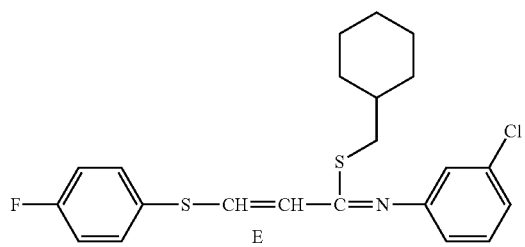 [SMILES: Fc1ccc(SC=CC(=Nc2cccc(Cl)c2)SCC2CCCCC2)cc1]

¹H-NMR (CDCl₃)δ(ppm): 0.92-1.31(5H, m), 1.50-1.90 (6H, m), 2.96(2H,d,J=6.8 Hz), 5.77(1H,d,J=15.5 Hz), 6.56 (1H,d,J=8.0 Hz), 6.67(1H,s), 6.97-7.06(3H,m), 7.15(1H,t, J=8.0 Hz), 7.28-7.40(3H, m)

Compound AA10-1339: cyclohexylmethyl N-(3-fluorophenyl)-3-(phenylthio)thioacrylimidate

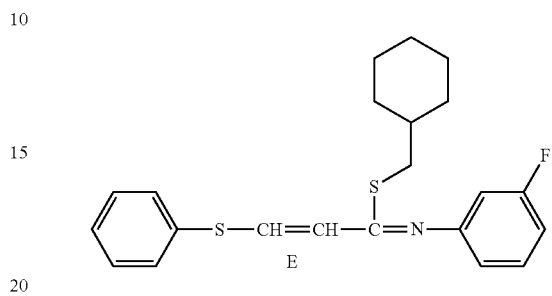

¹H-NMR (CDCl₃)δ(ppm): 0.92-1.33(5H, m), 1.49-1.92 (6H, m), 2.97(2H, d, J=6.8 Hz), 5.95(1H, d, J=15.5 Hz), 6.43(1H, d, J=10.1 Hz), 6.47(1H, d, J=8.0 Hz), 6.72(1H, td, J=8.0, 1.7 Hz), 7.18(1H, dd, J=14.7, 8.0 Hz), 7.24-7.46(6H, M).

Compound AA10-1340: cyclohexylmethyl N-(3-fluorophenyl)-3-(4-fluorophenylthio)thioacrylimidate

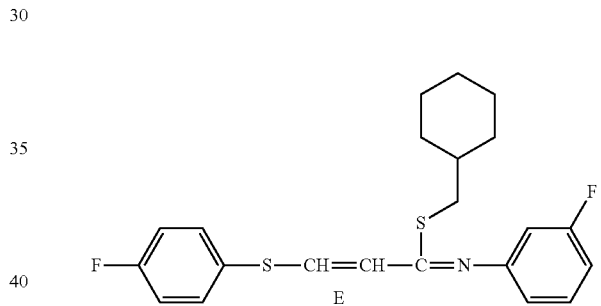

¹H-NMR (CDCl₃)δ(ppm): 0.94-1.31(5H, m), 1.50-1.91 (6H, m), 2.97(2H, d, J=6.8 Hz), 5.81(1H, d, J=15.5 Hz), 6.40(1H, d, J=10.1 Hz), 6.45(1H, d, J=8.0 Hz), 6.73(1H, td, J=8.0, 2.1 Hz), 7.01(2H,t,J=8.5 Hz), 7.17(1H,dd,J=14.7, 8.0 Hz), 7.29-7.40(3H, m).

EXAMPLE AA3

Compound AA8-2: 1-cyclopentylethyl 3-(4-fluorophenylthio)-N-(phenyl)thioacrylimidate

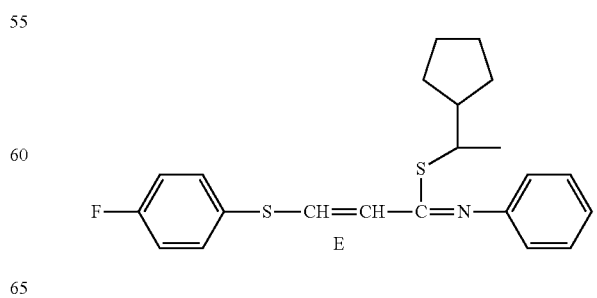

Ethynyl trimethyl silane (1.0 mL) was dissolved in dry THF (20 mL), n-butyllithium/hexane solution (1.57 mol./L; 5 mL) was added dropwise thereto at −78° C., and then it was warmed to 0° C. THF (2 mL) solution of phenyl isothiocyanate (0.88 mL) was added thereto, THF (2 mL) solution of 1-cyclopentylethyl methanesulfonate (1.55 g) was added thereto, and then it was refluxed for 7 hours. Saturated aqueous solution of ammonium chloride (10 mL) and water (10 mL) were added to the reaction solution, then it was extracted with t-butyl methyl ether (20 mL) The organic layer was washed with saturated aqueous solution of sodium chloride (20 mL), dried over anhydrous magnesium sulfate. Inorganic salt was filtered off and the filtrate was concentrated under reduced pressure to obtain brown oil (2.22 g). The residue was subjected to Florisil column chromatography (hexane/ethyl acetate=20/1) to obtain crude 1-cyclopentylethyl N-(phenyl)-3-(trimethylsilyl)thiopropynimidate (0.98 g). The obtained crude 1-cyclopentylethyl N-(phenyl)-3-(trimethylsilyl)thiopropynimidate (0.98 g) was dissolved to methanol (20 mL), a small amount of potassium carbonate was added thereto, and then stirred for 1 hour at room temperature. Furthermore, 4-fluorothiophenol (0.22 mL) was added to the mixture and stirred for overnight. The reaction solution was concentrated under reduced pressure. The residue was subjected to silica gel column chromatography (hexane/ethyl acetate=30/1) to obtain 1-cyclopentylethyl 3-(4-fluorophenylthio)-N-(phenyl)thioacrylimidate (0.43 g).

$^1$H-NMR (CDCl$_3$)δ(ppm): 1.26-1.89(11H, m), 2.00-2.10 (1H, m), 3.81-3.88(1H, m), 5.91(1H, dJ=15.4 Hz), 6.69(2H, dJ=7.6 Hz), 6.97-7.04(3H, m), 7.22-7.35(5H, m).

Below mentioned compounds were synthesized in a similar manner as the Example AA3.

Compound AA4-2: cyclobutylmethyl N-(4-fluorophenyl)-3-(4-fluorophenylthio)thioacrylimidate

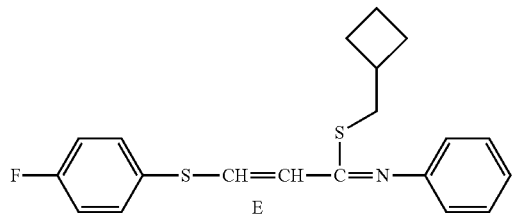 [SMILES: Fc1ccc(SC=CC(=Nc2ccccc2)SCC2CCC2)cc1]

$^1$H-NMR (CDCl$_3$)δ(ppm): 1.70-1.92(4H, m), 2.04-2.14 (2H, m), 2.57-2.65(1H, m), 3.15(2H,d,J=7.5 Hz), 5.93(1H,d, J=15.5 Hz), 6.68(2H, d, J=7.2 Hz), 6.96-7.05(3H, m), 7.22-7.34(5H, m)

EXAMPLE AB1

Compound AB35-2: 1-ethyl-2-methylbutyl 3-(4-fluorophenylthio)-N-(phenyl)thioacrylimidate

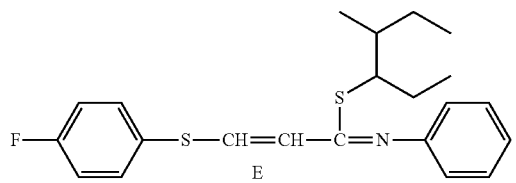

1-ethyl-2-methylbutyl N-phenyl-3-(trimethylsilyl)thiopropynimidate (0.47 g) was dissolved to methanol (10 mL), small amount of potassium carbonate was added to the solution under ice-cooling and then it was stirred for 30 minutes. Then methanol (3 mL) of 4-fluorothiophenol (0.105 mL) was added to the solution and the mixture was stirred for 18 hours at room temperature. The reaction mixture was concentrated under reduced pressure. The residue was subjected to medium pressure HPLC (hexane/ethyl acetate=98/2) to obtain 1-ethyl-2-methylbutyl 3-(4-fluorophenylthio)-N-(phenyl)thioacrylimidate (0.09 g).

$^1$H-NMR (CDCl$_3$)δ(ppm): 0.89-1.04(9H, m), 1.13-1.34 (1H, m), 1.49-1.78(4H, m), 3.86-3.91(0.75H, m), 3.97-4.01 (0.25H, m), 5.92(0.25H, d, J=15.4 Hz), 5.93(0.75H, d, J=15.4 Hz), 6.66(2H, d, J=7.6 Hz), 6.97-7.03(3H, m), 7.21-7.35(5H, m)

Below mentioned compounds were synthesized in a similar manner as the Example AB1.

Compound AB36-2: 1-ethyl3-methylbutyl 3-(4-fluorophenylthio)-N-(phenyl)thioacrylimidate

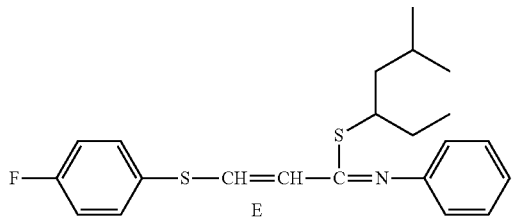 [SMILES: CCC(CC(C)C)SC(C=CSc1ccc(F)cc1)=Nc1ccccc1]

$^1$H-NMR (CDCl$_3$)δ(ppm): 0.92(6H,d,J=6.6 Hz), 1.00(3H, t,J=7.3 Hz), 1.40-1.86(5H, m), 3.89-3.95(1H, m), 5.92(1H, d, J=15.6 Hz), 6.67(2H, d, J=7.6 Hz), 6.96-7.04(3H, m), 7.21-7.35(5H, m)

EXAMPLE AB2

Compound AB42-2: 1-ethyl-2-methylpentyl 3-(4-fluorophenylthio)-N-(phenyl)thioacrylimidate

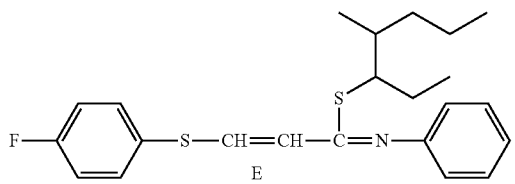 [SMILES: CCCC(C)C(CC)SC(C=CSc1ccc(F)cc1)=Nc1ccccc1]

1-ethyl-2-methylpentyl N-phenylpropynthioimidate (0.44 g) was dissolved to chloroform (8 mL), chloroform (3 mL) solution of 4-fluorothiophenol (0.16 g) was added to the solution under ice-cooling, and then it was stirred for 18 hours at room temperature. The reaction mixture was concentrated under reduced pressure. The obtained residue was subjected to medium pressure HPLC (hexane/ethyl acetate=98/2) to obtain 1-ethyl-2-methylpentyl 3-(4-fluorophenylthio)-N-(phenyl)thioacrylimidate (0.28 g) as pale yellow oil.

$^1$H-NMR (CDCl$_3$)δ(ppm): 0.88(3H, t, J=7.0 Hz), 0.93-1.04(6H, m$_3$), 1.14-1.89(7H, m), 3.85-3.98(1H, m), 5.92(1H, d, J=15.4 Hz), 6.66(2H, d, J=7.3 Hz), 6.96-7.03(3H, m), 7.21-7.35(5H, m)

Below mentioned compounds were synthesized in a similar manner as the Example AB2.

Compound AB92-2: 2-indanyl 3-(4-fluorophenylthio)-N-(phenyl)thioacrylimidate

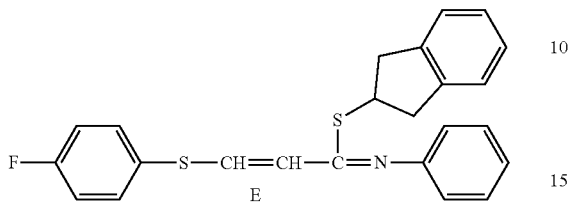

$^1$H-NMR (CDCl$_3$)δ(ppm): 3.01(1H,d,J=5.9 Hz), 3.05(1H, d,J=5.9 Hz), 3.48(1H, d, J=7.8 Hz), 3.52(1H, d, J=7.8 Hz), 4.45-4.51(1H, m), 5.95(1H, d, J=15.6 Hz), 6.73(2H, d, J=7.6 Hz), 6.96(2H, t, J=8.5 Hz), 7.04(1H, t, J=7.3 Hz), 7.14-7.27 (9H, m)

EXAMPLE 3

Compound AB8-2: 4-methylcyclohexyl 3-(4-fluorophenylthio)-N-(phenyl)thioacrylimidate

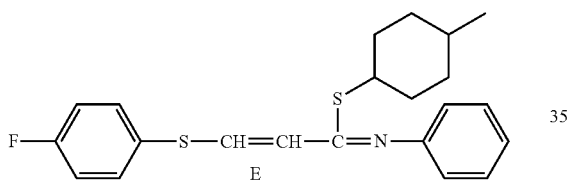

Etynyltrimethylsilane (3.5 mL) was dissolved to dry THF (70 mL), hexane solution of n-butyl lithium (1.58 mol./L; 17 mL) was added to the solution at −78° C. Then the mixtuer was allowed to warm to 0° C. Then, THF (5 mL) solution of phenyl isotiocyanate (3.2 mL) was added to the mixture, and then it was stirred for 20 minutes under ice-cooling. The reaction mixture was allowed to warm to room temperature, and THF was added thereto until total amount being 100 mL.

4-methylcyclohexyl methanesulfonate (1.01 g) and tetramethylethylenediamine (0.5 mL) was added to 20 mL of above solution. Then it was heated under reflux for 8.5 hours. Saturated aqueous solution of ammonium chloride (15 mL) and water (10 mL) was added to the reaction mixture, and then it was extracted with t-butylmethylether (20 mL). The obtained organic layer was washed with saturated aqueous solution of sodium chloride (20 mL), dried over anhydrous magnesium sulfate, and concentrated under reduced pressure to obtain black oil (1.82 g). The oil was subjected to Florisil column chromatography (hexane/ethyl acetate=20/1) to obtain 4-methylcyclohexyl N-phenyl3-(trimethylsilyl)thiopropynimidate (0.67 g).

Obtained 4-methylcyclohexyl N-phenyl 3-(trimethylsilyl) thiopropioimidate was dissolved to methanol (20 mL), and small amount of potassium carbonate was added to the solution at room temperature and it was stirred for 1 hour. After that, 4-fluorothiophenol (0.15 mL) was added to the mixture at room temperature and stirred overnight. The reaction mixture was concentrated under reduced pressure. The obtained residue was subjected to silica gel column chromatography (hexane/ethyl acetate=30/1) to obtain 4-methylcyclohexyl 3-(4-fluorophenylthio)-N-(phenyl)thioacrylimidate (0.30 g).

$^1$H-NMR (CDCl$_3$)δ(ppm): 0.87(1.5H, d J=6.5 Hz), 0.93 (1.5H, d J=6.5 Hz), 1.06-2.16(9H, m), 3.59(0.5H, tt J=12.1, 3.4 Hz), 4.15(0.5H, br t J=3.5 Hz), 5.92(1H, d J=15.5 Hz), 6.69(2H, d J=8.0 Hz), 6.96-7.04(3H, m), 7.22-7.36(5H, m).

Below mentioned compounds were synthesized in a similar manner as the Example AB3.

Compound AB7-2: 3-methylcyclohexyl 3-(4-fluorophenylthio)-N-(phenyl)thioacrylimidate

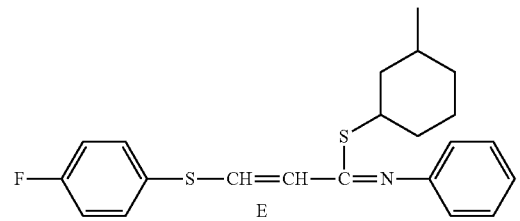 [SMILES: CC1CCCC(SC(C=CSc2ccc(F)cc2)=Nc2ccccc2)C1]

$^1$H-NMR (CDCl$_3$)δ(ppm): 0.87-2.12(12H, m), 3.66(0.2H, br), 4.23(0.8H, br), 5.91(d J=15.5 Hz), 5.93(d J=15.5 Hz) total 1H, 6.69(2H, d J=7.5 Hz), 6.97-7.04(3H, m), 7.22-7.36 (5H, m).

Compound AB6-2: 2-methylcyclohexyl 3-(4-fluorophenylthio)-N-(phenyl)thioacrylimidate

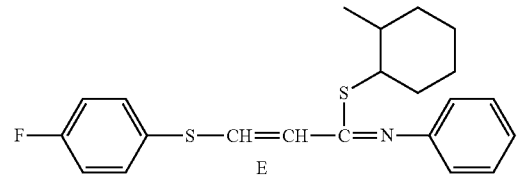 [SMILES: CC1CCCCC1SC(C=CSc1ccc(F)cc1)=Nc1ccccc1]

$^1$H-NMR (CDCl$_3$)δ(ppm): 1.01-1.08(3H, m), 1.27-1.79 (8H, m), 1.90-1.95(1H, m), 3.48-4.23(1H, m), 5.91(1H, d, J=15.4 Hz), 6.66-6.68(2H, m), 6.96-7.03(3H, m), 7.21-7.26 (2H, m), 7.30-7.35(3H, m)

Compound AB9-2: 2,3-dimethylcyclohexyl 3-(4-fluorophenylthio)-N-(phenyl)thioacrylimidate

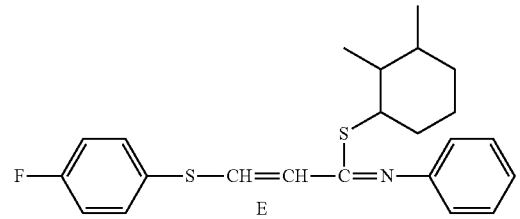 [SMILES: CC1CCCC(SC(C=CSc2ccc(F)cc2)=Nc2ccccc2)C1C]

¹H-NMR (CDCl₃)δ(ppm): 0.88-1.12(7H, m), 1.27-1.69 (6H, m), 2.00(1H, br), 4.28(1H, brs), 5.92(1H, d J=15.5 Hz), 6.67(2H, d J=7.7 Hz), 6.70-7.04(3H, m), 7.22-7.35(5H, m).

Compound AB46-2: 2-methyl-1-propylbutyl 3-(4-fluorophenylthio)-N-(phenyl)thioacrylimidate

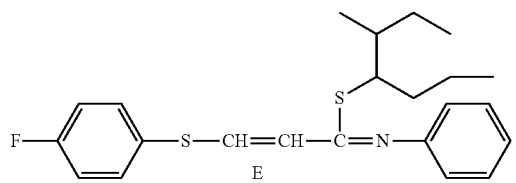 [SMILES: CCCC(SC(C=CSc1ccc(F)cc1)=Nc1ccccc1)C(C)CC]

¹H-NMR (CDCl₃)δ(ppm): 0.87-0.99(9H, m), 1.19-1.76 (7H, m), 3.98(0.6H, brs), 4.09(0.4H, brs), 5.92(d J=15.4 Hz), 5.92(d J=15.4 Hz): あわせて 1H, 6.66(2H, d J=7.8 Hz), 6.97-7.03(3H, m), 7.17-7.36(5H, m).

EXAMPLE AB4

Compound AB84-2: 2-ethyl-1-methylbutyl 3-(4-fluorophenylthio)-N-(phenyl)thioacrylimidate

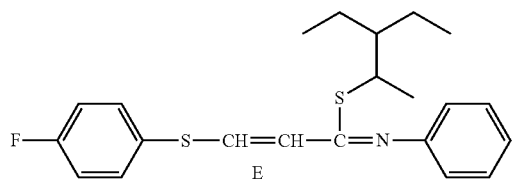 [SMILES: CCC(CC)C(C)SC(C=CSc1ccc(F)cc1)=Nc1ccccc1]

Etynyltrimethylsilane (0.7 mL) was dissolved to dry THF (15 mL), hexane solution of n-butyl lithium (1.58 mol./L; 3.2 mL) was added dropwise to the solution at −78° C., and then the mixture was allowed to warm to 0° C. After that, THF (2 mL) solution of phenyl isotiocyanate (0.61 mL) was added dropwise to the mixture, and then it was stirred for 30 minutes under ice-cooling. THF (1 mL) solution of 2-ethyl-1-methyl-butyl methanesulfonate (1.01 g) was added to the solution and heated under reflux for 6.5 hours. The reaction mixture was concentrated under reduced pressure. The obtained residue was subjected to Florisil column chromatography (hexane/ethyl acetate=20/1) to obtain 2-ethyl-1-methylbutyl N-phenyl-3-(trimethylsilyl)thiopropynimidate (0.74 g).

Obtained 2-ethyl-1-methylbutyl N-phenyl-3-(trimethylsilyl)thiopropynimidate was dissolved to methanol (15 mL), and then small amount of potassium carbonate was added to the solution at room temperature, and then it was stirred for 1 hour. After that, 4-fluorothiophenol (0.19 mL) was added to the mixture at room temperature and stirred for 2.7 hours. The reaction mixture was concentrated under reduced pressure. The obtained residue was subjected to silica gel column chromatography (hexane/ethyl acetate=20/1) and medium pressure HPLC (hexane/ethyl acetate=99/1) to obtain 2-ethyl-1-methylbutyl 3-(4-fluorophenylthio)-N-(phenyl) thioacrylimidate (0.43 g).

¹H-NMR (CDCl₃)δ(ppm): 0.93(6H, t J=7.2 Hz), 1.27-1.51 (8H, m), 4.12(1H, br), 5.93(1H, d J=15.6 Hz), 6.69(2H, d J=7.6 Hz), 6.97-7.04(3H, m), 7.18-7.35(5H, m)

Below mentioned compounds were synthesized in a similar manner as the Example AB4.

Compound AB31-2: 1,2-dimethylpentyl 3-(4-fluorophenylthio)-N-(phenyl)thioacrylimidate

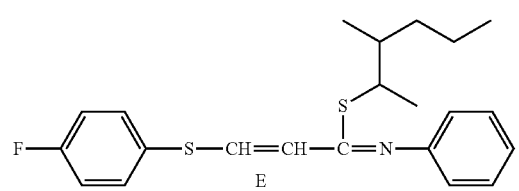

¹H-NMR (CDCl₃)δ(ppm): 0.89(3H, t J=6.8 Hz), 0.97(3H, t J=6.8 Hz), 1.18-1.41(7H,m), 1.78-1.86(1H,m), 3.91-4.01 (1H,m), 5.92(1H, dJ=15.5 Hz), 6.69(2H,dJ=9.0 Hz), 6.97-7.04(3H,m), 7.14-7.35(5H, m).

Compound AB45-2: 3-methyl-1-propylbutyl 3-(4-fluorophenylthio)-N-(phenyl)thioacrylimidate

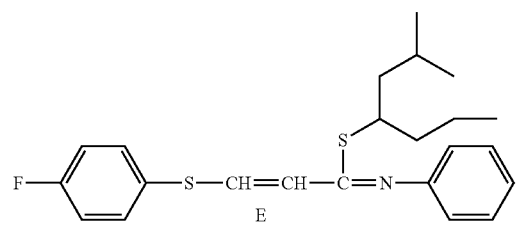 [SMILES: CCCC(CC(C)C)SC(C=CSc1ccc(F)cc1)=Nc1ccccc1]

¹H-NMR (CDCl₃)δ(ppm): 0.86-0.92(9H, m), 1.26-1.31 (2H, m), 1.40-1.66(5H,m), 1.79-1.85(1H,m), 3.95-4.02(1H, m), 5.93(1H, d,J=15.2 Hz), 6.66-6.68(2H,m), 6.93-7.02(3H, m), 7.20-7.25(2H, m), 7.29-7.32(2H, m)

Other examples of the compound (I) which can be produced in a similar manner as described above will be shown with the compound number.

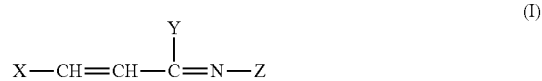

wherein X, Y and Z are any one of the combinations of the substituents shown in Table 1.

TABLE 1

| Compound Number | X | Y | Z | Stereochemistry of the —CH═CH— bond |
|---|---|---|---|---|
| 212 | *—S—(2-F-C6H4) | *—S—CH2—C6H5 | *—C6H5 | Z |
| 214 | *—S—(3-F-C6H4) | *—S—CH2—C6H5 | *—C6H5 | Z |
| 216 | *—S—(2-Cl-C6H4) | *—S—CH2—C6H5 | *—C6H5 | Z |
| 218 | *—S—(3-Cl-C6H4) | *—S—CH2—C6H5 | *—C6H5 | Z |
| 220 | *—S—(4-Cl-C6H4) | *—S—CH2—C6H5 | *—C6H5 | Z |
| 222 | *—S—(3-Br-C6H4) | *—S—CH2—C6H5 | *—C6H5 | Z |
| 224 | *—S—(4-Br-C6H4) | *—S—CH2—C6H5 | *—C6H5 | Z |
| 227 | *—S—(2-Me-C6H4) | *—S—CH2—C6H5 | *—C6H5 | Z |
| 229 | *—S—(4-Me-C6H4) | *—S—CH2—C6H5 | *—C6H5 | Z |
| 231 | *—S—(4-CF3-C6H4) | *—S—CH2—C6H5 | *—C6H5 | Z |
| 233 | *—S—(3-OMe-C6H4) | *—S—CH2—C6H5 | *—C6H5 | Z |
| 236 | *—S—CH2—(4-F-C6H4) | *—S—CH2—C6H5 | *—C6H5 | Z |

TABLE 1-continued

| Compound Number | X | Y | Z | Stereochemistry of the —CH=CH— bond |
|---|---|---|---|---|
| 238 | *—S—CH₂—C₆H₄—Me (4-Me) | *—S—CH₂—C₆H₅ | *—C₆H₅ | Z |
| 240 | *—S—CH₂—C₆H₄—Cl (4-Cl) | *—S—CH₂—C₆H₅ | *—C₆H₅ | Z |
| 242 | *—S—CH₂—C₆H₃—(2,4-Cl₂) | *—S—CH₂—C₆H₅ | *—C₆H₅ | Z |
| 244 | *—S—CH₂—C₆H₄—Me (2-Me) | *—S—CH₂—C₆H₅ | *—C₆H₅ | Z |
| 246 | *—S—CH₂—C₆H₄—OMe (4-OMe) | *—S—CH₂—C₆H₅ | *—C₆H₅ | Z |
| 247 | *—S—C₆H₄—OMe (4-OMe) | *—S—CH₂—C₆H₅ | *—C₆H₅ | Z |
| 249 | *—S—C₆H₃—(2,4-Cl₂) | *—S—CH₂—C₆H₅ | *—C₆H₅ | Z |
| 251 | *—S—C₆H₃—(3,5-Cl₂) | *—S—CH₂—C₆H₅ | *—C₆H₅ | Z |
| 253 | *—S—C₆H₃—(2,4-Me₂) | *—S—CH₂—C₆H₅ | *—C₆H₅ | Z |
| 255 | *—S—(2-pyridyl) | *—S—CH₂—C₆H₅ | *—C₆H₅ | Z |
| 257 | *—S—CH₂—C₆H₅ | *—S—CH₂—C₆H₅ | *—C₆H₅ | Z |

TABLE 1-continued

| Compound Number | X | Y | Z | Stereochemistry of the —CH=CH— bond |
|---|---|---|---|---|
| 342 | *—S-(2-F-C6H4) | *—S-CH2-cyclohexyl | *—C6H4-Me (para) | Z |
| 344 | *—S-(3-F-C6H4) | *—S-CH2-cyclohexyl | *—C6H4-Me (para) | Z |
| 346 | *—S-(2-Cl-C6H4) | *—S-CH2-cyclohexyl | *—C6H4-Me (para) | Z |
| 348 | *—S-(3-Cl-C6H4) | *—S-CH2-cyclohexyl | *—C6H4-Me (para) | Z |
| 350 | *—S-(4-Cl-C6H4) | *—S-CH2-cyclohexyl | *—C6H4-Me (para) | Z |
| 352 | *—S-(3-Br-C6H4) | *—S-CH2-cyclohexyl | *—C6H4-Me (para) | Z |
| 355 | *—S-(4-NO2-C6H4) | *—S-CH2-cyclohexyl | *—C6H4-Me (para) | Z |
| 358 | *—S-(4-Me-C6H4) | *—S-CH2-cyclohexyl | *—C6H4-Me (para) | Z |
| 360 | *—S-(4-CF3-C6H4) | *—S-CH2-cyclohexyl | *—C6H4-Me (para) | Z |
| 362 | *—S-(3-OMe-C6H4) | *—S-CH2-cyclohexyl | *—C6H4-Me (para) | Z |
| 364 | *—S-(4-OMe-C6H4) | *—S-CH2-cyclohexyl | *—C6H4-Me (para) | Z |
| 369 | *—S-(2-pyridyl) | *—S-CH2-cyclohexyl | *—C6H4-Me (para) | Z |

TABLE 1-continued
| Compound Number | X | Y | Z | Stereochemistry of the —CH=CH— bond |
|---|---|---|---|---|
| 372 | 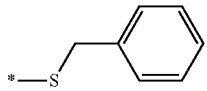 | 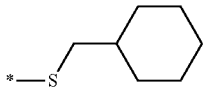 [SMILES: *SCC1CCCCC1] | 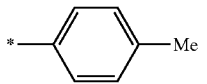 [SMILES: *c1ccc(C)cc1] | Z |
| 374 | 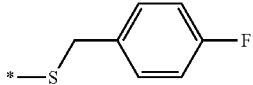 | 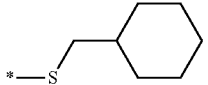 | 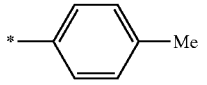 [SMILES: *c1ccc(C)cc1] | Z |
| 376 | 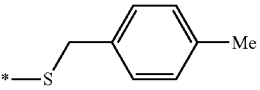 [SMILES: *SCc1ccc(C)cc1] | 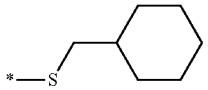 [SMILES: *SCC1CCCCC1] | 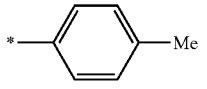 | Z |
| 378 | 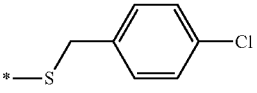 | 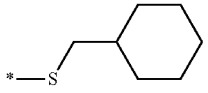 [SMILES: *SCC1CCCCC1] | 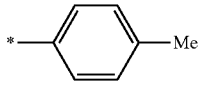 | Z |
| 380 | 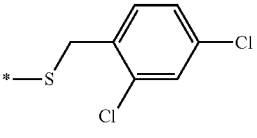 [SMILES: *SCc1ccc(Cl)cc1Cl] | 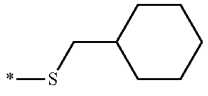 [SMILES: *SCC1CCCCC1] | 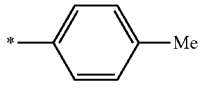 | Z |
| 382 | 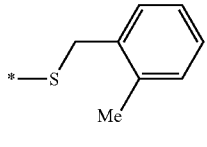 [SMILES: *SCc1ccccc1C] | 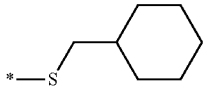 | 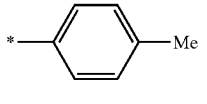 [SMILES: *c1ccc(C)cc1] | Z |
| 384 | 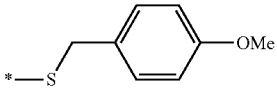 [SMILES: *SCc1ccc(OC)cc1] | 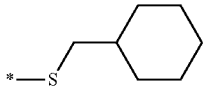 [SMILES: *SCC1CCCCC1] | 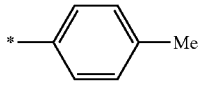 [SMILES: *c1ccc(C)cc1] | Z |
| 395 | 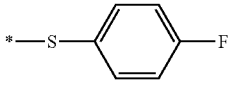 [SMILES: *Sc1ccc(F)cc1] | 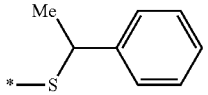 | 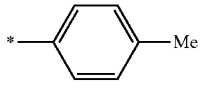 [SMILES: *c1ccc(C)cc1] | Z |
| 399 | 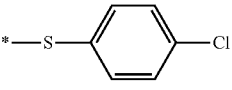 [SMILES: *Sc1ccc(Cl)cc1] | 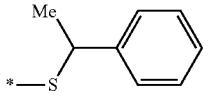 [SMILES: *SC(C)c1ccccc1] | 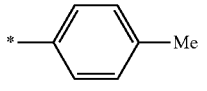 [SMILES: *c1ccc(C)cc1] | Z |
| 401 | 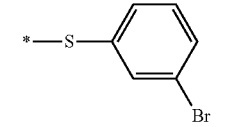 [SMILES: *Sc1cccc(Br)c1] | 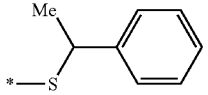 | 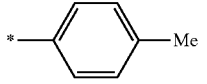 [SMILES: *c1ccc(C)cc1] | Z |
| 403 | 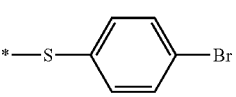 | 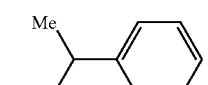 | 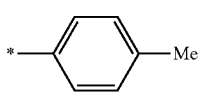 | Z |
| 406 | 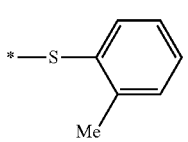 | 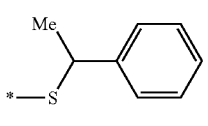 | 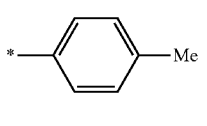 [SMILES: *c1ccc(C)cc1] | Z |

TABLE 1-continued

| Compound Number | X | Y | Z | Stereochemistry of the —CH=CH— bond |
|---|---|---|---|---|
| 414 | *—S-(3,5-dichlorophenyl) | *—S—CH(Me)-phenyl | *-(4-methylphenyl) | Z |
| 417 | *—S-(pyridin-2-yl) | *—S—CH(Me)-phenyl | *-(4-methylphenyl) | Z |
| 430 | *—S-(3-fluorophenyl) | *—S—CH2—CH(Me)2 | *-(4-methylphenyl) | Z |
| 436 | *—S-(4-chlorophenyl) | *—S—CH2—CH(Me)2 | *-(4-methylphenyl) | Z |
| 439 | *—S-(4-bromophenyl) | *—S—CH2—CH(Me)2 | *-(4-methylphenyl) | Z |
| 442 | *—S-(2-methylphenyl) | *—S—CH2—CH(Me)2 | *-(4-methylphenyl) | Z |
| 445 | *—S-(4-trifluoromethylphenyl) | *—S—CH2—CH(Me)2 | *-(4-methylphenyl) | Z |
| 453 | *—S-(pyridin-2-yl) | *—S—CH2—CH(Me)2 | *-(4-methylphenyl) | Z |
| 455 | *—S-(pyrimidin-2-yl) | *—S—CH2—CH(Me)2 | *-(4-methylphenyl) | Z |
| 457 | *—S—CH2-phenyl | *—S—CH2—CH(Me)2 | *-(4-methylphenyl) | Z |
| 459 | *—S—CH2-(4-fluorophenyl) | *—S—CH2—CH(Me)2 | *-(4-methylphenyl) | Z |
| 461 | *—S—CH2-(4-methylphenyl) | *—S—CH2—CH(Me)2 | *-(4-methylphenyl) | Z |

TABLE 1-continued
| Compound Number | X | Y | Z | Stereochemistry of the —CH=CH— bond |
|---|---|---|---|---|
| 463 | 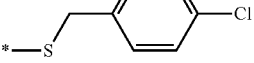 | 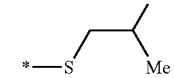 | 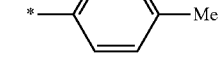 | Z |
| 465 | 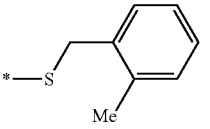 [SMILES: *SCc1ccccc1C] | 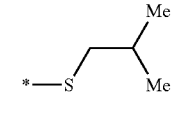 | 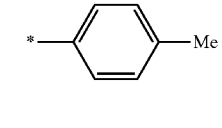 [SMILES: *c1ccc(C)cc1] | Z |
| 514 | 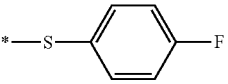 [SMILES: *Sc1ccc(F)cc1] | 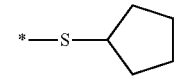 | 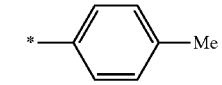 | |
| 515 | 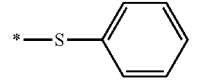 | 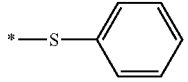 | 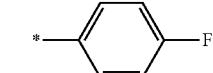 | |
| 516 | 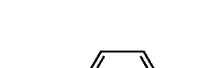 | *—S—C$_6$H$_{13}$ | 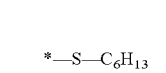 | |
| 517 | 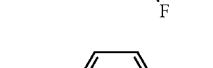 | 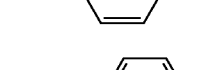 |  | |
| 518 | 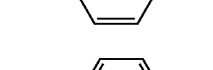 | 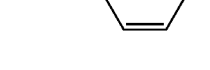 |  | |
| 519 | 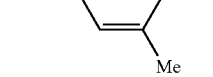 | 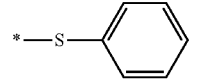 [SMILES: *Sc1ccccc1] | 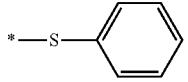 | |
| 520 | 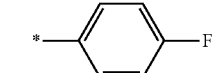 | 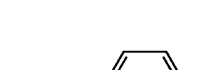 |  | |
| 521 | 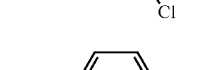 | 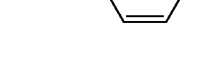 |  | |
| 522 | 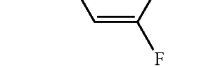 | 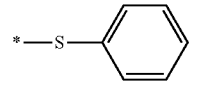 | 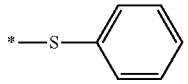 | |

TABLE 1-continued
| Compound Number | X | Y | Z | Stereochemistry of the —CH=CH— bond |
|---|---|---|---|---|
| 523 | 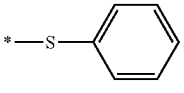 [SMILES: *Sc1ccccc1] | 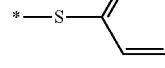 | 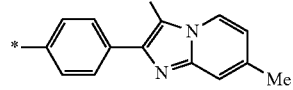 | |
| 524 | 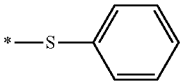 | 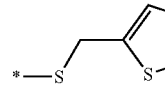 | 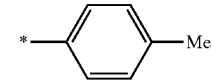 | |
| 525 | 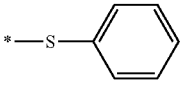 [SMILES: *Sc1ccccc1] | 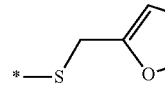 | 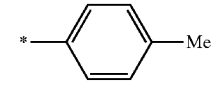 [SMILES: *c1ccc(C)cc1] | |
| 526 | 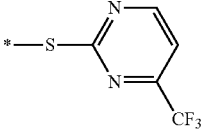 | 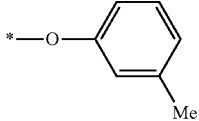 [SMILES: *Oc1cccc(C)c1] | 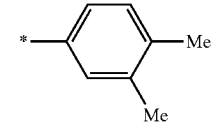 [SMILES: *c1ccc(C)c(C)c1] | |
| 527 | 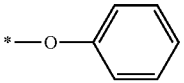 [SMILES: *Oc1ccccc1] | 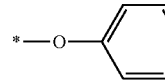 | 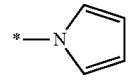 | |
| 528 | 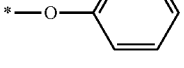 | 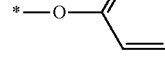 | 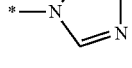 | |
| 529 | 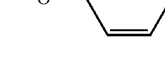 | 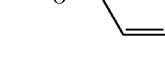 | 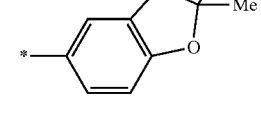 | |
| 530 | 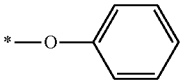 | 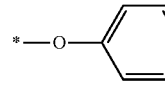 | 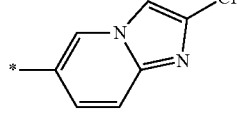 | |
| 531 | 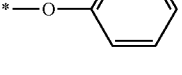 | 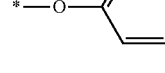 | 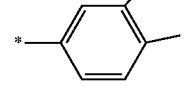 | |
| 532 | 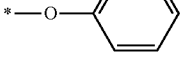 | 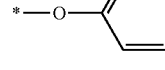 | 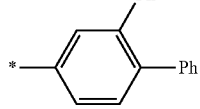 | |
| 533 | 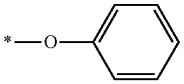 [SMILES: *Oc1ccccc1] | 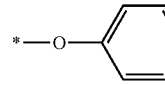 | 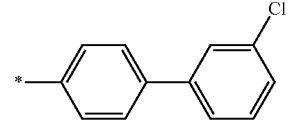 [SMILES: *c1ccc(-c2cccc(Cl)c2)cc1] | |
| 534 | 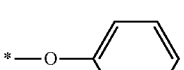 | 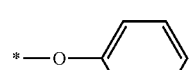 | 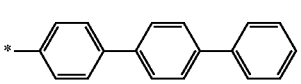 [SMILES: *c1ccc(-c2ccc(-c3ccccc3)cc2)cc1] | |

TABLE 1-continued

| Compound Number | X | Y | Z | Stereochemistry of the —CH=CH— bond |
|---|---|---|---|---|
| 535 | *—S—Ph | *—S—CH₂CH₂—OPh | *—C₆H₄—Me | |
| 536 | *—S—Ph | *—S—CH₂CH₂—OEt | *—C₆H₄—Me | |
| 537 | *—S—Ph | *—S—CH₂—CN | *—C₆H₄—Me | |
| 538 | *—S—Ph | *—S—CH₂—CO₂Bu | *—C₆H₄—Me | |
| 539 | *—S—Ph | *—S—CH₂CH₂—Cl | *—C₆H₄—Me | |
| 540 | *—S—Ph | *—S—CH₂CH₂—SMe | *—C₆H₄—Me | |
| 541 | *—S—Ph | *—S—CH₂CH₂—SPh | *—C₆H₄—Me | |
| 542 | *—S—Ph | *—S—CH₂—CH=CH—Ph | *—C₆H₄—Me | |
| 543 | *—S—Ph | *—S—CH₂—CH(CH₂Me)(Me) | *—C₆H₄—Me | |
| 544 | *—S—Ph | *—S—geranyl | *—C₆H₄—Me | |
| 545 | *—S—Ph | *—S—citronellyl | *—C₆H₄—Me | |
| 546 | *—S—Ph | *—S—CH(Me)CH₂CH(Me)₂ | *—C₆H₄—Me | |
| 547 | *—S—Ph | *—S—CH₂CH(Me)CH₂Me | *—C₆H₄—Me | |
| 548 | *—O—Ph | *—O—Ph | *—C₆H₄—(oxazol-2-yl) | |

TABLE 1-continued

| Compound Number | X | Y | Z | Stereochemistry of the —CH=CH— bond |
|---|---|---|---|---|
| 549 | *—O—C₆H₅ | *—O—C₆H₅ | *—(C₆H₄)—thiazole | |
| 550 | *—O—C₆H₅ | *—O—C₆H₅ | *—(C₆H₄)—(5-Me-1,3,4-oxadiazol-2-yl) | |
| 551 | *—O—C₆H₅ | *—O—C₆H₅ | *—(C₆H₄)—(5-Me-1,3,4-thiadiazol-2-yl) | |
| 552 | *—O—C₆H₅ | *—O—C₆H₅ | *—(2-Ph-thiazol-5-yl) | |
| 553 | *—O—C₆H₅ | *—O—C₆H₅ | *—(2-Ph-oxazol-5-yl) | |
| 554 | *—S—C₆H₅ | *—S—CH₂CH₂CH(Me)₂ | *—C₆H₄—Me | |
| 555 | *—S—C₆H₅ | *—S—CH₂CH₂CH₂CH(Me)₂ | *—C₆H₄—Me | |
| 556 | *—S—C₆H₅ | *—S—CH₂C(Me)=CH₂ | *—C₆H₄—Me | |
| 557 | *—S—C₆H₅ | *—S—C₆H₁₃ | *—C₆H₄—Me | |
| 558 | *—S—C₆H₅ | *—S—C₁₀H₂₁ | *—C₆H₄—Me | |
| 559 | *—S—(benzoxazol-2-yl) | *—S—(benzoxazol-2-yl) | *—C₆H₄—Me | |
| 560 | *—S—(4,5-diMe-thiazol-2-yl) | *—S—(4,5-diMe-thiazol-2-yl) | *—C₆H₄—Me | |
| 561 | *—S—(5-Me-1,3,4-thiadiazol-2-yl) | *—S—(5-Me-1,3,4-thiadiazol-2-yl) | *—C₆H₄—Me | |

TABLE 1-continued

| Compound Number | X | Y | Z | Stereochemistry of the —CH=CH— bond |
|---|---|---|---|---|
| 562 | *—S-[1,3,4-thiadiazol-2-yl-5-Me] | *—S-[1,3,4-thiadiazol-2-yl-5-Me] | *-[thien-3-yl] | |
| 563 | *—S-[benzothiazol-2-yl] | *—S-[benzothiazol-2-yl] | *-[quinolin-6-yl] | |
| 564 | *—S-Ph | *—S—CH$_2$—C≡C—Me | *-[4-Me-phenyl] | |
| 565 | *—S-Ph | *—O-[3-Me-phenyl] | *-[3,4-diF-phenyl] | |
| 566 | *—S-Ph | *—O-[3-Me-phenyl] | *-[4-F-3-Me-phenyl] | |
| 567 | *—S-Ph | *—O-[3-Me-phenyl] | *-[3-Cl-4-F-phenyl] | |
| 568 | *—S-Ph | *—O-[3-Me-phenyl] | *-[3-F-4-Me-phenyl] | |
| 569 | *—S-Ph | *—O-[3-Me-phenyl] | *-[3-Cl-4-Me-phenyl] | |
| 570 | *—S-[pyridin-2-yl] | *—O-[5-Me-pyridin-3-yl] | *-[quinolin-3-yl] | |
| 571 | *—S-[pyridin-2-yl] | *—O-[3-Me-phenyl] | *-[anthracen-2-yl] | |
| 572 | *—S-Ph | *—O-[3-Me-phenyl] | *-[4-(3-Cl-7-Me-imidazo[1,2-a]pyridin-2-yl)phenyl] | |

TABLE 1-continued

| Compound Number | X | Y | Z | Stereochemistry of the —CH=CH— bond |
|---|---|---|---|---|
| 573 | *—S-CH2-(2-thienyl) | *—S-CH2-(2-thienyl) | *—C6H4—Me (para) | |
| 574 | *—S-CH2-(2-furyl) | *—S-CH2-(2-furyl) | *—C6H4—Me (para) | |
| 575 | *—S—C6H4—F (para) | *—S-CH2CH2-OPh | *—C6H4—Me (para) | |
| 576 | *—S—C6H4—F (para) | *—S-CH2CH2-OEt | *—C6H4—Me (para) | |
| 577 | *—S—C6H4—F (para) | *—S-CH2-CN | *—C6H4—Me (para) | |
| 578 | *—S—C6H4—Me (para) | *—S-CH2-CO2Bu | *—C6H4—Me (para) | |
| 579 | *—S—C6H4—F (para) | *—S-CH2CH2-Cl | *—C6H4—Me (para) | |
| 580 | *—S—C6H4—F (para) | *—S-CH2CH2-SMe | *—C6H4—Me (para) | |
| 581 | *—S—C6H4—F (para) | *—S-CH2CH2-SPh | *—C6H4—Me (para) | |
| 582 | *—S—C6H4—Me (para) | *—S-CH2-CH=CH-Ph | *—C6H4—Me (para) | |
| 583 | *—S—C6H4—F (para) | *—S-CH2-CH(CH2Me)(Me) | *—C6H4—Me (para) | |
| 584 | *—S—C6H4—Me (para) | *—S-CH2CH2-C(Me)=CH-CH2CH2-CH=C(Me)2 | *—C6H4—Me (para) | |
| 585 | *—S—C6H4—F (para) | *—S-CH2CH2-CH(Me)-CH2CH2-CH=C(Me)2 | *—C6H4—Me (para) | |
| 586 | *—S—C6H4—Me (para) | *—S-CH(Me)-CH2-CH(Me)-Me | *—C6H4—Me (para) | |

TABLE 1-continued
| Compound Number | X | Y | Z | Stereochemistry of the —CH=CH— bond |
|---|---|---|---|---|
| 587 | 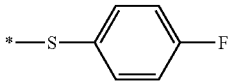 | 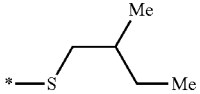 | 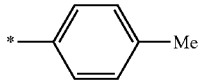 [SMILES: *c1ccc(C)cc1] | |
| 588 | 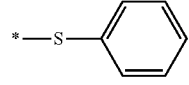 [SMILES: *Sc1ccccc1] | 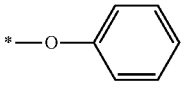 | 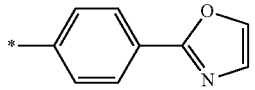 | |
| 589 | 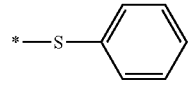 [SMILES: *Sc1ccccc1] | 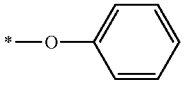 [SMILES: *Oc1ccccc1] | 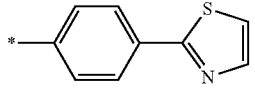 [SMILES: *c1ccc(-c2nccs2)cc1] | |
| 590 | 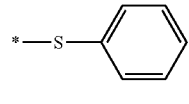 [SMILES: *Sc1ccccc1] | 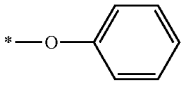 | 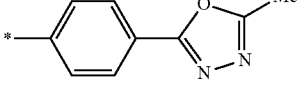 | |
| 591 | 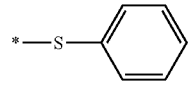 | 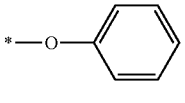 | 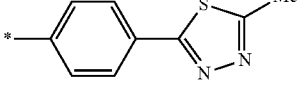 | |
| 592 | 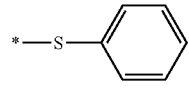 | 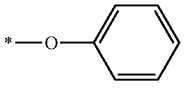 | 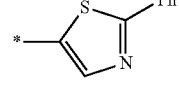 | |
| 593 | 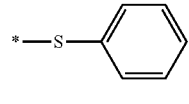 [SMILES: *Sc1ccccc1] | 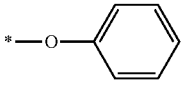 | 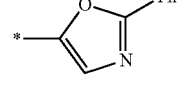 | |
| 594 | 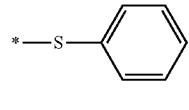 [SMILES: *Sc1ccccc1] | 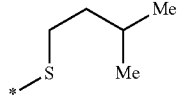 | 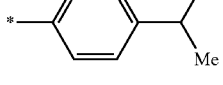 | |
| 595 | 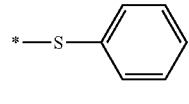 [SMILES: *Sc1ccccc1] | 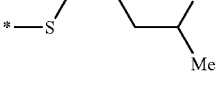 | 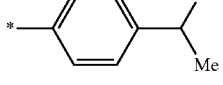 | |
| 596 | 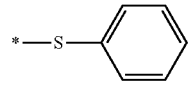 | 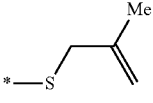 [SMILES: *SCC(=C)C] | 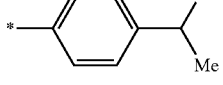 | |
| 597 | 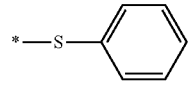 [SMILES: *Sc1ccccc1] | *—S—C$_6$H$_{13}$ | 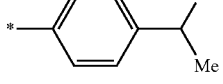 | |

Other specific examples of the compound (AAI) will be shown below.

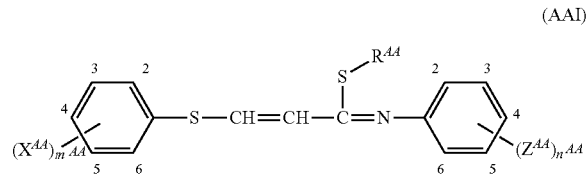

(AAI)

Compounds AA1-1 to AA1-5352 wherein $R^{AA}$ represents a cyclopropylmethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA1-2 to AA2-5352 wherein $R^{AA}$ represents a 1-cyclopropylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA1-3 to AA3-5352 wherein $R^{AA}$ represents a 1-cyclopropylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA1-4 to AA4-5352 wherein $R^{AA}$ represents a cyclobutylmethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA1-5 to AA5-5352 wherein $R^{AA}$ represents a 1-cyclobutylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA6-1 to AA6-5352 wherein $R^{AA}$ represents a 1-cyclobutylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA1-7 to AA7-5352 wherein $R^{AA}$ represents a cyclopentylmethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA8-1 to AA8-5352 wherein $R^{AA}$ represents a 1-cyclopentylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA9-1 to AA9-5352 wherein $R^{AA}$ represents a 1-cyclopentylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA10-1 to AA10-5352 wherein $R^{AA}$ represents a cyclohexylmethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA11-1 to AA11-5352 wherein $R^{AA}$ represents a 1-cyclohexylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA12-1 to AA12-5352 wherein $R^{AA}$ represents a 1-cyclohexylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA13-1 to AA13-5352 wherein $R^{AA}$ represents a 2-cyclopropylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA14-1 to AA14-5352 wherein $R^{AA}$ represents a 2-cyclopropylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA15-1 to AA15-5352 wherein $R^{AA}$ represents a 2-cyclopropyl 1-methylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA16-1 to AA16-5352 wherein $R^{AA}$ represents a 3-cyclopropylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA17-1 to AA17-5352 wherein $R^{AA}$ represents a 2-cyclobutylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA18-1 to AA18-5352 wherein $R^{AA}$ represents a 2-cyclobutylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA19-1 to AA19-5352 wherein $R^{AA}$ represents a 2-cyclobutyl 1-methylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA20-1 to AA20-5352 wherein $R^{AA}$ represents a 3-cyclobutylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA21-1 to AA21-5352 wherein $R^{AA}$ represents a 2-cyclopentylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA22-1 to AA22-5352 wherein $R^{AA}$ represents a 2-cyclopentylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA23-1 to AA23-5352 wherein $R^{AA}$ represents a 2-cyclopentyl 1-methylethyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA24-1 to AA24-5352 wherein $R^{AA}$ represents a 3-cyclopentylpropyl group, and $(X^{AA})_m{}^{AA}$, $(Z^{AA})_n{}^{AA}$ and geometric isomer of CH=CH corresponds to compound branch numbers −1 to −5352 among the following "combinations G".

Compounds AA25-1 to AA25-5352 wherein $R^{AA}$ represents a 2-cyclohexylethyl group, and $(X)_m{}^{AA}$, $(Z^{AA})_n{}^{AA}$ and geometric isomer of CH═CH corresponds to compound branch numbers −1 to −5352 among the following "combinations G".

Compounds AA26-1 to AA26-5352 wherein $R^{AA}$ represents a 2-cyclohexylpropyl group, and $(X^{AA})_m^{AA}$, $(Z^{AA})_n^{AA}$ and geometric isomer of CH═CH corresponds to compound branch numbers −1 to −5352 among the following "combinations G".

Compounds AA27-1 to AA27-5352 wherein $R^{AA}$ represents a 2-cyclohexyl1-methylethyl group, and $(X^{AA})_m^{AA}$, $(Z^{AA})_n^{AA}$ and geometric isomer of CH═CH corresponds to compound branch numbers −1 to −5352 among the following "combinations G".

Compounds AA28-1 to AA28-5352 wherein $R^{AA}$ represents a 3-cyclohexylpropyl group, and $(X^{AA})_m^{AA}$, $(Z^{AA})_n^{AA}$ and geometric isomer of CH═CH corresponds to compound branch numbers −1 to −5352 among the following "combinations G".

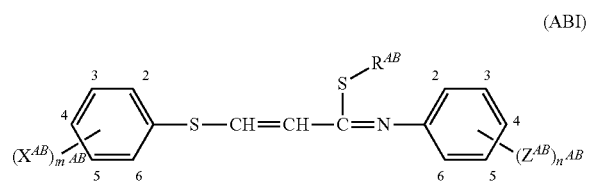

(ABI)

Compounds AB1-1 to AB1-6690 wherein $R^{AB}$ represents a 2-methylcyclopropyl group, and $(X^{AB})_m^{AB}$, $(Z^{AB})_n^{AB}$ and geometric isomer of CH═CH corresponds to compound branch numbers −1 to −6690 among the following "combinations G".

Compounds AB2-1 to AB2-6690 wherein $R^{AB}$ represents a 2-methylcyclobutyl group, and $(X^{AB})_m^{AB}$, $(Z^{AB})_n^{AB}$ and geometric isomer of CH═CH corresponds to compound branch numbers −1 to −6690 among the following "combinations G".

Compounds AB3-1 to AB3-6690 wherein $R^{AB}$ represents a 2-methylcyclopentyl group, and $(X^{AB})_m^{AB}$, $(Z^{AB})_n^{AB}$ and geometric isomer of CH═CH corresponds to compound branch numbers −1 to −6690 among the following "combinations G".

Compounds AB4-1 to AB4-6690 wherein $R^{AB}$ represents a 3-methylcyclopentyl group, and $(X^{AB})_m^{AB}$, $(Z^{AB})_n^{AB}$ and geometric isomer of CH═CH corresponds to compound branch numbers −1 to −6690 among the following "combinations G".

Compounds AB5-1 to AB5-6690 wherein $R^{AB}$ represents a 1-methylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB6-1 to AB6-6690 wherein $R^{AB}$ represents a 2-methylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB7-1 to AB7-6690 wherein $R^{AB}$ represents a 3-methylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB8-1 to AB8-6690 wherein $R^{AB}$ represents a 4-methylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB9-1 to AB9-6690 wherein RB represents a 2,3-dimethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB10-1 to AB10-6690 wherein $R^{AB}$ represents a 2,4-dimethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB11-1 to AB11-6690 wherein $R^{AB}$ represents a 2,5-dimethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB12-1 to AB12-6690 wherein $R^{AB}$ represents a 3,5-dimethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB13-1 to AB13-6690 wherein $R^{AB}$ represents a 3,3-dimethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB14-1 to AB14-6690 wherein $R^{AB}$ represents a 4,4-dimethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB15-1 to AB15-6690 wherein $R^{AB}$ represents a 4-ethylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB16-1 to AB16-6690 wherein $R^{AB}$ represents a 4-isopropylcyclohexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB17-1 to AB17-6690 wherein $R^{AB}$ represents a 1-methylhexyl group, and $(X^{AB})_m^{AB}$, $(Z^{AB})_n^{AB}$ and geometric isomer of CH═CH corresponds to compound branch numbers −1 to −6690 among the following "combinations G".

Compounds AB18-1 to AB18-6690 wherein $R^{AB}$ represents a 1-ethylpentyl group, and $(X^{AB})_m^{AB}$, $(Z^{AB})_n^{AB}$ and geometric isomer of CH═CH corresponds to compound branch numbers −1 to −6690 among the following "combinations G".

Compounds AB19-1 to AB19-6690 wherein $R^{AB}$ represents a 1-propylbutyl group, and $(X^{AB})_m^{AB}$, $(Z^{AB})_n^{AB}$ and geometric isomer of CH═CH corresponds to compound branch numbers −1 to −6690 among the following "combinations G".

Compounds AB20-1 to AB20-6690 wherein $R^{AB}$ represents a 1-methylheptyl group, and $(X^{AB})_m^{AB}$, $(Z^{AB})_n^{AB}$ and geometric isomer of CH═CH corresponds to compound branch numbers −1 to −6690 among the following "combinations G".

Compounds AB21-1 to AB21-6690 wherein $R^{AB}$ represents a 1-ethylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB22-1 to AB22-6690 wherein $R^{AB}$ represents a 1-propylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB23-1 to AB23-6690 wherein $R^{AB}$ represents a 1-methyloctyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB24-1 to AB24-6690 wherein $R^{AB}$ represents a 1-ethylheptyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB25-1 to AB25-6690 wherein $R^{AB}$ represents a 1-propylhexyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB26-1 to AB26-6690 wherein $R^{AB}$ represents a 1-butylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB27-1 to AB27-6690 wherein $R^{AB}$ represents a 1-methylnonyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB28-1 to AB28-6690 wherein $R^{AB}$ represents a 1-ethyloctyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB29-1 to AB29-6690 wherein $R^{AB}$ represents a 1-propylheptyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB30-1 to AB30-6690 wherein $R^{AB}$ represents a 1-butylhexyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB31-1 to AB31-6690 wherein $R^{AB}$ represents a 1,2-dimethylpentyl group, and $(X)_m{}^{AB}$, $(Z^{AB})_n{}^{AB}$ and geometric isomer of CH=CH corresponds to compound branch numbers −1 to −6690 among the following "combinations G".

Compounds AB32-1 to AB32-6690 wherein $R^{AB}$ represents a 1,3-dimethylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB33-1 to AB33-6690 wherein $R^{AB}$ represents a 1,4-dimethylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB34-1 to AB34-6690 wherein $R^{AB}$ represents a 1-(methylethyl)butyl group, and $(X^{AB})_m{}^{AB}$, $(Z^{AB})_m{}^{AB}$ and geometric isomer of CH=CH corresponds to compound branch numbers −1 to −6690 among the following "combinations G".

Compounds AB35-1 to AB35-6690 wherein $R^{AB}$ represents a 1-ethyl 2-methylbutyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB36-1 to AB36-6690 wherein $R^{AB}$ represents a 1-ethyl 3-methylbutyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB37-1 to AB37-6690 wherein $R^{AB}$ represents a 1,2-dimethylhexyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB38-1 to AB38-6690 wherein $R^{AB}$ represents a 1,3-dimethylhexyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB39-1 to AB39-6690 wherein $R^{AB}$ represents a 1,4-dimethylhexyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB40-1 to AB40-6690 wherein $R^{AB}$ represents a 1,5-dimethylhexyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB41-1 to AB41-6690 wherein $R^{AB}$ represents a 1-(methylethyl)pentyl group, and $(X^{AB})_m AB$, $(Z^{AB})_n{}^{AB}$ and geometric isomer of CH=CH corresponds to compound branch numbers −1 to −6690 among the following "combinations G".

Compounds AB42-1 to AB42-6690 wherein $R^{AB}$ represents a 1-ethyl 2-methylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB43-1 to AB43-6690 wherein $R^{AB}$ represents a 1-ethyl 3-methylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB44-1 to AB44-6690 wherein $R^{AB}$ represents a 1-ethyl 4-methylpentyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB45-1 to AB45-6690 wherein $R^{AB}$ represents a 3-methyl 1-propylbutyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB46-1 to AB46-6690 wherein $R^{AB}$ represents a 2-methyl 1-propylbutyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB47-1 to AB47-6690 wherein $R^{AB}$ represents a 1,2-dimethylheptyl group, and $(X^{AB})_m{}^{AB}$, $(Z^{AB})_n{}^{AB}$ and geometric isomer of CH=CH corresponds to compound branch numbers −1 to −6690 among the following "combinations G".

Compounds AB48-1 to AB48-6690 wherein $R^{AB}$ represents a 1,3-dimethylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB49-1 to AB49-6690 wherein $R^{AB}$ represents a 1,4-dimethylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB50-1 to AB50-6690 wherein $R^{AB}$ represents a 1,5-dimethylheptyl group, and $(X)_m^{AB}$, $(Z^{AB})_n^{AB}$ and geometric isomer of CH=CH corresponds to compound branch numbers −1 to −6690 among the following "combinations G".

Compounds AB51-1 to AB51-6690 wherein $R^{AB}$ represents a 1,6-dimethylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB52-1 to AB52-6690 wherein $R^{AB}$ represents a 1-(methylethyl)hexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB53-1 to AB53-6690 wherein $R^{AB}$ represents a 1-ethyl 1-methylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB54-1 to AB54-6690 wherein $R^{AB}$ represents a 1-ethyl 2-methylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB55-1 to AB55-6690 wherein $R^{AB}$ represents a 1-ethyl 3-methylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB56-1 to AB56-6690 wherein $R^{AB}$ represents a 1-ethyl 4-methylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB57-1 to AB57-6690 wherein $R^{AB}$ represents a 1-ethyl 5-methylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB58-1 to AB58-6690 wherein $R^{AB}$ represents a 1-(2-methylpropyl)pentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB59-1 to AB59-6690 wherein $R^{AB}$ represents a 1-(1-methylpropyl)pentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB60-1 to AB60-6690 wherein $R^{AB}$ represents a 2-methyl 1-propylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB61-1 to AB71-6690 wherein $R^{AB}$ represents a 3-methyl 1-propylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB62-1 to AB72-6690 wherein $R^{AB}$ represents a 4-methyl 1-propylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB63-1 to AB73-6690 wherein $R^{AB}$ represents a 1,2-dimethyloctyl group, and $(X^{AB})_m^{AB}$, $(Z^{AB})_n^{AB}$ and geometric isomer of CH=CH corresponds to compound branch numbers −1 to −6690 among the following "combinations G".

Compounds AB64-1 to AB74-6690 wherein $R^{AB}$ represents a 1,3-dimethyloctyl group, and $(X^{AB})_m^{AB}$, $(Z^{AB})_n^{AB}$ and geometric isomer of CH=CH corresponds to compound branch numbers −1 to −6690 among the following "combinations G".

Compounds AB65-1 to AB75-6690 wherein $R^{AB}$ represents a 1,4-dimethyloctyl group, and $(X^{AB})_m^{AB}$, $(Z^{AB})_n^{AB}$ and geometric isomer of CH=CH corresponds to compound branch numbers −1 to −6690 among the following "combinations G".

Compounds AB66-1 to AB76-6690 wherein $R^{AB}$ represents a 1,5-dimethyloctyl group, and $(X)_m^{AB}$, $(Z^{AB})_n^{AB}$ and geometric isomer of CH=CH corresponds to compound branch numbers −1 to −6690 among the following "combinations G".

Compounds AB67-1 to AB77-6690 wherein $R^{AB}$ represents a 1,6-dimethyloctyl group, and $(X^{AB})_m^{AB}$, $(Z^{AB})_n^{AB}$ and geometric isomer of CH=CH corresponds to compound branch numbers −1 to −6690 among the following "combinations G".

Compounds AB68-1 to AB78-6690 wherein $R^{AB}$ represents a 1,7-dimethyloctyl group, and $(X^{AB})_m^{AB}$, $(Z^{AB})_n^{AB}$ and geometric isomer of CH=CH corresponds to compound branch numbers −1 to −6690 among the following "combinations G".

Compounds AB69-1 to AB79-6690 wherein $R^{AB}$ represents a 1-(methylethyl)heptyl group, and $(X^{AB})_n^{AB}$, $(Z^{AB})_n^{AB}$ and geometric isomer of CH=CH corresponds to compound branch numbers −1 to −6690 among the following "combinations G".

Compounds AB70-1 to AB70-6690 wherein $R^{AB}$ represents a 1-ethyl 2-methylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB71-1 to AB71-6690 wherein $R^{AB}$ represents a 1-ethyl 3-methylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB72-1 to AB72-6690 wherein $R^{AB}$ represents a 1-ethyl 4-methylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB73-1 to AB73-6690 wherein $R^{AB}$ represents a 1-ethyl 5-methylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB74-1 to AB74-6690 wherein $R^{AB}$ represents a 1-ethyl 6-methylheptyl group, and $(X^{AB})_m^{AB}$, $(Z^{AB})_n^{AB}$ and geometric isomer of CH=CH corresponds to compound branch numbers −1 to −6690 among the following "combinations G".

Compounds AB75-1 to AB75-6690 wherein $R^{AB}$ represents a 1-(2-methylpropyl) hexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB76-1 to AB76-6690 wherein $R^{AB}$ represents a 1-(1-methylpropyl) hexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB77-1 to AB77-6690 wherein $R^{AB}$ represents a 2-methyl 1-propylhexyl group, and $(X^{AB})_m^{AB}$, $(Z^{AB})_n AB$ and geometric isomer of CH=CH corresponds to compound branch numbers −1 to −6690 among the following "combinations G".

Compounds AB78-1 to AB78-6690 wherein $R^{AB}$ represents a 3-methyl 1-propylhexyl group, and $(X^{AB})_m^{AB}$, $(Z^{AB})_n AB$ and geometric isomer of CH=CH corresponds to compound branch numbers −1 to −6690 among the following "combinations G".

Compounds AB79-1 to AB79-6690 wherein $R^{AB}$ represents a 4-methyl 1-propylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB80-1 to AB80-6690 wherein $R^{AB}$ represents a 5-methyl 1-propylhexyl group, and $(X^{AB})_m^{AB}$, $(Z^{AB})_n^{AB}$ and geometric isomer of CH=CH corresponds to compound branch numbers −1 to −6690 among the following "combinations G".

Compounds AB81-1 to AB81-6690 wherein $R^{AB}$ represents a 1-butyl 4-methylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB82-1 to AB82-6690 wherein $R^{AB}$ represents a 1-butyl 3-methylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB83-1 to AB83-6690 wherein $R^{AB}$ represents a 1-butyl 2-methylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB84-1 to AB84-6690 wherein $R^{AB}$ represents a 2-ethyl 1-methylbutyl group, and $(X^{AB})_m^{AB}$, $(Z^{AB})_n A$ and geometric isomer of CH=CH corresponds to compound branch numbers −1 to −6690 among the following "combinations G".

Compounds AB85-1 to AB85-6690 wherein $R^{AB}$ represents a 1,2-diethylbutyl group, and $(X^{AB})_m^{AB}$, $(Z^{AB})_n^{AB}$ and geometric isomer of CH=CH corresponds to compound branch numbers −1 to −6690 among the following "combinations G".

Compounds AB86-1 to AB86-6690 wherein $R^{AB}$ represents a 2-ethyl 1-propylbutyl group, and $(X^{AB})_m^{AB}$, $(Z^{AB})_n^{AB}$ and geometric isomer of CH=CH corresponds to compound branch numbers −1 to −6690 among the following "combinations G".

Compounds AB87-1 to AB87-6690 wherein $R^{AB}$ represents a 1,2-diethylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB88-1 to AB88-6690 wherein $R^{AB}$ represents a 1,3-diethylpentyl group, and $(X)_m^{AB}$, $(Z^{AB})_n^{AB}$ and geometric isomer of CH=CH corresponds to compound branch numbers −1 to −6690 among the following "combinations G".

2-ethyl 1-propylpentyl Compounds AB89-1 to AB89-6690 wherein $R^{AB}$ represents a group, and $(X^{AB})_m^{AB}$, $(Z^{AB})_n^{AB}$ and geometric isomer of CH=CH corresponds to compound branch numbers −1 to −6690 among the following "combinations G".

Compounds AB90-1 to AB90-6690 wherein $R^{AB}$ represents a 3-ethyl 1-propylpentyl group, and $(X^{AB})_m^{AB}$, $(Z^{AB})_n^{AB}$ and geometric isomer of CH=CH corresponds to compound branch numbers −1 to −6690 among the following "combinations G".

Compounds AB91-1 to AB91-6690 wherein $R^{AB}$ represents a 1-indanyl group, and $(X^{AB})_m^{AB}$, $(Z^{AB})_n^{AB}$ and geometric isomer of CH=CH corresponds to compound branch numbers −1 to −6690 among the following "combinations G".

Compounds AB92-1 to AB92-6690 wherein $R^{AB}$ represents a 2-indanyl group, and $(X^{AB})_m^{AB}$, $(Z^{AB})_n^{AB}$ and geometric isomer of CH=CH corresponds to compound branch numbers −1 to −6690 among the following "combinations G".

Compounds AB93-1 to AB93-6690 wherein $R^{AB}$ represents a 1,2,3,4-tetrahydro 1-naphtyl group, and $(X^{AB})_m^{AB}$, $(Z^{AB})_n^{AB}$ and geometric isomer of CH=CH corresponds to compound branch numbers −1 to −6690 among the following "combinations G".

Compounds AB94-1 to AB94-6690 wherein $R^{AB}$ represents a 1,2,3,4-tetrahydro 2-naphtyl group, and $(X^{AB})_m^{AB}$, $(Z^{AB})_n^{AB}$ and geometric isomer of CH=CH corresponds to compound branch numbers −1 to −6690 among the following "combinations G".

"Combinations G":

[compound branch number: $(X_{AA})_m^{AA}$ or $(X_{AB})_m^{AB}$, $(Z_{AA})_n^{AA}$ or $(Z_{AB})_n^{AB}$, geometric isomer of CH=CH double bond]= [−1:H,H,E], [−2:4-F,H,E], [−3:4-F,H,Z], [−4:4-Cl,H,E], [−5:4-Cl,H,Z], [−6:4-Br,H,E], [−7:4-I,H,E], [−8:4-Me,H,E], [−9:4-Me,H,Z], [−10:4-Et,H,E], [−11:4-$C_3H_7$,H,E], [−12:4-$(Me)_2$CH,H,E], [−13:4-$CF_3$,H,E], [−14:4-$CF_3$,H,Z], [−15:4-$C_2F_5$,H,E], [−16:4-$C_3F_7$,H,E], [−17:4-$(CF_3)_2$CF,H,E], [−18:4-$(CF_3)_2$CH,H,E], [−19:4-$CHF_2$,H,E], [−20:4-$CH_2F$,H,E], [−21:4-$CF_3CH_2$,H,E], [−22:4-MeO,H,E], [−23:4-MeO,H,Z], [−24:4-EtO,H,E], [−25:4-$C_3H_7O$,H,E], [−26:4-$(Me)_2$CHO,H,E], [−27:4-$NO_2$,H,E], [−28:4-$NO_2$,H,Z], [−29:3-F,H,E], [−30:3-F,H,Z], [−31:3-Cl,H,E], [−32:3-Cl,H,Z], [−33:3-Br,H,E], [−34:3-I,H,E], [−35:3-Me,H,E], [−36:3-Me,H,Z], [−37:3-Et,H,E], [−38:3-$C_3H_7$,H,E], [−39:3-$(Me)_2$CH,H,E], [−40:3-$CF_3$,H,E], [−41:3-$CF_3$,H,Z], [−42:3-$C_2F_5$,H,E], [−43:3-$C_3F_7$,H,E], [−44:3-$(CF_3)_2$CF,H,E], [−45:3-$(CF_3)_2$CH,H,E], [−46:3-$CHF_2$,H,E], [−47:3-$CHF_2$,H,Z], [−48:3-$CH_2F$,H,E], [−49:3-$CH_2F$,H,Z], [−50:3-$CF_3CH_2$,H,E], [−51:3-MeO,H,E], [−52:3-MeO,H,Z], [−53:3-EtO,H,E], [−54:3-$C_3H_7O$,H,E], [−55:3-$(Me)_2$CHO,H,E], [−56:3-$NO_2$,H,E], [−57:2-F,H,E], [−58:2-Cl,H,E], [−59:2-Br,H,E], [−60:2-I,H,E], [−61:2-Me,H,E], [−62:2-Et,H,E], [−63:2-$C_3H_7$,H,E],

[−64:2-(Me)₂CH,H,E], [−65:2-CF₃,H,E], [−66:2-C₂F₅,H,E], [−67:2-C₃F₇,H,E], [−68:2-(CF₃)₂CF,H,E], [−69:2-(CF₃)₂CH,H,E], [−70:2-CHF₂,H,E], [−71:2-CH₂F,H,E], [−72:2-CF₃CH₂,H,E], [−73:2-MeO,H,E], [−74:2-EtO,H,E], [−75:2-C₃H₇O,H,E], [−76:2-(Me)₂CHO,H,E], [−77:2-NO₂,H,E], [−78:2,3-F₂,H,E], [−79:2,4-F₂,H,E], [−80:2,5-F₂,H,E], [−81:2,6-F₂,H,E], [−82:3,4-F₂,H,E], [−83:3,4-F₂,H,Z], [−84:3,5-F₂,H,E], [−85:3,5-F₂,H,Z], [−86:2,3-Cl₂,H,E], [−87:2,3-Cl₂,H,Z], [−88:2,4-Cl₂,H,E], [−89:2,4-Cl₂,H,Z], [−90:2,5-Cl₂,H,E], [−91:2,5-Cl₂,H,Z], [−92:2,6-Cl₂,H,E], [−93:3,4-Cl₂,H,E], [−94:3,5-Cl₂,H,E], [−95:2,3-Br₂,H,E], [−96:2,4-Br₂,H,E], [−97:2,5-Br₂,H,E], [−98:2,6-Br₂,H,E], [−99:3,4-Br₂,H,E], [−100:3,5-Br₂,H,E], [−101:2,3-Me₂,H,E], [−102:2,4-Me₂,H,E], [−103:2,5-Me₂,H,E], [−104:2,6-Me₂,H,E], [−105:3,4-Me₂,H,E], [−106:3,5-Me₂,H,E], [−107:2,3-Et₂,H,E], [−108:2,4-Et₂,H,E], [−109:2,5-Et₂,H,E], [−110:2,6-Et₂,H,E], [−111:3,4-Et₂,H,E], [−112:3,5-Et₂,H,E], [−113:2,3-(CF₃)₂,H,E], [−114:2,4-(CF₃)₂,H,E], [−115:2,5-(CF₃)₂,H,E], [−116:2,6-(CF₃)₂,H,E], [−117:3,4-(CF₃)₂,H,E], [−118:3,5-(CF₃)₂,H,E], [−119:2,3-(CHF₂)₂,H,E], [−120:2,4-(CHF₂)₂,H,E], [−121:2,5-(CHF₂)₂,H,E], [−122:2,6-(CHF₂)₂,H,E], [−123:3,4-(CHF₂)₂,H,E], [−124:3,5-(CHF₂)₂,H,E], [−125:2,3-(CH₂F)₂,H,E], [−126:2,4-(CH₂F)₂,H,E], [−127:2,5-(CH₂F)₂,H,E], [−128:2,6-(CH₂F)₂,H,E], [−129:3,4-(CH₂F)₂,H,E], [−130:3,5-(CH₂F)₂,H,E], [−131:2,3-(MeO)₂,H,E], [−132:2,4-(MeO)₂,H,E], [−133:2,5-(MeO)₂,H,E], [−134:2,6-(MeO)₂,H,E], [−135:3,4-(MeO)₂,H,E], [−136:3,5-(MeO)₂,H,E], [−137:2,3-(EtO)₂,H,E], [−138:2,4-(EtO)₂,H,E], [−139:2,5-(EtO)₂,H,E], [−140:2,6-(EtO)₂,H,E], [−141:3,4-(EtO)₂,H,E], [−142:3,5-(EtO)₂,H,E], [−143:2-Cl-3-F,H,E], [−144:2-Cl-4-F,H,E], [−145:2-Cl-5-F,H,E], [−146:2-Cl-6-F,H,E], [−147:3-Cl-2-F,H,E], [−148:3-Cl-4-F,H,E], [−149:3-Cl-5-F,H,E], [−150:4-Cl-2-F,H,E], [−151:4-Cl-3-F,H,E], [−152:2-F-3-Me,H,E], [−153:2-F-4-Me,H,E], [−154:2-F-5-Me,H,E], [−155:2-F-6-Me,H,E], [−156:3-F-2-Me,H,E], [−157:3-F-4-Me,H,E], [−158:3-F-5-Me,H,E], [−159:4-F-2-Me,H,E], [−160:4-F-3-Me,H,E], [−161:2-Cl-3-Me,H,E], [−162:2-Cl-4-Me,H,E], [−163:2-Cl-5-Me,H,E], [−164:2-Cl-6-Me,H,E], [−165:3-Cl-2-Me,H,E], [−166:3-Cl-4-Me,H,E], [−167:3-Cl-5-Me,H,E], [−168:4-Cl-2-Me,H,E], [−169:4-Cl-3-Me,H,E], [−170:2-F-3-CF₃,H,E], [−171:2-F-4-CF₃,H,E], [−172:2-F-5-CF₃,H,E], [−173:2-F-6-CF₃,H,E], [−174:3-F-2-CF₃,H,E], [−175:3-F-4-CF₃,H,E], [−176:3-F-5-CF₃,H,E], [−177:4-F-2-CF₃,H,E], [−178:4-F-3-CF₃,H,E], [−179:2-Cl-3-CF₃,H,E], [−180:2-Cl-4-CF₃,H,E], [−181:2-Cl-5-CF₃,H,E], [−182:2-Cl-6-CF₃,H,E], [−183:3-Cl-2-CF₃,H,E], [−184:3-Cl-4-CF₃,H,E], [−185:3-Cl-5-CF₃,H,E], [−186:4-Cl-2-CF₃,H,E], [−187:4-Cl-3-CF₃,H,E], [−188:2-Me-3-CF₃,H,E], [−189:2-Me-4-CF₃,H,E], [−190:2-Me-5-CF₃,H,E], [−191:2-Me-6-CF₃,H,E], [−192:3-Me-2-CF₃,H,E], [−193:3-Me-4-CF₃,H,E], [−194:3-Me-5-CF₃,H,E], [−195:4-Me-2-CF₃,H,E], [−196:4-Me-3-CF₃,H,E], [−197:2-F-3-MeO,H,E], [−198:2-F-4-MeO,H,E], [−199:2-F-5-MeO,H,E], [−200:2-F-6-MeO,H,E], [−201:3-F-2-MeO,H,E], [−202:3-F-4-MeO,H,E], [−203:3-F-5-MeO,H,E], [−204:4-F-2-MeO,H,E], [−205:4-F-3-MeO,H,E], [−206:2-Cl-3-MeO,H,E], [−207:2-Cl-4-MeO,H,E], [−208:2-Cl-5-MeO,H,E], [−209:2-Cl-6-MeO,H,E], [−210:3-Cl-2-MeO,H,E], [−211:3-Cl-4-MeO,H,E], [−212:3-Cl-5-MeO,H,E], [−213:4-Cl-2-MeO,H,E], [−214:4-Cl-3-MeO,H,E], [−215:2-Me-3-MeO,H,E], [−216:2-Me-4-MeO,H,E], [−217:2-Me-5-MeO,H,E], [−218:2-Me-6-MeO,H,E], [−219:3-Me-2-MeO,H,E], [−220:3-Me-4-MeO,H,E], [−221:3-Me-5-MeO,H,E], [−222:4-Me-2-MeO,H,E], [−223:4-Me-3-MeO,H,E], [−224:H,4-F,E], [−225:4-F,4-F,E], [−226:4-F,4-F,Z], [−227:4-Cl,4-F,E], [−228:4-Cl,4-F,Z], [−229:4-Br,4-F,E], [−230:4-I,4-F,E], [−231:4-Me,4-F,E], [−232:4-Me,4-F,Z], [−233:4-Et,4-F,E], [−234:4-C₃H₇,4-F,E], [−235:4-(Me)₂CH,4-F,E], [−236:4-CF₃,4-F,E], [−237:4-CF₃,4-F,Z], [−238:4-C₂F₅,4-F,E], [−239:4-C₃F₇,4-F,E], [−240:4-(CF₃)₂CF,4-F,E], [−241:4-(CF₃)₂CH,4-F,E], [−242:4-CHF₂,4-F,E], [−243:4-CH₂F,4-F,E], [−244:4-CF₃CH₂,4-F,E], [−245:4-MeO,4-F,E], [−246:4-MeO,4-F,Z], [−247:4-EtO,4-F,E], [−248:4-C₃H₇O,4-F,E], [−249:4-(Me)₂CHO,4-F,E], [−250:4-NO₂,4-F,E], [−251:4-NO₂,4-F,Z], [−252:3-F,4-F,E], [−253:3-F,4-F,Z], [−254:3-Cl,4-F,E], [−255:3-Cl,4-F,Z], [−256:3-Br,4-F,E], [−257:3-I,4-F,E], [−258:3-Me,4-F,E], [−259:3-Me,4-F,Z], [−260:3-Et,4-F,E], [−261:3-C₃H₇,4-F,E], [−262:3-(Me)₂CH,4-F,E], [−263:3-CF₃,4-F,E], [−264:3-CF₃,4-F,Z], [−265:3-C₂F₅,4-F,E], [−266:3-C₃F₇,4-F,E], [−267:3-(CF₃)₂CF,4-F,E], [−268:3-(CF₃)₂CH,4-F,E], [−269:3-CHF₂,4-F,E], [−270:3-CHF₂,4-F,Z], [−271:3-CH₂F,4-F,E], [−272:3-CH₂F,4-F,Z], [−273:3-CF₃CH₂,4-F,E], [−274:3-MeO,4-F,E], [−275:3-MeO,4-F,Z], [−276:3-EtO,4-F,E], [−277:3-C₃H₇O,4-F,E], [−278:3-(Me)₂CHO,4-F,E], [−279:3-NO₂,4-F,E], [−280:2-F,4-F,E], [−281:2-Cl,4-F,E], [−282:2-Br,4-F,E], [−283:2-I,4-F,E], [−284:2-Me,4-F,E], [−285:2-Et,4-F,E], [−286:2-C₃H₇,4-F,E], [−287:2-(Me)₂CH,4-F,E], [−288:2-CF₃,4-F,E], [−289:2-C₂F₅,4-F,E], [−290:2-C₃F₇,4-F,E], [−291:2-(CF₃)₂CF,4-F,E], [−292:2-(CF₃)₂CH,4-F,E], [−293:2-CHF₂,4-F,E], [−294:2-CH₂F,4-F,E], [−295:2-CF₃CH₂,4-F,E], [−296:2-MeO,4-F,E], [−297:2-EtO,4-F,E], [−298:2-C₃H₇O,4-F,E], [−299:2-(Me)₂CHO,4-F,E], [−300:2-NO₂,4-F,E], [−301:2,3-F₂,4-F,E], [−302:2,4-F₂,4-F,E], [−303:2,5-F₂,4-F,E], [−304:2,6-F₂,4-F,E], [−305:3,4-F₂,4-F,E], [−306:3,4-F₂,4-F,Z], [−307:3,5-F₂,4-F,E], [−308:3,5-F₂,4-F,Z], [−309:2,3-Cl₂,4-F,E], [−310:2,3-Cl₂,4-F,Z], [−311:2,4-Cl₂,4-F,E], [−312:2,4-Cl₂,4-F,Z], [−313:2,5-Cl₂,4-F,E], [−314:2,5-Cl₂,4-F,Z], [−315:2,6-Cl₂,4-F,E], [−316:3,4-Cl₂,4-F,E], [−317:3,5-Cl₂,4-F,E], [−318:2,3-Br₂,4-F,E], [−319:2,4-Br₂,4-F,E], [−320:2,5-Br₂,4-F,E], [−321:2,6-Br₂,4-F,E], [−322:3,4-Br₂,4-F,E], [−323:3,5-Br₂,4-F,E], [−324:2,3-Me₂,4-F,E], [−325:2,4-Me₂,4-F,E], [−326:2,5-Me₂,4-F,E], [−327:2,6-Me₂,4-F,E], [−328:3,4-Me₂,4-F,E], [−329:3,5-Me₂,4-F,E], [−330:2,3-Et₂,4-F,E], [−331:2,4-Et₂,4-F,E], [−332:2,5-Et₂,4-F,E], [−333:2,6-Et₂,4-F,E], [−334:3,4-Et₂,4-F,E], [−335:3,5-Et₂,4-F,E], [−336:2,3-(CF₃)₂,4-F,E], [−337:2,4-(CF₃)₂,4-F,E], [−338:2,5-(CF₃)₂,4-F,E], [−339:2,6-(CF₃)₂,4-F,E], [−340:3,4-(CF₃)₂,4-F,E], [−341:3,5-(CF₃)₂,4-F,E], [−342:2,3-(CHF₂)₂,4-F,E], [−343:2,4-(CHF₂)₂,4-F,E], [−344:2,5-(CHF₂)₂,4-F,E], [−345:2,6-(CHF₂)₂,4-F,E], [−346:3,4-(CHF₂)₂,4-F,E], [−347:3,5-(CHF₂)₂,4-F,E], [−348:2,3-(CH₂F)₂,4-F,E], [−349:2,4-(CH₂F)₂,4-F,E], [−350:2,5-(CH₂F)₂,4-F,E], [−351:2,6-(CH₂F)₂,4-F,E], [−352:3,4-(CH₂F)₂,4-F,E], [−353:3,5-(CH₂F)₂,4-F,E], [−354:2,3-(MeO)₂,4-F,E], [−355:2,4-(MeO)₂,4-F,E], [−356:2,5-(MeO)₂,4-F,E], [−357:2,6-(MeO)₂,4-F,E], [−358:3,4-(MeO)₂,4-F,E], [−359:3,5-(MeO)₂,4-F,E], [−360:2,3-(EtO)₂,4-F,E], [−361:2,4-(EtO)₂,4-F,E], [−362:2,5-(EtO)₂,4-F,E], [−363:2,6-(EtO)₂,4-F,E], [−364:3,4-(EtO)₂,4-F,E], [−365:3,5-(EtO)₂,4-F,E], [−366:2-Cl-3-F,4-F,E], [−367:2-Cl-4-F,4-F,E], [−368:2-Cl-5-F,4-F,E], [−369:2-Cl-6-F,4-F,E], [−370:3-Cl-2-F,4-F,E], [−371:3-Cl-4-F,4-F,E], [−372:3-Cl-5-F,4-F,E], [−373:4-Cl-2-F,4-F,E], [−374:4-Cl-3-F,4-F,E], [−375:2-F-3-Me,4-F,E], [−376:2-F-4-Me,4-F,E], [−377:2-F-5-Me,4-F,E], [−378:2-F-6-Me,4-F,E], [−379:3-F-2-Me,4-F,E], [−380:3-F-4-Me,4-F,E], [−381:3-F-5-Me,4-F,E], [−382:4-F-2-Me,4-F,E], [−383:4-F-3-Me,4-F,E], [−384:2-Cl-3-Me,4-F,E], [−385:2-Cl-4-Me,4-F,E], [−386:2-Cl-5-Me,4-F,E], [−387:

2-Cl-6-Me,4-F,E], [−388:3-Cl-2-Me,4-F,E], [−389:3-Cl-4-Me,4-F,E], [−390:3-Cl-5-Me,4-F,E], [−391:4-Cl-2-Me,4-F,E], [−392:4-Cl-3-Me,4-F,E], [−393:2-F-3-CF$_3$,4-F,E], [−394:2-F-4-CF$_3$,4-F,E], [−395:2-F-5-CF$_3$,4-F,E], [−396:2-F-6-CF$_3$,4-F,E], [−397:3-F-2-CF$_3$,4-F,E], [−398:3-F-4-CF$_3$,4-F,E], [−399:3-F-5-CF$_3$,4-F,E], [−400:4-F-2-CF$_3$,4-F,E], [−401:4-F-3-CF$_3$,4-F,E], [−402:2-Cl-3-CF$_3$,4-F,E], [−403:2-Cl-4-CF$_3$,4-F,E], [−404:2-Cl-5-CF$_3$,4-F,E], [−405:2-Cl-6-CF$_3$,4-F,E], [−406:3-Cl-2-CF$_3$,4-F,E], [−407:3-Cl-4-CF$_3$,4-F,E], [−408:3-Cl-5-CF$_3$,4-F,E], [−409:4-Cl-2-CF$_3$,4-F,E], [−410:4-Cl-3-CF$_3$,4-F,E], [−411:2-Me-3-CF$_3$,4-F,E], [−412:2-Me-4-CF$_3$,4-F,E], [−413:2-Me-5-CF$_3$,4-F,E], [−414:2-Me-6-CF$_3$,4-F,E], [−415:3-Me-2-CF$_3$,4-F,E], [−416:3-Me-4-CF$_3$,4-F,E], [−417:3-Me-5-CF$_3$,4-F,E], [−418:4-Me-2-CF$_3$,4-F,E], [−419:4-Me-3-CF$_3$,4-F,E], [−420:2-F-3-MeO,4-F,E], [−421:2-F-4-MeO,4-F,E], [−422:2-F-5-MeO,4-F,E], [−423:2-F-6-MeO,4-F,E], [−424:3-F-2-MeO,4-F,E], [−425:3-F-4-MeO,4-F,E], [−426:3-F-5-MeO,4-F,E], [−427:4-F-2-MeO,4-F,E], [−428:4-F-3-MeO,4-F,E], [−429:2-Cl-3-MeO,4-F,E], [−430:2-Cl-4-MeO,4-F,E], [−431:2-Cl-5-MeO,4-F,E], [−432:2-Cl-6-MeO,4-F,E], [−433:3-Cl-2-MeO,4-F,E], [−434:3-Cl-4-MeO,4-F,E], [−435:3-Cl-5-MeO,4-F,E], [−436:4-Cl-2-MeO,4-F,E], [−437:4-Cl-3-MeO,4-F,E], [−438:2-Me-3-MeO,4-F,E], [−439:2-Me-4-MeO,4-F,E], [−440:2-Me-5-MeO,4-F,E], [−441:2-Me-6-MeO,4-F,E], [−442:3-Me-2-MeO,4-F,E], [−443:3-Me-4-MeO,4-F,E], [−444:3-Me-5-MeO,4-F,E], [−445:4-Me-2-MeO,4-F,E], [−446:4-Me-3-MeO,4-F,E], [−447:H,4-Cl,E], [−448:4-F,4-Cl,E], [−449:4-F,4-Cl,Z], [−450:4-Cl,4-Cl,E], [−451:4-Cl,4-Cl,Z], [−452:4-Br,4-Cl,E], [−453:4-I,4-Cl,E], [−454:4-Me,4-Cl,E], [−455:4-Me,4-Cl,Z], [−456:4-Et,4-Cl,E], [−457:4-C$_3$H$_7$,4-Cl,E], [−458:4-(Me)$_2$CH,4-Cl,E], [−459:4-CF$_3$,4-Cl,E], [−460:4-CF$_3$,4-Cl,Z], [−461:4-C$_2$F$_5$,4-Cl,E], [−462:4-C$_3$F$_7$,4-Cl,E], [−463:4-(CF$_3$)$_2$CF,4-Cl,E], [−464:4-(CF$_3$)$_2$CH,4-Cl,E], [−465:4-CHF$_2$,4-Cl,E], [−466:4-CH$_2$F,4-Cl,E], [−467:4-CF$_3$CH$_2$,4-Cl,E], [−468:4-MeO,4-Cl,E], [−469:4-MeO,4-Cl,Z], [−470:4-EtO,4-Cl,E], [−471:4-C$_3$H$_7$,4-Cl,E], [−472:4-(Me)$_2$CHO,4-Cl,E], [−473:4-NO$_2$, 4-Cl,E], [−474:4-NO$_2$, 4-Cl,Z], [−475:3-F, 4-Cl,E], [−476:3-F,4-Cl,Z], [−477:3-Cl,4-Cl,E], [−478:3-Cl,4-Cl,Z], [−479:3-Br,4-Cl,E], [−480:3-I,4-Cl,E], [−481:3-Me,4-Cl,E], [−482:3-Me,4-Cl,Z], [−483:3-Et,4-Cl,E], [−484:3-C$_3$H$_7$,4-Cl,E], [−485:3-(Me)$_2$CH,4-Cl,E], [−486:3-CF$_3$,4-Cl,E], [−487:3-CF$_3$,4-Cl,Z], [−488:3-C$_2$F$_5$,4-Cl,E], [−489:3-C$_3$F$_7$,4-Cl,E], [−490:3-(CF$_3$)$_2$CF,4-Cl,E], [−491:3-(CF$_3$)$_2$CH,4-Cl,E], [−492:3-CHF$_2$,4-Cl,E], [−493:3-CHF$_2$,4-Cl,Z], [−494:3-CH$_2$F,4-Cl,E], [−495:3-CH$_2$F,4-Cl,Z], [−496:3-CF$_3$CH$_2$, 4-Cl,E], [−497:3-MeO,4-Cl,E], [−498:3-MeO,4-Cl,Z], [−499:3-EtO,4-Cl,E], [−500:3-C$_3$H$_7$O,4-Cl,E], [−501:3-(Me)$_2$CHO,4-Cl,E], [−502:3-NO$_2$,4-Cl,E], [−503:2-F,4-Cl,E], [−504:2-Cl,4-Cl,E], [−505:2-Br,4-Cl,E], [−506:2-I,4-Cl,E], [−507:2-Me,4-Cl,E], [−508:2-Et,4-Cl,E], [−509:2-C$_3$H$_7$,4-Cl,E], [−510:2-(Me)$_2$CH,4-Cl,E], [−511:2-CF$_3$,4-Cl,E], [−512:2-C$_2$F$_5$,4-Cl,E], [−513:2-C$_3$F$_7$,4-Cl,E], [−514:2-(CF$_3$)$_2$CF,4-Cl,E], [−515:2-(CF$_3$)$_2$CH,4-Cl,E], [−516:2-CHF$_2$,4-Cl,E], [−517:2-CH$_2$F,4-Cl,E], [−518:2-CF$_3$CH$_2$,4-Cl,E], [−519:2-MeO,4-Cl,E], [−520:2-EtO,4-Cl,E], [−521:2-C$_3$H$_7$O,4-Cl,E], [−522:2-(Me)$_2$CHO,4-Cl,E], [−523:2-NO$_2$,4-Cl,E], [−524:2,3-F$_2$,4-Cl,E], [−525:2,4-F$_2$,4-Cl,E], [−526:2,5-F$_2$,4-Cl,E], [−527:2,6-F$_2$,4-Cl,E], [−528:3,4-F$_2$,4-Cl,E], [−529:3,4-F$_2$,4-Cl,Z], [−530:3,5-F$_2$,4-Cl,E], [−531:3,5-F$_2$,4-Cl,Z], [−532:2,3-Cl$_2$,4-Cl,E], [−533:2,3-Cl$_2$,4-Cl,Z], [−534:2,4-Cl$_2$,4-Cl,E], [−535:2,4-Cl$_2$,4-Cl,Z], [−536:2,5-Cl$_2$,4-Cl,E], [−537:2,5-Cl$_2$,4-Cl,Z], [−538:2,6-Cl$_2$,4-Cl,E], [−539:3,4-Cl$_2$,4-Cl,E], [−540:3,5-Cl$_2$,4-Cl,E], [−541:2,3-Br$_2$,4-Cl,E], [−542:2,4-Br$_2$,4-Cl,E], [−543:2,5-Br$_2$,4-Cl,E], [−544:2,6-Br$_2$,4-Cl,E], [−545:3,4-Br$_2$,4-Cl,E], [−546:3,5-Br$_2$,4-Cl,E], [−547:2,3-Me$_2$,4-Cl,E], [−548:2,4-Me$_2$,4-Cl,E], [−549:2,5-Me$_2$,4-Cl,E], [−550:2,6-Me$_2$,4-Cl,E], [−551:3,4-Me$_2$,4-Cl,E], [−552:3,5-Me$_2$,4-Cl,E], [−553:2,3-Et$_2$,4-Cl,E], [−554:2,4-Et$_2$,4-Cl,E], [−555:2,5-Et$_2$,4-Cl,E], [−556:2,6-Et$_2$,4-Cl,E], [−557:3,4-Et$_2$,4-Cl,E], [−558:3,5-Et$_2$,4-Cl,E], [−559:2,3-(CF$_3$)$_2$,4-Cl,E], [−560:2,4-(CF$_3$)$_2$,4-Cl,E], [−561:2,5-(CF$_3$)$_2$,4-Cl,E], [−562:2,6-(CF$_3$)$_2$,4-Cl,E], [−563:3,4-(CF$_3$)$_2$,4-Cl,E], [−564:3,5-(CF$_3$)$_2$,4-Cl,E], [−565:2,3-(CHF$_2$)$_2$,4-Cl,E], [−566:2,4-(CHF$_2$)$_2$,4-Cl,E], [−567:2,5-(CHF$_2$)$_2$,4-Cl,E], [−568:2,6-(CHF$_2$)$_2$,4-Cl,E], [−569:3,4-(CHF$_2$)$_2$,4-Cl,E], [−570:3,5-(CHF$_2$)$_2$,4-Cl,E], [−571:2,3-(CH$_2$F)$_2$,4-Cl,E], [−572:2,4-(CH$_2$F)$_2$,4-Cl,E], [−573:2,5-(CH$_2$F)$_2$,4-Cl,E], [−574:2,6-(CH$_2$F)$_2$,4-Cl,E], [−575:3,4-(CH$_2$F)$_2$,4-Cl,E], [−576:3,5-(CH$_2$F)$_2$,4-Cl,E], [−577:2,3-(MeO)$_2$,4-Cl,E], [−578:2,4-(MeO)$_2$,4-Cl,E], [−579:2,5-(MeO)$_2$,4-Cl,E], [−580:2,6-(MeO)$_2$,4-Cl,E], [−581:3,4-(MeO)$_2$,4-Cl,E], [−582:3,5-(MeO)$_2$,4-Cl,E], [−583:2,3-(EtO)$_2$,4-Cl,E], [−584:2,4-(EtO)$_2$,4-Cl,E], [−585:2,5-(EtO)$_2$,4-Cl,E], [−586:2,6-(EtO)$_2$,4-Cl,E], [−587:3,4-(EtO)$_2$,4-Cl,E], [−588:3,5-(EtO)$_2$,4-Cl,E], [−589:2-Cl-3-F,4-Cl,E], [−590:2-Cl-4-F, 4-Cl,E], [−591:2-Cl-5-F,4-Cl,E], [−592:2-Cl-6-F, 4-Cl,E], [−593:3-Cl-2-F, 4-Cl,E], [−594:3-Cl-4-F,4-Cl,E], [−595:3-Cl-5-F,4-Cl,E], [−596:4-Cl-2-F,4-Cl,E], [−597:4-Cl-3-F,4-Cl,E], [−598:2-F-3-Me,4-Cl,E], [−599:2-F-4-Me,4-Cl,E], [−600:2-F-5-Me,4-Cl,E], [−601:2-F-6-Me,4-Cl,E], [−602:3-F-2-Me,4-Cl,E], [−603:3-F-4-Me,4-Cl,E], [−604:3-F—5-Me,4-Cl,E], [−605:4-F-2-Me,4-Cl,E], [−606:4-F-3-Me,4-Cl,E], [−607:2-Cl-3-Me,4-Cl,E], [−608:2-Cl-4-Me,4-Cl,E], [−609:2-Cl-5-Me,4-Cl,E], [−610:2-Cl-6-Me,4-Cl,E], [−611:3-Cl-2-Me,4-Cl,E], [−612:3-Cl-4-Me,4-Cl,E], [−613:3-Cl-5-Me,4-Cl,E], [−614:4-Cl-2-Me,4-Cl,E], [−615:4-Cl-3-Me,4-Cl,E], [−616:2-F-3-CF$_3$,4-Cl,E], [−617:2-F-4-CF$_3$,4-Cl,E], [−618:2-F-5-CF$_3$,4-Cl,E], [−619:2-F-6-CF$_3$,4-Cl,E], [−620:3-F-2-CF$_3$,4-Cl,E], [−621:3-F-4-CF$_3$,4-Cl,E], [−622:3-F-5-CF$_3$,4-Cl,E], [−623:4-F-2-CF$_3$,4-Cl,E], [−624:4-F-3-CF$_3$,4-Cl,E], [−625:2-Cl-3-CF$_3$,4-Cl,E], [−626:2-Cl-4-CF$_3$,4-Cl,E], [−627:2-Cl-5-CF$_3$,4-Cl,E], [−628:2-Cl-6-CF$_3$,4-Cl,E], [−629:3-Cl-2-CF$_3$,4-Cl,E], [−630:3-Cl-4-CF$_3$,4-Cl,E], [−631:3-Cl-5-CF$_3$,4-Cl,E], [−632:4-Cl-2-CF$_3$,4-Cl,E], [−633:4-Cl-3-CF$_3$,4-Cl,E], [−634:2-Me-3-CF$_3$,4-Cl,E], [−635:2-Me-4-CF$_3$,4-Cl,E], [−636:2-Me-5-CF$_3$,4-Cl,E], [−637:2-Me-6-CF$_3$,4-Cl,E], [−638:3-Me-2-CF$_3$,4-Cl,E], [−639:3-Me-4-CF$_3$,4-Cl,E], [−640:3-Me-5-CF$_3$,4-Cl,E], [−641:4-Me-2-CF$_3$,4-Cl,E], [−642:4-Me-3-CF$_3$,4-Cl,E], [−643:2-F-3-MeO,4-Cl,E], [−644:2-F-4-MeO,4-Cl,E], [−645:2-F-5-MeO, 4-Cl,E], [−646:2-F-6-MeO, 4-Cl,E], [−647:3-F-2-MeO, 4-Cl,E], [−648:3-F-4-MeO,4-Cl,E], [−649:3-F-5-MeO,4-Cl,E], [−650:4-F-2-MeO,4-Cl,E], [−651:4-F-3-MeO,4-Cl,E], [−652:2-Cl-3-MeO,4-Cl,E], [−653:2-Cl-4-MeO,4-Cl,E], [−654:2-Cl-5-MeO,4-Cl,E], [−655:2-Cl-6-MeO,4-Cl,E], [−656:3-Cl-2-MeO,4-Cl,E], [−657:3-Cl-4-MeO, 4-Cl,E], [−658:3-Cl-5-MeO,4-Cl,E], [−659:4-Cl-2-MeO,4-Cl,E], [−660:4-Cl-3-MeO,4-Cl,E], [−661:2-Me-3-MeO,4-Cl,E], [−662:2-Me-4-MeO,4-Cl,E], [−663:2-Me-5-MeO,4-Cl,E], [−664:2-Me-6-MeO,4-Cl,E], [−665:3-Me-2-MeO,4-Cl,E], [−666:3-Me-4-MeO,4-Cl,E], [−667:3-Me-5-MeO,4-Cl,E], [−668:4-Me-2-MeO,4-Cl,E], [−669:4-Me-3-MeO,4-Cl,E], [−670:H,4-CF$_3$,E], [−671:4-F,4-CF$_3$,E], [−672:4-F,4-CF$_3$,Z], [−673:4-Cl,4-CF$_3$,E], [−674:4-Cl$_4$-CF$_3$,Z], [−675:4-Br,4-CF$_3$,E], [−676:4-I,4-CF$_3$,E], [−677:4-Me, 4-CF$_3$,E], [−678:4-Me, 4-CF$_3$,Z], [−679:4-Et,4-CF$_3$,E], [−680:4-

C₃H₇,4-CF₃,E], [−681:4-(Me)₂CH,4-CF₃,E], [−682:4-CF₃,4-CF₃,E], [−683:4-CF₃,4-CF₃,Z], [−684:4-C₂F₅,4-CF₃,E], [−685:4-C₃F₇, 4-CF₃,E], [−686:4-(CF₃)₂CF,4-CF₃,E], [−687:4-(CF₃)₂CH,4-CF₃,E], [−688:4-CHF₂,4-CF₃,E], [−689:4-CH₂F,4-CF₃,E], [−690:4-CF₃CH₂,4-CF₃,E], [−691:4-MeO, 4-CF₃,E], [−692:4-MeO,4-CF₃,Z], [−693:4-EtO,4-CF₃,E], [−694:4-C₃H₇O,4-CF₃,E], [−695:4-(Me)₂CHO,4-CF₃,E], [−696:4-NO₂,4-CF₃,E], [−697:4-NO₂,4-CF₃,Z], [−698:3-F,4-CF₃,E], [−699:3-F,4-CF₃,Z], [−700:3-Cl-4-CF₃,E], [−701:3-Cl, 4-CF₃,Z], [−702:3-Br, 4-CF₃,E], [−703:3-I,4-CF₃,E], [−704:3-Me,4-CF₃,E], [−705:3-Me,4-CF₃,Z], [−706:3-Et,4-CF₃,E], [−707:3-C₃H₇,4-CF₃,E], [−708:3-(Me)₂CH,4-CF₃,E], [−709:3-CF₃,4-CF₃,E], [−710:3-CF₃,4-CF₃,Z], [−711:3-C₂F₅,4-CF₃,E], [−712:3-C₃F₇,4-CF₃,E], [−713:3-(CF₃)₂CF,4-CF₃,E], [−714:3-(CF₃)₂CH,4-CF₃,E], [−715:3-CHF₂,4-CF₃,E], [−716:3-CHF₂,4-CF₃,Z], [−717:3-CH₂F, 4-CF₃,E], [−718:3-CH₂F, 4-CF₃,Z], [−719:3-CF₃CH₂,4-CF₃,E], [−720:3-MeO,4-CF₃,E], [−721:3-MeO,4-CF₃,Z], [−722:3-EtO,4-CF₃,E], [−723:3-C₃H₇O,4-CF₃,E], [−724:3-(Me)₂CHO,4-CF₃,E], [−725:3-NO₂,4-CF₃,E], [−726:2-F,4-CF₃,E], [−727:2-Cl,4-CF₃,E], [−728:2-Br,4-CF₃,E], [−729:2-I,4-CF₃,E], [−730:2-Me,4-CF₃,E], [−731:2-Et,4-CF₃,E], [−732:2-C₃H₇,4-CF₃,E], [−733:2-(Me)₂CH,4-CF₃,E], [−734:2-CF₃,4-CF₃,E], [−735:2-C₂F₅,4-CF₃,E], [−736:2-C₃F₇,4-CF₃,E], [−737:2-(CF₃)₂CF,4-CF₃,E], [−738:2-(CF₃)₂CH,4-CF₃,E], [−739:2-CHF₂,4-CF₃,E], [−740:2-CH₂F,4-CF₃,E], [−741:2-CF₃CH₂,4-CF₃,E], [−742:2-MeO,4-CF₃,E], [−743:2-EtO,4-CF₃,E], [−744:2-C₃H₇O,4-CF₃,E], [−745:2-(Me)₂CHO,4-CF₃,E], [−746:2-NO₂,4-CF₃,E], [−747:2,3-F₂,4-CF₃,E], [−748:2,4-F₂,4-CF₃,E], [−749:2,5-F₂,4-CF₃,E], [−750:2,6-F₂,4-CF₃,E], [−751:3,4-F₂,4-CF₃,E], [−752:3,4-F₂,4-CF₃,Z], [−753:3,5-F₂,4-CF₃,E], [−754:3,5-F₂,4-CF₃,Z], [−755:2,3-Cl₂,4-CF₃,E], [−756:2,3-Cl₂,4-CF₃,Z], [−757:2,4-Cl₂,4-CF₃,E], [−758:2,4-Cl₂,4-CF₃,Z], [−759:2,5-Cl₂,4-CF₃,E], [−760:2,5-Cl₂,4-CF₃,Z], [−761:2,6-Cl₂,4-CF₃,E], [−762:3,4-Cl₂,4-CF₃,E], [−763:3,5-Cl₂,4-CF₃,E], [−764:2,3-Br₂,4-CF₃,E], [−765:2,4-Br₂,4-CF₃,E], [−766:2,5-Br₂,4-CF₃,E], [−767:2,6-Br₂,4-CF₃,E], [−768:3,4-Br₂,4-CF₃,E], [−769:3,5-Br₂,4-CF₃,E], [−770:2,3-Me₂,4-CF₃,E], [−771:2,4-Me₂,4-CF₃,E], [−772:2,5-Me₂,4-CF₃,E], [−773:2,6-Me₂,4-CF₃,E], [−774:3,4-Me₂,4-CF₃,E], [−775:3,5-Me₂,4-CF₃,E], [−776:2,3-Et₂,4-CF₃,E], [−777:2,4-Et₂,4-CF₃,E], [−778:2,5-Et₂,4-CF₃,E], [−779:2,6-Et₂,4-CF₃,E], [−780:3,4-Et₂,4-CF₃,E], [−781:3,5-Et₂,4-CF₃,E], [−782:2,3-(CF₃)₂,4-CF₃,E], [−783:2,4-(CF₃)₂,4-CF₃,E], [−784:2,5-(CF₃)₂,4-CF₃,E], [−785:2,6-(CF₃)₂,4-CF₃,E], [−786:3,4-(CF₃)₂,4-CF₃,E], [−787:3,5-(CF₃)₂,4-CF₃,E], [−788:2,3-(CHF₂)₂,4-CF₃,E], [−789:2,4-(CHF₂)₂,4-CF₃,E], [−790:2,5-(CHF₂)₂,4-CF₃,E], [−791:2,6-(CHF₂)₂,4-CF₃,E], [−792:3,4-(CHF₂)₂,4-CF₃,E], [−793:3,5-(CHF₂)₂,4-CF₃,E], [−794:2,3-(CH₂F)₂,4-CF₃,E], [−795:2,4-(CH₂F)₂,4-CF₃,E], [−796:2,5-(CH₂F)₂,4-CF₃,E], [−797:2,6-(CH₂F)₂,4-CF₃,E], [−798:3,4-(CH₂F)₂,4-CF₃,E], [−799:3,5-(CH₂F)₂,4-CF₃,E], [−800:2,3-(MeO)₂,4-CF₃,E], [−801:2,4-(MeO)₂,4-CF₃,E], [−802:2,5-(MeO)₂,4-CF₃,E], [−803:2,6-(MeO)₂,4-CF₃,E], [−804:3,4-(MeO)₂,4-CF₃,E], [−805:3,5-(MeO)₂,4-CF₃,E], [−806:2,3-(EtO)₂,4-CF₃,E], [−807:2,4-(EtO)₂,4-CF₃,E], [−808:2,5-(EtO)₂,4-CF₃,E], [−809:2,6-(EtO)₂,4-CF₃,E], [−810:3,4-(EtO)₂,4-CF₃,E], [−811:3,5-(EtO)₂,4-CF₃,E], [−812:2-Cl-3-F,4-CF₃,E], [−813:2-Cl-4-F,4-CF₃,E], [−814:2-Cl-5-F,4-CF₃,E], [−815:2-Cl-6-F,4-CF₃,E], [−816:3-Cl-2-F,4-CF₃,E], [−817:3-Cl-4-F,4-CF₃,E], [−818:3-Cl-5-F,4-CF₃,E], [−819:4-Cl-2-F,4-CF₃,E], [−820:4-Cl-3-F,4-CF₃,E], [−821:2-F-3-Me,4-CF₃,E], [−822:2-F-4-Me,4-CF₃,E], [−823:2-F-5-Me,4-CF₃,E], [−824:2-F-6-Me,4-CF₃,E], [−825:3-F-2-Me,4-CF₃,E], [−826:3-F-4-Me,4-CF₃,E], [−827:3-F-5-Me,4-CF₃,E], [−828:4-F-2-Me,4-CF₃,E], [−829:4-F-3-Me,4-CF₃,E], [−830:2-Cl-3-Me,4-CF₃,E], [−831:2-Cl-4-Me,4-CF₃,E], [−832:2-Cl-5-Me,4-CF₃,E], [−833:2-Cl-6-Me,4-CF₃,E], [−834:3-Cl-2-Me,4-CF₃,E], [−835:3-Cl-4-Me,4-CF₃,E], [−836:3-Cl-5-Me,4-CF₃,E], [−837:4-Cl-2-Me,4-CF₃,E], [−838:4-Cl-3-Me,4-CF₃,E], [−839:2-F-3-CF₃,4-CF₃,E], [−840:2-F-4-CF₃,4-CF₃,E], [−841:2-F-5-CF₃,4-CF₃,E], [−842:2-F-6-CF₃,4-CF₃,E], [−843:3-F-2-CF₃,4-CF₃,E], [−844:3-F-4-CF₃,4-CF₃,E], [−845:3-F-5-CF₃,4-CF₃,E], [−846:4-F-2-CF₃,4-CF₃,E], [−847:4-F-3-CF₃,4-CF₃,E], [−848:2-Cl-3-CF₃,4-CF₃,E], [−849:2-Cl-4-CF₃,4-CF₃,E], [−850:2-Cl-5-CF₃,4-CF₃,E], [−851:2-Cl-6-CF₃,4-CF₃,E], [−852:3-Cl-2-CF₃,4-CF₃,E], [−853:3-Cl-4-CF₃,4-CF₃,E], [−854:3-Cl-5-CF₃,4-CF₃,E], [−855:4-Cl-2-CF₃,4-CF₃,E], [−856:4-Cl-3-CF₃,4-CF₃,E], [−857:2-Me-3-CF₃,4-CF₃,E], [−858:2-Me-4-CF₃,4-CF₃,E], [−859:2-Me-5-CF₃,4-CF₃,E], [−860:2-Me-6-CF₃,4-CF₃,E], [−861:3-Me-2-CF₃,4-CF₃,E], [−862:3-Me-4-CF₃,4-CF₃,E], [−863:3-Me-5-CF₃,4-CF₃,E], [−864:4-Me-2-CF₃,4-CF₃,E], [−865:4-Me-3-CF₃,4-CF₃,E], [−866:2-F-3-MeO,4-CF₃,E], [−867:2-F-4-MeO,4-CF₃,E], [−868:2-F-5-MeO,4-CF₃,E], [−869:2-F-6-MeO,4-CF₃,E], [−870:3-F-2-MeO,4-CF₃,E], [−871:3-F-4-MeO,4-CF₃,E], [−872:3-F-5-MeO,4-CF₃,E], [−873:4-F-2-MeO,4-CF₃,E], [−874:4-F-3-MeO,4-CF₃,E], [−875:2-Cl-3-MeO,4-CF₃,E], [−876:2-Cl-4-MeO,4-CF₃,E], [−877:2-Cl-5-MeO,4-CF₃,E], [−878:2-Cl-6-MeO,4-CF₃,E], [−879:3-Cl-2-MeO,4-CF₃,E], [−880:3-Cl-4-MeO,4-CF₃,E], [−881:3-Cl-5-MeO,4-CF₃,E], [−882:4-Cl-2-MeO,4-CF₃,E], [−883:4-Cl-3-MeO,4-CF₃,E], [−884:2-Me-3-MeO,4-CF₃,E], [−885:2-Me-4-MeO,4-CF₃,E], [−886:2-Me-5-MeO,4-CF₃,E], [−887:2-Me-6-MeO,4-CF₃,E], [−888:3-Me-2-MeO, 4-CF₃,E], [−889:3-Me-4-MeO,4-CF₃,E], [−890:3-Me-5-MeO, 4-CF₃,E], [−891:4-Me-2-MeO,4-CF₃,E], [−892:4-Me-3-MeO,4-CF₃,E],

[−893:H, 4-MeO,E], [−894:4-F, 4-MeO,E], [−895:4-F, 4-MeO,Z], [−896:4-Cl, 4-MeO,F], [−897:4-Cl, 4-MeO,Z], [−898:4-Br, 4-MeO,E], [−899:4-I,4-MeO,E], [−900:4-Me,4-MeO,E], [−901:4-Me, 4-MeO,Z], [−902:4-Et,4-MeO,E], [−903:4-C₃H₇,4-MeO,E], [−904:4-(Me)₂CH,4-MeO,E], [−905:4-CF₃,4-MeO,E], [−906:4-CF₃,4-MeO, Z], [−907:4-C₂F₅,4-MeO,E], [−908:4-C₃F₇,4-MeO,E], [−909:4-(CF₃)₂CF,4-MeO,E], [−910:4-(CF₃)₂CH,4-MeO,E], [−911:4-CHF₂-4-MeO,E], [−912:4-CH₂F,4-MeO,E], [−913:4-CF₃CH₂,4-MeO,E], [−914:4-MeO,4-MeO,E], [−915:4-MeO,4-MeO,Z], [−916:4-EtO,4-MeO,E], [−917:4-C₃H₇O,4-MeO,E], [−918:4-(Me)₂CHO,4-MeO,E], [−919:4-NO₂-4-MeO,E], [−920:4-NO₂,4-MeO,Z], [−921:3-F, 4-MeO,E], [−922:3-F, 4-MeO,Z], [−923:3-Cl-4-MeO,E], [−924:3-Cl, 4-MeO,Z], [−925:3-Br, 4-MeO,E], [−926:3-I,4-MeO,E], [−927:3-Me,4-MeO,E], [−928:3-Me,4-MeO,Z], [−929:3-Et,4-MeO,E], [−930:3-C₃H₇,4-MeO,E], [−931:3-(Me)₂CH,4-MeO,E], [−932:3-CF₃,4-MeO,E], [−933:3-CF₃,4-MeO,Z], [−934:3-C₂F₅,4-MeO,E], [−935:3-C₃F₇,4-MeO,E], [−936:3-(CF₃)₂CF,4-MeO,E], [−937:3-(CF₃)₂CH,4-MeO,E], [−938:3-CHF₂-4-MeO,E], [−939:3-CHF₂,4-MeO,Z], [−940:3-CH₂F, 4-MeO,E], [−941:3-CH₂F, 4-MeO, Z], [−942:3-CF₃CH₂,4-MeO,E], [−943:3-MeO,4-MeO,E], [−944:3-MeO,4-MeO,Z], [−945:3-EtO,4-MeO,E], [−946:3-C₃H₇O,4-MeO,E], [−947:3-(Me)₂CHO,4-MeO,E], [−948:3-NO₂,4-MeO,E], [−949:2-F,4-MeO,E], [−950:2-Cl,4-MeO,E], [−951:2-Br,4-MeO,E], [−952:2-I,4-MeO,E], [−953:2-Me,4-MeO,E], [−954:2-Et,4-MeO,E], [−955:2-C₃H₇,4-MeO,E], [−956:2-(Me)₂CH,4-MeO,E], [−957:2-CF₃,4-MeO,E], [−958:2-C₂F₅,4-

MeO,E], [-959:2-C₃F₇,4-MeO,E], [-960:2-(CF₃)₂CF,4-MeO,E], [-961:2-(CF₃)₂CH,4-MeO,E], [-962:2-CHF₂,4-MeO,E], [-963:2-CH₂F,4-MeO,E], [-964:2-CF₃CH₂,4-MeO,E], [-965:2-MeO,4-MeO,E], [-966:2-EtO,4-MeO,E], [-967:2-C₃H₇O,4-MeO,E], [-968:2-(Me)₂CHO,4-MeO,E], [-969:2-NO₂,4-MeO,E], [-970:2,3-F₂,4-MeO,E], [-971:2,4-F₂,4-MeO,E], [-972:2,5-F₂,4-MeO,E], [-973:2,6-F₂,4-MeO,E], [-974:3,4-F₂,4-MeO,E], [-975:3,4-F₂,4-MeO,Z], [-976:3,5-F₂,4-MeO,E], [-977:3,5-F₂,4-MeO,Z], [-978:2,3-Cl₂,4-MeO,E], [-979:2,3-Cl₂,4-MeO,Z], [-980:2,4-Cl₂,4-MeO,E], [-981:2,4-Cl₂,4-MeO,Z], [-982:2,5-Cl₂,4-MeO,E], [-983:2,5-Cl₂,4-MeO,Z], [-984:2,6-Cl₂,4-MeO,E], [-985:3,4-Cl₂,4-MeO,E], [-986:3,5-Cl₂,4-MeO,E], [-987:2,3-Br₂,4-MeO,E], [-988:2,4-Br₂,4-MeO,E], [-989:2,5-Br₂,4-MeO,E], [-990:2,6-Br₂,4-MeO,E], [-991:3,4-Br₂,4-MeO,E], [-992:3,5-Br₂,4-MeO,E], [-993:2,3-Me₂,4-MeO,E], [-994:2,4-Me₂,4-MeO,E], [-995:2,5-Me₂,4-MeO,E], [-996:2,6-Me₂,4-MeO,E], [-997:3,4-Me₂,4-MeO,E], [-998:3,5-Me₂,4-MeO,E], [-999:2,3-Et₂,4-MeO,E], [-1000:2,4-Et₂,4-MeO,E], [-1001:2,5-Et₂,4-MeO,E], [-1002:2,6-Et₂,4-MeO,E], [-1003:3,4-Et₂,4-MeO,E], [-1004:3,5-Et₂,4-MeO,E], [-1005:2,3-(CF₃)₂,4-MeO,E], [-1006:2,4-(CF₃)₂,4-MeO,E], [-1007:2,5-(CF₃)₂,4-MeO,E], [-1008:2,6-(CF₃)₂,4-MeO,E], [-1009:3,4-(CF₃)₂,4-MeO,E], [-1010:3,5-(CF₃)₂,4-MeO,E], [-1011:2,3-(CHF₂)₂,4-MeO,E], [-1012:2,4-(CHF₂)₂,4-MeO,E], [-1013:2,5-(CHF₂)₂,4-MeO,E], [-1014:2,6-(CHF₂)₂,4-MeO,E], [-1015:3,4-(CHF₂)₂,4-MeO,E], [-1016:3,5-(CHF₂)₂,4-MeO,E], [-1017:2,3-(CH₂F)₂,4-MeO,E], [-1018:2,4-(CH₂F)₂,4-MeO,E], [-1019:2,5-(CH₂F)₂,4-MeO,E], [-1020:2,6-(CH₂F)₂,4-MeO,E], [-1021:3,4-(CH₂F)₂,4-MeO,E], [-1022:3,5-(CH₂F)₂,4-MeO,E], [-1023:2,3-(MeO)₂,4-MeO,E], [-1024:2,4-(MeO)₂,4-MeO,E], [-1025:2,5-(MeO)₂,4-MeO,E], [-1026:2,6-(MeO)₂,4-MeO,E], [-1027:3,4-(MeO)₂,4-MeO,E], [-1028:3,5-(MeO)₂,4-MeO,E], [-1029:2,3-(EtO)₂,4-MeO,E], [-1030:2,4-(EtO)₂, 4-MeO,E], [-1031:2,5-(EtO)₂, 4-MeO,E], [-1032:2,6-(EtO)₂,4-MeO,E], [-1033:3,4-(EtO)₂,4-MeO,E], [-1034:3,5-(EtO)₂,4-MeO,E], [-1035:2-Cl-3-F,4-MeO,E], [-1036:2-Cl-4-F,4-MeO,E], [-1037:2-Cl-5-F,4-MeO,E], [-1038:2-Cl-6-F,4-MeO,E], [-1039:3-Cl-2-F,4-MeO,E], [-1040:3-Cl-4-F,4-MeO,E], [-1041:3-Cl-5-F,4-MeO,E], [-1042:4-Cl-2-F,4-MeO,E], [-1043:4-Cl-3-F,4-MeO,E], [-1044:2-F-3-Me,4-MeO,E], [-1045:2-F-4-Me,4-MeO,E], [-1046:2-F-5-Me,4-MeO,E], [-1047:2-F-6-Me,4-MeO,E], [-1048:3-F-2-Me,4-MeO,E], [-1049:3-F-4-Me,4-MeO,E], [-1050:3-F-5-Me,4-MeO,E], [-1051:4-F-2-Me,4-MeO,E], [-1052:4-F-3-Me,4-MeO,E], [-1053:2-Cl-3-Me,4-MeO,E], [-1054:2-Cl-4-Me,4-MeO,E], [-1055:2-Cl-5-Me,4-MeO,E], [-1056:2-Cl-6-Me,4-MeO,E], [-1057:3-Cl-2-Me,4-MeO,E], [-1058:3-Cl-4-Me,4-MeO,E], [-1059:3-Cl-5-Me,4-MeO,E], [-1060:4-Cl-2-Me,4-MeO,E], [-1061:4-Cl-3-Me,4-MeO,E], [-1062:2-F-3-CF₃,4-MeO,E], [-1063:2-F-4-CF₃,4-MeO,E], [-1064:2-F-5-CF₃,4-MeO,E], [-1065:2-F-6-CF₃,4-MeO,E], [-1066:3-F-2-CF₃,4-MeO,E], [-1067:3-F-4-CF₃,4-MeO,E], [-1068:3-F-5-CF₃,4-MeO,E], [-1069:4-F-2-CF₃,4-MeO,E], [-1070:4-F-3-CF₃,4-MeO,E], [-1071:2-Cl-3-CF₃,4-MeO,E], [-1072:2-Cl-4-CF₃,4-MeO,E], [-1073:2-Cl-5-CF₃,4-MeO,E], [-1074:2-Cl-6-CF₃,4-MeO,E], [-1075:3-Cl-2-CF₃,4-MeO,E], [-1076:3-Cl-4-CF₃,4-MeO,E], [-1077:3-Cl-5-CF₃,4-MeO,E], [-1078:4-Cl-2-CF₃,4-MeO,E], [-1079:4-Cl-3-CF₃,4-MeO,E], [-1080:2-Me-3-CF₃,4-MeO,E], [-1081:2-Me-4-CF₃,4-MeO,E], [-1082:2-Me-5-CF₃,4-MeO,E], [-1083:2-Me-6-CF₃,4-MeO,E], [-1084:3-Me-2-CF₃,4-MeO,E], [-1085:3-Me-4-CF₃,4-MeO,E], [-1086:3-Me-5-CF₃,4-MeO,E], [-1087:4-Me-2-CF₃,4-MeO,E], [-1088:4-Me-3-CF₃,4-MeO,E], [-1089:2-F-3-MeO,4-MeO,E], [-1090:2-F-4-MeO,4-MeO,E], [-1091:2-F-5-MeO,4-MeO,E], [-1092:2-F-6-MeO,4-MeO,E], [-1093:3-F-2-MeO,4-MeO,E], [-1094:3-F-4-MeO,4-MeO,E], [-1095:3-F-5-MeO,4-MeO,E], [-1096:4-F-2-MeO,4-MeO,E], [-1097:4-F-3-MeO,4-MeO,E], [-1098:2-Cl-3-MeO,4-MeO,E], [-1099:2-Cl-4-MeO,4-MeO,E], [-1100:2-Cl-5-MeO,4-MeO,E], [-1101:2-Cl-6-MeO,4-MeO,E], [-1102:3-Cl-2-MeO,4-MeO,E], [-1103:3-Cl-4-MeO,4-MeO,E], [-1104:3-Cl-5-MeO,4-MeO,E], [-1105:4-Cl-2-MeO,4-MeO,E], [-1106:4-Cl-3-MeO,4-MeO,E], [-1107:2-Me-3-MeO,4-MeO,E], [-1108:2-Me-4-MeO,4-MeO,E], [-1109:2-Me-5-MeO,4-MeO,E], [-1110:2-Me-6-MeO,4-MeO,E], [-1111:3-Me-2-MeO,4-MeO,E], [-1112:3-Me-4-MeO,4-MeO,E], [-1113:3-Me-5-MeO,4-MeO,E], [-1114:4-Me-2-MeO,4-MeO,E], [-1115:4-Me-3-MeO,4-MeO,E],

[-1116:H,4-(Me)₃CO,E], [-1117:4-F,4-(Me)₃CO,E], [-1118:4-F,4-(Me)₃CO,Z], [-1119:4-Cl,4-(Me)₃CO,E], [-1120:4-Cl,4-(Me)₃CO,Z], [-1121:4-Br,4-(Me)₃CO,E], [-1122:4-I,4-(Me)₃CO,E], [-1123:4-Me,4-(Me)₃CO,E], [-1124:4-Me,4-(Me)₃CO,Z], [-1125:4-Et,4-(Me)₃CO,E], [-1126:4-C₃H₇,4-(Me)₃CO,E], [-1127:4-(Me)₂CH,4-(Me)₃CO,E], [-1128:4-CF₃-4-(Me)₃CO,E], [-1129:4-CF₃,4-(Me)₃CO,Z], [-1130:4-C₂F₅,4-(Me)₃CO,E], [-1131:4-C₃F₇,4-(Me)₃CO,E], [-1132:4-(CF₃)₂CF,4-(Me)₃CO,E], [-1133:4-(CF₃)₂CH,4-(Me)₃CO,E], [-1134:4-CHF₂,4-(Me)₃CO,E], [-1135:4-CH₂F,4-(Me)₃CO,E], [-1136:4-CF₃CH₂,4-(Me)₃CO,E], [-1137:4-MeO,4-(Me)₃CO,E], [-1138:4-MeO,4-(Me)₃CO,Z], [-1139:4-EtO,4-(Me)₃CO,E], [-1140:4-C₃H₇O,4-(Me)₃CO,E], [-1141:4-(Me)₂CHO,4-(Me)₃CO,E], [-1142:4-NO₂,4-(Me)₃CO,E], [-1143:4-NO₂,4-(Me)₃CO,Z], [-1144:3-F,4-(Me)₃CO,E], [-1145:3-F,4-(Me)₃CO,Z], [-1146:3-Cl,4-(Me)₃CO,E], [-1147:3-Cl,4-(Me)₃CO,Z], [-1148:3-Br,4-(Me)₃CO,E], [-1149:3-I,4-(Me)₃CO,E], [-1150:3-Me,4-(Me)₃CO,E], [-1151:3-Me,4-(Me)₃CO,Z], [-1152:3-Et,4-(Me)₃CO,E], [-1153:3-C₃H₇,4-(Me)₃CO,E], [-1154:3-(Me)₂CH,4-(Me)₃CO,E], [-1155:3-CF₃, 4-(Me)₃CO,E], [-1156:3-CF₃,4-(Me)₃CO,Z], [-1157:3-C₂F₅, 4-(Me)₃CO,E], [-1158:3-C₃F₇,4-(Me)₃CO,E], [-1159:3-(CF₃)₂CF,4-(Me)₃CO,E], [-1160:3-(CF₃)₂CH,4-(Me)₃CO,E], [-1161:3-CHF₂, 4-(Me)₃CO,E], [-1162:3-CHF₂,4-(Me)₃CO,Z], [-1163:3-CH₂F,4-(Me)₃CO,E], [-1164:3-CH₂F,4-(Me)₃CO,Z], [-1165:3-CF₃CH₂, 4-(Me)₃CO,E], [-1166:3-MeO,4-(Me)₃CO,E], [-1167:3-MeO,4-(Me)₃CO,Z], [-1168:3-EtO,4-(Me)₃CO,E], [-1169:3-C₃H₇O,4-(Me)₃CO,E], [-1170:3-(Me)₂CHO,4-(Me)₃CO,E], [-1171:3-NO₂,4-(Me)₃CO,E], [-1172:2-F,4-(Me)₃CO,E], [-1173:2-Cl,4-(Me)₃CO,E], [-1174:2-Br,4-(Me)₃CO,E], [-1175:2-I,4-(Me)₃CO,E], [-1176:2-Me,4-(Me)₃CO,E], [-1177:2-Et,4-(Me)₃CO,E], [-1178:2-C₃H₇,4-(Me)₃CO,E], [-1179:2-(Me)₂CH,4-(Me)₃CO,E], [-1180:2-CF₃, 4-(Me)₃CO,E], [-1181:2-C₂F₅,4-(Me)₃CO,E], [-1182:2-C₃F₇,4-(Me)₃CO,E], [-1183:2-(CF₃)₂CF,4-(Me)₃CO,E], [-1184:2-(CF₃)₂CH, 4-(Me)₃CO,E], [-1185:2-CHF₂,4-(Me)₃CO,E], [-1186:2-CH₂F,4-(Me)₃CO,E], [-1187:2-CF₃CH₂,4-(Me)₃CO,E], [-1188:2-MeO,4-(Me)₃CO,E], [-1189:2-EtO,4-(Me)₃CO,E], [-1190:2-C₃H₇O,4-(Me)₃CO,E], [-1191:2-(Me)₂CHO,4-(Me)₃CO,E], [-1192:2-NO₂,4-(Me)₃CO,E], [-1193:2,3-F₂,4-(Me)₃CO,E], [-1194:2,4-F₂,4-(Me)₃CO,E], [-1195:2,5-F₂,4-(Me)₃CO,E], [-1196:2,6-F₂,4-(Me)₃CO,E], [-1197:3,4-F₂,4-(Me)₃CO,E], [-1198:3,4-F₂,4-(Me)₃CO,Z], [-1199:3,5-F₂,4-(Me)₃O,E], [-1200:3,5-F₂, 4-(Me)₃CO,Z], [−1201:2,3-Cl₂,4-(Me)₃CO,E], [−1202:2,3-Cl₂-4-(Me)₃CO,Z], [−1203:2,4-Cl₂,4-(Me)₃CO,E], [−1204:2,4-Cl₂,4-(Me)₃CO,Z], [−1205:2,5-Cl₂,4-(Me)₃CO,E], [−1206:2,5-Cl₂,4-(Me)₃CO,Z], [−1207:2,6-Cl₂,4-(Me)₃CO,E], [−1208:3,4-Cl₂,4-(Me)₃CO,E], [−1209:3,5-Cl₂,4-(Me)₃CO,E], [−1210:2,3-Br₂,4-(Me)₃CO,E], [−1211:2,4-Br₂,4-(Me)₃CO,E], [−1212:2,5-Br₂,4-(Me)₃CO,E], [−1213:2,6-Br₂,4-(Me)₃CO,E], [−1214:3,4-Br₂,4-(Me)₃CO,E], [−1215:3,5-Br₂,4-(Me)₃CO,E], [−1216:2,3-Me₂,4-(Me)₃CO,E], [−1217:2,4-Me₂,4-(Me)₃CO,E], [−1218:2,5-Me₂,4-(Me)₃CO,E], [−1219:2,6-Me₂,4-(Me)₃CO,E], [−1220:3,4-Me₂,4-(Me)₃CO,E], [−1221:3,5-Me₂,4-(Me)₃CO,E], [−1222:2,3-Et₂,4-(Me)₃CO,E], [−1223:2,4-Et₂,4-(Me)₃CO,E], [−1224:2,5-Et₂,4-(Me)₃CO,E], [−1225:2,6-Et₂,4-(Me)₃CO,E], [−1226:3,4-Et₂,4-(Me)₃CO,E], [−1227:3,5-Et₂,4-(Me)₃CO,E], [−1228:2,3-(CF₃)₂,4-(Me)₃CO,E], [−1229:2,4-(CF₃)₂,4-(Me)₃CO,E], [−1230:2,5-(CF₃)₂,4-(Me)₃CO,E], [−1231:2,6-(CF₃)₂,4-(Me)₃CO,E], [−1232:3,4-(CF₃)₂,4-(Me)₃CO,E], [−1233:3,5-(CF₃)₂,4-(Me)₃CO,E], [−1234:2,3-(HF₂)₂,4-(Me)₃CO,E], [−1235:2,4-(HF₂)₂,4-(Me)₃CO,E], [−1236:2,5-(HF₂)₂,4-(Me)₃CO,E], [−1237:2,6-(HF₂)₂,4-(Me)₃CO,E], [−1238:3,4-(HF₂)₂,4-(Me)₃CO,E], [−1239:3,5-(CHF₂)₂,4-(Me)₃CO,E], [−1240:2,3-(CH₂F)₂,4-(Me)₃CO,E], [−1241:2,4-(CH₂F)₂,4-(Me)₃CO,E], [−1242:2,5-(CH₂F)₂,4-(Me)₃CO,E], [−1243:2,6-(CH₂F)₂,4-(Me)₃CO,E], [−1244:3,4-(OH₂F)₂,4-(Me)₃CO,E], [−1245:3,5-(OH₂F)₂,4-(Me)₃CO,E], [−1246:2,3-(MeO)₂,4-(Me)₃CO,E], [−1247:2,4-(MeO)₂,4-(Me)₃CO,E], [−1248:2,5-(MeO)₂,4-(Me)₃CO,E], [−1249:2,6-(MeO)₂,4-(Me)₃CO,E], [−1250:3,4-(MeO)₂,4-(Me)₃CO,E], [−1251:3,5-(MeO)₂,4-(Me)₃O,E], [−1252:2,3-(EtO)₂,4-(Me)₃CO,E], [−1253:2,4-(EtO)₂,4-(Me)₃CO,E], [−1254:2,5-(EtO)₂,4-(Me)₃CO,E], [−1255:2,6-(EtO)₂,4-(Me)₃O,E], [−1256:3,4-(EtO)₂,4-(Me)₃CO,E], [−1257:3,5-(EtO)₂,4-(Me)₃O,E], [−1258:2-Cl-3-F,4-(Me)₃CO,E], [−1259:2-Cl-4-F,4-(Me)₃CO,E], [−1260:2-Cl-5-F,4-(Me)₃CO,E], [−1261:2-Cl-6-F,4-(Me)₃CO,E], [−1262:3-Cl-2-F,4-(Me)₃CO,E], [−1263:3-Cl-4-F,4-(Me)₃CO,E], [−1264:3-Cl-5-F,4-(Me)₃CO,E], [−1265:4-Cl-2-F,4-(Me)₃CO,E], [−1266:4-Cl-3-F,4-(Me)₃CO,E], [−1267:2-F-3-Me,4-(Me)₃CO,E], [−1268:2-F-4-Me,4-(Me)₃CO,E], [−1269:2-F-5-Me,4-(Me)₃CO,E], [−1270:2-F-6-Me,4-(Me)₃CO,E], [−1271:3-F-2-Me,4-(Me)₃CO,E], [−1272:3-F-4-Me,4-(Me)₃CO,E], [−1273:3-F-5-Me,4-(Me)₃CO,E], [−1274:4-F-2-Me,4-(Me)₃CO,E], [−1275:4-F-3-Me,4-(Me)₃CO,E], [−1276:2-Cl-3-Me,4-(Me)₃CO,E], [−1277:2-Cl-4-Me,4-(Me)₃CO,E], [−1278:2-Cl-5-Me,4-(Me)₃CO,E], [−1279:2-Cl-6-Me,4-(Me)₃CO,E], [−1280:3-Cl-2-Me,4-(Me)₃CO,E], [−1281:3-Cl-4-Me,4-(Me)₃CO,E], [−1282:3-Cl-5-Me,4-(Me)₃CO,E], [−1283:4-Cl-2-Me,4-(Me)₃CO,E], [−1284:4-Cl-3-Me,4-(Me)₃CO,E], [−1285:2-F-3-CF₃,4-(Me)₃CO,E], [−1286:2-F-4-CF₃,4-(Me)₃CO,E], [−1287:2-F-5-CF₃,4-(Me)₃CO,E], [−1288:2-F-6-CF₃,4-(Me)₃CO,E], [−1289:3-F-2-CF₃,4-(Me)₃CO,E], [−1290:3-F-4-CF₃,4-(Me)₃CO,E], [−1291:3-F-5-CF₃,4-(Me)₃CO,E], [−1292:4-F-2-CF₃,4-(Me)₃CO,E], [−1293:4-F-3-CF₃,4-(Me)₃CO,E], [−1294:2-Cl-3-CF₃,4-(Me)₃CO,E], [−1295:2-Cl-4-CF₃,4-(Me)₃CO,E], [−1296:2-Cl-5-CF₃,4-(Me)₃CO,E], [−1297:2-Cl-6-CF₃,4-(Me)₃CO,E], [−1298:3-Cl-2-CF₃,4-(Me)₃CO,E], [−1299:3-Cl-4-CF₃,4-(Me)₃CO,E], [−1300:3-Cl-5-CF₃,4-(Me)₃CO,E], [−1301:4-Cl-2-CF₃,4-(Me)₃CO,E], [−1302:4-Cl-3-F₃,4-(Me)₃CO,E], [−1303:2-Me-3-CF₃,4-(Me)₃CO,E], [−1304:2-Me-4-CF₃,4-(Me)₃CO,E], [−1305:2-Me-5-CF₃,4-(Me)₃CO,E], [−1306:2-Me-6-CF₃,4-(Me)₃CO,E], [−1307:3-Me-2-CF₃,4-(Me)₃CO,E], [−1308:3-Me-4-CF₃,4-(Me)₃CO,E], [−1309:3-Me-5-CF₃,4-(Me)₃CO,E], [−1310:4-Me-2-CF₃,4-(Me)₃CO,E], [−1311:4-Me-3-CF₃,4-(Me)₃CO,E], [−1312:2-F-3-MeO,4-(Me)₃CO,E], [−1313:2-F-4-MeO,4-(Me)₃CO,E], [−1314:2-F-5-MeO,4-(Me)₃CO,E], [−1315:2-F-6-MeO,4-(Me)₃CO,E], [−1316:3-F-2-MeO,4-(Me)₃CO,E], [−1317:3-F-4-MeO,4-(Me)₃CO,E], [−1318:3-F-5-MeO,4-(Me)₃CO,E], [−1319:4-F-2-MeO,4-(Me)₃CO,E], [−1320:4-F-3-MeO,4-(Me)₃CO,E], [−1321:2-Cl-3-MeO,4-(Me)₃CO,E], [−1322:2-Cl-4-MeO,4-(Me)₃CO,E], [−1323:2-Cl-5-MeO,4-(Me)₃CO,E], [−1324:2-Cl-6-MeO,4-(Me)₃CO,E], [−1325:3-Cl-2-MeO,4-(Me)₃CO,E], [−1326:3-Cl-4-MeO,4-(Me)₃CO,E], [−1327:3-Cl-5-MeO,4-(Me)₃CO,E], [−1328:4-Cl-2-MeO,4-(Me)₃CO,E], [−1329:4-Cl-3-MeO,4-(Me)₃CO,E], [−1330:2-Me-3-MeO,4-(Me)₃CO,E], [−1331:2-Me-4-MeO,4-(Me)₃CO,E], [−1332:2-Me-5-MeO,4-(Me)₃CO,E], [−1333:2-Me-6-MeO,4-(Me)₃CO,E], [−1334:3-Me-2-MeO,4-(Me)₃CO,E], [−1335:3-Me-4-MeO,4-(Me)₃CO,E], [−1336:3-Me-5-MeO,4-(Me)₃CO,E], [−1337:4-Me-2-MeO,4-(Me)₃CO,E], [−1338:4-Me-3-MeO,4-(Me)₃CO,E],

[−1339:H,3-F,E], [−1340:4-F,3-F,E], [−1341:4-F,3-F,Z], [−1342:4-Cl,3-F,E], [−1343:4-Cl,3-F,Z], [−1344:4-Br,3-F,E], [−1345:4-1,3-F,E], [−1346:4-Me,3-F,E], [−1347:4-Me,3-F,Z], [−1348:4-Et,3-F,E], [−1349:4-C₃H₇,3-F,E], [−1350:4-(Me)₂CH,3-F,E], [−1351:4-CF₃,3-F,E], [−1352:4-CF₃,3-F,Z], [−1353:4-C₂F₅,3-F,E], [−1354:4-C₃F₇,3-F,E], [−1355:4-(CF₃)₂CF,3-F,E], [−1356:4-(CF₃)₂CH,3-F,E], [−1357:4-CHF₂,3-F,E], [−1358:4-CH₂F,3-F,E], [−1359:4-CF₃CH₂,3-F,E], [−1360:4-MeO,3-F,E], [−1361:4-MeO,3-F,Z], [−1362:4-EtO,3-F,E], [−1363:4-C₃H₇O,3-F,E], [−1364:4-(Me)₂CHO,3-F,E], [−1365:4-NO₂,3-F,E], [−1366:4-NO₂,3-F,Z], [−1367:3-F,3-F,E], [−1368:3-F,3-F,Z], [−1369:3-Cl,3-F,E], [−1370:3-Cl,3-F,Z], [−1371:3-Br,3-F,E], [−1372:3-I,3-F,E], [−1373:3-Me,3-F,E], [−1374:3-Me,3-F,Z], [−1375:3-Et,3-F,E], [−1376:3-C₃H₇,3-F,E], [−1377:3-(Me)₂CH,3-F,E], [−1378:3-CF₃,3-F,E], [−1379:3-CF₃,3-F,Z], [−1380:3-C₂F₅,3-F,E], [−1381:3-C₃F₇,3-F,E], [−1382:3-(CF₃)₂CF,3-F,E], [−1383:3-(CF₃)₂CH,3-F,E], [−1384:3-CHF₂,3-F,E], [−1385:3-CHF₂,3-F,Z], [−1386:3-CH₂F,3-F,E], [−1387:3-CH₂F,3-F,Z], [−1388:3-CF₃CH₂,3-F,E], [−1389:3-MeO,3-F,E], [−1390:3-MeO,3-F,Z], [−1391:3-EtO,3-F,E], [−1392:3-C₃H₇O,3-F,E], [−1393:3-(Me)₂CHO,3-F,E], [−1394:3-NO₂,3-F,E], [−1395:2-F,3-F,E], [−1396:2-Cl,3-F,E], [−1397:2-Br,3-F,E], [−1398:2-I,3-F,E], [−1399:2-Me,3-F,E], [−1400:2-Et,3-F,E], [−1401:2-C₃H₇,3-F,E], [−1402:2-(Me)₂CH,3-F,E], [−1403:2-CF₃,3-F,E], [−1404:2-C₂F₅,3-F,E], [−1405:2-C₃F₇,3-F,E], [−1406:2-(CF₃)₂CF,3-F,E], [−1407:2-(CF₃)₂CH,3-F,E], [−1408:2-CHF₂,3-F,E], [−1409:2-CH₂F,3-F,E], [−1410:2-CF₃CH₂,3-F,E], [−1411:2-MeO,3-F,E], [−1412:2-EtO,3-F,E], [−1413:2-C₃H₇O,3-F,E], [−1414:2-(Me)₂CHO,3-F,E], [−1415:2-NO₂,3-F,E], [−1416:2,3-F₂,3-F,E], [−1417:2,4-F₂,3-F,E], [−1418:2,5-F₂,3-F,E], [−1419:2,6-F₂,3-F,E], [−1420:3,4-F₂,3-F,E], [−1421:3,4-F₂,3-F,Z], [−1422:3,5-F₂,3-F,E], [−1423:3,5-F₂,3-F,Z], [−1424:2,3-Cl₂,3-F,E], [−1425:2,3-Cl₂,3-F,Z], [−1426:2,4-Cl₂,3-F,E], [−1427:2,4-Cl₂,3-F,Z], [−1428:2,5-Cl₂,3-F,E], [−1429:2,5-Cl₂,3-F,Z], [−1430:2,6-Cl₂,3-F,E], [−1431:3,4-Cl₂,3-F,E], [−1432:3,5-Cl₂,3-F,E], [−1433:2,3-Br₂,3-F,E], [−1434:2,4-Br₂,3-F,E], [−1435:2,5-Br₂,3-F,E], [−1436:2,6-Br₂,3-F,E], [−1437:3,4-Br₂,3-F,E], [−1438:3,5-Br₂,3-F,E], [−1439:2,3-Me₂,3-F,E], [−1440:2,4-Me₂,3-F,E], [−1441:2,5-Me₂,3-F,E], [−1442:2,6-Me₂,3-F,E], [−1443:3,4-Me₂,3-F,E], [−1444:3,5-Me₂,3-F,E], [−1445:2,3-Et₂,3-F,E], [−1446:2,4-Et₂,3-F,E], [−1447:2,5-Et₂,3-F,E], [−1448:2,6-Et₂,3-F,E], [−1449:3,4-Et₂,3-F,E], [−1450:3,5-Et₂,3-F,E], [−1451:2,3-(CF₃)₂,3-F,E], [−1452:

2,4-(CF$_3$)$_2$,3-F,E], [–1453:2,5-(CF$_3$)$_2$,3-F,E], [–1454:2,6-(CF$_3$)$_2$,3-F,E], [–1455:3,4-(CF$_3$)$_2$,3-F,E], [–1456:3,5-(CF$_3$)$_2$,3-F,E], [–1457:2,3-(CHF$_2$)$_2$,3-F,E], [–1458:2,4-(CHF$_2$)$_2$,3-F,E], [–1459:2,5-(CHF$_2$)$_2$,3-F,E], [–1460:2,6-(CHF$_2$)$_2$,3-F,E], [–1461:3,4-(CHF$_2$)$_2$,3-F,E], [–1462:3,5-(CHF$_2$)$_2$,3-F,E], [–1463:2,3-(CH$_2$F)$_2$,3-F,E], [–1464:2,4-(CH$_2$F)$_2$,3-F,E], [–1465:2,5-(CH$_2$F)$_2$,3-F,E], [–1466:2,6-(CH$_2$F)$_2$,3-F,E], [–1467:3,4-(CH$_2$F)$_2$,3-F,E], [–1468:3,5-(CH$_2$F)$_2$,3-F,E], [–1469:2,3-(MeO)$_2$,3-F,E], [–1470:2,4-(MeO)$_2$,3-F,E], [–1471:2,5-(MeO)$_2$,3-F,E], [–1472:2,6-(MeO)$_2$,3-F,E], [–1473:3,4-(MeO)$_2$,3-F,E], [–1474:3,5-(MeO)$_2$,3-F,E], [–1475:2,3-(EtO)$_2$,3-F,E], [–1476:2,4-(EtO)$_2$,3-F,E], [–1477:2,5-(EtO)$_2$,3-F,E], [–1478:2,6-(EtO)$_2$,3-F,E], [–1479:3,4-(EtO)$_2$,3-F,E], [–1480:3,5-(EtO)$_2$,3-F,E], [–1481:2-Cl-3-F,3-F,E], [–1482:2-Cl-4-F,3-F,E], [–1483:2-Cl-5-F,3-F,E], [–1484:2-Cl-6-F,3-F,E], [–1485:3-Cl-2-F,3-F,E], [–1486:3-Cl-4-F,3-F,E], [–1487:3-Cl-5-F,3-F,E], [–1488:4-Cl-2-F,3-F,E], [–1489:4-Cl-3-F,3-F,E], [–1490:2-F-3-Me,3-F,E], [–1491:2-F-4-Me,3-F,E], [–1492:2-F-5-Me,3-F,E], [–1493:2-F-6-Me,3-F,E], [–1494:3-F-2-Me,3-F,E], [–1495:3-F-4-Me,3-F,E], [–1496:3-F-5-Me,3-F,E], [–1497:4-F-2-Me,3-F,E], [–1498:4-F-3-Me,3-F,E], [–1499:2-Cl-3-Me,3-F,E], [–1500:2-Cl-4-Me,3-F,E], [–1501:2-Cl-5-Me,3-F,E], [–1502:2-Cl-6-Me,3-F,E], [–1503:3-Cl-2-Me,3-F,E], [–1504:3-Cl-4-Me,3-F,E], [–1505:3-Cl-5-Me,3-F,E], [–1506:4-Cl-2-Me,3-F,E], [–1507:4-Cl-3-Me,3-F,E], [–1508:2-F-3-CF$_3$,3-F,E], [–1509:2-F-4-CF$_3$,3-F,E], [–1510:2-F-5-CF$_3$,3-F,E], [–1511:2-F-6-CF$_3$,3-F,E], [–1512:3-F-2-CF$_3$,3-F,E], [–1513:3-F-4-CF$_3$,3-F,E], [–1514:3-F-5-CF$_3$,3-F,E], [–1515:4-F-2-CF$_3$,3-F,E], [–1516:4-F-3-CF$_3$,3-F,E], [–1517:2-Cl-3-CF$_3$,3-F,E], [–1518:2-Cl-4-CF$_3$,3-F,E], [–1519:2-Cl-5-CF$_3$,3-F,E], [–1520:2-Cl-6-CF$_3$,3-F,E], [–1521:3-Cl-2-CF$_3$,3-F,E], [–1522:3-Cl-4-CF$_3$,3-F,E], [–1523:3-Cl-5-CF$_3$,3-F,E], [–1524:4-Cl-2-CF$_3$,3-F,E], [–1525:4-Cl-3-CF$_3$,3-F,E], [–1526:2-Me-3-CF$_3$,3-F,E], [–1527:2-Me-4-CF$_3$,3-F,E], [–1528:2-Me-5-CF$_3$,3-F,E], [–1529:2-Me-6-CF$_3$,3-F,E], [–1530:3-Me-2-CF$_3$,3-F,E], [–1531:3-Me-4-CF$_3$,3-F,E], [–1532:3-Me-5-CF$_3$,3-F,E], [–1533:4-Me-2-CF$_3$,3-F,E], [–1534:4-Me-3-CF$_3$,3-F,E], [–1535:2-F-3-MeO,3-F,E], [–1536:2-F-4-MeO,3-F,E], [–1537:2-F-5-MeO,3-F,E], [–1538:2-F-6-MeO,3-F,E], [–1539:3-F-2-MeO,3-F,E], [–1540:3-F-4-MeO,3-F,E], [–1541:3-F-5-MeO,3-F,E], [–1542:4-F-2-MeO,3-F,E], [–1543:4-F-3-MeO,3-F,E], [–1544:2-Cl-3-MeO,3-F,E], [–1545:2-Cl-4-MeO,3-F,E], [–1546:2-Cl-5-MeO,3-F,E], [–1547:2-Cl-6-MeO,3-F,E], [–1548:3-Cl-2-MeO,3-F,E], [–1549:3-Cl-4-MeO,3-F,E], [–1550:3-Cl-5-MeO,3-F,E], [–1551:4-Cl-2-MeO,3-F,E], [–1552:4-Cl-3-MeO,3-F,E], [–1553:2-Me-3-MeO,3-F,E], [–1554:2-Me-4-MeO,3-F,E], [–1555:2-Me-5-MeO,3-F,E], [–1556:2-Me-6-MeO,3-F,E], [–1557:3-Me-2-MeO,3-F,E], [–1558:3-Me-4-MeO,3-F,E], [–1559:3-Me-5-MeO,3-F,E], [–1560:4-Me-2-MeO,3-F,E], [–1561:4-Me-3-MeO,3-F,E], [–1562:H,3-Cl,E], [–1563:4-F,3-Cl,E], [–1564:4-F,3-Cl,Z], [–1565:4-Cl,3-Cl,E], [–1566:4-Cl,3-Cl,Z], [–1567:4-Br,3-Cl,E], [–1568:4-I,3-Cl,E], [–1569:4-Me,3-Cl,E], [–1570:4-Me,3-Cl,Z], [–1571:4-Et,3-Cl,E], [–1572:4-C$_3$H$_7$,3-Cl,E], [–1573:4-(Me)$_2$CH,3-Cl,E], [–1574:4-CF$_3$,3-Cl,E], [–1575:4-CF$_3$,3-Cl,Z], [–1576:4-C$_2$F$_5$,3-Cl,E], [–157 7:4-C$_3$F$_7$,3-Cl,E], [–1578:4-(CF$_3$)$_2$CF,3-Cl,E], [–1579:4-(CF$_3$)$_2$CH,3-Cl,E], [–1580:4-CHF$_2$,3-Cl,E], [–1581:4-CH$_2$F,3-Cl,E], [–1582:4-CF$_3$CH$_2$,3-Cl,E], [–1583:4-MeO,3-Cl,E], [–1584:4-MeO,3-Cl,E], [–1585:4-EtO,3-Cl,E], [–1586:4-C$_3$H$_7$O,3-Cl,E], [–1587:4-(Me)$_2$CHO,3-Cl,E], [–1588:4-NO$_2$,3-Cl,E], [–1589:4-NO$_2$,3-Cl,Z], [–15 90:3-F,3-Cl,E], [–1591:3-F,3-Cl,Z], [–1592:3-Cl,3-Cl,E], [–159 3:3-Cl,3-Cl,Z], [–1594:3-Br,3-Cl,E], [–1595:3-I,3-Cl,E], [–159 6:3-Me,3-Cl,E], [–1597:3-Me,3-Cl,Z], [–1598:3-Et,3-Cl,E], [–15 99:3-C$_3$H$_7$,3-Cl,E], [–1600:3-(Me)$_2$CH,3-Cl,E], [–1601:3-CF$_3$,3-Cl,E], [–1602:3-CF$_3$,3-Cl,Z], [–1603:3-C$_2$F$_5$,3-Cl,E], [–1604:3-C$_3$F$_7$,3-Cl,E], [–1605:3-(CF$_3$)$_2$CF,3-Cl,E], [–1606:3-(CF$_3$)$_2$CH,3-Cl,E], [–1607:3-CHF$_2$,3-Cl,E], [–1608:3-CHF$_2$,3-Cl,Z], [–1609:3-CH$_2$F,3-Cl,E], [–1610:3-CH$_2$F,3-Cl,Z], [–1611:3-CF$_3$CH$_2$,3-Cl,E], [–1612:3-MeO,3-Cl,E], [–1613:3-MeO,3-Cl,Z], [–1614:3-EtO,3-Cl,E], [–1615:3-C$_3$H$_7$O,3-Cl,E], [–1616:3-(Me)$_2$CHO,3-Cl,E], [–1617:3-NO$_2$,3-Cl,E], [–1618:2-F,3-Cl,E], [–1619:2-Cl,3-Cl,E], [–1620:2-Br,3-Cl,E], [–1621:2-I,3-Cl,E], [–1622:2-Me,3-Cl,E], [–1623:2-Et,3-Cl,E], [–1624:2-C$_3$H$_7$,3-Cl,E], [–1625:2-(Me)$_2$CH,3-Cl,E], [–1626:2-CF$_3$,3-Cl,E], [–1627:2-C$_2$F$_5$,3-Cl,E], [–1628:2-C$_3$F$_7$,3-Cl,E], [–1629:2-(CF$_3$)$_2$CF,3-Cl,E], [–1630:2-(CF$_3$)$_2$CH,3-Cl,E], [–1631:2-CHF$_2$,3-Cl,E], [–1632:2-CH$_2$F,3-Cl,E], [–1633:2-CF$_3$CH$_2$,3-Cl,E], [–1634:2-MeO,3-Cl,E], [–1635:2-EtO,3-Cl,E], [–1636:2-C$_3$H$_7$O,3-Cl,E], [–1637:2-(Me)$_2$CHO,3-Cl,E], [–1638:2-NO$_2$,3-Cl,E], [–1639:2,3-F$_2$,3-Cl,E], [–1640:2,4-F$_2$,3-Cl,E], [–1641:2,5-F$_2$,3-Cl,E], [–1642:2,6-F$_2$,3-Cl,E], [–1643:3,4-F$_2$,3-Cl,E], [–1644:3,4-F$_2$,3-Cl,Z], [–1645:3,5-F$_2$,3-Cl,E], [–1646:3,5-F$_2$,3-Cl,Z], [–1647:2,3-Cl$_2$,3-Cl,E], [–1648:2,3-Cl$_2$,3-Cl,Z], [–1649:2,4-Cl$_2$,3-Cl,E], [–1650:2,4-Cl$_2$,3-Cl,Z], [–1651:2,5-Cl$_2$,3-Cl,E], [–1652:2,5-Cl$_2$,3-Cl,Z], [–1653:2,6-Cl$_2$,3-Cl,E], [–1654:3,4-Cl$_2$,3-Cl,E], [–1655:3,5-Cl$_2$,3-Cl,E], [–1656:2,3-Br$_2$,3-Cl,E], [–1657:2,4-Br$_2$,3-Cl,E], [–1658:2,5-Br$_2$,3-Cl,E], [–1659:2,6-Br$_2$,3-Cl,E], [–1660:3,4-Br$_2$,3-Cl,E], [–1661:3,5-Br$_2$,3-Cl,E], [–1662:2,3-Me$_2$,3-Cl,E], [–1663:2,4-Me$_2$,3-Cl,E], [–1664:2,5-Me$_2$,3-Cl,E], [–1665:2,6-Me$_2$,3-Cl,E], [–1666:3,4-Me$_2$,3-Cl,E], [–1667:3,5-Me$_2$,3-Cl,E], [–1668:2,3-Et$_2$,3-Cl,E], [–1669:2,4-Et$_2$,3-Cl,E], [–1670:2,5-Et$_2$,3-Cl,E], [–1671:2,6-Et$_2$,3-Cl,E], [–1672:3,4-Et$_2$,3-Cl,E], [–1673:3,5-Et$_2$,3-Cl,E], [–1674:2,3-(CF$_3$)$_2$,3-Cl,E], [–1675:2,4-(CF$_3$)$_2$,3-Cl,E], [–1676:2,5-(CF$_3$)$_2$,3-Cl,E], [–1677:2,6-(CF$_3$)$_2$,3-Cl,E], [–1678:3,4-(CF$_3$)$_2$,3-Cl,E], [–1679:3,5-(CF$_3$)$_2$,3-Cl,E], [–1680:2,3-(CHF$_2$)$_2$,3-Cl,E], [–1681:2,4-(CHF$_2$)$_2$,3-Cl,E], [–1682:2,5-(CHF$_2$)$_2$,3-Cl,E], [–1683:2,6-(CHF$_2$)$_2$,3-Cl,E], [–1684:3,4-(CHF$_2$)$_2$,3-Cl,E], [–1685:3,5-(CHF$_2$)$_2$,3-Cl,E], [–1686:2,3-(CH$_2$F)$_2$,3-Cl,E], [–1687:2,4-(CH$_2$F)$_2$,3-Cl,E], [–1688:2,5-(CH$_2$F)$_2$,3-Cl,E], [–1689:2,6-(CH$_2$F)$_2$,3-Cl,E], [–1690:3,4-(CH$_2$F)$_2$,3-Cl,E], [–1691:3,5-(CH$_2$F)$_2$,3-Cl,E], [–1692:2,3-(MeO)$_2$,3-Cl,E], [–1693:2,4-(MeO)$_2$,3-Cl,E], [–1694:2,5-(MeO)$_2$,3-Cl,E], [–1695:2,6-(MeO)$_2$,3-Cl,E], [–1696:3,4-(MeO)$_2$,3-Cl,E], [–1697:3,5-(MeO)$_2$,3-Cl,E], [–1698:2,3-(EtO)$_2$,3-Cl,E], [–1699:2,4-(EtO)$_2$,3-Cl,E], [–1700:2,5-(EtO)$_2$,3-Cl,E], [–1701:2,6-(EtO)$_2$,3-Cl,E], [–1702:3,4-(EtO)$_2$,3-Cl,E], [–1703:3,5-(EtO)$_2$,3-Cl,E], [–1704:2-Cl-3-F,3-Cl,E], [–1705:2-Cl-4-F,3-Cl,E], [–1706:2-Cl-5-F,3-Cl,E], [–1707:2-Cl-6-F,3-Cl,E], [–1708:3-Cl-2-F,3-Cl,E], [–1709:3-Cl-4-F,3-Cl,E], [–1710:3-Cl-5-F,3-Cl,E], [–1711:4-Cl-2-F,3-Cl,E], [–1712:4-Cl-3-F,3-Cl,E], [–1713:2-F-3-Me,3-Cl,E], [–1714:2-F-4-Me,3-Cl,E], [–1715:2-F-5-Me,3-Cl,E], [–1716:2-F-6-Me,3-Cl,E], [–1717:3-F-2-Me,3-Cl,E], [–1718:3-F-4-Me,3-Cl,E], [–1719:3-F-5-Me,3-Cl,E], [–1720:4-F-2-Me,3-Cl,E], [–1721:4-F-3-Me,3-Cl,E], [–1722:2-Cl-3-Me,3-Cl,E], [–1723:2-Cl-4-Me,3-Cl,E], [–1724:2-Cl-5-Me,3-Cl,E], [–1725:2-Cl-6-Me,3-Cl,E], [–1726:3-Cl-2-Me,3-Cl,E], [–1727:3-Cl-4-Me,3-Cl,E], [–1728:3-Cl-5-Me,3-Cl,E], [–1729:4-Cl-2-Me,3-Cl,E], [–1730:4-Cl-3-Me,3-Cl,E], [–1731:2-F-3-CF$_3$,3-Cl,E], [–1732:2-F-4-CF$_3$,3-Cl,E], [–1733:2-F-5-CF$_3$,3-Cl,E], [–1734:2-F-6-CF$_3$,3-Cl,E],

[−1735:3-F-2-CF$_3$,3-Cl,E], [−1736:3-F-4-CF$_3$,3-Cl,E], [−1737:3-F-5-CF$_3$,3-Cl,E], [−1738:4-F-2-CF$_3$,3-Cl,E], [−1739:4-F-3-CF$_3$,3-Cl,E], [−1740:2-Cl-3-CF$_3$,3-Cl,E], [−1741:2-Cl-4-CF$_3$,3-Cl,E], [−1742:2-Cl-5-CF$_3$,3-Cl,E], [−1743:2-Cl-6-CF$_3$,3-Cl,E], [−1744:3-Cl-2-CF$_3$,3-Cl,E], [−1745:3-Cl-4-CF$_3$,3-Cl,E], [−1746:3-Cl-5-CF$_3$,3-Cl,E], [−1747:4-Cl-2-CF$_3$,3-Cl,E], [−1748:4-Cl-3-CF$_3$,3-Cl,E], [−1749:2-Me-3-CF$_3$,3-Cl,E], [−1750:2-Me-4-CF$_3$,3-Cl,E], [−1751:2-Me-5-CF$_3$,3-Cl,E], [−1752:2-Me-6-CF$_3$,3-Cl,E], [−1753:3-Me-2-CF$_3$,3-Cl,E], [−1754:3-Me-4-CF$_3$,3-Cl,E], [−1755:3-Me-5-CF$_3$,3-Cl,E], [−1756:4-Me-2-CF$_3$,3-Cl,E], [−1757:4-Me-3-CF$_3$,3-Cl,E], [−1758:2-F-3-MeO,3-Cl,E], [−1759:2-F-4-MeO,3-Cl,E], [−1760:2-F-5-MeO,3-Cl,E], [−1761:2-F-6-MeO,3-Cl,E], [−1762:3-F-2-MeO,3-Cl,E], [−1763:3-F-4-MeO,3-Cl,E], [−1764:3-F-5-MeO,3-Cl,E], [−1765:4-F-2-MeO,3-Cl,E], [−1766:4-F-3-MeO,3-Cl,E], [−1767:2-Cl-3-MeO,3-Cl,E], [−1768:2-Cl-4-MeO,3-Cl,E], [−1769:2-Cl-5-MeO,3-Cl,E], [−1770:2-Cl-6-MeO,3-Cl,E], [−1771:3-Cl-2-MeO,3-Cl,E], [−1772:3-Cl-4-MeO,3-Cl,E], [−1773:3-Cl-5-MeO,3-Cl,E], [−1774:4-Cl-2-MeO,3-Cl,E], [−1775:4-Cl-3-MeO,3-Cl,E], [−1776:2-Me-3-MeO,3-Cl,E], [−1777:2-Me-4-MeO,3-Cl,E], [−1778:2-Me-5-MeO,3-Cl,E], [−1779:2-Me-6-MeO,3-Cl,E], [−1780:3-Me-2-MeO,3-Cl,E], [−1781:3-Me-4-MeO,3-Cl,E], [−1782:3-Me-5-MeO,3-Cl,E], [−1783:4-Me-2-MeO,3-Cl,E], [−1784:4-Me-3-MeO,3-Cl,E],

[−1785:H,3-CF$_3$,E], [−1786:4-F,3-CF$_3$,E], [−1787:4-F,3-CF$_3$,Z], [−1788:4-Cl, 3-CF$_3$,E], [−1789:4-Cl, 3-CF$_3$,Z], [−1790:4-Br, 3-CF$_3$,E], [−1791:4-I,3-CF$_3$,E], [−1792:4-Me,3-CF$_3$,E], [−1793:4-Me,3-CF$_3$,Z], [−1794:4-Et, 3-CF$_3$,E], [−1795:4-C$_3$H$_7$, 3-CF$_3$,E], [−1796:4-(Me)$_2$CH, 3-CF$_3$,E], [−1797:4-CF$_3$,3-CF$_3$,E], [−1798:4-CF$_3$,3-CF$_3$,Z], [−1799:4-C$_2$F$_5$,3-CF$_3$,E], [−1800:4-C$_3$F$_7$,3-CF$_3$,E], [−1801:4-CF$_3$)$_2$CF,3-CF$_3$,E], [−1802:4-(CF$_3$)$_2$CH,3-CF$_3$,E], [−1803:4-CHF$_2$,3-CF$_3$,E], [−1804:4-CH$_2$F, 3-CF$_3$,E], [−1805:4-CF$_3$CH$_2$,3-CF$_3$,E], [−1806:4-MeO,3-CF$_3$,E], [−1807:4-MeO,3-CF$_3$,Z], [−1808:4-EtO,3-CF$_3$,E], [−1809:4-C$_3$H$_7$O,3-CF$_3$,E], [−1810:4-(Me)$_2$CHO,3-CF$_3$,E], [−1811:4-NO$_2$,3-CF$_3$,E], [−1812:4-NO$_2$,3-CF$_3$,Z], [−1813:3-F,3-CF$_3$,E], [−1814:3-F,3-CF$_3$,Z], [−1815:3-Cl, 3-CF$_3$,E], [−1816:3-Cl,3-CF$_3$,Z], [−1817:3-Br,3-CF$_3$,E], [−1818:3-I,3-CF$_3$,E], [−1819:3-Me,3-CF$_3$,E], [−1820:3-Me,3-CF$_3$,Z], [−1821:3-Et,3-CF$_3$,E], [−1822:3-Cl-3H$_7$,3-CF$_3$,E], [−1823:3-(Me)$_2$CH,3-CF$_3$,E], [−1824:3-CF$_3$,3-CF$_3$,E], [−1825:3-CF$_3$,3-CF$_3$,Z], [−1826:3-C$_2$F$_5$,3-CF$_3$,E], [−1827:3-C$_3$F$_7$,3-CF$_3$,E], [−1828:3-(CF$_3$)$_2$CF,3-CF$_3$,E], [−1829:3-(CF$_3$)$_2$CH,3-CF$_3$,E], [−1830:3-CHF$_2$,3-CF$_3$,E], [−1831:3-CHF$_2$,3-CF$_3$,Z], [−1832:3-CH$_2$F,3-CF$_3$,E], [−1833:3-CH$_2$F, 3-CF$_3$,Z], [−1834:3-CF$_3$CH$_2$,3-CF$_3$,E], [−1835:3-MeO,3-CF$_3$,E], [−1836:3-MeO,3-CF$_3$,Z], [−1837:3-EtO,3-CF$_3$,E], [−1838:3-C$_3$H$_7$O, 3-CF$_3$,E], [−1839:3-(Me)$_2$CHO, 3-CF$_3$,E], [−1840:3-NO$_2$,3-CF$_3$,E], [−1841:2-F,3-CF$_3$,E], [−1842:2-C$_{1-3}$-CF$_3$,E], [−1843:2-Br,3-CF$_3$,E], [−1844:2-I,3-CF$_3$,E], [−1845:2-Me,3-CF$_3$,E], [−1846:2-Et, 3-CF$_3$,E], [−1847:2-C$_3$H$_7$, 3-CF$_3$,E], [−1848:2-(Me)$_2$CH, 3-CF$_3$,E], [−1849:2-CF$_3$,3-CF$_3$,E], [−1850:2-C$_2$F$_5$,3-CF$_3$,E], [−1851:2-C$_3$F$_7$, 3-CF$_3$,E], [−1852:2-(CF$_3$)$_2$CF, 3-CF$_3$,E], [−1853:2-(CF$_3$)$_2$CH,3-CF$_3$,E], [−1854:2-CHF$_2$,3-CF$_3$,E], [−1855:2-CH$_2$F, 3-CF$_3$,E], [−1856:2-CF$_3$CH$_2$,3-CF$_3$,E], [−1857:2-MeO,3-CF$_3$,E], [−1858:2-EtO,3-CF$_3$,E], [−1859:2-C$_3$H$_7$O,3-CF$_3$,E], [−1860:2-(Me)$_2$CHO,3-CF$_3$,E], [−1861:2-NO$_2$,3-CF$_3$,E], [−1862:2,3-F$_2$,3-CF$_3$,E], [−1863:2,4-F$_2$,3-CF$_3$,E], [−1864:2,5-F$_2$,3-CF$_3$,E], [−1865:2,6-F$_2$,3-CF$_3$,E], [−1866:3,4-F$_2$,3-CF$_3$,E], [−1867:3,4-F$_2$,3-CF$_3$,Z], [−1868:3,5-F$_2$,3-CF$_3$,E], [−1869:3,5-F$_2$,3-CF$_3$,Z],

[−1870:2,3-Cl$_2$,3-CF$_3$,E], [−1871:2,3-Cl$_2$,3-CF$_3$,Z], [−1872:2,4-Cl$_2$,3-CF$_3$,E], [−1873:2,4-Cl$_2$,3-CF$_3$,Z], [−1874:2,5-Cl$_2$,3-CF$_3$,E], [−1875:2,5-Cl$_2$,3-CF$_3$,Z], [−1876:2,6-Cl$_2$,3-CF$_3$,E], [−1877:3,4-Cl$_2$,3-CF$_3$,E], [−1878:3,5-Cl$_2$,3-CF$_3$,E], [−1879:2,3-Br$_2$,3-CF$_3$,E], [−1880:2,4-Br$_2$,3-CF$_3$,E], [−1881:2,5-Br$_2$,3-CF$_3$,E], [−1882:2,6-Br$_2$,3-CF$_3$,E], [−1883:3,4-Br$_2$,3-CF$_3$,E], [−1884:3,5-Br$_2$,3-CF$_3$,E], [−1885:2,3-Me$_2$,3-CF$_3$,E], [−1886:2,4-Me$_2$,3-CF$_3$,E], [−1887:2,5-Me$_2$,3-CF$_3$,E], [−1888:2,6-Me$_2$,3-CF$_3$,E], [−1889:3,4-Me$_2$,3-CF$_3$,E], [−1890:3,5-Me$_2$,3-CF$_3$,E], [−1891:2,3-Et$_2$,3-CF$_3$,E], [−1892:2,4-Et$_2$,3-CF$_3$,E], [−1893:2,5-Et$_2$,3-CF$_3$,E], [−1894:2,6-Et$_2$,3-CF$_3$,E], [−1895:3,4-Et$_2$,3-CF$_3$,E], [−1896:3,5-Et$_2$,3-CF$_3$,E], [−1897:2,3-(CF$_3$)$_2$,3-CF$_3$,E], [−1898:2,4-(CF$_3$)$_2$,3-CF$_3$,E], [−1899:2,5-(CF$_3$)$_2$,3-CF$_3$,E], [−1900:2,6-(CF$_3$)$_2$,3-CF$_3$,E], [−1901:3,4-(CF$_3$)$_2$,3-CF$_3$,E], [−1902:3,5-(CF$_3$)$_2$,3-CF$_3$,E], [−1903:2,3-(CHF$_2$)$_2$,3-CF$_3$,E], [−1904:2,4-(CHF$_2$)$_2$,3-CF$_3$,E], [−1905:2,5-(CHF$_2$)$_2$,3-CF$_3$,E], [−1906:2,6-(CHF$_2$)$_2$,3-CF$_3$,E], [−1907:3,4-(CHF$_2$)$_2$,3-CF$_3$,E], [−1908:3,5-(CHF$_2$)$_2$,3-CF$_3$,E], [−1909:2,3-(CH$_2$F)$_2$,3-CF$_3$,E], [−1910:2,4-(CH$_2$F)$_2$,3-CF$_3$,E], [−1911:2,5-(CH$_2$F)$_2$,3-CF$_3$,E], [−1912:2,6-(CH$_2$F)$_2$,3-CF$_3$,E], [−1913:3,4-(CH$_2$F)$_2$,3-CF$_3$,E], [−1914:3,5-(CH$_2$F)$_2$,3-CF$_3$,E], [−1915:2,3-(MeO)$_2$,3-CF$_3$,E], [−1916:2,4-(MeO)$_2$,3-CF$_3$,E], [−1917:2,5-(MeO)$_2$,3-CF$_3$,E], [−1918:2,6-(MeO)$_2$,3-CF$_3$,E], [−1919:3,4-(MeO)$_2$,3-CF$_3$,E], [−1920:3,5-(MeO)$_2$,3-CF$_3$,E], [−1921:2,3-(EtO)$_2$,3-CF$_3$,E], [−1922:2,4-(EtO)$_2$,3-CF$_3$,E], [−1923:2,5-(EtO)$_2$,3-CF$_3$,E], [−1924:2,6-(EtO)$_2$,3-CF$_3$,E], [−1925:3,4-(EtO)$_2$,3-CF$_3$,E], [−1926:3,5-(EtO)$_2$,3-CF$_3$,E], [−1927:2-Cl-3-F,3-CF$_3$,E], [−1928:2-Cl-4-F,3-CF$_3$,E], [−1929:2-Cl-5-F,3-CF$_3$,E], [−1930:2-Cl-6-F,3-CF$_3$,E], [−1931:3-Cl-2-F,3-CF$_3$,E], [−1932:3-Cl-4-F,3-CF$_3$,E], [−1933:3-Cl-5-F,3-CF$_3$,E], [−1934:4-Cl-2-F,3-CF$_3$,E], [−1935:4-Cl-3-F,3-CF$_3$,E], [−1936:2-F-3-Me,3-CF$_3$,E], [−1937:2-F-4-Me,3-CF$_3$,E], [−1938:2-F-5-Me,3-CF$_3$,E], [−1939:2-F-6-Me,3-CF$_3$,E], [−1940:3-F-2-Me,3-CF$_3$,E], [−1941:3-F-4-Me,3-CF$_3$,E], [−1942:3-F-5-Me,3-CF$_3$,E], [−1943:4-F-2-Me,3-CF$_3$,E], [−1944:4-F-3-Me,3-CF$_3$,E], [−1945:2-Cl-3-Me,3-CF$_3$,E], [−1946:2-Cl-4-Me,3-CF$_3$,E], [−1947:2-Cl-5-Me,3-CF$_3$,E], [−1948:2-Cl-6-Me,3-CF$_3$,E], [−1949:3-Cl-2-Me,3-CF$_3$,E], [−1950:3-Cl-4-Me,3-CF$_3$,E], [−1951:3-Cl-5-Me,3-CF$_3$,E], [−1952:4-Cl-2-Me,3-CF$_3$,E], [−1953:4-Cl-3-Me,3-CF$_3$,E], [−1954:2-F-3-CF$_3$,3-CF$_3$,E], [−1955:2-F-4-CF$_3$,3-CF$_3$,E], [−1956:2-F-5-CF$_3$,3-CF$_3$,E], [−1957:2-F-6-CF$_3$,3-CF$_3$,E], [−1958:3-F-2-CF$_3$,3-CF$_3$,E], [−1959:3-F-4-CF$_3$,3-CF$_3$,E], [−1960:3-F-5-CF$_3$,3-CF$_3$,E], [−1961:4-F-2-CF$_3$,3-CF$_3$,E], [−1962:4-F-3-CF$_3$,3-CF$_3$,E], [−1963:2-Cl-3-CF$_3$,3-CF$_3$,E], [−1964:2-Cl-4-CF$_3$,3-CF$_3$,E], [−1965:2-Cl-5-CF$_3$,3-CF$_3$,E], [−1966:2-Cl-6-CF$_3$,3-CF$_3$,E], [−1967:3-Cl-2-CF$_3$,3-CF$_3$,E], [−1968:3-Cl-4-CF$_3$,3-CF$_3$,E], [−1969:3-Cl-5-CF$_3$,3-CF$_3$,E], [−1970:4-Cl-2-CF$_3$,3-CF$_3$,E], [−1971:4-Cl-3-CF$_3$,3-CF$_3$,E], [−1972:2-Me-3-CF$_3$,3-CF$_3$,E], [−1973:2-Me-4-CF$_3$,3-CF$_3$,E], [−1974:2-Me-5-CF$_3$,3-CF$_3$,E], [−1975:2-Me-6-CF$_3$,3-CF$_3$,E], [−1976:3-Me-2-CF$_3$,3-CF$_3$,E], [−1977:3-Me-4-CF$_3$,3-CF$_3$,E], [−1978:3-Me-5-CF$_3$,3-CF$_3$,E], [−1979:4-Me-2-CF$_3$,3-CF$_3$,E], [−1980:4-Me-3-CF$_3$,3-CF$_3$,E], [−1981:2-F-3-MeO,3-CF$_3$,E], [−1982:2-F-4-MeO,3-CF$_3$,E], [−1983:2-F-5-MeO,3-CF$_3$,E], [−1984:2-F-6-MeO,3-CF$_3$,E], [−1985:3-F-2-MeO,3-CF$_3$,E], [−1986:3-F-4-MeO,3-CF$_3$,E], [−1987:3-F-5-MeO,3-CF$_3$,E], [−1988:4-F-2-MeO,3-CF$_3$,E], [−1989:4-F-3-MeO,3-CF$_3$,E], [−1990:2-Cl-3-MeO,3-CF$_3$,E], [−1991:2-Cl-4-MeO,3-CF$_3$,E], [−1992:2-Cl-5-MeO,3-CF$_3$,E], [−1993:2-Cl-6-MeO,3-CF$_3$,E], [−1994:3-Cl-2-MeO,3-CF$_3$,E], [−1995:3-

Cl-4-MeO,3-CF₃,E], [−1996:3-Cl-5-MeO,3-CF₃,E], [−1997:4-Cl-2-MeO,3-CF₃,E], [−1998:4-Cl-3-MeO,3-CF₃,E], [−1999:2-Me-3-MeO,3-CF₃,E], [−2000:2-Me-4-MeO,3-CF₃,E], [−2001:2-Me-5-MeO,3-CF₃,E], [−2002:2-Me-6-MeO,3-CF₃,E], [−2003:3-Me-2-MeO,3-CF₃,E], [−2004:3-Me-4-MeO,3-CF₃,E], [−2005:3-Me-5-MeO,3-CF₃,E], [−2006:4-Me-2-MeO,3-CF₃,E], [−2007:4-Me-3-MeO,3-CF₃,E],

[−2008:H, 3-MeO,F]l, [−2009:4-F, 3-MeO,E], [−2010:4-F, 3-MeO, Z], [−2011:4-Cl,3-MeO,E], [−2012:4-Cl,3-MeO, Z], [−2013:4-Br,3-MeO,E], [−2014:4-I,3-MeO,E], [−2015:4-Me,3-MeO,E], [−2016:4-Me,3-MeO,Z], [−2017:4-Et, 3-MeO,E], [−2018:4-C₃H₇,3-MeO,E], [−2019:4-(Me)₂CH,3-MeO,E], [−2020:4-CF₃,3-MeO,E], [−2021:4-CF₃,3-MeO,Z], [−2022:4-C₂F₅,3-MeO,E], [−2023:4-C₃F₇,3-MeO,E], [−2024:4-(CF₃)₂CF,3-MeO,E], [−2025:4-(CF₃)₂CH,3-MeO,E], [−2026:4-CHF₂,3-MeO,E], [−2027:4-CH₂F,3-MeO,E], [−2028:4-CF₃CH₂,3-MeO,E], [−2029:4-MeO,3-MeO,E], [−2030:4-MeO,3-MeO,Z], [−2031:4-EtO,3-MeO,E], [−2032:4-C₃H₇O,3-MeO,E], [−2033:4-(Me)₂CHO,3-MeO,E], [−2034:4-NO₂,3-MeO,E], [−2035:4-NO₂,3-MeO,Z], [−2036:3-F,3-MeO,E], [−2037:3-F,3-MeO,Z], [−2038:3-Cl,3-MeO,E], [−2039:3-Cl,3-MeO,Z], [−2040:3-Br,3-MeO,E], [−2041:3-I,3-MeO,E], [−2042:3-Me,3-MeO,E], [−2043:3-Me,3-MeO, Z], [−2044:3-Et, 3-MeO,E], [−2045:3-C₃H₇,3-MeO,E], [−2046:3-(Me)₂CH,3-MeO,E], [−2047:3-CF₃,3-MeO,E], [−2048:3-CF₃,3-MeO, Z], [−2049:3-C₂F₅,3-MeO,E], [−2050:3-C₃F₇,3-MeO,E], [−2051:3-(CF₃)₂CF,3-MeO,E], [−2052:3-(CF₃)₂CH,3-MeO,E], [−2053:3-CHF₂,3-MeO,E], [−2054:3-CHF₂,3-MeO,Z], [−2055:3-CH₂F, 3-MeO,E], [−2056:3-CH₂F, 3-MeO, Z], [−2057:3-CF₃OCH₂,3-MeO,E], [−2058:3-MeO,3-MeO,E], [−2059:3-MeO,3-MeO,Z], [−2060:3-EtO,3-MeO,E], [−2061:3-C₃H₇O,3-MeO,E], [−2062:3-(Me)₂CHO,3-MeO,E], [−2063:3-NO₂,3-MeO,E], [−2064:2-F, 3-MeO,E], [−2065:2-Cl,3-MeO,E], [−2066:2-Br,3-MeO,E], [−2067:2-I,3-MeO,E], [−2068:2-Me,3-MeO,E], [−2069:2-Et,3-MeO,E], [−2070:2-C₃H₇,3-MeO,E], [−2071:2-(Me)₂CH,3-MeO,E], [−2072:2-CF₃,3-MeO,E], [−2073:2-C₂F₅,3-MeO,E], [−2074:2-C₃F₇,3-MeO,E], [−2075:2-(CF₃)₂CF,3-MeO,E], [−2076:2-(CF₃)₂CH,3-MeO,E], [−2077:2-CHF₂,3-MeO,E], [−2078:2-CH₂F,3-MeO,E], [−2079:2-CF₃CH₂,3-MeO,E], [−2080:2-MeO,3-MeO,E], [−2081:2-EtO,3-MeO,E], [−2082:2-C₃H₇O,3-MeO,E], [−2083:2-(Me)₂CHO,3-MeO,E], [−2084:2-NO₂,3-MeO,E], [−2085:2,3-F₂,3-MeO,E], [−2086:2,4-F₂,3-MeO,E], [−2087:2,5-F₂,3-MeO,E], [−2088:2,6-F₂,3-MeO,E], [−2089:3,4-F₂,3-MeO,E], [−2090:3,4-F₂,3-MeO,Z], [−2091:3,5-F₂,3-MeO,E], [−2092:3,5-F₂,3-MeO,Z], [−2093:2,3-Cl₂,3-MeO,E], [−2094:2,3-Cl₂,3-MeO, Z], [−2095:2,4-Cl₂,3-MeO,E], [−2096:2,4-Cl₂,3-MeO,Z], [−2097:2,5-Cl₂,3-MeO,E], [−2098:2,5-Cl₂,3-MeO,Z], [−2099:2,6-Cl₂,3-MeO,E], [−2100:3,4-Cl₂,3-MeO,E], [−2101:3,5-Cl₂,3-MeO,E], [−2102:2,3-Br₂,3-MeO,E], [−2103:2,4-Br₂,3-MeO,E], [−2104:2,5-Br₂,3-MeO,E], [−2105:2,6-Br₂,3-MeO,E], [−2106:3,4-Br₂,3-MeO,E], [−2107:3,5-Br₂,3-MeO,E], [−2108:2,3-Me₂,3-MeO,E], [−2109:2,4-Me₂,3-MeO,E], [−2110:2,5-Me₂,3-MeO,E], [−2111:2,6-Me₂,3-MeO,E], [−2112:3,4-Me₂,3-MeO,E], [−2113:3,5-Me₂,3-MeO,E], [−2114:2,3-Et₂,3-MeO,E], [−2115:2,4-Et₂,3-MeO,E], [−2116:2,5-Et₂,3-MeO,E], [−2117:2,6-Et₂,3-MeO,E], [−2118:3,4-Et₂,3-MeO,E], [−2119:3,5-Et₂,3-MeO,E], [−2120:2,3-(CF₃)₂,3-MeO,E], [−2121:2,4-(CF₃)₂,3-MeO,E], [−2122:2,5-(CF₃)₂,3-MeO,E], [−2123:2,6-(CF₃)₂,3-MeO,E], [−2124:3,4-(CF₃)₂,3-MeO,E], [−2125:3,5-(CF₃)₂,3-MeO,E], [−2126:2,3-(CHF₂)₂,3-MeO,E], [−2127:2,4-(CHF₂)₂,3-MeO,E], [−2128:2,5-(CHF₂)₂,3-MeO,E], [−2129:2,6-(CHF₂)₂,3-MeO,E], [−2130:3,4-(CHF₂)₂,3-MeO,E], [−2131:3,5-(CHF₂)₂,3-MeO,E], [−2132:2,3-(CH₂F)₂,3-MeO,E], [−2133:2,4-(CH₂F)₂,3-MeO,E], [−2134:2,5-(CH₂F)₂,3-MeO,E], [−2135:2,6-(CH₂F)₂,3-MeO,E], [−2136:3,4-(CH₂F)₂,3-MeO,E], [−2137:3,5-(CH₂F)₂,3-MeO,E], [−2138:2,3-(MeO)₂,3-MeO,E], [−2139:2,4-(MeO)₂,3-MeO,E], [−2140:2,5-(MeO)₂,3-MeO,E], [−2141:2,6-(MeO)₂,3-MeO,E], [−2142:3,4-(MeO)₂,3-MeO,E], [−2143:3,5-(MeO)₂,3-MeO,E], [−2144:2,3-(EtO)₂,3-MeO,E], [−2145:2,4-(EtO)₂,3-MeO,E], [−2146:2,5-(EtO)₂,3-MeO, E], [−2147:2,6-(EtO)₂,3-MeO,E], [−2148:3,4-(EtO)₂,3-MeO,E], [−2149:3,5-(EtO)₂,3-MeO,E], [−2150:2-Cl-3-F,3-MeO,E], [−2151:2-Cl-4-F,3-MeO,E], [−2152:2-Cl-5-F,3-MeO,E], [−2153:2-Cl-6-F,3-MeO,E], [−2154:3-Cl-2-F,3-MeO,E], [−2155:3-Cl-4-F,3-MeO,E], [−2156:3-Cl-5-F,3-MeO,E], [−2157:4-Cl-2-F,3-MeO,E], [−2158:4-Cl-3-F,3-MeO,E], [−2159:2-F-3-Me,3-MeO,E], [−2160:2-F-4-Me,3-MeO,E], [−2161:2-F-5-Me,3-MeO,E], [−2162:2-F-6-Me,3-MeO,E], [−2163:3-F-2-Me,3-MeO,E], [−2164:3-F-4-Me,3-MeO,E], [−2165:3-F-5-Me,3-MeO,E], [−2166:4-F-2-Me,3-MeO,E], [−2167:4-F-3-Me,3-MeO,E], [−2168:2-Cl-3-Me,3-MeO,E], [−2169:2-Cl-4-Me,3-MeO,E], [−2170:2-Cl-5-Me,3-MeO,E], [−2171:2-Cl-6-Me,3-MeO,E], [−2172:3-Cl-2-Me,3-MeO,E], [−2173:3-Cl-4-Me,3-MeO,E], [−2174:3-Cl-5-Me,3-MeO,E], [−2175:4-Cl-2-Me,3-MeO,E], [−2176:4-Cl-3-Me,3-MeO,E], [−2177:2-F-3-CF₃,3-MeO,E], [−2178:2-F-4-CF₃,3-MeO,E], [−2179:2-F-5-CF₃,3-MeO,E], [−2180:2-F-6-CF₃,3-MeO,E], [−2181:3-F-2-CF₃,3-MeO,E], [−2182:3-F-4-CF₃,3-MeO,E], [−2183:3-F-5-CF₃,3-MeO,E], [−2184:4-F-2-CF₃,3-MeO,E], [−2185:4-F-3-CF₃,3-MeO,E], [−2186:2-Cl-3-CF₃,3-MeO,E], [−2187:2-Cl-4-CF₃,3-MeO,E], [−2188:2-Cl-5-CF₃,3-MeO,E], [−2189:2-Cl-6-CF₃,3-MeO,E], [−2190:3-Cl-2-CF₃,3-MeO,E], [−2191:3-Cl-4-CF₃,3-MeO,E], [−2192:3-Cl-5-CF₃,3-MeO,E], [−2193:4-Cl-2-CF₃,3-MeO,E], [−2194:4-Cl-3-CF₃,3-MeO,E], [−2195:2-Me-3-CF₃,3-MeO,E], [−2196:2-Me-4-CF₃,3-MeO,E], [−2197:2-Me-5-CF₃,3-MeO,E], [−2198:2-Me-6-CF₃,3-MeO,E], [−2199:3-Me-2-CF₃,3-MeO,E], [−2200:3-Me-4-CF₃,3-MeO,E], [−2201:3-Me-5-CF₃,3-MeO,E], [−2202:4-Me-2-CF₃,3-MeO,E], [−2203:4-Me-3-CF₃,3-MeO,E], [−2204:2-F-3-MeO,3-MeO,E], [−2205:2-F-4-MeO,3-MeO,E], [−2206:2-F-5-MeO,3-MeO,E], [−2207:2-F-6-MeO,3-MeO,E], [−2208:3-F-2-MeO,3-MeO,E], [−2209:3-F-4-MeO,3-MeO,E], [−2210:3-F-5-MeO,3-MeO,E], [−2211:4-F-2-MeO,3-MeO,E], [−2212:4-F-3-MeO,3-MeO,E], [−2213:2-Cl-3-MeO,3-MeO,E], [−2214:2-Cl-4-MeO,3-MeO,E], [−2215:2-Cl-5-MeO,3-MeO,E], [−2216:2-Cl-6-MeO,3-MeO,E], [−2217:3-Cl-2-MeO,3-MeO,E], [−2218:3-Cl-4-MeO,3-MeO,E], [−2219:3-Cl-5-MeO,3-MeO,E], [−2220:4-Cl-2-MeO,3-MeO,E], [−2221:4-Cl-3-MeO,3-MeO,E], [−2222:2-Me-3-MeO,3-MeO,E], [−2223:2-Me-4-MeO,3-MeO,E], [−2224:2-Me-5-MeO,3-MeO,E], [−2225:2-Me-6-MeO,3-MeO,E], [−2226:3-Me-2-MeO,3-MeO,E], [−2227:3-Me-4-MeO,3-MeO,E], [−2228:3-Me-5-MeO,3-MeO,E], [−2229:4-Me-2-MeO,3-MeO,E], [−2230:4-Me-3-MeO,3-MeO,E],

[−2231:H,3-(Me)₃CO,E], [−2232:4-F,3-(Me)₃CO,E], [−2233:4-F,3-(Me)₃CO,Z], [−2234:4-Cl,3-(Me)₃CO,E], [−2235:4-Cl,3-(Me)₃CO,Z], [−2236:4-Br,3-(Me)₃CO,E], [−2237:4-I,3-(Me)₃CO,E], [−2238:4-Me,3-(Me)₃CO,E], [−2239:4-Me,3-(Me)₃CO,Z], [−2240:4-Et,3-(Me)₃CO,E], [−2241:4-C₃H₇,3-(Me)₃CO,E], [−2242:4-(Me)₂CH,3-(Me)₃CO,E], [−2243:4-CF₃,3-(Me)₃CO,E], [−2244:4-CF₃,3-(Me)₃CO,Z], [−2245:4-C₂F₅,3-(Me)₃CO,E],

[−2246:4-$C_3F_7$,3-(Me)$_3$CO,E], [−2247:4-(CF$_3$)$_2$CF,3-(Me)$_3$CO,E], [−2248:4-(CF$_3$)$_2$CH,3-(Me)$_3$CO,E], [−2249:4-CHF$_2$,3-(Me)$_3$CO,E], [−2250:4-CH$_2$F,3-(Me)$_3$CO,E], [−2251:4-CF$_3$CH$_2$,3-(Me)$_3$CO,E], [−2252:4-MeO,3-(Me)$_3$CO,E], [−2253:4-MeO,3-(Me)$_3$CO,Z], [−2254:4-EtO,3-(Me)$_3$CO,E], [−2255:4-$C_3H_7$O,3-(Me)$_3$CO,E], [−2256:4-(Me)$_2$CHO,3-(Me)$_3$CO,E], [−2257:4-NO$_2$,3-(Me)$_3$CO,E], [−2258:4-NO$_2$,3-(Me)$_3$CO,Z], [−2259:3-F,3-(Me)$_3$CO,E], [−2260:3-F,3-(Me)$_3$CO,Z], [−2261:3-Cl,3-(Me)$_3$CO,E], [−2262:3-Cl,3-(Me)$_3$CO,Z], [−2263:3-Br,3-(Me)$_3$CO,E], [−2264:3-I,3-(Me)$_3$CO,E], [−2265:3-Me,3-(Me)$_3$CO,E], [−2266:3-Me,3-(Me)$_3$CO,Z], [−2267:3-Et,3-(Me)$_3$CO,E], [−2268:3-$C_3H_7$,3-(Me)$_3$CO,E], [−2269:3-(Me)$_2$CH,3-(Me)$_3$CO,E], [−2270:3-CF$_3$,3-(Me)$_3$CO,E], [−2271:3-CF$_3$,3-(Me)$_3$CO,Z], [−2272:3-$C_2F_5$,3-(Me)$_3$CO,E], [−2273:3-$C_3F_7$,3-(Me)$_3$CO,E], [−2274:3-(CF$_3$)$_2$CF,3-(Me)$_3$CO,E], [−2275:3-(CF$_3$)$_2$CH,3-(Me)$_3$CO,E], [−2276:3-CHF$_2$,3-(Me)$_3$CO,E], [−2277:3-CHF$_2$,3-(Me)$_3$CO,Z], [−2278:3-CH$_2$F,3-(Me)$_3$CO,E], [−2279:3-CH$_2$F,3-(Me)$_3$CO,Z], [−2280:3-CF$_3$CH$_2$,3-(Me)$_3$CO,E], [−2281:3-MeO,3-(Me)$_3$CO,E], [−2282:3-MeO,3-(Me)$_3$CO,Z], [−2283:3-EtO,3-(Me)$_3$CO,E], [−2284:3-$C_3H_7$O,3-(Me)$_3$CO,E], [−2285:3-(Me)$_2$CHO,3-(Me)$_3$CO,E], [−2286:3-NO$_2$,3-(Me)$_3$CO,E], [−2287:2-F,3-(Me)$_3$CO,E], [−2288:2-Cl,3-(Me)$_3$CO,E], [−2289:2-Br,3-(Me)$_3$CO,E], [−2290:2-I,3-(Me)$_3$CO,E], [−2291:2-Me,3-(Me)$_3$CO,E], [−2292:2-Et,3-(Me)$_3$CO,E], [−2293:2-$C_3H_7$,3-(Me)$_3$CO,E], [−2294:2-(Me)$_2$CH,3-(Me)$_3$CO,E], [−2295:2-CF$_3$,3-(Me)$_3$CO,E], [−2296:2-$C_2F_5$,3-(Me)$_3$CO,E], [−2297:2-$C_3F_7$,3-(Me)$_3$CO,E], [−2298:2-(CF$_3$)$_2$CF,3-(Me)$_3$CO,E], [−2299:2-(CF$_3$)$_2$CH,3-(Me)$_3$CO,E], [−2300:2-CHF$_2$,3-(Me)$_3$CO,E], [−2301:2-CH$_2$F,3-(Me)$_3$CO,E], [−2302:2-CF$_3$CH$_2$,3-(Me)$_3$CO,E], [−2303:2-MeO,3-(Me)$_3$CO,E], [−2304:2-EtO,3-(Me)$_3$CO,E], [−2305:2-$C_3H_7$O,3-(Me)$_3$CO,E], [−2306:2-(Me)$_2$CHO,3-(Me)$_3$CO,E], [−2307:2-NO$_2$,3-(Me)$_3$CO,E], [−2308:2,3-F$_2$,3-(Me)$_3$CO,E], [−2309:2,4-F$_2$,3-(Me)$_3$CO,E], [−2310:2,5-F$_2$,3-(Me)$_3$CO,E], [−2311:2,6-F$_2$,3-(Me)$_3$CO,E], [−2312:3,4-F$_2$,3-(Me)$_3$CO,E], [−2313:3,4-F$_2$,3-(Me)$_3$CO,Z], [−2314:3,5-F$_2$,3-(Me)$_3$O,E], [−2315:3,5-F$_2$,3-(Me)$_3$CO,Z], [−2316:2,3-Cl$_2$,3-(Me)$_3$CO,E], [−2317:2,3-Cl$_2$,3-(Me)$_3$CO,Z], [−2318:2,4-Cl$_2$,3-(Me)$_3$CO,E], [−2319:2,4-Cl$_2$,3-(Me)$_3$CO,Z], [−2320:2,5-Cl$_2$,3-(Me)$_3$CO,E], [−2321:2,5-Cl$_2$,3-(Me)$_3$CO,Z], [−2322:2,6-Cl$_2$,3-(Me)$_3$CO,E], [−2323:3,4-Cl$_2$,3-(Me)$_3$CO,E], [−2324:3,5-Cl$_2$,3-(Me)$_3$CO,E], [−2325:2,3-Br$_2$,3-(Me)$_3$CO,E], [−2326:2,4-Br$_2$,3-(Me)$_3$CO,E], [−2327:2,5-Br$_2$,3-(Me)$_3$CO,E], [−2328:2,6-Br$_2$,3-(Me)$_3$CO,E], [−2329:3,4-Br$_2$,3-(Me)$_3$CO,E], [−2330:3,5-Br$_2$,3-(Me)$_3$CO,E], [−2331:2,3-Me$_2$,3-(Me)$_3$CO,E], [−2332:2,4-Me$_2$,3-(Me)$_3$CO,E], [−2333:2,5-Me$_2$,3-(Me)$_3$O,E], [−2334:2,6-Me$_2$,3-(Me)$_3$CO,E], [−2335:3,4-Me$_2$,3-(Me)$_3$CO,E], [−2336:3,5-Me$_2$,3-(Me)$_3$O,E], [−2337:2,3-Et$_2$,3-(Me)$_3$CO,E], [−2338:2,4-Et$_2$,3-(Me)$_3$CO,E], [−2339:2,5-Et$_2$,3-(Me)$_3$CO,E], [−2340:2,6-Et$_2$,3-(Me)$_3$CO,E], [−2341:3,4-Et$_2$,3-(Me)$_3$CO,E], [−2342:3,5-Et$_2$,3-(Me)$_3$CO,E], [−2343:2,3-(CF$_3$)$_2$,3-(Me)$_3$CO,E], [−2344:2,4-(CF$_3$)$_2$,3-(Me)$_3$CO,E], [−2345:2,5-(CF$_3$)$_2$,3-(Me)$_3$CO,E], [−2346:2,6-(CF$_3$)$_2$,3-(Me)$_3$CO,E], [−2347:3,4-(CF$_3$)$_2$,3-(Me)$_3$CO,E], [−2348:3,5-(CF$_3$)$_2$,3-(Me)$_3$CO,E], [−2349:2,3-(HF$_2$)$_2$,3-(Me)$_3$O,E], [−2350:2,4-(HF$_2$)$_2$,3-(Me)$_3$CO,E], [−2351:2,5-(HF$_2$)$_2$,3-(Me)$_3$CO,E], [−2352:2,6-(HF$_2$)$_2$,3-(Me)$_3$CO,E], [−2353:3,4-(HF$_2$)$_2$,3-(Me)$_3$CO,E], [−2354:3,5-(CHF$_2$)$_2$,3-(Me)$_3$CO,E], [−2355:2,3-(CH$_2$F)$_2$,3-(Me)$_3$CO,E], [−2356:2,4-(CH$_2$F)$_2$,3-(Me)$_3$CO,E], [−2357:2,5-(CH$_2$F)$_2$,3-(Me)$_3$CO,E], [−2358:2,6-(CH$_2$F)$_2$,3-(Me)$_3$CO,E], [−2359:3,4-(CH$_2$F)$_2$,3-(Me)$_3$CO,E], [−2360:3,5-(CH$_2$F)$_2$,3-(Me)$_3$CO,E], [−2361:2,3-(MeO)$_2$,3-(Me)$_3$CO,E], [−2362:2,4-(MeO)$_2$,3-(Me)$_3$Cl,E], [−2363:2,5-(MeO)$_2$,3-(Me)$_3$CO,E], [−2364:2,6-(MeO)$_2$,3-(Me)$_3$CO,E], [−2365:3,4-(MeO)$_2$,3-(Me)$_3$CO,E], [−2366:3,5-(MeO)$_2$,3-(Me)$_3$O,E], [−2367:2,3-(EtO)$_2$,3-(Me)$_3$CO,E], [−2368:2,4-(EtO)$_2$,3-(Me)$_3$CO,E], [−2369:2,5-(EtO)$_2$,3-(Me)$_3$CO,E], [−2370:2,6-(EtO)$_2$,3-(Me)$_3$CO,E], [−2371:3,4-(EtO)$_2$,3-(Me)$_3$CO,E], [−2372:3,5-(EtO)$_2$,3-(Me)$_3$CO,E], [−2373:2-Cl-3-F,3-(Me)$_3$CO,E], [−2374:2-Cl-4-F,3-(Me)$_3$CO,E], [−2375:2-Cl-5-F,3-(Me)$_3$CO,E], [−2376:2-Cl-6-F,3-(Me)$_3$CO,E], [−2377:3-Cl-2-F,3-(Me)$_3$CO,E], [−2378:3-Cl-4-F,3-(Me)$_3$CO,E], [−2379:3-Cl-5-F,3-(Me)$_3$CO,E], [−2380:4-Cl-2-F,3-(Me)$_3$CO,E], [−2381:4-Cl-3-F,3-(Me)$_3$CO,E], [−2382:2-F-3-Me,3-(Me)$_3$CO,E], [−2383:2-F-4-Me,3-(Me)$_3$CO,E], [−2384:2-F-5-Me,3-(Me)$_3$CO,E], [−2385:2-F-6-Me,3-(Me)$_3$CO,E], [−2386:3-F-2-Me,3-(Me)$_3$CO,E], [−2387:3-F-4-Me,3-(Me)$_3$CO,E], [−2388:3-F-5-Me,3-(Me)$_3$CO,E], [−2389:4-F-2-Me,3-(Me)$_3$CO,E], [−2390:4-F-3-Me,3-(Me)$_3$CO,E], [−2391:2-Cl-3-Me,3-(Me)$_3$CO,E], [−2392:2-Cl-4-Me,3-(Me)$_3$CO,E], [−2393:2-Cl-5-Me,3-(Me)$_3$CO,E], [−2394:2-Cl-6-Me,3-(Me)$_3$CO,E], [−2395:3-Cl-2-Me,3-(Me)$_3$CO,E], [−2396:3-Cl-4-Me,3-(Me)$_3$CO,E], [−2397:3-Cl-5-Me,3-(Me)$_3$CO,E], [−2398:4-Cl-2-Me,3-(Me)$_3$CO,E], [−2399:4-Cl-3-Me,3-(Me)$_3$CO,E], [−2400:2-F-3-CF$_3$,3-(Me)$_3$CO,E], [−2401:2-F-4-CF$_3$,3-(Me)$_3$CO,E], [−2402:2-F-5-CF$_3$,3-(Me)$_3$CO,E], [−2403:2-F-6-CF$_3$,3-(Me)$_3$CO,E], [−2404:3-F-2-CF$_3$,3-(Me)$_3$CO,E], [−2405:3-F-4-CF$_3$,3-(Me)$_3$CO,E], [−2406:3-F-5-CF$_3$,3-(Me)$_3$CO,E], [−2407:4-F-2-CF$_3$,3-(Me)$_3$CO,E], [−2408:4-F-3-CF$_3$,3-(Me)$_3$CO,E], [−2409:2-Cl-3-CF$_3$,3-(Me)$_3$CO,E], [−2410:2-Cl-4-CF$_3$,3-(Me)$_3$CO,E], [−2411:2-Cl-5-CF$_3$,3-(Me)$_3$CO,E], [−2412:2-Cl-6-CF$_3$,3-(Me)$_3$CO,E], [−2413:3-Cl-2-CF$_3$,3-(Me)$_3$CO,E], [−2414:3-Cl-4-CF$_3$,3-(Me)$_3$CO,E], [−2415:3-Cl-5-CF$_3$,3-(Me)$_3$CO,E], [−2416:4-Cl-2-CF$_3$,3-(Me)$_3$CO,E], [−2417:4-Cl-3-F,3-(Me)$_3$CO,E], [−2418:2-Me-3-CF$_3$,3-(Me)$_3$CO,E], [−2419:2-Me-4-CF$_3$,3-(Me)$_3$CO,E], [−2420:2-Me-5-CF$_3$,3-(Me)$_3$CO,E], [−2421:2-Me-6-CF$_3$,3-(Me)$_3$CO,E], [−2422:3-Me-2-CF$_3$,3-(Me)$_3$CO,E], [−2423:3-Me-4-CF$_3$,3-(Me)$_3$CO,E], [−2424:3-Me-5-CF$_3$,3-(Me)$_3$CO,E], [−2425:4-Me-2-CF$_3$,3-(Me)$_3$CO,E], [−2426:4-Me-3-CF$_3$,3-(Me)$_3$CO,E], [−2427:2-F-3-MeO,3-(Me)$_3$O,E], [−2428:2-F-4-MeO,3-(Me)$_3$O,E], [−2429:2-F-5-MeO,3-(Me)$_3$CO,E], [−2430:2-F-6-MeO,3-(Me)$_3$CO,E], [−2431:3-F-2-MeO,3-(Me)$_3$CO,E], [−2432:3-F-4-MeO,3-(Me)$_3$CO,E], [−2433:3-F-5-MeO,3-(Me)$_3$CO,E], [−2434:4-F-2-MeO,3-(Me)$_3$CO,E], [−2435:4-F-3-MeO,3-(Me)$_3$CO,E], [−2436:2-Cl-3-MeO,3-(Me)$_3$CO,E], [−2437:2-Cl-4-MeO,3-(Me)$_3$CO,E], [−2438:2-Cl-5-MeO,3-(Me)$_3$CO,E], [−2439:2-Cl-6-MeO,3-(Me)$_3$CO,E], [−2440:3-Cl-2-MeO,3-(Me)$_3$CO,E], [−2441:3-Cl-4-MeO,3-(Me)$_3$CO,E], [−2442:3-Cl-5-MeO,3-(Me)$_3$CO,E], [−2443:4-Cl-2-MeO,3-(Me)$_3$CO,E], [−2444:4-Cl-3-MeO,3-(Me)$_3$CO,E], [−2445:2-Me-3-MeO,3-(Me)$_3$CO,E], [−2446:2-Me-4-MeO,3-(Me)$_3$CO,E], [−2447:2-Me-5-MeO,3-(Me)$_3$CO,E], [−2448:2-Me-6-MeO,3-(Me)$_3$CO,E], [−2449:3-Me-2-MeO,3-(Me)$_3$CO,E], [−2450:3-Me-4-MeO,3-(Me)$_3$CO,E], [−2451:3-Me-5-MeO,3-(Me)$_3$CO,E], [−2452:4-Me-2-MeO,3-(Me)$_3$CO,E], [−2453:4-Me-3-MeO,3-(Me)$_3$CO,E],

[−2454:H,2-F,E], [−2455:4-F,2-F,E], [−2456:4-F,2-F,Z], [−2457:4-Cl$_2$-F,E], [−2458:4-Cl$_2$-F,Z], [−2459:4-Br,2-F,E], [−2460:4-I,2-F,E], [−2461:4-Me,2-F,E], [−2462:4-Me,2-F,Z], [−2463:4-Et,2-F,E], [−2464:4-$C_3H_7$,2-F,E], [−2465:4-(Me)$_2$CH,2-F,E], [−2466:4-CF$_3$,2-F,E], [−2467:4-CF$_3$,2-F,Z], [−2468:4-$C_2F_5$,2-F,E], [−2469:4-$C_3F_7$,2-F,E], [−2470:4-(CF$_3$)$_2$CF,2-F,E], [−2471:4-(CF$_3$)$_2$CH,2-F,

E], [-2472:4-CHF$_2$,2-F,E], [-2473:4-CH$_2$F,2-F,E], [-2474:4-CF$_3$CH$_2$,2-F,E], [-2475:4-MeO,2-F,E], [-2476:4-MeO,2-F,Z], [-2477:4-EtO,2-F,E], [-2478:4-C$_3$H$_7$O,2-F,E], [-2479:4-(Me)$_2$CHO,2-F,E], [-2480:4-NO$_2$,2-F,E], [-2481:4-NO$_2$,2-F,Z], [-2482:3-F,2-F,E], [-2483:3-F,2-F,Z], [-2484:3-Cl,2-F,E], [-2485:3-Cl,2-F,Z], [-2486:3-Br,2-F,E], [-2487:3-I,2-F,E], [-2488:3-Me,2-F,E], [-2489:3-Me,2-F,Z], [-2490:3-Et,2-F,E], [-2491:3-C$_3$H$_7$,2-F,E], [-2492:3-(Me)$_2$CH,2-F,E], [-2493:3-CF$_3$,2-F,E], [-2494:3-CF$_3$,2-F,Z], [-2495:3-C$_2$F$_5$,2-F,E], [-2496:3-C$_3$F$_7$,2-F,E], [-2497:3-(CF$_3$)$_2$CF,2-F,E], [-2498:3-(CF$_3$)$_2$CH,2-F,E], [-2499:3-CHF$_2$,2-F,E], [-2500:3-CHF$_2$,2-F,Z], [-2501:3-CH$_2$F,2-F,E], [-2502:3-CH$_2$F,2-F,Z], [-2503:3-CF$_3$CH$_2$,2-F,E], [-2504:3-MeO,2-F,E], [-2505:3-MeO,2-F,Z], [-2506:3-EtO,2-F,E], [-2507:3-C$_3$H$_7$O,2-F,E], [-2508:3-(Me)$_2$CHO,2-F,E], [-2509:3-NO$_2$,2-F,E], [-2510:2-F,2-F,E], [-2511:2-Cl,2-F,E], [-2512:2-Br,2-F,E], [-2513:2-I,2-F,E], [-2514:2-Me,2-F,E], [-2515:2-Et,2-F,E], [-2516:2-C$_3$H$_7$,2-F,E], [-2517:2-(Me)$_2$CH,2-F,E], [-2518:2-CF$_3$,2-F,E], [-2519:2-C$_2$F$_5$,2-F,E], [-2520:2-C$_3$F$_7$,2-F,E], [-2521:2-(CF$_3$)$_2$CF,2-F,E], [-2522:2-(CF$_3$)$_2$CH,2-F,E], [-2523:2-CHF$_2$,2-F,E], [-2524:2-CH$_2$F,2-F,E], [-2525:2-CF$_3$CH$_2$,2-F,E], [-2526:2-MeO,2-F,E], [-2527:2-EtO,2-F,E], [-2528:2-C$_3$H$_7$O,2-F,E], [-2529:2-(Me)$_2$CHO,2-F,E], [-2530:2-NO$_2$,2-F,E], [-2531:2,3-F$_2$,2-F,E], [-2532:2,4-F$_2$,2-F,E], [-2533:2,5-F$_2$,2-F,E], [-2534:2,6-F$_2$,2-F,E], [-2535:3,4-F$_2$,2-F,E], [-2536:3,4-F$_2$,2-F,Z], [-2537:3,5-F$_2$,2-F,E], [-2538:3,5-F$_2$,2-F,Z], [-2539:2,3-Cl$_2$,2-F,E], [-254:2,3-Cl$_2$,2-F,Z], [-2541:2,4-Cl$_2$,2-F,E], [-2542:2,4Cl$_2$,2-F,Z], [-2543:2,5Cl$_2$,2-F,E], [-2544:2,5-Cl$_2$,2-F,Z], [-2545:2,6-Cl$_2$,2-F,E], [-2546:3,4-Cl$_2$,2-F,E], [-2547:3,5-Cl$_2$,2-F,E], [-2548:2,3-Br$_2$,2-F,E], [-2549:2,4-Br$_2$,2-F,E], [-255:2,5Br$_2$,2-F,E], [-2551:2,6Br$_2$,2-F,E], [-2552:34-Br$_2$,2-F,E], [-2553:3,5-Br$_2$,2-F,E], [-2554:2,3Me$_2$,2-F,E], [-2555:2,4-Me$_2$,2-F,E], [-2556:2,5-Me$_2$,2-F,E], [-2557:2,6-Me$_2$,2-F,E], [-2558:3,4-Me$_2$,2-F,E], [-2559:3,5Me$_2$,2-F,E], [-2560:2,3-Et$_2$,2-F,E], [-2561:2,4-Et$_2$,2-F,E], [-2562:2,5Et$_2$,2-F,E], [-2563:2,6-Et$_2$,2-F,E], [-2564:3,4Et$_2$,2-F,E], [-2565:3,5Et$_2$,2-F,E], [-2566:2,3-(CF)$_2$,2-F,E], [-2567:2,4-(CF)$_2$,2-F,E], [-2568:2,5-(CF$_3$)$_2$,2-F,E], [-2569:2,6-(CF)$_2$,2-F,E], [-2570:3,4-(CF$_3$)$_2$,2-F,E], [-2571:3,5-(CF$_3$)$_2$,2-F,E], [-2572:2,3-(CHF$_2$)$_2$,2-F,E]-[-2573:2,4-(CHF$_2$)$_2$,2-F,E], [-2574:2,5-(CHF$_2$)$_2$,2-F,E], [-2575:2,6-(CHF$_2$)$_2$,2-F,E], [-2576:3,4-(CHF$_2$)$_2$,2-F,E], [-2577:3,5-(CHF$_2$)$_2$,2-F,E], [-2578:2,3-(CH$_2$F)$_2$,2-F,E], [-2579:2,4-(CH$_2$F)$_2$,2-F,E], [-2580:2,5-(CH$_2$F)$_2$,2-F,E], [-2581:2,6-(CH$_2$F)$_2$,2-F,E], [-2582:3,4-(OH$_2$F)$_2$,2-F,E], [-2583:3,5-(OH$_2$F)$_2$,2-F,E], [-2584:2,3-(MeO)$_2$,2-F,E], [-2585:2,4-(MeO)$_2$,2-F,E], [-2586:2,5-(MeO)$_2$,2-F,E], [-2587:2,6-(MeO)$_2$,2-F,E], [-2588:3,4-(MeO)$_2$,2-F,E], [-2589:3,5-(MeO)$_2$,2-F,E], [-2590:2,3-(EtO)$_2$,2-F,E], [-2591:2,4-(EtO)$_2$,2-F,E], [-2592:2,5-(EtO)$_2$,2-F,E], [-2593:2,6-(EtO)$_2$,2-F,E], [-2594:3,4-(EtO)$_2$,2-F,E], [-2595:3,5-(EtO)$_2$,2-F,E], [-2596:2-Cl-3-F,2-F,E], [-2597:2-Cl-4-F,2-F,E], [-2598:2-Cl-5-F,2-F,E], [-2599:2-Cl-6-F,2-F,E], [-2600:3-Cl-2-F,2-F,E], [-2601:3-Cl-4-F,2-F,E], [-2602:3-Cl-5-F,2-F,E], [-2603:4-Cl-2-F,2-F,E], [-2604:4-Cl-3-F,2-F,E], [-2605:2-F-3-Me,2-F,E], [-2606:2-F-4-Me,2-F,E], [-2607:2-F-5-Me,2-F,E], [-2608:2-F-6-Me,2-F,E], [-2609:3-F-2-Me,2-F,E], [-2610:3-F-4-Me,2-F,E], [-2611:3-F-5-Me,2-F,E], [-2612:4-F-2-Me,2-F,E], [-2613:4-F-3-Me,2-F,E], [-2614:2-Cl-3-Me,2-F,E], [-2615:2-Cl-4-Me,2-F,E], [-2616:2-Cl-5-Me,2-F,E], [-2617:2-Cl-6-Me,2-F,E], [-2618:3-Cl-2-Me,2-F,E], [-2619:3-Cl-4-Me,2-F,E], [-2620:3-Cl-5-Me,2-F,E], [-2621:4-Cl-2-Me,2-F,E], [-2622:4-Cl-3-Me,2-F,E], [-2623:2-F-3-CF$_3$,2-F,E], [-2624:2-F-4-CF$_3$,2-F,E], [-2625:2-F-5-CF$_3$,2-F,E], [-2626:2-F-6-CF$_3$,2-F,E], [-2627:3-F-2-CF$_3$,2-F,E], [-2628:3-F-4-CF$_3$,2-F,E], [-2629:3-F-5-CF$_3$,2-F,E], [-2630:4-F-2-CF$_3$,2-F,E], [-2631:4-F-3-CF$_3$,2-F,E], [-2632:2-Cl-3-CF$_3$,2-F,E], [-2633:2-Cl-4-CF$_3$,2-F,E], [-2634:2-Cl-5-CF$_3$,2-F,E], [-2635:2-Cl-6-CF$_3$,2-F,E], [-2636:3-Cl-2-CF$_3$,2-F,E], [-2637:3-Cl-4-CF$_3$,2-F,E], [-2638:3-Cl-5-CF$_3$,2-F,E], [-2639:4-Cl-2-CF$_3$,2-F,E], [-2640:4-Cl-3-CF$_3$,2-F,E], [-2641:2-Me-3-CF$_3$,2-F,E], [-2642:2-Me-4-CF$_3$,2-F,E], [-2643:2-Me-5-CF$_3$,2-F,E], [-2644:2-Me-6-CF$_3$,2-F,E], [-2645:3-Me-2-CF$_3$,2-F,E], [-2646:3-Me-4-CF$_3$,2-F,E], [-2647:3-Me-5-CF$_3$,2-F,E], [-2648:4-Me-2-CF$_3$,2-F,E], [-2649:4-Me-3-CF$_3$,2-F,E], [-2650:2-F-3-MeO,2-F,E], [-2651:2-F-4-MeO,2-F,E], [-2652:2-F-5-MeO,2-F,E], [-2653:2-F-6-MeO,2-F,E], [-2654:3-F-2-MeO,2-F,E], [-2655:3-F-4-MeO,2-F,E], [-2656:3-F-5-MeO,2-F,E], [-2657:4-F-2-MeO,2-F,E], [-2658:4-F-3-MeO,2-F,E], [-2659:2-Cl-3-MeO,2-F,E], [-2660:2-Cl-4-MeO,2-F,E], [-2661:2-Cl-5-MeO,2-F,E], [-2662:2-Cl-6-MeO,2-F,E], [-2663:3-Cl-2-MeO,2-F,E], [-2664:3-Cl-4-MeO,2-F,E], [-2665:3-Cl-5-MeO,2-F,E], [-2666:4-Cl-2-MeO,2-F,E], [-2667:4-Cl-3-MeO,2-F,E], [-2668:2-Me-3-MeO,2-F,E], [-2669:2-Me-4-MeO,2-F,E], [-2670:2-Me-5-MeO,2-F,E], [-2671:2-Me-6-MeO,2-F,E], [-2672:3-Me-2-MeO,2-F,E], [-2673:3-Me-4-MeO,2-F,E], [-2674:3-Me-5-MeO,2-F,E], [-2675:4-Me-2-MeO,2-F,E], [-2676:4-Me-3-MeO,2-F,E], [-2677:H, 2-Cl,E], [-2678:4-F, 2-Cl,E], [-2679:4-F, 2-Cl, Z], [-2680:4-Cl,2-Cl,E], [-2681:4-Cl,2-Cl,Z], [-2682:4-Br,2-Cl,E], [-2683:4-I,2-Cl,E], [-2684:4-Me, 2-Cl,E], [-2685:4-Me, 2-Cl, Z], [-2686:4-Et,2-Cl,E], [-2687:4-C$_3$H$_7$,2-Cl,E], [-2688:4-(Me)$_2$CH,2-Cl,E], [-2689:4-CF$_3$,2-Cl,E], [-2690:4-CF$_3$,2-Cl,Z], [-2691:4-Cl-2F$_5$, 2-Cl,E], [-2692:4-C$_3$F$_7$,2-Cl,E], [-2693:4-(CF$_3$)$_2$CF,2-Cl,E], [-2694:4-(CF$_3$)$_2$CH,2-Cl,E], [-2695:4-CHF$_2$,2-Cl,E], [-2696:4-CH$_2$F,2-Cl,E], [-2697:4-CF$_3$CH$_2$,2-Cl,E], [-2698:4-MeO,2-Cl,E], [-2699:4-MeO,2-Cl,Z], [-2700:4-EtO,2-Cl,E], [-2701:4-C$_3$H$_7$O,2-Cl,E], [-2702:4-(Me)$_2$CHO,2-Cl,E], [-2703:4-NO$_2$,2-Cl,E], [-2704:4-NO$_2$,2-Cl,Z], [-2705:3-F,2-Cl,E], [-2706:3-F,2-Cl,Z], [-2707:3-Cl,2-Cl,E], [-2708:3-Cl,2-Cl,Z], [-2709:3-Br,2-Cl,E], [-2710:3-I,2-Cl,E], [-2711:3-Me, 2-Cl,E], [-2712:3-Me, 2-Cl, Z], [-2713:3-Et,2-Cl,E], [-2714:3-C$_3$H$_7$,2-Cl,E], [-2715:3-(Me)$_2$CH,2-Cl,E], [-2716:3-CF$_3$,2-Cl,E], [-2717:3-CF$_3$,2-Cl,E], [-2718:3-C$_2$F$_5$,2-Cl,E], [-2719:3-C$_3$F$_7$,2-Cl,E], [-2720:3-(CF$_3$)$_2$CF,2-Cl,E], [-2721:3-(CF$_3$)$_2$CH,2-Cl,E], [-2722:3-CHF$_2$,2-Cl,E], [-2723:3-CHF$_2$,2-Cl,Z], [-2724:3-CH$_2$F,2-Cl,E], [-2725:3-CH$_2$F,2-Cl,Z], [-2726:3-CF$_3$CH$_2$,2-Cl,E], [-2727:3-MeO,2-Cl,E], [-2728:3-MeO,2-Cl,Z], [-2729:3-EtO,2-Cl,E], [-2730:3-C$_3$H$_7$O,2-Cl,E], [-2731:3-(Me)$_2$CHO,2-Cl,E], [-2732:3-NO$_2$,2-Cl,E], [-2733:2-F,2-Cl,E], [-2734:2-Cl,2-Cl,E], [-2735:2-Br, 2-Cl,E], [-2736:2-I,2-Cl,E], [-2737:2-Me,2-Cl,E], [-2738:2-Et,2-Cl,E], [-2739:2-C$_3$H$_7$,2-Cl,E], [-2740:2-(Me)$_2$CH,2-Cl,E], [-2741:2-CF$_3$,2-Cl,E], [-2742:2-C$_2$F$_5$,2-Cl,E], [-2743:2-C$_3$F$_7$,2-Cl,E], [-2744:2-(CF$_3$)$_2$CF,2-Cl,E], [-2745:2-(CF$_3$)$_2$CH,2-Cl,E], [-2746:2-CHF$_2$,2-Cl,E], [-2747:2-CH$_2$F,2-Cl,E], [-2748:2-CF$_3$CH$_2$,2-Cl,E], [-2749:2-MeO,2-Cl,E], [-2750:2-EtO,2-Cl,E], [-2751:2-C$_3$H$_7$O,2-Cl,E], [-2752:2-(Me)$_2$CHO,2-Cl,E], [-2753:2-NO$_2$,2-Cl,E], [-2754:2,3-F$_2$,2-Cl,E], [-2755:2,4-F$_2$,2-Cl,E], [-2756:2,5-F$_2$,2-Cl,E], [-2757:2,6-F$_2$,2-Cl,E], [-2758:3,4-F$_2$,2-Cl,E], [-2759:3,4-F$_2$,2-Cl,Z], [-2760:3,5-F$_2$,2-Cl,E], [-2761:3,5-F$_2$,2-Cl,Z], [-2762:2,3Cl$_2$,2Cl,E], [-2763:2,3-Cl$_2$,2-Cl, Z], [-2764:2,4-Cl$_2$,2-Cl,E], [-2765:2,4-Cl$_2$,2-Cl,Z], [-2766:2,5-Cl$_2$,2-Cl,E], [-2767:

2,5Cl₂,2Cl,Z], [–2768:2,6-Cl₂,2-Cl,E], [–2769:3,4-Cl₂, 2Cl,E], [–2770:3,5Cl₂,2-Cl,E], [–2771:2,3-Br₂,2-Cl,E], [–2772:2,4Br₂,2-Cl,E], [–2773:2,5-Br₂,2-Cl,E], [–2774:2, 6-Br₂,2-Cl,E], [–2775:3,4Br₂,2-Cl,E], [–2776:3,5-Br₂,2-Cl,E], [–2777:2,3-Me₂,2Cl,E], [–2778:2,4-Me₂,2-Cl,E], [–2779:2,5-Me₂,2Cl,E], [–278:2,6Me₂2Cl,E], [–2781:3, 4-Me₂,2-Cl,E], [–2782:3,5-Me₂,2-Cl,E], [–2783:2,3Et₂, 2-Cl,E], [–2784:2,4-Et₂2Cl,E], [–2785:2,5Et₂,2Cl,E], [–2786:2,6-Et₂,2>Cl,E], [–2787:3,4-Et₂,2-Cl,E], [–2788: 3,5Et₂,2-Cl,E], [–2789:2,3-(CF₃)₂,2-Cl,E], [–279:2,4-(CF₃)₂,2-Cl,E], [–2791:2,5-CF₃)₂,2-Cl,E], [–2792:2,6-(CF₃)₂,2Cl,E], [–2793:3,4-(CF₃)₂,2-Cl,E], [–2794:3,5-(CF₃)₂,2Cl,E], [–2795:2,3-(CHF₂)₂,2-Cl,E], [–2796:2,4-(CHF₂)₂,2-Cl,E], [–2797:2,5-(CHF₂)₂,2-Cl,E], [–2798:2, 6-(CHF₂)₂,2-Cl,E], [–2799:3,4-(CHF₂)₂,2Cl,E], [–2800: 3,5-(CHF₂)₂,2-Cl,E], [–2801:2,3-(CH₂F)₂2Cl,E], [–2802: 2,4-(CH₂F)₂,2-Cl,E], [–283:2,5-(CH₂F)₂2Cl,E], [–2804: 2,6-(CH₂F)₂,2-Cl,E], [–2805:3,4-(CH₂F)₂,2-Cl,E], [–2806:3,5-(CH₂F)₂,2-Cl,E], [–2807:2,3-(MeO)₂,2-Cl, E], [–2808:2,4-(MeO)₂,2-Cl,E], [–2809:2,5-(MeO)₂,2Cl, E], [–2810:2,6-(MeO)₂,2-Cl,E], [–2811:3,4-(MeO)₂,2-Cl, E], [2812:3,5-(MeO)₂,2Cl,E], [–2813:2,3-(EtO)₂,2-Cl,E], [–2814:2,4-(EtO)₂,2-Cl,E], [–2815:2,5-(EtO)₂,2-Cl,E], [–2816:2,6-(EtO)₂,2-Cl,E], [–2817:3,4-(EtO)₂,2Cl,E], [–2818:35-(EtO)₂,2-Cl,E], [–2819:2-Cl-3-F, 2-Cl,E], [–2820:2-Cl-4-F, 2-Cl,E], [–2821:2-Cl-5-F, 2-Cl,E], [–2822:2-Cl-6-F, 2-Cl,E], [–2823:3-Cl-2-F,2-Cl,E], [–2824:3-Cl-4-F,2-Cl,E], [–2825:3-Cl-5-F 2-Cl,E], [–2826:4-Cl-2-F, 2-Cl,E], [–2827:4-Cl-3-F, 2-Cl,E], [–2828:2-F-3-Me,2-Cl,E], [–2829:2-F-4-Me,2-Cl,E], [–2830:2-F-5-Me,2-Cl,E], [–2831:2-F-6-Me,2-Cl,E], [–2832:3-F-2-Me,2-Cl,E], [–2833:3-F-4-Me,2-Cl,E], [–2834:3-F-5-Me,2-Cl,E], [–2835:4-F-2-Me,2-Cl,E], [–2836:4-F-3-Me,2-Cl,E], [–2837:2-Cl-3-Me,2-Cl,E], [–2838:2-Cl-4-Me,2-Cl,E], [–2839:2-Cl-5-Me,2-Cl,E], [–2840:2-Cl-6-Me,2-Cl,E], [–2841:3-Cl-2-Me,2-Cl,E], [–2842:3-Cl-4-Me,2-Cl,E], [–2843:3-Cl-5-Me,2-Cl,E], [–2844:4-Cl-2-Me,2-Cl,E], [–2845:4-Cl-3-Me,2-Cl,E], [–2846:2-F-3-CF₃,2-Cl,E], [–2847:2-F-4-CF₃,2-Cl,E], [–2848:2-F-5-CF₃,2-Cl,E], [–2849:2-F-6-CF₃,2-Cl,E], [–2850:3-F-2-CF₃,2-Cl,E], [–2851:3-F-4-CF₃,2-Cl,E], [–2852:3-F-5-CF₃,2-Cl,E], [–2853:4-F-2-CF₃,2-Cl,E], [–2854:4-F-3-CF₃,2-Cl,E], [–2855:2-Cl-3-CF₃,2-Cl,E], [–2856:2-Cl-4-CF₃,2-Cl,E], [–2857:2-Cl-5-CF₃,2-Cl,E], [–2858:2-Cl-6-CF₃,2-Cl,E], [–2859:3-Cl-2-CF₃,2-Cl,E], [–2860:3-Cl-4-CF₃,2-Cl,E], [–2861:3-Cl-5-CF₃,2-Cl,E], [–2862:4-Cl-2-CF₃,2-Cl,E], [–2863:4-Cl-3-CF₃,2-Cl,E], [–2864:2-Me-3-CF₃,2-Cl,E], [–2865:2-Me-4-CF₃,2-Cl, E], [–2866:2-Me-5-CF₃,2-Cl,E], [–2867:2-Me-6-CF₃,2-Cl,E], [–2868:3-Me-2-CF₃,2-Cl,E], [–2869:3-Me-4-CF₃, 2-Cl,E], [–2870:3-Me-5-CF₃,2-Cl,E], [–2871:4-Me-2-CF₃,2-Cl,E], [–2872:4-Me-3-CF₃,2-Cl,E], [–2873:2-F-3-MeO,2-Cl,E], [–2874:2-F-4-MeO,2-Cl,E], [–2875:2-F-5-MeO,2-Cl,E], [–2876:2-F-6-MeO,2-Cl,E], [–2877:3-F-2-MeO,2-Cl,E], [–2878:3-F-4-MeO,2-Cl,E], [–2879:3-F-5-MeO,2-Cl,E], [–2880:4-F-2-MeO,2-Cl,E], [–2881:4-F-3-MeO,2-Cl,E], [–2882:2-Cl-3-MeO,2-Cl,E], [–2883:2-Cl-4-MeO,2-Cl,E], [–2884:2-Cl-5-MeO,2-Cl,E], [–2885:2-Cl-6-MeO,2-Cl,E], [–2886:3-Cl-2-MeO,2-Cl,E], [–2887: 3-Cl-4-MeO,2-Cl,E], [–2888:3-Cl-5-MeO,2-Cl,E], [–2889:4-Cl-2-MeO,2-Cl,E], [–2890:4-Cl-3-MeO,2-Cl, E], [–2891:2-Me-3-MeO,2-Cl,E], [–2892:2-Me-4-MeO, 2-Cl,E], [–2893:2-Me-5-MeO,2-Cl,E], [–2894:2-Me-6-MeO,2-Cl,E], [–2895:3-Me-2-MeO,2-Cl,E], [–2896:3-Me-4-MeO,2-Cl,E], [–2897:3-Me-5-MeO,2-Cl,E], [–2898:4-Me-2-MeO,2-Cl,E], [–2899:4-Me-3-MeO,2-Cl, E], [–2900:H,2-CF₃,E], [–2901:4-F,2-CF₃,E], [–2902:4-F, 2-CF₃,Z], [–2903:4 Cl,2-CF₃,E], [–2904:4 Cl,2-CF₃,Z], [–2905:4-Br,2-CF₃,E], [–2906:4-I,2-CF₃,E], [–2907:4-Me, 2-CF₃,E], [–2908:4-Me,2-CF₃,Z], [–2909: 4-Et, 2-CF₃,E], [–2910:4-C₃H₇,2-CF₃,E], [–2911:4-(Me)₂CH,2-CF₃,E], [–2912:4 CF₃,2-CF₃,E], [–2913:4-CF₃,2-CF₃,Z], [–2914:4-C₂F₅,2-CF₃,E], [–2915:4C₃F₇,2-CF₃, E], [–2916:4-(CF₃)₂CF, 2-CF₃,E], [–2917:4-(CF₃)₂CH-2-CF₃,E], [–2918:4-CHF₂,2-CF₃,E], [–2919:4-CH₂F, 2-CF₃,E], [–2920:4-CF₃CH₂, 2-CF₃,E], [–2921:4-MeO,2-CF₃,E], [–2922:4-MeO,2-CF₃,Z], [–2923:4-EtO,2-CF₃, E], [–2924:4-C₃H₇,2-CF₃,E], [–2925:4-Me)₂CHO,2-CF₃, E], [–2926:4-N₂,2-CF₃,E], [–2927:4 N₂,2-CF₃,Z], [–2928:3-F,2-CF₃,E], [–2929:3-F,2-CF₃,Z], [–2930:3-Cl, 2-CF₃,E], [–2931:3-Cl,2-CF₃,Z], [–2932:3 Br,2-CF₃,E], [–2933:3-I,2-CF₃,E], [–2934:3-Me,2-CF₃,E], [–2935:3-Me,2-CF₃,Z], [–2936:3-Et,2-CF₃,E], [–2937:3-C₃H₇,2-CF₃,E], [–2938:3-(Me)₂CH,2-CF₃,E], [–2939:3-CF₃,2-CF₃,E], [–2940:3-CF₃,2-CF₃,Z], [–2941:3-C₂F₅,2-CF₃, E], [–2942:3-C₃F₇,2-CF₃,E], [–2943:3-(CF₃)₂CF,2-CF₃, E], [–2944:3-CF₃)₂CH,2-CF₃,E], [–2945:3-CHF₂,2-CF₃, E], [–2946:3-CHF₂,2-CF₃,Z], [–2947:3-CH₂F, 2-CF₃,E], [–2948:3 CH₂F, 2-CF₃,Z, 2949:3-CF₃CH₂,2-CF₃,E], [–2950:3-MeO,2-CF₃,E], [–2951:3-MeO,2-CF₃,Z], [–2952:3-EtO,2-CF₃,E], [–2953:3 C₃H₇,2-CF₃,E], [–2954:3-(Me)₂CHO,2-CF₃,E], [–2955:3 NO₂,2-CF₃,E], [–2956:2-F,2-CF₃,E], [–2957:2-Cl,2-CF₃,E], [–2958:2-Br,2-CF₃,E], [–29592:1,2-CF₃,E], [–2960:2-Me,2-CF₃, E], [–2961:2 Et,2-CF₃,E], [–2962:2-C₃H₇,2-CF₃,E], [–2963:2-(Me)₂CH,2-CF₃,E], [–2964:2-CF₃,2-CF₃,E], [–2965:2-C₂F₅,2-CF₃,E], [–2966:2-C₃F₇,2-CF₃,E], [–2967:2-(CF₃)₂CF,2-CF₃,E], [–2968:2-(CF₃)₂CH,2-CF₃,E], [–2969:2-CHF₂,2-CF₃,E], [–2970:2CH₂F, 2-CF₃, E], [–2971:2-CF₃CH₂,2-CF₃,E], [–2972:2-MeO,2-CF₃, E], [–2973:2 EtO,2-CF₃,E], [–2974:2-C₃H₇,2-CF₃,E], [–2975:2-(Me)₂CHO,2-CF₃,E], [2976:2-NO₂,2-CF₃,E], [–2977:2,3-F₂,2-CF₃,E], [–2978:2,4-F₂-2-CF₃,E], [–2979: 2,5-F₂,2-CF₃,E], [–2980:2,6-F₂,2-CF₃,E], [–2981:3,4-F₂, 2-CF₃,E], [–2982:3,4-F₂,2-CF₃,Z], [–2983:3,5-F₂2-CF₃, E], [–2984:3,5-F₂,2-CF₃,Z], [––2985:2,3-Cl₂,2-CF₃,E], [–2986:2,3-Cl₂,2-CF₃,Z], [–2987:2,4-Cl₂,2-CF₃,E], [–2988:2,4-Cl₂2-CF₃,Z], [–2989:2,5-Cl₂,2-CF₃,E], [–2990:2,5-Cl₂,2-CF₃,Z], [–2991:2,6-Cl₂,CF₃,E], [–2992:3,4-Cl₂,2-CF₃,E], [–2993:3,5-Cl₂,2-CF₃,E], [–2994:2,3-Br₂,2-CF₃,E], [–2995:2,4-Br₂,2-CF₃,E], [–2996:2,5-Br₂,2-CF₃,E], [–2997:2,6-Br₂,2-CF₃,E], [–2998:3,4-Br₂,2-CF₃,E], [–2999:3,5-Br₂,2-CF₃,E], [–3000:2,3-Me₂,2-CF₃,E], [–3001:2,4-Me₂,2-CF₃,E], [–3002:2,5-Me₂,2-CF₃,E], [–3003:2,6-Me₂,2-CF₃,E], [–3004:3,4-Me₂,2-CF₃,E], [–3005:3,5-Me₂,2-CF₃,E], [–3006:2,3-Et₂,2-CF₃,E], [–307:2,4-Et₂,2-CF₃,E], [–3008:2,5-Et₂,2-CF₃,E], [–3009:2,6-Et₂,2-CF₃,E], [–3010:3,4-Et₂2-CF₃,E], [–3011:3,5-Et₂,2-CF₃,E], [–3012:2,3-(CF₃)₂,2-CF₃,E], [–3013:2,4-(CF₃)₂,2-CF₃, E], [–3014:2,5-CF₃)₂,2-CF₃,E], [–3015:2,6-(CF₃)₂,2-CF₃,E], [–3016:3,4-(CF₃)₂,2-CF₃,E], [–3017:3,5-(CF₃)₂, 2-CF₃,E], [–3018:2,3-(CHF₂)₂,2-CF₃,E], [–3019:2,4-(CHF₂)₂,2-CF₃,E], [–3020:2,5-(CHF₂)₂,2-CF₃,E], [–3021:2,6-(CHF₂)₂,2-CF₃,E], [–3022:3,4-(CHF₂)₂,2-CF₃,E], [–3023:3,5-(CHF₂)₂,2-CF₃,E], [–3024:2,3-(CH₂F)₂,2-CF₃,E], [–3025:2,4-(CH₂F)₂,2-CF₃,E], [–3026:2,5-(CH₂F)₂,2-CF₃,E], [–3027:2,6-(CH₂F)₂,2-CF₃,E], [–3028:3,4-(CH₂F)₂,2-CF₃,E], [–3029:3,5-(CH₂F)₂,2-CF₃,E], [–3030:2,3-(MeO)₂,2-CF₃,E], [–3031: 2,4-(MeO)₂,2-CF₃,E], [–3032:2,5-(MeO)₂,2-CF₃,E], [–3033:2,6-(MeO)₂,2-CF₃,E], [–3034:3,4-(MeO)₂,2-CF₃, E], [–3035:3,5-(MeO)₂,2-CF₃,E], [–3036:2,3-(EtO)₂,2-CF₃,E], [–3037:2,4-(EtO)₂,2-CF₃,E], [–3038:2,5-(EtO)₂,

2-CF₃,E], [−3039:2,6-(EtO)₂,2-CF₃,E], [−3040:3,4-(EtO)₂,2-CF₃,E], [−3041:3,5-(EtO)₂,2-CF₃,E], [−3042:2-Cl-3-F,2-CF₃,E], [−3043:2-Cl-4-F,2-CF₃,E], [−3044:2-Cl-5-F,2-CF₃,E], [−3045:2-Cl-6-F,2-CF₃,E], [−3046:3-Cl-2-F,2-CF₃,E], [−3047:3-Cl-4-F,2-CF₃,E], [−3048:3-Cl-5-F,2-CF₃,E], [−3049:4-Cl-2-F,2-CF₃,E], [−3050:4-Cl-3-F,2-CF₃,E], [−3051:2-F-3-Me,2-CF₃,E], [−3052:2-F-4-Me,2-CF₃,E], [−3053:2-F-5-Me,2-CF₃,E], [−3054:2-F-6-Me,2-CF₃,E], [−3055:3-F-2-Me,2-CF₃,E], [−3056:3-F-4-Me,2-CF₃,E], [−3057:3-F-5-Me,2-CF₃,E], [−3058:4-F-2-Me,2-CF₃,E], [−3059:4-F-3-Me,2-CF₃,E], [−3060:2-Cl-3-Me,2-CF₃,E], [−3061:2-Cl-4-Me,2-CF₃,E], [−3062:2-Cl-5-Me,2-CF₃,E], [−3063:2-Cl-6-Me,2-CF₃,E], [−3064:3-Cl-2-Me,2-CF₃,E], [−3065:3-Cl-4-Me,2-CF₃,E], [−3066:3-Cl-5-Me,2-CF₃,E], [−3067:4-Cl-2-Me,2-CF₃,E], [−3068:4-Cl-3-Me,2-CF₃,E], [−3069:2-F-3-CF₃,2-CF₃,E], [−3070:2-F-4-CF₃,2-CF₃,E], [−3071:2-F-5-CF₃,2-CF₃,E], [−3072:2-F-6-CF₃,2-CF₃,E], [−3073:3-F-2-CF₃,2-CF₃,E], [−3074:3-F-4-CF₃,2-CF₃,E], [−3075:3-F-5-CF₃,2-CF₃,E], [−3076:4-F-2-CF₃,2-CF₃,E], [−3077:4-F-3-CF₃,2-CF₃,E], [−3078:2-Cl-3-CF₃,2-CF₃,E], [−3079:2-Cl-4-CF₃,2-CF₃,E], [−3080:2-Cl-5-CF₃,2-CF₃,E], [−3081:2-Cl-6-CF₃,2-CF₃,E], [−3082:3-Cl-2-CF₃,2-CF₃,E], [−3083:3-Cl-4-CF₃,2-CF₃,E], [−3084:3-Cl-5-CF₃,2-CF₃,E], [−3085:4-Cl-2-CF₃,2-CF₃,E], [−3086:4-Cl-3-CF₃,2-CF₃,E], [−3087:2-Me-3-CF₃,2-CF₃,E], [−3088:2-Me-4-CF₃,2-CF₃,E], [−3089:2-Me-5-CF₃,2-CF₃,E], [−3090:2-Me-6-CF₃,2-CF₃,E], [−3091:3-Me-2-CF₃,2-CF₃,E], [−3092:3-Me-4-CF₃,2-CF₃,E], [−3093:3-Me-5-CF₃,2-CF₃,E], [−3094:4-Me-2-CF₃,2-CF₃,E], [−3095:4-Me-3-CF₃,2-CF₃,E], [−3096:2-F-3-MeO,2-CF₃,E], [−3097:2-F-4-MeO,2-CF₃,E], [−3098:2-F-5-MeO,2-CF₃,E], [−3099:2-F-6-MeO,2-CF₃,E], [−3100:3-F-2-MeO,2-CF₃,E], [−3101:3-F-4-MeO,2-CF₃,E], [−3102:3-F-5-MeO,2-CF₃,E], [−3103:4-F-2-MeO,2-CF₃,E], [−3104:4-F-3-MeO,2-CF₃,E], [−3105:2-Cl-3-MeO,2-CF₃,E], [−3106:2-Cl-4-MeO,2-CF₃,E], [−3107:2-Cl-5-MeO,2-CF₃,E], [−3108:2-Cl-6-MeO,2-CF₃,E], [−3109:3-Cl-2-MeO,2-CF₃,E], [−3110:3-Cl-4-MeO,2-CF₃,E], [−3111:3-Cl-5-MeO,2-CF₃,E], [−3112:4-Cl-2-MeO,2-CF₃,E], [−3113:4-Cl-3-MeO,2-CF₃,E], [−3114:2-Me-3-MeO,2-CF₃,E], [−3115:2-Me-4-MeO,2-CF₃,E], [−3116:2-Me-5-MeO,2-CF₃,E], [−3117:2-Me-6-MeO,2-CF₃,E], [−3118:3-Me-2-MeO,2-CF₃,E], [−3119:3-Me-4-MeO,2-CF₃,E], [−3120:3-Me-5-MeO,2-CF₃,E], [−3121:4-Me-2-MeO,2-CF₃,E], [−3122:4-Me-3-MeO,2-CF₃,E],

[−3123:H, 2-MeO,E], [−3124:4-F, 2-MeO,E], [−3125:4-F, 2-MeO, Z], [−3126:4-Cl,2-MeO,E], [−3127:4-Cl,2-MeO, Z], [−3128:4-Br,2-MeO,E], [−3129:4-I,2-MeO,E], [−3130:4-Me, 2-MeO,E], [−3131:4-Me, 2-MeO,Z], [−3132:4-Et,2-MeO,E], [−3133:4-C₃H₇,2-MeO,E], [−3134:4-(Me)₂CH,2-MeO,E], [−3135:4-CF₃,2-MeO,E], [−3136:4-CF₃,2-MeO,Z], [−3137:4-C₂F₅,2-MeO,E], [−3138:4-C₃F₇,2-MeO,E], [−3139:4-(CF₃)₂CF,2-MeO,E], [−3140:4-(CF₃)₂CH,2-MeO,E], [−3141:4-CHF₂,2-MeO,E], [−3142:4-CH₂F,2-MeO,E], [−3143:4-CF₃CH₂,2-MeO,E], [−3144:4-MeO,2-MeO,E], [−3145:4-MeO,2-MeO,Z], [−3146:4-EtO,2-MeO,E], [−3147:4-C₃H₇O,2-MeO,E], [−3148:4-(Me)₂CHO,2-MeO,E], [−3149:4-NO₂,2-MeO,E], [−3150:4-NO₂,2-MeO,Z], [−3151:3-F,2-MeO,E], [−3152:3-F,2-MeO,Z], [−3153:3-Cl₂-MeO,E], [−3154:3-Cl₂-MeO,Z], [−3155:3-Br, 2-MeO,E], [−3156:3-I,2-MeO,E], [−3157:3-Me, 2-MeO,E], [−3158:3-Me,2-MeO,Z], [−3159:3-Et,2-MeO,E], [−3160:3-C₃H₇,2-MeO,E], [−3161:3-(Me)₂CH,2-MeO,E], [−3162:3-CF₃,2-MeO,E], [−3163:3-CF₃,2-MeO, Z], [−3164:3-C₂F₅,2-MeO,E], [−3165:3-C₃F₇,2-MeO,E], [−3166:3-(CF₃)₂CF,2-MeO,E], [−3167:3-(CF₃)₂CH,2-MeO,E], [−3168:3-CHF₂,2-MeO,E], [−3169:3-CHF₂,2-MeO, Z], [−3170:3-CH₂F,2-MeO,E], [−3171:3-CH₂F, 2-MeO, Z], [−3172:3-CF₃CH₂,2-MeO,E], [−3173:3-MeO,2-MeO,E], [−3174:3-MeO,2-MeO,Z], [−3175:3-EtO,2-MeO,E], [−3176:3-C₃H₇O,2-MeO,E], [−3177:3-(Me)₂CHO,2-MeO,E], [−3178:3-NO₂,2-MeO,E], [−3179:2-F, 2-MeO,E], [−3180:2-Cl, 2-MeO,E], [−3181:2-Br, 2-MeO,E], [−3182:2-I,2-MeO,E], [−3183:2-Me,2-MeO,E], [−3184:2-Et,2-MeO,E], [−3185:2-C₃H₇,2-MeO,E], [−3186:2-(Me)₂CH,2-MeO,E], [−3187:2-CF₃,2-MeO,E], [−3188:2-C₂F₅,2-MeO,E], [−3189:2-C₃F₇,2-MeO,E], [−3190:2-(CF₃)₂CF,2-MeO,E], [−3191:2-(CF₃)₂CH,2-MeO,E], [−3192:2-CHF₂,2-MeO,E], [−3193:2-CH₂F,2-MeO,E], [−3194:2-CF₃CH₂,2-MeO,E], [−3195:2-MeO,2-MeO,E], [−3196:2-EtO,2-MeO,E], [−3197:2-C₃H₇O,2-MeO,E], [−3198:2-(Me)₂CHO,2-MeO,E], [−3199:2-NO₂,2-MeO,E], [−3200:2,3-F₂,2-MeO,E], [−3201:2,4-F₂,2-MeO,E], [−3202:2,5-F₂,2-MeO,E], [−3203:2,6-F₂,2-MeO,E], [−3204:3,4-F₂,2-MeO,E], [−3205:3,4-F₂,2-MeO,Z], [−3206:3,5-F₂,2-MeO,E], [−3207:3,5-F₂,2-MeO,Z], [−3208:2,3-Cl₂,2-MeO,E], [−3209:2,3-Cl₂,2-MeO,Z], [−3210:2,4-Cl₂,2-MeO,E], [−3211:2,4-Cl₂,2-MeO,Z], [−3212:2,5-Cl₂,2-MeO,E], [−3213:2,5-Cl₂,2-MeO,Z], [−3214:2,6-Cl₂,2-MeO,E], [−3215:3,4-Cl₂,2-MeO,E], [−3216:3,5-Cl₂,2-MeO,E], [−3217:2,3-Br₂,2-MeO,E], [−3218:2,4-Br₂,2-MeO,E], [−3219:2,5-Br₂,2-MeO,E], [−3220:2,6-Br₂,2-MeO,E], [−3221:3,4-Br₂,2-MeO,E], [−3222:3,5-Br₂,2-MeO,E], [−3223:2,3-Me₂,2-MeO,E], [−3224:2,4-Me₂,2-MeO,E], [−3225:2,5-Me₂,2-MeO,E], [−3226:2,6-Me₂,2-MeO,E], [−3227:3,4-Me₂,2-MeO,E], [−3228:3,5-Me₂,2-MeO,E], [−3229:2,3-Et₂,2-MeO,E], [−3230:2,4-Et₂,2-MeO,E], [−3231:2,5-Et₂,2-MeO,E], [−3232:2,6-Et₂,2-MeO,E], [−3233:3,4-Et₂,2-MeO,E], [−3234:3,5-Et₂,2-MeO,E], [−3235:2,3-(CF₃)₂,2-MeO,E], [−3236:2,4-(CF₃)₂,2-MeO,E], [−3237:2,5-(CF₃)₂,2-MeO,E], [−3238:2,6-(CF₃)₂,2-MeO,E], [−3239:3,4-(CF₃)₂,2-MeO,E], [−3240:3,5-(CF₃)₂,2-MeO,E], [−3241:2,3-(CHF₂)₂,2-MeO,E], [−3242:2,4-(CHF₂)₂,2-MeO,E], [−3243:2,5-(CHF₂)₂,2-MeO,E], [−3244:2,6-(CHF₂)₂,2-MeO,E], [−3245:3,4-(CHF₂)₂,2-MeO,E], [−3246:3,5-(CHF₂)₂,2-MeO,E], [−3247:2,3-(CH₂F)₂,2-MeO,E], [−3248:2,4-(CH₂F)₂,2-MeO,E], [−3249:2,5-(CH₂F)₂,2-MeO,E], [−3250:2,6-(CH₂F)₂,2-MeO,E], [−3251:3,4-(CH₂F)₂,2-MeO,E], [−3252:3,5-(CH₂F)₂,2-MeO,E], [−3253:2,3-(MeO)₂,2-MeO,E], [−3254:2,4-(MeO)₂,2-MeO,E], [−3255:2,5-(MeO)₂,2-MeO,E], [−3256:2,6-(MeO)₂,2-MeO,E], [−3257:3,4-(MeO)₂,2-MeO,E], [−3258:3,5-(MeO)₂,2-MeO,E], [−3259:2,3-(EtO)₂,2-MeO,E], [−3260:2,4-(EtO)₂,2-MeO,E], [−3261:2,5-(EtO)₂,2-MeO,E], [−3262:2,6-(EtO)₂,2-MeO,E], [−3263:3,4-(EtO)₂,2-MeO,E], [−3264:3,5-(EtO)₂,2-MeO,E], [−3265:2-Cl-3-F,2-MeO,E], [−3266:2-Cl-4-F,2-MeO,E], [−3267:2-Cl-5-F,2-MeO,E], [−3268:2-Cl-6-F,2-MeO,E], [−3269:3-Cl-2-F,2-MeO,E], [−3270:3-Cl-4-F,2-MeO,E], [−3271:3-Cl-5-F,2-MeO,E], [−3272:4-Cl-2-F,2-MeO,E], [−3273:4-Cl-3-F,2-MeO,E], [−3274:2-F-3-Me,2-MeO,E], [−3275:2-F-4-Me,2-MeO,E], [−3276:2-F-5-Me,2-MeO,E], [−3277:2-F-6-Me,2-MeO,E], [−3278:3-F-2-Me,2-MeO,E], [−3279:3-F-4-Me,2-MeO,E], [−3280:3-F-5-Me,2-MeO,E], [−3281:4-F-2-Me,2-MeO,E], [−3282:4-F-3-Me,2-MeO,E], [−3283:2-Cl-3-Me,2-MeO,E], [−3284:2-Cl-4-Me,2-MeO,E], [−3285:2-Cl-5-Me,2-MeO,E], [−3286:2-Cl-6-Me,2-MeO,E], [−3287:3-Cl-2-Me,2-MeO,E], [−3288:3-Cl-4-Me,2-MeO,E], [−3289:3-Cl-5-Me,2-MeO,E], [−3290:4-Cl-2-Me,2-MeO,E], [−3291:4-Cl-3-Me,2-MeO,E], [−3292:2-F-3-CF₃,2-MeO,E], [−3293:2-F-4-CF₃,2-MeO,

E], [-3294:2-F-5-CF$_3$,2-MeO,E], [-3295:2-F-6-CF$_3$,2-MeO,E], [-3296:3-F-2-CF$_3$,2-MeO,E], [-3297:3-F-4-CF$_3$,2-MeO,E], [-3298:3-F-5-CF$_3$,2-MeO,E], [-3299:4-F-2-CF$_3$,2-MeO,E], [-3300:4-F-3-CF$_3$,2-MeO,E], [-3301:2-Cl-3-CF$_3$,2-MeO,E], [-3302:2-Cl-4-CF$_3$,2-MeO,E], [-3303:2-Cl-5-CF$_3$,2-MeO,E], [-3304:2-Cl-6-CF$_3$,2-MeO,E], [-3305:3-Cl-2-CF$_3$,2-MeO,E], [-3306:3-Cl-4-CF$_3$,2-MeO,E], [-3307:3-Cl-5-CF$_3$,2-MeO,E], [-3308:4-Cl-2-CF$_3$,2-MeO,E], [-3309:4-Cl-3-CF$_3$,2-MeO,E], [-3310:2-Me-3-CF$_3$,2-MeO,E], [-3311:2-Me-4-CF$_3$,2-MeO,E], [-3312:2-Me-5-CF$_3$,2-MeO,E], [-3313:2-Me-6-CF$_3$,2-MeO,E], [-3314:3-Me-2-CF$_3$,2-MeO,E], [-3315:3-Me-4-CF$_3$,2-MeO,E], [-3316:3-Me-5-CF$_3$,2-MeO,E], [-3317:4-Me-2-CF$_3$,2-MeO,E], [-3318:4-Me-3-CF$_3$,2-MeO,E], [-3319:2-F-3-MeO,2-MeO,E], [-3320:2-F-4-MeO,2-MeO,E], [-3321:2-F-5-MeO,2-MeO,E], [-3322:2-F-6-MeO,2-MeO,E], [-3323:3-F-2-MeO,2-MeO,E], [-3324:3-F-4-MeO,2-MeO,E], [-3325:3-F-5-MeO,2-MeO,E], [-3326:4-F-2-MeO,2-MeO,E], [-3327:4-F-3-MeO,2-MeO,E], [-3328:2-Cl-3-MeO,2-MeO,E], [-3329:2-Cl-4-MeO,2-MeO,E], [-3330:2-Cl-5-MeO,2-MeO,E], [-3331:2-Cl-6-MeO,2-MeO,E], [-3332:3-Cl-2-MeO,2-MeO,E], [-3333:3-Cl-4-MeO,2-MeO,E], [-3334:3-Cl-5-MeO,2-MeO,E], [-3335:4-Cl-2-MeO,2-MeO,E], [-3336:4-Cl-3-MeO,2-MeO,E], [-3337:2-Me-3-MeO,2-MeO,E], [-3338:2-Me-4-MeO,2-MeO,E], [-3339:2-Me-5-MeO,2-MeO,E], [-3340:2-Me-6-MeO,2-MeO,E], [-3341:3-Me-2-MeO,2-MeO,E], [-3342:3-Me-4-MeO,2-MeO,E], [-3343:3-Me-5-MeO,2-MeO,E], [-3344:4-Me-2-MeO,2-MeO,E], [-3345:4-Me-3-MeO,2-MeO,E],
[-3346:H,2-(Me)$_3$CO,E], [-3347:4-F,2-(Me)$_3$CO,E], [-3348:4-F,2-(Me)$_3$CO,Z], [-3349:4-Cl,2-(Me)$_3$CO,E], [-3350:4-Cl,2-(Me)$_3$CO,Z], [-3351:4-Br,2-(Me)$_3$CO,E], [-3352:4-I,2-(Me)$_3$CO,E], [-3353:4-Me,2-(Me)$_3$CO,E], [-3354:4-Me,2-(Me)$_3$CO,Z], [-3355:4-Et,2-(Me)$_3$CO,E], [-3356:4-C$_3$H$_7$,2-(Me)$_3$CO,E], [-3357:4-(Me)$_2$CH,2-(Me)$_3$CO,E], [-3358:4-CF$_3$,2-(Me)$_3$CO,E], [-3359:4-CF$_3$,2-(Me)$_3$CO,Z], [-3360:4-C$_2$F$_5$,2-(Me)$_3$CO,E], [-3361:4-C$_3$F$_7$, 2-(Me)$_3$CO,E], [-3362:4-(CF$_3$)$_2$CF,2-(Me)$_3$CO,E], [-3363:4-(CF$_3$)$_2$CH,2-(Me)$_3$CO,E], [-3364:4-CHF$_2$,2-(Me)$_3$CO,E], [-3365:4-CH$_2$F,2-(Me)$_3$CO,E], [-3366:4-CF$_3$CH$_2$,2-(Me)$_3$CO,E], [-3367:4-MeO,2-(Me)$_3$CO,E], [-3368:4-MeO,2-(Me)$_3$CO,Z], [-3369:4-EtO,2-(Me)$_3$CO,E], [-3370:4-C$_3$H$_7$O,2-(Me)$_3$CO,E], [-3371:4-(Me)$_2$CHO,2-(Me)$_3$CO,E], [-3372:4-NO$_2$,2-(Me)$_3$CO,E], [-3373:4-NO$_2$,2-(Me)$_3$CO,Z], [-3374:3-F,2-(Me)$_3$CO,E], [-3375:3-F,2-(Me)$_3$CO,Z], [-3376:3-Cl$_2$,2-(Me)$_3$CO,E], [-3377:3-Cl,2-(Me)$_3$CO,Z], [-3378:3-Br,2-(Me)$_3$CO,E], [-3379:3-I,2-(Me)$_3$CO,E], [-3380:3-Me,2-(Me)$_3$CO,E], [-3381:3-Me,2-(Me)$_3$CO,Z], [-3382:3-Et,2-(Me)$_3$CO,E], [-3383:3-C$_3$H$_7$,2-(Me)$_3$CO,E], [-3384:3-(Me)$_2$CH,2-(Me)$_3$CO,E], [-3385:3-CF$_3$,2-(Me)$_3$CO,E], [-3386:3-CF$_3$,2-(Me)$_3$CO,Z], [-3387:3-C$_2$F$_5$,2-(Me)$_3$CO,E], [-3388:3-C$_3$F$_7$,2-(Me)$_3$CO,E], [-3389:3-(CF$_3$)$_2$CF,2-(Me)$_3$CO,E], [-3390:3-(CF$_3$)$_2$CH,2-(Me)$_3$CO,E], [-3391:3-CHF$_2$,2-(Me)$_3$CO,E], [-3392:3-CHF$_2$,2-(Me)$_3$O,Z], [-3393:3-CH$_2$F,2-(Me)$_3$CO,E], [-3394:3-CH$_2$F,2-(Me)$_3$CO,Z], [-3395:3-CF$_3$CH$_2$,2-(Me)$_3$CO,E], [-3396:3-MeO,2-(Me)$_3$CO,E], [-3397:3-MeO,2-(Me)$_3$CO,Z], [-3398:3-EtO,2-(Me)$_3$CO,E], [-3399:3-C$_3$H$_7$O,2-(Me)$_3$CO,E], [-3400:3-(Me)$_2$CHO,2-(Me)$_3$CO,E], [-3401:3-NO$_2$,2-(Me)$_3$CO,E], [-3402:2-F,2-(Me)$_3$CO,E], [-3403:2-Cl,2-(Me)$_3$CO,E], [-3404:2-Br,2-(Me)$_3$CO,E], [-3405:2-I,2-(Me)$_3$CO,E], [-3406:2-Me,2-(Me)$_3$CO,E], [-3407:2-Et,2-(Me)$_3$CO,E], [-3408:2-C$_3$H$_7$,2-(Me)$_3$CO,E], [-3409:2-(Me)$_2$CH,2-(Me)$_3$CO,E], [-3410:2-CF$_3$,2-(Me)$_3$CO,E], [-3411:2-C$_2$F$_5$,2-(Me)$_3$CO,E], [-3412:2-C$_3$F$_7$,2-(Me)$_3$CO,E], [-3413:2-(CF$_3$)$_2$CF,2-(Me)$_3$CO,E], [-3414:2-(CF$_3$)$_2$CH, 2-(Me)$_3$CO,E], [-3415:2-CHF$_2$,2-(Me)$_3$CO,E], [-3416:2-CH$_2$F,2-(Me)$_3$CO,E], [-3417:2-CF$_3$CH$_2$,2-(Me)$_3$CO,E], [-3418:2-MeO,2-(Me)$_3$CO,E], [-3419:2-EtO,2-(Me)$_3$CO,E], [-3420:2-C$_3$H$_7$O,2-(Me)$_3$CO,E], [-3421:2-(Me)$_2$CHO,2-(Me)$_3$CO,E], [-3422:2-NO$_2$,2-(Me)$_3$CO,E], [-3423:2,3-F$_2$,2-(Me)$_3$CO,E], [-3424:2,4-F$_2$,2-(Me)$_3$CO,E], [-3425:2,5-F$_2$,2-(Me)$_3$CO,E], [-3426:2,6-F$_2$,2-(Me)$_3$CO,E], [-3427:3,4-F$_2$,2-(Me)$_3$CO,E], [-3428:3,4-F$_2$,2-(Me)$_3$CO,Z], [-3429:3,5-F$_2$,2-(Me)$_3$CO,E], [-3430:3,5-F$_2$,2-(Me)$_3$CO,Z], [-3431:2,3-Cl$_2$,2-(Me)$_3$CO,E], [-3432:2,3-Cl$_2$,2-(Me)$_3$CO,Z], [-3433:2,4-Cl$_2$,2-(Me)$_3$CO,E], [-3434:2,4-Cl$_2$,2-(Me)$_3$CO,Z], [-3435:2,5-Cl$_2$,2-(Me)$_3$CO,E], [-3436:2,5-Cl$_2$,2-(Me)$_3$CO,Z], [-3437:2,6-Cl$_2$,2-(Me)$_3$CO,E], [-3438:34-Cl$_2$,2-(Me)$_3$CO,E], [-3439:3,5-Cl$_2$,2-(Me)$_3$CO,E], [-3440:2,3-Br$_2$,2-(Me)$_3$CO,E], [-3441:2,4-Br$_2$,2-(Me)$_3$CO,E], [-3442:2,5-Br$_2$,2-(Me)$_3$CO,E], [-3443:2,6-Br$_2$,2-(Me)$_3$CO,E], [-3444:3,4-Br$_2$,2-(Me)$_3$CO,E], [-3445:3,5-Br$_2$,2-(Me)$_3$CO,E], [-3446:2,3-Me$_2$,2-(Me)$_3$CO,E], [-3447:2,4-Me$_2$,2-(Me)$_3$CO,E], [-3448:2,5-Me$_2$,2-(Me)$_3$O,E], [-3449:2,6-Me$_2$,2-(Me)$_3$CO,E], [-3450:3,4-Me$_2$,2-(Me)$_3$CO,E], [-3451:3,5-Me$_2$,2-(Me)$_3$CO,E], [-3452:2,3-Et$_2$,2-(Me)$_3$CO,E], [-3453:2,4-Et$_2$,2-(Me)$_3$CO,E], [-3454:2,5-Et$_2$,2-(Me)$_3$CO,E], [-3455:2,6-Et$_2$,2-(Me)$_3$CO,E], [-3456:3,4-Et$_2$,2-(Me)$_3$CO,E], [-3457:3,5-Et$_2$,2-(Me)$_3$CO,E], [-3458:2,3-(CF$_3$)$_2$,2-(Me)$_3$CO,E], [-3459:2,4-(CF$_3$)$_2$,2-(Me)$_3$CO,E], [-3460:2,5-(CF$_3$)$_2$,2-(Me)$_3$CO,E], [-3461:2,6-(CF$_3$)$_2$,2-(Me)$_3$CO,E], [-3462:3,4-(CF$_3$)$_2$,2-(Me)$_3$CO,E], [-3463:3,5-(CF$_3$)$_2$,2-(Me)$_3$CO,E], [-3464:2,3-(HF$_2$)$_2$,2-(Me)$_3$CO,E], [-3465:2,4-(HF$_2$)$_2$,2-(Me)$_3$CO,E], [-3466:2,5-(HF$_2$)$_2$,2-(Me)$_3$CO,E], [-3467:2,6-(HF$_2$)$_2$,2-(Me)$_3$CO,E], [-3468:3,4-(HF$_2$)$_2$,2-(Me)$_3$CO,E], [-3469:3,5-(CHF$_2$)$_2$,2-(Me)$_3$CO,E], [-3470:2,3-(CH$_2$F)$_2$,2-(Me)$_3$CO,E], [-3471:2,4-(OH$_2$F)$_2$,2-(Me)$_3$CO,E], [-3472:2,5-(CH$_2$F)$_2$,2-(Me)$_3$CO,E], [-3473:2,6-(CH$_2$F)$_2$,2-(Me)$_3$CO,E], [-3474:3,4-(OH$_2$F)$_2$,2-(Me)$_3$CO,E], [-3475:3,5-(OH$_2$F)$_2$,2-(Me)$_3$CO,F ], [-3476:2,3-(MeO)$_2$,2-(Me)$_3$CO,E], [-3477:2,4-(MeO)$_2$,2-(Me)$_3$CO,E], [-3478:2,5-(MeO)$_2$,2-(Me)$_3$CO,E], [-3479:2,6-(MeO)$_2$,2-(Me)$_3$CO,E], [-3480:3,4-(MeO)$_2$,2-(Me)$_3$CO,E], [-3481:3,5-(MeO)$_2$,2-(Me)$_3$O,E], [-3482:2,3-(EtO)$_2$,2-(Me)$_3$CO,E], [-3483:2,4-(EtO)$_2$,2-(Me)$_3$CO,E], [-3484:2,5-(EtO)$_2$,2-(Me)$_3$CO,E], [-3485:2,6-(EtO)$_2$,2-(Me)$_3$O,E], [-3486:3,4-(EtO)$_2$,2-(Me)$_3$O,E], [-3487:3,5-(EtO)$_2$,2-(Me)$_3$O,E], [-3488:2-Cl-3-F,2-(Me)$_3$CO,E], [-3489:2-Cl-4-F,2-(Me)$_3$CO,E], [-3490:2-Cl-5-F,2-(Me)$_3$CO,E], [-3491:2-Cl-6-F,2-(Me)$_3$O,E], [-3492:3-Cl-2-F,2-(Me)$_3$CO,E], [-3493:3-Cl-4-F,2-(Me)$_3$O,E], [-3494:3-Cl-5-F,2-(Me)$_3$CO,E], [-3495:4-Cl-2-F,2-(Me)$_3$CO,E], [-3496:4-Cl-3-F,2-(Me)$_3$CO,E], [-3497:2-F-3-Me,2-(Me)$_3$CO,E], [-3498:2-F-4-Me,2-(Me)$_3$CO,E], [-3499:2-F-5-Me,2-(Me)$_3$CO,E], [-3500:2-F-6-Me,2-(Me)$_3$CO,E], [-3501:3-F-2-Me,2-(Me)$_3$CO,E], [-3502:3-F-4-Me,2-(Me)$_3$CO,E], [-3503:3-F-5-Me,2-(Me)$_3$CO,E], [-3504:4-F-2-Me,2-(Me)$_3$CO,E], [-3505:4-F-3-Me,2-(Me)$_3$O,E], [-3506:2-Cl-3-Me,2-(Me)$_3$CO,E], [-3507:2-Cl-4-Me,2-(Me)$_3$CO,E], [-3508:2-Cl-5-Me,2-(Me)$_3$CO,E], [-3509:2-Cl-6-Me,2-(Me)$_3$CO,E], [-3510:3-Cl-2-Me,2-(Me)$_3$CO,E], [-3511:3-Cl-4-Me,2-(Me)$_3$CO,E], [-3512:3-Cl-5-Me,2-(Me)$_3$CO,E], [-3513:4-Cl-2-Me,2-(Me)$_3$CO,E], [-3514:4-Cl-3-Me,2-(Me)$_3$CO,E], [-3515:2-F-3-CF$_3$,2-(Me)$_3$O,E], [-3516:2-F-4-CF$_3$,2-(Me)$_3$O,E], [-3517:2-F-5-CF$_3$,2-(Me)$_3$O,E], [-3518:2-F-6-CF$_3$,2-(Me)$_3$CO,E], [-3519:3-F-2-CF$_3$,2-(Me)$_3$CO,E], [-3520:3-F-4-CF$_3$,2-(Me)$_3$CO,E], [-3521:3-F-5-CF$_3$,2-(Me)$_3$CO,E], [-3522:4-F-2-CF$_3$,2-(Me)$_3$CO,

E], [-3523:4-F-3-CF₃,2-(Me)₃CO,E], [-3524:2-Cl-3-CF₃,2-(Me)₃CO,E], [-3525:2-Cl-4-CF₃,2-(Me)₃CO,E], [-3526:2-Cl-5-CF₃,2-(Me)₃CO,E], [-3527:2-Cl-6-CF₃,2-(Me)₃CO,E], [-3528:3-Cl-2-CF₃,2-(Me)₃CO,E], [-3529:3-Cl-4-CF₃,2-(Me)₃CO,E], [-3530:3-Cl-5-CF₃,2-(Me)₃CO,E], [-3531:4-Cl-2-CF₃,2-(Me)₃CO,E], [-3532:4-Cl-3-CF₃,2-(Me)₃CO,E], [-3533:2-Me-3-CF₃,2-(Me)₃CO,E], [-3534:2-Me-4-CF₃,2-(Me)₃CO,E], [-3535:2-Me-5-CF₃,2-(Me)₃CO,E], [-3536:2-Me-6-CF₃,2-(Me)₃CO,E], [-3537:3-Me-2-CF₃,2-(Me)₃CO,E], [-3538:3-Me-4-CF₃,2-(Me)₃CO,E], [-3539:3-Me-5-CF₃,2-(Me)₃CO,E], [-3540:4-Me-2-CF₃,2-(Me)₃CO,E], [-3541:4-Me-3-CF₃,2-(Me)₃CO,E], [-3542:2-F-3-MeO,2-(Me)₃CO,E], [-3543:2-F-4-MeO,2-(Me)₃CO,E], [-3544:2-F-5-MeO,2-(Me)₃CO,E], [-3545:2-F-6-MeO,2-(Me)₃CO,E], [-3546:3-F-2-MeO,2-(Me)₃CO,E], [-3547:3-F-4-MeO,2-(Me)₃CO,E], [-3548:3-F-5-MeO,2-(Me)₃CO,E], [-3549:4-F-2-MeO,2-(Me)₃CO,E], [-3550:4-F-3-MeO,2-(Me)₃CO,E], [-3551:2-Cl-3-MeO,2-(Me)₃CO,E], [-3552:2-Cl-4-MeO,2-(Me)₃CO,E], [-3553:2-Cl-5-MeO,2-(Me)₃CO,E], [-3554:2-Cl-6-MeO,2-(Me)₃CO,E], [-3555:3-Cl-2-MeO,2-(Me)₃CO,E], [-3556:3-Cl-4-MeO,2-(Me)₃CO,E], [-3557:3-Cl-5-MeO,2-(Me)₃CO,E], [-3558:4-Cl-2-MeO,2-(Me)₃CO,E], [-3559:4-Cl-3-MeO,2-(Me)₃CO,E], [-3560:2-Me-3-MeO,2-(Me)₃CO,E], [-3561:2-Me-4-MeO,2-(Me)₃CO,E], [-3562:2-Me-5-MeO,2-(Me)₃CO,E], [-3563:2-Me-6-MeO,2-(Me)₃CO,E], [-3564:3-Me-2-MeO,2-(Me)₃CO,E], [-3565:3-Me-4-MeO,2-(Me)₃CO,E], [-3566:3-Me-5-MeO,2-(Me)₃CO,E], [-3567:4-Me-2-MeO,2-(Me)₃CO,E], [-3568:4-Me-3-MeO,2-(Me)₃CO,E], [-3569:H,2,3-F₂,E], [-3570:4-F,2,3-F₂,E], [-3571:4-F,2,3-F₂,Z], [-3572:4-Cl, 2,3-F₂,E], [-3573:4-Cl, 2,3-F₂,Z], [-3574:4-Br,2,3-F₂,E], [-3575:4-I,2,3-F₂,E], [-3576:4-Me, 2,3-F₂,E], [-3577:4-Me,2,3-F₂,Z], [-3578:4-Et,2,3-F₂,E], [-3579:4-C₃H₇,2,3-F₂,E], [-3580:4-(Me)₂CH,2,3-F₂,E], [-3581:4-CF₃,2,3-F₂,E], [-3582:4-CF₃,2,3-F₂,Z], [-3583:4-C₂F₅,2,3-F₂,E], [-3584:4-C₃F₇,2,3-F₂,E], [-3585:4-(CF₃)₂CF,2,3-F₂,E], [-3586:4-(CF₃)₂CH,2,3-F₂,E], [-3587:4-CHF₂,2,3-F₂,E], [-3588:4-CH₂F,2,3-F₂,E], [-3589:4-CF₃CH₂,2,3-F₂,E], [-3590:4-MeO,2,3-F₂,E], [-3591:4-MeO,2,3-F₂,Z], [-3592:4-EtO,2,3-F₂,E], [-3593:4-C₃H₇O,2,3-F₂,E], [-3594:4-(Me)₂CHO,2,3-F₂,E], [-3595:4-NO₂,2,3-F₂,E], [-3596:4-NO₂, 2,3-F₂,Z], [-3597:3-F,2,3-F₂,E], [-3598:3-F,2,3-F₂,Z], [-3599:3-C₁₋₂,₃-F₂,E], [-3600:3-C₁₋₂,₃-F₂,Z], [-3601:3-Br,2,3-F₂,E], [-3602:3-I,2,3-F₂,E], [-3603:3-Me,2,3-F₂,E], [-3604:3-Me,2,3-F₂,Z], [-3605:3-Et,2,3-F₂,E], [-3606:3-C₃H₇,2,3-F₂,E], [-3607:3-(Me)₂CH,2,3-F₂,E], [-3608:3-CF₃,2,3-F₂,E], [-3609:3-CF₃,2,3-F₂,Z], [-3610:3-C₂F₅,2,3-F₂,E], [-3611:3-C₃F₇, 2,3-F₂,E], [-3612:3-(CF₃)₂CF,2,3-F₂,E], [-3613:3-(CF₃)₂CH,2,3-F₂,E], [-3614:3-CHF₂,2,3-F₂,E], [-3615:3-CHF₂,2,3-F₂,Z], [-3616:3-CH₂F,2,3-F₂,E], [-3617:3-CH₂F, 2,3-F₂,Z], [-3618:3-CF₃CH₂,2,3-F₂,E], [-3619:3-MeO,2,3-F₂,E], [-3620:3-MeO,2,3-F₂,Z], [-3621:3-EtO,2,3-F₂,E], [-3622:3-C₃H₇O,2,3-F₂,E], [-3623:3-(Me)₂CHO,2,3-F₂,E], [-3624:3-NO₂,2,3-F₂,E], [-3625:2-F,2,3-F₂,E], [-3626:2-Cl,2,3-F₂,E], [-3627:2-Br,2,3-F₂,E], [-3628:2-I,2,3-F₂,E], [-3629:2-Me,2,3-F₂,E], [-3630:2-Et,2,3-F₂,E], [-3631:2-C₃H₇,2,3-F₂,E], [-3632:2-(Me)₂CH,2,3-F₂,E], [-3633:2-CF₃,2,3-F₂,E], [-3634:2-C₂F₅,2,3-F₂,E], [-3635:2-C₃F₇, 2,3-F₂,E], [-3636:2-(CF₃)₂CF,2,3-F₂,E], [-3637:2-(CF₃)₂CH,2,3-F₂,E], [-3638:2-CHF₂,2,3-F₂,E], [-3639:2-CH₂F, 2,3-F₂,E], [-3640:2-CF₃CH₂,2,3-F₂,E], [-3641:2-MeO,2,3-F₂,E], [-3642:2-EtO,2,3-F₂,E], [-3643:2-C₃H₇O,2,3-F₂,E], [-3644:2-(Me)₂CHO,2,3-F₂,E], [-3645:2-NO₂,2,3-F₂,E], [-3646:2,3-F₂,2,3-F₂,E], [-3647:2,4-F₂,2,3-F₂,E], [-3648:2,5-F₂,2,3-F₂,E], [-3649:2,6-F₂,2,3-F₂,E], [-3650:3,4-F₂,2,3-F₂,E], [-3651:3,4-F₂,2,3-F₂,Z], [-3652:3,5-F₂,2,3-F₂,E], [-3653:3,5-F₂,2,3-F₂,Z], [-3654:2,3-Cl₂,2,3-F₂,E], [-3655:2,3-Cl₂,2,3-F₂,Z], [-3656:2,4-Cl₂,2,3-F₂,E], [-3657:2,4-Cl₂,2,3-F₂,Z], [-3658:2,5-Cl₂,2,3-F₂,E], [-3659:2,5-Cl₂,2,3-F₂,Z], [-3660:2,6-Cl₂,2,3-F₂,E], [-3661:3,4-Cl₂,2,3-F₂,E], [-3662:3,5-Cl₂,2,3-F₂,E], [-3663:2,3-Br₂,2,3-F₂,E], [-3664:2,4-Br₂,2,3-F₂,E], [-3665: 2,5-Br₂,2,3-F₂,E], [-3666:2,6-Br₂,2,3-F₂,E], [-3667:3,4-Br₂, 2,3-F₂,E], [-3668:3,5-Br₂,2,3-F₂,E], [-3669:2,3-Me₂,2,3-F₂,E], [-3670:2,4-Me₂,2,3-F₂,E], [-3671:2,5-Me₂,2,3-F₂,E], [-3672:2,6-Me₂,2,3-F₂,E], [-3673:3,4-Me₂,2,3-F₂,E], [-3674:3,5-Me₂,2,3-F₂,E], [-3675:2,3-Et₂,2,3-F₂,E], [-3676:2,4-Et₂,2,3-F₂,E], [-3677:2,5-Et₂,2,3-F₂,E], [-3678:2,6-Et₂,2,3-F₂,E], [-3679:3,4-Et₂,2,3-F₂,E], [-3680:3,5-Et₂,2,3-F₂,E], [-3681:2,3-(CF₃)₂,2,3-F₂,E], [-3682:2,4-(CF₃)₂,2,3-F₂,E], [-3683:2,5-(CF₃)₂,2,3-F₂,E], [-3684:2,6-(CF₃)₂,2,3-F₂,E], [-3685:3,4-(CF₃)₂,2,3-F₂,E], [-3686:3,5-(CF₃)₂,2,3-F₂,E], [-3687:2,3-(CHF₂)₂,2,3-F₂,E], [-3688:2,4-(CHF₂)₂,2,3-F₂,E], [-3689:2,5-(CHF₂)₂,2,3-F₂,E], [-3690:2,6-(CHF₂)₂,2,3-F₂,E], [-3691:3,4-(CHF₂)₂,2,3-F₂,E], [-3692:3,5-(CHF₂)₂,2,3-F₂,E], [-3693:2,3-(CH₂F)₂,2,3-F₂,E], [-3694:2,4-(CH₂F)₂,2,3-F₂,E], [-3695:2,5-(CH₂F)₂,2,3-F₂,E], [-3696:2,6-(CH₂F)₂,2,3-F₂,E], [-3697:3,4-(CH₂F)₂,2,3-F₂,E], [-3698:3,5-(CH₂F)₂,2,3-F₂,E], [-3699:2,3-(MeO)₂,2,3-F₂,E], [-3700:2,4-(MeO)₂,2,3-F₂,E], [-3701:2,5-(MeO)₂,2,3-F₂,E], [-3702:2,6-(MeO)₂,2,3-F₂,E], [-3703:3,4-(MeO)₂,2,3-F₂,E], [-3704:3,5-(MeO)₂,2,3-F₂,E], [-3705:2,3-(EtO)₂,2,3-F₂,E], [-3706:2,4-(EtO)₂,2,3-F₂,E], [-3707:2,5-(EtO)₂,2,3-F₂,E], [-3708:2,6-(EtO)₂,2,3-F₂,E], [-3709:3,4-(EtO)₂,2,3-F₂,E], [-3710:3,5-(EtO)₂,2,3-F₂,E], [-3711:2-Cl-3-F,2,3-F₂,E], [-3712:2-Cl-4-F,2,3-F₂,E], [-3713:2-Cl-5-F,2,3-F₂,E], [-3714:2-Cl-6-F,2,3-F₂,E], [-3715:3-Cl-2-F,2,3-F₂,E], [-3716:3-Cl-4-F,2,3-F₂,E], [-3717:3-Cl-5-F,2,3-F₂,E], [-3718:4-Cl-2-F,2,3-F₂,E], [-3719:4-Cl-3-F,2,3-F₂,E], [-3720:2-F-3-Me,2,3-F₂,E], [-3721:2-F-4-Me,2,3-F₂,E], [-3722:2-F-5-Me,2,3-F₂,E], [-3723:2-F-6-Me,2,3-F₂,E], [-3724:3-F-2-Me,2,3-F₂,E], [-3725:3-F-4-Me,2,3-F₂,E], [-3726:3-F-5-Me,2,3-F₂,E], [-3727:4-F-2-Me,2,3-F₂,E], [-3728:4-F-3-Me,2,3-F₂,E], [-3729:2-Cl-3-Me,2,3-F₂,E], [-3730:2-Cl-4-Me,2,3-F₂,E], [-3731:2-Cl-5-Me,2,3-F₂,E], [-3732:2-Cl-6-Me,2,3-F₂,E], [-3733:3-Cl-2-Me,2,3-F₂,E], [-3734:3-Cl-4-Me,2,3-F₂,E], [-3735:3-Cl-5-Me,2,3-F₂,E], [-3736:4-Cl-2-Me,2,3-F₂,E], [-3737:4-Cl-3-Me,2,3-F₂,E], [-3738:2-F-3-CF₃,2,3-F₂,E], [-3739:2-F-4-CF₃,2,3-F₂,E], [-3740:2-F-5-CF₃,2,3-F₂,E], [-3741:2-F-6-CF₃,2,3-F₂,E], [-3742:3-F-2-CF₃,2,3-F₂,E], [-3743:3-F-4-CF₃,2,3-F₂,E], [-3744:3-F-5-CF₃,2,3-F₂,E], [-3745:4-F-2-CF₃,2,3-F₂,E], [-3746:4-F-3-CF₃,2,3-F₂,E], [-3747:2-Cl-3-CF₃,2,3-F₂,E], [-3748:2-Cl-4-CF₃,2,3-F₂,E], [-3749:2-Cl-5-CF₃,2,3-F₂,E], [-3750:2-Cl-6-CF₃,2,3-F₂,E], [-3751:3-Cl-2-CF₃,2,3-F₂,E], [-3752:3-Cl-4-CF₃, 2,3-F₂,E], [-3753:3-Cl-5-CF₃,2,3-F₂,E], [-3754:4-Cl-2-CF₃,2,3-F₂,E], [-3755:4-Cl-3-CF₃,2,3-F₂,E], [-3756:2-Me-3-CF₃,2,3-F₂,E], [-3757:2-Me-4-CF₃,2,3-F₂,E], [-3758:2-Me-5-CF₃,2,3-F₂,E], [-3759:2-Me-6-CF₃,2,3-F₂,E], [-3760:3-Me-2-CF₃,2,3-F₂,E], [-3761:3-Me-4-CF₃,2,3-F₂,E], [-3762:3-Me-5-CF₃,2,3-F₂,E], [-3763:4-Me-2-CF₃,2,3-F₂,E], [-3764:4-Me-3-CF₃,2,3-F₂,E], [-3765:2-F-3-MeO,2,3-F₂,E], [-3766:2-F-4-MeO,2,3-F₂,E], [-3767:2-F-5-MeO,2,3-F₂,E], [-3768:2-F-6-MeO,2,3-F₂,E], [-3769:3-F-2-MeO,2,3-F₂,E], [-3770:3-F-4-MeO,2,3-F₂,E], [-3771:3-F-5-MeO,2,3-F₂,E], [-3772:4-F-2-MeO,2,3-F₂,E], [-3773:4-F-3-

MeO,2,3-F₂,E], [−3774:2-Cl-3-MeO,2,3-F₂,E], [−3775:2-Cl-4-MeO,2,3-F₂,E], [−3776:2-Cl-5-MeO,2,3-F₂,E], [−3777:2-Cl-6-MeO,2,3-F₂,E], [−3778:3-Cl-2-MeO,2,3-F₂,E], [−3779:3-Cl-4-MeO,2,3-F₂,E], [−3780:3-Cl-5-MeO,2,3-F₂,E], [−3781:4-Cl-2-MeO,2,3-F₂,E], [−3782:4-Cl-3-MeO,2,3-F₂,E], [−3783:2-Me-3-MeO,2,3-F₂,E], [−3784:2-Me-4-MeO,2,3-F₂,E], [−3785:2-Me-5-MeO,2,3-F₂,E], [−3786:2-Me-6-MeO,2,3-F₂,E], [−3787:3-Me-2-MeO,2,3-F₂,E], [−3788:3-Me-4-MeO,2,3-F₂,E], [−3789:3-Me-5-MeO,2,3-F₂,E], [−3790:4-Me-2-MeO,2,3-F₂,E], [−3791:4-Me-3-MeO, 2,3-F₂,E],

[−3792:H,2,4-F₂,E], [−3793:4-F,2,4-F₂,E], [−3794:4-F,2,4-F₂,Z], [−3795:4-Cl,2,4-F₂,E], [−3796:4-Cl,2,4-F₂,Z], [−3797:4-Br,2,4-F₂,E], [−3798:4-I,2,4-F₂,E], [−3799:4-Me, 2,4-F₂,E], [−3800:4-Me,2,4-F₂,Z], [−3801:4-Et,2,4-F₂,E], [−3802:4-C₃H₇,2,4-F₂,E], [−3803:4-(Me)₂CH,2,4-F₂,E], [−3804:4-CF₃,2,4-F₂,E], [−3805:4-CF₃,2,4-F₂,Z], [−3806:4-C₂F₅,2,4-F₂,E], [−3807:4-C₃F₇,2,4-F₂,E], [−3808:4-(CF₃)₂CF,2,4-F₂,E], [−3809:4-(CF₃)₂CH,2,4-F₂,E], [−3810:4-CHF₂,2,4-F₂,E], [−3811:4-CH₂F,2,4-F₂,E], [−3812:4-CF₃CH₂,2,4-F₂,E], [−3813:4-MeO,2,4-F₂,E], [−3814:4-MeO,2,4-F₂,Z], [−3815:4-EtO,2,4-F₂,E], [−3816:4-C₃H₇O,2,4-F₂,E], [−3817:4-(Me)₂CHO,2,4-F₂,E], [−3818:4-NO₂,2,4-F₂,E], [−3819:4-NO₂,2,4-F₂,Z], [−3820:3-F,2,4-F₂,E], [−3821:3-F,2,4-F₂,Z], [−3822:3-Cl,2,4-F₂,E], [−3823:3-Cl,2,4-F₂,Z], [−3824:3-Br,2,4-F₂,E], [−3825:3-I,2,4-F₂,E], [−3826:3-Me, 2,4-F₂,E], [−3827:3-Me, 2,4-F₂,Z], [−3828:3-Et,2,4-F₂,E], [−3829:3-C₃H₇,2,4-F₂,E], [−3830:3-(Me)₂CH,2,4-F₂,E], [−3831:3-CF₃,2,4-F₂,E], [−3832:3-CF₃,2,4-F₂,Z], [−3833:3-C₂F₅,2,4-F₂,E], [−3834:3-C₃F₇, 2,4-F₂,E], [−3835:3-(CF₃)₂CF,2,4-F₂,E], [−3836:3-(CF₃)CH,2,4-F₂,E], [−3837:3-CHF₂,2,4-F₂,E], [−3838:3-CHF₂,2,4-F₂,Z], [−3839:3-CH₂F, 2,4-F₂,E], [−3840:3-CH₂F, 2,4-F₂,Z], [−3841:3-CF₃CH₂,2,4-F₂,E], [−3842:3-MeO,2,4-F₂,E], [−3843:3-MeO,2,4-F₂,Z], [−3844:3-EtO,2,4-F₂,E], [−3845:3-C₃H₇O,2,4-F₂,E], [−3846:3-(Me)₂CHO,2,4-F₂,E], [−3847:3-NO₂,2,4-F₂,E], [−3848:2-F,2,4-F₂,E], [−3849:2-Cl,2,4-F₂,E], [−3850:2-Br,2,4-F₂,E], [−3851:2-I,2,4-F₂,E], [−3852:2-Me,2,4-F₂,E], [−3853:2-Et,2,4-F₂,E], [−3854:2-C₃H₇,2,4-F₂,E], [−3855:2-(Me)₂CH,2,4-F₂,E], [−3856:2-CF₃,2,4-F₂,E], [−3857:2-C₂F₅,2,4-F₂,E], [−3858:2-C₃F₇,2,4-F₂,E], [−3859:2-(CF₃)₂CF,2,4-F₂,E], [−3860:2-(CF₃)₂CH,2,4-F₂,E], [−3861:2-CHF₂,2,4-F₂,E], [−3862:2-CH₂F,2,4-F₂,E], [−3863:2-CF₃CH₂,2,4-F₂,E], [−3864:2-MeO,2,4-F₂,E], [−3865:2-EtO,2,4-F₂,E], [−3866:2-C₃H₇O,2,4-F₂,E], [−3867:2-(Me)₂CHO,2,4-F₂,E], [−3868:2-NO₂,2,4-F₂,E], [−3869:2,3-F₂,2,4-F₂,E], [−3870:2,4-F₂,2,4-F₂,E], [−3871:2,5-F₂, 2,4-F₂,E], [−3872:2,6-F₂,2,4-F₂,E], [−3873:3,4-F₂,2,4-F₂,E], [−3874:3,4-F₂,2,4-F₂,Z], [−3875:3,5-F₂,2,4-F₂,E], [−3876:3,5-F₂,2,4-F₂,Z], [−3877:2,3-Cl₂,2,4-F₂,E], [−3878:2,3-Cl₂,2,4-F₂,Z], [−3879:2,4-Cl₂,2,4-F₂,E], [−3880:2,4-Cl₂,2,4-F₂,Z], [−3881:2,5-Cl₂,2,4-F₂,E], [−3882:2,5-Cl₂,2,4-F₂,Z], [−3883:2,6-Cl₂, 2,4-F₂,E], [−3884:3,4-Cl₂,2,4-F₂,E], [−3885:3,5-Cl₂,2,4-F₂,E], [−3886:2,3-Br₂,2,4-F₂,E], [−3887:2,4-Br₂,2,4-F₂,E], [−3888:2,5-Br₂,2,4-F₂,E], [−3889:2,6-Br₂,2,4-F₂,E], [−3890:3,4-Br₂,2,4-F₂,E], [−3891:3,5-Br₂,2,4-F₂,E], [−3892:2,3-Me₂,2,4-F₂,E], [−3893:2,4-Me₂,2,4-F₂,E], [−3894:2,5-Me₂,2,4-F₂,E], [−3895:2,6-Me₂,2,4-F₂,E], [−3896:3,4-Me₂,2,4-F₂,E], [−3897:3,5-Me₂,2,4-F₂,E], [−3898:2,3-Et₂,2,4-F₂,E], [−3899:2,4-Et₂,2,4-F₂,E], [−3900:2,5-Et₂,2,4-F₂,E], [−3901:2,6-Et₂,2,4-F₂,E], [−3902:3,4-Et₂,2,4-F₂,E], [−3903:3,5-Et₂,2,4-F₂,E], [−3904:2,3-(CF₃)₂,2,4-F₂,E], [−3905:2,4-(CF₃)₂,2,4-F₂,E], [−3906:2,5-(CF₃)₂,2,4-F₂,E], [−3907:2,6-(CF₃)₂,2,4-F₂,E], [−3908:3,4-(CF₃)₂,2,4-F₂,E], [−3909:3,5-(CF₃)₂,2,4-F₂,E], [−3910:2,3-(CHF₂)₂,2,4-F₂,E], [−3911:2,4-(CHF₂)₂,2,4-F₂,E], [−3912:2,5-(CHF₂)₂,2,4-F₂,E], [−3913:2,6-(CHF₂)₂,2,4-F₂,E], [−3914:3,4-(CHF₂)₂,2,4-F₂,E], [−3915:3,5-(CHF₂)₂,2,4-F₂,E], [−3916:2,3-(CH₂F)₂,2,4-F₂,E], [−3917:2,4-(CH₂F)₂,2,4-F₂,E], [−3918:2,5-(CH₂F)₂,2,4-F₂,E], [−3919:2,6-(CH₂F)₂,2,4-F₂,E], [−3920:3,4-(CH₂F)₂,2,4-F₂,E], [−3921:3,5-(CH₂F)₂,2,4-F₂,E], [−3922:2,3-(MeO)₂,2,4-F₂,E], [−3923:2,4-(MeO)₂,2,4-F₂,E], [−3924:2,5-(MeO)₂,2,4-F₂,E], [−3925:2,6-(MeO)₂,2,4-F₂,E], [−3926:3,4-(MeO)₂,2,4-F₂,E], [−3927:3,5-(MeO)₂,2,4-F₂,E], [−3928:2,3-(EtO)₂,2,4-F₂,E], [−3929:2,4-(EtO)₂,2,4-F₂,E], [−3930:2,5-(EtO)₂,2,4-F₂,E], [−3931:2,6-(EtO)₂, 2,4-F₂,E], [−3932:3,4-(EtO)₂,2,4-F₂,E], [−3933:3,5-(EtO)₂,2,4-F₂,E], [−3934:2-Cl-3-F,2,4-F₂,E], [−3935:2-Cl-4-F,2,4-F₂,E], [−3936:2-Cl-5-F,2,4-F₂,E], [−3937:2-Cl-6-F,2,4-F₂,E], [−3938:3-Cl-2-F,2,4-F₂,E], [−3939:3-Cl-4-F,2,4-F₂,E], [−3940:3-Cl-5-F,2,4-F₂,E], [−3941:4-Cl-2-F,2,4-F₂,E], [−3942:4-Cl-3-F,2,4-F₂,E], [−3943:2-F-3-Me,2,4-F₂,E], [−3944:2-F-4-Me,2,4-F₂,E], [−3945:2-F-5-Me,2,4-F₂,E], [−3946:2-F-6-Me,2,4-F₂,E], [−3947:3-F-2-Me,2,4-F₂,E], [−3948:3-F-4-Me,2,4-F₂,E], [−3949:3-F-5-Me,2,4-F₂,E], [−3950:4-F-2-Me,2,4-F₂,E], [−3951:4-F-3-Me,2,4-F₂,E], [−3952:2-Cl-3-Me,2,4-F₂,E], [−3953:2-Cl-4-Me,2,4-F₂,E], [−3954:2-Cl-5-Me,2,4-F₂,E], [−3955:2-Cl-6-Me,2,4-F₂,E], [−3956:3-Cl-2-Me,2,4-F₂,E], [−3957:3-Cl-4-Me,2,4-F₂,E], [−3958:3-Cl-5-Me,2,4-F₂,E], [−3959:4-Cl-2-Me,2,4-F₂,E], [−3960:4-Cl-3-Me,2,4-F₂,E], [−3961:2-F-3-CF₃,2,4-F₂,E], [−3962:2-F-4-CF₃,2,4-F₂,E], [−3963:2-F-5-CF₃,2,4-F₂,E], [−3964:2-F-6-CF₃,2,4-F₂,E], [−3965:3-F-2-CF₃,2,4-F₂,E], [−3966:3-F-4-CF₃,2,4-F₂,E], [−3967:3-F-5-CF₃,2,4-F₂,E], [−3968:4-F-2-CF₃,2,4-F₂,E], [−3969:4-F-3-CF₃,2,4-F₂,E], [−3970:2-Cl-3-CF₃,2,4-F₂,E], [−3971:2-Cl-4-CF₃,2,4-F₂,E], [−3972:2-Cl-5-CF₃,2,4-F₂,E], [−3973:2-Cl-6-CF₃, 2,4-F₂,E], [−3974:3-Cl-2-CF₃,2,4-F₂,E], [−3975:3-Cl-4-CF₃,2,4-F₂,E], [−3976:3-Cl-5-CF₃,2,4-F₂,E], [−3977:4-Cl-2-CF₃,2,4-F₂,E], [−3978:4-Cl-3-CF₃,2,4-F₂,E], [−3979:2-Me-3-CF₃,2,4-F₂,E], [−3980:2-Me-4-CF₃,2,4-F₂,E], [−3981:2-Me-5-CF₃,2,4-F₂,E], [−3982:2-Me-6-CF₃,2,4-F₂,E], [−3983:3-Me-2-CF₃,2,4-F₂,E], [−3984:3-Me-4-CF₃,2,4-F₂,E], [−3985:3-Me-5-CF₃,2,4-F₂,E], [−3986:4-Me-2-CF₃,2,4-F₂,E], [−3987:4-Me-3-CF₃,2,4-F₂,E], [−3988:2-F-3-MeO,2,4-F₂,E], [−3989:2-F-4-MeO,2,4-F₂,E], [−3990:2-F-5-MeO,2,4-F₂,E], [−3991:2-F-6-MeO,2,4-F₂,E], [−3992:3-F-2-MeO,2,4-F₂,E], [−3993:3-F-4-MeO,2,4-F₂,E], [−3994:3-F-5-MeO,2,4-F₂,E], [−3995:4-F-2-MeO,2,4-F₂,E], [−3996:4-F-3-MeO, 2,4-F₂,E], [−3997:2-Cl-3-MeO,2,4-F₂,E], [−3998:2-Cl-4-MeO,2,4-F₂,E], [−3999:2-Cl-5-MeO, 2,4-F₂,E], [−4000:2-Cl-6-MeO, 2,4-F₂,E], [−4001:3-Cl-2-MeO,2,4-F₂,E], [−4002:3-Cl-4-MeO,2,4-F₂,E], [−4003:3-Cl-5-MeO,2,4-F₂,E], [−4004:4-Cl-2-MeO,2,4-F₂,E], [−4005:4-Cl-3-MeO,2,4-F₂,E], [−4006:2-Me-3-MeO,2,4-F₂,E], [−4007:2-Me-4-MeO,2,4-F₂,E], [−4008:2-Me-5-MeO,2,4-F₂,E], [−4009:2-Me-6-MeO,2,4-F₂,E], [−4010:3-Me-2-MeO,2,4-F₂,E], [−4011:3-Me-4-MeO,2,4-F₂,E], [−4012:3-Me-5-MeO,2,4-F₂,E], [−4013:4-Me-2-MeO,2,4-F₂,E], [−4014:4-Me-3-MeO,2,4-F₂,E],

[−4015:H,2,5-F₂,E], [−4016:4-F,2,5-F₂,E], [−4017:4-F,2,5-F₂,Z], [−4018:4-Cl, 2,5-F₂,E], [−4019:4-Cl, 2,5-F₂,Z], [−4020:4-Br,2,5-F₂,E], [−4021:4-I,2,5-F₂,E], [−4022:4-Me, 2,5-F₂,E], [−4023:4-Me,2,5-F₂,Z], [−4024:4-Et,2,5-F₂,E], [−4025:4-C₃H₇,2,5-F₂,E], [−4026:4-(Me)₂CH,2,5-F₂,E], [−4027:4-CF₃,2,5-F₂,E], [−4028:4-CF₃,2,5-F₂,Z], [−4029:4-C₂F₅,2,5-F₂,E], [−4030:4-C₃F₇, 2,5-F₂,E], [−4031:4-(CF₃)₂CF,2,5-F₂,E], [−4032:4-(CF₃)₂CH,2,5-F₂,E], [−4033:4-CHF₂,2,5-F₂,E], [−4034:4-CH₂F,2,5-

F₂,E], [-4035:4-CF₃CH₂,2,5-F₂,E], [-4036:4-MeO,2,5-F₂,E], [-4037:4-MeO,2,5-F₂,Z], [-4038:4-EtO,2,5-F₂,E], [-4039:4-C₃H₇O,2,5-F₂,E], [-4040:4-(Me)₂CHO,2,5-F₂,E], [-4041:4-NO₂,2,5-F₂,E], [-4042:4-NO₂,2,5-F₂,Z], [-4043:3-F,2,5-F₂,E], [-4044:3-F,2,5-F₂,Z], [-4045:3-Cl,2,5-F₂,E], [-4046:3-Cl,2,5-F₂,Z], [-4047:3-Br,2,5-F₂,E], [-4048:3-I,2,5-F₂,E], [-4049:3-Me,2,5-F₂,E], [-4050:3-Me,2,5-F₂,Z], [-4051:3-Et,2,5-F₂,E], [-4052:3-C₃H₇,2,5-F₂,E], [-4053:3-(Me)₂CH,2,5-F₂,E], [-4054:3-CF₃,2,5-F₂,E], [-4055:3-CF₃,2,5-F₂,Z], [-4056:3-C₂F₅,2,5-F₂,E], [-4057:3-C₃F₇,2,5-F₂,E], [-4058:3-(CF₃)₂CF,2,5-F₂,E], [-4059:3-(CF₃)CH,2,5-F₂,E], [-4060:3-CHF₂,2,5-F₂,E], [-4061:3-CHF₂,2,5-F₂,Z], [-4062:3-CH₂F,2,5-F₂,E], [-4063:3-CH₂F,2,5-F₂,Z], [-4064:3-CF₃CH₂,2,5-F₂,E], [-4065:3-MeO,2,5-F₂,E], [-4066:3-MeO,2,5-F₂,Z], [-4067:3-EtO,2,5-F₂,E], [-4068:3-C₃H₇O,2,5-F₂,E], [-4069:3-(Me)₂CHO,2,5-F₂,E], [-4070:3-NO₂,2,5-F₂,E], [-4071:2-F,2,5-F₂,E], [-4072:2-Cl,2,5-F₂,E], [-4073:2-Br,2,5-F₂,E], [-4074:2-I,2,5-F₂,E], [-4075:2-Me,2,5-F₂,E], [-4076:2-Et,2,5-F₂,E], [-4077:2-C₃H₇,2,5-F₂,E], [-4078:2-(Me)₂CH,2,5-F₂,E], [-4079:2-CF₃,2,5-F₂,E], [-4080:2-C₂F₅,2,5-F₂,E], [-4081:2-C₃F₇,2,5-F₂,E], [-4082:2-(CF₃)₂CF,2,5-F₂,E], [-4083:2-(CF₃)₂CH,2,5-F₂,E], [-4084:2-CHF₂,2,5-F₂,E], [-4085:2-CH₂F,2,5-F₂,E], [-4086:2-CF₃CH₂,2,5-F₂,E], [-4087:2-MeO,2,5-F₂,E], [-4088:2-EtO,2,5-F₂,E], [-4089:2-C₃H₇O,2,5-F₂,E], [-4090:2-(Me)₂CHO,2,5-F₂,E], [-4091:2-NO₂,2,5-F₂,E], [-4092:2,3-F₂,2,5-F₂,E], [-4093:2,4-F₂,2,5-F₂,E], [-4094:2,5-F₂,2,5-F₂,E], [-4095:2,6-F₂,2,5-F₂,E], [-4096:3,4-F₂,2,5-F₂,E], [-4097:3,4-F₂,2,5-F₂,Z], [-4098:3,5-F₂,2,5-F₂,E], [-4099:3,5-F₂,2,5-F₂,Z], [-4100:2,3-Cl₂,2,5-F₂,E], [-4101:2,3-Cl₂,2,5-F₂,Z], [-4102:2,4-Cl₂,2,5-F₂,E], [-4103:2,4-Cl₂,2,5-F₂,Z], [-4104:2,5-Cl₂,2,5-F₂,E], [-4105:2,5-Cl₂,2,5-F₂,Z], [-4106:2,6-Cl₂,2,5-F₂,E], [-4107:3,4-Cl₂,2,5-F₂,E], [-4108:3,5-Cl₂,2,5-F₂,E], [-4109:2,3-Br₂,2,5-F₂,E], [-4110:2,4-Br₂,2,5-F₂,E], [-4111:2,5-Br₂,2,5-F₂,E], [-4112:2,6-Br₂,2,5-F₂,E], [-4113:3,4-Br₂,2,5-F₂,E], [-4114:3,5-Br₂,2,5-F₂,E], [-4115:2,3-Me₂,2,5-F₂,E], [-4116:2,4-Me₂,2,5-F₂,E], [-4117:2,5-Me₂,2,5-F₂,E], [-4118:2,6-Me₂,2,5-F₂,E], [-4119:3,4-Me₂,2,5-F₂,E], [-4120:3,5-Me₂,2,5-F₂,E], [-4121:2,3-Et₂,2,5-F₂,E], [-4122:2,4-Et₂,2,5-F₂,E], [-4123:2,5-Et₂,2,5-F₂,E], [-4124:2,6-Et₂,2,5-F₂,E], [-4125:3,4-Et₂,2,5-F₂,E], [-4126:3,5-Et₂,2,5-F₂,E], [-4127:2,3-(CF₃)₂,2,5-F₂,E], [-4128:2,4-(CF₃)₂,2,5-F₂,E], [-4129:2,5-(CF₃)₂,2,5-F₂,E], [-4130:2,6-(CF₃)₂,2,5-F₂,E], [-4131:3,4-(CF₃)₂,2,5-F₂,E], [-4132:3,5-(CF₃)₂,2,5-F₂,E], [-4133:2,3-(CHF₂)₂,2,5-F₂,E], [-4134:2,4-(CHF₂)₂,2,5-F₂,E], [-4135:2,5-(CHF₂)₂,2,5-F₂,E], [-4136:2,6-(CHF₂)₂,2,5-F₂,E], [-4137:3,4-(CHF₂)₂,2,5-F₂,E], [-4138:3,5-(CHF₂)₂,2,5-F₂,E], [-4139:2,3-(0H₂F)₂,2,5-F₂,E], [-4140:2,4-(CH₂F)₂,2,5-F₂,E], [-4141:2,5-(0H₂F)₂,2,5-F₂,E], [-4142:2,6-(CH₂F)₂,2,5-F₂,E], [-4143:3,4-(CH₂F)₂,2,5-F₂,E], [-4144:3,5-(CH₂F)₂,2,5-F₂,E], [-4145:2,3-(MeO)₂,2,5-F₂,E], [-4146:2,4-(MeO)₂,2,5-F₂,E], [-4147:2,5-(MeO)₂,2,5-F₂,E], [-4148:2,6-(MeO)₂,2,5-F₂,E], [-4149:3,4-(MeO)₂,2,5-F₂,E], [-4150:3,5-(MeO)₂,2,5-F₂,E], [-4151:2,3-(EtO)₂,2,5-F₂,E], [-4152:2,4-(EtO)₂,2,5-F₂,E], [-4153:2,5-(EtO)₂,2,5-F₂,E], [-4154:2,6-(EtO)₂,2,5-F₂,E], [-4155:3,4-(EtO)₂,2,5-F₂,E], [-4156:3,5-(EtO)₂,2,5-F₂,E], [-4157:2-Cl-3-F,2,5-F₂,E], [-4158:2-Cl-4-F,2,5-F₂,E], [-4159:2-Cl-5-F, 2,5-F₂,E], [-4160:2-Cl-6-F, 2,5-F₂,E], [-4161:3-Cl-2-F,2,5-F₂,E], [-4162:3-Cl-4-F,2,5-F₂,E], [-4163:3-Cl-5-F, 2,5-F₂,E], [-4164:4-Cl-2-F, 2,5-F₂, F], [-4165:4-Cl-3-F, 2,5-F₂,E], [-4166:2-F-3-Me,2,5-F₂,E], [-4167:2-F-4-Me,2,5-F₂,E], [-4168:2-F-5-Me,2,5-F₂,E], [-4169:2-F-6-Me,2,5-F₂,E], [-4170:3-F-2-Me,2,5-F₂,E], [-4171:3-F-4-Me,2,5-F₂,E], [-4172:3-F-5-Me,2,5-F₂,E], [-4173:4-F-2-Me, 2,5-F₂,E], [-4174:4-F-3-Me, 2,5-F₂,F], [-4175:2-Cl-3-Me, 2,5-F₂,E], [-4176:2-Cl-4-Me, 2,5-F₂, F], [-4177:2-Cl-5-Me, 2,5-F₂,E], [-4178:2-Cl-6-Me, 2,5-F₂, F], [-4179:3-Cl-2-Me,2,5-F₂,E], [-4180:3-Cl-4-Me,2,5-F₂,E], [-4181:3-Cl-5-Me,2,5-F₂,E], [-4182:4-Cl-2-Me,2,5-F₂,E], [-4183:4-Cl-3-Me,2,5-F₂,E], [-4184:2-F-3-CF₃,2,5-F₂,E], [-4185:2-F-4-CF₃,2,5-F₂,E], [-4186:2-F-5-CF₃,2,5-F₂,E], [-4187:2-F-6-CF₃, 2,5-F₂,E], [-4188:3-F-2-CF₃,2,5-F₂,E], [-4189:3-F-4-CF₃,2,5-F₂,E], [-4190:3-F-5-CF₃,2,5-F₂,E], [-4191:4-F-2-CF₃,2,5-F₂,E], [-4192:4-F-3-CF₃,2,5-F₂,E], [-4193:2-Cl-3-CF₃,2,5-F₂,E], [-4194:2-Cl-4-CF₃,2,5-F₂,E], [-4195:2-Cl-5-CF₃,2,5-F₂,E], [-4196:2-Cl-6-CF₃,2,5-F₂,E], [-4197:3-Cl-2-CF₃,2,5-F₂,E], [-4198:3-Cl-4-CF₃,2,5-F₂,E], [-4199:3-Cl-5-CF₃,2,5-F₂,E], [-4200:4-Cl-2-CF₃,2,5-F₂,E], [-4201:4-Cl-3-CF₃,2,5-F₂,E], [-4202:2-Me-3-CF₃,2,5-F₂,E], [-4203:2-Me-4-CF₃,2,5-F₂,E], [-4204:2-Me-5-CF₃,2,5-F₂,E], [-4205:2-Me-6-CF₃,2,5-F₂,E], [-4206:3-Me-2-CF₃,2,5-F₂,E], [-4207:3-Me-4-CF₃,2,5-F₂,E], [-4208:3-Me-5-CF₃,2,5-F₂,E], [-4209:4-Me-2-CF₃,2,5-F₂,E], [-4210:4-Me-3-CF₃,2,5-F₂,E], [-4211:2-F-3-MeO,2,5-F₂,E], [-4212:2-F-4-MeO,2,5-F₂,E], [-4213:2-F-5-MeO,2,5-F₂,E], [-4214:2-F-6-MeO,2,5-F₂,E], [-4215:3-F-2-MeO,2,5-F₂,E], [-4216:3-F-4-MeO,2,5-F₂,E], [-4217:3-F-5-MeO,2,5-F₂,E], [-4218:4-F-2-MeO, 2,5-F₂,E], [-4219:4-F-3-MeO, 2,5-F₂,E], [-4220:2-Cl-3-MeO,2,5-F₂,E], [-4221:2-Cl-4-MeO,2,5-F₂,E], [-4222:2-Cl-5-MeO,2,5-F₂,E], [-4223:2-Cl-6-MeO,2,5-F₂,E], [-4224:3-Cl-2-MeO,2,5-F₂,E], [-4225:3-Cl-4-MeO,2,5-F₂,E], [-4226:3-Cl-5-MeO,2,5-F₂,E], [-4227:4-Cl-2-MeO,2,5-F₂,E], [-4228:4-Cl-3-MeO,2,5-F₂,E], [-4229:2-Me-3-MeO,2,5-F₂,E], [-4230:2-Me-4-MeO,2,5-F₂,E], [-4231:2-Me-5-MeO,2,5-F₂,E], [-4232:2-Me-6-MeO,2,5-F₂,E], [-4233:3-Me-2-MeO,2,5-F₂,E], [-4234:3-Me-4-MeO,2,5-F₂,E], [-4235:3-Me-5-MeO,2,5-F₂,E], [-4236:4-Me-2-MeO,2,5-F₂,E], [-4237:4-Me-3-MeO,2,5-F₂,E],

[-4238:H,3,4-F₂,E], [-4239:4-F,3,4-F₂,E], [-4240:4-F,3,4-F₂,Z], [-4241:4-Cl,3,4-F₂,E], [-4242:4-Cl,3,4-F₂,Z], [-4243:4-Br,3,4-F₂,E], [-4244:4-I,3,4-F₂,E], [-4245:4-Me,3,4-F₂,E], [-4246:4-Me,3,4-F₂,Z], [-4247:4-Et,3,4-F₂,E], [-4248:4-C₃H₇,3,4-F₂,E], [-4249:4-(Me)₂CH,3,4-F₂,E], [-4250:4-CF₃,3,4-F₂,E], [-4251:4-CF₃,3,4-F₂,Z], [-4252:4-C₂F₅,3,4-F₂,E], [-4253:4-C₃F₇,3,4-F₂,E], [-4254:4-(CF₃)₂CF,3,4-F₂,E], [-4255:4-(CF₃)₂CH,3,4-F₂,E], [-4256:4-CHF₂,3,4-F₂,E], [-4257:4-CH₂F,3,4-F₂,E], [-4258:4-CF₃CH₂,3,4-F₂,E], [-4259:4-MeO,3,4-F₂,E], [-4260:4-MeO,3,4-F₂,Z], [-4261:4-EtO,3,4-F₂,E], [-4262:4-C₃H₇O,3,4-F₂,E], [-4263:4-(Me)₂CHO,3,4-F₂,E], [-4264:4-NO₂,3,4-F₂,E], [-4265:4-NO₂, 3,4-F₂,Z], [-4266:3-F,3,4-F₂,E], [-4267:3-F,3,4-F₂,Z], [-4268:3-Cl,3,4-F₂,E], [-4269:3-Cl,3,4-F₂,Z], [-4270:3-Br,3,4-F₂,E], [-4271:3-I,3,4-F₂,E], [-4272:3-Me,3,4-F₂,E], [-4273:3-Me,3,4-F₂,Z], [-4274:3-Et,3,4-F₂,E], [-4275:3-C₃H₇,3,4-F₂,E], [-4276:3-(Me)₂CH,3,4-F₂,E], [-4277:3-CF₃,3,4-F₂,E], [-4278:3-CF₃,3,4-F₂,Z], [-4279:3-C₂F₅,3,4-F₂,E], [-4280:3-C₃F₇,3,4-F₂,E], [-4281:3-(CF₃)₂CF,3,4-F₂,E], [-4282:3-(CF₃)₂CH,3,4-F₂,E], [-4283:3-CHF₂,3,4-F₂,E], [-4284:3-CHF₂,3,4-F₂,Z], [-4285:3-CH₂F,3,4-F₂,E], [-4286:3-CH₂F,3,4-F₂,Z], [-4287:3-CF₃CH₂,3,4-F₂,E], [-4288:3-MeO,3,4-F₂,E], [-4289:3-MeO,3,4-F₂,Z], [-4290:3-EtO,3,4-F₂,E], [-4291:3-C₃H₇O,3,4-F₂,E], [-4292:3-(Me)₂CHO,3,4-F₂,E], [-4293:3-NO₂,3,4-F₂,E], [-4294:2-F,3,4-F₂,E], [-4295:2-Cl,3,4-F₂,E], [-4296:2-Br,3,4-F₂,E], [-4297:2-I,3,4-F₂,E], [-4298:2-Me,3,4-F₂,

E], [−4299:2-Et,3,4-F$_2$,E], [−4300:2-C$_3$H$_7$,3,4-F$_2$,E], [−4301:2-(Me)$_2$CH,3,4-F$_2$,E], [−4302:2-CF$_3$,3,4-F$_2$,E], [−4303:2-C$_2$F$_5$,3,4-F$_2$,E], [−4304:2-C$_3$F$_7$,3,4-F$_2$,E], [−4305:2-(CF$_3$)$_2$CF,3,4-F$_2$,E], [−4306:2-(CF$_3$)$_2$CH,3,4-F$_2$,E], [−4307:2-CHF$_2$,3,4-F$_2$,E], [−4308:2-CH$_2$F,3,4-F$_2$,E], [−4309:2-CF$_3$CH$_2$,3,4-F$_2$,E], [−4310:2-MeO,3,4-F$_2$,E], [−4311:2-EtO,3,4-F$_2$,E], [−4312:2-C$_3$H$_7$O,3,4-F$_2$,E], [−4313:2-(Me)$_2$CHO,3,4-F$_2$,E], [−4314:2-NO$_2$,3,4-F$_2$,E], [−4315:2,3-F$_2$,3,4-F$_2$,E], [−4316:2,4-F$_2$,3,4-F$_2$,E], [−4317:2,5-F$_2$,3,4-F$_2$,E], [−4318:2,6-F$_2$,3,4-F$_2$,E], [−4319:3,4-F$_2$,3,4-F$_2$,E], [−4320:3,4-F$_2$,3,4-F$_2$,Z], [−4321:3,5-F$_2$,3,4-F$_2$,E], [−4322:3,5-F$_2$,3,4-F$_2$,Z], [−4323:2,3-Cl$_2$,3,4-F$_2$,E], [−4324:2,3-Cl$_2$,3,4-F$_2$,Z], [−4325:2,4-Cl$_2$,3,4-F$_2$,E], [−4326:2,4-Cl$_2$,3,4-F$_2$,Z], [−4327:2,5-Cl$_2$,3,4-F$_2$,E], [−4328:2,5-Cl$_2$,3,4-F$_2$,Z], [−4329:2,6-Cl$_2$, 3,4-F$_2$,E], [−4330:3,4-Cl$_2$,3,4-F$_2$,E], [−4331:3,5-Cl$_2$,3,4-F$_2$,E], [−4332:2,3-Br$_2$,3,4-F$_2$,E], [−4333:2,4-Br$_2$,3,4-F$_2$,E], [−4334:2,5-Br$_2$,3,4-F$_2$,E], [−4335:2,6-Br$_2$,3,4-F$_2$,E], [−4336:3,4-Br$_2$, 3,4-F$_2$,E], [−4337:3,5-Br$_2$,3,4-F$_2$,E], [−4338:2,3-Me$_2$,3,4-F$_2$,E], [−4339:2,4-Me$_2$,3,4-F$_2$,E], [−4340:2,5-Me$_2$,3,4-F$_2$,E], [−4341:2,6-Me$_2$,3,4-F$_2$,E], [−4342:3,4-Me$_2$,3,4-F$_2$,E], [−4343:3,5-Me$_2$,3,4-F$_2$,E], [−4344:2,3-Et$_2$,3,4-F$_2$,E], [−4345:2,4-Et$_2$,3,4-F$_2$,E], [−4346:2,5-Et$_2$,3,4-F$_2$,E], [−4347:2,6-Et$_2$,3,4-F$_2$,E], [−4348:3,4-Et$_2$,3,4-F$_2$,E], [−4349:3,5-Et$_2$,3,4-F$_2$,E], [−4350:2,3-(CF$_3$)$_2$,3,4-F$_2$,E], [−4351:2,4-(CF$_3$)$_2$,3,4-F$_2$,E], [−4352:2,5-(CF$_3$)$_2$,3,4-F$_2$,E], [−4353:2,6-(CF$_3$)$_2$,3,4-F$_2$,E], [−4354:3,4-(CF$_3$)$_2$,3,4-F$_2$,E], [−4355:3,5-(CF$_3$)$_2$,3,4-F$_2$,E], [−4356:2,3-(CHF$_2$)$_2$,3,4-F$_2$,E], [−4357:2,4-(CHF$_2$)$_2$,3,4-F$_2$,E], [−4358:2,5-(CHF$_2$)$_2$,3,4-F$_2$,E], [−4359:2,6-(CHF$_2$)$_2$,3,4-F$_2$,E], [−4360:3,4-(CHF$_2$)$_2$,3,4-F$_2$,E], [−4361:3,5-(CHF$_2$)$_2$,3,4-F$_2$,E], [−4362:2,3-(CH$_2$F)$_2$,3,4-F$_2$,E], [4363:2,4-(CH$_2$F)$_2$,3,4-F$_2$,E], [−4364:2,5-(CH$_2$F)$_2$,3,4-F$_2$,E], [−4365:2,6-(CH$_2$F)$_2$,3,4-F$_2$,E], [−4366:3,4-(CH$_2$F)$_2$,3,4-F$_2$,E], [−4367:3,5-(CH$_2$F)$_2$,3,4-F$_2$,E], [−4368:2,3-(MeO)$_2$,3,4-F$_2$,E], [−4369:2,4-(MeO)$_2$,3,4-F$_2$,E], [−4370:2,5-(MeO)$_2$,3,4-F$_2$,E], [−4371:2,6-(MeO)$_2$,3,4-F$_2$,E], [−4372:3,4-(MeO)$_2$,3,4-F$_2$,E], [−4373:3,5-(MeO)$_2$,3,4-F$_2$,E], [−4374:2,3-(EtO)$_2$,3,4-F$_2$,E], [−4375:2,4-(EtO)$_2$,3,4-F$_2$,E], [−4376:2,5-(EtO)$_2$,3,4-F$_2$,E], [−4377:2,6-(EtO)$_2$, 3,4-F$_2$,E], [−4378:3,4-(EtO)$_2$,3,4-F$_2$,E], [−4379:3,5-(EtO)$_2$,3,4-F$_2$,E], [−4380:2-Cl-3-F,3,4-F$_2$,E], [−4381:2-Cl-4-F,3,4-F$_2$,E], [−4382:2-Cl-5-F,3,4-F$_2$,E], [−4383:2-Cl-6-F,3,4-F$_2$,E], [−4384:3-Cl-2-F,3,4-F$_2$,E], [−4385:3-Cl-4-F,3,4-F$_2$,E], [−4386:3-Cl-5-F,3,4-F$_2$,E], [−4387:4-Cl-2-F,3,4-F$_2$,E], [−4388:4-Cl-3-F,3,4-F$_2$,E], [−4389:2-F-3-Me,3,4-F$_2$,E], [−4390:2-F-4-Me,3,4-F$_2$,E], [−4391:2-F-5-Me,3,4-F$_2$,E], [−4392:2-F-6-Me,3,4-F$_2$,E], [−4393:3-F-2-Me,3,4-F$_2$,E], [−4394:3-F-4-Me,3,4-F$_2$,E], [−4395:3-F-5-Me,3,4-F$_2$,E], [−4396:4-F-2-Me,3,4-F$_2$,E], [−4397:4-F-3-Me,3,4-F$_2$,E], [−4398:2-Cl-3-Me,3,4-F$_2$,E], [−4399:2-Cl-4-Me,3,4-F$_2$,E], [−4400:2-Cl-5-Me,3,4-F$_2$,E], [−4401:2-Cl-6-Me,3,4-F$_2$,E], [−4402:3-Cl-2-Me,3,4-F$_2$,E], [−4403:3-Cl-4-Me,3,4-F$_2$,E], [−4404:3-Cl-5-Me,3,4-F$_2$,E], [−4405:4-Cl-2-Me,3,4-F$_2$,E], [−4406:4-Cl-3-Me,3,4-F$_2$,E], [−4407:2-F-3-CF$_3$,3,4-F$_2$,E], [−4408:2-F-4-CF$_3$,3,4-F$_2$,E], [−4409:2-F-5-CF$_3$,3,4-F$_2$,E], [−4410:2-F-6-CF$_3$,3,4-F$_2$,E], [−4411:3-F-2-CF$_3$,3,4-F$_2$,E], [−4412:3-F-4-CF$_3$,3,4-F$_2$,E], [−4413:3-F-5-CF$_3$,3,4-F$_2$,E], [−4414:4-F-2-CF$_3$,3,4-F$_2$,E], [−4415:4-F-3-CF$_3$,3,4-F$_2$,E], [−4416:2-Cl-3-CF$_3$,3,4-F$_2$,E], [−4417:2-Cl-4-CF$_3$,3,4-F$_2$,E], [−4418:2-Cl-5-CF$_3$,3,4-F$_2$,E], [−4419:2-Cl-6-CF$_3$,3,4-F$_2$,E], [−4420:3-Cl-2-CF$_3$,3,4-F$_2$,E], [−4421:3-Cl-4-CF$_3$, 3,4-F$_2$,E], [−4422:3-Cl-5-CF$_3$,3,4-F$_2$,E], [−4423:4-Cl-2-CF$_3$,3,4-F$_2$,E], [−4424:4-Cl-3-CF$_3$,3,4-F$_2$,E], [−4425:2-Me-3-CF$_3$,3,4-F$_2$,E], [−4426:2-Me-4-CF$_3$,3,4-F$_2$,E], [−4427:2-Me-5-CF$_3$,3,4-F$_2$,E], [−4428:2-Me-6-CF$_3$,3,4-F$_2$,E], [−4429:3-Me-2-CF$_3$,3,4-F$_2$,E], [−4430:3-Me-4-CF$_3$,3,4-F$_2$,E], [−4431:3-Me-5-CF$_3$,3,4-F$_2$,E], [−4432:4-Me-2-CF$_3$,3,4-F$_2$,E], [−4433:4-Me-3-CF$_3$,3,4-F$_2$,E], [−4434:2-F-3-MeO,3,4-F$_2$,E], [−4435:2-F-4-MeO,3,4-F$_2$,E], [−4436:2-F-5-MeO,3,4-F$_2$,E], [−4437:2-F-6-MeO,3,4-F$_2$,E], [−4438:3-F-2-MeO,3,4-F$_2$,E], [−4439:3-F-4-MeO,3,4-F$_2$,E], [−4440:3-F-5-MeO,3,4-F$_2$,E], [−4441:4-F-2-MeO,3,4-F$_2$,E], [−4442:4-F-3-MeO,3,4-F$_2$,E], [−4443:2-Cl-3-MeO,3,4-F$_2$,E], [−4444:2-Cl-4-MeO,3,4-F$_2$,E], [−4445:2-Cl-5-MeO,3,4-F$_2$,E], [−4446:2-Cl-6-MeO,3,4-F$_2$,E], [−4447:3-Cl-2-MeO,3,4-F$_2$,E], [−4448:3-Cl-4-MeO,3,4-F$_2$,E], [−4449:3-Cl-5-MeO,3,4-F$_2$,E], [−4450:4-Cl-2-MeO,3,4-F$_2$,E], [−4451:4-Cl-3-MeO,3,4-F$_2$,E], [−4452:2-Me-3-MeO,3,4-F$_2$,E], [−4453:2-Me-4-MeO,3,4-F$_2$,E], [−4454:2-Me-5-MeO,3,4-F$_2$,E], [−4455:2-Me-6-MeO,3,4-F$_2$,E], [−4456:3-Me-2-MeO,3,4-F$_2$,E], [−4457:3-Me-4-MeO,3,4-F$_2$,E], [−4458:3-Me-5-MeO,3,4-F$_2$,E], [−4459:4-Me-2-MeO,3,4-F$_2$,E], [−4460:4-Me-3-MeO, 3,4-F$_2$,E], [−4461:H,3,5-Cl$_2$,E], [−4462:4-F,3,5-Cl$_2$,E], [−4463:4-F,3,5-Cl$_2$,Z], [−4464:4-Cl,3,5-Cl$_2$,E], [−4465:4-Cl,3,5-Cl$_2$,Z], [−4466:4-Br,3,5-Cl$_2$,E], [−4467:4-I,3,5-Cl$_2$,E], [−4468:4-Me,3,5-Cl$_2$,E], [−4469:4-Me,3,5-Cl$_2$,Z], [−4470:4-Et,3,5-Cl$_2$,E], [−4471:4-C$_3$H$_7$,3,5-Cl$_2$,E], [−4472:4-(Me)$_2$CH,3,5-Cl$_2$,E], [−4473:4-CF$_3$,3,5-Cl$_2$,E], [−4474:4-CF$_3$,3,5-Cl$_2$,Z], [−4475:4-C$_2$F$_5$,3,5-Cl$_2$,E], [−4476:4-C$_3$F$_7$,3,5-Cl$_2$,E], [−4477:4-(CF$_3$)$_2$CF,3,5-Cl$_2$,E], [−4478:4-(CF$_3$)$_2$CH,3,5-Cl$_2$,E], [−4479:4-CHF$_2$,3,5-Cl$_2$,E], [−4480:4-CH$_2$F,3,5-Cl$_2$,E], [−4481:4-CF$_3$CH$_2$,3,5-Cl$_2$,E], [−4482:4-MeO,3,5-Cl$_2$,E], [−4483:4-MeO, 3,5-Cl$_2$,Z], [−4484:4-EtO, 3,5-Cl$_2$,E], [−4485:4-C$_3$H$_7$O,3,5-Cl$_2$,E], [−4486:4-(Me)$_2$CHO, 3,5-Cl$_2$,E], [−4487:4-NO$_2$,3,5-Cl$_2$,E], [−4488:4-NO$_2$,3,5-Cl$_2$,Z], [−4489:3-F,3,5-Cl$_2$,E], [−4490:3-F,3,5-Cl$_2$,Z], [−4491:3-Cl,3,5-Cl$_2$,E], [−4492:3-Cl,3,5-Cl$_2$,Z], [−4493:3-Br, 3,5-Cl$_2$,E], [−4494:3-I,3,5-Cl$_2$,E], [−4495:3-Me,3,5-Cl$_2$,E], [−4496:3-Me,3,5-Cl$_2$,Z], [−4497:3-Et,3,5-Cl$_2$,E], [−4498:3-C$_3$H$_7$,3,5-Cl$_2$,E], [−4499:3-(Me)$_2$CH, 3,5-Cl$_2$,E], [−4500:3-CF$_3$,3,5-Cl$_2$,E], [−4501:3-CF$_3$,3,5-Cl$_2$,Z], [−4502:3-C$_2$F$_5$, 3,5-Cl$_2$,E], [−4503:3-C$_3$F$_7$,3,5-Cl$_2$,E], [−4504:3-(CF$_3$)$_2$CF,3,5-Cl$_2$,E], [−4505:3-(CF$_3$)$_2$CH,3,5-Cl$_2$,E], [−4506:3-CHF$_2$,3,5-Cl$_2$,E], [−4507:3-CHF$_2$,3,5-Cl$_2$,Z], [−4508:3-CH$_2$F,3,5-Cl$_2$,E], [−4509:3-CH$_2$F,3,5-Cl$_2$, Z], [−4510:3-CF$_3$CH$_2$,3,5-Cl$_2$,E], [−4511:3-MeO, 3,5-Cl$_2$,E], [−4512:3-MeO,3,5-Cl$_2$,Z], [−4513:3-EtO,3,5-Cl$_2$,E], [−4514:3-C$_3$H$_7$O,3,5-Cl$_2$,E], [−4515:3-(Me)$_2$CHO,3,5-Cl$_2$,E], [−4516:3-NO$_2$,3,5-Cl$_2$,E], [−4517:2-F,3,5-Cl$_2$,E], [−4518:2-Cl,3,5-Cl$_2$,E], [−4519:2-Br,3,5-Cl$_2$,E], [−4520:2-I,3,5-Cl$_2$,E], [−4521:2-Me,3,5-Cl$_2$,E], [−4522:2-Et,3,5-Cl$_2$,E], [−4523:2-C$_3$H$_7$,3,5-Cl$_2$,E], [−4524:2-(Me)$_2$CH,3,5-Cl$_2$,E], [−4525:2-CF$_3$,3,5-Cl$_2$,E], [−4526:2-C$_2$F$_5$,3,5-Cl$_2$,E], [−4527:2-C$_3$F$_7$,3,5-Cl$_2$,E], [−4528:2-(CF$_3$)$_2$CF,3,5-Cl$_2$,E], [−4529:2-(CF$_3$)$_2$CH,3,5-Cl$_2$,E], [−4530:2-CHF$_2$,3,5-Cl$_2$,E], [−4531:2-CH$_2$F,3,5-Cl$_2$,E], [−4532:2-CF$_3$CH$_2$,3,5-Cl$_2$,E], [−4533:2-MeO,3,5-Cl$_2$,E], [−4534:2-EtO,3,5-Cl$_2$,E], [−4535:2-C$_3$H$_7$O,3,5-Cl$_2$,E], [−4536:2-(Me)$_2$CHO,3,5-Cl$_2$,E], [−4537:2-NO$_2$,3,5-Cl$_2$,E], [−4538:2,3-F$_2$,3,5-Cl$_2$,E], [−4539:2,4-F$_2$,3,5-Cl$_2$,E], [−4540:2,5-F$_2$,3,5-Cl$_2$,E], [−4541:2,6-F$_2$,3,5-Cl$_2$,E], [−4542:3,4-F$_2$,3,5-Cl$_2$,E], [−4543:3,4-F$_2$,3,5-Cl$_2$,Z], [−4544:3,5-F$_2$,3,5-Cl$_2$,E], [−4545:3,5-F$_2$,3,5-Cl$_2$,Z], [−4546:2,3-Cl$_2$,3,5-Cl$_2$,E], [−4547:2,3-Cl$_2$,3,5-Cl$_2$,Z], [−4548:2,4-Cl$_2$,3,5-Cl$_2$,E], [−4549:2,4-Cl$_2$,3,5-Cl$_2$,Z], [−4550:2,5-Cl$_2$,3,5-Cl$_2$,E], [−4551:2,5-Cl$_2$,3,5-Cl$_2$,E], [−4552:2,6-Cl$_2$,3,5-Cl$_2$,E], [−4553:3,4-Cl$_2$,3,5-Cl$_2$,E], [−4554:3,5-Cl$_2$,3,5-Cl$_2$,E], [−4555:2,3-Br$_2$,3,5-Cl$_2$,E], [−4556:2,4-Br$_2$,3,5-Cl$_2$,E], [−4557:2,5-Br$_2$,3,5-Cl$_2$,E], [−4558:2,6-Br$_2$,3,5-Cl$_2$,E],

[-4559:3,4-Br₂,3,5-Cl₂,E], [-4560:3,5-Br₂,3,5-Cl₂,E], [-4561:2,3-Me₂,3,5-Cl₂,E], [-4562:2,4-Me₂,3,5-Cl₂,E], [-4563:2,5-Me₂,3,5-Cl₂,E], [-4564:2,6-Me₂,3,5-Cl₂,E], [-4565:3,4-Me₂,3,5-Cl₂,E], [-4566:3,5-Me₂,3,5-Cl₂,E], [-4567:2,3-Et₂,3,5-Cl₂,E], [-4568:2,4-Et₂,3,5-Cl₂,E], [-4569:2,5-Et₂,3,5-Cl₂,E], [-4570:2,6-Et₂,3,5-Cl₂,E], [-4571:3,4-Et₂,3,5-Cl₂,E], [-4572:3,5-Et₂,3,5-Cl₂,E], [-4573:2,3-(CF₃)₂,3,5-Cl₂,E], [-4574:2,4-(CF₃)₂,3,5-Cl₂,E], [-4575:2,5-(CF₃)₂,3,5-Cl₂,E], [-4576:2,6-(CF₃)₂,3,5-Cl₂,E], [-4577:3,4-(CF₃)₂,3,5-Cl₂,E], [-4578:3,5-(CF₃)₂,3,5-Cl₂,E], [-4579:2,3-(CHF₂)₂,3,5-Cl₂,E], [-4580:2,4-(CHF₂)₂,3,5-Cl₂,E], [-4581:2,5-(CHF₂)₂,3,5-Cl₂,E], [-4582:2,6-(CHF₂)₂,3,5-Cl₂,E], [-4583:3,4-(CHF₂)₂,3,5-Cl₂,E], [-4584:3,5-(CHF₂)₂,3,5-Cl₂,E], [-4585:2,3-(CH₂F)₂,3,5-Cl₂,E], [-4586:2,4-(CH₂F)₂,3,5-Cl₂,E], [-4587:2,5-(CH₂F)₂,3,5-Cl₂,E], [-4588:2,6-(CH₂F)₂,3,5-Cl₂,E], [-4589:3,4-(CH₂F)₂,3,5-Cl₂,E], [-4590:3,5-(CH₂F)₂,3,5-Cl₂,E], [-4591:2,3-(MeO)₂,3,5-Cl₂,E], [-4592:2,4-(MeO)₂,3,5-Cl₂,E], [-4593:2,5-(MeO)₂,3,5-Cl₂,E], [-4594:2,6-(MeO)₂,3,5-Cl₂,E], [-4595:3,4-(MeO)₂,3,5-Cl₂,E], [-4596:3,5-(MeO)₂,3,5-Cl₂,E], [-4597:2,3-(EtO)₂,3,5-Cl₂,E], [-4598:2,4-(EtO)₂,3,5-Cl₂,E], [-4599:2,5-(EtO)₂,3,5-Cl₂,E], [-4600:2,6-(EtO)₂,3,5-Cl₂,E], [-4601:3,4-(EtO)₂,3,5-Cl₂,E], [-4602:3,5-(EtO)₂,3,5-Cl₂,E], [-4603:2-Cl-3-F,3,5-Cl₂,E], [-4604:2-Cl-4-F,3,5-Cl₂,E], [-4605:2-Cl-5-F,3,5-Cl₂,E], [-4606:2-Cl-6-F,3,5-Cl₂,E], [-4607:3-Cl-2-F,3,5-Cl₂,E], [-4608:3-Cl-4-F,3,5-Cl₂,E], [-4609:3-Cl-5-F,3,5-Cl₂,E], [-4610:4-Cl-2-F,3,5-Cl₂,E], [-4611:4-Cl-3-F,3,5-Cl₂,E], [-4612:2-F-3-Me,3,5-Cl₂,E], [-4613:2-F-4-Me,3,5-Cl₂,E], [-4614:2-F-5-Me,3,5-Cl₂,E], [-4615:2-F-6-Me,3,5-Cl₂,E], [-4616:3-F-2-Me,3,5-Cl₂,E], [-4617:3-F-4-Me,3,5-Cl₂,E], [-4618:3-F-5-Me,3,5-Cl₂,E], [-4619:4-F-2-Me,3,5-Cl₂,E], [-4620:4-F-3-Me,3,5-Cl₂,E], [-4621:2-Cl-3-Me,3,5-Cl₂,E], [-4622:2-Cl-4-Me,3,5-Cl₂,E], [-4623:2-Cl-5-Me,3,5-Cl₂,E], [-4624:2-Cl-6-Me,3,5-Cl₂,E], [-4625:3-Cl-2-Me,3,5-Cl₂,E], [-4626:3-Cl-4-Me,3,5-Cl₂,E], [-4627:3-Cl-5-Me,3,5-Cl₂,E], [-4628:4-Cl-2-Me,3,5-Cl₂,E], [-4629:4-Cl-3-Me,3,5-Cl₂,E], [-4630:2-F-3-CF₃,3,5-Cl₂,E], [-4631:2-F-4-CF₃,3,5-Cl₂,E], [-4632:2-F-5-CF₃,3,5-Cl₂,E], [-4633:2-F-6-CF₃,3,5-Cl₂,E], [-4634:3-F-2-CF₃,3,5-Cl₂,E], [-4635:3-F-4-CF₃,3,5-Cl₂,E], [-4636:3-F-5-CF₃,3,5-Cl₂,E], [-4637:4-F-2-CF₃,3,5-Cl₂,E], [-4638:4-F-3-CF₃,3,5-Cl₂,E], [-4639:2-Cl-3-CF₃,3,5-Cl₂,E], [-4640:2-Cl-4-CF₃,3,5-Cl₂,E], [-4641:2-Cl-5-CF₃,3,5-Cl₂,E], [-4642:2-Cl-6-CF₃,3,5-Cl₂,E], [-4643:3-Cl-2-CF₃,3,5-Cl₂,E], [-4644:3-Cl-4-CF₃,3,5-Cl₂,E], [-4645:3-Cl-5-CF₃,3,5-Cl₂,E], [-4646:4-Cl-2-CF₃,3,5-Cl₂,E], [-4647:4-Cl-3-CF₃,3,5-Cl₂,E], [-4648:2-Me-3-CF₃,3,5-Cl₂,E], [-4649:2-Me-4-CF₃,3,5-Cl₂,E], [-4650:2-Me-5-CF₃,3,5-Cl₂,E], [-4651:2-Me-6-CF₃,3,5-Cl₂,E], [-4652:3-Me-2-CF₃,3,5-Cl₂,E], [-4653:3-Me-4-CF₃,3,5-Cl₂,E], [-4654:3-Me-5-CF₃,3,5-Cl₂,E], [-4655:4-Me-2-CF₃,3,5-Cl₂,E], [-4656:4-Me-3-CF₃,3,5-Cl₂,E], [-4657:2-F-3-MeO,3,5-Cl₂,E], [-4658:2-F-4-MeO,3,5-Cl₂,E], [-4659:2-F-5-MeO,3,5-Cl₂,E], [-4660:2-F-6-MeO,3,5-Cl₂,E], [-4661:3-F-2-MeO,3,5-Cl₂,E], [-4662:3-F-4-MeO,3,5-Cl₂,E], [-4663:3-F-5-MeO,3,5-Cl₂,E], [-4664:4-F-2-MeO,3,5-Cl₂,E], [-4665:4-F-3-MeO,3,5-Cl₂,E], [-4666:2-Cl-3-MeO,3,5-Cl₂,E], [-4667:2-Cl-4-MeO,3,5-Cl₂,E], [-4668:2-Cl-5-MeO,3,5-Cl₂,E], [-4669:2-Cl-6-MeO,3,5-Cl₂,E], [-4670:3-Cl-2-MeO,3,5-Cl₂,E], [-4671:3-Cl-4-MeO,3,5-Cl₂,E], [-4672:3-Cl-5-MeO,3,5-Cl₂,E], [-4673:4-Cl-2-MeO,3,5-Cl₂,E], [-4674:4-Cl-3-MeO,3,5-Cl₂,E], [-4675:2-Me-3-MeO,3,5-Cl₂,E], [-4676:2-Me-4-MeO,3,5-Cl₂,E], [-4677:2-Me-5-MeO,3,5-Cl₂,E], [-4678:2-Me-6-MeO,3,5-Cl₂,E], [-4679:3-Me-2-MeO,3,5-Cl₂,E], [-4680:3-Me-4-MeO,3,5-Cl₂,E], [-4681:3-Me-5-MeO,3,5-Cl₂,E], [-4682:4-Me-2-MeO,3,5-Cl₂,E], [-4683:4-Me-3-MeO,3,5-Cl₂,E],

[-4684:H,3-Cl-4-F,E], [-4685:4-F,3-Cl-4-F,E], [-4686:4-F,3-Cl-4-F,Z], [-4687:4-Cl,3-Cl-4-F,E], [-4688:4-Cl,3-Cl-4-F,Z], [-4689:4-Br,3-Cl-4-F,E], [-4690:4-I,3-Cl-4-F,E], [-4691:4-Me,3-Cl-4-F,E], [-4692:4-Me,3-Cl-4-F,Z], [-4693:4-Et,3-Cl-4-F,E], [-4694:4-C₃H₇,3-Cl-4-F,E], [-4695:4-(Me)₂CH,3-Cl-4-F,E], [-4696:4-CF₃,3-Cl-4-F,E], [-4697:4-CF₃,3-Cl-4-F,Z], [-4698:4-C₂F₅,3-Cl-4-F,E], [-4699:4-C₃F₇,3-Cl-4-F,E], [-4700:4-(CF₃)₂CF,3-Cl-4-F,E], [-4701:4-(CF₃)₂CH,3-Cl-4-F,E], [-4702:4-CHF₂,3-Cl-4-F,E], [-4703:4-CH₂F,3-Cl-4-F,E], [-4704:4-CF₃CH₂,3-Cl-4-F,E], [-4705:4-MeO,3-Cl-4-F,E], [-4706:4-MeO,3-Cl-4-F,Z], [-4707:4-EtO,3-Cl-4-F,E], [-4708:4-C₃H₇O,3-Cl-4-F,E], [-4709:4-(Me)₂CHO,3-Cl-4-F,E], [-4710:4-NO₂,3-Cl-4-F,E], [-4711:4-NO₂,3-Cl-4-F,Z], [-4712:3-F,3-Cl-4-F,E], [-4713:3-F,3-Cl-4-F,Z], [-4714:3-Cl,3-Cl-4-F,E], [-4715:3-Cl,3-Cl-4-F,Z], [-4716:3-Br,3-Cl-4-F,E], [-4717:3-I,3-Cl-4-F,E], [-4718:3-Me,3-Cl-4-F,E], [-4719:3-Me,3-Cl-4-F,Z], [-4720:3-Et,3-Cl-4-F,E], [-4721:3-C₃H₇,3-Cl-4-F,E], [-4722:3-(Me)₂CH,3-Cl-4-F,E], [-4723:3-CF₃,3-Cl-4-F,E], [-4724:3-CF₃,3-Cl-4-F,Z], [-4725:3-C₂F₅,3-Cl-4-F,E], [-4726:3-C₃F₇,3-Cl-4-F,E], [-4727:3-(CF₃)₂CF,3-Cl-4-F,E], [-4728:3-(CF₃)₂CH,3-Cl-4-F,E], [-4729:3-CHF₂,3-Cl-4-F,E], [-4730:3-CHF₂,3-Cl-4-F,Z], [-4731:3-CH₂F,3-Cl-4-F,E], [-4732:3-CH₂F,3-Cl-4-F,Z], [-4733:3-CF₃CH₂,3-Cl-4-F,E], [-4734:3-MeO,3-Cl-4-F,E], [-4735:3-MeO,3-Cl-4-F,Z], [-4736:3-EtO,3-Cl-4-F,E], [-4737:3-C₃H₇O,3-Cl-4-F,E], [-4738:3-(Me)₂CHO,3-Cl-4-F,E], [-4739:3-NO₂,3-Cl-4-F,E], [-4740:2-F,3-Cl-4-F,E], [-4741:2-Cl,3-Cl-4-F,E], [-4742:2-Br,3-Cl-4-F,E], [-4743:2-I,3-Cl-4-F,E], [-4744:2-Me,3-Cl-4-F,E], [-4745:2-Et,3-Cl-4-F,E], [-4746:2-C₃H₇,3-Cl-4-F,E], [-4747:2-(Me)₂CH,3-Cl-4-F,E], [-4748:2-CF₃,3-Cl-4-F,E], [-4749:2-C₂F₅,3-Cl-4-F,E], [-4750:2-C₃F₇,3-Cl-4-F,E], [-4751:2-(CF₃)₂CF,3-Cl-4-F,E], [-4752:2-(CF₃)₂CH,3-Cl-4-F,E], [-4753:2-CHF₂,3-Cl-4-F,E], [-4754:2-CH₂F,3-Cl-4-F,E], [-4755:2-CF₃CH₂,3-Cl-4-F,E], [-4756:2-MeO,3-Cl-4-F,E], [-4757:2-EtO,3-Cl-4-F,E], [-4758:2-C₃H₇O,3-Cl-4-F,E], [-4759:2-(Me)₂CHO,3-Cl-4-F,E], [-4760:2-NO₂,3-Cl-4-F,E], [-4761:2,3-F₂,3-Cl-4-F,E], [-4762:2,4-F₂,3-Cl-4-F,E], [-4763:2,5-F₂,3-Cl-4-F,E], [-4764:2,6-F₂,3-Cl-4-F,E], [-4765:3,4-F₂,3-Cl-4-F,E], [-4766:3,4-F₂,3-Cl-4-F,Z], [-4767:3,5-F₂,3-Cl-4-F,E], [-4768:3,5-F₂,3-Cl-4-F,Z], [-4769:2,3-Cl₂,3-Cl-4-F,E], [-4770:2,3-Cl₂,3-Cl-4-F,Z], [-4771:2,4-Cl₂,3-Cl-4-F,E], [-4772:2,4-Cl₂,3-Cl-4-F,Z], [-4773:2,5-Cl₂,3-Cl-4-F,E], [-4774:2,5-Cl₂,3-Cl-4-F,Z], [-4775:2,6-Cl₂,3-Cl-4-F,E], [-4776:3,4-Cl₂,3-Cl-4-F,E], [-4777:3,5-Cl₂,3-Cl-4-F,E], [-4778:2,3-Br₂,3-Cl-4-F,E], [-4779:2,4-Br₂,3-Cl-4-F,E], [-4780:2,5-Br₂,3-Cl-4-F,E], [-4781:2,6-Br₂,3-Cl-4-F,E], [-4782:3,4-Br₂,3-Cl-4-F,E], [-4783:3,5-Br₂,3-Cl-4-F,E], [-4784:2,3-Me₂,3-Cl-4-F,E], [-4785:2,4-Me₂,3-Cl-4-F,E], [-4786:2,5-Me₂,3-Cl-4-F,E], [-4787:2,6-Me₂,3-Cl-4-F,E], [-4788:3,4-Me₂,3-Cl-4-F,E], [-4789:3,5-Me₂,3-Cl-4-F,E], [-4790:2,3-Et₂,3-Cl-4-F,E], [-4791:2,4-Et₂,3-Cl-4-F,E], [-4792:2,5-Et₂,3-Cl-4-F,E], [-4793:2,6-Et₂,3-Cl-4-F,E], [-4794:3,4-Et₂,3-Cl-4-F,E], [-4795:3,5-Et₂,3-Cl-4-F,E], [-4796:2,3-(CF₃)₂,3-Cl-4-F,E], [-4797:2,4-(CF₃)₂,3-Cl-4-F,E], [-4798:2,5-(CF₃)₂,3-Cl-4-F,E], [-4799:2,6-(CF₃)₂,3-Cl-4-F,E], [-4800:3,4-(CF₃)₂,3-Cl-4-F,E], [-4801:3,5-(CF₃)₂,3-Cl-4-F,E], [-4802:2,3-(CHF₂)₂,3-Cl-4-F,E], [-4803:2,4-(CHF₂)₂,3-Cl-4-F,E], [-4804:2,5-(CHF₂)₂,3-Cl-4-F,E], [-4805:2,6-(CHF₂)₂,3-Cl-4-F,E], [-4806:3,4-(CHF₂)₂,3-Cl-4-F,E], [-4807:3,5-

(CHF$_2$)$_2$,3-Cl-4-F,E], [−4808:2,3-(CH$_2$F)$_2$,3-Cl-4-F,E], [−4809:2,4-(CH$_2$F)$_2$,3-Cl-4-F,E], [−4810:2,5-(CH$_2$F)$_2$,3-Cl-4-F,E], [−4811:2,6-(CH$_2$F)$_2$,3-Cl-4-F,E], [−4812:3,4-(CH$_2$F)$_2$,3-Cl-4-F,E], [−4813:3,5-(CH$_2$F)$_2$,3-Cl-4-F,E], [−4814:2,3-(MeO)$_2$,3-Cl-4-F,E], [−4815:2,4-(MeO)$_2$,3-Cl-4-F,E], [−4816:2,5-(MeO)$_2$,3-Cl-4-F,E], [−4817:2,6-(MeO)$_2$,3-Cl-4-F,E], [−4818:3,4-(MeO)$_2$,3-Cl-4-F,E], [−4819:3,5-(MeO)$_2$,3-Cl-4-F,E], [−4820:2,3-(EtO)$_2$,3-Cl-4-F,E], [−4821:2,4-(EtO)$_2$,3-Cl-4-F,E], [−4822:2,5-(EtO)$_2$,3-Cl-4-F,E], [−4823:2,6-(EtO)$_2$,3-Cl-4-F,E], [−4824:3,4-(EtO)$_2$,3-Cl-4-F,E], [−4825:3,5-(EtO)$_2$,3-Cl-4-F,E], [−4826:2-Cl-3-F,3-Cl-4-F,E], [−4827:2-Cl-4-F,3-Cl-4-F,E], [−4828:2-Cl-5-F,3-Cl-4-F,E], [−4829:2-Cl-6-F,3-Cl-4-F,E], [−4830:3-Cl-2-F,3-Cl-4-F,E], [−4831:3-Cl-4-F,3-Cl-4-F,E], [−4832:3-Cl-5-F,3-Cl-4-F,E], [−4833:4-Cl-2-F,3-Cl-4-F,E], [−4834:4-Cl-3-F,3-Cl-4-F,E], [−4835:2-F-3-Me,3-Cl-4-F,E], [−4836:2-F-4-Me,3-Cl-4-F,E], [−4837:2-F-5-Me,3-Cl-4-F,E], [−4838:2-F-6-Me,3-Cl-4-F,E], [−4839:3-F-2-Me,3-Cl-4-F,E], [−4840:3-F-4-Me,3-Cl-4-F,E], [−4841:3-F-5-Me,3-Cl-4-F,E], [−4842:4-F-2-Me,3-Cl-4-F,E], [−4843:4-F-3-Me,3-Cl-4-F,E], [−4844:2-Cl-3-Me,3-Cl-4-F,E], [−4845:2-Cl-4-Me,3-Cl-4-F,E], [−4846:2-Cl-5-Me,3-Cl-4-F,E], [−4847:2-Cl-6-Me,3-Cl-4-F,E], [−4848:3-Cl-2-Me,3-Cl-4-F,E], [−4849:3-Cl-4-Me,3-Cl-4-F,E], [−4850:3-Cl-5-Me,3-Cl-4-F,E], [−4851:4-Cl-2-Me,3-Cl-4-F,E], [−4852:4-Cl-3-Me,3-Cl-4-F,E], [−4853:2-F-3-CF$_3$,3-Cl-4-F,E], [−4854:2-F-4-CF$_3$,3-Cl-4-F,E], [−4855:2-F-5-CF$_3$,3-Cl-4-F,E], [−4856:2-F-6-CF$_3$,3-Cl-4-F,E], [−4857:3-F-2-CF$_3$,3-Cl-4-F,E], [−4858:3-F-4-CF$_3$,3-Cl-4-F,E], [−4859:3-F-5-CF$_3$,3-Cl-4-F,E], [−4860:4-F-2-CF$_3$,3-Cl-4-F,E], [−4861:4-F-3-CF$_3$,3-Cl-4-F,E], [−4862:2-Cl-3-CF$_3$,3-Cl-4-F,E], [−4863:2-Cl-4-CF$_3$,3-Cl-4-F,E], [−4864:2-Cl-5-CF$_3$,3-Cl-4-F,E], [−4865:2-Cl-6-CF$_3$,3-Cl-4-F,E], [−4866:3-Cl-2-CF$_3$,3-Cl-4-F,E], [−4867:3-Cl-4-CF$_3$,3-Cl-4-F,E], [−4868:3-Cl-5-CF$_3$,3-Cl-4-F,E], [−4869:4-Cl-2-CF$_3$,3-Cl-4-F,E], [−4870:4-Cl-3-CF$_3$,3-Cl-4-F,E], [−4871:2-Me-3-CF$_3$,3-Cl-4-F,E], [−4872:2-Me-4-CF$_3$,3-Cl-4-F,E], [−4873:2-Me-5-CF$_3$,3-Cl-4-F,E], [−4874:2-Me-6-CF$_3$,3-Cl-4-F,E], [−4875:3-Me-2-CF$_3$,3-Cl-4-F,E], [−4876:3-Me-4-CF$_3$,3-Cl-4-F,E], [−4877:3-Me-5-CF$_3$,3-Cl-4-F,E], [−4878:4-Me-2-CF$_3$,3-Cl-4-F,E], [−4879:4-Me-3-CF$_3$,3-Cl-4-F,E], [−4880:2-F-3-MeO,3-Cl-4-F,E], [−4881:2-F-4-MeO,3-Cl-4-F,E], [−4882:2-F-5-MeO,3-Cl-4-F,E], [−4883:2-F-6-MeO,3-Cl-4-F,E], [−4884:3-F-2-MeO,3-Cl-4-F,E], [−4885:3-F-4-MeO,3-Cl-4-F,E], [−4886:3-F-5-MeO,3-Cl-4-F,E], [−4887:4-F-2-MeO,3-Cl-4-F,E], [−4888:4-F-3-MeO,3-Cl-4-F,E], [−4889:2-Cl-3-MeO,3-Cl-4-F,E], [−4890:2-Cl-4-MeO,3-Cl-4-F,E], [−4891:2-Cl-5-MeO,3-Cl-4-F,E], [−4892:2-Cl-6-MeO,3-Cl-4-F,E], [−4893:3-Cl-2-MeO,3-Cl-4-F,E], [−4894:3-Cl-4-MeO,3-Cl-4-F,E], [−4895:3-Cl-5-MeO,3-Cl-4-F,E], [−4896:4-Cl-2-MeO,3-Cl-4-F,E], [−4897:4-Cl-3-MeO,3-Cl-4-F,E], [−4898:2-Me-3-MeO,3-Cl-4-F,E], [−4899:2-Me-4-MeO,3-Cl-4-F,E], [−4900:2-Me-5-MeO,3-Cl-4-F,E], [−4901:2-Me-6-MeO,3-Cl-4-F,E], [−4902:3-Me-2-MeO,3-Cl-4-F,E], [−4903:3-Me-4-MeO,3-Cl-4-F,E], [−4904:3-Me-5-MeO,3-Cl-4-F,E], [−4905:4-Me-2-MeO,3-Cl-4-F,E], [−4906:4-Me-3-MeO,3-Cl-4-F,E],

[−4907:H,4-Cl-3-F,E], [−4908:4-F,4-Cl-3-F,E], [−4909:4-F,4-Cl-3-F,Z], [−4910:4-Cl,4-Cl-3-F,E], [−4911:4-Cl,4-Cl-3-F,Z], [−4912:4-Br,4-Cl-3-F,E], [−4913:4-I,4-Cl-3-F,E], [−4914:4-Me,4-Cl-3-F,E], [−4915:4-Me,4-Cl-3-F,Z], [−4916:4-Et,4-Cl-3-F,E], [−4917:4-C$_3$H$_7$,4-Cl-3-F,E], [−4918:4-(Me)$_2$CH,4-Cl-3-F,E], [−4919:4-CF$_3$,4-Cl-3-F,E], [−4920:4-CF$_3$,4-Cl-3-F,Z], [−4921:4-C$_2$F$_5$,4-Cl-3-F,E], [−4922:4-C$_3$F$_7$,4-Cl-3-F,E], [−4923:4-(CF$_3$)$_2$CF,4-Cl-3-F,E], [−4924:4-(CF$_3$)$_2$CH,4-Cl-3-F,E], [−4925:4-CHF$_2$,4-Cl-3-F,E], [−4926:4-CH$_2$F,4-Cl-3-F,E], [−4927:4-CF$_3$CH$_2$,4-Cl-3-F,E], [−4928:4-MeO,4-Cl-3-F,E], [−4929:4-MeO,4-Cl-3-F,Z], [−4930:4-EtO,4-Cl-3-F,E], [−4931:4-C$_3$H$_7$O,4-Cl-3-F,E], [−4932:4-(Me)$_2$CHO,4-Cl-3-F,E], [−4933:4-NO$_2$,4-Cl-3-F,E], [−4934:4-NO$_2$,4-Cl-3-F,Z], [−4935:3-F,4-Cl-3-F,E], [−4936:3-F,4-Cl-3-F,Z], [−4937:3-Cl,4-Cl-3-F,E], [−4938:3-Cl,4-Cl-3-F,Z], [−4939:3-Br,4-Cl-3-F,E], [−4940:3-I,4-Cl-3-F,E], [−4941:3-Me,4-Cl-3-F,E], [−4942:3-Me,4-Cl-3-F,Z], [−4943:3-Et,4-Cl-3-F,E], [−4944:3-C$_3$H$_7$,4-Cl-3-F,E], [−4945:3-(Me)$_2$CH,4-Cl-3-F,E], [−4946:3-CF$_3$,4-Cl-3-F,E], [−4947:3-CF$_3$,4-Cl-3-F,Z], [−4948:3-C$_2$F$_5$,4-Cl-3-F,E], [−4949:3-C$_3$F$_7$,4-Cl-3-F,E], [−4950:3-(CF$_3$)$_2$CF,4-Cl-3-F,E], [−4951:3-(CF$_3$)$_2$CH,4-Cl-3-F,E], [−4952:3-CHF$_2$,4-Cl-3-F,E], [−4953:3-CHF$_2$,4-Cl-3-F,Z], [−4954:3-CH$_2$F,4-Cl-3-F,E], [−4955:3-CH$_2$F,4-Cl-3-F,Z], [−4956:3-CF$_3$CH$_2$,4-Cl-3-F,E], [−4957:3-MeO,4-Cl-3-F,E], [−4958:3-MeO,4-Cl-3-F,Z], [−4959:3-EtO,4-Cl-3-F,E], [−4960:3-C$_3$H$_7$O,4-Cl-3-F,E], [−4961:3-(Me)$_2$CHO,4-Cl-3-F,E], [−4962:3-NO$_2$,4-Cl-3-F,E], [−4963:2-F,4-Cl-3-F,E], [−4964:2-Cl,4-Cl-3-F,E], [−4965:2-Br,4-Cl-3-F,E], [−4966:2-I,4-Cl-3-F,E], [−4967:2-Me,4-Cl-3-F,E], [−4968:2-Et,4-Cl-3-F,E], [−4969:2-C$_3$H$_7$,4-Cl-3-F,E], [−4970:2-(Me)$_2$CH,4-Cl-3-F,E], [−4971:2-CF$_3$,4-Cl-3-F,E], [−4972:2-C$_2$F$_5$,4-Cl-3-F,E], [−4973:2-C$_3$F$_7$,4-Cl-3-F,E], [−4974:2-(CF$_3$)$_2$CF,4-Cl-3-F,E], [−4975:2-(CF$_3$)$_2$CH,4-Cl-3-F,E], [−4976:2-CHF$_2$,4-Cl-3-F,E], [−4977:2-CH$_2$F,4-Cl-3-F,E], [−4978:2-CF$_3$CH$_2$,4-Cl-3-F,E], [−4979:2-MeO,4-Cl-3-F,E], [−4980:2-EtO,4-Cl-3-F,E], [−4981:2-C$_3$H$_7$O,4-Cl-3-F,E], [−4982:2-(Me)$_2$CHO,4-Cl-3-F,E], [−4983:2-NO$_2$,4-Cl-3-F,E], [−4984:2,3-F$_2$,4-Cl-3-F,E], [−4985:2,4-F$_2$,4-Cl-3-F,E], [−4986:2,5-F$_2$,4-Cl-3-F,E], [−4987:2,6-F$_2$,4-Cl-3-F,E], [−4988:3,4-F$_2$,4-Cl-3-F,E], [−4989:3,4-F$_2$,4-Cl-3-F,Z], [−4990:3,5-F$_2$, 4-Cl-3-F,E], [−4991:3,5-F$_2$, 4-Cl-3-F,Z], [−4992:2,3-Cl$_2$,4-Cl-3-F,E], [−4993:2,3-Cl$_2$,4-Cl-3-F,Z], [−4994:2,4-Cl$_2$,4-Cl-3-F,E], [−4995:2,4-Cl$_2$,4-Cl-3-F,Z], [−4996:2,5-Cl$_2$,4-Cl-3-F,E], [−4997:2,5-Cl$_2$,4-Cl-3-F,Z], [−4998:2,6-Cl$_2$,4-Cl-3-F,E], [−4999:3,4-Cl$_2$,4-Cl-3-F,E], [−5000:3,5-Cl$_2$,4-Cl-3-F,E], [−5001:2,3-Br$_2$,4-Cl-3-F,E], [−5002:2,4-Br$_2$,4-Cl-3-F,E], [−5003:2,5-Br$_2$,4-Cl-3-F,E], [−5004:2,6-Br$_2$,4-Cl-3-F,E], [−5005:3,4-Br$_2$,4-Cl-3-F,E], [−5006:3,5-Br$_2$,4-Cl-3-F,E], [−5007:2,3-Me$_2$,4-Cl-3-F,E], [−5008:2,4-Me$_2$,4-Cl-3-F,E], [−5009:2,5-Me$_2$,4-Cl-3-F,E], [−5010:2,6-Me$_2$,4-Cl-3-F,E], [−5011:3,4-Me$_2$,4-Cl-3-F,E], [−5012:3,5-Me$_2$,4-Cl-3-F,E], [−5013:2,3-Et$_2$,4-Cl-3-F,E], [−5014:2,4-Et$_2$,4-Cl-3-F,E], [−5015:2,5-Et$_2$,4-Cl-3-F,E], [−5016:2,6-Et$_2$,4-Cl-3-F,E], [−5017:3,4-Et$_2$,4-Cl-3-F,E], [−5018:3,5-Et$_2$,4-Cl-3-F,E], [−5019:2,3-(CF$_3$)$_2$,4-Cl-3-F,E], [−5020:2,4-(CF$_3$)$_2$,4-Cl-3-F,E], [−5021:2,5-(CF$_3$)$_2$,4-Cl-3-F,E], [−5022:2,6-(CF$_3$)$_2$,4-Cl-3-F,E], [−5023:3,4-(CF$_3$)$_2$,4-Cl-3-F,E], [−5024:3,5-(CF$_3$)$_2$,4-Cl-3-F,E], [−5025:2,3-(CHF$_2$)$_2$,4-Cl-3-F,E], [−5026:2,4-(CHF$_2$)$_2$,4-Cl-3-F,E], [−5027:2,5-(CHF$_2$)$_2$,4-Cl-3-F,E], [−5028:2,6-(CHF$_2$)$_2$,4-Cl-3-F,E], [−5029:3,4-(CHF$_2$)$_2$,4-Cl-3-F,E], [−5030:3,5-(CHF$_2$)$_2$,4-Cl-3-F,E], [−5031:2,3-(CH$_2$F)$_2$,4-Cl-3-F,E], [−5032:2,4-(CH$_2$F)$_2$,4-Cl-3-F,E], [−5033:2,5-(CH$_2$F)$_2$,4-Cl-3-F,E], [−5034:2,6-(CH$_2$F)$_2$,4-Cl-3-F,E], [−5035:3,4-(CH$_2$F)$_2$,4-Cl-3-F,E], [−5036:3,5-(CH$_2$F)$_2$,4-Cl-3-F,E], [−5037:2,3-(MeO)$_2$,4-Cl-3-F,E], [−5038:2,4-(MeO)$_2$,4-Cl-3-F,E], [−5039:2,5-(MeO)$_2$,4-Cl-3-F,E], [−5040:2,6-(MeO)$_2$,4-Cl-3-F,E], [−5041:3,4-(MeO)$_2$,4-Cl-3-F,E], [−5042:3,5-(MeO)$_2$,4-Cl-3-F,E], [−5043:2,3-(EtO)$_2$,4-Cl-3-F,E], [−5044:2,4-(EtO)$_2$,4-Cl-3-F,E], [−5045:2,5-(EtO)$_2$,4-Cl-3-F,E], [−5046:2,6-(EtO)$_2$,4-Cl-3-F,E], [−5047:3,4-(EtO)$_2$,4-Cl-3-F,E], [−5048:3,5-(EtO)$_2$,4-Cl-3-F,E],

[−5049:2-Cl-3-F,4-Cl-3-F,E], [−5050:2-Cl-4-F,4-Cl-3-F, E], [−5051:2-Cl-5-F,4-Cl-3-F,E], [−5052:2-Cl-6-F,4-Cl-3-F,E], [−5053:3-Cl-2-F,4-Cl-3-F,E], [−5054:3-Cl-4-F,4-Cl-3-F,E], [−5055:3-Cl-5-F,4-Cl-3-F,E], [−5056:4-Cl-2-F,4-Cl-3-F,E], [−5057:4-Cl-3-F,4-Cl-3-F,E], [−5058:2-F-3-Me,4-Cl-3-F,E], [−5059:2-F-4-Me,4-Cl-3-F,E], [−5060:2-F-5-Me,4-Cl-3-F,E], [−5061:2-F-6-Me,4-Cl-3-F,E], [−5062:3-F-2-Me,4-Cl-3-F,E], [−5063:3-F-4-Me,4-Cl-3-F,E], [−5064:3-F-5-Me,4-Cl-3-F,E], [−5065:4-F-2-Me,4-Cl-3-F,E], [−5066:4-F-3-Me,4-Cl-3-F,E], [−5067:2-Cl-3-Me,4-Cl-3-F,E], [−5068:2-Cl-4-Me,4-Cl-3-F,E], [−5069:2-Cl-5-Me,4-Cl-3-F,E], [−5070:2-Cl-6-Me,4-Cl-3-F,E], [−5071:3-Cl-2-Me,4-Cl-3-F,E], [−5072:3-Cl-4-Me,4-Cl-3-F,E], [−5073:3-Cl-5-Me,4-Cl-3-F,E], [−5074:4-Cl-2-Me,4-Cl-3-F,E], [−5075:4-Cl-3-Me,4-Cl-3-F,E], [−5076:2-F-3-$CF_3$,4-Cl-3-F,E], [−5077:2-F-4-$CF_3$,4-Cl-3-F,E], [−5078:2-F-5-$CF_3$,4-Cl-3-F,E], [−5079:2-F-6-$CF_3$,4-Cl-3-F,E], [−5080:3-F-2-$CF_3$,4-Cl-3-F,E], [−5081:3-F-4-$CF_3$,4-Cl-3-F,E], [−5082:3-F-5-$CF_3$,4-Cl-3-F,E], [−5083:4-F-2-$CF_3$,4-Cl-3-F,E], [−5084:4-F-3-$CF_3$,4-Cl-3-F,E], [−5085:2-Cl-3-$CF_3$,4-Cl-3-F,E], [−5086:2-Cl-4-$CF_3$,4-Cl-3-F,E], [−5087:2-Cl-5-$CF_3$,4-Cl-3-F,E], [−5088:2-Cl-6-$CF_3$,4-Cl-3-F,E], [−5089:3-Cl-2-$CF_3$,4-Cl-3-F,E], [−5090:3-Cl-4-$CF_3$,4-Cl-3-F,E], [−5091:3-Cl-5-$CF_3$,4-Cl-3-F,E], [−5092:4-Cl-2-$CF_3$,4-Cl-3-F,E], [−5093:4-Cl-3-$CF_3$,4-Cl-3-F,E], [−5094:2-Me-3-$CF_3$,4-Cl-3-F,E], [−5095:2-Me-4-$CF_3$,4-Cl-3-F,E], [−5096:2-Me-5-$CF_3$,4-Cl-3-F,E], [−5097:2-Me-6-$CF_3$,4-Cl-3-F,E], [−5098:3-Me-2-$CF_3$,4-Cl-3-F,E], [−5099:3-Me-4-$CF_3$,4-Cl-3-F,E], [−5100:3-Me-5-$CF_3$,4-Cl-3-F,E], [−5101:4-Me-2-$CF_3$,4-Cl-3-F,E], [−5102:4-Me-3-$CF_3$,4-Cl-3-F,E], [−5103:2-F-3-MeO,4-Cl-3-F,E], [−5104:2-F-4-MeO,4-Cl-3-F,E], [−5105:2-F-5-MeO,4-Cl-3-F,E], [−5106:2-F-6-MeO,4-Cl-3-F,E], [−5107:3-F-2-MeO,4-Cl-3-F,E], [−5108:3-F-4-MeO,4-Cl-3-F,E], [−5109:3-F-5-MeO,4-Cl-3-F,E], [−5110:4-F-2-MeO,4-Cl-3-F,E], [−5111:4-F-3-MeO,4-Cl-3-F,E], [−5112:2-Cl-3-MeO,4-Cl-3-F,E], [−5113:2-Cl-4-MeO,4-Cl-3-F,E], [−5114:2-Cl-5-MeO,4-Cl-3-F,E], [−5115:2-Cl-6-MeO,4-Cl-3-F,E], [−5116:3-Cl-2-MeO,4-Cl-3-F,E], [−5117:3-Cl-4-MeO,4-Cl-3-F,E], [−5118:3-Cl-5-MeO,4-Cl-3-F,E], [−5119:4-Cl-2-MeO,4-Cl-3-F,E], [−5120:4-Cl-3-MeO,4-Cl-3-F,E], [−5121:2-Me-3-MeO,4-Cl-3-F,E], [−5122:2-Me-4-MeO,4-Cl-3-F,E], [−5123:2-Me-5-MeO,4-Cl-3-F,E], [−5124:2-Me-6-MeO,4-Cl-3-F,E], [−5125:3-Me-2-MeO, 4-Cl-3-F,E], [−5126:3-Me-4-MeO,4-Cl-3-F,E], [−5127:3-Me-5-MeO, 4-Cl-3-F,E], [−5128:4-Me-2-MeO,4-Cl-3-F,E], [−5129:4-Me-3-MeO, 4-Cl-3-F,E],

[−5130:H,3-F-4-$(Me)_3$CO,E], [−5131:4-F,3-F-4-$(Me)_3$CO, E], [−5132:4-F,3-F-4-$(Me)_3$CO,Z], [−5133:4-Cl,3-F-4-$(Me)_3$CO,E], [−5134:4-Cl,3-F-4-$(Me)_3$CO,Z], [−5135:4-Br,3-F-4-$(Me)_3$CO,E], [−5136:4-I,3-F-4-$(Me)_3$CO,E], [−5137:4-Me,3-F-4-$(Me)_3$CO,E], [−5138:4-Me,3-F-4-$(Me)_3$CO,Z], [−5139:4-Et,3-F-4-$(Me)_3$CO,E], [−5140:4-$C_3H_7$,3-F-4-$(Me)_3$CO,E], [−5141:4-$(Me)_2$CH,3-F-4-$(Me)_3$CO,E], [−5142:4-$CF_3$,3-F-4-$(Me)_3$CO,E], [−5143:4-$CF_3$,3-F-4-$(Me)_3$CO,Z], [−5144:4-$C_2F_5$,3-F-4-$(Me)_3$CO,E], [−5145:4-$C_3F_7$,3-F-4-$(Me)_3$CO,E], [−5146:4-$(CF_3)_2$CF,3-F-4-$(Me)_3$CO,E], [−5147:4-$(CF_3)_2$CH,3-F-4-$(Me)_3$CO,E], [−5148:4-$CHF_2$,3-F-4-$(Me)_3$CO,E], [−5149:4-$CH_2F$,3-F-4-$(Me)_3$CO,E], [−5150:4-$CF_3CH_2$,3-F-4-$(Me)_3$CO,E], [−5151:4-MeO,3-F-4-$(Me)_3$CO,E], [−5152:4-MeO,3-F-4-$(Me)_3$CO,Z], [−5153:4-EtO,3-F-4-$(Me)_3$CO,E], [−5154:4-$C_3H_7$O,3-F-4-$(Me)_3$CO,E], [−5155:4-$(Me)_2$CHO,3-F-4-$(Me)_3$CO,E], [−5156:4-$NO_2$,3-F-4-$(Me)_3$CO,E], [−5157:4-$NO_2$,3-F-4-$(Me)_3$CO,Z], [−5158:3-F,3-F-4-$(Me)_3$CO,E], [−5159:3-F,3-F-4-$(Me)_3$CO,Z], [−5160:3-Cl,3-F-4-$(Me)_3$CO,E], [−5161:3-Cl,3-F-4-$(Me)_3$CO,Z], [−5162:3-Br,3-F-4-$(Me)_3$CO,E], [−5163:3-I,3-F-4-$(Me)_3$CO,E], [−5164:3-Me,3-F-4-$(Me)_3$CO,E], [−5165:3-Me,3-F-4-$(Me)_3$CO,Z], [−5166:3-Et,3-F-4-$(Me)_3$CO,E], [−5167:3-$C_3H_7$,3-F-4-$(Me)_3$CO,E], [−5168:3-$(Me)_2$CH,3-F-4-$(Me)_3$CO,E], [−5169:3-$CF_3$,3-F-4-$(Me)_3$CO,E], [−5170:3-$CF_3$,3-F-4-$(Me)_3$CO,Z], [−5171:3-$C_2F_5$,3-F-4-$(Me)_3$CO,E], [−5172:3-$C_3F_7$,3-F-4-$(Me)_3$CO,E], [−5173:3-$(CF_3)_2$CF,3-F-4-$(Me)_3$CO,E], [−5174:3-$(CF_3)_2$CH,3-F-4-$(Me)_3$CO,E], [−5175:3-$CHF_2$,3-F-4-$(Me)_3$CO,E], [−5176:3-$CHF_2$,3-F-4-$(Me)_3$CO,Z], [−5177:3-$CH_2F$,3-F-4-$(Me)_3$CO,E], [−5178:3-$CH_2F$,3-F-4-$(Me)_3$CO,Z], [−5179:3-$CF_3CH_2$,3-F-4-$(Me)_3$CO,E], [−5180:3-MeO,3-F-4-$(Me)_3$CO,E], [−5181:3-MeO,3-F-4-$(Me)_3$CO,Z], [−5182:3-EtO,3-F-4-$(Me)_3$CO,E], [−5183:3-$C_3H_7$O,3-F-4-$(Me)_3$CO,E], [−5184:3-$(Me)_2$CHO,3-F-4-$(Me)_3$CO,E], [−5185:3-$NO_2$,3-F-4-$(Me)_3$CO,E], [−5186:2-F,3-F-4-$(Me)_3$CO,E], [−5187:2-Cl,3-F-4-$(Me)_3$CO,E], [−5188:2-Br,3-F-4-$(Me)_3$CO,E], [−5189:2-I,3-F-4-$(Me)_3$CO,E], [−5190:2-Me,3-F-4-$(Me)_3$CO,E], [−5191:2-Et,3-F-4-$(Me)_3$CO,E], [−5192:2-$C_3H_7$,3-F-4-$(Me)_3$CO,E], [−5193:2-$(Me)_2$OH, 3-F-4-$(Me)_3$CO,E], [−5194:2-$CF_3$,3-F-4-$(Me)_3$CO,E], [−5195:2-$C_2F_5$,3-F-4-$(Me)_3$CO,E], [−5196:2-$C_3F_7$,3-F-4-$(Me)_3$CO,E], [−5197:2-$(CF_3)_2$CF,3-F-4-$(Me)_3$CO,E], [−5198:2-$(CF_3)_2$CH,3-F-4-$(Me)_3$CO,E], [−5199:2-$CHF_2$,3-F-4-$(Me)_3$CO,E], [−5200:2-$CH_2F$,3-F-4-$(Me)_3$CO,E], [−5201:2-$CF_3CH_2$,3-F-4-$(Me)_3$CO,E], [−5202:2-MeO,3-F-4-$(Me)_3$CO,E], [−5203:2-EtO,3-F-4-$(Me)_3$CO,E], [−5204:2-$C_3H_7$O,3-F-4-$(Me)_3$CO,E], [−5205:2-$(Me)_2$CHO,3-F-4-$(Me)_3$CO,E], [−5206:2-$NO_2$,3-F-4-$(Me)_3$CO,E], [−5207:2,3-$F_2$,3-F-4-$(Me)_3$CO,E], [−5208:2,4-$F_2$,3-F-4-$(Me)_3$CO,E], [−5209:2,5-$F_2$,3-F-4-$(Me)_3$CO,E], [−5210:2,6-$F_2$,3-F-4-$(Me)_3$CO,E], [−5211:3,4-$F_2$,3-F-4-$(Me)_3$CO,E], [−5212:3,4-$F_2$,3-F-4-$(Me)_3$CO,Z], [−5213:3,5-$F_2$,3-F-4-$(Me)_3$CO,E], [−5214:3,5-$F_2$,3-F-4-$(Me)_3$CO,Z], [−5215:2,3-$Cl_2$,3-F-4-$(Me)_3$CO,E], [−5216:2,3-$Cl_2$,3-F-4-$(Me)_3$CO,Z], [−5217:2,4-$Cl_2$,3-F-4-$(Me)_3$CO,E], [−5218:2,4-$Cl_2$,3-F-4-$(Me)_3$CO,Z], [−5219:2,5-$Cl_2$,3-F-4-$(Me)_3$CO,E], [−5220:2,5-$Cl_2$,3-F-4-$(Me)_3$CO,Z], [−5221:2,6-$Cl_2$,3-F-4-$(Me)_3$CO,E], [−5222:3,4-$Cl_2$,3-F-4-$(Me)_3$CO,E], [−5223:3,5-$Cl_2$,3-F-4-$(Me)_3$CO,E], [−5224:2,3-$Br_2$,3-F-4-$(Me)_3$CO,E], [−5225:2,4-$Br_2$,3-F-4-$(Me)_3$CO,E], [−5226:2,5-$Br_2$,3-F-4-$(Me)_3$CO,E], [−5227:2,6-$Br_2$,3-F-4-$(Me)_3$CO,E], [−5228:3,4-$Br_2$,3-F-4-$(Me)_3$CO,E], [−5229:3,5-$Br_2$,3-F-4-$(Me)_3$CO,E], [−5230:2,3-$Me_2$,3-F-4-$(Me)_3$CO,E], [−5231:2,4-$Me_2$,3-F-4-$(Me)_3$CO,E], [−5232:2,5-$Me_2$,3-F-4-$(Me)_3$CO,E], [−5233:2,6-$Me_2$,3-F-4-$(Me)_3$CO,E], [−5234:3,4-$Me_2$,3-F-4-$(Me)_3$CO,E], [−5235:3,5-$Me_2$,3-F-4-$(Me)_3$CO,E], [−5236:2,3-$Et_2$,3-F-4-$(Me)_3$CO,E], [−5237:2,4-$Et_2$,3-F-4-$(Me)_3$CO,E], [−5238:2,5-$Et_2$,3-F-4-$(Me)_3$CO,E], [−5239:2,6-$Et_2$,3-F-4-$(Me)_3$CO,E], [−5240:3,4-$Et_2$,3-F-4-$(Me)_3$CO,E], [−5241:3,5-$Et_2$,3-F-4-$(Me)_3$CO,E], [−5242:2,3-$(CF_3)_2$,3-F-4-$(Me)_3$CO,E], [−5243:2,4-$(CF_3)_2$,3-F-4-$(Me)_3$CO,E], [−5244:2,5-$(CF_3)_2$,3-F-4-$(Me)_3$CO,E], [−5245:2,6-$(CF_3)_2$,3-F-4-$(Me)_3$CO,E], [−5246:3,4-$(CF_3)_2$,3-F-4-$(Me)_3$CO,E], [−5247:3,5-$(CF_3)_2$,3-F-4-$(Me)_3$CO,E], [−5248:2,3-$(CHF_2)_2$,3-F-4-$(Me)_3$CO,E], [−5249:2,4-$(CHF_2)_2$,3-F-4-$(Me)_3$CO,E], [−5250:2,5-$(CHF_2)_2$,3-F-4-$(Me)_3$CO,E], [−5251:2,6-$(CHF_2)_2$,3-F-4-$(Me)_3$CO,E], [−5252:3,4-$(CHF_2)_2$,3-F-4-$(Me)_3$CO,E], [−5253:3,5-$(CHF_2)_2$,3-F-4-$(Me)_3$CO,E], [−5254:2,3-$(CH_2F)_2$,3-F-4-$(Me)_3$CO,E], [−5255:2,4-$(CH_2F)_2$,3-F-4-$(Me)_3$CO,E], [−5256:2,5-$(CH_2F)_2$,3-F-4-$(Me)_3$CO,E], [−5257:2,6-$(CH_2F)_2$,3-F-4-$(Me)_3$CO,E], [−5258:3,4-$(CH_2F)_2$,3-F-4-$(Me)_3$CO,E], [−5259:3,5-$(CH_2F)_2$,3-F-4-$(Me)_3$CO,E], [−5260:2,3-

(MeO)₂,3-F-4-(Me)₃CO,E], [−5261:2,4-(MeO)₂,3-F-4-(Me)₃O,E], [−5262:2,5-(MeO)₂,3-F-4-(Me)₃CO,E], [−5263:2,6-(MeO)₂,3-F-4-(Me)₃O,E], [−5264:3,4-(MeO)₂,3-F-4-(Me)₃O,E], [−5265:3,5-(MeO)₂,3-F-4-(Me)₃CO,E], [−5266:2,3-(EtO)₂,3-F-4-(Me)₃CO,E], [−5267:2,4-(EtO)₂,3-F-4-(Me)₃CO,E], [−5268:2,5-(EtO)₂,3-F-4-(Me)₃O,E], [−5269:2,6-(EtO)₂,3-F-4-(Me)₃CO,E], [−5270:3,4-(EtO)₂,3-F-4-(Me)₃CO,E], [−5271:3,5-(EtO)₂,3-F-4-(Me)₃CO,E], [−5272:2-Cl-3-F,3-F-4-(Me)₃CO,E], [−5273:2-Cl-4-F,3-F-4-(Me)₃CO,E], [−5274:2-Cl-5-F,3-F-4-(Me)₃CO,E], [−5275:2-Cl-6-F,3-F-4-(Me)₃CO,E], [−5276:3-Cl-2-F,3-F-4-(Me)₃CO,E], [−5277:3-Cl-4-F,3-F-4-(Me)₃CO,E], [−5278:3-Cl-5-F,3-F-4-(Me)₃CO,E], [−5279:4-Cl-2-F,3-F-4-(Me)₃CO,E], [−5280:4-Cl-3-F,3-F-4-(Me)₃CO,E], [−5281:2-F-3-Me,3-F-4-(Me)₃CO,E], [−5282:2-F-4-Me,3-F-4-(Me)₃CO,E], [−5283:2-F-5-Me,3-F-4-(Me)₃CO,E], [−5284:2-F-6-Me,3-F-4-(Me)₃CO,E], [−5285:3-F-2-Me,3-F-4-(Me)₃CO,E], [−5286:3-F-4-Me,3-F-4-(Me)₃CO,E], [−5287:3-F-5-Me,3-F-4-(Me)₃CO,E], [−5288:4-F-2-Me,3-F-4-(Me)₃CO,E], [−5289:4-F-3-Me,3-F-4-(Me)₃O,E], [−5290:2-Cl-3-Me,3-F-4-(Me)₃CO,E], [−5291:2-Cl-4-Me,3-F-4-(Me)₃CO,E], [−5292:2-Cl-5-Me,3-F-4-(Me)₃CO,E], [−5293:2-Cl-6-Me,3-F-4-(Me)₃CO,E], [−5294:3-Cl-2-Me,3-F-4-(Me)₃CO,E], [−5295:3-Cl-4-Me,3-F-4-(Me)₃CO,E], [−5296:3-Cl-5-Me,3-F-4-(Me)₃CO,E], [−5297:4-Cl-2-Me,3-F-4-(Me)₃CO,E], [−5298:4-Cl-3-Me,3-F-4-(Me)₃O,E], [−5299:2-F-3-CF₃,3-F-4-(Me)₃CO,E], [−5300:2-F-4-CF₃,3-F-4-(Me)₃CO,E], [−5301:2-F-5-CF₃,3-F-4-(Me)₃CO,E], [−5302:2-F-6-CF₃,3-F-4-(Me)₃CO,E], [−5303:3-F-2-CF₃,3-F-4-(Me)₃CO,E], [−5304:3-F-4-CF₃,3-F-4-(Me)₃CO,E], [−5305:3-F-5-CF₃,3-F-4-(Me)₃CO,E], [−5306:4-F-2-CF₃,3-F-4-(Me)₃CO,E], [−5307:4-F-3-CF₃,3-F-4-(Me)₃CO,E], [−5308:2-Cl-3-CF₃,3-F-4-(Me)₃CO,E], [−5309:2-Cl-4-CF₃,3-F-4-(Me)₃CO,E], [−5310:2-Cl-5-CF₃,3-F-4-(Me)₃CO,E], [−5311:2-Cl-6-CF₃,3-F-4-(Me)₃CO,E], [−5312:3-Cl-2-CF₃,3-F-4-(Me)₃CO,E], [−5313:3-Cl-4-CF₃,3-F-4-(Me)₃CO,E], [−5314:3-Cl-5-CF₃,3-F-4-(Me)₃CO,E], [−5315:4-Cl-2-CF₃,3-F-4-(Me)₃CO,E], [−5316:4-Cl-3-CF₃,3-F-4-(Me)₃CO,E], [−5317:2-Me-3-CF₃,3-F-4-(Me)₃CO,E], [−5318:2-Me-4-CF₃,3-F-4-(Me)₃CO,E], [−5319:2-Me-5-CF₃,3-F-4-(Me)₃CO,E], [−5320:2-Me-6-CF₃,3-F-4-(Me)₃CO,E], [−5321:3-Me-2-CF₃,3-F-4-(Me)₃CO,E], [−5322:3-Me-4-CF₃,3-F-4-(Me)₃CO,E], [−5323:3-Me-5-CF₃,3-F-4-(Me)₃CO,E], [−5324:4-Me-2-CF₃,3-F-4-(Me)₃CO,E], [−5325:4-Me-3-CF₃,3-F-4-(Me)₃CO,E], [−5326:2-F-3-MeO,3-F-4-(Me)₃CO,E], [−5327:2-F-4-MeO,3-F-4-(Me)₃CO,E], [−5328:2-F-5-MeO,3-F-4-(Me)₃CO,E], [−5329:2-F-6-MeO,3-F-4-(Me)₃CO,E], [−5330:3-F-2-MeO,3-F-4-(Me)₃CO,E], [−5331:3-F-4-MeO,3-F-4-(Me)₃CO,E], [−5332:3-F-5-MeO,3-F-4-(Me)₃CO,E], [−5333:4-F-2-MeO,3-F-4-(Me)₃CO,E], [−5334:4-F-3-MeO,3-F-4-(Me)₃CO,E], [−5335:2-Cl-3-MeO,3-F-4-(Me)₃CO,E], [−5336:2-Cl-4-MeO,3-F-4-(Me)₃CO,E], [−5337:2-Cl-5-MeO,3-F-4-(Me)₃CO,E], [−5338:2-Cl-6-MeO,3-F-4-(Me)₃CO,E], [−5339:3-Cl-2-MeO,3-F-4-(Me)₃CO,E], [−5340:3-Cl-4-MeO,3-F-4-(Me)₃CO,E], [−5341:3-Cl-5-MeO,3-F-4-(Me)₃CO,E], [−5342:4-Cl-2-MeO,3-F-4-(Me)₃CO,E], [−5343:4-Cl-3-MeO,3-F-4-(Me)₃CO,E], [−5344:2-Me-3-MeO,3-F-4-(Me)₃CO,E], [−5345:2-Me-4-MeO,3-F-4-(Me)₃CO,E], [−5346:2-Me-5-MeO,3-F-4-(Me)₃CO,E], [−5347:2-Me-6-MeO,3-F-4-(Me)₃CO,E], [−5348:3-Me-2-MeO,3-F-4-(Me)₃CO,E], [−5349:3-Me-4-MeO,3-F-4-(Me)₃CO,E], [−5350:3-Me-5-MeO,3-F-4-(Me)₃CO,E], [−5351:4-Me-2-MeO,3-F-4-(Me)₃CO,E], [−5352:4-Me-3-MeO,3-F-4-(Me)₃CO,E], [−5353:H,4-Me,E], [−5354:4-F,4-Me,E], [−5355:4-F,4-Me,Z], [−5356:4-Cl,4-Me,E], [−5357:4-Cl,4-Me,Z], [−5358:4-Br,4-Me,E], [−5359:4-I,4-Me,E], [−5360:4-Me,4-Me,E], [−5361:4-Me,4-Me,Z], [−5362:4-Et,4-Me,E], [−5363:4-C₃H₇,4-Me,E], [−5364:4-(Me)₂CH,4-Me,E], [−5365:4-CF₃,4-Me,E], [−5366:4-CF₃,4-Me,Z], [−5367:4-C₂F₅,4-Me,E], [−5368:4-C₃F₇,4-Me,E], [−5369:4-(CF₃)₂CF,4-Me,E], [−5370:4-(CF₃)₂CH,4-Me,E], [−5371:4-CHF₂,4-Me,E], [−5372:4-CH₂F,4-Me,E], [−5373:4-CF₃CH₂,4-Me,E], [−5374:4-MeO,4-Me,E], [−5375:4-MeO,4-Me,Z], [−5376:4-EtO,4-Me,E], [−5377:4-C₃H₇O,4-Me,E], [−5378:4-(Me)₂CHO,4-Me,E], [−5379:4-NO₂,4-Me,E], [−5380:4-NO₂,4-Me,Z], [−5381:3-F,4-Me,E], [−5382:3-F,4-Me,Z], [−5383:3-Cl,4-Me,E], [−5384:3-Cl,4-Me,Z], [−5385:3-Br,4-Me,E], [−5386:3-I,4-Me,E], [−5387:3-Me,4-Me,E], [−5388:3-Me,4-Me,Z], [−5389:3-Et,4-Me,E], [−5390:3-C₃H₇,4-Me,E], [−5391:3-(Me)₂CH,4-Me,E], [−5392:3-CF₃,4-Me,E], [−5393:3-CF₃,4-Me,Z], [−5394:3-C₂F₅,4-Me,E], [−5395:3-C₃F₇,4-Me,E], [−5396:3-(CF₃)₂CF,4-Me,E], [−5397:3-(CF₃)₂CH,4-Me,E], [−5398:3-CHF₂,4-Me,E], [−5399:3-CHF₂,4-Me,Z], [−5400:3-CH₂F,4-Me,E], [−5401:3-CH₂F,4-Me,Z], [−5402:3-CF₃CH₂,4-Me,E], [−5403:3-MeO,4-Me,E], [−5404:3-MeO,4-Me,Z], [−5405:3-EtO,4-Me,E], [−5406:3-C₃H₇O,4-Me,E], [−5407:3-(Me)₂CHO,4-Me,E], [−5408:3-NO₂,4-Me,E], [−5409:2-F,4-Me,E], [−5410:2-Cl,4-Me,E], [−5411:2-Br,4-Me,E], [−5412:2-I,4-Me,E], [−5413:2-Me,4-Me,E], [−5414:2-Et,4-Me,E], [−5415:2-C₃H₇,4-Me,E], [−5416:2-(Me)₂CH,4-Me,E], [−5417:2-CF₃,4-Me,E], [−5418:2-C₂F₅,4-Me,E], [−5419:2-C₃F₇,4-Me,E], [−5420:2-(CF₃)₂CF,4-Me,E], [−5421:2-(CF₃)₂CH,4-Me,E], [−5422:2-CHF₂,4-Me,E], [−5423:2-CH₂F,4-Me,E], [−5424:2-CF₃CH₂,4-Me,E], [−5425:2-MeO,4-Me,E], [−5426:2-EtO,4-Me,E], [−5427:2-C₃H₇O,4-Me,E], [−5428:2-(Me)₂CHO,4-Me,E], [−5429:2-NO₂,4-Me,E], [−5430:2,3-F₂,4-Me,E], [−5431:2,4-F₂,4-Me,E], [−5432:2,5-F₂,4-Me,E], [−5433:2,6-F₂,4-Me,E], [−5434:3,4-F₂,4-Me,E], [−5435:3,4-F₂,4-Me,Z], [−5436:3,5-F₂,4-Me,E], [−5437:3,5-F₂,4-Me,Z], [−5438:2,3-Cl₂,4-Me,E], [−5439:2,3-Cl₂,4-Me,Z], [−5440:2,4-Cl₂,4-Me,E], [−5441:2,4-Cl₂,4-Me,Z], [−5442:2,5-Cl₂,4-Me,E], [−5443:2,5-Cl₂,4-Me,Z], [−5444:2,6-Cl₂,4-Me,E], [−5445:3,4-Cl₂,4-Me,E], [−5446:3,5-Cl₂,4-Me,E], [−5447:2,3-Br₂,4-Me,E], [−5448:2,4-Br₂,4-Me,E], [−5449:2,5-Br₂,4-Me,E], [−5450:2,6-Br₂,4-Me,E], [−5451:3,4-Br₂,4-Me,E], [−5452:3,5-Br₂,4-Me,E], [−5453:2,3-Me₂,4-Me,E], [−5454:2,4-Me₂,4-Me,E], [−5455:2,5-Me₂,4-Me,E], [−5456:2,6-Me₂,4-Me,E], [−5457:3,4-Me₂,4-Me,E], [−5458:3,5-Me₂,4-Me,E], [−5459:2,3-Et₂,4-Me,E], [−5460:2,4-Et₂,4-Me,E], [−5461:2,5-Et₂,4-Me,E], [−5462:2,6-Et₂,4-Me,E], [−5463:3,4-Et₂,4-Me,E], [−5464:3,5-Et₂,4-Me,E], [−5465:2,3-(CF₃)₂,4-Me,E], [−5466:2,4-(CF₃)₂,4-Me,E], [−5467:2,5-(CF₃)₂,4-Me,E], [−5468:2,6-(CF₃)₂,4-Me,E], [−5469:3,4-(F₃)₂,4-Me,E], [−5470:3,5-(F₃)₂,4-Me,E], [−5471:2,3-(CHF₂)₂,4-Me,E], [−5472:2,4-(CHF₂)₂,4-Me,E], [−5473:2,5-(CHF₂)₂,4-Me,E], [−5474:2,6-(CHF₂)₂,4-Me,E], [−5475:3,4-(CHF₂)₂,4-Me,E], [−5476:3,5-(CHF₂)₂,4-Me,E], [−5477:2,3-(CH₂F)₂,4-Me,E], [−5478:2,4-(CH₂F)₂,4-Me,E], [−5479:2,5-(CH₂F)₂,4-Me,E], [−5480:2,6-(CH₂F)₂,4-Me,E], [−5481:3,4-(CH₂F)₂,4-Me,E], [−5482:3,5-(CH₂F)₂,4-Me,E], [−5483:2,3-(MeO)₂,4-Me,E], [−5484:2,4-(MeO)₂,4-Me,E], [−5485:2,5-(MeO)₂,4-Me,E], [−5486:2,6-(MeO)₂,4-Me,E], [−5487:3,4-(MeO)₂,4-Me,E], [−5488:3,5-(MeO)₂,4-Me,E], [−5489:2,3-(EtO)₂,4-Me,E], [−5490:2,4-(EtO)₂,4-Me,E], [−5491:2,5-(EtO)₂,4-Me,E], [−5492:2,6-(EtO)₂,4-Me,E], [−5493:3,4-(EtO)₂,4-Me,E], [−5494:3,5-(EtO)₂,

4-Me,E], [–5495:2-Cl-3-F,4-Me,E], [–5496:2-Cl-4-F,4-Me,E], [–5497:2-Cl-5-F,4-Me,E], [–5498:2-Cl-6-F,4-Me,E], [–5499:3-Cl-2-F,4-Me,E], [–5500:3-Cl-4-F,4-Me,E], [–5501:3-Cl-5-F,4-Me,E], [–5502:4-Cl-2-F,4-Me,E], [–5503:4-Cl-3-F,4-Me,E], [–5504:2-F-3-Me,4-Me,E], [–5505:2-F-4-Me,4-Me,E], [–5506:2-F-5-Me,4-Me,E], [–5507:2-F-6-Me,4-Me,E], [–5508:3-F-2-Me,4-Me,E], [–5509:3-F-4-Me,4-Me,E], [–5510:3-F-5-Me,4-Me,E], [–5511:4-F-2-Me,4-Me,E], [–5512:4-F-3-Me,4-Me,E], [–5513:2-Cl-3-Me,4-Me,E], [–5514:2-Cl-4-Me,4-Me,E], [–5515:2-Cl-5-Me,4-Me,E], [–5516:2-Cl-6-Me,4-Me,E], [–5517:3-Cl-2-Me,4-Me,E], [–5518:3-Cl-4-Me,4-Me,E], [–5519:3-Cl-5-Me,4-Me,E], [–5520:4-Cl-2-Me,4-Me,E], [–5521:4-Cl-3-Me,4-Me,E], [–5522:2-F-3-$CF_3$,4-Me,E], [–5523:2-F-4-$CF_3$,4-Me,E], [–5524:2-F-5-$CF_3$,4-Me,E], [–5525:2-F-6-$CF_3$,4-Me,E], [–5526:3-F-2-$CF_3$,4-Me,E], [–5527:3-F-4-$CF_3$,4-Me,E], [–5528:3-F-5-$CF_3$,4-Me,E], [–5529:4-F-2-$CF_3$,4-Me,E], [–5530:4-F-3-$CF_3$,4-Me,E], [–5531:2-Cl-3-$CF_3$,4-Me,E], [–5532:2-Cl-4-$CF_3$,4-Me,E], [–5533:2-Cl-5-$CF_3$,4-Me,E], [–5534:2-Cl-6-$CF_3$,4-Me,E], [–5535:3-Cl-2-$CF_3$,4-Me,E], [–5536:3-Cl-4-$CF_3$,4-Me,E], [–5537:3-Cl-5-$CF_3$,4-Me,E], [–5538:4-Cl-2-$CF_3$,4-Me,E], [–5539:4-Cl-3-$CF_3$,4-Me,E], [–5540:2-Me-3-$CF_3$,4-Me,E], [–5541:2-Me-4-$CF_3$,4-Me,E], [–5542:2-Me-5-$CF_3$,4-Me,E], [–5543:2-Me-6-$CF_3$,4-Me,E], [–5544:3-Me-2-$CF_3$,4-Me,E], [–5545:3-Me-4-$CF_3$,4-Me,E], [–5546:3-Me-5-$CF_3$,4-Me,E], [–5547:4-Me-2-$CF_3$,4-Me,E], [–5548:4-Me-3-$CF_3$,4-Me,E], [–5549:2-F-3-MeO,4-Me,E], [–5550:2-F-4-MeO,4-Me,E], [–5551:2-F-5-MeO,4-Me,E], [–5552:2-F-6-MeO,4-Me,E], [–5553:3-F-2-MeO,4-Me,E], [–5554:3-F-4-MeO,4-Me,E], [–5555:3-F-5-MeO,4-Me,E], [–5556:4-F-2-MeO,4-Me,E], [–5557:4-F-3-MeO,4-Me,E], [–5558:2-Cl-3-MeO,4-Me,E], [–5559:2-Cl-4-MeO,4-Me,E], [–5560:2-Cl-5-MeO,4-Me,E], [–5561:2-Cl-6-MeO,4-Me,E], [–5562:3-Cl-2-MeO,4-Me,E], [–5563:3-Cl-4-MeO,4-Me,E], [–5564:3-Cl-5-MeO,4-Me,E], [–5565:4-Cl-2-MeO,4-Me,E], [–5566:4-Cl-3-MeO,4-Me,E], [–5567:2-Me-3-MeO,4-Me,E], [–5568:2-Me-4-MeO,4-Me,E], [–5569:2-Me-5-MeO,4-Me,E], [–5570:2-Me-6-MeO,4-Me,E], [–5571:3-Me-2-MeO,4-Me,E], [–5572:3-Me-4-MeO,4-Me,E], [–5573:3-Me-5-MeO,4-Me,E], [–5574:4-Me-2-MeO,4-Me,E], [–5575:4-Me-3-MeO,4-Me,E], [–5576:H,3-Me,E], [–5577:4-F,3-Me,E], [–5578:4-F,3-Me,Z], [–5579:4-Cl,3-Me,E], [–5580:4-Cl,3-Me,Z], [–5581:4-Br,3-Me,E], [–5582:4-I,3-Me,E], [–5583:4-Me,3-Me,E], [–5584:4-Me,3-Me,Z], [–5585:4-Et,3-Me,E], [–5586:4-$C_3H_7$,3-Me,E], [–5587:4-(Me)$_2$CH,3-Me,E], [–5588:4-$CF_3$,3-Me,E], [–5589:4-$CF_3$,3-Me,Z], [–5590:4-$C_2F_5$,3-Me,E], [–5591:4-$C_3F_7$,3-Me,E], [–5592:4-(CF$_3$)$_2$CF,3-Me,E], [–5593:4-(CF$_3$)$_2$CH,3-Me,E], [–5594:4-CHF$_2$,3-Me,E], [–5595:4-CH$_2$F,3-Me,E], [–5596:4-CF$_3$CH$_2$,3-Me,E], [–5597:4-MeO,3-Me,E], [–5598:4-MeO,3-Me,Z], [–5599:4-EtO,3-Me,E], [–5600:4-$C_3H_7$O,3-Me,E], [–5601:4-(Me)$_2$CHO,3-Me,E], [–5602:4-NO$_2$,3-Me,E], [–5603:4-NO$_2$,3-Me,Z], [–5604:3-F,3-Me,E], [–5605:3-F,3-Me,Z], [–5606:3-Cl,3-Me,E], [–5607:3-Cl,3-Me,Z], [–5608:3-Br,3-Me,E], [–5609:3-I,3-Me,E], [–5610:3-Me,3-Me,E], [–5611:3-Me,3-Me,Z], [–5612:3-Et,3-Me,E], [–5613:3-$C_3H_7$,3-Me,E], [–5614:3-(Me)$_2$CH,3-Me,E], [–5615:3-CF$_3$,3-Me,E], [–5616:3-CF$_3$,3-Me,Z], [–5617:3-$C_2F_5$,3-Me,E], [–5618:3-$C_3F_7$,3-Me,E], [–5619:3-(CF$_3$)$_2$CF,3-Me,E], [–5620:3-(CF$_3$)$_2$CH,3-Me,E], [–5621:3-CHF$_2$,3-Me,E], [–5622:3-CHF$_2$,3-Me,Z], [–5623:3-CH$_2$F,3-Me,E], [–5624:3-CH$_2$F,3-Me,Z], [–5625:3-CF$_3$CH$_2$,3-Me,E], [–5626:3-MeO,3-Me,E], [–5627:3-MeO,3-Me,Z], [–5628:3-EtO,3-Me,E], [–5629:3-$C_3H_7$O,3-Me,E], [–5630:3-(Me)$_2$CHO,3-Me,E], [–5631:3-NO$_2$,3-Me,E], [–5632:2-F,3-Me,E], [–5633:2-Cl,3-Me,E], [–5634:2-Br,3-Me,E], [–5635:2-I,3-Me,E], [–5636:2-Me,3-Me,E], [–5637:2-Et,3-Me,E], [–5638:2-$C_3H_7$,3-Me,E], [–5639:2-(Me)$_2$CH,3-Me,E], [–5640:2-CF$_3$,3-Me,E], [–5641:2-$C_2F_5$,3-Me,E], [–5642:2-$C_3F_7$,3-Me,E], [–5643:2-(CF$_3$)$_2$CF,3-Me,E], [–5644:2-(CF$_3$)$_2$CH,3-Me,E], [–5645:2-CHF$_2$,3-Me,E], [–5646:2-CH$_2$F,3-Me,E], [–5647:2-CF$_3$CH$_2$,3-Me,E], [–5648:2-MeO,3-Me,E], [–5649:2-EtO,3-Me,E], [–5650:2-$C_3H_7$O,3-Me,E], [–5651:2-(Me)$_2$CHO,3-Me,E], [–5652:2-NO$_2$,3-Me,E], [–5653:2,3-F$_2$,3-Me,E], [–5654:2,4-F$_2$,3-Me,E], [–5655:2,5-F$_2$,3-Me,E], [–5656:2,6-F$_2$,3-Me,E], [–5657:3,4-F$_2$,3-Me,E], [–5658:3,4-F$_2$,3-Me,Z], [–5659:3,5-F$_2$,3-Me,E], [–5660:3,5-F$_2$,3-Me,Z], [–5661:2,3-Cl$_2$,3-Me,E], [–5662:2,3-Cl$_2$,3-Me,Z], [–5663:2,4-Cl$_2$,3-Me,E], [–5664:2,4-Cl$_2$,3-Me,Z], [–5665:2,5-Cl$_2$,3-Me,E], [–5666:2,5-Cl$_2$,3-Me,Z], [–5667:2,6-Cl$_2$,3-Me,E], [–5668:3,4-Cl$_2$,3-Me,E], [–5669:3,5-Cl$_2$,3-Me,E], [–5670:2,3-Br$_2$,3-Me,E], [–5671:2,4-Br$_2$,3-Me,E], [–5672:2,5-Br$_2$,3-Me,E], [–5673:2,6-Br$_2$,3-Me,E], [–5674:3,4-Br$_2$,3-Me,E], [–5675:3,5-Br$_2$,3-Me,E], [–5676:2,3-Me$_2$,3-Me,E], [–5677:2,4-Me$_2$,3-Me,E], [–5678:2,5-Me$_2$,3-Me,E], [–5679:2,6-Me$_2$,3-Me,E], [–5680:3,4-Me$_2$,3-Me,E], [–5681:3,5-Me$_2$,3-Me,E], [–5682:2,3-Et$_2$,3-Me,E], [–5683:2,4-Et$_2$,3-Me,E], [–5684:2,5-Et$_2$,3-Me,E], [–5685:2,6-Et$_2$,3-Me,E], [–5686:3,4-Et$_2$,3-Me,E], [–5687:3,5-Et$_2$,3-Me,E], [–5688:2,3-(CF$_3$)$_2$,3-Me,E], [–5689:2,4-(CF$_3$)$_2$,3-Me,E], [–5690:2,5-(CF$_3$)$_2$,3-Me,E], [–5691:2,6-(CF$_3$)$_2$,3-Me,E], [–5692:3,4-(CF$_3$)$_2$,3-Me,E], [–5693:3,5-(CF$_3$)$_2$,3-Me,E], [–5694:2,3-(CHF$_2$)$_2$,3-Me,E], [–5695:2,4-(CHF$_2$)$_2$,3-Me,E], [–5696:2,5-(CHF$_2$)$_2$,3-Me,E], [–5697:2,6-(CHF$_2$)$_2$,3-Me,E], [–5698:3,4-(CHF$_2$)$_2$,3-Me,E], [–5699:3,5-(CHF$_2$)$_2$,3-Me,E], [–5700:2,3-(CH$_2$F)$_2$,3-Me,E], [–5701:2,4-(CH$_2$F)$_2$,3-Me,E], [–5702:2,5-(CH$_2$F)$_2$,3-Me,E], [–5703:2,6-(CH$_2$F)$_2$,3-Me,E], [–5704:3,4-(CH$_2$F)$_2$,3-Me,E], [–5705:3,5-(CH$_2$F)$_2$,3-Me,E], [–5706:2,3-(MeO)$_2$,3-Me,E], [–5707:2,4-(MeO)$_2$,3-Me,E], [–5708:2,5-(MeO)$_2$,3-Me,E], [–5709:2,6-(MeO)$_2$,3-Me,E], [–5710:3,4-(MeO)$_2$,3-Me,E], [–5711:3,5-(MeO)$_2$,3-Me,E], [–5712:2,3-(EtO)$_2$,3-Me,E], [–5713:2,4-(EtO)$_2$,3-Me,E], [–5714:2,5-(EtO)$_2$,3-Me,E], [–5715:2,6-(EtO)$_2$,3-Me,E], [–5716:3,4-(EtO)$_2$,3-Me,E], [–5717:3,5-(EtO)$_2$,3-Me,E], [–5718:2-Cl-3-F,3-Me,E], [–5719:2-Cl-4-F,3-Me,E], [–5720:2-Cl-5-F,3-Me,E], [–5721:2-Cl-6-F,3-Me,E], [–5722:3-Cl-2-F,3-Me,E], [–5723:3-Cl-4-F,3-Me,E], [–5724:3-Cl-5-F,3-Me,E], [–5725:4-Cl-2-F,3-Me,E], [–5726:4-Cl-3-F,3-Me,E], [–5727:2-F-3-Me,3-Me,E], [–5728:2-F-4-Me,3-Me,E], [–5729:2-F-5-Me,3-Me,E], [–5730:2-F-6-Me,3-Me,E], [–5731:3-F-2-Me,3-Me,E], [–5732:3-F-4-Me,3-Me,E], [–5733:3-F-5-Me,3-Me,E], [–5734:4-F-2-Me,3-Me,E], [–5735:4-F-3-Me,3-Me,E], [–5736:2-Cl-3-Me,3-Me,E], [–5737:2-Cl-4-Me,3-Me,E], [–5738:2-Cl-5-Me,3-Me,E], [–5739:2-Cl-6-Me,3-Me,E], [–5740:3-Cl-2-Me,3-Me,E], [–5741:3-Cl-4-Me,3-Me,E], [–5742:3-Cl-5-Me,3-Me,E], [–5743:4-Cl-2-Me,3-Me,E], [–5744:4-Cl-3-Me,3-Me,E], [–5745:2-F-3-CF$_3$,3-Me,E], [–5746:2-F-4-CF$_3$,3-Me,E], [–5747:2-F-5-CF$_3$,3-Me,E], [–5748:2-F-6-CF$_3$,3-Me,E], [–5749:3-F-2-CF$_3$,3-Me,E], [–5750:3-F-4-CF$_3$,3-Me,E], [–5751:3-F-5-CF$_3$,3-Me,E], [–5752:4-F-2-CF$_3$,3-Me,E], [–5753:4-F-3-CF$_3$,3-Me,E], [–5754:2-Cl-3-CF$_3$,3-Me,E], [–5755:2-Cl-4-CF$_3$,3-Me,E], [–5756:2-Cl-5-CF$_3$,3-Me,E], [–5757:2-Cl-6-CF$_3$,3-Me,E], [–5758:3-Cl-2-CF$_3$,3-Me,E], [–5759:3-Cl-4-CF$_3$,3-Me,E], [–5760:3-Cl-5-CF$_3$,3-Me,E], [–5761:4-Cl-2-CF$_3$,3-Me,E], [–5762:4-Cl-3-CF$_3$,3-Me,E], [–5763:2-Me-3-CF$_3$,3-Me,E],

[-5764:2-Me-4-CF$_3$,3-Me,E], [-5765:2-Me-5-CF$_3$,3-Me,E], [-5766:2-Me-6-CF$_3$,3-Me,E], [-5767:3-Me-2-CF$_3$,3-Me,E], [-5768:3-Me-4-CF$_3$,3-Me,E], [-5769:3-Me-5-CF$_3$,3-Me,E], [-5770:4-Me-2-CF$_3$,3-Me,E], [-5771:4-Me-3-CF$_3$,3-Me,E], [-5772:2-F-3-MeO,3-Me,E], [-5773:2-F-4-MeO,3-Me,E], [-5774:2-F-5-MeO,3-Me,E], [-5775:2-F-6-MeO,3-Me,E], [-5776:3-F-2-MeO,3-Me,E], [-5777:3-F-4-MeO,3-Me,E], [-5778:3-F-5-MeO,3-Me,E], [-5779:4-F-2-MeO,3-Me,E], [-5780:4-F-3-MeO,3-Me,E], [-5781:2-Cl-3-MeO,3-Me,E], [-5782:2-Cl-4-MeO,3-Me,E], [-5783:2-Cl-5-MeO,3-Me,E], [-5784:2-Cl-6-MeO,3-Me,E], [-5785:3-Cl-2-MeO,3-Me,E], [-5786:3-Cl-4-MeO,3-Me,E], [-5787:3-Cl-5-MeO,3-Me,E], [-5788:4-Cl-2-MeO,3-Me,E], [-5789:4-Cl-3-MeO,3-Me,E], [-5790:2-Me-3-MeO,3-Me,E], [-5791:2-Me-4-MeO,3-Me,E], [-5792:2-Me-5-MeO,3-Me,E], [-5793:2-Me-6-MeO,3-Me,E], [-5794:3-Me-2-MeO,3-Me,E], [-5795:3-Me-4-MeO,3-Me,E], [-5796:3-Me-5-MeO,3-Me,E], [-5797:4-Me-2-MeO,3-Me,E], [-5798:4-Me-3-MeO,3-Me,E],

[-5799:H,2-Me,E], [-5800:4-F,2-Me,E], [-5801:4-F,2-Me,Z], [-5802:4-Cl,2-Me,E], [-5803:4-Cl,2-Me,Z], [-5804:4-Br,2-Me,E], [-5805:4-I,2-Me,E], [-5806:4-Me,2-Me,E], [-5807:4-Me,2-Me,Z], [-5808:4-Et,2-Me,E], [-5809:4-C$_3$H$_7$,2-Me,E], [-5810:4-(Me)$_2$CH,2-Me,E], [-5811:4-CF$_3$,2-Me,E], [-5812:4-CF$_3$,2-Me,Z], [-5813:4-C$_2$F$_5$,2-Me,E], [-5814:4-C$_3$F$_7$,2-Me,E], [-5815:4-(CF$_3$)$_2$CF,2-Me,E], [-5816:4-(CF$_3$)$_2$CH,2-Me,E], [-5817:4-CHF$_2$,2-Me,E], [-5818:4-CH$_2$F,2-Me,E], [-5819:4-CF$_3$CH$_2$,2-Me,E], [-5820:4-MeO,2-Me,E], [-5821:4-MeO,2-Me,Z], [-5822:4-EtO,2-Me,E], [-5823:4-C$_3$H$_7$O,2-Me,E], [-5824:4-(Me)$_2$CHO,2-Me,E], [-5825:4-NO$_2$,2-Me,E], [-5826:4-NO$_2$,2-Me,Z], [-5827:3-F,2-Me,E], [-5828:3-F,2-Me,Z], [-5829:3-Cl,2-Me,E], [-5830:3-Cl,2-Me,Z], [-5831:3-Br,2-Me,E], [-5832:3-I,2-Me,E], [-5833:3-Me,2-Me,E], [-5834:3-Me,2-Me,Z], [-5835:3-Et,2-Me,E], [-5836:3-C$_3$H$_7$,2-Me,E], [-5837:3-(Me)$_2$CH,2-Me,E], [-5838:3-CF$_3$,2-Me,E], [-5839:3-CF$_3$,2-Me,Z], [-5840:3-C$_2$F$_5$,2-Me,E], [-5841:3-C$_3$F$_7$,2-Me,E], [-5842:3-(CF$_3$)$_2$CF,2-Me,E], [-5843:3-(CF$_3$)$_2$CH,2-Me,E], [-5844:3-CHF$_2$,2-Me,E], [-5845:3-CHF$_2$,2-Me,Z], [-5846:3-CH$_2$F,2-Me,E], [-5847:3-CH$_2$F,2-Me,Z], [-5848:3-CF$_3$CH$_2$,2-Me,E], [-5849:3-MeO,2-Me,E], [-5850:3-MeO,2-Me,Z], [-5851:3-EtO,2-Me,E], [-5852:3-C$_3$H$_7$O,2-Me,E], [-5853:3-(Me)$_2$CHO,2-Me,E], [-5854:3-NO$_2$,2-Me,E], [-5855:2-F,2-Me,E], [-5856:2-Cl,2-Me,E], [-5857:2-Br,2-Me,E], [-5858:2-I,2-Me,E], [-5859:2-Me,2-Me,E], [-5860:2-Et,2-Me,E], [-5861:2-C$_3$H$_7$,2-Me,E], [-5862:2-(Me)$_2$CH,2-Me,E], [-5863:2-CF$_3$,2-Me,E], [-5864:2-C$_2$F$_5$,2-Me,E], [-5865:2-C$_3$F$_7$,2-Me,E], [-5866:2-(CF$_3$)$_2$CF,2-Me,E], [-5867:2-(CF$_3$)$_2$CH,2-Me,E], [-5868:2-CHF$_2$,2-Me,E], [-5869:2-CH$_2$F,2-Me,E], [-5870:2-CF$_3$CH$_2$,2-Me,E], [-5871:2-MeO,2-Me,E], [-5872:2-EtO,2-Me,E], [-5873:2-C$_3$H$_7$O,2-Me,E], [-5874:2-(Me)$_2$CHO,2-Me,E], [-5875:2-NO$_2$,2-Me,E], [-5876:2,3-F$_2$,2-Me,E], [-5877:2,4-F$_2$,2-Me,E], [-5878:2,5-F$_2$,2-Me,E], [-5879:2,6-F$_2$,2-Me,E], [-5880:3,4-F$_2$,2-Me,E], [-5881:3,4-F$_2$,2-Me,Z], [-5882:3,5-F$_2$,2-Me,E], [-5883:3,5-F$_2$,2-Me,Z], [-5884:2,3-Cl$_2$,2-Me,E], [-5885:2,3-Cl$_2$,2-Me,Z], [-5886:2,4-Cl$_2$,2-Me,E], [-5887:2,4-Cl$_2$,2-Me,Z], [-5888:2,5-Cl$_2$,2-Me,E], [-5889:2,5-Cl$_2$,2-Me,Z], [-5890:2,6-Cl$_2$,2-Me,E], [-5891:3,4-Cl$_2$,2-Me,E], [-5892:3,5-Cl$_2$,2-Me,E], [-5893:2,3-Br$_2$,2-Me,E], [-5894:2,4-Br$_2$,2-Me,E], [-5895:2,5-Br$_2$,2-Me,E], [-5896:2,6-Br$_2$,2-Me,E], [-5897:3,4-Br$_2$,2-Me,E], [-5898:3,5-Br$_2$,2-Me,E], [-5899:2,3-Me$_2$,2-Me,E], [-5900:2,4-Me$_2$,2-Me,E], [-5901:2,5-Me$_2$,2-Me,E], [-5902:2,6-Me$_2$,2-Me,E], [-5903:3,4-Me$_2$,2-Me,E], [-5904:3,5-Me$_2$,2-Me,E], [-5905:2,3-Et$_2$,2-Me,E], [-5906:2,4-Et$_2$,2-Me,E], [-5907:2,5-Et$_2$,2-Me,E], [-5908:2,6-Et$_2$,2-Me,E], [-5909:3,4-Et$_2$,2-Me,E], [-5910:3,5-Et$_2$,2-Me,E], [-5911:2,3-(CF$_3$)$_2$,2-Me,E], [-5912:2,4-(CF$_3$)$_2$,2-Me,E], [-5913:2,5-(CF$_3$)$_2$,2-Me,E], [-5914:2,6-(CF$_3$)$_2$,2-Me,E], [-5915:3,4-(CF$_3$)$_2$,2-Me,E], [-5916:3,5-(CF$_3$)$_2$,2-Me,E], [-5917:2,3-(CHF$_2$)$_2$,2-Me,E], [-5918:2,4-(CHF$_2$)$_2$,2-Me,E], [-5919:2,5-(CHF$_2$)$_2$,2-Me,E], [-5920:2,6-(CHF$_2$)$_2$,2-Me,E], [-5921:3,4-(CHF$_2$)$_2$,2-Me,E], [-5922:3,5-(CHF$_2$)$_2$,2-Me,E], [-5923:2,3-(CH$_2$F)$_2$,2-Me,E], [-5924:2,4-(CH$_2$F)$_2$,2-Me,E], [-5925:2,5-(CH$_2$F)$_2$,2-Me,E], [-5926:2,6-(CH$_2$F)$_2$,2-Me,E], [-5927:3,4-(CH$_2$F)$_2$,2-Me,E], [-5928:3,5-(CH$_2$F)$_2$,2-Me,E], [-5929:2,3-(MeO)$_2$,2-Me,E], [-5930:2,4-(MeO)$_2$,2-Me,E], [-5931:2,5-(MeO)$_2$,2-Me,E], [-5932:2,6-(MeO)$_2$,2-Me,E], [-5933:3,4-(MeO)$_2$,2-Me,E], [-5934:3,5-(MeO)$_2$,2-Me,E], [-5935:2,3-(EtO)$_2$,2-Me,E], [-5936:2,4-(EtO)$_2$,2-Me,E], [-5937:2,5-(EtO)$_2$,2-Me,E], [-5938:2,6-(EtO)$_2$,2-Me,E], [-5939:3,4-(EtO)$_2$,2-Me,E], [-5940:3,5-(EtO)$_2$,2-Me,E], [-5941:2-Cl-3-F,2-Me,E], [-5942:2-Cl-4-F,2-Me,E], [-5943:2-Cl-5-F,2-Me,E], [-5944:2-Cl-6-F,2-Me,E], [-5945:3-Cl-2-F,2-Me,E], [-5946:3-Cl-4-F,2-Me,E], [-5947:3-Cl-5-F,2-Me,E], [-5948:4-Cl-2-F,2-Me,E], [-5949:4-Cl-3-F,2-Me,E], [-5950:2-F-3-Me,2-Me,E], [-5951:2-F-4-Me,2-Me,E], [-5952:2-F-5-Me,2-Me,E], [-5953:2-F-6-Me,2-Me,E], [-5954:3-F-2-Me,2-Me,E], [-5955:3-F-4-Me,2-Me,E], [-5956:3-F-5-Me,2-Me,E], [-5957:4-F-2-Me,2-Me,E], [-5958:4-F-3-Me,2-Me,E], [-5959:2-Cl-3-Me,2-Me,E], [-5960:2-Cl-4-Me,2-Me,E], [-5961:2-Cl-5-Me,2-Me,E], [-5962:2-Cl-6-Me,2-Me,E], [-5963:3-Cl-2-Me,2-Me,E], [-5964:3-Cl-4-Me,2-Me,E], [-5965:3-Cl-5-Me,2-Me,E], [-5966:4-Cl-2-Me,2-Me,E], [-5967:4-Cl-3-Me,2-Me,E], [-5968:2-F-3-CF$_3$,2-Me,E], [-5969:2-F-4-CF$_3$,2-Me,E], [-5970:2-F-5-CF$_3$,2-Me,E], [-5971:2-F-6-CF$_3$,2-Me,E], [-5972:3-F-2-CF$_3$,2-Me,E], [-5973:3-F-4-CF$_3$,2-Me,E], [-5974:3-F-5-CF$_3$,2-Me,E], [-5975:4-F-2-CF$_3$,2-Me,E], [-5976:4-F-3-CF$_3$,2-Me,E], [-5977:2-Cl-3-CF$_3$,2-Me,E], [-5978:2-Cl-4-CF$_3$,2-Me,E], [-5979:2-Cl-5-CF$_3$,2-Me,E], [-5980:2-Cl-6-CF$_3$,2-Me,E], [-5981:3-Cl-2-CF$_3$,2-Me,E], [-5982:3-Cl-4-CF$_3$,2-Me,E], [-5983:3-Cl-5-CF$_3$,2-Me,E], [-5984:4-Cl-2-CF$_3$,2-Me,E], [-5985:4-Cl-3-CF$_3$,2-Me,E], [-5986:2-Me-3-CF$_3$,2-Me,E], [-5987:2-Me-4-CF$_3$,2-Me,E], [-5988:2-Me-5-CF$_3$,2-Me,E], [-5989:2-Me-6-CF$_3$,2-Me,E], [-5990:3-Me-2-CF$_3$,2-Me,E], [-5991:3-Me-4-CF$_3$,2-Me,E], [-5992:3-Me-5-CF$_3$,2-Me,E], [-5993:4-Me-2-CF$_3$,2-Me,E], [-5994:4-Me-3-CF$_3$,2-Me,E], [-5995:2-F-3-MeO,2-Me,E], [-5996:2-F-4-MeO,2-Me,E], [-5997:2-F-5-MeO,2-Me,E], [-5998:2-F-6-MeO,2-Me,E], [-5999:3-F-2-MeO,2-Me,E], [-6000:3-F-4-MeO,2-Me,E], [-6001:3-F—5-MeO,2-Me,E], [-6002:4-F-2-MeO,2-Me,E], [-6003:4-F-3-MeO,2-Me,E], [-6004:2-Cl-3-MeO,2-Me,E], [-6005:2-Cl-4-MeO,2-Me,E], [-6006:2-Cl-5-MeO,2-Me,E], [-6007:2-Cl-6-MeO,2-Me,E], [-6008:3-Cl-2-MeO,2-Me,E], [-6009:3-Cl-4-MeO,2-Me,E], [-6010:3-Cl-5-MeO,2-Me,E], [-6011:4-Cl-2-MeO,2-Me,E], [-6012:4-Cl-3-MeO,2-Me,E], [-6013:2-Me-3-MeO,2-Me,E], [-6014:2-Me-4-MeO,2-Me,E], [-6015:2-Me-5-MeO,2-Me,E], [-6016:2-Me-6-MeO,2-Me,E], [-6017:3-Me-2-MeO,2-Me,E], [-6018:3-Me-4-MeO,2-Me,E], [-6019:3-Me-5-MeO,2-Me,E], [-6020:4-Me-2-MeO,2-Me,E], [-6021:4-Me-3-MeO,2-Me,E],

[-6022:H,3,4-Me$_2$,E], [-6023:4-F,3,4-Me$_2$,E], [-6024:4-F,3,4-Me$_2$,Z], [-6025:4-Cl,3,4-Me$_2$,E], [-6026:4-Cl,3,4-Me$_2$,Z], [-6027:4-Br,3,4-Me$_2$,E], [-6028:4-I,3,4-Me$_2$,E],

[-6029:4-Me, 3,4-Me$_2$,E], [-6030:4-Me,3,4-Me$_2$,Z], [-6031:4-Et,3,4-Me$_2$,E], [-6032:4-C$_3$H$_7$,3,4-Me$_2$,E], [-6033:4-(Me)$_2$CH,3,4-Me$_2$,E], [-6034:4-CF$_3$,3,4-Me$_2$,E], [-6035:4-CF$_3$,3,4-Me$_2$,Z], [-6036:4-C$_2$F$_5$,3,4-Me$_2$,E], [-6037:4-C$_3$F$_7$,3,4-Me$_2$,E], [-6038:4-(CF$_3$)$_2$CF,3,4-Me$_2$,E], [-6039:4-(CF$_3$)$_2$CH, 3,4-Me$_2$,E], [-6040:4-CHF$_2$,3,4-Me$_2$,E], [-6041:4-CH$_2$F,3,4-Me$_2$,E], [-6042:4-CF$_3$CH$_2$,3,4-Me$_2$,E], [-6043:4-MeO,3,4-Me$_2$,E], [-6044:4-MeO, 3,4-Me$_2$,Z], [-6045:4-EtO, 3,4-Me$_2$,E], [-6046:4-C$_3$H$_7$O,3,4-Me$_2$,E], [-6047:4-(Me)$_2$CHO, 3,4-Me$_2$,E], [-6048:4-NO$_2$, 3,4-Me$_2$,E], [-6049:4-NO$_2$,3,4-Me$_2$,Z], [-6050:3-F,3,4-Me$_2$,E], [-6051:3-F,3,4-Me$_2$,Z], [-6052:3-Cl,3,4-Me$_2$,E], [-6053:3-Cl,3,4-Me$_2$,Z], [-6054:3-Br,3,4-Me$_2$,E], [-6055:3-I,3,4-Me$_2$,E], [-6056:3-Me,3,4-Me$_2$,E], [-6057:3-Me,3,4-Me$_2$,Z], [-6058:3-Et,3,4-Me$_2$,E], [-6059:3-C$_3$H$_7$,3,4-Me$_2$,E], [-6060:3-(Me)$_2$CH,3,4-Me$_2$,E], [-6061:3-CF$_3$,3,4-Me$_2$,E], [-6062:3-CF$_3$,3,4-Me$_2$,Z], [-6063:3-C$_2$F$_5$, 3,4-Me$_2$,E], [-6064:3-C$_3$F$_7$,3,4-Me$_2$,E], [-6065:3-(CF$_3$)$_2$CF,3,4-Me$_2$,E], [-6066:3-(CF$_3$)$_2$CH,3,4-Me$_2$,E], [-6067:3-CHF$_2$,3,4-Me$_2$,E], [-6068:3-CHF$_2$,3,4-Me$_2$,Z], [-6069:3-CH$_2$F,3,4-Me$_2$,E], [-6070:3-CH$_2$F,3,4-Me$_2$,Z], [-6071:3-CF$_3$CH$_2$,3,4-Me$_2$,E], [-6072:3-MeO, 3,4-Me$_2$,E], [-6073:3-MeO,3,4-Me$_2$,Z], [-6074:3-EtO,3,4-Me$_2$,E], [-6075:3-C$_3$H$_7$O,3,4-Me$_2$,E], [-6076:3-(Me)$_2$CHO,3,4-Me$_2$,E], [-6077:3-NO$_2$,3,4-Me$_2$,E], [-6078:2-F,3,4-Me$_2$,E], [-6079:2-Cl,3,4-Me$_2$,E], [-6080:2-Br, 3,4-Me$_2$,E], [-6081:2-I,3,4-Me$_2$,E], [-6082:2-Me,3,4-Me$_2$,E], [-6083:2-Et,3,4-Me$_2$,E], [-6084:2-C$_3$H$_7$,3,4-Me$_2$,E], [-6085:2-(Me)$_2$CH,3,4-Me$_2$,E], [-6086:2-CF$_3$,3,4-Me$_2$,E], [-6087:2-C$_2$F$_5$,3,4-Me$_2$,E], [-6088:2-C$_3$F$_7$,3,4-Me$_2$,E], [-6089:2-(CF$_3$)$_2$CF,3,4-Me$_2$,E], [-6090:2-(CF$_3$)$_2$CH,3,4-Me$_2$,E], [-6091:2-CHF$_2$, 3,4-Me$_2$,E], [-6092:2-CH$_2$F, 3,4-Me$_2$,E], [-6093:2-CF$_3$CH$_2$, 3,4-Me$_2$,E], [-6094:2-MeO,3,4-Me$_2$,E], [-6095:2-EtO,3,4-Me$_2$,E], [-6096:2-C$_3$H$_7$O,3,4-Me$_2$,E], [-6097:2-(Me)$_2$CHO,3,4-Me$_2$,E], [-6098:2-NO$_2$,3,4-Me$_2$,E], [-6099:2,3-F$_2$,3,4-Me$_2$,E], [-6100:2,4-F$_2$,3,4-Me$_2$,E], [-6101:2,5-F$_2$,3,4-Me$_2$,E], [-6102:2,6-F$_2$,3,4-Me$_2$,E], [-6103:3,4-F$_2$,3,4-Me$_2$,E], [-6104:3,4-F$_2$,3,4-Me$_2$,Z], [-6105:3,5-F$_2$,3,4-Me$_2$,E], [-6106:3,5-F$_2$,3,4-Me$_2$,Z], [-6107:2,3-Cl$_2$,3,4-Me$_2$,E], [-6108:2,3-Cl$_2$,3,4-Me$_2$,Z], [-6109:2,4-Cl$_2$,3,4-Me$_2$,E], [-6110:2,4-Cl$_2$,3,4-Me$_2$,Z], [-6111:2,5-Cl$_2$,3,4-Me$_2$,E], [-6112:2,5-Cl$_2$,3,4-Me$_2$,Z], [-6113:2,6-Cl$_2$,3,4-Me$_2$,E], [-6114:3,4-Cl$_2$,34-Me$_2$,E], [-6115:3,5-Cl$_2$,3,4-Me$_2$,E], [-6116:2,3-Br$_2$,3,4-Me$_2$,E], [-6117:2,4-Br$_2$,3,4-Me$_2$,E], [-6118:2,5-Br$_2$,3,4-Me$_2$,E], [-6119:2,6-Br$_2$,3,4-Me$_2$,E], [-6120:3,4-Br$_2$,3,4-Me$_2$,E], [-6121:3,5-Br$_2$,3,4-Me$_2$,E], [-6122:2,3-Me$_2$,3,4-Me$_2$,E], [-6123:2,4-Me$_2$,3,4-Me$_2$,E], [-6124:2,5-Me$_2$,3,4-Me$_2$,E], [-6125:2,6-Me$_2$,3,4-Me$_2$,E], [-6126:3,4-Me$_2$,3,4-Me$_2$,E], [-6127:3,5-Me$_2$,3,4-Me$_2$,E], [-6128:2,3-Et$_2$,3,4-Me$_2$,E], [-6129:2,4-Et$_2$,3,4-Me$_2$,E], [-6130:2,5-Et$_2$,3,4-Me$_2$,E], [-6131:2,6-Et$_2$,3,4-Me$_2$,E], [-6132:3,4-Et$_2$,3,4-Me$_2$,E], [-6133:3,5-Et$_2$,3,4-Me$_2$,E], [-6134:2,3-(CF$_3$)$_2$,3,4-Me$_2$,E], [-6135:2,4-(CF$_3$)$_2$,3,4-Me$_2$,E], [-6136:2,5-(CF$_3$)$_2$,3,4-Me$_2$,E], [-6137:2,6-(CF$_3$)$_2$,3,4-Me$_2$,E], [-6138:3,4-(CF$_3$)$_2$,3,4-Me$_2$,E], [-6139:3,5-(CF$_3$)$_2$,3,4-Me$_2$,E], [-6140:2,3-(CHF$_2$)$_2$,3,4-Me$_2$,E], [-6141:2,4-(CHF$_2$)$_2$,3,4-Me$_2$,E], [-6142:2,5-(CHF$_2$)$_2$,3,4-Me$_2$,E], [-6143:2,6-(CHF$_2$)$_2$,3,4-Me$_2$,E], [-6144:3,4-(CHF$_2$)$_2$,3,4-Me$_2$,E], [-6145:3,5-(CHF$_2$)$_2$,3,4-Me$_2$,E], [-6146:2,3-(CH$_2$F)$_2$,3,4-Me$_2$,E], [-6147:2,4-(CH$_2$F)$_2$,3,4-Me$_2$,E], [-6148:2,5-(CH$_2$F)$_2$,3,4-Me$_2$,E], [-6149:2,6-(CH$_2$F)$_2$,3,4-Me$_2$,E], [-6150:3,4-(CH$_2$F)$_2$,3,4-Me$_2$,E], [-6151:3,5-(CH$_2$F)$_2$,3,4-Me$_2$,E], [-6152:2,3-(MeO)$_2$,3,4-Me$_2$,E], [-6153:2,4-(MeO)$_2$,3,4-Me$_2$,E], [-6154:2,5-(MeO)$_2$,3,4-Me$_2$,E], [-6155:2,6-(MeO)$_2$,3,4-Me$_2$,E], [-6156:3,4-(MeO)$_2$,3,4-Me$_2$,E], [-6157:3,5-(MeO)$_2$,3,4-Me$_2$,E], [-6158:2,3-(EtO)$_2$,3,4-Me$_2$,E], [-6159:2,4-(EtO)$_2$,3,4-Me$_2$,E], [-6160:2,5-(EtO)$_2$,3,4-Me$_2$,E], [-6161:2,6-(EtO)$_2$,3,4-Me$_2$,E], [-6162:3,4-(EtO)$_2$,3,4-Me$_2$,E], [-6163:3,5-(EtO)$_2$,3,4-Me$_2$,E], [-6164:2-Cl-3-F,3,4-Me$_2$,E], [-6165:2-Cl-4-F,3,4-Me$_2$,E], [-6166:2-Cl-5-F,3,4-Me$_2$,E], [-6167:2-Cl-6-F,3,4-Me$_2$,E], [-6168:3-Cl-2-F,3,4-Me$_2$,E], [-6169:3-Cl-4-F,3,4-Me$_2$,E], [-6170:3-Cl-5-F,3,4-Me$_2$,E], [-6171:4-Cl-2-F,3,4-Me$_2$,E], [-6172:4-Cl-3-F,3,4-Me$_2$,E], [-6173:2-F-3-Me,3,4-Me$_2$,E], [-6174:2-F-4-Me,3,4-Me$_2$,E], [-6175:2-F-5-Me,3,4-Me$_2$,E], [-6176:2-F-6-Me, 3,4-Me$_2$,E], [-6177:3-F-2-Me, 3,4-Me$_2$,E], [-6178:3-F-4-Me,3,4-Me$_2$,E], [-6179:3-F-5-Me,3,4-Me$_2$,E], [-6180:4-F-2-Me,3,4-Me$_2$,E], [-6181:4-F-3-Me,3,4-Me$_2$,E], [-6182:2-Cl-3-Me,3,4-Me$_2$,E], [-6183:2-Cl-4-Me,3,4-Me$_2$,E], [-6184:2-Cl-5-Me,3,4-Me$_2$,E], [-6185:2-Cl-6-Me,3,4-Me$_2$,E], [-6186:3-Cl-2-Me,3,4-Me$_2$,E], [-6187:3-Cl-4-Me,3,4-Me$_2$,E], [-6188:3-Cl-5-Me,3,4-Me$_2$,E], [-6189:4-Cl-2-Me,3,4-Me$_2$,E], [-6190:4-Cl-3-Me,3,4-Me$_2$,E], [-6191:2-F-3-CF$_3$,3,4-Me$_2$,E], [-6192:2-F-4-CF$_3$,3,4-Me$_2$,E], [-6193:2-F-5-CF$_3$,3,4-Me$_2$,E], [-6194:2-F-6-CF$_3$,3,4-Me$_2$,E], [-6195:3-F-2-CF$_3$,3,4-Me$_2$,E], [-6196:3-F-4-CF$_3$,3,4-Me$_2$,E], [-6197:3-F-5-CF$_3$,3,4-Me$_2$,E], [-6198:4-F-2-CF$_3$,3,4-Me$_2$,E], [-6199:4-F-3-CF$_3$,3,4-Me$_2$,E], [-6200:2-Cl-3-CF$_3$,3,4-Me$_2$,E], [-6201:2-Cl-4-CF$_3$,3,4-Me$_2$,E], [-6202:2-Cl-5-CF$_3$,3,4-Me$_2$,E], [-6203:2-Cl-6-CF$_3$,3,4-Me$_2$,E], [-6204:3-Cl-2-CF$_3$,3,4-Me$_2$,E], [-6205:3-Cl-4-CF$_3$,3,4-Me$_2$,E], [-6206:3-Cl-5-CF$_3$,3,4-Me$_2$,E], [-6207:4-Cl-2-CF$_3$,3,4-Me$_2$,E], [-6208:4-Cl-3-CF$_3$,3,4-Me$_2$,E], [-6209:2-Me-3-CF$_3$,3,4-Me$_2$,E], [-6210:2-Me-4-CF$_3$,3,4-Me$_2$,E], [-6211:2-Me-5-CF$_3$,3,4-Me$_2$,E], [-6212:2-Me-6-CF$_3$,3,4-Me$_2$,E], [-6213:3-Me-2-CF$_3$, 3,4-Me$_2$,E], [-6214:3-Me-4-CF$_3$,3,4-Me$_2$,E], [-6215:3-Me-5-CF$_3$,3,4-Me$_2$,E], [-6216:4-Me-2-CF$_3$,3,4-Me$_2$,E], [-6217:4-Me-3-CF$_3$,3,4-Me$_2$,E], [-6218:2-F-3-MeO,3,4-Me$_2$,E], [-6219:2-F-4-MeO,3,4-Me$_2$,E], [-6220:2-F-5-MeO,3,4-Me$_2$,E], [-6221:2-F-6-MeO,3,4-Me$_2$,E], [-6222:3-F-2-MeO,3,4-Me$_2$,E], [-6223:3-F-4-MeO,3,4-Me$_2$,E], [-6224:3-F-5-MeO,3,4-Me$_2$,E], [-6225:4-F-2-MeO,3,4-Me$_2$,E], [-6226:4-F-3-MeO,3,4-Me$_2$,E], [-6227:2-Cl-3-MeO,3,4-Me$_2$,E], [-6228:2-Cl-4-MeO,3,4-Me$_2$,E], [-6229:2-Cl-5-MeO,3,4-Me$_2$,E], [-6230:2-Cl-6-MeO,3,4-Me$_2$,E], [-6231:3-Cl-2-MeO,3,4-Me$_2$,E], [-6232:3-Cl-4-MeO,3,4-Me$_2$,E], [-6233:3-Cl-5-MeO,3,4-Me$_2$,E], [-6234:4-Cl-2-MeO,3,4-Me$_2$,E], [-6235:4-Cl-3-MeO,3,4-Me$_2$,E], [-6236:2-Me-3-MeO,3,4-Me$_2$,E], [-6237:2-Me-4-MeO,3,4-Me$_2$,E], [-6238:2-Me-5-MeO,3,4-Me$_2$,E], [-6239:2-Me-6-MeO,3,4-Me$_2$,E], [-6240:3-Me-2-MeO,3,4-Me$_2$,E], [-6241:3-Me-4-MeO,3,4-Me$_2$,E], [-6242:3-Me-5-MeO,3,4-Me$_2$,E], [-6243:4-Me-2-MeO,3,4-Me$_2$,E], [-6244:4-Me-3-MeO,3,4-Me$_2$,E],

[-6245:H,3-F-4-Me,E], [-6246:4-F,3-F-4-Me,E], [-6247:4-F,3-F-4-Me,Z], [-6248:4-Cl,3-F-4-Me,E], [-6249:4-Cl,3-F-4-Me,Z], [-6250:4-Br,3-F-4-Me,E], [-6251:4-I,3-F-4-Me,E], [-6252:4-Me,3-F-4-Me,E], [-6253:4-Me,3-F-4-Me,Z], [-6254:4-Et,3-F-4-Me,E], [-6255:4-C$_3$H$_7$,3-F-4-Me,E], [-6256:4-(Me)$_2$CH,3-F-4-Me,E], [-6257:4-CF$_3$,3-F-4-Me,E], [-6258:4-CF$_3$,3-F-4-Me,Z], [-6259:4-C$_2$F$_5$,3-F-4-Me,E], [-6260:4-C$_3$F$_7$,3-F-4-Me,E], [-6261:4-(CF$_3$)$_2$CF,3-F-4-Me,E], [-6262:4-(CF$_3$)$_2$CH,3-F-4-Me,E], [-6263:4-CHF$_2$,3-F-4-Me,E], [-6264:4-CH$_2$F,3-F-4-Me,E], [-6265:4-CF$_3$CH$_2$,3-F-4-Me,E], [-6266:4-MeO,3-F-4-Me,E], [-6267:4-MeO,3-F-4-Me,Z], [-6268:4-EtO,3-F-4-Me,E], [-6269:4-C$_3$H$_7$O,3-F-4-Me,E], [-6270:4-(Me)$_2$CHO,3-F-4-Me,E], [-6271:4-NO$_2$,3-F-4-Me,E], [-6272:4-NO$_2$,3-F-4-Me,Z], [-6273:3-F, 3-F-4-

Me,E], [-6274:3-F, 3-F-4-Me, Z], [-6275:3-Cl,3-F-4-Me,E], [-6276:3-Cl,3-F-4-Me,Z], [-6277:3-Br,3-F-4-Me,E], [-6278:3-I,3-F-4-Me,E], [-6279:3-Me,3-F-4-Me,E], [-6280:3-Me,3-F-4-Me,Z], [-6281:3-Et,3-F-4-Me,E], [-6282:3-$C_3H_7$,3-F-4-Me,E], [-6283:3-$(Me)_2CH$,3-F-4-Me,E], [-6284:3-$CF_3$,3-F-4-Me,E], [-6285:3-$CF_3$,3-F-4-Me,Z], [-6286:3-$C_2F_5$,3-F-4-Me,E], [-6287:3-$C_3F_7$,3-F-4-Me,E], [-6288:3-$(CF_3)_2CF$,3-F-4-Me,E], [-6289:3-$(CF_3)_2CH$,3-F-4-Me,E], [-6290:3-$CHF_2$,3-F-4-Me,E], [-6291:3-$CHF_2$,3-F-4-Me,Z], [-6292:3-$CH_2F$,3-F-4-Me,E], [-6293:3-$CH_2F$,3-F-4-Me,Z], [-6294:3-$CF_3CH_2$,3-F-4-Me,E], [-6295:3-MeO,3-F-4-Me,E], [-6296:3-MeO,3-F-4-Me,Z], [-6297:3-EtO,3-F-4-Me,E], [-6298:3-$C_3H_7O$,3-F-4-Me,E], [-6299:3-$(Me)_2CHO$,3-F-4-Me,E], [-6300:3-$NO_2$,3-F-4-Me,E], [-6301:2-F,3-F-4-Me,E], [-6302:2-Cl,3-F-4-Me,E], [-6303:2-Br,3-F-4-Me,E], [-6304:2-I,3-F-4-Me,E], [-6305:2-Me,3-F-4-Me,E], [-6306:2-Et,3-F-4-Me,E], [-6307:2-$C_3H_7$,3-F-4-Me,E], [-6308:2-$(Me)_2CH$,3-F-4-Me,E], [-6309:2-$CF_3$,3-F-4-Me,E], [-6310:2-$C_2F_5$,3-F-4-Me,E], [-6311:2-$C_3F_7$,3-F-4-Me,E], [-6312:2-$(CF_3)_2CF$,3-F-4-Me,E], [-6313:2-$(CF_3)_2CH$,3-F-4-Me,E], [-6314:2-$CHF_2$,3-F-4-Me,E], [-6315:2-$CH_2F$,3-F-4-Me,E], [-6316:2-$CF_3CH_2$,3-F-4-Me,E], [-6317:2-MeO,3-F-4-Me,E], [-6318:2-EtO,3-F-4-Me,E], [-6319:2-$C_3H_7O$,3-F-4-Me,E], [-6320:2-$(Me)_2CHO$,3-F-4-Me,E], [-6321:2-$NO_2$,3-F-4-Me,E], [-6322:2,3-$F_2$,3-F-4-Me,E], [-6323:2,4-$F_2$,3-F-4-Me,E], [-6324:2,5-$F_2$,3-F-4-Me,E], [-6325:2,6-$F_2$,3-F-4-Me,E], [-6326:3,4-$F_2$,3-F-4-Me,E], [-6327:3,4-$F_2$,3-F-4-Me,Z], [-6328:3,5-$F_2$,3-F-4-Me,E], [-6329:3,5-$F_2$,3-F-4-Me,Z], [-6330:2,3-$Cl_2$,3-F-4-Me,E], [-6331:2,3-$Cl_2$,3-F-4-Me,Z], [-6332:2,4-$Cl_2$,3-F-4-Me,E], [-6333:2,4-$Cl_2$,3-F-4-Me,Z], [-6334:2,5-$Cl_2$,3-F-4-Me,E], [-6335:2,5-$Cl_2$,3-F-4-Me,Z], [-6336:2,6-$Cl_2$,3-F-4-Me,E], [-6337:3,4-$Cl_2$,3-F-4-Me,E], [-6338:3,5-$Cl_2$,3-F-4-Me,E], [-6339:2,3-$Br_2$,3-F-4-Me,E], [-6340:2,4-$Br_2$,3-F-4-Me,E], [-6341:2,5-$Br_2$,3-F-4-Me,E], [-6342:2,6-$Br_2$,3-F-4-Me,E], [-6343:3,4-$Br_2$,3-F-4-Me,E], [-6344:3,5-$Br_2$,3-F-4-Me,E], [-6345:2,3-$Me_2$,3-F-4-Me,E], [-6346:2,4-$Me_2$,3-F-4-Me,E], [-6347:2,5-$Me_2$,3-F-4-Me,E], [-6348:2,6-$Me_2$,3-F-4-Me,E], [-6349:3,4-$Me_2$,3-F-4-Me,E], [-6350:3,5-$Me_2$,3-F-4-Me,E], [-6351:2,3-$Et_2$,3-F-4-Me,E], [-6352:2,4-$Et_2$,3-F-4-Me,E], [-6353:2,5-$Et_2$,3-F-4-Me,E], [-6354:2,6-$Et_2$,3-F-4-Me,E], [-6355:3,4-$Et_2$,3-F-4-Me,E], [-6356:3,5-$Et_2$,3-F-4-Me,E], [-6357:2,3-$(CF_3)_2$,3-F-4-Me,E], [-6358:2,4-$(CF_3)_2$,3-F-4-Me,E], [-6359:2,5-$(CF_3)_2$,3-F-4-Me,E], [-6360:2,6-$(CF_3)_2$,3-F-4-Me,E], [-6361:3,4-$(CF_3)_2$,3-F-4-Me,E], [-6362:3,5-$(CF_3)_2$,3-F-4-Me,E], [-6363:2,3-$(CHF_2)_2$,3-F-4-Me,E], [-6364:2,4-$(CHF_2)_2$,3-F-4-Me,E], [-6365:2,5-$(CHF_2)_2$,3-F-4-Me,E], [-6366:2,6-$(CHF_2)_2$,3-F-4-Me,E], [-6367:3,4-$(CHF_2)_2$,3-F-4-Me,E], [-6368:3,5-$(CHF_2)_2$,3-F-4-Me,E], [-6369:2,3-$(CH_2F)_2$,3-F-4-Me,E], [-6370:2,4-$(CH_2F)_2$,3-F-4-Me,E], [-6371:2,5-$(CH_2F)_2$,3-F-4-Me,E], [-6372:2,6-$(CH_2F)_2$,3-F-4-Me,E], [-6373:3,4-$(CH_2F)_2$,3-F-4-Me,E], [-6374:3,5-$(CH_2F)_2$,3-F-4-Me,E], [-6375:2,3-$(MeO)_2$,3-F-4-Me,E], [-6376:2,4-$(MeO)_2$,3-F-4-Me,E], [-6377:2,5-$(MeO)_2$,3-F-4-Me,E], [-6378:2,6-$(MeO)_2$,3-F-4-Me,E], [-6379:3,4-$(MeO)_2$,3-F-4-Me,E], [-6380:3,5-$(MeO)_2$,3-F-4-Me,E], [-6381:2,3-$(EtO)_2$,3-F-4-Me,E], [-6382:2,4-$(EtO)_2$,3-F-4-Me,E], [-6383:2,5-$(EtO)_2$,3-F-4-Me,E], [-6384:2,6-$(EtO)_2$,3-F-4-Me,E], [-6385:3,4-$(EtO)_2$,3-F-4-Me,E], [-6386:3,5-$(EtO)_2$,3-F-4-Me,E], [-6387:2-Cl-3-F,3-F-4-Me,E], [-6388:2-Cl-4-F,3-F-4-Me,E], [-6389:2-Cl-5-F,3-F-4-Me,E], [-6390:2-Cl-6-F,3-F-4-Me,E], [-6391:3-Cl-2-F,3-F-4-Me,E], [-6392:3-Cl-4-F,3-F-4-Me,E], [-6393:3-Cl-5-F,3-F-4-Me,E], [-6394:4-Cl-2-F,3-F-4-Me,E], [-6395:4-Cl-3-F,3-F-4-Me,E], [-6396:2-F-3-Me,3-F-4-Me,E], [-6397:2-F-4-Me,3-F-4-Me,E], [-6398:2-F-5-Me,3-F-4-Me,E], [-6399:2-F-6-Me,3-F-4-Me,E], [-6400:3-F-2-Me,3-F-4-Me,E], [-6401:3-F-4-Me,3-F-4-Me,E], [-6402:3-F-5-Me,3-F-4-Me,E], [-6403:4-F-2-Me,3-F-4-Me,E], [-6404:4-F-3-Me,3-F-4-Me,E], [-6405:2-Cl-3-Me,3-F-4-Me,E], [-6406:2-Cl-4-Me,3-F-4-Me,E], [-6407:2-Cl-5-Me,3-F-4-Me,E], [-6408:2-Cl-6-Me,3-F-4-Me,E], [-6409:3-Cl-2-Me,3-F-4-Me,E], [-6410:3-Cl-4-Me,3-F-4-Me,E], [-6411:3-Cl-5-Me,3-F-4-Me,E], [-6412:4-Cl-2-Me,3-F-4-Me,E], [-6413:4-Cl-3-Me,3-F-4-Me,E], [-6414:2-F-3-$CF_3$,3-F-4-Me,E], [-6415:2-F-4-$CF_3$,3-F-4-Me,E], [-6416:2-F-5-$CF_3$,3-F-4-Me,E], [-6417:2-F-6-$CF_3$,3-F-4-Me,E], [-6418:3-F-2-$CF_3$,3-F-4-Me,E], [-6419:3-F-4-$CF_3$,3-F-4-Me,E], [-6420:3-F-5-$CF_3$,3-F-4-Me,E], [-6421:4-F-2-$CF_3$,3-F-4-Me,E], [-6422:4-F-3-$CF_3$,3-F-4-Me,E], [-6423:2-Cl-3-$CF_3$,3-F-4-Me,E], [-6424:2-Cl-4-$CF_3$,3-F-4-Me,E], [-6425:2-Cl-5-$CF_3$,3-F-4-Me,E], [-6426:2-Cl-6-$CF_3$,3-F-4-Me,E], [-6427:3-Cl-2-$CF_3$,3-F-4-Me,E], [-6428:3-Cl-4-$CF_3$,3-F-4-Me,E], [-6429:3-Cl-5-$CF_3$,3-F-4-Me,E], [-6430:4-Cl-2-$CF_3$,3-F-4-Me,E], [-6431:4-Cl-3-$CF_3$,3-F-4-Me,E], [-6432:2-Me-3-$CF_3$,3-F-4-Me,E], [-6433:2-Me-4-$CF_3$,3-F-4-Me,E], [-6434:2-Me-5-$CF_3$,3-F-4-Me,E], [-6435:2-Me-6-$CF_3$,3-F-4-Me,E], [-6436:3-Me-2-$CF_3$,3-F-4-Me,E], [-6437:3-Me-4-$CF_3$,3-F-4-Me,E], [-6438:3-Me-5-$CF_3$,3-F-4-Me,E], [-6439:4-Me-2-$CF_3$,3-F-4-Me,E], [-6440:4-Me-3-$CF_3$,3-F-4-Me,E], [-6441:2-F-3-MeO,3-F-4-Me,E], [-6442:2-F-4-MeO,3-F-4-Me,E], [-6443:2-F-5-MeO,3-F-4-Me,E], [-6444:2-F-6-MeO,3-F-4-Me,E], [-6445:3-F-2-MeO,3-F-4-Me,E], [-6446:3-F-4-MeO,3-F-4-Me,E], [-6447:3-F-5-MeO,3-F-4-Me,E], [-6448:4-F-2-MeO,3-F-4-Me,E], [-6449:4-F-3-MeO,3-F-4-Me,E], [-6450:2-Cl-3-MeO,3-F-4-Me,E], [-6451:2-Cl-4-MeO,3-F-4-Me,E], [-6452:2-Cl-5-MeO,3-F-4-Me,E], [-6453:2-Cl-6-MeO,3-F-4-Me,E], [-6454:3-Cl-2-MeO,3-F-4-Me,E], [-6455:3-Cl-4-MeO,3-F-4-Me,E], [-6456:3-Cl-5-MeO,3-F-4-Me,E], [-6457:4-Cl-2-MeO,3-F-4-Me,E], [-6458:4-Cl-3-MeO,3-F-4-Me,E], [-6459:2-Me-3-MeO,3-F-4-Me,E], [-6460:2-Me-4-MeO,3-F-4-Me,E], [-6461:2-Me-5-MeO,3-F-4-Me,E], [-6462:2-Me-6-MeO,3-F-4-Me,E], [-6463:3-Me-2-MeO,3-F-4-Me,E], [-6464:3-Me-4-MeO,3-F-4-Me,E], [-6465:3-Me-5-MeO,3-F-4-Me,E], [-6466:4-Me-2-MeO,3-F-4-Me,E], [-6467:4-Me-3-MeO,3-F-4-Me,E],

[-6468:H,4-F-3-Me,E], [-6469:4-F,4-F-3-Me,E], [-6470:4-F,4-F-3-Me,Z], [-6471:4-Cl,4-F-3-Me,E], [-6472:4-Cl,4-F-3-Me,Z], [-6473:4-Br,4-F-3-Me,E], [-6474:4-I,4-F-3-Me,E], [-6475:4-Me,4-F-3-Me,E], [-6476:4-Me,4-F-3-Me,Z], [-6477:4-Et,4-F-3-Me,E], [-6478:4-$C_3H_7$,4-F-3-Me,E], [-6479:4-$(Me)_2CH$,4-F-3-Me,E], [-6480:4-$CF_3$,4-F-3-Me,E], [-6481:4-$CF_3$,4-F-3-Me,Z], [-6482:4-$C_2F_5$,4-F-3-Me,E], [-6483:4-$C_3F_7$,4-F-3-Me,E], [-6484:4-$(CF_3)_2CF$,4-F-3-Me,E], [-6485:4-$(CF_3)_2CH$,4-F-3-Me,E], [-6486:4-$CHF_2$,4-F-3-Me,E], [-6487:4-$CH_2F$,4-F-3-Me,E], [-6488:4-$CF_3CH_2$,4-F-3-Me,E], [-6489:4-MeO,4-F-3-Me,E], [-6490:4-MeO,4-F-3-Me,Z], [-6491:4-EtO,4-F-3-Me,E], [-6492:4-$C_3H_7O$,4-F-3-Me,E], [-6493:4-$(Me)_2CHO$,4-F-3-Me,E], [-6494:4-$NO_2$, 4-F-3-Me,E], [-6495:4-$NO_2$, 4-F-3-Me,Z], [-6496:3-F,4-F-3-Me,E], [-6497:3-F,4-F-3-Me,Z], [-6498:3-Cl,4-F-3-Me,E], [-6499:3-Cl,4-F-3-Me,Z], [-6500:3-Br,4-F-3-Me,E], [-6501:3-I,4-F-3-Me,E], [-6502:3-Me,4-F-3-Me,E], [-6503:3-Me,4-F-3-Me,Z], [-6504:3-Et,4-F-3-Me,E], [-6505:3-$C_3H_7$,4-F-3-Me,E], [-6506:3-$(Me)_2CH$,4-F-3-Me,E], [-6507:3-$CF_3$,4-F-3-Me,E], [-6508:3-$CF_3$,4-F-3-Me,Z], [-6509:3-$C_2F_5$,4-F-3-Me,E], [-6510:3-$C_3F_7$,4-F-

3-Me,E], [−6511:3-(CF₃)₂CF,4-F-3-Me,E], [−6512:3-(CF₃)₂CH,4-F-3-Me,E], [−6513:3-CHF₂,4-F-3-Me,E], [−6514:3-CHF₂,4-F-3-Me,Z], [−6515:3-CH₂F,4-F-3-Me,E], [−6516:3-CH₂F,4-F-3-Me,Z], [−6517:3-CF₃CH₂,4-F-3-Me,E], [−6518:3-MeO,4-F-3-Me,E], [−6519:3-MeO,4-F-3-Me,Z], [−6520:3-EtO,4-F-3-Me,E], [−6521:3-C₃H₇O,4-F-3-Me,E], [−6522:3-(Me)₂CHO,4-F-3-Me,E], [−6523:3-NO₂,4-F-3-Me,E], [−6524:2-F,4-F-3-Me,E], [−6525:2-Cl,4-F-3-Me,E], [−6526:2-Br,4-F-3-Me,E], [−6527:2-I,4-F-3-Me,E], [−6528:2-Me,4-F-3-Me,E], [−6529:2-Et,4-F-3-Me,E], [−6530:2-C₃H₇,4-F-3-Me,E], [−6531:2-(Me)₂CH,4-F-3-Me,E], [−6532:2-CF₃,4-F-3-Me,E], [−6533:2-C₂F₅,4-F-3-Me,E], [−6534:2-C₃F₇,4-F-3-Me,E], [−6535:2-(CF₃)₂CF,4-F-3-Me,E], [−6536:2-(CF₃)₂CH,4-F-3-Me,E], [−6537:2-CHF₂,4-F-3-Me,E], [−6538:2-CH₂F,4-F-3-Me,E], [−6539:2-CF₃CH₂,4-F-3-Me,E], [−6540:2-MeO,4-F-3-Me,E], [−6541:2-EtO,4-F-3-Me,E], [−6542:2-C₃H₇O,4-F-3-Me,E], [−6543:2-(Me)₂CHO,4-F-3-Me,E], [−6544:2-NO₂,4-F-3-Me,E], [−6545:2,3-F₂,4-F-3-Me,E], [−6546:2,4-F₂-4-F-3-Me,E], [−6547:2,5-F₂,4-F-3-Me,E], [−6548:2,6-F₂,4-F-3-Me,E], [−6549:3,4-F₂,4-F-3-Me,E], [−6550:3,4-F₂,4-F-3-Me,Z], [−6551:3,5-F₂,4-F-3-Me,E], [−6552:3,5-F₂,4-F-3-Me,Z], [−6553:2,3-Cl₂,4-F-3-Me,E], [−6554:2,3-Cl₂,4-F-3-Me,Z], [−6555:2,4-Cl₂,4-F-3-Me,E], [−6556:2,4-Cl₂,4-F-3-Me,Z], [−6557:2,5-Cl₂,4-F-3-Me,E], [−6558:2,5-Cl₂,4-F-3-Me,Z], [−6559:2,6-Cl₂,4-F-3-Me,E], [−6560:3,4-Cl₂,4-F-3-Me,E], [−6561:3,5-Cl₂,4-F-3-Me,E], [−6562:2,3-Br₂,4-F-3-Me,E], [−6563:2,4-Br₂,4-F-3-Me,E], [−6566:3,4-Br₂,4-F-3-Me,E], [−6567:3,5-Br₂,4-F-3-Me,E], [−6568:2,3-Me₂,4-F-3-Me,E], [−6569:2,4-Me₂,4-F-3-Me,E], [−6570:2,5-Me₂,4-F-3-Me,E], [−6571:2,6-Me₂,4-F-3-Me,E], [−6572:3,4-Me₂,4-F-3-Me,E], [−6573:3,5-Me₂,4-F-3-Me,E], [−6574:2,3-Et₂,4-F-3-Me,E], [−6575:2,4-Et₂,4-F-3-Me,E], [−6576:2,5-Et₂,4-F-3-Me,E], [−6577:2,6-Et₂,4-F-3-Me,E], [−6578:3,4-Et₂,4-F-3-Me,E], [−6579:3,5-Et₂,4-F-3-Me,E], [−6580:2,3-(CF₃)₂,4-F-3-Me,E], [−6581:2,4-(CF₃)₂,4-F-3-Me,E], [−6582:2,5-(CF₃)₂,4-F-3-Me,E], [−6583:2,6-(CF₃)₂,4-F-3-Me,E], [−6584:3,4-(CF₃)₂,4-F-3-Me,E], [−6585:3,5-(CF₃)₂,4-F-3-Me,E], [−6586:2,3-(CHF₂)₂,4-F-3-Me,E], [−6587:2,4-(CHF₂)₂,4-F-3-Me,E], [−6588:2,5-(CHF₂)₂,4-F-3-Me,E], [−6589:2,6-(CHF₂)₂,4-F-3-Me,E], [−6590:3,4-(CHF₂)₂,4-F-3-Me,E], [−6591:3,5-(CHF₂)₂,4-F-3-Me,E], [−6592:2,3-(CH₂F)₂,4-F-3-Me,E], [−6593:2,4-(CH₂F)₂,4-F-3-Me,E], [−6594:2,5-(CH₂F)₂,4-F-3-Me,E], [−6595:2,6-(CH₂F)₂,4-F-3-Me,E], [−6596:3,4-(CH₂F)₂,4-F-3-Me,E], [−6597:3,5-(CH₂F)₂,4-F-3-Me,E], [−6598:2,3-(MeO)₂,4-F-3-Me,E], [−6599:2,4-(MeO)₂,4-F-3-Me,E], [−6600:2,5-(MeO)₂,4-F-3-Me,E], [−6601:2,6-(MeO)₂,4-F-3-Me,E], [−6602:3,4-(MeO)₂,4-F-3-Me,E], [−6603:3,5-(MeO)₂,4-F-3-Me,E], [−6604:2,3-(EtO)₂,4-F-3-Me,E], [−6605:2,4-(EtO)₂,4-F-3-Me,E], [−6606:2,5-(EtO)₂,4-F-3-Me,E], [−6607:2,6-(EtO)₂,4-F-3-Me,E], [−6608:3,4-(EtO)₂,4-F-3-Me,E], [−6609:3,5-(EtO)₂,4-F-3-Me,E], [−6610:2-Cl-3-F,4-F-3-Me,E], [−6611:2-Cl-4-F,4-F-3-Me,E], [−6612:2-Cl-5-F,4-F-3-Me,E], [−6613:2-Cl-6-F,4-F-3-Me,E], [−6614:3-Cl-2-F,4-F-3-Me,E], [−6615:3-Cl-4-F,4-F-3-Me,E], [−6616:3-Cl-5-F,4-F-3-Me,E], [−6617:4-Cl-2-F,4-F-3-Me,E], [−6618:4-Cl-3-F,4-F-3-Me,E], [−6619:2-F-3-Me,4-F-3-Me,E], [−6620:2-F-4-Me,4-F-3-Me,E], [−6621:2-F-5-Me,4-F-3-Me,E], [−6622:2-F-6-Me,4-F-3-Me,E], [−6623:3-F-2-Me,4-F-3-Me,E], [−6624:3-F-4-Me,4-F-3-Me,E], [−6625:3-F-5-Me,4-F-3-Me,E], [−6626:4-F-2-Me,4-F-3-Me,E], [−6627:4-F-3-Me,4-F-3-Me,E], [−6628:2-Cl-3-Me,4-F-3-Me,E], [−6629:2-Cl-4-Me,4-F-3-Me,E], [−6630:2-Cl-5-Me,4-F-3-Me,E], [−6631:2-Cl-6-Me,4-F-3-Me,E], [−6632:3-Cl-2-Me,4-F-3-Me,E], [−6633:3-Cl-4-Me,4-F-3-Me,E], [−6634:3-Cl-5-Me,4-F-3-Me,E], [−6635:4-Cl-2-Me,4-F-3-Me,E], [−6636:4-Cl-3-Me,4-F-3-Me,E], [−6637:2-F-3-CF₃,4-F-3-Me,E], [−6638:2-F-4-CF₃,4-F-3-Me,E], [−6639:2-F-5-CF₃,4-F-3-Me,E], [−6640:2-F-6-CF₃,4-F-3-Me,E], [−6641:3-F-2-CF₃,4-F-3-Me,E], [−6642:3-F-4-CF₃,4-F-3-Me,E], [−6643:3-F-5-CF₃,4-F-3-Me,E], [−6644:4-F-2-CF₃,4-F-3-Me,E], [−6645:4-F-3-CF₃,4-F-3-Me,E], [−6646:2-Cl-3-CF₃,4-F-3-Me,E], [−6647:2-Cl-4-CF₃,4-F-3-Me,E], [−6648:2-Cl-5-CF₃,4-F-3-Me,E], [−6649:2-Cl-6-CF₃,4-F-3-Me,E], [−6650:3-Cl-2-CF₃,4-F-3-Me,E], [−6651:3-Cl-4-CF₃,4-F-3-Me,E], [−6652:3-Cl-5-CF₃,4-F-3-Me,E], [−6653:4-Cl-2-CF₃,4-F-3-Me,E], [−6654:4-Cl-3-CF₃,4-F-3-Me,E], [−6655:2-Me-3-CF₃,4-F-3-Me,E], [−6656:2-Me-4-CF₃,4-F-3-Me,E], [−6657:2-Me-5-CF₃,4-F-3-Me,E], [−6658:2-Me-6-CF₃,4-F-3-Me,E], [−6659:3-Me-2-CF₃,4-F-3-Me,E], [−6660:3-Me-4-CF₃,4-F-3-Me,E], [−6661:3-Me-5-CF₃,4-F-3-Me,E], [−6662:4-Me-2-CF₃,4-F-3-Me,E], [−6663:4-Me-3-CF₃,4-F-3-Me,E], [−6664:2-F-3-MeO,4-F-3-Me,E], [−6665:2-F-4-MeO,4-F-3-Me,E], [−6666:2-F-5-MeO,4-F-3-Me,E], [−6667:2-F-6-MeO,4-F-3-Me,E], [−6668:3-F-2-MeO,4-F-3-Me,E], [−6669:3-F-4-MeO,4-F-3-Me,E], [−6670:3-F-5-MeO,4-F-3-Me,E], [−6671:4-F-2-MeO,4-F-3-Me,E], [−6672:4-F-3-MeO,4-F-3-Me,E], [−6673:2-Cl-3-MeO,4-F-3-Me,E], [−6674:2-Cl-4-MeO,4-F-3-Me,E], [−6675:2-Cl-5-MeO,4-F-3-Me,E], [−6676:2-Cl-6-MeO,4-F-3-Me,E], [−6677:3-Cl-2-MeO,4-F-3-Me,E], [−6678:3-Cl-4-MeO,4-F-3-Me,E], [−6679:3-Cl-5-MeO,4-F-3-Me,E], [−6680:4-Cl-2-MeO,4-F-3-Me,E], [−6681:4-Cl-3-MeO,4-F-3-Me,E], [−6682:2-Me-3-MeO,4-F-3-Me,E], [−6683:2-Me-4-MeO,4-F-3-Me,E], [−6684:2-Me-5-MeO,4-F-3-Me,E], [−6685:2-Me-6-MeO,4-F-3-Me,E], [−6686:3-Me-2-MeO,4-F-3-Me,E], [−6687:3-Me-4-MeO,4-F-3-Me,E], [−6688:3-Me-5-MeO,4-F-3-Me,E], [−6689:4-Me-2-MeO,4-F-3-Me,E], [−6690:4-Me-3-MeO,4-F-3-Me,E].

In the above-described "combinations G", for example, when $(X^{AA})_m{}^{AA}$ is "H", it is meant that m=0, when $(X^{AA})_m{}^{AA}$ is "4-F", it is meant that $m^{AA}=1$ and X is a fluorine atom substituting on 4 position, when $(X^{AA})_m{}^{AA}$ is "2,3-(CF₃)₂", it is meant that $m^{AA}=2$, one of $X^{AA}$s is a trifluoromethyl group substituting on 2 position and the other of $X^{AA}$s is a trifluoromethyl group substituting on 3 position;

when $(Z^{AA})_m{}^{AA}$ is "H", it is meant that $n^{AA}=0$, when $(Z^{AA})_n{}^{AA}$ is "4-MeO", it is meant that $n^{AA}=1$ and $Z^{AA}$ is a methoxy group substituting on 4 position, when $(Z^{AA})_n{}^{AA}$ is "3-F-4-(Me)₃CO", it is meant that $n^{AA}=2$, one of $Z^{AA}$s is a fluorine atom substituting on 3 position and the other of $Z^{AA}$s is a t-butoxy group substituting on 4 position;

when geometric isomerism in double bond in CH=CH is "E", it is meant that geometric isomerism in double bond in CH=CH in the formula (I) is E (entgegen) body, and when geometric isomerism in double bond in CH=CH is "Z", it is meant that geometric isomerism in double bond in CH=CH in the formula (I) is Z (zusammen) body.

Next, Reference Production Example will be shown.

REFERENCE PRODUCTION EXAMPLE 1

N-Benzyloxy-3-(phenylthio)acrylimidoyl bromide

Pyridine (2.7 ml) was added to THF (80 ml) solution of 3-(phenylthio)acryloyl chloride (3.0 g) and hydrochloric acid salt of O-benzylhydroxylamine (2.6 g) under ice-cooling and stirred at the same temperature for one hour and at room temperature for three hours. The reaction mixture was concentrated under reduced pressure. Chloroform (150 ml) was added to the residue, washed successively with 1N hydrochloric acid, pure water and aqueous saturated sodium chloride solution, dried over anhydrous magnesium sulfate and concentrated under reduced pressure. The residue was subjected to silica gel column chromatography (hexane:ethyl acetate 2:1) to obtain N-benzyloxy-3-(phenylthio)acrylamide (3.5 g) as colorless oil. N-benzyloxy-3-(phenylthio) acrylamide (1.0 g) was dissolved to acetonitrile (70 ml), carbon tetrabromide (2.3 g) and triphenylphosphine (1.8 g) were added thereto under ice-cooling, then heat refluxing for four hours. The reaction mixture was concentrated under reduced pressure. The residue was subjected to silica gel column chromatography (hexane:ethyl acetate 20:1) to obtain N-benzyloxy-3-(phenylthio)acrylimidoyl bromide (1.1 g) as light yellow oil.

$^1$H-NMR (CDCl$_3$) δ(ppm): 5.21(1.7H,s), 5.35(0.3H,s), 6.05(0.17H,d,J=10.4 Hz), 6.14(0.83H,d,J=14.7 Hz), 6.70 (0.17H,d,J=10.4 Hz), 7.21-7.48(10.83H,m)

REFERENCE PRODUCTION EXAMPLE 2

N-Phenyl-3-(phenylthio)acrylamide

3-Phenylthioacrylic acid (6.74 g) was suspended to toluene (50 ml), then thionyl chloride (5.00 ml) and one drop of DMF were added thereto. The mixture was stirred on the 60° C. oil bath for 30 minutes. The reaction mixture was concentrated under reduced pressure. The residue was added dropwise to acetonitrile (60 ml) solution of aniline (8.5 ml) under ice-cooling, and stirred at the same temperature for three hours. The reaction mixture was poured into 250 ml of ice-water, and adjusted to pH 3 with concentrated hydrochloric acid. The precipitated crystal was collected by filtration, washed with water and dried to obtain N-phenyl-3-(phenylthio)acrylamide (9.09 g) as light brown crystal.

$^1$H-NMR (CDCl$_3$) δ(ppm): 5.78(0.84H,d J=14.6 Hz), 5.98 (0.16H,d J=9.8 Hz), 7.00-7.59(11.16H,m), 7.84(0.84H,d J=14.6 Hz)

Below mentioned compounds were synthesized in a similar manner as above.

N-(4-Chlorophenyl)-3-(phenylthio)acrylamide $^1$H-NMR (CDCl$_3$) δ(ppm): 5.74(0.92H, d J=15.0 Hz), 5.96 (0.08H, d J=9.9 Hz), 7.03-7.59(9.08H, m), 7.84(0.92H, d J=14.9 Hz) N-(3-Chlorophenyl)-3-(phenylthio)acrylamide $^1$H-NMR (CDCl$_3$) δ(ppm): 5.74(0.94H, d J=14.9 Hz), 5.97 (0.06H, d J=9.7 Hz), 7.03-7.67(9.06H, m), 7.85(1H, d J=14.9 Hz) N-(2-Chlorophenyl)-3-(phenylthio)acrylamide $^1$H-NMR (CDCl$_3$) δ(ppm): 5.88(1H, d J=15.1 Hz), 6.98-7.08(1H, m), 7.22-7.58(8H, m), 7.88(1H, d J=15.1 Hz) N-Phenyl-3-(phenoxy)acrylamide $^1$H-NMR (CDCl$_3$) δ(ppm): 5.70(1H, d, J=12.0 Hz), 7.07-7.20(5H, m), 7.30-7.39(4H, m), 7.52-7.54(2H,m), 7.89(1H, d,J=12.0 Hz) N-(4-Methoxyphenyl)-3-(phenylthio)acrylamide $^1$H-NMR (CDCl$_3$) δ(ppm): 3.78(3H, s), 5.77(1H, d J=14.7 Hz), 6.81-6.88(1H, m), 6.97-7.04(2H, m), 7.24-7.55(5H, m), 7.81(1H, d J=14.7 Hz)

N-(2-Fluorophenyl)-3-(phenylthio)acrylamide $^1$H-NMR (CDCl$_3$) δ(ppm): 5.82(1H, d J=14.7 Hz), 6.98-7.57(9H, m), 7.86(1H, d J=14.7 Hz)

N-(3-Pyridyl)-3-(phenylthio)acrylamide $^1$H-NMR (CDCl$_3$) δ(ppm): 5.87(0.81H, d J=14.7 Hz), 6.11 (0.19H, d J=9.9 Hz), 7.18-7.58(5.19H, m, Ar—H), 7.85(0.81H, d J=14.7 Hz), 8.17-8.30(2H, m), 8.49-8.65(2H, m)

REFERENCE PRODUCTION EXAMPLE 3

N-Phenyl-3-(cyclohexylthio)acrylamide

Thionyl chloride (0.58 ml) and one drop of DMF were added to the suspension of toluene (15 ml) of 3-(cyclohexylthio)thioacrylic acid (1.0 g) at room temperature, and it was stirred on the 80° C. oil bath for 1.5 minutes. The reaction mixture was concentrated under reduced pressure. Acetonitrile (20 ml) was added to the residue, then aniline (0.50 g) and triethylamine (0.73 ml) were added to the mixture under ice-cooling. The mixture was stirred at the same temperature for three hours, then it was concentrated under reduced pressure. 1N hydrochloric acid (50 ml) was added to the residue, and extracted with ethyl acetate (100 ml). The organic layer was successively washed with water and aqueous saturated sodium chloride solution, dried over anhydrous magnesium sulfate and concentrated under reduced pressure. The residue was separated and purified by silica gel column chromatography (hexane:ethyl acetate=5:1) to obtain E form of N-phenyl-3-(cyclohexylthio)acrylamide (0.60 g) and Z form (0.38 g).

E form $^1$H-NMR (CDCl$_3$) δ(ppm): 1.26-1.49(5H,m), 1.60-1.65 (1H,m), 1.77-1.80(2H,m), 2.01-2.04(2H,m), 3.01-3.07(1H, m), 5.95(1H,d,J=14.8 Hz), 7.08-7.11(1H,m), 7.08-7.11(1H, m), 7.24(1H,brs), 7.29-7.33(2H,m), 7.53-7.55(2H,m), 7.77 (1H,d,J=14.8 Hz)

Z form $^1$H-NMR (CDCl$_3$) δ(ppm): 1.25-1.48(5H,m), 1.59-1.64 (1H,m), 1.79-1.83(2H,m), 2.01-2.04(2H,m), 2.79-2.84(1H, m), 5.90(1H,d,J=10.4 Hz), 7.05-7.10(2H,m), 7.23(1H,brs), 7.26-7.31(2H,m), 7.54-7.62(2H,m)

REFERENCE PRODUCTION EXAMPLE 4

N-(4-Methylphenyl)-3-(phenylthio)acrylamide p-Toluidine (2.46 g) was dissolved to acetonitrile (20 ml), then acetonitrile (3 ml) solution of 3-(phenylthio)acryloyl chloride (2.0 g) was added dropwise thereto under ice-cooling. The mixture was stirred at room temperature for 1.5 hours. The reaction mixture was poured into 50 ml of ice-water, and adjusted to pH 4 with concentrated hydrochloric acid. The precipitated crystal was collected by filtration, washed with water and dried to obtain N-(4-methylphenyl)-3-(phenylthio)acrylamide (2.62 g) as light brown crystal.

$^1$H-NMR (CDCl$_3$) δ(ppm): 2.28(3H, s), 5.86(0.8H, d J=14.3 Hz), 5.99(0.2H, d J=9.9 Hz), 7.02-7.15(2H, m), 7.28-7.63(7.2H, m), 7.84(0.67H, d J=14.4 Hz), 7.95(0.13H, d J=14.5 Hz)

Below mentioned compounds were synthesized in a similar manner as above.

N-(4-Fluorophenyl)-3-(phenylthio)acrylamide $^1$H-NMR (CDCl$_3$) δ(ppm): 5.76(0.77H, d J=14.7 Hz), 5.96 (0.23H, d J=9.4 Hz), 6.93-7.60(9.23H, m), 7.83(0.77H, d J=14.7 Hz)

N-(3-Fluorophenyl)-3-(phenylthio)acrylamide

¹H-NMR (CDCl₃) δ(ppm): 5.77(0.77H, d J=14.5 Hz), 5.99 (0.23H, d J=9.97 Hz), 6.73-6.84(1H, m), 7.10-7.63(8.23H, m), 7.84(1H, d J=14.5 Hz)

N-(4-Trifluoromethylphenyl)-3-(phenylthio)acrylamide

¹H-NMR (CDCl₃) δ(ppm): 5.74(0.83H, d J=14.4 Hz), 5.99 (0.17H, d J=9.7 Hz), 7.23-7.77(9.17H, m), 7.90(0.83H, d J=14.4 Hz)

N-(4-Methylphenyl)-3-(phenoxy)acrylamide

¹H-NMR (CDCl₃) δ(ppm): 2.31(3H,s), 5.70(1H,d,J=11.6 Hz), 7.05-7.19(5H,m), 7.23(1H,brs), 7.34-7.40(4H,m), 7.87(1H,d,J=11.6 Hz)

N-(4-Methoxyphenyl)-3-(phenoxy)acrylamide

¹H-NMR (CDCl₃) δ(ppm): 3.78(3H,s), 5.69(1H,d,J=11.6 Hz), 6.84-6.86(2H,m), 7.06-7.08(2H,m), 7.15-7.19(2H,m), 7.34-7.43(3H,m), 7.87(1H,d,J=11.6 Hz)

N-(2-Chlorophenyl)-3-(phenoxy)acrylamide

¹H-NMR (CDCl₃) δ(ppm): 5.75(1H,d,J=11.7 Hz), 7.01-7.05(1H,m), 7.09-7.12(2H,m), 7.18-7.30(2H,m), 7.35-7.41(3H,m), 7.48(1H,brs), 7.92(1H,d,J=11.7 Hz), 8.43(1H,d,J=8.3 Hz)

N-(3,5-Dichlorophenyl)-3-(phenoxy)acrylamide

¹H-NMR (CDCl₃) δ(ppm): 5.66(1H,d,J=11.6 Hz), 7.06-7.08(3H,m), 7.18-7.21(1H,m), 7.26(1H,s), 7.36-7.51(2H,m), 7.51(2H,s), 7.90(1H,d,J=11.6 Hz)

N-(3,4,5-Trichlorophenyl)-3-(phenoxy)acrylamide

¹H-NMR (CDCl₃) δ(ppm): 5.63(1H,d,J=11.6 Hz), 7.07-7.09(3H,m), 7.19-7.23(1H,m), 7.37-7.41(2H,m), 7.67(2H,s), 7.91(1H,d,J=11.6 Hz)

N-(3-Methylphenyl)-3-(phenoxy)acrylamide

¹H-NMR (CDCl₃) δ(ppm): 2.33(3H,s), 5.70(1H,d,J=11.6 Hz), 6.92(1H,d,J=7.5 Hz), 7.06-7.09(2H,m), 7.15(1H, brs), 7.16-7.21(2H,m), 7.29-7.39(4H,m), 7.88(1H,d,J=11.6 Hz)

N-(3,4-Dimethylphenyl)-3-(phenoxy)acrylamide

¹H-NMR (CDCl₃) δ(ppm): 2.21(3H,s), 2.23(3H,s), 5.69(1H,d,J=11.6 Hz), 7.05-7.10(4H,m), 7.15-7.19(1H,m), 7.23(1H, br.), 7.32-7.38(3H,m), 7.87(1H,d,J=11.6 Hz)

N-[3-(1-Methylethyl)phenyl]-3-(phenoxy)acrylamide

¹H-NMR (CDCl₃) δ(ppm): 1.24(6H,d,J=7.5 Hz), 2.89(1H, sept, J=7.5 Hz), 5.70(1H,d,J=11.6 Hz), 6.98(1H,d,J=7.5 Hz), 7.07-7.09(2H,m), 7.16-7.24(3H,m), 7.35-7.43(4H,m), 7.90(1H,d,J=11.6 Hz)

N-[4-(1-Methylethyl)phenyl]-3-(phenoxy)acrylamide

¹H-NMR (CDCl₃) δ(ppm): 1.23(6H,d,J=7.5 Hz), 2.88(1H, sept, J=7.5 Hz), 5.70(1H,d,J=11.6 Hz), 6.98(1H,d,J=7.5 Hz), 7.07-7.09(3H,m), 7.16-7.19(3H,m), 7.35-7.39(3H,m), 7.43(1H, brs), 7.88(1H,d,J=11.6 Hz)

N-(4-Fluorophenyl)-3-(phenoxy)acrylamide

¹H-NMR (CDCl₃) δ(ppm): 5.67(1H,d,J=11.6 Hz), 7.00-7.10(5H,m), 7.17-7.21(1H,m), 7.36-7.40(2H,m), 7.48(2H, br.), 7.90(1H,d,J=11.6 Hz)

N-(4-Bromophenyl)-3-(phenoxy)acrylamide

¹H-NMR (CDCl₃) δ(ppm): 5.67(1H,d,J=11.6 Hz), 7.06-7.09(2H,m), 7.17-7.21(2H,m), 7.35-7.45(6H,m), 7.89(1H,d, J=11.6 Hz)

N-(3-Methoxyphenyl)-3-(phenoxy)acrylamide

¹H-NMR (CDCl₃) δ(ppm): 3.80(3H,s), 5.69(1H,d,J=11.7 Hz), 6.66(1H, dd, J₁=8.3 Hz, J₂=1.7 Hz,), 6.98(1H,d,J=7.8 Hz), 7.06-7.09(2H,m), 7.16-7.23(3H,m), 7.35-7.39(3H,m), 7.89(1H,d,J=11.7 Hz)

N-(4-Iodophenyl)-3-(phenoxy)acrylamide

¹H-NMR (CDCl₃) δ(ppm): 5.67(1H,d,J=11.6 Hz), 7.06-7.08(2H,m), 7.15-7.21(2H,m), 7.31-7.39(4H,m), 7.60-7.62(2H,m), 7.88(1H,d,J=11.6 Hz)

N-(5-Indanyl)-3-(phenoxy)acrylamide

¹H-NMR (CDCl₃) δ(ppm): 2.00-2.10(2H,m), 2.84-2.90(4H,m), 5.70(1H,d,J=11.6 Hz), 7.07-7.19(6H,m), 7.35-7.39(2H,m), 7.48(1H, brs), 7.87(1H,d,J=11.6 Hz)

N-[4-(Methylthio)phenyl]-3-(phenoxy)acrylamide

¹H-NMR (CDCl₃) δ(ppm): 2.46(3H,s), 5.68(1H,d,J=11.7 Hz), 7.07-7.09(3H,m), 7.17-7.25(3H,m), 7.35-7.40(2H,m), 7.46(2H, br.), 7.89(1H,d,J=11.7 Hz)

N-(Benzo-1,4-dioxane-6-yl)-3-(phenoxy)acrylamide

¹H-NMR (CDCl₃) δ(ppm): 4.23(4H,s), 5.67(1H,d,J=11.6 Hz), 6.80(1H,d,J=8.7 Hz), 6.90(1H, brs), 7.01(1H, brs), 7.06-7.09(2H,m), 7.15-7.19(2H,m), 7.35-7.39(2H,m), 7.87(1H,d, J=11.6 Hz)

N-(4-Benzylphenyl)-3-(phenoxy)acrylamide

¹H-NMR (CDCl₃) δ(ppm): 3.95(2H,s), 5.67(1H,d,J=11.6 Hz), 6.98(1H, brs), 7.08-7.10(2H,m), 7.13-7.21(6H,m), 7.28-7.30(2H,m), 7.35-7.43(4H,m), 7.89(1H,d,J=11.6 Hz)

N-(4-Trifluoromethoxyphenyl)-3-(phenoxy)acrylamide

¹H-NMR (CDCl₃) δ(ppm): 5.68(1H,d,J=11.6 Hz), 7.07-7.10(2H,m), 7.14-7.21(4H,m), 7.36-7.40(2H,m), 7.55-7.58(2H,m), 7.91(1H,d,J=11.6 Hz)

N-(3-Biphenyl)-3-(phenoxy)acrylamide

¹H-NMR (CDCl₃) δ(ppm): 5.74(1H, d, J=11.8 Hz), 7.06-7.59(14H, m), 7.80(1H, brs), 7.91(1H, d, J=11.8 Hz)

N-(4-Benzoylphenyl)-3-(phenoxy)acrylamide

¹H-NMR (CDCl₃) δ(ppm): 5.78(1H, d, J=11.8 Hz), 7.11-7.84(14H, m), 7.33(1H, brs), 7.94(1H, d, J=11.8 Hz)

N-(4-Acetylphenyl)-3-(phenoxy)acrylamide $^1$H-NMR (CDCl$_3$) δ(ppm): 2.58(3H, s), 5.69(1H, d, J=11.8 Hz), 7.09-7.96(9H, m), 7.25(1H, brs), 7.94(1H, d, J=11.8 Hz)

N-(4-Methoxycarbonylphenyl)-3-(phenoxy)acrylamide $^1$H-NMR (CDCl$_3$) δ(ppm): 3.90(3H, s), 5.68(1H, d, J=11.6 Hz), 7.09-7.64(7H, m), 7.58(1H, brs), 7.93(1H, d, J=11.6 Hz), 8.00-8.02(2H, m)

3-(Phenoxy)-N-(quinoline-6-yl)acrylamide $^1$H-NMR (CDCl$_3$) δ(ppm): 3.70(1H, brs), 6.00(1H, d, J=12.0 Hz), 7.24-9.08(11H, m), 7.87(1H, d, J=12.0 Hz)

3-(Phenoxy)-N-(3,4,5-trimethylphenyl)acrylamide $^1$H-NMR (CDCl$_3$) δ(ppm): 2.13(3H, s), 2.26(6H, s), 5.68 (1H, d, J=11.6 Hz), 6.98(1H, brs), 7.07-7.39(7H, m), 7.87 (1H, d, J=11.6 Hz)

N-[4-(1,1-Dimethylethylthio)phenyl]-3-(phenoxy)acrylamide $^1$H-NMR (CDCl$_3$) δ(ppm): 1.27(9H, s), 1.68(1H, brs), 5.70(1H, d, J=11.6 Hz), 7.08-7.53(9H, m), 7.90(1H, d, J=11.6 Hz)

3-(Phenoxy)-N-(3-thienyl)acrylamide $^1$H-NMR (CDCl$_3$) δ(ppm): 5.67(1H,d,J=11.8 Hz), 7.01 (1H,dd,J$_1$=5.2 Hz, J$_2$=1.3 Hz), 7.06-7.09(2H,m), 7.16-7.24 (2H,m), 7.35-7.39(2H,m), 7.46(1H,brs), 7.59(1H,brs), 7.89 (1H,d,J=11.8 Hz)

REFERENCE PRODUCTION EXAMPLE 5

N-(3-Methylphenyl)-3-(phenylthio)acrylamide

THF (45 ml) solution of 3-(phenylthio)acryloyl chloride (3.03 g) was added to THF (45 ml) solution of triethylamine (2.09 ml) under ice-cooling. 3-methylaniline (1.62 g) was added to the mixture under ice-cooling and stirred at room temperature for ten hours. The reaction solution was concentrated under reduced pressure. Ice cooled 1N hydrochloric acid (40 ml) and ethyl acetate (200 ml) were added to the residue and separated to two layer. The organic layer was washed with aqueous saturated sodium chloride solution (40 ml) twice, dried over anhydrous magnesium sulfate, filtered off inorganic salt and concentrated under reduced pressure to obtain N-(3-methylphenyl)-3-(phenylthio)acrylamide (3.46 g).

$^1$H-NMR (CDCl$_3$) δ(ppm): 2.33(3H,s), 5.77(0.83H, d J=14.6 Hz), 5.97(0.17H, d J=9.9 Hz), 6.86-6.96(2H, m), 7.12-7.58(7.17H, m), 7.84(0.83H, d J=14.6 Hz)

Below mentioned compounds were synthesized in a similar manner as above.

N-(4-Bromophenyl)-3-(phenylthio)acrylamide $^1$H-NMR (CDCl$_3$) δ(ppm): 5.60(0.13H,d,J=14.5 Hz), 5.76 (0.67H,d,J=14.7 Hz), 5.96(0.18H,d,J=9.9 Hz), 7.13-7.59 (9.18H,m), 7.84(0.67H,d,J=14.4 Hz), 7.95(0.13H,d,J=14.5 Hz)

N-(4-Nitrophenyl)-3-(phenylthio)acrylamide $^1$H-NMR (CDCl$_3$) δ(ppm): 5.73(0.71H,d,J=14.3 Hz), 6.01 (0.29H,d,J=9.6 Hz), 7.34-7.59(6H,m), 7.70(1H,d, =9.2 Hz), 7.81(0.29H,d,J=9.6 Hz), 7.95(0.71H,d,J=14.3 Hz), 8.17-8.25 (2H,m)

N-(3,4-Dichlorophenyl)-3-(phenoxy)acrylamide $^1$H-NMR (CDCl$_3$) δ(ppm): 5.65(1H,d,J=11.6 Hz), 7.07-7.09(2H,m), 7.13(1H,brs), 7.18-7.22(1H,m), 7.35-7.40(4H, m), 7.78(1H,s), 7.90(1H,d,J=11.6 Hz)

N-(4-Cyanophenyl)-3-(phenylthio)acrylamide $^1$H-NMR (CDCl$_3$) δ(ppm): 5.75(0.71H,d,J=15.0 Hz), 6.00 (0.23H,d,J=9.9 Hz), 7.29-7.79(9.23H,m), 7.91(0.77H,d, J=15.0 Hz)

N-(4-Ethylphenyl)-3-(phenylthio)acrylamide $^1$H-NMR (CDCl$_3$) δ(ppm): 1.20(2H,t,J=7.6 Hz), 2.60(3H, q,J=7.6 Hz), 5.79(0.83H,d,J=14.8 Hz), 5.98(0.17H,d,J=9.9 Hz), 7.06-7.22(3.17H,m), 7.30-7.56(6H,m), 7.82(0.83H,d, J=14.8 Hz)

N-[4-(1-Methylethyl)phenyl]-3-(phenylthio)acrylamide $^1$H-NMR (CDCl$_3$) δ(ppm): 1.22(6H,d,J=7.0 Hz), 2.87(1H, sept, J=7.0 Hz), 5.78(0.83H,d, J=14.6 Hz), 5.97(0.17H,d, J=10.1 Hz), 6.97-7.57(9.17H, m), 7.82(0.83H,d, J=14.6 Hz)

N-(4-Propylphenyl)-3-(phenylthio)acrylamide $^1$H-NMR (CDCl$_3$) δ(ppm): 0.93(2H, t, J=7.5 Hz), 1.61(3H, sext, J=7.5 Hz), 2.54(2H,t, J=7.5 Hz), 5.79(0.83H,d, J=14.5 Hz), 5.97(0.17H,d, J=9.9 Hz), 6.98-7.59(9.17H,m), 7.82(0.83H,d, J=14.5 Hz)

N-[4-(1,1-Dimethylethyl)phenyl]-3-(phenylthio)acrylamide $^1$H-NMR (CDCl$_3$) δ(ppm): 1.30(9H,s), 5.64(0.08H,d, J=15.2 Hz), 5.78(0.75H,d,J=14.5 Hz), 5.97(0.17H,d,J=10.1 Hz), 7.07-7.18(2H,m), 7.24-7.68(7.27H,m), 7.79(0.64H, d,J=14.6 Hz), 7.86(0.09H,d,J=15.3 Hz)

N-(4-Phenylthiophenyl)-3-(phenoxy)acrylamide $^1$H-NMR (CDCl$_3$) δ(ppm): 5.68(1H,d,J=11.6 Hz), 7.08-7.10(3H,m), 7.18-7.27(6H,m), 7.35-7.40(4H,m), 7.50-7.52 (2H,m), 7.90(1H,d,J=11.6 Hz) N-(4-Propylphenyl)-3-(phenylthio)acrylamide $^1$H-NMR (CDCl$_3$) δ(ppm): 1.06-1.47(6H, m), 1.58-1.93 (4H,m), 2.35-2.51(1H,m), 5.64(0.09H,d, J=15.3 Hz), 5.86 (0.64H,d, J=14.6 Hz), 6.00(0.27H,d, J=10.1 Hz), 7.16-7.58 (9.17H,m), 7.83(0.75H,d, J=14.5 Hz), 7.88(0.08H,d, J=15.2 Hz)

N-(4-Cyclohexylthiophenyl)-3-(phenoxy)acrylamide $^1$H-NMR (CDCl$_3$) δ(ppm): 1.19-1.35(6H, m), 1.57-1.62 (1H, m), 1.75-1.77(2H, m), 1.94-1.96(2H, m), 2.96-3.05(1H, m), 5.68(1H, d, J=11.6 Hz), 7.00-7.48(10H, m), 7.90(1H, d, J=11.6 Hz)

N-(4-Phenoxyphenyl)-3-(phenylthio)acrylamide $^1$H-NMR (CDCl$_3$) δ(ppm): 5.64(0.09H,d,J=15.1 Hz), 6.03 (0.64H,d, J=14.8 Hz), 6.11(0.27H,d, J=9.9 Hz), 6.83-6.95 (4H,m), 6.98-7.07(1H,m), 7.16-7.58(9.27H,m), 7.83(0.75H, d, J=14.5 Hz), 7.88(0.08H,d, J=15.2 Hz)

N-[4-(1,1-Dimethylethyloxy)phenyl]-3-(phenoxy)acrylamide $^1$H-NMR (CDCl$_3$) δ(ppm): 1.32(9H,s), 5.69(1H,d, J=11.6 Hz), 6.94-6.96(2H,m), 7.02(1H,brs), 7.08-7.10(2H,m), 7.16-7.20(1H,m), 7.36-7.40(1H,m), 7.89(1H,d,J=11.6 Hz)

3-(Phenoxy)-N-(4-piperidinophenyl)acrylamide $^1$H-NMR (CDCl$_3$) δ(ppm): 1.56-1.61(2H,m), 1.67-1.73 (4H,m), 3.09-3.12(4H,m), 5.68(1H,d,J=11.6 Hz), 6.89(2H,d, J=8.9 Hz), 7.00(1H, brs), 7.07(2H,d,J=8.0 Hz), 7.15-7.19 (1H,m), 7.34-7.38(4H,m), 7.86(1H,d,J=11.6 Hz)

3-(Phenylthio)-N-(2,2,2-trifluoroethyl)acrylamide $^1$H-NMR (CDCl$_3$) δ(ppm): 3.90-4.02(2H,m), 5.65(0.77H, d, J=14.5 Hz), 5.66(0.77H,br.), 5.88(0.23H,d, J=9.9 Hz), 5.90 (0.23H,br.), 7.20(0.23H,d, J=9.9 Hz), 7.33-7.49(5H,m), 7.80 (0.77H, d, J=14.5 Hz)

3-(Phenylthio)-N-(1-phenylethylideneamino)acrylamide $^1$H-NMR (CDCl$_3$) δ(ppm): 2.20(2.4H,s), 2.29(0.6H,s), 6.89(0.8H,d, J=15.1 Hz), 7.04(0.2H,d,J=10.2 Hz), 7.36-7.60 (10.2H,m), 7.95(0.8H,d, J=15.1 Hz), 8.69(0.8H,brs), 8.90 (0.2H,brs)

REFERENCE PRODUCTION EXAMPLE 6

N-Benzenesulfonyl-3-(phenylthio)acrylamide

Sodium hydride (55% in oil; 0.48 g) was added to THF (30 ml) solution of 3-(phenylthio)acryloyl chloride (1.0 g) and benzenesulfoneamide (0.87 g) under ice-cooling, and stirred at the same temperature for two hours and at room temperature for two hours. The reaction mixture was concentrated under reduced pressure. 1N hydrochloric acid (50 ml) was added to the residue, and extracted with chloroform (50 ml) twice. The organic layer was washed with aqueous saturated sodium chloride solution, dried over anhydrous magnesium sulfate, and concentrated under reduced pressure. The obtained crystal was washed with tert-butyl methyl ether, collected by filtration, dried under reduced pressure to obtain N-benzenesulfonyl-3-(phenylthio)acrylamide (1.4 g).

$^1$H-NMR (CDCl$_3$) δ(ppm): 5.62(0.8H,d,J=14.7 Hz), 5.99 (0.2H,d, J=10.1 Hz), 7.34-7.66(8.2H,m), 7.86(0.8H,d, J=14.7 Hz), 7.99-8.01(1.6H,m), 8.10-8.12(0.4H,m), 8.48(0.8H,brs), 8.72(0.2H,brs)

REFERENCE PRODUCTION EXAMPLE 7

Isopropyl N-phenyl-3-(trimethylsilyl)thiopropioimidate

Ethynyltrimethylsilane (0.93 g) was dissolved to dry THF (30 ml), n-butyl lithium/hexane solution (1.6 mol/l; 5.6 ml) was added dropwise thereto at −78° C., then it was warmed to 0° C. The reaction mixture was cooled to −78° C., THF (5 ml) solution of phenyl isothiocyanate (1.24 g) was added dropwise to the reaction mixture.

Then it was gradually warmed to 0° C. After that, THF (5 ml) solution of 2-iodopropane (1.52 g) was added dropwise thereto under ice-cooling, then stirred for 14 hours at room temperature. The reaction solution was concentrated. The residue was subjected to silica gel column chromatography (hexane/ethyl acetate=15/1) to obtain isopropyl N-phenyl-3-(trimethylsilyl)thiopropioimidate (1.7 g).

$^1$H-NMR (CDCl$_3$) δ(ppm): 0.09(6H,s), 0.28(3H,s), 1.37 (0.33H,d, J=6.7 Hz), 1.40(0.66H,d, J=6.7 Hz), 3.82-3.98(1H, m), 6.85-7.36(5H,m)

Below mentioned compounds were synthesized in a similar manner as above.

Methyl 3-(trimethylsilyl)-N-phenyl-thiopropioimidate $^1$H-NMR (CDCl$_3$) δ(ppm): 0.10(6H,s), 0.30(3H,s), 2.34 (3H,s), 2.51(0.67H,s), 2.54(0.33H,s), 6.83-7.40(5H,m)

Benzyl 3-(trimethylsilyl)-N-phenyl-thiopropioimidate $^1$H-NMR (CDCl$_3$) δ(ppm): 0.10(6H,s), 0.28(3H,s), 4.37 (1.5H,s), 4.60(0.5H,s), 6.85-7.43(10H,m)

2-Propenyl 3-(trimethylsilyl)-N-phenyl-thiopropioimidate $^1$H-NMR (CDCl$_3$) δ(ppm): 0.10(6H,s), 0.28(3H,s), 3.72-3.82(2H,m), 5.10-5.35(2H,m), 5.80-6.02(1H,m), 6.83-7.39 (5H,m)

2-Propynyl 3-(trimethylsilyl)-N-phenyl-thiopropioimidate $^1$H-NMR (CDCl$_3$) δ(ppm): 0.11(6H,s), 0.31(3H,s), 2.21 (0.66H,t, J=2.6 Hz), 2.26(0.33H,t, J=2.6 Hz), 3.82(1.3H,d, J=2.6 Hz), 3.90(0.7H,d, J=2.6 Hz), 6.88-7.38(5H,m)

1-Phenethyl 3-(trimethylsilyl)-N-phenyl-thiopropioimidate $^1$H-NMR (CDCl$_3$) δ(ppm): 0.09(6H,s), 0.31(3H,s), 1.77 (2H,d, J=7.2 Hz), 2.05(1H,d, J=7.2 Hz), 5.07(0.66H,q,J=7.2 Hz), 5.12(0.33H,q, J=7.2 Hz), 7.02-7.47(10H,m)

cyclohexyl 3-(trimethylsilyl)-N-phenyl-thiopropioimidate $^1$H-NMR (CDCl$_3$) δ(ppm): 0.09(6H,s), 0.30(3H,s), 1.13-1.80(8H,m), 2.04-2.18(2H,m), 3.52-3.64(0.33H,m), 3.75-3.87(0.66H,m), 6.87-7.36(5H,m)

Ethyl N-(4-methylphenyl)-3-trimethylsilyl-thiopropioimidate $^1$H-NMR (CDCl$_3$) δ(ppm): 0.12(6H,s), 0.29(3H,s), 1.23-1.38(3H,m), 2.33(3H,s), 3.07-3.13(2H,m), 6.82(1H,d J=8.3 Hz), 6.99(1H,d J=8.3 Hz), 7.09-7.15(2H,m)

Propyl N-(4-methylphenyl)-3-trimethylsilyl-thiopropioimidate $^1$H-NMR (CDCl$_3$) δ(ppm): 0.12(6H,s), 0.29(3H,s), 0.93-1.05(3H,m), 1.66-1.78(2H,m), 2.33(3H,s), 3.04-3.10(2H,m), 6.83(1H,d, J=8.2 Hz), 6.99(1H,d, J=8.4 Hz), 7.10(1H,d, J=8.0 Hz), 7.15(1H,d J=7.7 Hz)

Butyl N-(4-methylphenyl)-3-trimethylsilyl-thiopropioimidate $^1$H-NMR (CDCl$_3$) δ(ppm): 0.12(6H,s), 0.29(3H,s), 0.88-1.00(3H,m), 1.37-1.50(2H,m), 1.62-1.77(2H,m), 2.33(3H,s), 3.06-3.13(2H,m), 6.83(1H,d, J=8.2 Hz), 6.99(1H,d, J=8.2 Hz), 7.10(1H,d, J=8.0 Hz), 7.15(1H,d J=8.0 Hz)

2-Methylpropyl N-(4-methylphenyl)-3-trimethylsilyl-thiopropioimidate $^1$H-NMR (CDCl$_3$) δ(ppm): 0.12(6H,s), 0.29(3H,s), 0.98 (2H,dJ=6.8 Hz), 1.03(4H,d,J=6.3 Hz), 1.88-2.00(1H,m), 2.32(1.8H,s), 2.33(1.2H,s), 2.99(0.8H,d,J=7.0 Hz), 3.03 (1.2H,d,J=6.5 Hz), 6.83(1H,d,J=8.2 Hz), 6.87(1H,d,J=8.2 Hz), 7.10(1H,d,J=8.2 Hz), 7.15(1H,d,J=8.0 Hz)

1-Methylpropyl N-(4-methylphenyl)-3-trimethylsilyl-thiopropioimidate $^1$H-NMR (CDCl$_3$) δ(ppm): 0.12(6H,s), 0.29(3H,s), 0.98 (1.3H,t, J=8.5 Hz), 1.03(1.7H,t, J=8.5 Hz), 1.36(1.3H,d, J=7.0 Hz), 1.39(1.7H,d, J=6.7 Hz), 1.60-1.78(2H,m), 2.33 (3H,s), 3.64(0.4H,q, J=6.3 Hz), 3.83(0.6H,q, J=6.8 Hz), 6.83 (1H,d, J=8.5 Hz), 7.00(1H,d, J=8.2 Hz), 7.10(1H,d, J=8.0 Hz), 7.15(1H,d, J=7.7 Hz)

cyclopentyl N-(4-methylphenyl)-3-trimethylsilyl-thiopropioimidate $^1$H-NMR (CDCl$_3$) δ(ppm): 0.11(6H,s), 0.28(3H,s), 1.61-1.75(6H,m), 2.15-2.18(2H,m), 2.32(3H,s), 3.88-3.91(0.4H, m), 3.98-4.02(0.6H,m), 6.83(1H,d, J=8.2 Hz), 7.00(1H,d, J=8.2 Hz), 7.10(1H,d, J=8.2 Hz), 7.15(1H,d, J=8.2 Hz)

3,3-Dimethyl-2-propenyl N-(4-methylphenyl)-3-trimethylsilyl-thiopropioimidate $^1$H-NMR (CDCl$_3$) δ(ppm): 0.12(6H,s), 0.29(3H,s), 1.66-1.74(6H,m), 2.32(0.8H,s), 2.33(2.2H,s), 3.64(2H,d J=7.3 Hz), 5.15-5.23(1H,m), 6.83(1H,d,J=8.3 Hz), 7.01(1H,d, J=8.0 Hz), 7.00-7.15(2H,m)

cyclohexyl N-(4-methylphenyl)-3-trimethylsilyl-thiopropioimidate $^1$H-NMR (CDCl$_3$) δ(ppm): 0.12(4.5H,s), 0.30(4.5H,s), 1.26-1.52(6H,m), 1.77(2H,brs), 2.10(2H,brs), 2.33(3H,s), 3.56-3.84(1H,m), 6.82(1H,d,J=8.2 Hz), 6.99(1H,d,J=8.2 Hz), 7.10(1H,d,J=8.5 Hz), 7.15(1H,d,J=8.5 Hz)

Pentyl N-(4-methylphenyl)-3-trimethylsilyl-thiopropioimidate $^1$H-NMR (CDCl$_3$) δ(ppm): 0.12(6H,s), 0.29(3H,s), 0.87-0.92(3H,m), 1.32-1.43(4H,m), 1.63-1.74(2H,m), 2.33(3H,s), 3.05-3.12(2H,m), 6.83(1H,d,J=8.2 Hz), 6.99(1H,d,J=8.5 Hz), 7.10(1H,d,J=8.0 Hz), 7.15(1H,d,J=8.0 Hz)

Decyl N-(4-methylphenyl)-3-trimethylsilyl-thiopropioimidate $^1$H-NMR (CDCl$_3$) δ(ppm): 0.12(6H, s), 0.29(3H, s), 0.88 (3H, t, J=6.9 Hz), 1.26-1.71(16H, m), 2.33(3H, s), 3.05-3.11 (2H, m), 6.82(1H, d, J=8.3 Hz), 6.99(1H, d, J=8.3 Hz), 7.10 (1H, d, J=8.0 Hz), 7.14(1H, d, J=8.0 Hz)

REFERENCE PRODUCTION EXAMPLE 8

Isopropyl N-Phenyl-thiopropioimidate

Isopropyl N-phenyl-3-(trimethylsilyl)thiopropioimidate (1.6 g) was dissolved to methanol (50 ml), small amount of potassium carbonate was added thereto under ice-cooling, then stirred for minutes. The reaction solution was poured into aqueous solution of sodium chloride, and it was extracted with ethyl acetate. The organic layer was washed with water, dried and distilled off the solvent to obtain isopropyl N-phenyl-thiopropioimidate (1.1 g).

$^1$H-NMR (CDCl$_3$) δ(ppm): 1.38(1.5H,d,J=6.8 Hz), 1.41 (4.5H,d,J=7.0 Hz), 3.20(0.8H,s), 3.40(0.2H,s), 3.80-4.20 (1H,m), 6.88-7.38(5H,m)

Below mentioned compounds were synthesized in a similar manner as above.

Methyl N-phenyl-thiopropioimidate $^1$H-NMR (CDCl$_3$) δ(ppm): 2.35(2H,s), 2.37(1H,s), 3.25 (0.66H,s), 2.49(0.33H,s), 6.98-7.37(5H,m)

Benzyl N-phenyl-thiopropioimidate $^1$H-NMR (CDCl$_3$) δ(ppm): 3.25(0.75H,s), 3.51(0.25H,s), 4.38(1.3H,s), 4.60(0.7H,s), 6.88-7.42(10H,m)

2-Propenyl N-phenyl-thiopropioimidate $^1$H-NMR (CDCl$_3$) δ(ppm): 3.25(0.8H,s), 3.46(0.2H,s), 3.77-3.82(2H,m), 5.13-5.35(2H,m), 5.82-6.03(1H,m), 6.88-7.38(5H,m)

2-Propynyl N-phenyl-thiopropioimidate $^1$H-NMR (CDCl$_3$) δ(ppm): 2.22(0.8H,t,J=2.6 Hz), 2.26 (0.2H,t,J=2.6 Hz), 3.29(0.8H,s), 3.52(0.2H,s), 3.86(0.4H,d, J=2.6 Hz), 3.92(1.6H,d,J=2.6 Hz), 6.88-7.38(5H,m)

1-Phenethyl N-phenyl-thiopropioimidate $^1$H-NMR (CDCl$_3$) δ(ppm): 1.76(1.5H,d,J=6.8 Hz), 2.05 (0.5H,d, J=6.8 Hz), 3.21(0.75H,s), 3.44(0.25H,s), 5.08 (0.75H,q,J=7.0 Hz), 5.22(0.25H,q, 7.0 Hz), 6.98-7.55(10H, m). 88-7.38(5H,m)

cyclohexyl N-phenyl-thiopropioimidate $^1$H-NMR (CDCl$_3$) δ(ppm): 1.27-1.80(8H,m), 2.05-2.14 (2H,m), 3.20(0.66H,s), 3.38(0.33H,s), 3.55-3.66(0.33H,s), 3.80-3.90(0.66H,s), 6.88-7.48(5H,m)

Ethyl N-(4-methylphenyl)-thiopropioimidate $^1$H-NMR (CDCl$_3$) δ(ppm): 1.25(3H,m), 2.33(3H,s), 2.89 (0.2H,q, J=7.3 Hz), 3.12(1.8H,q, J=7.3 Hz), 3.24(0.75H,s) 3.40(0.25H,s) 6.75-7.17(4H,m)

Propyl N-(4-methylphenyl)-thiopropioimidate $^1$H-NMR (CDCl$_3$) δ(ppm): 0.95-1.08(3H,m), 1.67-1.79 (2H,m), 2.33(3H,s), 3.07-3.13(2H,m), 3.24(0.75H,s), 3.40 (0.25H,s), 6.84(0.5H,d, J=8.3 Hz), 6.93(1.5H,d, J=8.3 Hz), 7.10-7.17(2H,m)

Butyl N-(4-methylphenyl)-thiopropioimidate $^1$H-NMR (CDCl$_3$) δ(ppm): 0.88-1.00(3H,m), 1.34-1.50 (2H,m), 1.63-1.77(2H,m), 2.31(0.4H,s), 2.33(2.6H,s), 3.09-3.15(2H,m), 3.25(0.75H,s), 3.40(0.25H,s), 6.84(0.5H,d, J=8.2 Hz), 6.94(1.5H, d, J=8.2 Hz), 7.08-7.17(2H,m)

2-Methylpropyl N-(4-methylphenyl)-thiopropioimidate $^1$H-NMR (CDCl$_3$) δ(ppm): 0.98(1.5H,d J=6.5 Hz), 1.04 (4.5H,d, J=6.8 Hz), 1.87-2.04(1H,m), 2.33(2.25H,s), 2.34 (0.75H,s), 3.01(0.5H,d,J=6.8 Hz), 3.05(1.5H,d,J=6.5 Hz), 3.25(0.75H,s), 3.40(0.25H,s), 6.84(0.5H,d,J=8.2 Hz), 6.93 (1.5H,d,J=8.5 Hz), 7.12(1.5H,d,J=8.0 Hz), 7.16(0.5H,d, J=8.0 Hz)

1-Methylpropyl N-(4-methylphenyl)-thiopropioimidate $^1$H-NMR (CDCl$_3$) δ(ppm): 0.98(1H,t,J=7.3 Hz), 1.03(2H, t,J=7.3 Hz), 1.36(1H,d,J=6.8 Hz), 1.40(2H,d,J=7.1 Hz), 1.59-1.78(2H,m), 2.33(3H,s), 3.22(0.75H,s), 3.37(0.25H,s), 3.68 (0.25H,q, J=6.8 Hz), 3.86(0.75H,q,J=6.8 Hz), 6.83(0.5H,d, J=8.3 Hz), 6.94(1.5H,d,J=8.0 Hz), 7.14(2H,m)

cyclopentyl N-(4-methylphenyl)-thiopropioimidate $^1$H-NMR (CDCl$_3$) δ(ppm): 1.59-1.76(6H,m), 2.16-2.23 (2H,m), 2.33(3H,s), 3.23(0.7H,s), 3.39(0.3H,s), 3.92-4.05 (1H,m), 6.83(0.5H,d J=8.5 Hz), 6.93(1.5H,d J=8.2 Hz), 7.11-7.16(2H,m)

3,3-Dimethyl-2-propenyl N-(4-methylphenyl)-thiopropioimidate $^1$H-NMR (CDCl$_3$) δ(ppm): 1.62-1.77(6H,m), 2.32(1H,s), 2.33(2H,s), 3.24(0.75H,s), 3.44(0.25H,s), 3.78(2H,d,J=7.8 Hz), 6.84(0.5H,d,J=8.3 Hz), 6.95(1.5H,d,J=8.3 Hz), 7.12-7.15(2H,m)

cyclohexyl N-(4-methylphenyl)-thiopropioimidate $^1$H-NMR (CDCl$_3$) δ(ppm): 1.24-1.53(6H,m), 1.73-1.75 (2H,m), 2.08-2.10(2H,m), 2.33(3H,s), 3.22(0.7H,s), 3.37(0.3H,s), 3.58-3.86(1H,m), 6.83(0.5H,d,J=8.2 Hz), 6.93 (1.5H,d,J=8.2 Hz), 7.11-7.16(2H,m)

Pentyl N-(4-methylphenyl)-thiopropioimidate $^1$H-NMR (CDCl$_3$) δ(ppm): 0.91(3H,t,J=7.2 Hz), 1.31-1.45 (4H,m), 1.63-1.75(2H,m), 2.33(3H,s), 3.07-3.13(2H,m), 3.24(0.7H,s), 3.40(0.3H,s), 6.84(0.5H,d,J=8.5 Hz), 6.93(1.5H,d, J=8.2 Hz), 7.12-7.17(2H,m)

Decyl N-(4-methyl-phenyl)-thiopropioimidate $^1$H-NMR (CDCl$_3$) δ(ppm): 0.88(3H, t, J=6.8 Hz), 1.26-1.74(16H, m), 2.33(3H, s), 3.08-3.13(2H, m), 3.24(0.75H, s), 3.40(0.25H, s), 6.83(0.5H, d, J=8.3 Hz), 6.94(1.5H, d, J=8.3 Hz), 7.12(1.5H, d, J=8.0 Hz), 7.15(0.5H, d, J=8.0 Hz)

REFERENCE PRODUCTION EXAMPLE AA1 cyclohexylmethyl N-(4-chlorophenyl)-3-(trimethylsilyl)thiopropynimidate

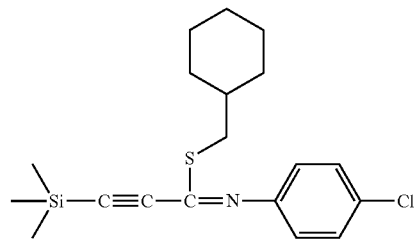 [SMILES: C[Si](C)(C)C#CC(=Nc1ccc(Cl)cc1)SCC1CCCCC1]

Ethynyl trimethyl silane (0.89 g) was dissolved to dry THF (15 mL), n-butyl lithium/hexane solution (1.6 mol./L; 5 mL) was added thereto at −78° C., and then it was warmed to 0° C. The mixture was cooled to −78° C., THF (4 mL) solution of 4-chlorophenyl isothiocyanate (1.44 g) was added dropwise, and then the mixture was allowed to warm to 0° C. THF (5 mL) solution of bromomethylcyclohexane (1.52 g) was added thereto under ice-cooling, and then the mixture was stirred at 50° C. for 6 hours. The reaction solution was concentrated. The residue was subjected to silica gel column chromatography (hexane/ethyl acetate=20/1) to obtain cyclohexylmethyl N-(4-chlorophenyl)-3-(trimethylsilyl)thiopropynimidate (0.34 g).

$^1$H-NMR (CDCl$_3$) δ(ppm): 0.12(6H, s), 0.29(3H, s), 0.91-1.07(5H, m), 1.60-1.88(6H, m), 3.00-3.03(2H, m), 6.85(0.6H, d, J=8.5 Hz), 6.98(1.4H, d, J=8.7 Hz), 7.26(1.2H, d, J=8.7 Hz), 7.30(0.8H, d, J=8.5 Hz)

Below mentioned compounds were synthesized in a similar manner as the Reference Production Example AA1.

cyclohexylmethyl N-(4-methoxyphenyl)-3-(trimethylsilyl)thiopropynimidate

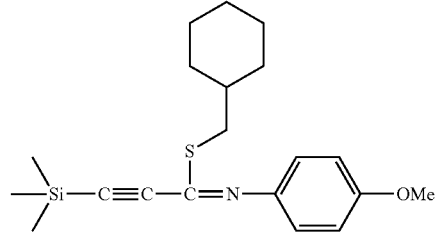 [SMILES: COc1ccc(N=C(C#C[Si](C)(C)C)SCC2CCCCC2)cc1]

$^1$H-NMR (CDCl$_3$) δ(ppm): 0.15(6H, s), 0.29(3H, s), 0.92-1.28(5H, m), 1.60-1.88(6H, m), 3.00-3.04(2H, m), 3.81(3H, s), 6.84-6.95(2.8H, m), 7.12(1.2H, d, J=8.8 Hz)

cyclohexylmethyl
N-phenyl-3-(trimethylsilyl)thiopropynimidate cyclohexylmethyl N-(3-methylphenyl)-3-(trimethyl-
silyl)thiopropynimidate

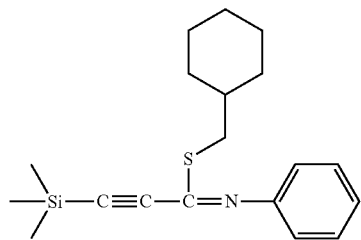 [SMILES: C[Si](C)(C)C#CC(=Nc1ccccc1)SCC1CCCCC1]

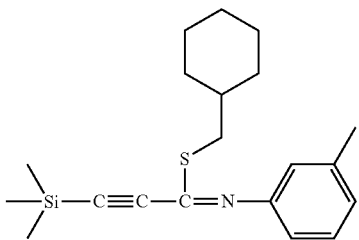

$^1$H-NMR (CDCl$_3$) δ(ppm): 0.09(6H, s), 0.29(3H, s), 0.90-1.27(5H, m), 1.58-1.89(6H, m), 2.99(0.7H, d, J=7.1 Hz), 3.04(1.3H, d, J=6.6 Hz), 6.91(0.7H, d, J=8.5 Hz), 7.02(1.3H, d, J=8.5 Hz), 7.08-7.14(1H, m), 7.27-7.36(2H, m)

$^1$H-NMR (CDCl$_3$) δ(ppm): 0.11(6H, s), 0.29(3H, s), 0.86-1.32(5H, m), 1.57-1.91(6H, m), 2.33(2H, s), 2.34(1H, s), 2.99(0.7H, d, J=7.0 Hz), 3.03(1.3H, d, J=7.0 Hz), 6.71(0.7H, d, J=6.8 Hz), 6.82-6.89(1.3H, m), 6.90-6.96(1H, m), 7.15-7.25(1H, m).

1-cyclohexylethyl N-(4-methylphenyl)-3-(trimethyl-
silyl)thiopropynimidate cyclohexylmethyl N-(3-chlorophenyl)-3-(trimethyl-
silyl)thiopropynimidate

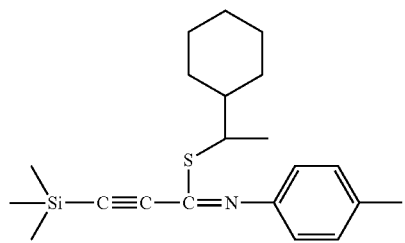

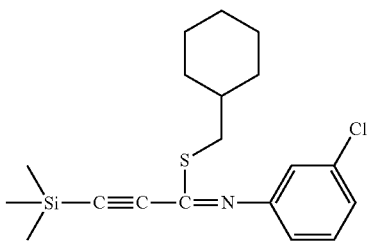

$^1$H-NMR (CDCl$_3$) δ(ppm): 0.12(6H, s), 0.28(3H, s,), 0.96-1.27(6H, m), 1.31(1.3H, d, J=7.2 Hz), 1.36(1.7H, d, J=7.0 Hz), 1.67-1.82(5H, m), 2.30(0.8H, s), 2.32(2.2H, s), 3.65-3.72(0.4H, m), 3.86-3.92(0.6H,m), 6.73-6.77(0.5H,m), 6.83(0.6H,d,J=8.2 Hz), 6.98(0.9H, d, J=8.5 Hz), 7.09(1.3H, d, J=8.0 Hz), 7.14(0.7H, d, J=8.2 Hz)

$^1$H-NMR (CDCl$_3$) δ(ppm): 0.12(7.2H, s), 0.30(1.8H, s), 0.87-1.32(5H,m), 1.54-1.92(6H,m), 2.98-3.05(2H,m), 6.76-6.80(0.2H, m), 6.87-6.93(1H, m), 7.05-7.12(1.8H, m), 7.20-7.29(1H, m).

1-cyclohexylethyl
N-phenyl-3-(trimethylsilyl)thiopropynimidate cyclohexylmethyl N-(3-methoxyphenyl)-3-(trimeth-
ylsilyl)thiopropynimidate

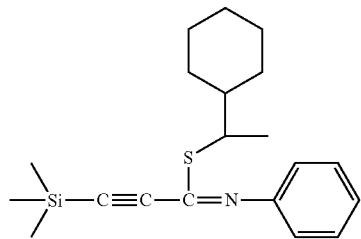 [SMILES: CC(SC(C#C[Si](C)(C)C)=Nc1ccccc1)C1CCCCC1]

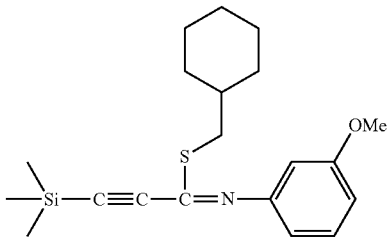 [SMILES: COc1cccc(N=C(C#C[Si](C)(C)C)SCC2CCCCC2)c1]

$^1$H-NMR (CDCl$_3$) δ(ppm): 0.09(6H, s), 0.29(3H,s), 1.00-1.28(5H, m), 1.32(1H, d, J=7.1 Hz), 1.37(2H, d, J=7.1 Hz), 1.57-1.86(6H, m), 3.66-3.72(0.3H, m), 3.87-3.94(0.7H, m), 6.90(0.7H, d, J=8.3 Hz), 7.03(1.3H, d, J=8.3 Hz), 7.08-7.14(1H, m), 7.28-7.36(2H, m)

$^1$H-NMR (CDCl$_3$) δ(ppm): 0.11(6H, s), 0.29(3H, s), 0.88-1.31(5H, m), 1.56-1.92(6H, m), 2.99(0.7H, d, J=6.9 Hz), 3.03(1.3H, d, J=6.9 Hz), 3.79(1H, s), 3.80(2H, s), 6.47(0.3H, t, J=2.2 Hz), 6.49-6.53(0.3H, m), 6.59(0.7H, t, J=2.2 Hz), 6.61-6.65(0.7H, m), 6.65-6.70(1H, m), 7.20(0.7H, t, J=8.1 Hz), 7.24(0.3H, t, J=8.1 Hz)

cyclohexylmethyl N-(3-fluorophenyl)-3-(trimethylsi-lyl)thiopropynimidate

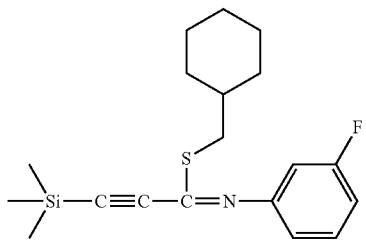 [SMILES: C[Si](C)(C)C#CC(=Nc1cccc(F)c1)SCC1CCCCC1]

¹H-NMR (CDCl₃) δ(ppm): 0.11(6.5H, s), 0.30(2.5H, s), 0.87-1.32(5H, m), 1.56-1.92(6H, m), 3.00(0.6H, d, J=7.0 Hz), 3.03(1.4H, d, J=7.0 Hz), 6.61-6.70(0.6H, m), 6.74-6.85(2.4H, m), 7.20-7.33(1H, m)

cyclopentylmethyl N-(4-methylphenyl)-3-(trimethyl-silyl)thiopropynimidate

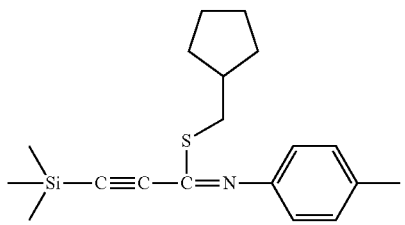

¹H-NMR (CDCl₃) δ(ppm): 0.12(6H, s), 0.29(3H, s), 1.17-1.36(2H, m), 1.50-1.90(6H, m), 2.12-2.37(4H, m), 3.09-3.17(2H, m), 6.80-7.17(4H, m)

cyclopentylmethyl N-phenyl3-(trimethylsilyl)thiopropynimidate

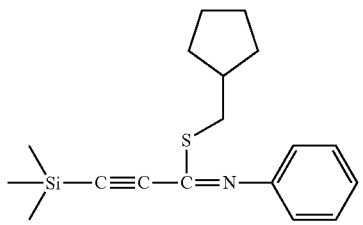 [SMILES: C[Si](C)(C)C#CC(=Nc1ccccc1)SCC1CCCC1]

¹H-NMR (CDCl₃) δ(ppm): 0.10(6H, s), 0.30(3H, s), 1.10-1.38(2H, m), 1.50-1.92(6H, m), 2.12-2.28(1H, m), 3.11-3.18(2H, m), 6.88-7.17(3H, m), 7.26-7.39(2H, m)

cyclohexylmethyl N-(4-fluorophenyl)-3-(trimethylsi-lyl)thiopropynimidate

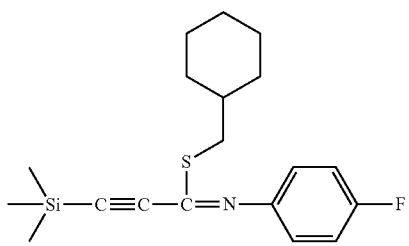 [SMILES: C[Si](C)(C)C#CC(=Nc1ccc(F)cc1)SCC1CCCCC1]

¹H-NMR (CDCl₃) δ(ppm): 0.12(6H, s), 0.29(3H, s), 0.89-1.28(5H, m), 1.59-1.88(6H, m), 3.00-3.03(2H, m), 6.86-7.05(4H, m)

Reference Production Example AA2 cyclopropylmethyl N-phenyl-3-(trimethylsilyl)thiopropynimidate

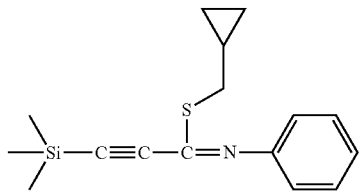 [SMILES: C[Si](C)(C)C#CC(=Nc1ccccc1)SCC1CC1]

Ethynyl trimethyl silane (0.7 mL) was dissolved to dry THF (15 mL), n-butyl lithium/hexane solution (1.58 mol./L; 3.5 mL) was added thereto at −78° C., and then it was warmed to 0° C. The mixture was cooled to −78° C., THF (2 mL) solution of phenyl isothiocyanate (0.65 mL) was added dropwise, and then the mixture was stirred for 40 minutes under ice-cooling. Bromomethylcyclopropane (0.53 mL) was added thereto, and then the mixture was stirred at room temperature for 5 hours. Saturated aqueous solution of ammonium chloride (15 mL) and water (10 mL) was added to the reaction solution, and extracted with t-butyl methyl ether (25 mL). The organic layer was washed with saturated aqueous solution of sodium chloride (25 mL), dried over anhydrous magnesium sulfate. Inorganic salt was filtered off to obtain brown oil (1.44 g). This material was Kugelrohr distilled at 0.3 mmHg at 180° C. for 5 minutes to obtain cyclopropylmethyl N-phenyl-3-(trimethylsilyl)thiopropynimidate (0.91 g).

¹H-NMR (CDCl₃) δ(ppm): 0.10(5H, s), 0.26-0.34(5H, m), 0.56-0.63(2H, m), 1.08-1.18(1H, m), 3.06(d, J=6.8 Hz), 3.08 (d, J=6.8 Hz) total 2H, 6.91-7.15(3H, m), 7.28-7.37(2H, m).

Reference Production Example AA3 cyclohexylmethyl N-(4-chlorophenyl)thiopropynimidate

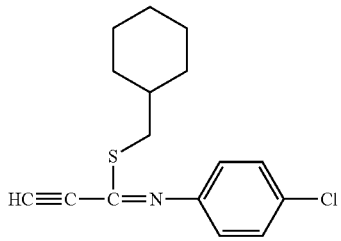 [SMILES: C#CC(=Nc1ccc(Cl)cc1)SCC1CCCCC1]

cyclohexylmethyl N-(4-chlorophenyl)-3-(trimethylsilyl) thiopropynimidate (0.34 g) was dissolved to methanol (5 mL), a small amount of potassium carbonate was added thereto under ice-cooling and stirred for minutes. The reaction solution was poured into aqueous solution of sodium chloride, and extracted with ethyl acetate. The organic layer was washed with water, dried. The solvent was distilled off to obtain cyclohexylmethyl N-(4-chlorophenyl)thiopropynimidate (0.27 g).

¹H-NMR (CDCl₃) δ(ppm): 1.01-1.28(5H, m), 1.60-1.88 (6H, m), 3.02-3.05(2H, m), 3.28(0.75H, s), 3.46(0.25H, s), 6.86(0.5H, d, J=8.8 Hz), 6.94(1.5H, d, J=8.8 Hz), 7.28(1.5H, d, J=8.8 Hz), 7.31(0.5H, d, J=8.8 Hz)

Below mentioned compounds were synthesized in a similar manner as the Reference Production Example AA3.

cyclohexylmethyl N-(4-methoxyphenyl)thiopropynimidate

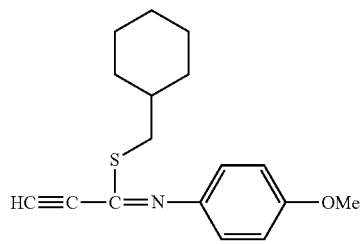 [SMILES: C#CC(=Nc1ccc(OC)cc1)SCC1CCCCC1]

$^1$H-NMR (CDCl$_3$) δ(ppm): 0.93-1.28(5H, m), 1.60-1.89 (6H, m), 3.02-3.05(2H, m), 3.29(0.75H, s), 3.40(0.25H, s), 3.80(3H, s), 6.88-6.96(2.7H, m), 7.05(1.3H, d, J=8.8 Hz)

cyclohexylmethyl N-(phenyl)thiopropynimidate

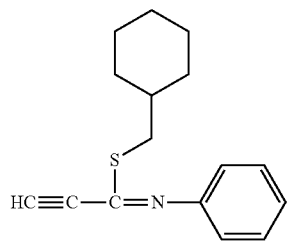

$^1$H-NMR (CDCl$_3$) δ(ppm): 0.92-1.28(5H, m), 1.59-1.89 (6H, m), 3.02(0.5H, d, J=6.8 Hz), 3.06(1.5H, d, J=6.6 Hz), 3.24(0.75H, s), 3.43(0.25H, s), 6.92(0.4H, d, J=7.3 Hz), 7.00 (1.6H, d, J=8.3 Hz), 7.11-7.15(1H, m), 7.31-7.37(2H, m).

1-cyclohexylethyl N-(phenyl)thiopropynimidate

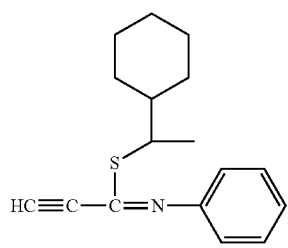 [SMILES: C#CC(=Nc1ccccc1)SC(C)C1CCCCC1]

$^1$H-NMR (CDCl$_3$) δ(ppm): 1.00-1.29(5H, m), 1.33(0.7H, d, J=7.1 Hz), 1.38(2.3H, d, J=7.1 Hz), 1.56-1.79(6H, m), 3.21(0.8H, s), 3.38(0.2H, s), 3.67-3.74(0.2H, m), 3.89-3.96 (0.8H, m), 6.91(0.5H, d, J=8.3 Hz), 7.00(1.5H, d, J=8.3 Hz), 7.10-7.15(1H, m), 7.30-7.37(2H, m)

cyclohexylmethyl N-(3-chlorophenyl)thiopropynimidate

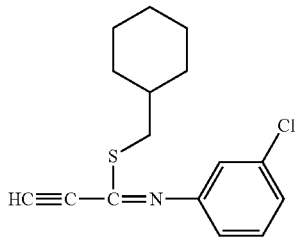 [SMILES: C#CC(=Nc1cccc(Cl)c1)SCC1CCCCC1]

cyclohexylmethyl N-(3-methoxyphenyl)thiopropynimidate

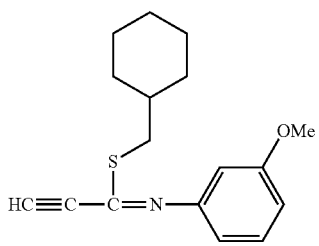 [SMILES: C#CC(=Nc1cccc(OC)c1)SCC1CCCCC1]

cyclohexylmethyl N-(3-fluorophenyl)thiopropynimidate

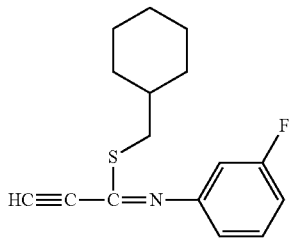 [SMILES: C#CC(=Nc1cccc(F)c1)SCC1CCCCC1]

cyclopentylmethyl N-(phenyl)thiopropynimidate

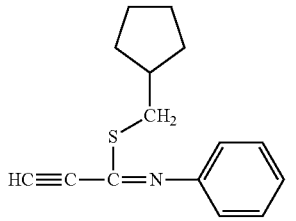 [SMILES: C#CC(=Nc1ccccc1)SCC1CCCC1]

$^1$H-NMR (CDCl$_3$) δ(ppm): 1.15-1.37(2H, m), 1.47-1.93 (6H, m), 2.07-2.27(1H, m). 2.12-2.20(2H, m), 3.23(0.7H, s), 3.43(0.3H, s), 6.87-7.18(3H, m), 7.27-7.38(2H, m)

cyclohexylmethyl
N-(4-fluorophenyl)thiopropynimidate

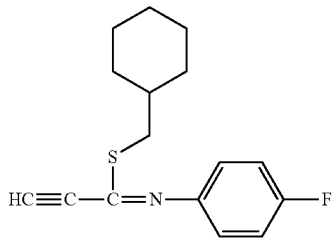 [SMILES: C#CC(=Nc1ccc(F)cc1)SCC1CCCCC1]

¹H-NMR (CDCl₃) δ(ppm): 0.96-1.27(5H, m), 1.62-1.88 (6H, m), 2.99-3.05(2H, m), 3.28(0.6H, s), 3.53(0.4H, s), 6.70-7.06(4H, m)

Reference Production Example AB1

1-ethyl-2-methylpentyl
N-phenyl-3-(trimethylsilyl)thiopropynimidate

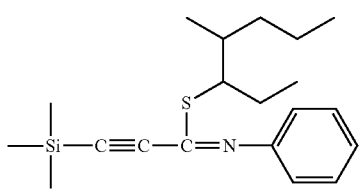 [SMILES: CCCC(C)C(CC)SC(C#C[Si](C)(C)C)=Nc1ccccc1]

Ethynyltrimethylsilane (0.60 g) was dissolved to dry THF (10 mL), hexane solution of n-butyl lithium (1.60 mol./L; 3.4 mL) was added dropwise at −78° C., and then the mixture was allowed to warm to 0° C. The mixture was cooled to −78° C., then THF (3 mL) solution of phenyl isotiocyanate (0.77 g) was added dropwise to the mixture. The reaction mixture was allowed to warm to 0° C. THF (5 mL) solution of 1-ethyl-2-methylpentyl methanesulfonate (1.37 g) was added dropwise to the mixture under ice-cooling, and then heated under reflux for 4 hours. The reaction mixture was concentrated and obtained residue was subjected to silica gel column chromatography (hexane/ethyl acetate=20/1) to obtain 1-ethyl-2-methylpentyl N-phenyl 3-(trimethylsilyl)thiopropynimidate (0.60 g).

¹H-NMR (CDCl₃) δ(ppm): 0.09(6H, s), 0.29(3H, s), 0.83-1.96(16H, m), 3.64-3.73(0.3H, m), 3.88-4.00(0.7H, m), 6.91 (0.6H, d, J=8.5 Hz), 7.00-7.03(1.2H, m), 7.07-7.14(1H, m), 7.27-7.36(2.2H, m)

Below mentioned compounds were synthesized in a similar manner as the Reference Production Example AB1.

1-ethyl-2-methylbutyl
N-phenyl-3-(trimethylsilyl)thiopropynimidate

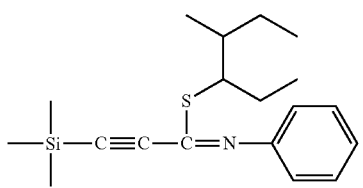 [SMILES: CCC(C)C(CC)SC(C#C[Si](C)(C)C)=Nc1ccccc1]

¹H-NMR (CDCl₃) δ(ppm): 0.09(6H, s), 0.28(3H, s), 0.84-1.07(9H, m), 1.11-1.37(1H, m), 1.42-1.84(4H, m), 3.65-4.04 (1H, m), 6.91(0.6H, d, J=7.5 Hz), 7.02(1.4H, d, J=7.2 Hz), 7.09(1H, t, J=7.3 Hz), 7.26-7.35(2H, m)

1-ethyl-3-methylbutyl
N-phenyl-3-(trimethylsilyl)thiopropynimidate

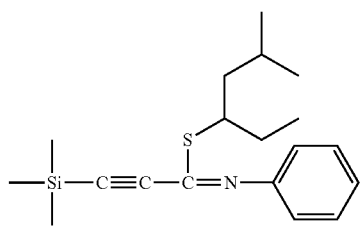 [SMILES: CCC(CC(C)C)SC(C#C[Si](C)(C)C)=Nc1ccccc1]

¹H-NMR (CDCl₃) δ(ppm): 0.09(6H, s), 0.28(3H, s), 0.89-1.05(9H, m), 1.38-1.89(5H, m), 3.71-3.98(1H, m), 6.90(0.7H, d, J=7.3 Hz), 7.03(1.3H, d, J=7.1 Hz), 7.09(1H, t, J=7.2 Hz), 7.27-7.35(2H, m)

2-indanyl-N-phenyl3-(trimethylsilyl)thiopropynimidate

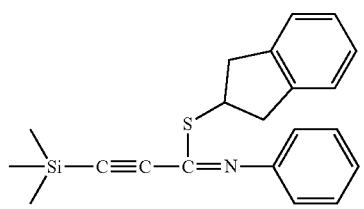 [SMILES: C[Si](C)(C)C#CC(=Nc1ccccc1)SC1Cc2ccccc2C1]

¹H-NMR (CDCl₃) δ(ppm): 0.09(6H, s), 0.29(3H, s), 2.99-3.09(2H, m), 3.47-3.56(2H, m), 4.37-4.44(0.3H, m), 4.50-4.58(0.7H, m), 6.90(0.6H, d, J=8.5 Hz), 7.06-7.23(6.4H, m), 7.28-7.34(2H, m)

Reference Production Example AB2

1-ethyl-2-methylpentyl N-(phenyl)thiopropynimidate

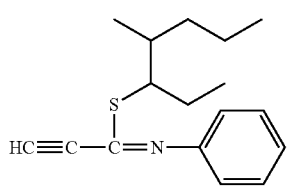 [SMILES: C#CC(=Nc1ccccc1)SC(CC)C(C)CCC]

1-ethyl-2-methylpentyl N-phenyl-3-(trimethylsilyl)thiopropynimidate (0.60 g) was dissolved to methanol (12 mL), small amount of potassium carbonate was added to the solution under ice-cooling, and then stirred for 30 minutes. The reaction mixture was poured into saturated aqueous solution of sodium chloride. It was extracted with ethyl acetate. Obtained organic layer was washed with water, dried, and the solvent was distilled off to obtain 1-ethyl-2-methylpentyl N-(phenyl)thiopropynimidate (0.44 g).

¹H-NMR (CDCl₃) δ(ppm): 0.84-1.98(16H, m), 3.23(0.5H, s), 3.24(0.3H, s), 3.38(0.13H, s), 3.39(0.07H, s), 3.63-3.71

(0.2H, m), 3.91-4.03(0.8H, m), 6.92(0.5H, d, J=8.6 Hz), 6.97-7.01(1.5H, m), 7.10-7.16(1H, m), 7.31-7.37(2H, m)

Below mentioned compounds were synthesized in a similar manner as the Reference Production Example AB2.

1-ethyl-2-methylbutyl N-(phenyl)thiopropynimidate

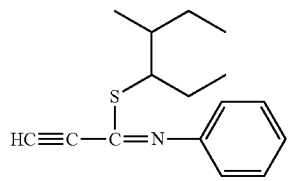 [SMILES: C#CC(=Nc1ccccc1)SC(CC)C(C)CC]

1-ethyl-3-methylbutyl N-(phenyl)thiopropynimidate

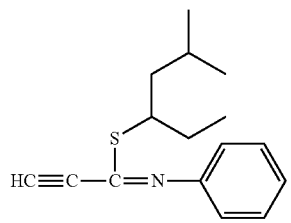 [SMILES: C#CC(=Nc1ccccc1)SC(CC)CC(C)C]

2-indanyl N-(phenyl)thiopropynimidate

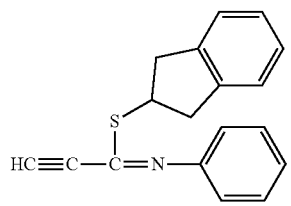 [SMILES: C#CC(=Nc1ccccc1)SC1Cc2ccccc2C1]

$^1$H-NMR (CDCl$_3$) δ(ppm) 2.98-3.09(2H, m), 3.22(0.75H, s), 3.46(0.25H, s), 3.48-3.57(2H, m), 4.43-4.59(1H, m), 6.91 (0.4H, d, J=8.5 Hz), 7.05(1.6H, d, J=8.5 Hz), 7.12-7.36(7H, m)

Then, Formulation Examples will be shown. All parts are by weight.

Formulation Example 1

Into a mixture of 35 parts of xylene and 35 parts of N,N-dimethylformamide, 10 parts of any one of the present compounds (1) to (599) is dissolved, and then 14 parts of polyoxyethylene styrylphenyl ether and 6 parts of calcium dodecylbenzenesulfonate are added. The mixture is stirred thoroughly to obtain a 10% emulsion.

Formulation Example 2

To a mixture of 4 parts of sodium laurylsulfate, 2 parts of calcium ligninsulfonate, 20 parts of synthetic hydrous silicon oxide fine powder and 54 parts of diatomaceous earth, 20 parts of any one of the present compounds (1) to (599) is added. The mixture is stirred thoroughly to obtain a 20% wettable agent.

Formulation Example 3

To 2 parts of any one of the present compounds (1) to (599), 1 part of synthetic hydrous silicon oxide fine powder, 2 parts of calcium ligninsulfonate, 30 parts of bentonite and 65 parts of kaolin clay are added, and then stirred thoroughly. Then, an appropriate amount of water is added to the mixture. The mixture is further stirred, granulated with a granulator, and forced-air dried to obtain a 2% granule.

Formulation Example 4

Into an appropriate amount of acetone, 1 part of any one of the present compounds (1) to (599) is dissolved, and then parts of synthetic hydrous silicon oxide fine powder, 0.3 part of PAP and 93.7 parts of fubasami clay are added. The mixture is stirred thoroughly. Then, acetone is removed from the mixture by evaporation to obtain a 1% powder.

Formulation Example 5

A mixture of 10 parts of any one of the present compounds (1) to (599); 35 parts of white carbon containing 50 parts of polyoxyethylene alkyl ether sulfate ammonium salt; and 55 parts of water is finely ground by a wet grinding method to obtain a 10% flowable agent.

Formulation Example 6

In 5 parts of xylene and 5 parts of trichloroethane, 0.1 part of any one of the present compounds (1) to (599) is dissolved. The solution is mixed with 89.9 parts of deodorized kerosene to obtain a 0.1% oil.

Formulation Example 7

In 0.5 ml of acetone, 10 mg of any one of the present compounds (1) to (599) is dissolved. The solution is mixed uniformly with 5 g of a solid feed powder for an animal (solid feed powder for rearing and breeding CE-2, manufactured by CLEA Japan, Inc.), and then dried by evaporation of acetone to obtain poison bait.

Then, it will be shown by Test Examples that the present compound is effective in controlling pests.

A mixture of 10 parts of the compound; 35 parts of white carbon containing 50 parts of polyoxyethylene alkyl ether sulfate ammonium salt; and 55 parts of water is finely ground by a wet grinding method to obtain a formulation.

The formulation was diluted with water so that the active ingredient concentration became 500 ppm, to prepare test pesticidal solution used in the Test Example 1 to 8.

Test Example 1

Spodoptela litura

In the bottom of polyethylene cup (diameter: 5.5 cm), filter paper having the same diameter was laid. Insecta LF (artificial diet; Nippon Nosan kogyo Co.) which was sliced to 6 mm thin and cut half was put on it. Then 2 ml of abovementioned test pesticidal solution was impregnated. After air-dried, five fourth-instar larvae of tobacco cutworms (Spodoptela litura) were put in the cup and put a lid on. After 6 days, the number of dead larvae was examined. The mortality was calculated by the below formula, and the result is shown by the index number. 4: mortality 100%, 3: mortality 80 to 99%, 2: mortality 60 to 79%, 1: mortality to 59%, 0: mortality 0 to 29% mortality(%)={(the number of dead larvae)/(the number of test larvae)}×100

Compounds (1), (2), (3), (4), (6), (7), (9), (10), (11), (13), (14), (15), (16), (19), (20), (21), (22), (23), (24), (25), (26), (30), (31), (34), (35), (37), (38), (40), (41), (43), (44), (45), (46), (47), (50), (51), (53), (54), (55), (56), (57), (58), (59), (61), (63), (64), (65), (67), (69), (70), (71), (72), (73), (74), (75), (76), (77), (78), (80), (81), (83), (84), (86), (87), (88), (91), (97), (101), (102), (103), (104), (105), (106), (107), (108), (110), (111), (112), (113), (114), (115), (118), (119), (121), (123), (136), (142), (146), (149), (151), (152), (156), (157), (159), (166), (167), (168), (169), (174), (175), (177), (180), (184) to (187), (189), (193) to (195), (198), (200), (203) to (205), (211) to (237), (239) to (241), (247) to (252), (254) to (256), (258) to (260), (263) to (273), (277) to (307), (316), (317), (321), (322), (324), (325), (330), (332) to (339), (341) to (370), (373), (377), (385), (386), (388) to (401), (410) to (418), (427) to (453), (458), (459), (461) to (463), (469) to (490), (493), (495) to (502), (505), (507), (513), (598) and (599) were shown index number 3 or more. Then efficient insecticidal activity is observed.

Test Example 2

Adoxophyes orana

In the bottom of polyethylene cup (diameter: 5.5 cm), filter paper having the same diameter was placed. Silkmate 2S (artificial diet; Nippon Nosan kogyo Co.) which was sliced to 2 mm thin was put on it. Then 1 ml of above mentioned test pesticidal solution was impregnated. After air-dried, thirty first-instar larvae of summer fruit tortrix (*Adoxophyes orana*) were put in the cup. After 7 days, the number of survived larvae was examined. The mortality was calculated by the below formula, and the result is shown by the index number. 4: mortality 100%, 3: mortality 80 to 99%, 2: mortality 60 to 79%, 1: mortality to 59%, 0: mortality 0 to 29% mortality(%)={(the number of test larvae−the number of survived larvae)/(the number of test larvae)}×100

Compounds (1), (2), (3), (4), (6), (7), (9), (10), (11), (13), (14), (15), (16), (19), (20), (21), (22), (23), (24), (25), (26), (30), (31), (34), (35), (37), (38), (40), (41), (42), (43), (44), (45), (46), (47), (48), (50), (51), (52), (53), (54), (56), (57), (58), (59), (63), (64), (65), (69), (70), (71), (72), (73), (74), (75), (76), (77), (78), (80), (81), (83), (84), (86), (87), (88), (91), (92), (97), (100), (101), (102), (103), (104), (105), (106), (107), (108), (110), (111), (112), (113), (114), (115), (118), (119), (120), (121), (122), (123), (128), (136), (146), (149), (151), (152), (156), (157), (159), (162), (166), (167), (168), (169), (170), (174) to (180), (184) to (187), (189), (192) to (195), (198) to (200), (203) to (205), (211) to (237), (239) to (243), (247) to (261), (263) to (308), (311), (315) to (317), (321) to (325), (330) to (339), (341) to (379), (381), (383), (385), (386), (388) to (400), (410) to (415), (424), (428) to (453), (458), (459), (462), (463), (469) to (490), (492), (493), (495) to (502), (505), (507), (513), (598) and (599) were shown index number 3 or more. Then efficient insecticidal activity is observed.

Test Example 3

Aphis gossypii

A cucumber in a first-leaf stage which was grown in 1 ounce cup was inoculated with thirty first-instar larvae of cotton aphids (*Aphis gossypii*). After one day, 20 ml of above mentioned test pesticidal solution was sprayed. After 6 days, the number of survived larvae was examined. The surviving rate based on untreated check was calculated by the below formula, and the result is shown by the index number. 4: surviving rate 0%, 3: surviving rate 1 to 10%, 2: surviving rate 11 to 40%, 1: surviving rate 41 to 70%, 0: surviving rate more than 70% surviving rate(%)=(the number of survived larvae on the treated cucumber)/the number of test larvae on the untreated cucumber)×100

Compounds (1), (2), (3), (4), (8), (9), (10), (12), (14), (15), (16), (17), (18), (19), (20), (23), (24), (25), (26), (27), (29), (30), (31), (34), (35), (37), (38), (41), (45), (46), (47), (54), (63), (64), (69), (70), (73), (74), (81), (84), (85), (87), (88), (91), (103), (106), (111), (117), (118), (119), (130), (155), (157), (158), (159), (174), (177), (180), (187), (192), (198), (203), (259), (263) to (271), (278) to (281), (284), (288), (290) to (302), (307), (321), (322), (324), (330), (333) to (335), (341) to (345), (347) to (365), (367) to (371), (373), (386), (388), (393) to (397), (407), (409), (410), (415), (416), (428) to (431), (433) to (438), (440) to (449), (451), (458), (459), (463) to (465), (469) to (476), (480) to (484), (486) to (488), (497), (498), (501), (502), (505), (513), (598) and (599) were shown index number 3 or more. Then efficient insecticidal activity is observed.

Test Example 4

Nilaparvata lugens

A rice plants grown until the second or third foliage in 90 ml plastic cup were cut into the same height of 5 cm. 20 ml of above mentioned test pesticidal solution was sprayed. After air-dried, thirty first to second-instar larvae of brown rice planthopper (*Nilaparvata lugens*) were set free on the rice plants and put a lid on. After 6 days, the number of survived larvae was examined. The surviving rate based on untreated check was calculated by the below formula, and the result is shown by the index number. 4: surviving rate 0%, 3: surviving rate 1 to 10%, 2: surviving rate 11 to 40%, 1: surviving rate 41 to 70%, 0: surviving rate more than 70% surviving rate(%)=(the number of survived larvae on treated rice/the number of test larvae on untreated rice)×100

Compounds (1), (2), (3), (16), (18), (20), (24), (25), (30), (31), (32), (33), (35), (37), (38), (43), (45), (47), (50), (54), (56), (57), (58), (59), (64), (69), (74), (75), (81), (84), (87), (103), (130), (151), (156), (157), (158), (159), (170), (174), (175), (177), (186), (187), (189) to (194), (198), (198), (203), (264) to (268), (280), (281), (284), (286), (288), (290), (292) to (297), (302), (321), (322), (324), (333), (334), (341), (344), (345), (347) to (354), (356) to (364), (367), (368), (370), (386), (388), (393) to (395), (407), (409), (428) to (432), (434) to (438), (441) to (449), (451), (463), (464), (469) to (476), (481), (482), (486) to (488), (490), (491), (497), (505), (513), (598) and (599) were shown index number 3 or more. Then efficient insecticidal activity is observed.

Test Example 5

Musca domestica

In the bottom of a polyethylene cup (diameter: 5.5 cm), filter paper having the same diameter was laid. After 0.7 ml of above mentioned test pesticidal solution was dropped on the filter paper and 30 mg of sucrose as diet was uniformly scattered. Ten female adult houseflies (*Musca domestica*) were left in the cup and put a lid on. After 24 hours, the number of dead insect was examined. The mortality was calculated by the below formula, and the result is shown by the index number. 4: mortality 100%, 3: mortality 70 to 99%, 2: mortality 40 to 69%, 1: mortality to 39%, 0: mortality 0 to 9% mortality(%)={(the number of dead insect)/(the number of test insect)}×100

Compounds (1), (2), (3), (4), (6), (9), (10), (13), (14), (16), (20), (23), (24), (25), (26), (30), (31), (34), (35), (37), (38), (40), (41), (43), (46), (47), (50), (54), (56), (57), (58), (59), (63), (64), (65), (66), (69), (70), (71), (72), (73), (74), (75), (81), (84), (86), (87), (91), (97), (98), (102), (103), (105), (106), (108), (111), (118), (119), (120), (121), (122), (136), (146), (149), (156), (157), (162), (163), (166), (174), (177), (185) to (187), (198), (203) to (205), (234), (259), (263) to (268), (278) to (281), (284), (286) to (302), (304), (305), (307), (321), (324), (332) to (334), (343), (354), (363), (368) to (370), (429) to (432), (434) to (437), (440), (443), (446), (447), (469) to (477), (480), (482), (486) to (488), (490), (497), (498) and (505) were shown index number 3 or more. Then efficient insecticidal activity is observed.

Test Example 6

Blattalla germanica

In the bottom of a polyethylene cup (diameter: 5.5 cm), filter paper having the same diameter was laid. After 0.7 ml of above mentioned test pesticidal solution was dropped on the filter paper and 30 mg of sucrose as diet was uniformly scattered. Two male adult German cockroach (Blattalla germanica) were left in the cup and put a lid on. After 6 days, the number of dead insect was examined. The mortality was calculated by the below formula, and the result is shown by the index number. 4: mortality 100%, 2: mortality 50%, 0: mortality 0% mortality(%)={(the number of dead insect)/(the number of test insect)}×100

Compounds (1), (2), (3), (4), (9), (10), (13), (14), (16), (24), (25), (26), (30), (31), (34), (35), (37), (38), (40), (41), (43), (45), (46), (47), (50), (54), (58), (69), (72), (73), (74), (75), (87), (102), (103), (106), (107), (108), (111), (123), (146), (151), (156), (157), (166), (174), (175), (177), (180), (186), (187), (198), (200), (203), (204), (219), (228), (260), (263) to (268), (270) to (272), (274), (278) to (281), (284) to (286), (293), (295), (297), (321), (322), (324), (333), (334), (348), (388), (389), (394), (395), (398), (399), (428) to (449), (451), (452), (454), (456), (462), (463), (467), (469) to (476), (480) to (483), (485) to (487), (490), (495), (497), (501), (502), (505), (513) and (599) were shown index number 4.

Test Example 7

Culex pipiens pallens 0.7 ml of above mentioned test pesticidal solution was added to 100 ml of ion-exchanged water (concentration of active ingredient: 3.5 ppm). 20 last-instar larvae of common mosquitoes (*Culex pipiens pallens*) were left in the water. After one day, the number of dead larvae was examined. The mortality was calculated by the below formula, and the result is shown by the index number. 4: mortality 91 to 100%, 2: mortality 10 to 90%, 0: mortality 0 to 10% mortality(%)={(the number of dead larvae)/(the number of test larvae)}×100

Compounds (1), (2), (3), (4), (6), (7), (9), (10), (13), (14), (16), (19), (20), (23), (24), (25), (26), (30), (31), (34), (35), (37), (38), (40), (41), (42), (43), (45), (46), (47), (50), (51), (53), (54), (56), (57), (58), (59), (63), (64), (65), (66), (69), (70), (71), (72), (73), (74), (75), (77), (78), (80), (81), (84), (86), (87), (88), (98), (100), (102), (103), (104), (105), (106), (107), (108), (111), (113), (114), (115), (118), (119), (121), (123), (128), (133), (136), (146), (150), (156), (157), (159), (162), (163), (166), (174), (175), (177), (180), (186), (187), (192) to (195), (198) to (201), (203) to (205), (213), (215) to (217), (223), (225) to (229), (234) to (238), (243), (256), (259) to (273), (278) to (281), (284) to (308), (316), (317), (321), (322), (324) to (328), (330) to (336), (338) to (355), (357) to (364), (368) to (370), (382), (385), (386), (388), (392) to (395), (401), (418), (419), (428) to (449), (452) to (455), (459), (465), (466), (469) to (483), (485) to (490), (492), (493), (495) to (497), (501), (502), (505), (507), (513), (598) and (599) were shown index number 4.

Test Example 8

Tetranychus urticae

A kidney beans were planted in a 3 ounce cup, and grown for one week. A leaf of kidney beans which many two-spotted spider mites (*Tetranychus urticae*) were parasited was cut and put on the leaves of before-mentioned kidney beans and placed for one day. After removing the leaf which many two-spotted spider mites (*Tetranychus urticae*) had been parasited, 20 ml of above-mentioned test pesticidal solution was sprayed. After 8 days, the number of survived female insect was examined. The result is shown by the index number. 4: survived female insect 0 to 3, 3: survived female insect 4 to 10, 2: survived female insect 11 to 20, 1: survived female insect 21 to 30, 0: survived female insect 31 or more Compounds (17), (28), (29), (32), (33), (194), (272), (396), (409), (418), (436), (452), (480), (481), (486), (497), (499) and (501) were shown index number 3 or more.

Test Example 9

Plutella xylostella 0.075 ml of the mixture of xylene and N,N-dimethylformamide (xylene:N,N-dimethylformamide=1:1) and 0.04 ml of the mixture of xylene and Sorpol 3005X (TOHO Chemical Industry Co. LTD) (xylene:Sorpol 3005X=1:9) were added to 30 mg of the each test compound. The mixture was diluted with water so that the active ingredient concentration came to 500 ppm to prepare test solution. The test solution was applied to a cabbage (*Brassicae oleracea*) in a forth-leaf stage at a rate 20 ml per pot. After air-drying, the ground part of the cabbage was cut off and the ground part of the cabbage was put in a polyethylene cup (volume 100 ml) with five second-instar worm of diamondback (*Plutella xylostella*). It was placed at 25° C.

After five days, the number of dead worm was examined. The mortality was calculated by the below formula, and the result is shown by the index number. 4: mortality 100%, 3: mortality 80 to 99%, 2: mortality 60 to 79%, 1: mortality 30 to 59%, 0: mortality 0 to 29% mortality(%)={(the number of dead larvae)/(the number of test larvae)}×100

Compounds (1), (2), (3), (4), (5), (6), (7), (8), (9), (10), (11), (13), (14), (15), (16), (17), (18), (19), (20), (21), (22), (23), (24), (25), (26), (27), (29), (30), (31), (34), (35), (37), (38), (40), (41), (42), (43), (44), (45), (46), (47), (50), (51), (52), (53), (54), (56), (57), (59), (63), (64), (65), (69), (70), (71), (72), (73), (74), (75), (76), (77), (78), (79), (80), (81), (83), (84), (86), (87), (88), (91), (95), (100), (101), (102), (103), (105), (106), (107), (108), (109), (110), (111), (112), (113), (114), (115), (116), (117), (118), (119), (120), (121), (122), (123), (133), (139), (145), (146), (149), (151), (156), (157), (158), (159), (163), (165), (166), (167), (168), (169), (174), (175), (177), (185), (186), (189), (191), (193), (194), (198) to (205), (211) to (221), (223) to (236), (239) to (242), (245), (247), (248), (252), (254), (256), (258) to (260), (263) to (273), (278) to (282), (284) to (302), (304), (307), (321), (322), (324), (325), (330) to (339), (341) to (371), (373), (375), (377), (379), (380), (386), (388) to (419), (422), (428) to (438), (441) to (449), (451), (452), (454), (457), (458), (462), (463), (465), (466), (469) to (475), (477) to (490), (493), (495) to (502), (505), (507), (513), (598) and (599) were shown index number 3 or more. Then efficient insecticidal activity is observed.

Test Example 10

Bemisia argentifolii 0.1 ml of the mixture of xylene and N,N-dimethylformamide (xylene:N,N-dimethylformamide=1:1) and 0.04 ml of the mixture of xylene and Sorpol 3005X (TOHO Chemical Industry Co. LTD) (xylene:Sorpol 3005X=1:9) were added to 40 mg of the each test compound. The mixture was diluted with water as that the active ingredient concentration came to prescribed concentration. Furthermore, spreader (Dain: Takeda Pharmaceutical Co. LTD) was added at the amount 1/3000 based on the mixture to prepare test solution.
Cabbage was planted in a 3-ounce cup, and grown about three weeks. All leaves excluding the second true leaf were cut off. On the second true leaf, imagoes of silver leaf white fly (*Bemisia argentifolii*) were released and allowed to lay eggs for three days and the imagoes were removed. The cabbage was retained in a greenhouse for 8 days. Then the test solution was sprayed in an amount of 20 ml per cup. After seven days, the mortality was examined. The result is shown by the index number.
4: mortality 100%, 3: mortality 90 to 99%, 2: mortality 60 to 89%, 1: mortality 30 to 59%, 0: mortality 0 to 29%
When the concentration of the active ingredient is 200 ppm, compounds (1) to (4), (7) to (20), (23), (25), (26), (28) to (35), (37), (38), (40), (41), (43), (45), (46), (50), (51), (53), (54), (56), (58), (59), (63), (69) to (76), (80), (81), (87), (88), (91), (101), (103), (105), (106), (111), (113), (117), (123), (125), (130), (156) to (158), (174), (184) to (187), (189), (193), (194), (200), (202) to (210), (219), (225), (228), (230), (232), (234), (248), (250), (258), (260), (263) to (266), (268) to (271), (278) to (281), (284) to (294), (296), (298), (299), (301), (302), (305), (307), (321), (324), (325), (357), (388), (389), (459), (463), (469) to (476), (469) to (476), (481), (482) and (497) were shown index number 3 or more.
When the concentration of the active ingredient is 50 ppm, compounds (21), (24), (344), (348), (350), (352), (355), (358), (360), (364), (368), (394), (395), (398), (430), (436), (442) and (445) were shown index number 3 or more.
When the concentration of the active ingredient is 12.5 ppm, compounds (333) and (431) were shown index number 3 or more.

Test Example 11

Haemaphysalis longicornis 0.5 mg of the test compound was dissolved to 1 ml of acetone. Onto one side of filter paper having 5 cm×10 cm, the solution was applied uniformly and then air-dried. Thereafter, the filter paper was folded in half and fixed by paper clips at the side to form bag like shape. Ten *Haemaphysalis longicornis* was put into the bag, and then the bag was closed with a paper clip. After 2 days, the number of dead insects was examined.
Compounds (1), (2), (3), (4), (24), (26), (28), (29), (35), (37), (43), (45), (48), (50), (51), (52), (54), (59), (63), (69), (75), (77), (80), (88), (101), (102), (103), (104), (106), (107), (111), (113), (118), (119), (120), (121), (122), (123), (130), (146), (156), (186), (187), (188), (189), (195), (207), (208), (264), (265), (266), (267), (278), (280), (284), (321), (324), (333), (334), (341), (428), (429), (430), (431), (433), (434), (435), (441), (442), (443), (446), (447), (469), (470), (471), (472), (473), (474), (475), (469) to (475), (480) and (513) were shown the mortality 100%.

Test Example 12

Plutella xylostella 0.1 ml of the mixture of xylene and N,N-dimethylformamide (xylene:N,N-dimethylformamide=1:1) and 0.04 ml of the mixture of xylene and Sorpol 3005X (TOHO Chemical Industry Co. LTD) (xylene:Sorpol 3005X=1:9) were added to 16 mg of the each test compound. The mixture was diluted with water as that the active ingredient concentration came to 200 ppm. Furthermore, spreader (Dain: Takeda Pharmaceutical Co. LTD) was added at the amount 1/3000 based on the mixture to prepare test solution. The test solution was applied to a cabbage (*Brassicae oleracea*) in a fifth-leaf stage at a rate 20 ml per pot. After air-drying, ten third-instar worm of diamondback (*Plutella xylostella*) was placed onto the cabbage, and the cabbage was covered with a cup having holes. After five days, the number of dead worm was examined. The mortality was calculated by the below formula, and the result is shown by the index number. 4: mortality 100%, 3: mortality 80 to 99%, 2: mortality 60 to 79%, 1: mortality to 59%, 0: mortality 0 to 29% mortality(%)={(the number of dead larvae)/(the number of test larvae)}×100

Compounds (32), (33), (130) and (196) were shown index number 3 or more.

Test Example 13

Spodoptela litura 0.1 ml of the mixture of xylene and N,N-dimethylformamide (xylene:N,N-dimethylformamide=1:1) and 0.04 ml of the mixture of xylene and Sorpol 3005X (TOHO Chemical Industry Co. LTD) (xylene:Sorpol 3005X=1:9) were added to 16 mg of the each test compound. The mixture was diluted with water as that the active ingredient concentration came to prescribed concentration. Furthermore, spreader (Dain: Takeda Pharmaceutical Co. LTD) was added at the amount 1/3000 based on the mixture to prepare test solution. The test solution was applied to a cabbage (*Brassicae oleracea*) in a fifth-leaf stage at a rate 20 ml per pot. After air-drying, ten fourth-instar worm of common cutworm (*Spodoptela litura*) was placed onto the cabbage, and the cabbage was covered with a cup having holes. After four days, the number of dead worm was examined. The mortality was calculated by the below formula, and the result is shown by the index number. 4: mortality 100%, 3: mortality 80 to 99%, 2: mortality 60 to 79%, 1: mortality to 59%, 0: mortality 0 to 29% mortality(%)={(the number of dead larvae)/(the number of test larvae)}×100

When the concentration of the active ingredient was 200 ppm, compounds (5), (8), (12), (17), (18), (27), (29), (32), (33), (117), (125), (126), (158) and (196) were shown index number 3 or more.

When the concentration of the active ingredient was 50 ppm, compound (130) was shown index number 3 or more.

Test Example 14

Adoxophyes orana 0.1 ml of the mixture of xylene and N,N-dimethylformamide (xylene:N,N-dimethylformamide=1:1) and 0.04 ml of the mixture of xylene and Sorpol 3005X (TOHO Chemical Industry Co. LTD) (xylene:Sorpol 3005X=1:9) were added to 16 mg of the each test compound. The mixture was diluted with water as that the active ingredient concentration came to prescribed concentration. Furthermore, spreader (Dain: Takeda Pharmaceutical Co. LTD) was added at the amount 1/3000 based on the mixture to prepare test solution. The test solution was applied to an apple seedling having about 12 to 15 cm height planted in a 3 ounce cup at a rate 20 ml per pot. After air-drying, about sixty first-instar larvae of summer fruit tortrix (*Adoxophyes orana*) were put on the apple, and the apple was covered by polyethylene cup. After 7 days, the number of survived larvae was examined. The mortality was calculated by the below formula, and the result is shown by the index number. 4: mortality 100%, 3: mortality 80 to 99%, 2: mortality 60 to 79%, 1: mortality 30 to 59%, 0: mortality 0 to 29% mortality(%)={(the number of test larvae−the number of survived larvae)/(the number of test larvae)}×100

When the concentration of the active ingredient was 200 ppm, compounds (5), (8), (12), (17), (18), (27), (117), (125), (126), (131) and (196) were shown index number 3 or more.

When the concentration of the active ingredient was 50 ppm, compounds (29), (154) and (158) were shown index number 3 or more.

When the concentration of the active ingredient was 12.5 ppm, compound (32), (33) and (130) was shown index number 3 or more.

Industrial Applicability

According to the present invention, the compound (I) or a salt thereof is useful for an active ingredient of a pesticidal composition because it has an excellent controlling activity against pests.

We claim:

1. An iminopropene compound given by the formula (I) or a salt thereof:

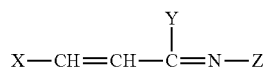

(I)

wherein,

X represents $SX^4$ or $S(O)_m X^5$,

Y represents $OY^1$,

Z represents a cyano group, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{91})Z^A$, $C(=O)OZ^B$, $C(=Q^{92})NZ^D Z^E$, $SO_2 Z^F$, $NZ^G Z^H$, $OZ^K$ or $N=C(Z^I)_2$, $X^4$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{41})X^{A4}$, $C(=O)OX^{B4}$, $C(=Q^{42})NX^{D4}X^{E4}$ or $S(O)_n X^{F4}$, $X^5$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Y^1$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{51})Y^{A1}$, $C(=O)OY^{B1}$, $C(=Q^{52})NY^{D1}Y^{E1}$, $S(O)_p Y^{F1}$ or $N=C(Y^{I1})_2$, $X^{A4}, Y^{A1}$ and $Z^A$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $X^{B4}, Y^{B1}$ and $Z^B$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $X^{D4}, Y^{D1}$ and $Z^D$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or $OG^{a1}$, and $X^{E4}, Y^{E1}$ and $Z^E$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $X^{D4}$ and $X^{E4}$, $Y^{D1}$ and $Y^{E1}$ and $Z^D$ and $Z^E$ represent a ring structure together with the nitrogen which is bonded with each other, $Y^{E1}$ and $Z^F$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $X^{F4}$ a represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Z^G$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{G1})G^{A1}$, $C(=O)OG^{B1}$, $C(=Q^{G2})NG^{D1}G^{E1}$ or $SO_2G^{F1}$, and $Z^H$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $Z^G$ and $Z^H$ represent a ring structure together with the nitrogen which is bonded with each other, $Y^{I1}$ and $Z^I$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $OG^{a2}$, $SG^{a3}$ or $NG^{G1}G^{H1}$, alternatively, represent a ring structure together with the carbon which is bonded with each other, $Z^K$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{K1})G^{A2}$, $C(=O)OG^{B2}$, $C(=Q^{k2})NG^{D2}G^{E2}$ or $SO_2G^{F2}$, $G^{a1}$, $G^{a2}$ and $G^{a3}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{A1}$ and $G^{A2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{B1}$ and $G^{B2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $G^{D1}$ and $G^{D2}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or $OG^{d1}$, and $G^{E1}$ and $G^{E2}$ represent each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{D1}$ and $G^{E1}$, and $G^{D2}$ and $G^{E2}$ represent a ring structure together with the nitrogen which is bonded with each other, $G^{F1}$ and $G^{F2}$ represent each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $G^{G1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=Q^{Ga})G^{A1\text{-}1}$, $C(=O)OG^{B1\text{-}1}$, $C(=Q^{Gb})NG^{D1\text{-}1}G^{E1\text{-}1}$ or $SO_2G^{F1\text{-}1}$, and $G^{H1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{G1}$ and $G^{H1}$ represent a ring structure together with the nitrogen which is bonded with each other, $G^{d1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{A1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $G^{B1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, $G^{D1-1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, an amino group optionally substituted, a cyano group or OL, and $G^{E1-1}$ represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, $G^{D1-1}$ and $G^{E1-1}$ represent a ring structure together with the nitrogen which is bonded with each other, $G^{F1-1}$ represents a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted, L represents a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, $Q^{41}, Q^{42}, Q^{51}, Q^{52}, Q^{91}, Q_{92}, Q^{G1}, Q^{G2}, Q^{K1}, Q^{K2}, Q^{Ga}$ and $Q^{Gb}$ represent each independently oxygen or sulfur, m represents an integer of 1 or 2, n and p represent each independently an integer of 0 or 2, and here, 1) if X is a benzoyloxy group and Y is a methoxy group, then, Z is not a 2-(benzoylamino)vinyl group, and
2) if X is a methoxy group and Y is a trifluoromethylsulfonyloxy group, then, Z is not a 3-vinyloxypropyl group.

2. The compound according to claim 1, wherein

X is $SX^4$ or $S(O)_2X^5$ $X^4$ and $X^5$ are each independently a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $C(=Q^{21})X^{42}$ (wherein, $Q^{21}$ is an oxygen atom, and $X^{42}$ is a lower alkyl group optionally substituted), Y is $OY^1$ (wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{J1})_2$, )

Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the carbon which is bonded with each other).

3. The compound according to claim 2, wherein
X is $SX^4$
(wherein, $X^4$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted),
Y is $OY^1$
(wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{I1})_2$,)

Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^I)_2$ (wherein, $Z^I$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, and alternatively, are formed a ring structure together with the carbon which is bonded with each other).

4. The compound according to claim 3, wherein
X is $SX^4$
(wherein, $X^4$ is a lower alkyl group optionally substituted, a higher alkyl group, a lower alkenyl group optionally substituted, a lower cycloalkyl group optionally substituted, an aromatic hydrocarbon group optionally substituted or a heterocyclic group optionally substituted),
Y is $OY^1$
(wherein, $Y^1$ is a lower alkyl group optionally substituted, an aromatic hydrocarbon group optionally substituted, a heterocyclic group optionally substituted or $N=C(Y^{I1})_2$ ($Y^{I1}$s are each independently a lower alkyl group or an aromatic hydrocarbon group)), and Z is a lower alkyl group optionally substituted, an aromatic hydrocarbon group optionally substituted, a heterocyclic group optionally substituted, a lower alkoxycarbonyl group, an aromatic hydrocarbon sulfonyl group optionally substituted, an amino group substituted with an aromatic hydrocarbon group and optionally substituted with a lower alkyl group, an aromatic hydrocarbon oxy group, a lower alkoxy group substituted with at least one aromatic hydrocarbon group or a lower alkylidene amino group substituted with at least one aromatic hydrocarbon group.

5. The compound according to claim 4, wherein
X is $SX^4$
(wherein, $X^4$ is a lower alkyl group optionally substituted with at least one substituent selected from the group consisting of (1) an aromatic hydrocarbon group optionally substituted with at least one halogen, lower alkyl group or lower alkoxy group and (2) a heterocyclic group optionally substituted with at least one halogen; a higher alkyl group; a lower alkenyl group; a lower cycloalkyl group; an aromatic hydrocarbon group optionally substituted with one or more independent substituent(s) selected from the group consisting of (1) a halogen atom, (2) a nitro group, (3) a lower alkyl group, (4) a lower haloalkyl group and (5) a lower alkoxy group; or a heterocyclic group optionally substituted with one or more lower alkyl group(s)),
Y is $OY^1$ (wherein, $Y^1$ is a lower alkyl group optionally substituted with at least one substituent selected from the group consisting of (1) an aromatic hydrocarbon group optionally substituted with at least one lower alkyl group, (2) an aromatic hydrocarbon group substituted with at least one halogen and (3) a heterocyclic group substituted with at least one halogen; an aromatic hydrocarbon group optionally substituted with one or more independent substituent(s) selected from the group consisting of (1) a halogen, (2) a cyano group, (3) a nitro group, (4) a lower alkyl group, (5) an amino group, (6) a lower alkylthio group, (7) a lower alkylsulfonyl group, (8) a lower cycloalkyl group, (9) an aromatic hydrocarbon group, (10) a lower alkoxycarbonyl group, (11) a lower alkoxy group, (12) a heterocyclic group, (13) a lower alkylene group and (14) a lower alkylenedioxy group; a heterocyclic group; or a lower alkylidene amino group optionally substituted at least one aromatic hydrocarbon group), and Z is a lower alkyl group substituted with at least one halogen; an aromatic hydrocarbon group optionally substituted with one or more independent substituent(s) selected from the group consisting of (1) a halogen, (2) a nitro group, (3) a cyano group, (4) a lower alkyl group, (5) a lower alkoxy group, (6) a lower haloalkyl group, (7) a lower cycloalkyl group and (8) an aromatic hydrocarbon oxy group; a heterocyclic group; a lower alkoxycarbonyl group; an aromatic hydrocarbon sulfonyl group; an amino group substituted with an aromatic hydrocarbon group and optionally substituted with a lower alkyl group; an aromatic hydrocarbon oxy group; a lower alkoxy group substituted with at least one aromatic hydrocarbon group, or a lower alkylidene amino group substituted with at least one aromatic hydrocarbon group.

6. The compound according to claim 2, wherein
X is $S(O)_2X^5$
(wherein, $X^5$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted, or $C(=Q^{21})X^{42}$ (wherein, $Q^{21}$ is an oxygen atom, and $X^{42}$ is a lower alkyl group optionally substituted), Y is $OY^1$
(wherein, $Y^1$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or $N=C(Y^{J1})_2$,)

Z is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, an aromatic hydrocarbon group optionally substituted, a heterocyclic group optionally substituted, $C(=O)OZ^B$ (wherein, $Z^B$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), $SO_2Z^F$ (wherein, $Z^F$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted, a heterocyclic group optionally substituted or an amino group optionally substituted), $NZ^GZ^H$ (wherein, $Z^G$ and $Z^H$ are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, alternatively, are formed a ring structure together with the nitrogen which is bonded with each other), $OZ^K$ (wherein, $Z^K$ is a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted), or $N=C(Z^J)_2$ (wherein, $Z^J$s are each independently a hydrogen atom, a lower alkyl group optionally substituted, a higher alkyl group, a lower cycloalkyl group optionally substituted, a lower alkenyl group optionally substituted, a higher alkenyl group, a lower cycloalkenyl group optionally substituted, a lower alkynyl group optionally substituted, a higher alkynyl group, an aromatic hydrocarbon group optionally substituted or a heterocyclic group optionally substituted, and alternatively, are formed a ring structure together with the carbon which is bonded with each other).

7. The compound according to claim 6, wherein
X is $S(O)_2X^5$
(wherein $X^5$ is an aromatic hydrocarbon group optionally substituted),
Y is $OY^1$
(wherein, $Y^1$ and $Y^4$ are an aromatic hydrocarbon group optionally substituted), and
Z is an aromatic hydrocarbon group optionally substituted.

8. A pesticidal composition comprising the compound according to claim 1 or a salt thereof as an active ingredient, and an inert carrier.

* * * * *